United States Patent
Mongkolsapaya et al.

(10) Patent No.: US 12,030,927 B2
(45) Date of Patent: Jul. 9, 2024

(54) ANTIBODIES CAPABLE OF BINDING TO THE SPIKE PROTEIN OF CORONAVIRUS SARS-CoV-2

(71) Applicant: RQ BIOTECHNOLOGY LIMITED, London (GB)

(72) Inventors: Juthathip Mongkolsapaya, Oxford (GB); Gavin Screaton, Oxford (GB)

(73) Assignee: RQ Biotechnology Limited, London (GB)

( * ) Notice: Subject to any disclaimer, the term of this patent is extended or adjusted under 35 U.S.C. 154(b) by 0 days.

(21) Appl. No.: 18/171,216

(22) Filed: Feb. 17, 2023

(65) Prior Publication Data

US 2023/0265170 A1  Aug. 24, 2023

(30) Foreign Application Priority Data

| Feb. 18, 2022 | (GB) | 2202232 |
| Mar. 11, 2022 | (GB) | 2203423 |
| May 9, 2022 | (GB) | 2206777 |
| Aug. 26, 2022 | (GB) | 2212470 |
| Sep. 26, 2022 | (GB) | 2214036 |
| Oct. 18, 2022 | (GB) | 2215418 |
| Feb. 10, 2023 | (GB) | 2301959 |

(51) Int. Cl.
*C07K 16/10* (2006.01)
*A61P 31/14* (2006.01)
*A61K 39/00* (2006.01)

(52) U.S. Cl.
CPC .............. *C07K 16/10* (2013.01); *A61P 31/14* (2018.01); *A61K 2039/505* (2013.01); *C07K 2317/52* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,122,427 A | 10/1978 | Karsh |
| 4,573,477 A | 3/1986 | Namekawa et al. |
| 5,088,498 A | 2/1992 | Beach et al. |
| 5,111,825 A | 5/1992 | Nishiyama et al. |
| 5,122,464 A | 6/1992 | Wilson et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,573,012 A | 11/1996 | McEwan |
| 5,580,717 A | 12/1996 | Dower et al. |
| 5,585,097 A | 12/1996 | Bolt et al. |
| 5,624,821 A | 4/1997 | Winter et al. |
| 5,648,260 A | 7/1997 | Winter et al. |
| 5,658,727 A | 8/1997 | Barbas et al. |
| 5,677,425 A | 10/1997 | Bodmer et al. |
| 5,693,780 A | 12/1997 | Newman et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,821,047 A | 10/1998 | Garrard et al. |
| 5,869,046 A | 2/1999 | Presta et al. |
| 5,965,726 A | 10/1999 | Pavlakis et al. |
| 5,969,108 A | 10/1999 | McCafferty et al. |
| 6,121,022 A | 9/2000 | Presta et al. |
| 6,165,745 A | 12/2000 | Ward et al. |
| 6,174,666 B1 | 1/2001 | Pavlakis et al. |
| 6,194,551 B1 | 2/2001 | Idusogie et al. |
| 6,277,375 B1 | 8/2001 | Ward |
| 6,291,664 B1 | 9/2001 | Pavlakis et al. |
| 6,314,312 B1 | 11/2001 | Wessels et al. |
| 6,414,132 B1 | 7/2002 | Pavlakis et al. |
| 6,602,684 B1 | 8/2003 | Umana et al. |
| 6,737,056 B1 | 5/2004 | Presta |
| 6,794,498 B2 | 9/2004 | Pavlakis et al. |
| 6,946,292 B2 | 9/2005 | Kanda et al. |
| 7,214,775 B2 | 5/2007 | Hanai et al. |
| 7,658,921 B2 | 2/2010 | Dall-Acqua et al. |
| 7,709,226 B2 | 5/2010 | Foote |
| 8,498,828 B2 | 7/2013 | Sasaki |

(Continued)

FOREIGN PATENT DOCUMENTS

| CN | 101198434 A | 6/2008 |
| CN | 102192769 A | 9/2011 |

(Continued)

OTHER PUBLICATIONS

Lefranc et al., Antibodies (Basel). Oct. 18, 2022;11(4):65. doi: 10.3390/antib11040065. PMID: 36278618 PMCID: PMC9624366.*
Nutalai et al., Cell. Jun. 9, 2022;185(12):2116-2131.e18. doi: 10.1016/j.cell.2022.05.014. Epub May 20, 2022. PMID: 35662412.*
Janeway et al., Immunobiology, 3rd edition, Garland Publishing Inc., 1997, pp. 3:1-3:11.*
Rudikoff et al., Proc Natl Acad Sci U S A. Mar. 1982;79(6):1979-83. doi: 10.1073/pnas.79.6.1979. PMID: 6804947.*
Edwards et al., J Mol Biol. Nov. 14, 2003;334(1):103-18. doi: 10.1016/j.jmb.2003.09.054. PMID: 14596803.*

(Continued)

*Primary Examiner* — Michael Szperka
(74) *Attorney, Agent, or Firm* — Sterne, Kessler, Goldstein & Fox P.L.L.C.

(57) ABSTRACT

The invention relates to antibodies useful for the prevention, treatment and/or diagnosis of coronavirus infections, and diseases and/or complications associated with coronavirus infections, including COVID-19. In particular, the invention relates to antibodies capable of binding to the spike protein of coronavirus SARS-CoV-2 and uses thereof.

26 Claims, 65 Drawing Sheets

Specification includes a Sequence Listing.

(56) References Cited

U.S. PATENT DOCUMENTS

| | | |
|---|---|---|
| 8,591,886 B2 | 11/2013 | Ponath et al. |
| 10,098,572 B2 | 10/2018 | Schwenk et al. |
| 10,207,072 B2 | 2/2019 | Dunn et al. |
| 10,271,739 B2 | 4/2019 | Freeman et al. |
| 10,787,501 B1 | 9/2020 | Babb et al. |
| 11,053,304 B1 | 7/2021 | Glanville et al. |
| 11,253,223 B2 | 2/2022 | Souzy et al. |
| 11,345,741 B2 | 5/2022 | Crowe et al. |
| 2002/0115923 A1 | 8/2002 | Erbel |
| 2004/0014194 A1 | 1/2004 | Beyer et al. |
| 2004/0167389 A1 | 8/2004 | Brabrand |
| 2004/0242997 A1 | 12/2004 | Griffin et al. |
| 2006/0079782 A1 | 4/2006 | Beach et al. |
| 2006/0253928 A1 | 11/2006 | Bakker et al. |
| 2006/0285071 A1 | 12/2006 | Erickson et al. |
| 2007/0178551 A1 | 8/2007 | Gerngross |
| 2007/0248600 A1 | 10/2007 | Hansen et al. |
| 2008/0060092 A1 | 3/2008 | Dickey et al. |
| 2009/0048518 A1 | 2/2009 | Furnam |
| 2010/0076315 A1 | 3/2010 | Erkamp et al. |
| 2010/0081929 A1 | 4/2010 | Suzuki |
| 2011/0121996 A1 | 5/2011 | Griffin et al. |
| 2011/0208060 A1 | 8/2011 | Haase et al. |
| 2013/0030285 A1 | 1/2013 | Vaillant et al. |
| 2013/0079628 A1 | 3/2013 | Groszmann et al. |
| 2013/0165005 A1 | 6/2013 | Berard-Andersen et al. |
| 2014/0213902 A1 | 7/2014 | Nagae et al. |
| 2014/0233794 A1 | 8/2014 | Oh et al. |
| 2014/0302058 A1 | 10/2014 | Bowen et al. |
| 2015/0223782 A1 | 8/2015 | Yamagata et al. |
| 2015/0238169 A1 | 8/2015 | Mizukami |
| 2016/0000409 A1 | 1/2016 | Bruder et al. |
| 2017/0281769 A1 | 10/2017 | Eriksson et al. |
| 2018/0256075 A1 | 9/2018 | Souzy et al. |
| 2021/0038119 A1 | 2/2021 | Souzy et al. |
| 2021/0261650 A1 | 8/2021 | Corti et al. |
| 2021/0277092 A1 | 9/2021 | Crowe et al. |
| 2021/0292393 A1 | 9/2021 | Westendorf et al. |
| 2021/0300999 A1 | 9/2021 | Crowe et al. |
| 2021/0332110 A1 | 10/2021 | Nussenzweig et al. |
| 2021/0355196 A1 | 11/2021 | Esser et al. |
| 2022/0041694 A1 | 2/2022 | Gasser et al. |
| 2022/0281958 A1 | 3/2022 | Crowe et al. |
| 2023/0242626 A1 | 8/2023 | Schmelzer et al. |

FOREIGN PATENT DOCUMENTS

| | | |
|---|---|---|
| CN | 102469957 A | 5/2012 |
| CN | 103584847 A | 2/2014 |
| CN | 103930168 A | 7/2014 |
| CN | 103948401 A | 7/2014 |
| CN | 104703548 A | 6/2015 |
| CN | 104840218 A | 8/2015 |
| CN | 104873224 A | 9/2015 |
| GB | 2443433 A | 5/2008 |
| JP | H05-168633 A | 7/1993 |
| JP | 2010504829 A | 2/2010 |
| JP | 2014502854 A | 2/2014 |
| WO | WO-8605807 A1 | 10/1986 |
| WO | WO-8901036 A1 | 2/1989 |
| WO | WO-9002809 A1 | 3/1990 |
| WO | WO-9110737 A1 | 7/1991 |
| WO | WO-9201047 A1 | 1/1992 |
| WO | WO-9218619 A1 | 10/1992 |
| WO | WO-9311236 A1 | 6/1993 |
| WO | WO-9420021 A2 | 9/1994 |
| WO | WO-9429351 A2 | 12/1994 |
| WO | WO-9515982 A2 | 6/1995 |
| WO | WO-9520401 A1 | 8/1995 |
| WO | WO-9713844 A1 | 4/1997 |
| WO | WO-9734631 A1 | 9/1997 |
| WO | WO-9823289 A1 | 6/1998 |
| WO | WO-9954342 A1 | 10/1999 |
| WO | WO-0042072 A2 | 7/2000 |
| WO | WO-0061739 A1 | 10/2000 |
| WO | WO-0129246 A1 | 4/2001 |
| WO | WO-0230954 A1 | 4/2002 |
| WO | WO-0231140 A1 | 4/2002 |
| WO | WO-02060919 A2 | 8/2002 |
| WO | WO-03011878 A2 | 2/2003 |
| WO | WO-2004049951 A1 | 6/2004 |
| WO | WO-2004065540 A2 | 8/2004 |
| WO | WO-2005007200 A1 | 1/2005 |
| WO | WO-2006057911 A2 | 6/2006 |
| WO | WO-2007032329 A1 | 3/2007 |
| WO | WO-2007039818 A2 | 4/2007 |
| WO | WO-2007106120 A2 | 9/2007 |
| WO | WO-2009036379 A2 | 3/2009 |
| WO | WO-2009128963 A2 | 10/2009 |
| WO | WO-2010052476 A1 | 5/2010 |
| WO | WO-2010105256 A1 | 9/2010 |
| WO | WO-2011135288 A2 | 11/2011 |
| WO | WO-2011139718 A1 | 11/2011 |
| WO | WO-2012009568 A2 | 1/2012 |
| WO | WO-2012130831 A1 | 10/2012 |
| WO | WO-2012142031 A1 | 10/2012 |
| WO | WO-2013165690 A1 | 11/2013 |
| WO | WO-2013169338 A1 | 11/2013 |
| WO | WO-2014111860 A2 | 7/2014 |
| WO | WO-2015179535 A1 | 11/2015 |
| WO | WO-2015197772 A1 | 12/2015 |
| WO | WO-2017186908 A1 | 11/2017 |
| WO | WO-2018160722 A1 | 9/2018 |
| WO | WO-2020061159 A1 | 3/2020 |
| WO | WO-2021045836 A1 | 3/2021 |
| WO | WO-2021195418 A1 | 3/2021 |
| WO | WO-2021158521 A1 | 8/2021 |
| WO | WO-2021163265 A1 | 8/2021 |
| WO | WO-2021183195 A1 | 9/2021 |
| WO | WO-2021203053 A1 | 10/2021 |
| WO | WO-2021231237 A2 | 11/2021 |
| WO | WO-2021233834 A1 | 11/2021 |
| WO | WO-2022026475 A2 | 2/2022 |
| WO | WO-2022034044 A1 | 2/2022 |
| WO | WO-2022035197 A1 | 2/2022 |
| WO | WO-2022167815 A1 | 8/2022 |
| WO | WO-2022167816 A2 | 8/2022 |
| WO | WO-2023084055 A1 | 5/2023 |
| WO | WO-2023079086 A1 | 11/2023 |

OTHER PUBLICATIONS

Llyod et al., Protein Eng Des Sel. Mar. 2009;22(3):159-68. doi: 10.1093/protein/gzn058. Epub Oct. 29, 2008. PMID: 18974080.*

Goel et al., J Immunol. Dec. 15, 2004; 173(12):7358-67 PMID: 15585860 DOI: 10.4049/jimmunol.173.12.7358.*

Lescar et al., J Biol Chem. Jul. 28, 1995;270(30):18067-76. doi: 10.1074/jbc.270.30.18067. PMID: 7629116.*

Kanyavuz et al., Nat Rev Immunol. Jun. 2019;19(6):355-368. doi: 10.1038/S41577-019-0126-7. PMID: 30718829.*

Dall'Acqua et al., J Biol Chem. Aug. 18, 2006;281(33):23514-24. doi: 10.1074/jbc.M604292200. Epub Jun. 21, 2006. PMID: 16793771.*

Baum, A., et al., "Antibody cocktail to SARS-CoV-2 spike protein prevents rapid mutational escape seen with individual antibodies," Science 369(6506):1014-1018, American Association for the Advancement of Science, United States (Aug. 2020).

Caly, L., et al., "The FDA-approved drug ivermectin inhibits the replication of SARS-CoV-2 in vitro," Antiviral Res 178:104787, Elsevier, Netherlands (Jun. 2020).

Cao, Y., et al., "BA.2.12.1, BA.4 and BA.5 escape antibodies elicited by Omicron infection," Nature 608(7923):593-602, Nature Portfolio, Germany (Aug. 2022).

Cele, S., et al., "Omicron extensively but incompletely escapes Pfizer BNT162b2 neutralization," Nature 602(7898):654-656, Nature Portfolio, Germany (Feb. 2022).

Dejnirattisai, W., et al., "Antibody evasion by the p. 1 strain of SARS-CoV-2," Cell 184(11):2939-2954.e9, Cell Press, United States (May 2021).

Dejnirattisai, W., et al., "SARS-CoV-2 Omicron-B.1.1.529 leads to widespread escape from neutralizing antibody responses," Cell 185(3):467-484.e15, Cell Press, United States (Feb. 2022).

(56) References Cited

OTHER PUBLICATIONS

Dejnirattisai, W., et al., "The antigenic anatomy of SARS-CoV-2 receptor binding domain," Cell 184(8):2183-2200.e22, Cell Press, United States (Apr. 2021).
Del Rio, C., and Malani, P.N., "COVID-19 in 2022-The Beginning of the End or the End of the Beginning?," JAMA 327(24):2389-2390, American Medical Association, United States (Jun. 2022).
Di Genova, C., et al., "Production, Titration, Neutralisation, Storage and Lyophilisation of Severe Acute Respiratory Syndrome Coronavirus 2 (SARS-CoV-2) Lentiviral Pseudotypes," Bio Protoc 11(21):e4236, Bio Protocol, United States (Nov. 2021).
Dong, J., et al., "Genetic and structural basis for SARS-CoV-2 variant neutralization by a two-antibody cocktail," Nat Microbiol 6(10):1233-1244, Nature Portfolio, Germany (Oct. 2021).
Flaxman, A., et al., "Reactogenicity and immunogenicity after a late second dose or a third dose of ChAdOx1 nCoV-19 in the UK: a substudy of two randomised controlled trials (COV001 and COV002)," Lancet 398(10304):981-990, Elsevier, Netherlands (Sep. 2021).
Folegatti, P.M., et al., "Safety and immunogenicity of the ChAdOx1 nCoV-19 vaccine against SARS-CoV-2: a preliminary report of a phase 1/2, single-blind, randomised controlled trial," The Lancet 396(10249):467-478, Elsevier, Netherlands (Aug. 2020).
Zhou, D., et al., "Structural basis for the neutralization of SARS-CoV-2 by an antibody from a convalescent patient," Nat Struct Mol Biol 27(10):950-958, Nature Portfolio, Germany (Oct. 2020).
Gobeil, S.M.C., et al., "Effect of natural mutations of SARS-CoV-2 on spike structure, conformation, and antigenicity," Science 373(6555):eabi6226, American Association for the Advancement of Science, United States (Aug. 2021).
Hinton, P.R., et al., "Engineered human IgG antibodies with longer serum half-lives in primates," J Biol Chem 279(8):6213-6216, American Society for Biochemistry and Molecular Biology, United States (Feb. 2004).
Huo, J., et al., "A delicate balance between antibody evasion and ACE2 affinity for Omicron BA.2.75," Cell Rep 42(1):111903, Cell Press, United States (Jan. 2023).
Huo, J., et al., "Humoral responses against SARS-CoV-2 Omicron BA.2.11, BA.2.12.1 and BA.2.13 from vaccine and BA.1 serum," Cell Discov 8(1):119, Springer Nature, Germany (Nov. 2022).
Huo, J., et al., Neutralizing nanobodies bind SARS-CoV-2 spike RBD and block interaction with ACE2, Nat Struct Mol Biol 27(9):846-854, Nature Portfolio, Germany (Sep. 2020).
Idusogie, E.E., et al., "Engineered antibodies with increased activity to recruit complement," J Immunol 166(4):2571-2575, American Association for Immunologists, United States (Feb. 2001).
Iketani, S., et al., "Antibody evasion properties of SARS-CoV-2 Omicron sublineages," Nature 604(7906):553-556, Nature Portfolio, Germany (Apr. 2022).
Lazar, G.A., et al., "Engineered antibody Fc variants with enhanced effector function," Proc Natl Acad Sci USA 103(11):4005-4010, National Academy of Sciences, United States (Mar. 2006).
Liu, C., et al., "Reduced neutralization of SARS-CoV-2 B.1.617 by vaccine and convalescent serum," Cell 184(16):4220-4236.e13, Cell Press, United States (Aug. 2021).
Liu, C., et al., "The antibody response to SARS-CoV-2 Beta underscores the antigenic distance to other variants," Cell Host Microbe 30(1):53-68.e12, Cell Press, United States (Jan. 2022).
Nie, J., et al., "Establishment and validation of a pseudovirus neutralization assay for SARS-CoV-2," Emerg Microbes Infect 9(1):680-686, Taylor & Francis, United Kingdom (Dec. 2020).
Nutalai, R., et al., "Potent cross-reactive antibodies following Omicron breakthrough in vaccinees," Cell 185(12):2116-2131.e18, Cell Press, United States (Jun. 2022).
Polack, F.P., et al., "Safety and Efficacy of the BNT162b2 mRNA Covid-19 Vaccine," N Engl J Med 383(27):2603-2615, Massachusetts Medical Society, United States (Dec. 2020).
Richards, J.O., et al., "Optimization of antibody binding to FcgammaRIIa enhances macrophage phagocytosis of tumor cells," Mol Cancer Ther 7(8):2517-2527, American Association for Cancer Research, United States (Aug. 2008).
Ryan, M.C., et al., "Antibody targeting of B-cell maturation antigen on malignant plasma cells," Mol Cancer Ther 6(11):3009-3018, Springer Science+Business Media, Germany (Nov. 2007).
Sun, Y., and Ho, M., et al., "Emerging antibody-based therapeutics against SARS-CoV-2 during the global pandemic, " Antib Ther 3(4):246-256, Oxford University Press, United Kingdom (Nov. 2020).
Supasa, P., et al., "Reduced neutralization of SARS-CoV-2 B.1.1.7 variant by convalescent and vaccine sera," Cell 184(8):2201-2211.e7, Cell Press, United States (Apr. 2021).
Suzuki, R., et al., "Attenuated fusogenicity and pathogenicity of SARS-CoV-2 Omicron variant," Nature 603(7902):700-705, Nature Portfolio, Germany (Mar. 2022).
Tuekprakhon, A., et al., "Antibody escape of SARS-CoV-2 Omicron BA.4 and BA.5 from vaccine and BA.1 serum," Cell 185(14):2422-2433.e13, Cell Press, United States (Jul. 2022).
Vaccaro, C., et al., "Engineering the Fc region of immunoglobulin G to modulate in vivo antibody levels," Nat Biotechnol 23(10):1283-1288, Nature Portfolio, Germany (Oct. 2005).
Van Der Straten, K., et al., "Antigenic cartography using sera from sequence-confirmed SARS-CoV-2 variants of concern infections reveals antigenic divergence of Omicron," Immunity 55(9):1725-1731.e4, Cell Press, United States (Sep. 2022).
Walter, T.S., et al., "A procedure for setting up high-throughput nanolitre crystallization experiments. I. Protocol design and validation," J Appl Cryst 36:308-314, International Union of Crystallography, United Kingdom (2003).
Weinreich, D.M., et al., "REGN-COV2, a Neutralizing Antibody Cocktail, in Outpatients with Covid-19," N Engl J Med 384(3):238-251, Massachusetts Medical Society, United States (Jan. 2021).
Westendorf, K., et al., "LY-CoV1404 (bebtelovimab) potently neutralizes SARS-CoV-2 variants," Cell Rep 39(7):110812, Cell Press, United States (May 2022).
Yuan, M., et al., "A broad and potent neutralization epitope in SARS-related coronaviruses," bioRxiv 2022.03.13.484037, Cold Spring Harbor Laboratory, United States (Mar. 2022).
Zahradnik, J., et al., "SARS-CoV-2 variant prediction and antiviral drug design are enabled by RBD in vitro evolution," Nat Microbiol 6(9):1188-1198, Nature Portfolio, Germany (Sep. 2021).
Zhou, D., et al., "Evidence of escape of SARS-CoV-2 variant B.1.351 from natural and vaccine-induced sera," Cell 184(9):2348-2361.e6, Cell Press, United States (Apr. 2021).
Pinto, D., et al., "Cross-neutralization of SARS-CoV-2 by a human monoclonal SARS-CoV antibody," Nature 583(7815):290-295, Nature Portfolio, Germany (Jul. 2020).
Cao, Y., et al., "Potent Neutralizing Antibodies against SARS-CoV-2 Identified by High-Throughput Single-Cell Sequencing of Convalescent Patients' B Cells," Cell 182(1):73-84, Cell Press, United States (Jul. 2020).
Hu, Y.F., et al., "In-Silico Analysis of Monoclonal Antibodies against SARS-CoV-2 Omicron," Viruses 14(2):390, Cell Press, United States (Feb. 2022).
Vanblargan, L.A., et al., "An infectious SARS-CoV-2 B.1.1.529 Omicron virus escapes neutralization by therapeutic monoclonal antibodies," Nat Med 28(3):490-495, Nature Portfolio, Germany (Mar. 2022).
Wang, P., et al., "Antibody resistance of SARS-CoV-2 variants B.1.351 and B.1.1.7," Nature 593(7857):130-135, Nature Portfolio, Germany (May 2021).
Yuan, M., et al. "Structural basis of a shared antibody response to SARS-CoV-2," Science 369(6507):1119-1123, American Association for the Advancement of Science, United States (Aug. 2020).
Zost, S.J., et al., "Potently neutralizing and protective human antibodies against SARS-CoV-2," Nature 584(7821):443-449, Nature Portfolio, Germany (Aug. 2020).
Gaudinski, M.R., et al., "Safety, tolerability, pharmacokinetics, and immunogenicity of the therapeutic monoclonal antibody mAb114 targeting Ebola virus glycoprotein (VRC 608): an open-label phase 1 study," Lancet 393(10174):889-898, Elsevier, Netherlands (Mar. 2019).
Hansen, J., et al., "Studies in humanized mice and convalescent humans yield a SARS-CoV-2 antibody cocktail," Science

(56) References Cited

OTHER PUBLICATIONS

369(6506):1010-1014, American Association for the Advancement of Science, United States (Aug. 2020).

Chiu, M.L., et al., "Antibody Structure and Function: The Basis for Engineering Therapeutics," Antibodies (Basel) 8(4):55, MDPI, Switzerland (Dec. 2019).

Kang, T.H., et al., "Boosting therapeutic potency of antibodies by taming Fc domain functions," Exp Mol Med 51(11):1-9, Nature Portfolio, Germany (Nov. 2019).

Chen, R.E., et al., "In vivo monoclonal antibody efficacy against SARS-CoV-2 variant strains," Nature 596(7870):103-108, Nature Portfolio, Germany (Aug. 2021).

Vanblargan, L.A., et al., "A potently neutralizing SARS-CoV-2 antibody inhibits variants of concern by utilizing unique binding residues in a highly conserved epitope," Immunity 54(10):2399-2416, Cell Press, United States (Oct. 2021).

Kramer, K.J., et al., "Potent neutralization of SARS-CoV-2 variants of concern by an antibody with an uncommon genetic signature and structural mode of spike recognition," Cell Rep 37(1):109784, Cell Press, United States (Oct. 2021).

Kreuzberger, N., et al., "SARS-cov-2-neutralising monoclonal antibodies for treatment of COVID-19," Cochrane Database Syst Rev 9(9):CD013825, Wiley, United States (Sep. 2000).

Jin, D., et al., "Analysis of the molecular mechanism of SARS-CoV-2 antibodies," Biochem Biophys Res Commun 566:45-52, Elsevier, Netherlands (Aug. 2021).

Wu, Y., et al., "Identification of Human Single-Domain Antibodies against SARS-CoV-2," Cell Host Microbe 27(6):891-898, Cell Press, United States (Jun. 2020).

Callaway, E., "COVID super-immunity: one of the pandemic's great puzzles," Nature 598(7881):393-394, Nature Portfolio, Germany (Oct. 2021).

Co-pending Application, U.S. Appl. No. 18/052,840, inventors Schmelzer, A., et al., filed Nov. 4, 2022 (Not yet Published).

Algaissi. A., et al., "SARS-CoV-2 S1 and N-based Serological Assays Reveal Rapid Seroconversion and Induction of Specific Antibody Response in COVID-19 Patients," Scientific Reports 10(1):16561, Nature Publishing Group, England (Oct. 2020).

Andreano, E., et al., "SARS-CoV-2 Escape in Vitro from a Highly Neutralizing COVID-19 Convalescent Plasma," bioRxiv 2020.12.28.424451, Cold Spring Harbor Laboratory, United States (Dec. 2020).

Bailey, J. R., et al., "Broadly Neutralizing Antibodies With Few Somatic Mutations and Hepatitis C Virus Clearance," JCI Insight 2(9):e92872, American Society for Clinical Investigation, United States (May 2017).

Barzon, L., et al., "Infection Dynamics in a Traveller With Persistent Shedding of Zika Virus RNA in Semen for Six Months After Returning From Haiti to Italy, Jan. 2016," Euro Surveillance 21(32):30316, European Centre for Disease Prevention and Control (ECDC), Sweden (Aug. 2016).

Baum, A., et al., "REGN-COV2 Antibodies Prevent and Treat SARS-CoV-2 Infection in Rhesus Macaques and Hamsters," Science 370(6520):1110-1115, American Association for the Advancement of Science, United States (Nov. 2020).

Benton, D. J., et al., "Receptor Binding and Priming of the Spike Protein of SARS-CoV-2 for Membrane Fusion," Nature 588(7837):327-330, Nature Publishing Group, England (Sep. 2020).

Bepler, T., et al., "Topaz-Denoise: General Deep Denoising Models for cryoEM and cryoET," Nature Communications 11(1):5208, Nature Pub. Group, England (Oct. 2020).

Brouwer, P. J. M., et al., "Potent Neutralizing Antibodies From COVID-19 Patients Define Multiple Targets of Vulnerability," Science 369(6504):643-650, American Association for the Advancement of Science, United States (Aug. 2020).

Case, J. B., et al., "Neutralizing Antibody and Soluble ACE2 Inhibition of a Replication-Competent VSV-SARS-CoV-2 and a clinical isolate of SARS-CoV-2," Cell Host & Microbe 28(3):475-485, Cell Press, United States (Sep. 2020).

Chen, Z., et al., "Human Neutralizing Monoclonal Antibody Inhibition of Middle East Respiratory Syndrome Coronavirus Replication in the Common Marmoset," The Journal of Infectious Diseases 215(12):1807-1815, Oxford University Press, United States (Jun. 2017).

Chng, J., et al., "Cleavage Efficient 2A Peptides for High Level Monoclonal Antibody Expression in CHO Cells, " mAbs 7(2):403-12, Taylor & Francis, United States (2015).

Choi, J.H., et al., "Characterization of a Human Monoclonal Antibody Generated from a B-cell Specific for a Prefusion-stabilized Spike Protein of Middle East Respiratory Syndrome Coronavirus," PloS One 15(5):e0232757, Public Library of Science, United States (May 2020).

Cornwell, O., et al., "Comparing Hydrogen Deuterium Exchange and Fast Photochemical Oxidation of Proteins: a Structural Characterisation of Wild-Type and DeltaN6 Beta2-Microglobulin," Journal of the American Society for Mass Spectrometry 29(12):2413-2426, ACS Publications, United States (Dec. 2018).

Corti, D., et al., "Prophylactic and Postexposure Efficacy of a Potent Human Monoclonal Antibody Against MERS Coronavirus," Proceedings of the National Academy of Sciences of the United States of America 112(33):10473-10478, National Academy of Sciences, United States (Aug. 2015).

Dinnon, K.H., et al., "A Mouse-adapted SARS-CoV-2 Model for the Evaluation of COVID-19 Medical Countermeasures," bioRxiv 2020.05.06.081497, Cold Spring Harbor Laboratory, United States (May 2020).

Duffy, M.R., et al., "Zika Virus Outbreak on Yap Island, Federated States of Micronesia," The New England Journal of Medicine 360(24):2536-2543, Massachusetts Medical Society, United States (Jun. 2009).

Emsley, P. and Cowtan, K., "Coot: Model-building Tools for Molecular Graphics," Acta crystallographica. Section D, Biological Crystallography 60(Pt 12 Pt 1):2126-2132, Wiley-Blackwell, United States (Dec. 2004).

Galloway, S. E., et al., "Emergence of SARS-CoV-2 B.1.1.7 Lineage - United States, Dec. 29, 2020-Jan. 12, 2021," Morbidity and Mortality Weekly Report 70(3):95-99, Centers for Disease Control, United States (Jan. 2021).

Giang, E., et al., "Human Broadly Neutralizing Antibodies to the Envelope Glycoprotein Complex of Hepatitis C Virus," Proceedings of the National Academy of Sciences of the United States of America 109(16):6205-6210, National Academy of Sciences, United States (Apr. 2012).

Gornet, M.E., et al., "Zika Virus in Semen: What We Know and What We Need to Know," Seminars in Reproductive Medicine 34(5):285-292, Thieme Medical Publishers, United States (Sep. 2016).

Greaney, A. J., et al., "Complete Mapping of Mutations to the SARS-CoV-2 Spike Receptor- Binding Domain that Escape Antibody Recognition," Cell Host & Microbe 29(1):44-57, Cell Press, United States (Jan. 2021).

Greaney, A. J., et al., "Comprehensive Mapping of Mutations to the SARS-CoV-2 Receptor-binding Domain That Affect Recognition by Polyclonal Human Serum Antibodies," bioRxiv 2020.2012.2031.425021 29(3):463-476 (Jan. 2021).

Halfon, P., et al., "Semen May Harbor HIV Despite Effective HAART: Another Piece in the Puzzle," PloS one 5(5):e10569, Public Library of Science, United States (May 2010).

Hoffmann, M., et al., "SARS-CoV-2 Cell Entry Depends on ACE2 and TMPRSS2 and Is Blocked by a Clinically Proven Protease Inhibitor," Cell 181(2):271-280, Cell Press, United States (Apr. 2020).

Huang, C. C., et al., "Structural Basis of Tyrosine Sulfation and VH-gene Usage in Antibodies That Recognize the HIV Type 1 Coreceptor-binding Site on gp120," Proceedings of the National Academy of Sciences of the United States of America 101(9):2706-2711, National Academy of Sciences, United States (Mar. 2004).

Huo, J. et al., "Neutralization of SARS-CoV-2 by Destruction of the Prefusion Spike," Cell Host & Microbe 28(3):445-454, Cell Press, United States (Sep. 2020).

(56) References Cited

OTHER PUBLICATIONS

Ianevski, A., et al., "Synergyfinder: A Web Application for Analyzing Drug Combination Dose-response Matrix Data," Bioinformatics 33(15):2413-2415, Oxford University Press, United Kingdom (Aug. 2017).
Jiang, L., et al., "Neutralizing Antibodies against SARS-CoV-2 and Other Human Coronaviruses," Trends in Immunology 41(5):355-359, Elsevier Science Ltd., United Kingdom (May 2020).
Jiang, L., et al., "Potent Neutralization of MERS-CoV by Human Neutralizing Monoclonal Antibodies to the Viral Spike Glycoprotein," Science Translational Medicine 6(234):234ra59, American Association for the Advancement of Science, United States (Apr. 2014).
Joyce, M. G., et al., "Vaccine-Induced Antibodies that Neutralize Group 1 and Group 2 Influenza A Viruses," Cell 166(3):609-623, Cell Press, United States (Jul. 2016).
Ju, B. et al., "Human Neutralizing Antibodies Elicited by SARS-CoV-2 Infection," Nature 584(7819):115-119, Nature Publishing Group, United States (May 2020).
Kabsch, W., "XDS," Acta Crystallographica. Section D, Biological Crystallography 66(Pt 2):125-132, Wiley-Blackwell, United States (Feb. 2010).
Klimstra, W. B., et al., "SARS-CoV-2 Growth, Furin-cleavage-site Adaptation and Neutralization Using Serum From Acutely Infected Hospitalized COVID-19 Patients," The Journal of General Virology 101(11):1156-1169, Microbiology Society, United Kingdom (Aug. 2020).
Kreer, C., et al., "Longitudinal Isolation of Potent Near-Germline SARS-CoV-2-Neutralizing Antibodies from COVID-19 Patients," Cell 182(4):843-854, Cell Press, United States (Aug. 2020).
Laha, S., et al., "Characterizations of SARS-CoV-2 Mutational Profile, Spike Protein Stability and Viral Transmission," Infection, Genetics and Evolution 85:104445, Elsevier Science, Netherlands (Jun. 2020).
Lan, J., et al., "Structure of the SARS-CoV-2 Spike Receptor-binding Domain Bound to the ACE2 Receptor," Nature 581(7807):215-220, Nature Publishing Group, United Kingdom (Mar. 2020).
Letko, M., et al., "Functional Assessment of Cell Entry and Receptor Usage for SARS-CoV-2 and Other Lineage B Betacoronaviruses," Nature Microbiology 5(4):562-569, Nature Publishing Group, United Kingdom (Mar. 2020).
Leung, K., et al., "Early Transmissibility Assessment of the N501Y Mutant Strains of SARS-CoV-2 in the United Kingdom, Oct. to Nov. 2020," Euro Surveillance 26(1):2002106, European Centre for Disease Prevention and Control (ECDC), Sweden (Jan. 2021).
Li, Q., et al., "The Impact of Mutations in SARS-CoV-2 Spike on Viral Infectivity and Antigenicity," Cell 182(5):1284-1294, Cell Press, United States (Sep. 2020).
Li, W., et al., "Angiotensin-converting Enzyme 2 Is a Functional Receptor for the SARS Coronavirus," Nature 426(6965):450-454, Nature Publishing Group, United Kingdom (Nov. 2003).
Liu, L., et al., "Potent Neutralizing Antibodies Against Multiple Epitopes on SARS-CoV-2 Spike," Nature 584(7821):450-456, Nature Publishing Group, England (Jul. 2020).
Liu, Z., et al., "Landscape Analysis of Escape Variants Identifies SARS-CoV-2 Spike Mutations That Attenuate Monoclonal and Serum Antibody Neutralization," bioRxiv 2020.11.06.372037, Cold Spring Harbor Laboratory, United States (Nov. 2020).
Long, Q. X., et al., "Antibody Responses to SARS-CoV-2 in Patients With COVID-19," Nature Medicine 26(6):845-848, Nature Publishing Company, United States (Jun. 2020).
McCoy, A. J., et al., "Phaser Crystallographic Software," Journal of Applied Crystallography 40(Pt 4):658-674, Wiley Online Library, United States (Aug. 2007).
Mukherjee, S., et al., "Enhancing Dengue Virus Maturation Using a Stable Furin Over-expressing Cell Line," Virology 497:33-40, Academic Press, United States (Oct. 2016).
Nielsen, S. C. A., et al., "Human B Cell Clonal Expansion and Convergent Antibody Responses to SARS-CoV-2," Cell Host & Microbe 28(4):516-525, Cell Press, United States (Oct. 2020).

Niu, P., et al., "Ultrapotent Human Neutralizing Antibody Repertoires Against Middle East Respiratory Syndrome Coronavirus From a Recovered Patient," The Journal of Infectious Diseases 218(8):1249-1260, Oxford University Press, United States (Sep. 2018).
Otwinowski, J., et al., "Inferring the Shape of Global Epistasis," Proceedings of the National Academy of Sciences of the United States of America 115(32):E7550-E7558, National Academy of Sciences, United States (Aug. 2018).
Pappas, L., et al., "Rapid Development of Broadly Influenza Neutralizing Antibodies Through Redundant Mutations," Nature 516(7531):418-422, Nature Publishing Group, England (Dec. 2014).
Piccoli, L., et al., "Mapping Neutralizing and Immunodominant Sites on the SARS-CoV-2 Spike Receptor-Binding Domain by Structure-Guided High-Resolution Serology," Cell 183(4):1024-1042, Cell Press, United States (Nov. 2020).
Pillay, T.S., "Gene of the Month: the 2019-nCoV/SARS-CoV-2 Novel Coronavirus Spike Protein," Journal of Clinical Pathology 73(7):366-369, BMJ Pub. Group, United Kingdom (May 2020).
Plante, J. A., et al., "Spike Mutation D614G Alters SARS-CoV-2 Fitness," Nature 592(7852):116-121, Nature Publishing Group, United Kingdom (Oct. 2020).
Purpura, L.J., et al., "Zika Virus in Semen: Lessons From Ebola," The Lancet. Infectious Diseases 16(10):1107-1108, The Lancet Pub., United States (Oct. 2016).
Rappuoli, R., et al., "Reverse Vaccinology 2.0: Human Immunology Instructs Vaccine Antigen Design," The Journal of Experimental Medicine 213(4):469-481, Rockefeller University Press, United States (Apr. 2016).
Robbiani, D. F., et al., "Convergent Antibody Responses to SARS-CoV-2 in Convalescent Individuals," Nature 584(7821):437-442, Nature Publishing Group, United Kingdom (Jun. 2020).
Robbiani, D. F., et al., "Convergent Antibody Responses to SARS-CoV-2 Infection in Convalescent Individuals," bioRxiv 2020.05.13.092619, Cold Spring Harbor Laboratory, United States (May 2020).
Rockx, B., et al., "Structural Basis for Potent Cross-neutralizing Human Monoclonal Antibody Protection Against Lethal Human and Zoonotic Severe Acute Respiratory Syndrome Coronavirus Challenge," Journal of Virology 82(7):3220-3235, American Society For Microbiology, United States (Apr. 2008).
Rogers, T. F., et al., "Isolation of Potent SARS-CoV-2 Neutralizing Antibodies and Protection From Disease in a Small Animal Model," Science 369(6506):956-963, American Association for the Advancement of Science, United States (Aug. 2020).
Sawatzki, K., et al., "Ferrets Not Infected by SARS-CoV-2 in a High-exposure Domestic Setting," bioRxiv, 14 pages, 2020.2008.2021.254995 (Aug. 2020).
Sheehan, K. C. F., et al., "Blocking Monoclonal Antibodies Specific for Mouse IFN-alpha/beta Receptor Subunit 1 (IFNAR-1) From Mice Immunized by in Vivo Hydrodynamic Transfection," Journal of Interferon & Cytokine Research 26(11):804-819, Mary Ann Liebert, United States (Nov. 2006).
Shi, R., et al., "A Human Neutralizing Antibody Targets the Receptor-binding Site of SARS-CoV-2," Nature 584(7819):120-124, Nature Publishing Group, United Kingdom (May 2020).
Soto, C., et al., "High Frequency of Shared Clonotypes in Human B Cell Receptor Repertoires," Nature 566(7744):398-402, Nature Publishing Group, United Kingdom (Jul. 2020).
Starr, T. N., et al., "Deep Mutational Scanning of SARS-CoV-2 Receptor Binding Domain Reveals Constraints on Folding and ACE2 Binding," Cell 182(5):1295-1310, Cell Press, United States (Sep. 2020).
Starr, T. N., et al., "Prospective Mapping of Viral Mutations That Escape Antibodies Used to Treat COVID-19," bioRxiv 2020.11.30.405472, Cold Spring Harbor Laboratory, United States (Jan. 2021).
Sui, J., et al., "Potent Neutralization of Severe Acute Respiratory Syndrome (SARS) Coronavirus by a Human mAb to S1 Protein That Blocks Receptor Association," Proceedings of the National Academy of Sciences of the United States of America 101(8):2536-2541, National Academy of Sciences, United States (Feb. 2004).

(56) References Cited

OTHER PUBLICATIONS

Sui, J., et al., "Structural and Functional Bases for Broad-spectrum Neutralization of Avian and Human Influenza a Viruses," Nature Structural & Molecular Biology 16(3):265-273, Nature Pub. Group, United States (Mar. 2009).

Tang, X.C., et al., "Identification of Human Neutralizing Antibodies Against MERS-CoV and Their Role in Virus Adaptive Evolution," Proceedings of the National Academy of Sciences of the United States of America 111(19):E2018-E2026, National Academy of Sciences, United States (May 2014).

Tegally, H., et al., "Emergence and Rapid Spread of a New Severe Acute Respiratory Syndrome-related Coronavirus 2 (SARS-CoV-2) Lineage With Multiple Spike Mutations in South Africa," medRxiv, 2020.2012.2021.20248640 (Dec. 2020).

Ter Meulen, J., et al., "Human Monoclonal Antibody as Prophylaxis for SARS Coronavirus Infection in Ferrets," Lancet 363(9427):2139-2141, Elsevier, United Kingdom (Jun. 2004).

Ter Meulen, J., et al., "Human Monoclonal Antibody Combination Against Sars Coronavirus: Synergy and Coverage of Escape Mutants," PLoS Medicine 3(7):e237, Public Library of Science, United States (Jul. 2006).

Tian, C., et al., "Immunodominance of the VH1-46 Antibody Gene Segment in the Primary Repertoire of Human Rotavirus-specific B Cells Is Reduced in the Memory Compartment Through Somatic Mutation of Nondominant Clones," Journal of Immunology 180(5):3279-3288, American Association of Immunologists, United States (Mar. 2008).

Tortorici, M. A., et al., "Ultrapotent Human Antibodies Protect Against SARS-CoV-2 Challenge via Multiple Mechanisms," Science 370(6519):950-957, American Association for the Advancement of Science, United States (Sep. 2020).

Valk, S.J., et al., "Convalescent Plasma or Hyperimmune Immunoglobulin for People With COVID-19: A Rapid Review," The Cochrane Database of Systematic Reviews 5(5):CD013600, Wiley, United Kingdom (May 2020).

Voloch, C. M., et al., "Genomic Characterization of a Novel SARS-CoV-2 Lineage From Rio De Janeiro, Brazil," medRxiv, 2020.2012.2023.20248598 (Mar. 2021).

Wahba, L., et al., "An Extensive Meta-Metagenomic Search Identifies SARS-CoV-2-Homologous Sequences in Pangolin Lung Viromes," mSphere 5(3):e00160-20, American Society for Microbiology, United States (May 2020).

Walls, A. C., et al., "Tectonic Conformational Changes of a Coronavirus Spike Glycoprotein Promote Membrane Fusion," Proceedings of the National Academy of Sciences of the United States of America 114(42):11157-11162, National Academy of Sciences, United States (Oct. 2017).

Wan, Y., et al., "Receptor Recognition by the Novel Coronavirus from Wuhan: an Analysis Based on Decade-Long Structural Studies of SARS Coronavirus," Journal of Virology 94(7):e00127-20, American Society For Microbiology, United States (Jan. 2020).

Wang, L., et al., "Importance of Neutralizing Monoclonal Antibodies Targeting Multiple Antigenic Sites on the Middle East Respiratory Syndrome Coronavirus Spike Glycoprotein To Avoid Neutralization Escape," Journal of Virology 92(10):e02002-17, American Society For Microbiology, United States (Mar. 2018).

Wang, N., et al., "Structural Definition of a Neutralization-Sensitive Epitope on the Mers-Cov S1-NTD," Cell Reports 28(13):3395-3405, Cell Press, United States (Sep. 2019).

Weisblum, Y., et al., "Escape From Neutralizing Antibodies by SARS-CoV-2 Spike Protein Variants," eLife (Oct. 2020).

Weitkamp, J. H., et al., "Infant and Adult Human B Cell Responses to Rotavirus Share Common Immunodominant Variable Gene Repertoires," Journal of Immunology 171(9):4680-4688, American Association of Immunologists, United States (Nov. 2003).

Wheatley, A. K., et al., "H5N1 Vaccine-Elicited Memory B Cells Are Genetically Constrained by the IGHV Locus in the Recognition of a Neutralizing Epitope in the Hemagglutinin Stem," Journal of Immunology 195(2):602-610, American Association of Immunologists, United States (Jul. 2015).

Wibmer, C. K., et al., "SARS-CoV-2 501Y.V2 Escapes Neutralization by South African COVID-19 Donor Plasma," bioRxiv 2021.01.18.427166, Cold Spring Harbor Laboratory, United States (Mar. 2021).

Williams, W. B., et al., "HIV-1 Vaccines. Diversion of HIV-1 Vaccine-induced Immunity by gp41-microbiota Cross-reactive Antibodies," Science 349(6249):aab 1253, American Association for the Advancement of Science, United States (Aug. 2015).

Winn, M. D., et al., "Overview of the CCP4 Suite and Current Developments," Acta crystallographica. Section D, Biological crystallography 67(Pt 4):235-242, Wiley-Blackwell, United States (Apr. 2011).

Wrapp, D., et al., "Cryo-EM Structure of the 2019-nCoV Spike in the Prefusion Conformation," Science 367(6483):1260-1263, American Association for the Advancement of Science, United States (Feb. 2020).

Wrobel, A. G., et al., "SARS-CoV-2 and Bat RaTG13 Spike Glycoprotein Structures Inform on Virus Evolution and Furin-cleavage Effects," Nature Structural & Molecular Biology 27(8):763-767, Nature Pub. Group, United States (Jul. 2020).

Wu, X., et al., "Focused Evolution of HIV-1 Neutralizing Antibodies Revealed by Structures and Deep Sequencing," Science 333(6049):1593-1602, American Association for the Advancement of Science, United States (Sep. 2011).

Xie, X., et al., "An Infectious cDNA Clone of SARS-CoV-2," Cell Host & Microbe 27(5):841-848, Cell Press, United States (Apr. 2020).

Ying, T., et al., "Exceptionally Potent Neutralization of Middle East Respiratory Syndrome Coronavirus by Human Monoclonal Antibodies," Journal of Virology 88(14):7796-7805, American Society For Microbiology, United States (Jul. 2014).

Yuan, M., et al., "A Highly Conserved Cryptic Epitope in the Receptor Binding Domains of SARS-CoV-2 and SARS-CoV," Science 368(6491):630-633, American Association for the Advancement of Science, United States (Apr. 2020).

Yuan, M., et al., "Structural Basis of a Shared Antibody Response to SARS-CoV-2," Science 369(6507):1119-1123, American Association for the Advancement of Science, United States (Jul. 2020).

Zhang, S., et al., "Structural Definition of a Unique Neutralization Epitope on the Receptor-Binding Domain of MERS-CoV Spike Glycoprotein," Cell Reports 24(2):441-452, Cell Press, United States (Jul. 2018).

Zhou, P., et al., "A Pneumonia Outbreak Associated With a New Coronavirus of Probable Bat Origin," Nature 579(7798):270-273, Nature Publishing Group, United Kingdom (Feb. 2020).

Zhou, T., et al., "Structural Repertoire of HIV-1-Neutralizing Antibodies Targeting the CD4 Supersite in 14 Donors," Cell 161(6):1280-1292, Cell Press, United States (Jun. 2015).

Zhu, N., et al., "A Novel Coronavirus from Patients with Pneumonia in China, 2019," The New England Journal of Medicine 382(8):727-733, Massachusetts Medical Society, United States (Feb. 2020).

Zhu, Z., et al., "Potent Cross-reactive Neutralization of SARS Coronavirus Isolates by Human Monoclonal Antibodies," Proceedings of the National Academy of Sciences of the United States of America 104(29):12123-12128, National Academy of Sciences, United States (Jul. 2007).

Zost, S. J., et al., "Rapid Isolation and Profiling of a Diverse Panel of Human Monoclonal Antibodies Targeting the SARS-CoV-2 Spike Protein," Nature Medicine 26(9):1422-1427, Nature Publishing Company, United States (Sep. 2020).

Tian, X., et al., "Potent binding of 2019 novel coronavirus spike protein by a SARS coronavirus-specific human monoclonal antibody," Emerg Microbes Infect 9(1):382-385, Taylor and Francis Ltd., United Kingdom (Feburary 2020).

Cheung, R.C., et al., "Epitope-specific antibody response to the surface antigen of duck hepatitis B virus in infected ducks," Virology 176(2):546-552, Academic Press, United States (1990).

Genbank, "Severe acute respiratory syndrome coronavirus 2 isolate Wuhan-Hu-1, complete genome," Accession No. MN908947.3, accessed at URL:[https://www.ncbi.nlm.nih.gov/nuccore/MN908947.3/], accessed on Oct. 14, 2021, 11 pages.

(56) References Cited

OTHER PUBLICATIONS

International Search Report and Written Opinion for International Application No. PCT/EP2021/063008, European Patent Office, Netherlands, mailed on Oct. 12, 2021, 22 pages.

International Search Report and Written Opinion for International Application No. PCT/EP2021/072203, European Patent Office, Netherlands, mailed on Dec. 8, 2021, 19 pages.

Sazinsky, S.L., et al., "Aglycosylated immunoglobulin G1 variants productively engage activating Fc receptors," Proc Natl Acad Sci USA 105(51):20167-20172, National Academy of Science, United States (Dec. 2008).

Tkaczyk, C., et al., "Identification of Anti-alpha Toxin Monoclonal Antibodies That Reduce the Severity of *Staphylococcus aureus* Dermonecrosis and Exhibit a Correlation Between Affinity and Potency," Clinical and Vaccine Immunology 19(3):377-385, American Society for Microbiology, United States (Mar. 2012).

Wang, C., et al., "A human monoclonal antibody blocking SARS-CoV-2 infection," bioRxiv 2020.03.11.987958, Cold Spring Harbor Laboratory, United States (Mar. 2020).

Wu, Y., et al., "A noncompeting pair of human neutralizing antibodies block COVID-19 virus binding to its receptor ACE2," Science 368(6496):1274-1278, with Supplementary Materials, American Association for the Advancement of Science, United States (Jun. 2020).

Yu, X-Q., et al., "Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults," Antimicrob Agents Chemother 61(1):e01020-16, American Society for Microbiology, United States (Dec. 2016).

Pinto, D., et al., "Structural and Functional Analysis of a potent sarbecovirus neutralizing antibody," bioRxiv, Cold Spring Harbor Laboratory, United States (Apr. 2020).

Walker, L.M., et al., "Passive immunotherapy of viral infections: super-antibodies enter the fray," Nat Rev Immunol 18(5):297-308, Springer Nature, Germany (May 2018).

Douthwaite, J., et al., "A CD80-Biased CTLA4-Ig Fusion Protein with Superior In Vivo Efficacy by Simultaneous Engineering of Affinity, Selectivity, Stability, and FcRn Binding," J Immunol 198(1):528-537, American Association of Immunologists, United States (Jan. 2017).

Third Party Observation submitted in International Application PCT/EP2021/063008 submitted on Sep. 19, 2022, filing date: May 17, 2021.

Ng, O., et al., "Substitution at Aspartic Acid 1128 in the SARS Coronavirus Spike Glycoprotein Mediated Escape from a S2 Domain-Targeting Neutralizing Monoclonal Antibody," PLOS One 9(7):e102415, Plos One, United States (Jul. 2014).

Popov, D., et al., "Treatment of Covid-19 Infection, A Rationale for Current and Future Pharmacological Approach," EC Pulmonology and Respiratory Medicine 9(4):38-58, ECPRM, United Kingdom (Mar. 2020).

Cherian, S., et al., "Perspectives for repurposing drugs for the coronavirus disease 2019," Indian J Med Res 151:160-171, Wolters Kluwer, Netherlands (Mar. 2020).

Sheahan, T., et al., "Comparative therapeutic efficacy of remdesivir and combination lopinavir, ritonavir, and interfereon beta against MERS-CoV," Nat Commun 11:222, Springer, Germany (Jan. 2020).

Abdiche, Y. N., et al., "Exploring Blocking Assays using Octet, Proteon, and Biacore Biosensors," Analytical Biochemistry 386(2):172-180, Elsevier, United States (2009).

Al-Lazikani, B., et al., "Standard conformations for the canonical structures of immunoglobulins, " Journal of Molecular Biology 273(4):927-948, Elsevier, United Kingdom (Nov. 1997).

Ames, R. S., et al., "Conversion of Murine Fabs Isolated From a Combinatorial Phage Display Library to Full Length Immunoglobulins," Journal of Immunological Methods 184(2):177-186, Elsevier, Netherlands (1995).

Bricogne, G., "Direct phase determination by entropy maximization and likelihood ranking: status report and perspectives," Acta Crystallographica. Section D, Biological Crystallography 49(Pt1):37-60, Wiley-Blackwell, United States (1993).

Bricogne, G., "[23] Bayesian statistical viewpoint on structure determination: Basic concepts and examples," Methods in Enzymology 276:361-423, Academic Press, United States (1997).

Brinkmann, U., et al., "Phage Display of Disulfide-stabilized Fv Fragments," Journal of Immunological Methods 182(1):41-50, Elsevier, Netherlands (1995).

Burton, D. R. and Barbas, C. F. 3rd., "Human Antibodies From Combinatorial Libraries," Advances in Immunology 57:191-280, Academic Press, United States (1994).

Champe, M., et al., "Monoclonal antibodies that block the activity of leukocyte function-associated antigen 1 recognize three discrete epitopes in the inserted domain of CD11a," The Journal of Biological Chemistry 270(3):1388-1394, American Society for Biochemistry and Molecular Biology, United States (1995).

Chayen, N. E., et al., "The Role of Oil in Macromolecular Crystallization," Structure 5(10):1269-1274, Cell Press, United States (1997).

Chothia, C., and Lesk, A. M., "Canonical Structures for the Hypervariable Regions of Immunoglobulins," Journal of Molecular Biology 196(4):901-917, Elsevier Science, United States (Aug. 1987).

Chothia, C., et al., "Structural Repertoire of the Human VH Segments," Journal of Molecular Biology 227(3):799-817, Academic Press, United Kingdom (1992).

Clackson, T., et al., "Making Antibody Fragments using Phage Display Libraries," Nature 352(6336):624-628, Nature Publishing Group, United Kingdom (Aug. 1991).

Coales, S. J., et al., "Epitope mapping by amide hydrogen/deuterium exchange coupled with immobilization of antibody, on-line proteolysis, liquid chromatography and mass spectrometry," Rapid Communications in Mass Spectrometry 23(5):639-647, John Wiley And Sons Ltd., United Kingdom (Mar. 2009).

Cockett, M. I., et al., "High level expression of tissue inhibitor of metalloproteinases in Chinese hamster ovary cells using glutamine synthetase gene amplification," Biotechnology 8(7):662-667, Nature Publishing Group, United Kingdom (1990).

Cunningham, B.C., and Wells, J. A., "High-resolution Epitope Mapping of hGH-receptor Interactions by Alanine-scanning Mutagenesis," Science 244(4908):1081-1085, American Association for the Advancement of Science, United States (Jun. 1989).

Dall'Acqua, W. F., et al., "Properties of Human IgGls Engineered for Enhanced Binding to the Neonatal Fc Receptor (FcRn)," The Journal of Biological Chemistry 281(33):23514-23524, American Society for Biochemistry and Molecular Biology, United States (Aug. 2006).

Davies, J., et al., "Expression of GnTIII in a Recombinant Anti-CD20 CHO Production Cell Line: Expression of Antibodies with Altered Glycoforms Leads to an Increase in ADCC through Higher Affinity for FC gamma RIII," Biotechnology and Bioengineering 74(4):288-294, Wiley, United States (2001).

Ferrara, C., et al., "Modulation of therapeutic antibody effector functions by glycosylation engineering: Influence of Golgi enzyme localization domain and co-expression of heterologous β1, 4-N-acetylglucosaminyltransferase III and Golgi α-mannosidase II," Biotechnology and Bioengineering 93(5):851-861, Wiley, United States (2006).

Foecking, M. K., et al., "Powerful and versatile enhancer-promoter unit for mammalian expression vectors," Gene 45(1):101-105, Elsevier, Netherlands (1986).

Giege, R., et al., "Crystallogenesis of biological macromolecules: facts and perspectives," Acta Crystallographica. Section D, Biological Crystallography 50(Pt4):339-350, Wiley-Blackwell, United States (1994).

Grams, et al., "Assessment of the reproducibility of the indirect ultrasound method of measuring diaphragm mobility," Clinical Physiology and Functional Imaging 34(1):18-25, Wiley-Blackwell, United States (2014).

Hammerling, G. J., et al., eds., "Appendix: Production of Antibody-Producing Hybridomas in the Rodent Systems" in Monoclonal Antibodies and T -Cell Hybridomas: Perspectives and Technical Advances, pp. 563-587, Elsevier, Netherlands (1981).

(56) References Cited

OTHER PUBLICATIONS

Harlow, E., and Lane, D., "Chapter 10: Cell Staining" in Antibodies: A Laboratory Manual, pp. 386-389, 2nd Edition, Cold Spring Harbor Press (1988).

International Search Report and Written Opinion directed to related International Patent Application No. PCT/EP2016/077426, mailed Feb. 3, 2017; 10 pages.

Jones, P.T., et al., "Replacing the Complementarity-determining Regions in a Human Antibody with those from a Mouse," Nature 321(6069):522-525, Nature Publishing Group, United Kingdom (May 1986).

Kabat, E. A. and Wu, T. T., "Attempts to Locate Complementarity-Determining Residues in the Variable Positions of Light and Heavy Chains," Annals of the New York Academy of Sciences 190:382-393, Blackwell, United States (1971).

Kanda, Y., et al., "Comparison of Biological Activity Among Nonfucosylated Therapeutic IgG1 Antibodies with Three Different N-Linked Fc Oligosaccharides: The High-Mannose, Hybrid, and Complex Types," Glycobiology 17(1):104-118, IRL Press at Oxford University Press, United Kingdom (2007).

Kettleborough, C. A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).

Kilpatrick, K. E., et al., "Rapid Development of Affinity Matured Monoclonal Antibodies Using RIMMS," Hybridoma 16(4):381-389, Mary Ann Liebert Inc., United States (1997).

Kim, S. J., et al., "Guided Selection of Human Antibody Light Chains Against TAG-72 Using a Phage Display Chain Shuffling Approach," Journal of Microbiology 45(6):572-577, Microbiological Society Of Korea, Korea (2007).

Kirkland, T. N., et al., "Analysis of the fine specificity and cross-reactivity of monoclonal anti-lipid A antibodies," Journal of Microbiology 137(11):3614-3619, Microbiological Society Of Korea, Korea (1986).

Kohler, G., and Milstein, C., "Continuous Cultures of Fused Cells Secreting Antibody of Predefined Specificity," Nature 256(5517):495-497, Macmillan Journals Ltd., United Kingdom (Aug. 1975).

Kuroki, M., et al., "Serological mapping of the TAG-72 tumor-associated antigen using 19 distinct monoclonal antibodies," Cancer Research 50(16):4872-4879, American Association for Cancer Research, United States (1990).

Kuroki, M., et al., "Biochemical characterization of 25 distinct carcinoembryonic antigen (CEA) epitopes recognized by 57 monoclonal antibodies and categorized into seven groups in terms of domain structure of the CEA molecule," Hybridoma 11(4):391-407, Mary Ann Liebert, United States (1992).

Kuroki, M., et al., "Determination of epitope specificities of a large number of monoclonal antibodies by solid-phase mutual inhibition assays using biotinylated antigen," Immunological Investigations 21(6):523-538, Informa Healthcare, United Kingdom (1992).

Lefranc, M. P., et al., "IMGT, the International ImMunoGeneTics Database," Nucleic Acids Research 27(1):209-212, Oxford University Press, United Kingdom (1999).

Lefranc, M.P., et al., "The IMGT Unique Numbering for Immunoglobulins, T Cell Receptors and Ig-like Domains," The Immunologist 7:132-136, Hogrefe & Huber Publishers, Germany (1999).

Maccallum, R. M., et al., "Antibody-antigen Interactions: Contact Analysis and Binding Site Topography," Journal of Molecular Biology 262(5):732-745, Academic Press, United Kingdom (Oct. 1996).

Martin, A. C. R., "Chapter 31: Protein Sequence and Structure Analysis of Antibody Variable Domains" in Antibody Engineering, Kontermann and Dubel, eds., pp. 422-439, Springer-Verlag, Germany (2001).

McPherson, A., "Crystallization of Proteins From Polyethylene Glycol," The Journal of Biological Chemistry 251(20):6300-6303, American Society for Biochemistry and Molecular Biology, United States (1976).

McPherson, A., "Current Approaches to Macromolecular Crystallization," European Journal of Biochemistry 189(1):1-23, Blackwell Science Ltd, United Kingdom (1990).

Moldenhauer, G., et al., "Identity of HML-1 antigen on intestinal intraepithelial T cells and of B-ly7 antigen on hairy cell leukaemia," Scandinavian Journal of Immunology 32(2):77-82, Blackwell Scientific Publications, United Kingdom (1990).

Morel, G. A., et al., "Monoclonal antibodies to bovine serum albumin: affinity and specificity determinations," Molecular Immunology 25(1):7-15, Pergamon Press, United Kingdom (1988).

Niwa, R., et al., "Enhancement of the Antibody-Dependent Cellular Cytotoxicity of Low-Fucose IgG1 Is Independent of Fcgammariiia Functional Polymorphism," Clinical Cancer Research 10(18 Pt 1):6248-6255, American Association for Cancer Research, United States (2004).

Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).

Presta, L. G., et al., "Engineering Therapeutic Antibodies for Improved Function," Biochemical Society Transactions 30(4):487-490, Portland Press, United Kingdom (2002).

Rader, C., et al., "A Phage Display Approach for Rapid Antibody Humanization: Designed Combinatorial V Gene Libraries," Proc Natl Acad Sci USA 95(15):8910-8915, National Academy of Sciences, United States (Jul. 1998).

Riechmann, L., et al., "Reshaping Human Antibodies for Therapy," Nature 332(6162):323-327, Nature Publishing Group, United States (Mar. 1988).

Roguska, M. A., et al., "Humanization of Murine Monoclonal Antibodies through Variable Domain Resurfacing," Proc Natl Acad Sci USA 91(3):969-973, National Academy of Sciences, United States (Feb. 1994).

Roguska, M.A., et al., "A Comparison of Two Murine Monoclonal Antibodies Humanized by CDR-grafting and Variable Domain Resurfacing, " Protein Engineering 9(10):895-904, Oxford University Press, United Kingdom (1996).

Roversi, P., et al., "Modelling prior distributions of atoms for macromolecular refinement and completion," Acta Crystallographica. Section D, Biological Crystallography 56(Pt10):1316-1323, International Union of Crystallography by Munksgaard, United States (2000).

Shields, R. L., et al., "High resolution mapping of the binding site on human IgG1 for Fc gamma RI, Fc gamma RII, Fc gamma RIII, and FcRn and design of IgG1 variants with improved binding to the Fc gamma R," The Journal of Biological Chemistry 276(9):6591-6604, American Society for Biochemistry and Molecular Biology, United States (Mar. 2001).

Shields, R. L., et al., "Lack of Fucose on Human IgG1 N-linked Oligosaccharide Improves Binding to Human Fcgamma RIII and Antibody-Dependent Cellular Toxicity," The Journal of Biological Chemistry 277(30):26733-26740, American Society for Biochemistry and Molecular Biology, United States (2002).

Shinkawa, T., et al., "The absence of fucose but not the presence of galactose or bisecting N-acetylglucosamine of human IgG1 complex-type oligosaccharides shows the critical role of enhancing antibody-dependent cellular cytotoxicity," The Journal of Biological Chemistry 278(5):3466-3473, American Society for Biochemistry and Molecular Biology, United States (2003).

Smith, P., et al., "Mouse Model Recapitulating Human Fcγ Receptor Structural and Functional Diversity," Proc Natl Acad Sci USA 109(16):6181-6186, National Academy of Sciences, United States (2012).

Stahli, C., et al., "Distinction of epitopes by monoclonal antibodies," Methods in Enzymology 92:242-253, Academic Press, United States (1983).

Tramontano, A., et al., "Framework Residue 71 is a Major Determinant of the Position and Conformation of the Second Hypervariable Region in the VH Domains of Immunoglobulins," Journal of Molecular Biology 215(1):175-182, Elsevier, United Kingdom (1990).

(56) References Cited

OTHER PUBLICATIONS

Umana, P., et al., "Engineered Glycoforms of an Antineuroblastoma IgG1 with Optimized Antibody-Dependent Cellular Cytotoxic Activity," Nature Biotechnology 17(2):176-180, Nature America Publishing, United States (1999).
Verhoeyen, M., et al., "Reshaping Human Antibodies: Grafting an Antilysozyme Activity," Science 239(4847):1534-1536, American Association for the Advancement of Science, United States (Mar. 1988).
Wagener, C., et al., "Monoclonal antibodies for carcinoembryonic antigen and related antigens as a model system: a systematic approach for the determination of epitope specificities of monoclonal antibodies," Journal of Immunology 130(5):2308-2315, American Association of Immunologists, United States (1983).
Wagener, C., et al., "Use of biotin-labeled monoclonal antibodies and avidin-peroxidase conjugates for the determination of epitope specificities in a solid-phase competitive enzyme immunoassay," Journal of Immunological Methods 68(1-2):269-274, Elsevier, Netherlands (1984)././.
Wein et al., 'Ultrasound based respiratory motion compensation in the abdomen' 2008 Workshop on Image Guidance and Computer Assistance for Soft Tissue Interventions. Vol 32, No. 294, pp. 1-8.
Xiao, X., et al., "The Costimulatory Receptor OX40 Inhibits Interleukin-17 Expression through Activation of Repressive Chromatin Remodeling Pathways," Immunity 44:1271-1283, Cell Press, United States (Jun. 2016).
"Guidance for Industry," FDA.gov, accessed at https://www.fda.gov/media/72309/download, published Jul. 2005, accessed on Dec. 26, 2022, 30 pages.
Zheng, Z., et al., "Monoclonal antibodies for the S2 subunit of spike of SARS-CoV-1 cross-react with the newly-emerged SARS-CoV-2," Eurosurveillance 25:19-28, European Centre for Disease Prevention and Control, Sweden (Jul. 2020).
Zohar, T., et al., "Dissecting antibody-mediated protection against SARS-CoV-2," Nature Reviews Immunology 20:392-394, Springer, Germany (Jun. 2020).
Moore, J.P., et al., "COVID-19 Vaccines: "Warp Speed" Needs Mind Melds, Not Warped Minds," Journal of Virology 94:e01083-20 (Jun. 2020).
Third Party Observation submitted in International Application No. PCT/EP2021/072203, submitted on Dec. 12, 2022, filing date: Aug. 9, 2021, 8 pages.
International Search Report and Written Opinion for International Application No. PCT/US2021/024215, European Patent Office, Netherlands, mailed on Jun. 24, 2021, 13 pages.
Kussie, P.H., et al., "A single engineered amino acid substitution changes antibody fine specificity," J Immunol 152(1):146-152, American Association of Immunologists, United States (Jan. 1994).
International Search Report and Written Opinion for International Application No. PCT/EP2022/080837, European Patent Office, Netherlands, mailed on Mar. 6, 2023, 20 pages.
Tomar, D., et al., "Molecular basis of high viscosity in concentrated antibody solutions: strategies for high concentration drug product development," MAbs 8(2):216-28 (2016).
Viola, M., et al., "Subcutaneous delivery of monoclonal antibodies: How do we get there?," J Control Release 286:301-314 (Sep. 2018).
Whitaker, N., et al., "A Formulation Development Approach to Identify and Select Stable Ultra-High-Concentration Monoclonal Antibody Formulations With Reduced Viscosities," J Pharm Sci 106(11):3230-3241 (Nov. 2017).
Uchiyama, S., "Liquid formulation for antibody drugs," Biochim Biophys Acta 1844(11):2041-2052 (Nov. 2014).
Kang, J., et al., "Rapid formulation development for monoclonal antibodies—Bioprocess International," accessed at http://www.bioprocessintl.com/manufacturing/formulation/rapid-formulation-development-for-monclonal-antibodies/, Apr. 12, 2016, 6 pages.
Dong, J., et al., "Genetic and Structural Basis for Recognition of SARS-CoV-2 Spike Protein b a Two-Antibody Cocktail," bioRxiv 2021.01.27.428529, Cold Spring Harbor Laboratory, United States (Mar. 2021).
Kamath, A.V., "Translational pharmacokinetics and pharmacodynamics of monoclonal antibodies," Drug Discov Today Technol 21-22:75-83, Elsevier Ltd., United Kingdom (Sep.-Dec. 2016).
International Search Report and Written Opinion for International Application No. PCT/EP2023/061297, European Patent Office, Netherlands, mailed on Sep. 15, 2023, 31 pages.
Kumar, S., et al., "Current status of therapeutic monoclonal antibodies against SARS-CoV-2," PLoS Pathog 17(9):e1009885, Public Library of Science, United States (Sep. 2021).
Asdaq, S.M.B., et al., "A Patent Review on the Therapeutic Application of Monoclonal Antibodies in COVID-19," Int J Mol Sci 22(21):11953, Multidisciplinary Digital Publishing Institute (MDPI), Switzerland (Nov. 2021).
Takashita, E., et al., "Efficacy of Antibodies and Antiviral Drugs against Covid-19 Omicron Variant," N Engl J Med 386(10):995-998, Massachusetts Medical Society, United States (Jan. 2022).
Corti, D., et al., "Tackling COVID-19 with neutralizing monoclonal antibodies," Cell 184(12):3086-3108, Cell Press, United States (Jun. 2021).
Starr, T.N., et al., "SARS-CoV-2 Rbd antibodies that maximize breadth and resistance to escape," Nature 597(7874):97-102, Nature Publishing Group, United Kingdom (Sep. 2021).
Saunders, K.O., "Conceptual Approaches to Modulating Antibody Effector Functions and Circulation Half-Life," Front Immunol 10:1296, Frontiers Media S.A., Switzerland (Jun. 2019).
Gershoni, J.M., et al., "Epitope mapping—The first step in developing epitope-based vaccines," BioDrugs 21(3): 145-156, Adis International Ltd., United Kingdom (2007).
Winkler, K., et al., "Changing the antigen binding specificity by single point mutations of an anti-p24 (HIV-1) antibody," J Immunol 165(8):4505-4514, American Association of Immunologists, United States (Oct. 2000).
Janeway, C.A., et al., "Structure of the Antibody Molecule and Immunoglobulin Genes," Chapter 3 in Immunobiology: The Immune System in Health and Disease, $3^{rd}$ Edition, p. 3:1-3:11, Garland Publishing Inc., New York (1997).
Rudikoff, S., et al., "Single amino acid substitution altering antigen-binding specificity," Proc Natl Acad Sci USA 79(6):1979-1983, National Academy of Sciences, United States (Mar. 1982).
Edwards, B.M., et al., "The remarkable flexibility of the human antibody repertoire; isolation of over one thousand different antibodies to a single protein, BLyS," J Mol Biol 334(1):103-118, Elsevier, Netherlands (Nov. 2003).
Lloyd, C., et al., "Modelling the human immune response: performance of a 1011 human antibody repertoire against a broad panel of therapeutically relevant antigens," Protein Eng Des Sel 22(3):159-168, Oxford University Press, United Kingdom (Mar. 2009).
Goel, M., et al., "Plasticity within the antigen-combining site may manifest as molecular mimicry in the humoral immune response," J Immunol 173(12):7358-7367, The American Association of Immunologists, United States (Dec. 2004).
Kanyavuz, A., et al., "Breaking the law: unconventional strategies for antibody diversification," Nat Rev Immunol 19(6):355-368, Springer Nature Limited, Germany (Jun. 2019).
International Search Report and Written Opinion for International Application No. PCT/EP2023/054109, European Patent Office, Netherlands, mailed on May 16, 2023, 18 pages.
Li, T., et al., "Ultrapotent SARS-CoV-2 neutralizing antibodies with protective efficacy against newly emerged mutational variants," bioRxiv 2021.04.19.440481v1, Cold Spring Harbor Laboratory, United States (Apr. 2021).
Wang, L., et al., "Antibodies with potent and broad neutralizing activity against antigenically diverse and highly transmissible SARS-CoV-2 variants," bioRxiv 2021.02.25.432969, Cold Spring Harbor Laboratory, United States (Mar. 2021).
Zhou, B., et al., "An elite broadly neutralizing antibody protects SARS-CoV-2 Omicron variant challenge," bioRxiv 2022.01.05. 475037, Cold Spring Harbor Laboratory, United States (Jan. 2022).
Yuan, M., et al., "Structural basis of a public antibody response to SARS-CoV-2," Science 369(6507):1119-1123, American Association for the Advancement of Science, United States (Aug. 2020).

(56) References Cited

OTHER PUBLICATIONS

Mendoza-Salazar, I., et al., "Anti-SARS-CoV-2 Omicron Antibodies Isolated from a SARS-CoV-2 Delta Semi-Immune Phage Display Library," Antibodies 11(1):13, MDPI, Switzerland (Feb. 2022).

Chi, X., et al., "An ultrapotent RBD-targeted biparatopic nanobody neutralizes broad SARS-CoV-2 variants," Signal Transduct Target Ther 7(1):44, Springer, Germany (Feb. 2022).

International Search Report and Written Opinion for International Application No. PCT/EP2022/081676 European Patent Office, Netherlands, mailed on Feb. 10, 2023, 13 pages.

Co-pending Application, U.S. Appl. No. 18/446,782, inventors Gasser, R., et al., filed Aug. 9, 2023 (Not yet Published).

Co-pending Application, U.S. Appl. No. 18/264,226, inventors Screaton, G., et al., filed Aug. 3, 2023 (Not yet Published).

Co-pending Application, U.S. Appl. No. 18/264,241, inventors Screaton, G., et al., filed Aug. 3, 2023 (Not yet Published).

Adams, P.D., et al., "PHENIX: A Comprehensive Python-based System for Macromolecular Structure Solution," Acta Crystallographica. Section D, Biological Crystallography 66(Pt 2):213-221, Wiley-Blackwell, United States (2010).

Chen, Z., et al., "Extremely potent monoclonal antibodies neutralize Omicron and other SARS-CoV-2 variants," medRxiv 2022.01.12.22269023, Cold Spring Harbor Laboratory, United States (Jan. 2022).

Cameroni, E., et al., "Broadly neutralizing antibodies overcome SARS-CoV-2 Omicron antigenic shift," Nature 602:664-670, Springer, Germany (Feb. 2022).

* cited by examiner

E

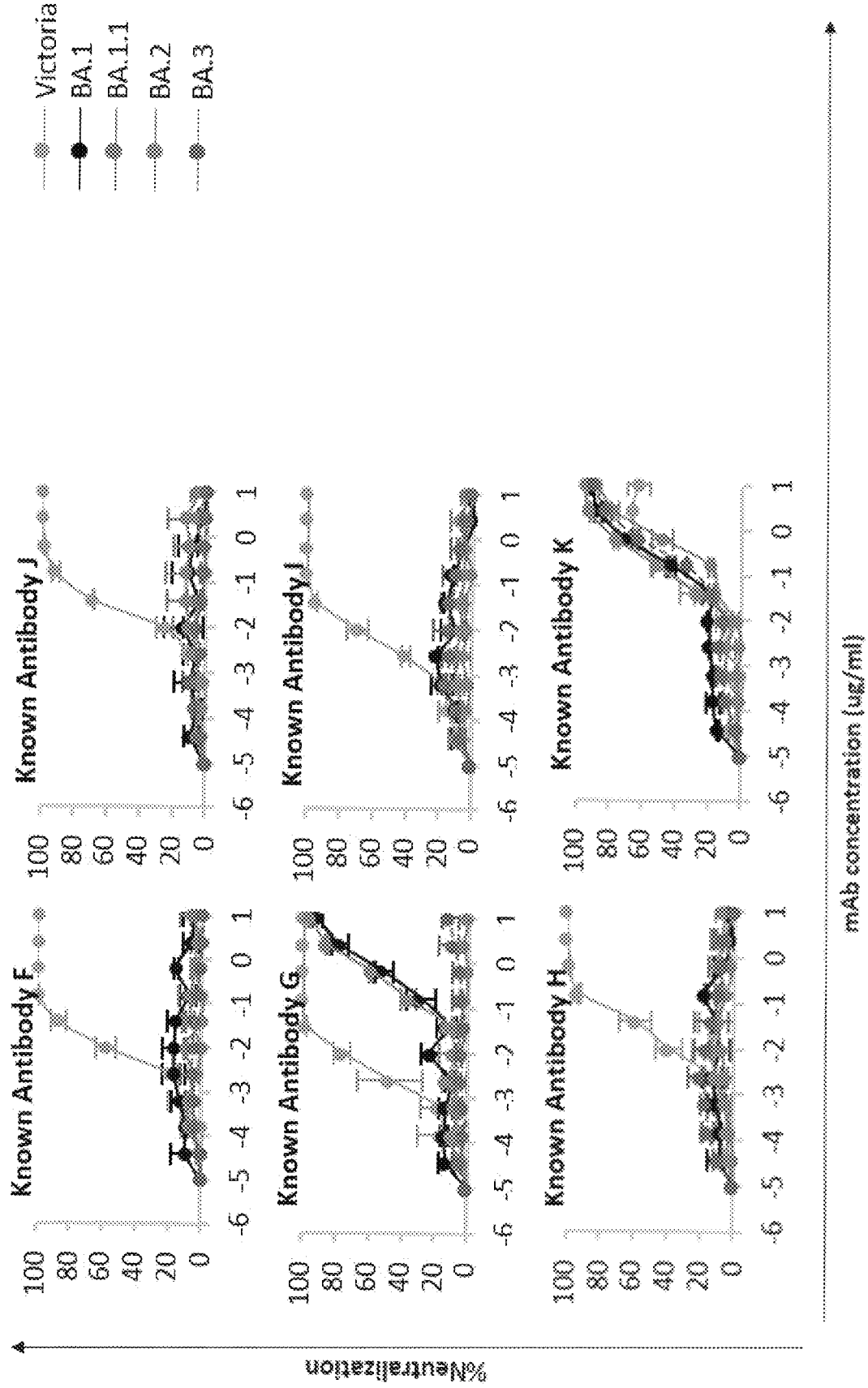

D

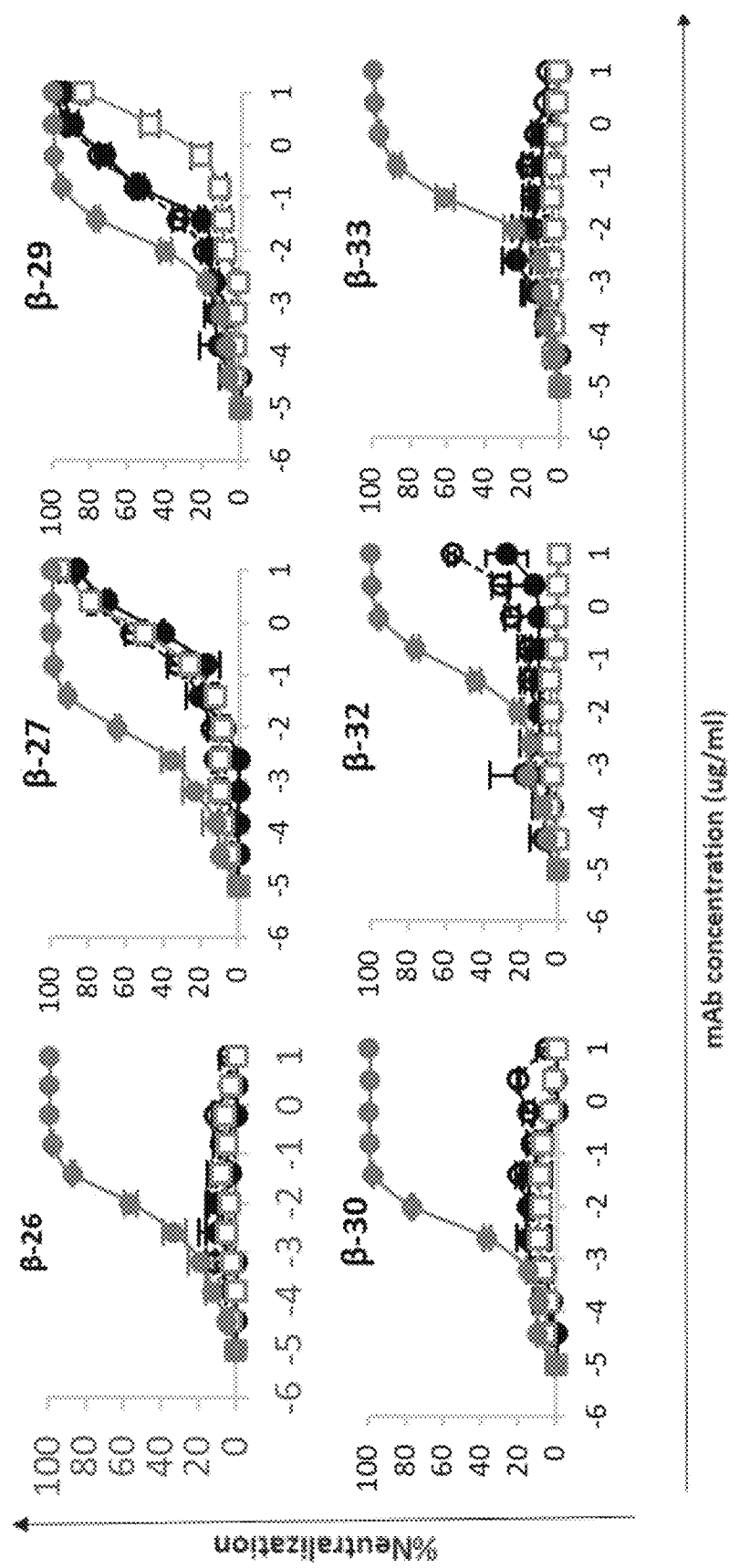

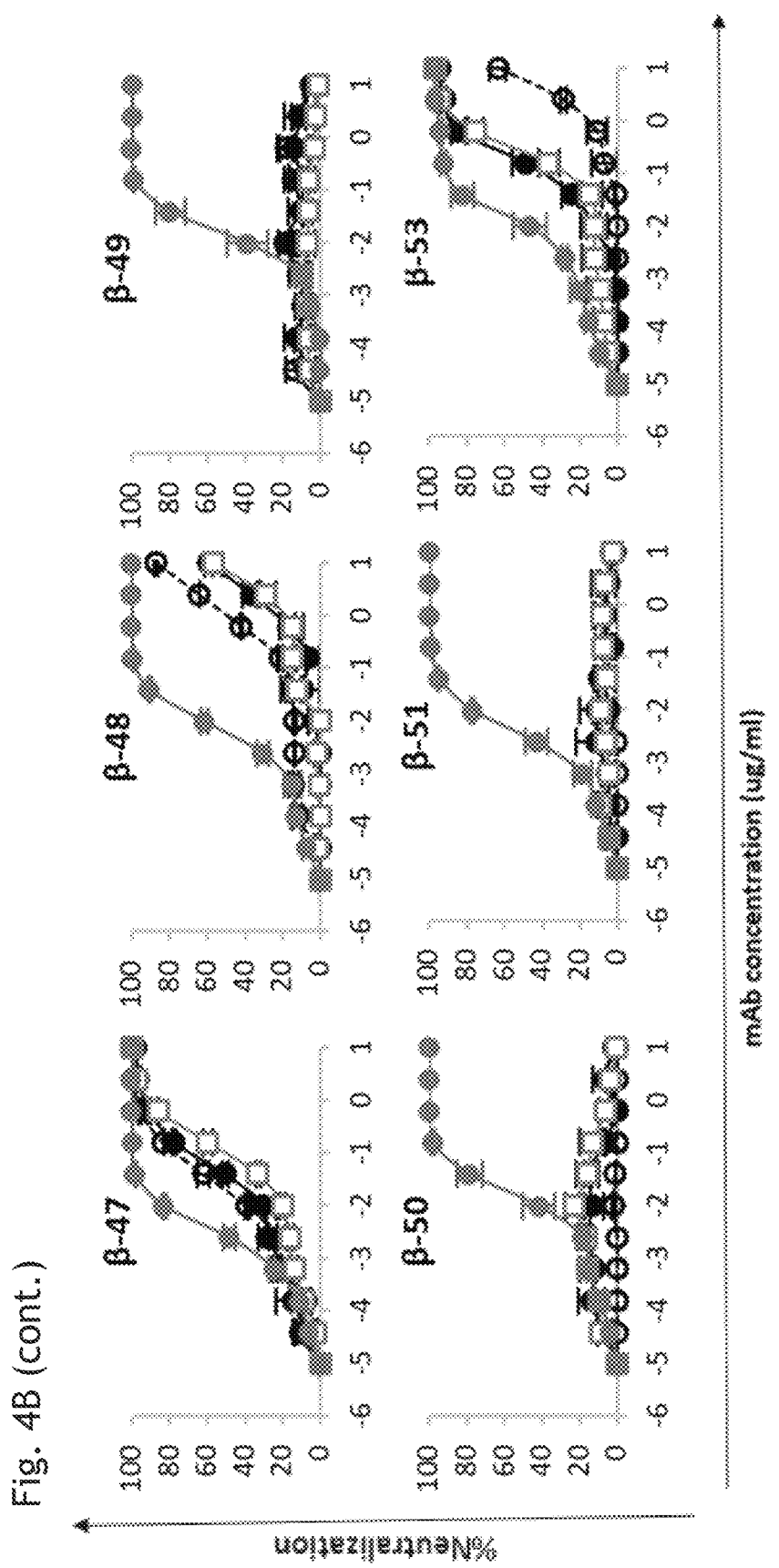

A

Fig. 6 (cont.)
B
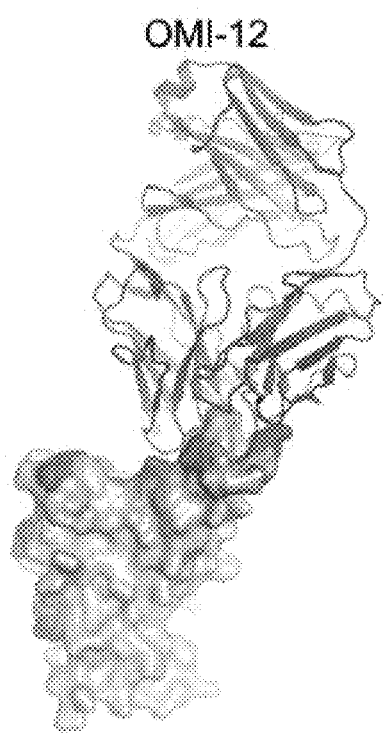
C
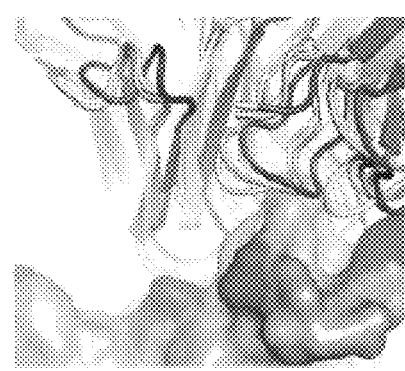
D
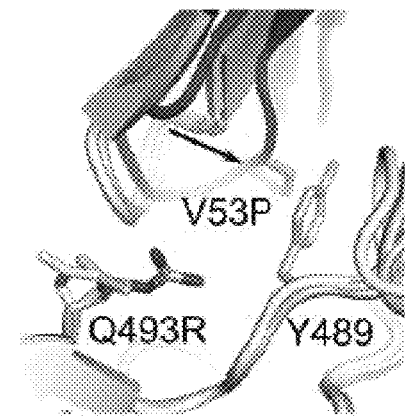

| | | NT |
|---|---|---|
| BA.1 | A67V,Δ69-70,T95I,G142D,Δ143-145,N211I,Δ212, ins214EPE | |
| BA.1.1 | A67V,Δ69-70,T95I,G142D,Δ143-145,N211I,Δ212, ins214EPE | |
| BA.2 | T19I,Δ24-26,A27S, G142D, V213G | |
| BA.3 | A67V,Δ69-70,T95I,G142D, Δ143-145,N211I,Δ212 | |
| BA.4/5 | T19I,Δ24-26,A27S, Δ69-70, G142D, V213G | |

| | | RBD |
|---|---|---|
| BA.1 | G339D, S371L,S373P,S375F, K417N,N440K,G446S | |
| BA.1.1 | G339D,R346K,S371L,S373P,S375F, K417N,N440K,G446S | |
| BA.2 | G339D, S371F,S373P,S375F,T376A,D405N,R408S,K417N,N440K | |
| BA.3 | G339D, S371F,S373P,S375F, D405N, K417N,N440K,G446S | |
| BA.4/5 | G339D, S371F,S373P,S375F,T376A,D405N,R408S,K417N,N440K, | |
| BA.1 | S477N,T478K,E484A, Q493R,G496S,Q498R,N501Y,Y505H | |
| BA.1.1 | S477N,T478K,E484A, Q493R,G496S,Q498R,N501Y,Y505H | |
| BA.2 | S477N,T478K,E484A, Q493R, Q498R,N501Y,Y505H | |
| BA.3 | S477N,T478K,E484A, Q493R, Q498R,N501Y,Y505H | |
| BA.4/5 | L452R,S477N,T478K,E484A,F486V, Q498R,N501Y,Y505H | |

BA.1   T547K,D614G,H655Y,N679K,P681H,N764K,D796Y,N856K,Q954H,N969K,L981F
BA.1.1 T547K,D614G,H655Y,N679K,P681H,N764K,D796Y,N856K,Q954H,N969K,L981F
BA.2         D614G,H655Y,N679K,P681H,N764K,D796Y,       Q954H,N969K
BA.3         D614G,H655Y,N679K,P681H,N746K,D796Y,       Q954H,N969K
BA.4/5       D614G,H655Y,N679K,P681H,N764K, D796Y,      Q954H,N969K

B

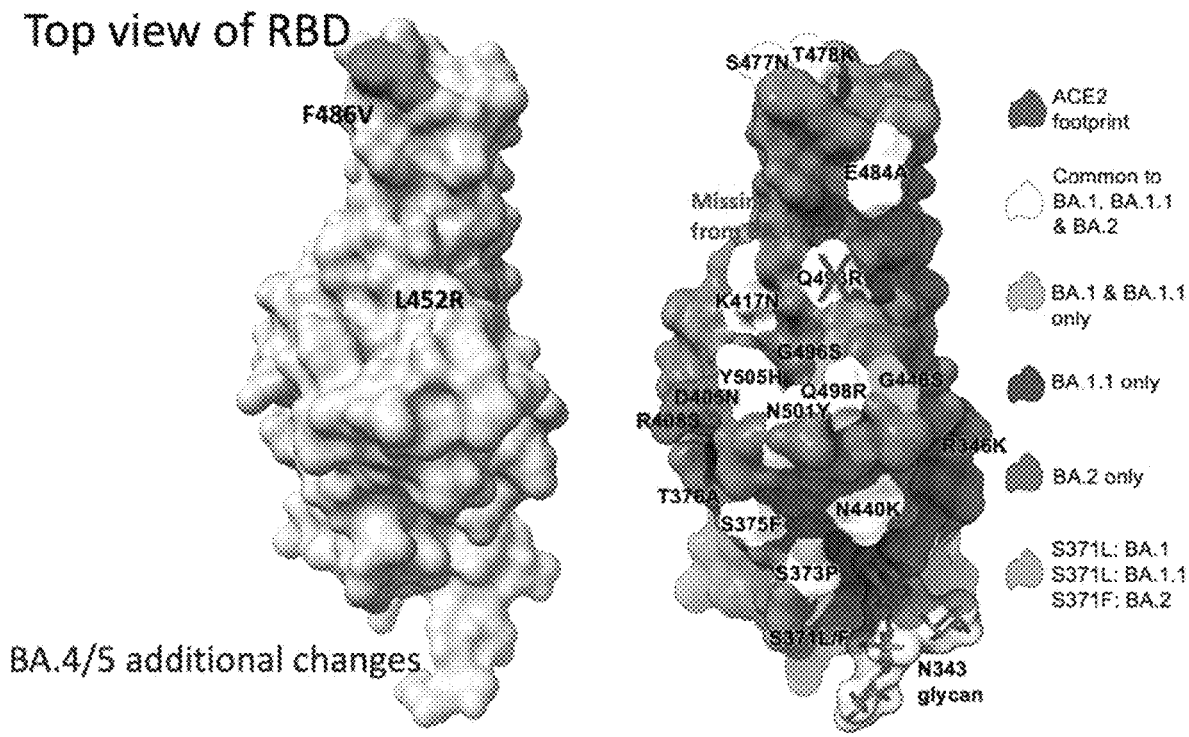

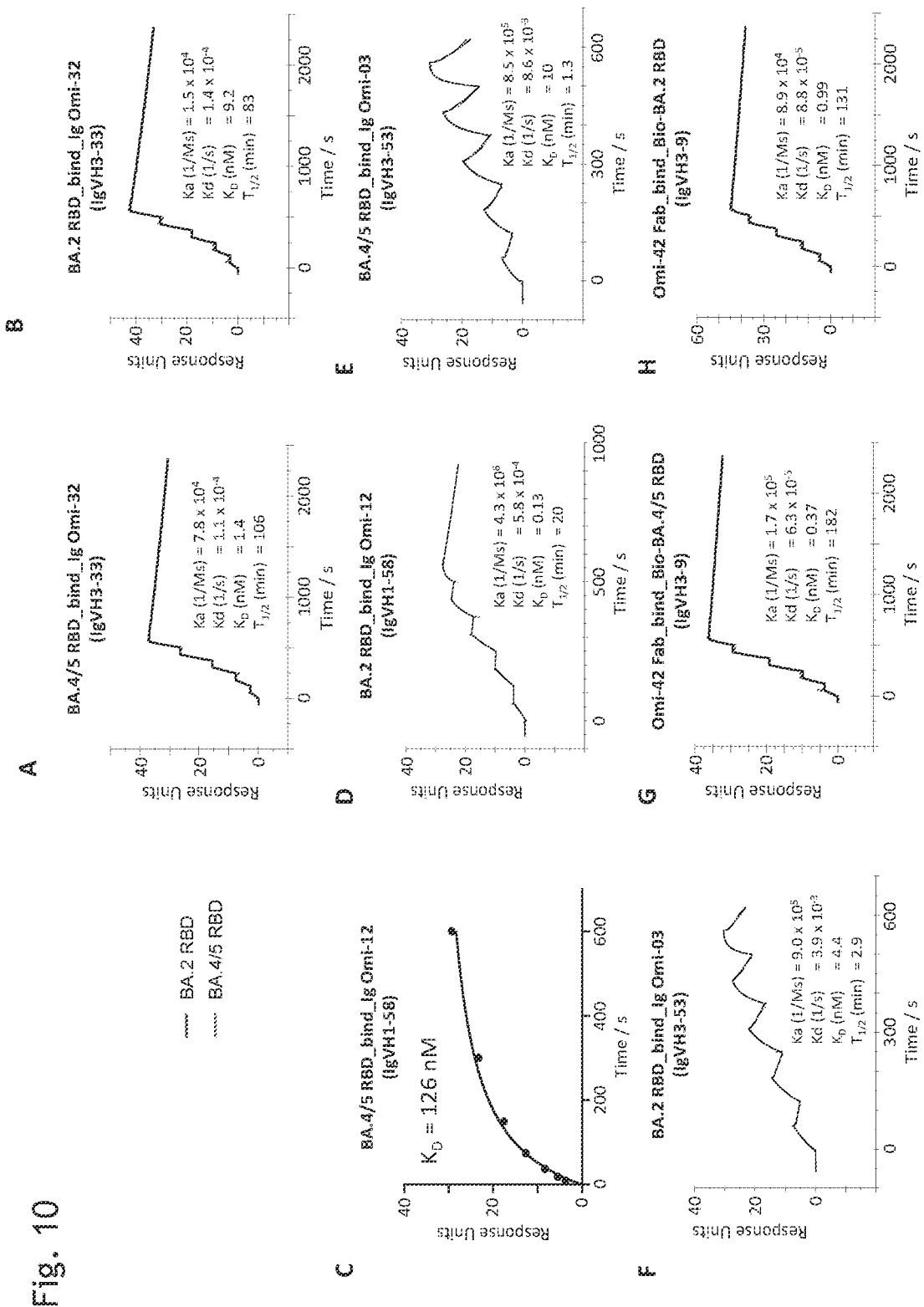

Fig. 12
A
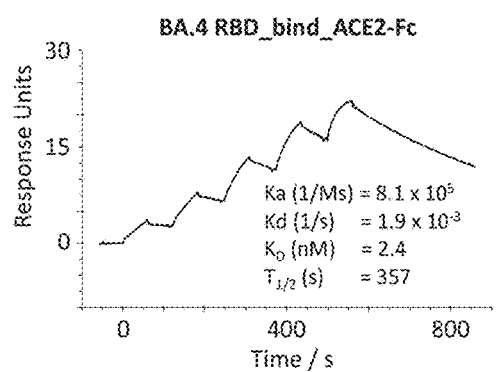
B
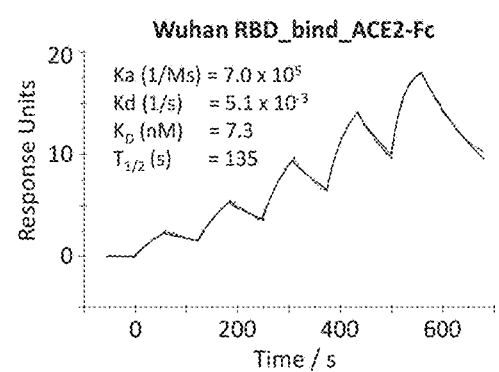
C
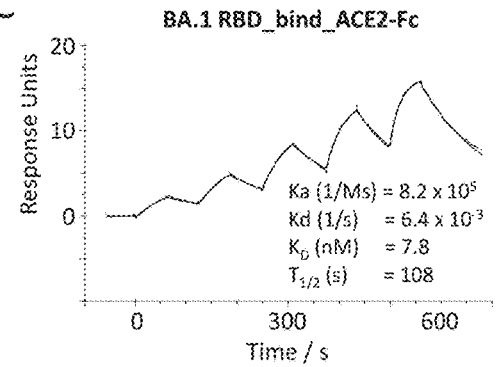
D
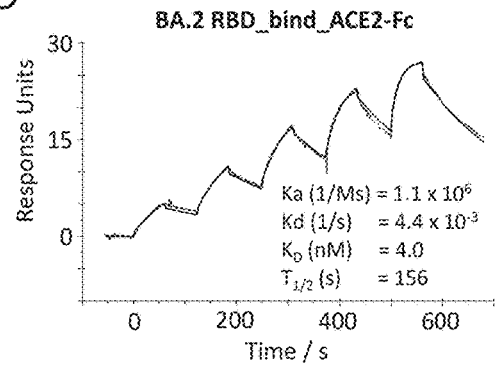
E
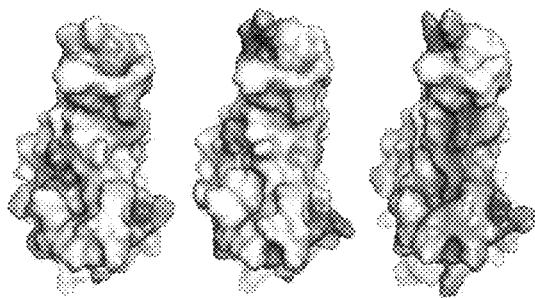
F G
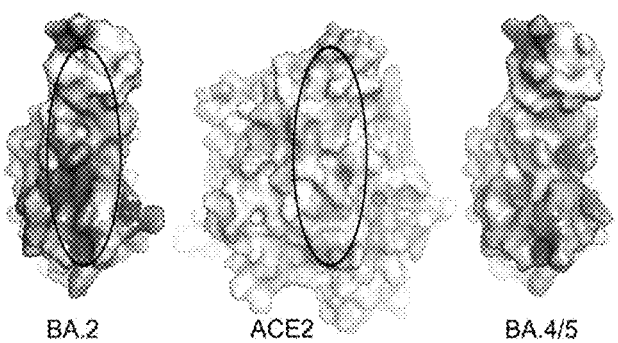

Fig. 26

Fig. 28
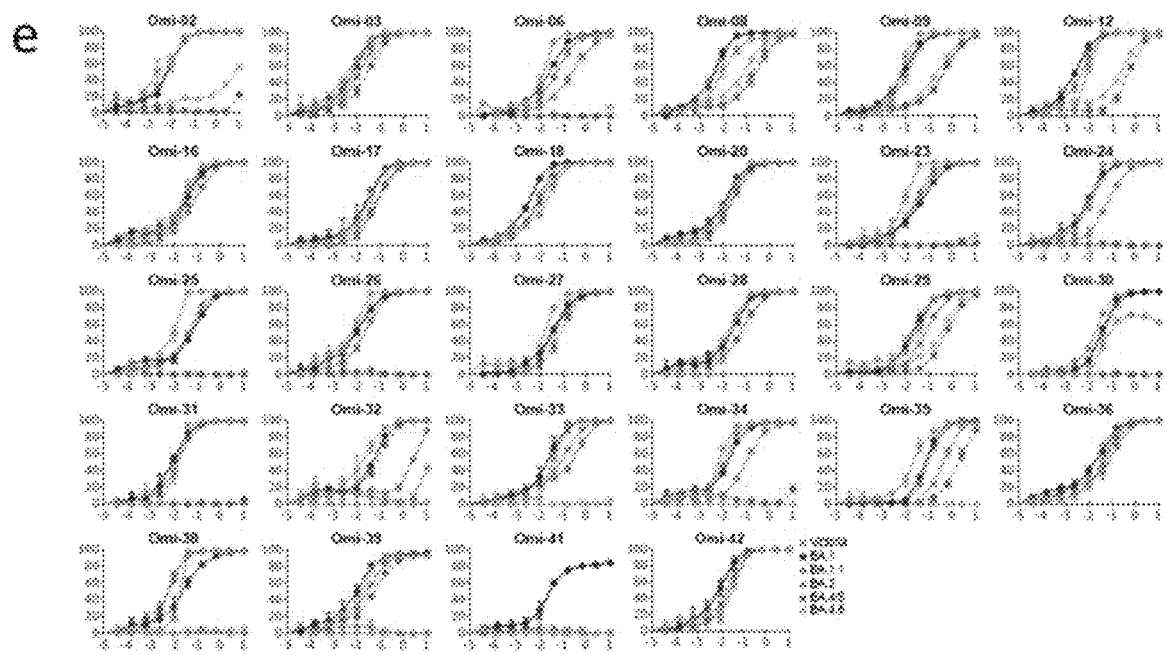
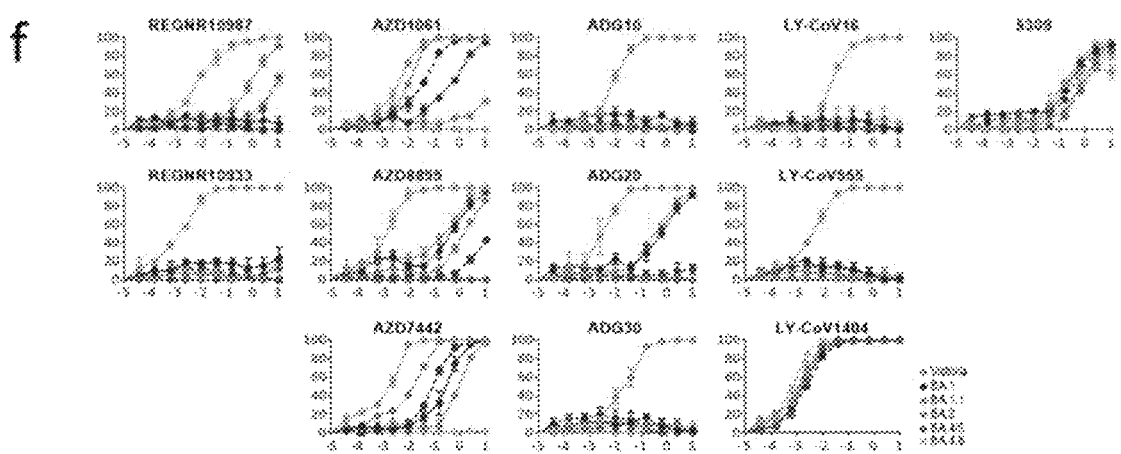

Fig. 35

Compiled IC50 titres of BA.1 mAb, data for various viruses

ANTIBODIES CAPABLE OF BINDING TO THE SPIKE PROTEIN OF CORONAVIRUS SARS-CoV-2

CROSS REFERENCE TO RELATED APPLICATIONS

This application claims priority to GB Application No. 2202232.1 (filed Feb. 18, 2022), GB Application No. 2203423.5 (filed Mar. 11, 2022), GB Application No. 2206777.1 (filed May 9, 2022), GB Application No. 2212470.5 (filed Aug. 26, 2022), GB Application No. 2214036.2 (filed Sep. 26, 2022), GB Application No. 2215418.1 (filed Oct. 18, 2022), and GB Application No. 2301959.9 (filed Feb. 10, 2023), each of which is herein incorporated by reference in its entirety.

REFERENCE TO SEQUENCE LISTING SUBMITTED ELECTRONICALLY

The content of the electronically submitted sequence listing (Name: 2943_2240005_Seqlisting_ST26; Size: 858,636 bytes; and Date of Creation: Feb. 17, 2023) filed with the application is incorporated herein by reference in its entirety.

FIELD OF INVENTION

The invention relates to antibodies useful for the prevention, treatment and/or diagnosis of coronavirus infections, and diseases and/or complications associated with coronavirus infections, including COVID-19.

BACKGROUND OF THE INVENTION

A severe viral acute respiratory syndrome named COVID-19 was first reported in Wuhan, China in December 2019. The virus rapidly disseminated globally leading to the pandemic with >200M confirmed infections and over 4.4M deaths in 12 months. The causative agent, SARS-CoV-2, is a beta coronavirus, related to SARS-CoV-1 and MERS coronaviruses, all of which cause severe respiratory syndromes.

Tremendous advances in our understanding of the disease and the virus have been made in the months since the identification of SARS-CoV-2 as the causative agent a of COVID-19. There are now a number of proven treatments including dexamethasone and Tocilizumab as well as monoclonal antibodies (mAbs), which have been shown to be effective when used in both prophylactic and therapeutic settings (Baum et al., 2020, Science 369, 1014-1018). Despite these advances, the pandemic is far from under control, leading to successive waves of infection.

Coronaviruses have four structural proteins: nucleocapsid, envelope, membrane and spike (S) proteins. The spike protein is the most prominent surface protein. It has an elongated trimeric structure and is responsible for engagement of target cells and triggering fusion of viral and host membranes. The spike protein from SARS-CoV-2 and SARS-CoV-1 both use angiotensin-converting enzyme 2 (ACE2) as a cell surface receptor. ACE2 is expressed in a number of tissues, including epithelial cells of the upper and lower respiratory tracts.

The S protein consists of two subunits, S1, which mediates receptor binding, and S2, responsible for viral and host cell membrane fusion. It is a dynamic structure capable of transitioning to a post-fusion state by cleavage between S1 and S2 following receptor binding or trypsin treatment. In some SARS-CoV-2 sequences a furin protease cleavage site is inserted between the S1 and S2 subunits, and a mutation of the cleavage site attenuates disease in animal models. The S1 fragment occupies the membrane distal tip of S and can be subdivided into an N-terminal domain (NTD) and receptor binding domain (RBD). While both regions are immunogenic, the RBD contains the interacting surface for ACE2 binding. Although usually packed down against the top of S2, RBDs can swing upwards to engage ACE2. Monoclonal antibodies (mAbs) recognize one or both of 'up' and 'down' conformations.

The S protein is relatively conserved between SARS-CoV-2 and SARS-CoV-1 (76%), but the RBD and NTD are less conserved (74% and 50% respectively) than the S2 domain (90%). Conservation with MERS-CoV and the seasonal human coronaviruses is much lower (19-21%). Overall, SARS-CoV-2 antibodies show limited cross-reactivity, even with SARS-CoV-1.

S is involved in viral attachment to target cells via the interaction of cell surface expressed ACE2 with the S receptor binding motif (otherwise known as the ACE-2 footprint), a 25 amino acid patch that lies at the tip of the receptor binding domain (RBD), in the S1 fragment of spike. Following attachment, cleavage of S releases S1, allowing a major conformational change in S2 exposing the hydrophobic fusion loop, to execute fusion of viral and host cell membranes, releasing the viral genome into the host cell cytoplasm to initiate viral replication. Analysis of large panels of mAbs generated from SARS-CoV-2 infected individuals reveals mAbs binding to multiple epitopes across S1 and S2. The majority of mAbs generated against the original strains of SARS-CoV-2, although able to bind S with high affinity, show little or no neutralizing activity. Genomic surveillance of SARS-CoV-2 has identified many thousands of mutations in structural and non-structural proteins. However, towards the end of 2020, viral variants were described that rapidly became the dominant strains locally and led to global spread and their designation of variants of concern (VoC).

Alpha (B.1.1.7) was first identified in the UK, with increased transmission. B.1.1.7 harbours 9 amino-acid changes in the spike, including N501Y in the ACE2 interacting surface. Beta (501Y.V2 also known as B.1.351) was first reported in South Africa. Gamma (P.1, 501Y.V2) was first reported in Brazil, which have 10 and 12 amino-acid changes in the spike protein, respectively. Delta was first reported from India and has now spread globally, causing outbreaks in a number of countries. Omicron BA.1 was first reported in late November 2021 in Southern Africa and spread around the world, becoming the dominant variant in many countries and almost completely displaced Delta.

A succession of sub-lineages of Omicron have emerged, including BA.1.1, BA.2, BA.2.12.1, BA.2.75 and BA.4/5, which have outcompeted preceding strains to become regionally or globally dominant. Over 30 mutations are found in the Omicron S protein, including 15 substitutions in the RBD, leading to increased transmissibility (Suzuki et al., 2022 "Attenuated fusogenicity and pathogenicity of SARS-CoV-2 Omicron variant." *Nature* 603, 700-705) and widespread large reductions in neutralizing antibody titres (Dejnirattisai et al., 2022 "SARS-CoV-2 Omicron-B.1.1.529 leads to widespread escape from neutralizing antibody responses." *Cell* 185, 467-484 e415).

Omicron BA.2 was reported at nearly the same time as BA.1. The proportion of Omicron infections caused by BA.2 has been increasing in several countries and it became the dominant sub-lineage in Denmark and India.

BA.1.1, containing an additional R346K mutation in RBD, at one point accounted for about 40% of Omicron sequences globally, and about 35-60% in the UK and the USA (Iketani et al., 2022 "Antibody evasion properties of SARS-CoV-2 Omicron sublineages." *Nature* 604, 553-556), but was soon outcompeted by BA.2. BA.2, which contains 8 unique substitutions in S, including 6 within the RBD, and lacks 13 mutations found in BA.1 (Nutalai et al., 2022), has become the dominant strain across the world as of August 2022. Recently, BA.2.12.1 has been identified in multiple countries, and caused a large regional outbreak in the North America (58% of the sequences as of May 25, 2022) (Del Rio and Malani, 2022, "COVID-19 in 2022—The Beginning of the End or the End of the Beginning?" *JAMA* 327, 2389-2390).

It is now becoming clear that BA.2 has a small transmission advantage against BA.1 although there is no evidence of increased disease severity. In early April 2022, two new Omicron lineages were reported from Gauteng in South Africa and designated BA.4 and BA.5. BA.4 and BA.5 (which have identical S sequences) became the dominant Omicron strains in Gauteng, fueling a new wave of infection in South Africa.

Since June 2022, BA.4/5, which has both higher receptor binding affinity and a markedly enhanced escape from antibody responses (Tuekprakhon et al., 2022 "Antibody escape of SARS-CoV-2 Omicron BA.4 and BA.5 from vaccine and BA.1 serum." *Cell* 185, 2422-2433 e2413) quickly spread from South Africa across the world and has now become the new globally dominant strain, with BA.5 in the ascendency in many regions. These variants (particularly BA.5) now account for the majority of sequenced cases in many countries.

In early May 2022, a new Omicron sub-lineage designated as BA.2.75 emerged in India. This strain has since spread to many countries including the UK, US, Australia, Germany and Canada. However, the true prevalence of BA.2.75 is difficult to determine as sequencing in many countries is patchy and has been greatly scaled back.

All of these variants contain multiple mutations in S and include changes in the RBD, NTD and in some cases the furin cleavage site between S1 and S2. The RBD mutations found in Alpha (N501Y), Beta (K417N, E484K, N501Y), Gamma (K417T, E484K, N501Y) and Delta (L452R, T478K) are located in or closely adjacent to the ACE2 interacting surface where they have the potential to modulate ACE2 interaction and disrupt the binding of neutralizing antibodies. Increased affinity of ACE2 interaction has been dominated for Alpha, Beta, Gamma and Delta (7, 19, 19, 2-fold, respectively) and may play a role in increasing viral transmissibility. Omicron contains an unprecedented number of mutations concentrated in the Spike (S) gene which carries 30 substitutions plus the deletion of 6 and insertion of 3 residues. Omicron BA.1 (RBD mutations of G339D, S371L, S373P, S375F, K417N, N440K, G446S, S477N, T478K, E484A, Q493R, G496S, Q498R, N501Y, Y505H) contains unique mutations S371L, G446S and G496S and in some isolates R346K (BA.1.1), while BA.2 carries S371F, T376A, D405N and R408S. BA.3 contains no unique mutations relative to BA.1 and BA.2 and appears to be a fusion of the two, being BA.1-like at the N terminus and switching to become BA.2-like at the C-terminus from the mutation G496S.

BA.2.75 contains multiple mutational changes in the S protein compared to BA.2, including four substitutions in the NTD (W152R, F157L, I210V and G257S) and four in the RBD: D339H, G446S, N460K and R493Q.

Three new variants related to BA.2, namely BA.2.11, BA.2.12.1 and BA.2.13, have also been detected in multiple countries. These contain a single mutation of L452R, L452Q and L452M compared to the BA.2 Spike receptor-binding domain (RBD) respectively (FIG. 29). Among them, BA.2.12.1, first identified in New York, became dominant in the US, accounting for about 58% of SARS-CoV-2 isolates as of May 25, 2022. While L452R is found in Delta and Kappa variants, and L452Q in Lambda, L452M is novel.

Considering the physico-chemical properties of the side chain of residue 452, BA.2.13 would be expected to be a relatively modest change; L to M will increase the size of the side chain but it remains hydrophobic. L to Q in BA.2.12.1 introduces some polar character, whilst BA.2.11 is the most radical with L to R introducing a large basic amino acid.

Further variants, BA.4 and BA.5, which have identical S sequences, appear to have evolved from BA.2. The sequences of BA.4 and BA.5 are highly related to the sequence of BA.2, but contain additional mutations. In particular, residues 69 and 70 of the NTD have been deleted (also found in Alpha, BA.1 and BA.3) and they contain two additional substitutions in the RBD: L452R (also found in Delta) and F486V. Finally BA.4 and BA.5 lack the Q493R change seen in BA.1 and BA.2, reverting to Q493 as in the Victoria/Wuhan strain. When looking at the RBD, BA.4 and BA.5 have assembled mutations at all of the previously described positions in the VoC Alpha (N501Y), Beta (K417N, E484K, N501Y), Gamma (K417T, E484K, N501Y), Delta (L452, T478K), the only difference is E484A in BA.4 and BA.5 rather than E484K Beta and Gamma.

As of September 2022, a new variant related to BA.4/5, designated BA.4.6, has emerged and expanded in the United States where BA.5 dominates (87.5% prevalence as of 10th September 2022, tripling from less than 2% of sequences in early July 2022 to over 6% in mid-August 2022). Compared to BA.4/5, BA.4.6 contains two extra mutations in the Spike protein (S), R346T in the RBD and N658S in the C-terminal domain. The R346T mutation has raised concern for enhanced antibody evasion over BA.4/5, as the R346K mutation in BA.1.1 reduced serum neutralisation compared to BA.1 and impaired the activity of a number of monoclonal antibodies (mAbs) (Nutalai, et al., 2022). SARS-CoV-2 detection kits using monoclonal antibodies have also been developed. Examples include lateral flow tests by, e.g. Innova (SARS-CoV-2 Antigen Rapid Qualitative Test) and Quidel (Sofia 2 SARS Antigen FIA). However, these tests are reported to be highly inaccurate.

As of January 2023, further variants have emerged such as BQ.1 and XBB, which carry up to 8 additional RBD amino-acid substitutions compared to BA.2.

Structure function mapping of panels of monoclonal antibodies (mAbs) isolated from infected cases has led to considerable understanding of the antigenicity of S and mechanisms of neutralization. The majority of potent neutralizing antibodies bind at or in close proximity to the footprint of ACE2 and function by blocking ACE2 interaction, thereby preventing cellular attachment and infection. A second site of interaction of potent mAbs is in proximity to N-linked glycan at position N343, exemplified by S309, these antibodies do not block ACE2 interaction but may function to destabilize the S trimer. The third group of potent mAbs bind to the N-terminal domain in S1 and their mode of action is at present unclear. Another RBD epitope of potential interest lies outside of the ACE2 footprint and whilst mAbs binding here are not potent neutralizers they can nevertheless effectively protect in vivo (Huo et al., 2020; Sun et al., 2021; Yuan et al., 2020; Zhou et al., 2020).

Following BA.5 several new trends were observed in the evolution of Omicron: i) the emergence of 'second generation' BA.2 variants (including derivatives of BA.5)—variants with long phylogenetic branch lengths, multiple antigenic mutations and a lack of genetic intermediates, for example BA.2.75, BJ.1, BS.1, BA.2.10.4 and BA.2.3.20 (van der Straten et al. 2022. *Immunity* 55, 1725-1731) and ii) accelerated antigenic drift, seen both in BA.5 (Tuekprakhon et al., 2022) and within these second generation BA.2 lineages, notably BQ.1 and BA.2.75 (https://nextstrain.org/nextclade/sars-cov-2/21L). Finally, recombination between two of these second-generation variants (BJ.1 and BM.1.1.1) has produced XBB. Many of these variants show a large degree of convergent evolution in known antigenic RBD residues, and mutations lie in areas that may threaten the binding of neutralizing antibodies, leading to further escape from protection from infection afforded by vaccine or previous SARS-CoV-2 infection, including prior Omicron infection.

At present a number of lineages are growing rapidly from within both the BA.2 and BA.5 branches. Most striking is the large degree of convergent evolution, particularly at antigenic RBD positions such as 346, 444, 446, 452, 460, 486, 490, and 494. These lineages include examples from the BA.4/5 branch (which naturally contains L452R, F486V and the reversion R493Q), such as BA.4.6 and BF.7 (R346T), BA.4.7 (R346S), BQ.1 (K444T, N460K) and BQ.1.1 (R346T, K444T, N460K); from the BA.2.75 branch (which naturally contains G446S, N460K and the reversion R493Q), BA.2.75.2 (R346T and F486V), BN.1 (R346T, K356T, F490S). There are also examples of several other second generation BA.2 variant lines such as BJ.1 (aka BA.2.10.1.1; R346T, L368I, V445P, G446S, V483A and F490V), BA.2.10.4 (G446S, F486P, S494P and the R493Q reversion), BS.1 (BA.2.3.2.1; R346T, L452R, N460K, G476S), BA.2.3.20 (K444R, N450D, L452M, N460K, E484R and the Q493R reversion), and finally a BA.2.75× BJ.1 recombinant, XBB (which relative to BA.2 contains R346T, L368I, V445P, G446S, N460K, F486S, F490S).

These second-generation BA.2 variants have become dominant globally, with BQ.1 alone accounting for 50% of infections as of 27 Dec. 2022 (https://cov-spectrum.org/explore/World/AllSamples/Past6M) and XBB.1.5 (XBB.1+ F486P) expanding rapidly in North America).

Outside the RBD the degree of convergent evolution is lesser but still present. Many of the second-generation BA.2 variant lineages contain deletions or mutations in the NTD, often similar to that seen in the VoCs, for example Δ~144 in BJ.1 and BA.2.10.4 (previously seen in Alpha and BA.1) and NSP12 G671S in BJ.1, BA.2.75 and BA.2.10.4 (previously seen in Delta).

All currently approved SARS-CoV-2 vaccines are designed to induce antibody (and T-cell) responses to S and contain the S sequence found in the original Wuhan strain.

There is therefore particular concern as to whether the S mutations in the VoCs could cause immune escape, leading to vaccine failure or susceptibility to repeat infections in previously infected individuals.

The extensive mutational burden in Omicron S disrupts the activity of the majority of mAb binding to the three sites of binding of potent antibodies described above, the ACE-2 footprint, around the N343 glycan and the NTD. This leads to severe knock down or complete loss of the neutralizing capacity of serum from natural infection or vaccination, which has contributed to the increased transmissibility and explosive spread of Omicron.

It is an object of the invention to identify further and improved antibodies useful for preventing, treating and/or diagnosing coronavirus infections, and diseases and/or complications associated with coronavirus infections, including COVID-19, especially the Omicron variants of concern (VoCs) and as-yet-unidentified variants having further mutations in the ACE-2 footprint, RBD and/or NTD in the spike protein of SARS-CoV-2.

SUMMARY OF THE INVENTION

The inventors identified 28 human monoclonal antibodies (mAbs) recognizing the spike protein of SARS-CoV-2 (see Table 3). These antibodies showed potent neutralisation activity against SARS-CoV-2. Some of the Table 3 antibodies demonstrated potent neutralization effects that were broadly effective against the hCoV-19/Wuhan/WIV04/2019 strain, as well as SARS-CoV-2 strains from various lineages, such as Victoria (Wuhan+S247R), Alpha, Beta, Gamma, Delta, Omicron, including Omicron BA.2.11, Omicron BA.2.12.1, Omicron BA.2.13, Omicron Omicron BA.2.3.20, Omicron BA.2.10.4, Omicron BA.1, Omicron BA.1.1, Omicron BA.2, Omicron BA.2.75, BA.2.75.2, Omicron BA.3, Omicron BA.4.6, Omicron BA.4/5, Omicron BJ.1, Omicron BS.1, Omicron BN.1, Omicron XBB, and/or Omicron XBB.1 strains.

Many of the Table 3 mAbs used public V-genes (V-genes shared by the majority of the population). The inventors have previously shown that it is possible to generate further antibodies by swapping the light and heavy chains of the antibodies in Tables 1, 2 and 3 which are derived from the same public V-genes. Antibodies derived from the same public V-genes provided particularly useful mixed-chain antibodies.

In particular, the inventors found that antibodies Omi02, Omi03, Omi12, Omi18, Omi28, Omi39 and Omi42 were particularly effective at cross-neutralising SARS-CoV-2 strains Victoria, Alpha, Beta, Gamma, Delta and Omicron.

Accordingly, the invention provides an antibody capable of binding to the spike protein of coronavirus SARS-CoV-2, wherein the antibody comprises at least three CDRs of any one of the 28 antibodies in Table 3.

The invention provides an antibody capable of binding to the spike protein of coronavirus SARS-CoV-2, wherein the antibody comprises at least three CDRs of antibody Omi12, or of any one of the 27 antibodies in Table 3.

The invention also provides a combination of antibodies comprising two or more antibodies according to the invention.

The invention also provides a combination of antibodies comprising (a) an antibody of the invention; and (b) an antibody comprising at least three CDRs of an antibody in Table 1 or Table 2. For example, the antibody may comprise (i) at least four, five, or all six CDRs of an antibody in Table 1 or Table 2; (ii) a heavy chain variable domain comprising or consist of an amino acid sequence having at least 80% sequence identity to the heavy chain variable domain of an antibody in Table 1 or Table 2; (iii) a light chain variable domain comprising or consisting of an amino acid sequence having at least 80% sequence identity to the light chain variable domain of an antibody in Table 1 or Table 2; and/or (iv) a heavy chain variable domain and a light chain variable domain comprising or consisting of an amino acid sequence having at least 80% identity to the heavy chain variable domain and light chain domain, respectively, of an antibody in Table 1 or Table 2.

The invention also provides one or more polynucleotides encoding an antibody of the invention, one or more vectors comprising said polynucleotides, or a host cell comprising said vectors.

The invention also provides a method for producing an antibody that is capable of binding to the spike protein of coronavirus SARS-CoV-2, comprising culturing the host cell of the invention and isolating the antibody from said culture.

The invention also provides a pharmaceutical composition comprising: (a) an antibody or a combination of antibodies of the invention, and (b) at least one pharmaceutically acceptable diluent or carrier.

The invention also provides an antibody, a combination of antibodies or a pharmaceutical composition of the invention, for use in a method for treatment of the human or animal body by therapy.

The invention also provides an antibody, a combination of antibodies or a pharmaceutical composition of the invention, for use in a method of treating or preventing coronavirus infection, or a disease or complication associated with coronavirus infection.

The invention also provides a method of treating or preventing coronavirus infection, or a disease or complication associated with coronavirus infection in a subject, comprising administering a therapeutically effective amount of an antibody, a combination of antibodies or the pharmaceutical composition of the invention, to said subject.

The invention also provides a method of identifying the presence of coronavirus, or a protein fragment thereof, in a sample, comprising (i) contacting the sample with an antibody or combination of antibodies of the invention, and (ii) detecting the presence or absence of an antibody-antigen complex, wherein the presence of the antibody-antigen complex indicates the presence of coronavirus, or a fragment thereof, in the sample.

The invention also provides a method of treating or preventing coronavirus infection, or a disease or complication associated therewith, in a subject, comprising identifying the presence of coronavirus according to the method of the invention, and treating the subject with the antibody or combination according to the invention, an anti-viral or an anti-inflammatory agent.

The invention provides the use of an antibody, a combination of antibodies or a pharmaceutical composition of the invention, for preventing, treating and/or diagnosing coronavirus infection, or a disease or complication associated therewith.

The invention also provides the use of an antibody, a combination of antibodies or a pharmaceutical composition of the invention, for the manufacture of a medicament for treating or preventing coronavirus infection, or a disease or complication associated therewith.

BRIEF DESCRIPTION OF THE FIGURES

FIG. 1 relates only to the first 22 Omicron antibodies disclosed in Tables 13 and 14 (i.e. Omi02 to Omi35). (A) FRNT50 titres against Victoria and Omicron BA.1 from the donors for the production of Omicron mAb are shown. (B) FACS plots showing the sorting of B cells using full length Omicron S. (C) Proportion of RBD and NTD binding antibodies found in the Omicron mAb compared to early pandemic mAb. (D) Heavy and Light chain variable gene usage. (E) Somatic mutations found in the potent Omicron mAb (FRNT50<100 ng/ml) compared to the early pandemic set.

FIG. 9. The Omicron sub-lineage compared to BA.4/5. (A) Comparison of S protein mutations of Omicron BA.1, BA.1.1, BA.2, BA.3 and BA.4/5 with NTD and RBD boundaries indicated. (B) Position of RBD mutations (grey surface with the ACE2 footprint in dark green). Mutations common to all Omicron lineages are shown in white (Q493R which is reverted in BA.4/5 is shown with a cross), those common to BA.1 and BA.1.1 in cyan, those unique to BA.1.1 in blue and those unique to BA.2 in magenta. Residue 371 (yellow) is mutated in all Omicron viruses but differs between BA.1 and BA.2. The N343 glycan is shown as sticks with a transparent surface FIG. 10. Surface plasmon resonance (SPR) analysis of interaction between BA.2 or BA.4/5 RBD and selected mAbs. Binding of BA.4/5 RBD is severely reduced compared to that of BA.2, so that the binding could not be accurately determined, as shown by a single-injection of 200 nM RBD over sample flow cells containing IgG Omi-31. (A-B; D-H) Sensorgrams (Red: original binding curve; black: fitted curve) showing the interactions between BA.2 or BA.4/5 RBD and selected mAbs, with kinetics data shown. (C) Determination of the affinity of BA.4/5 RBD to Omi-12 using a 1:1 binding equilibrium analysis.

FIG. 12. ACE2 RBD affinity. (A)-(D) SPR sensorgrams showing ACE2 binding of BA.4/5 RBD (A) in comparison to ancestral (Wuhan) (B), BA.1 (C) and BA.2 RBD (D). The data for Wuhan, BA.1 and BA.2 have been reported previously in (Nutalai et al., 2022). (E)-(G) Electrostatic surfaces, (E) from left to right, early pandemic, Delta and BA.1 RBD respectively, (F) open book view of BA.2 RBD and ACE2 of the BA.2 RBD/ACE2 complex (PDB 7ZF7), and (G) BA.4/5 RBD (modelled based on the structure of BA.2 RBD). The lozenges on ACE2 and RBD show the interaction areas.

FIG. 6. ACE2/RBD affinity and antigenic mapping FIG. 14. Neutralization curves for VH1-58 mAb. Pseudoviral neutralization curves for early pandemic mAb 253 (Dejnirattisai et al., 2021a) and Beta-47 (Liu et al., 2021b) against Victoria and the panel of Omicron lineage constructs.

FIG. 26. Primers for site-directed PCR mutagenesis of the BA.2.75 RBD Site-directed PCR mutagenesis was performed using the BA.2 Spike construct as the template. D339H, G446S, N460K and R493Q mutations were introduced using the primers shown.

FIG. 35. Heat map of IC50 neutralization titres for the panel of BA.1 (Omi) mAb. Pseudoviral neutralization IC50 titres for indicated mAb against a panel of pseudoviruses expressing variant S sequences. Live virus IC50 values against variants found earlier in the pandemic are included for comparison. Data for live virus assays and pseudoviral data for Victoria, BA.2 and BA.4/5 were previously reported in Tuekprakon et al. (2022).

DETAILED DESCRIPTION OF THE INVENTION

Antibodies of the Invention

Figure 1:
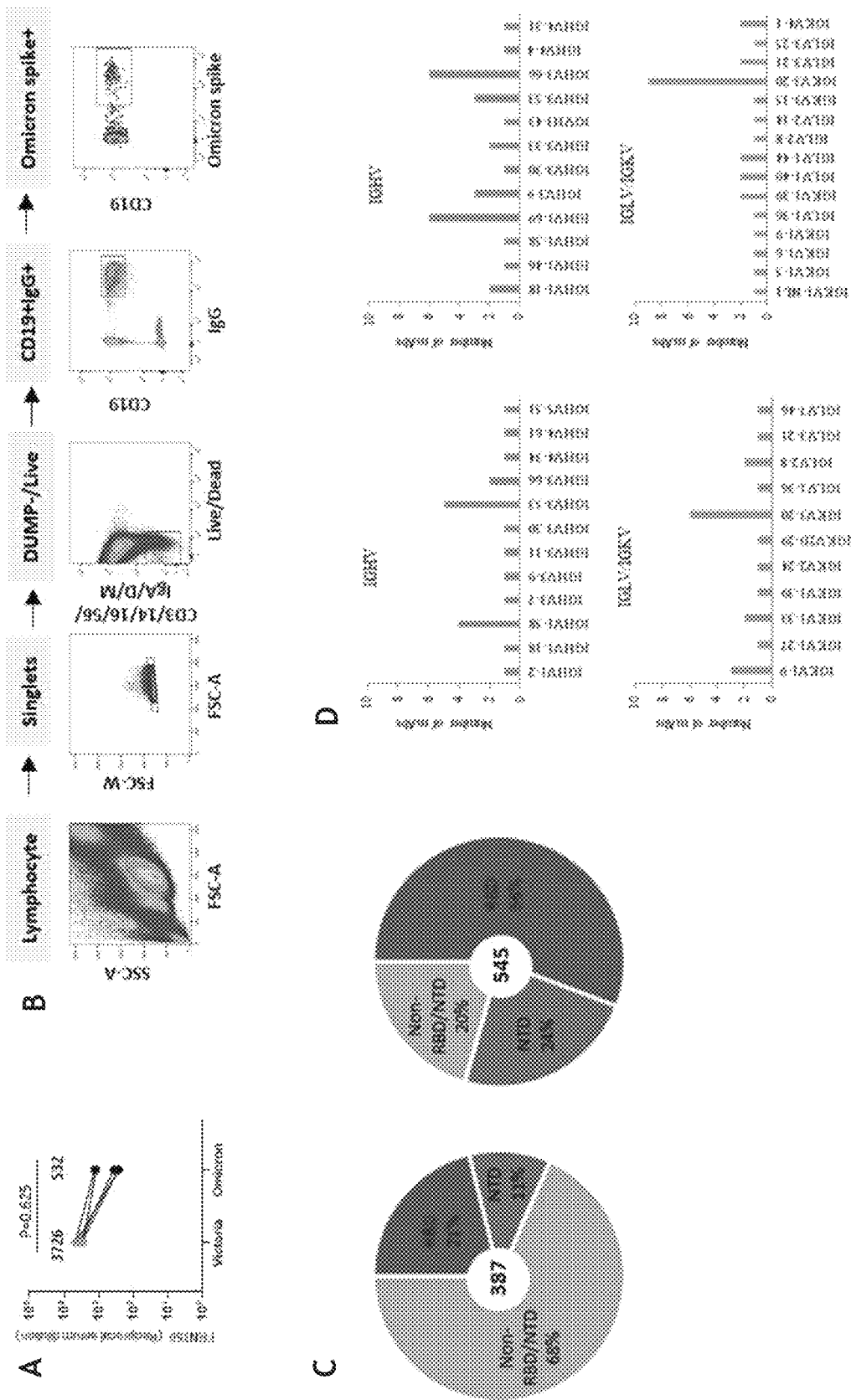
FIG. 1. The BA.2 sub-lineage of Omicron and generation of a panel of Omicron mAb.
Figure 1:
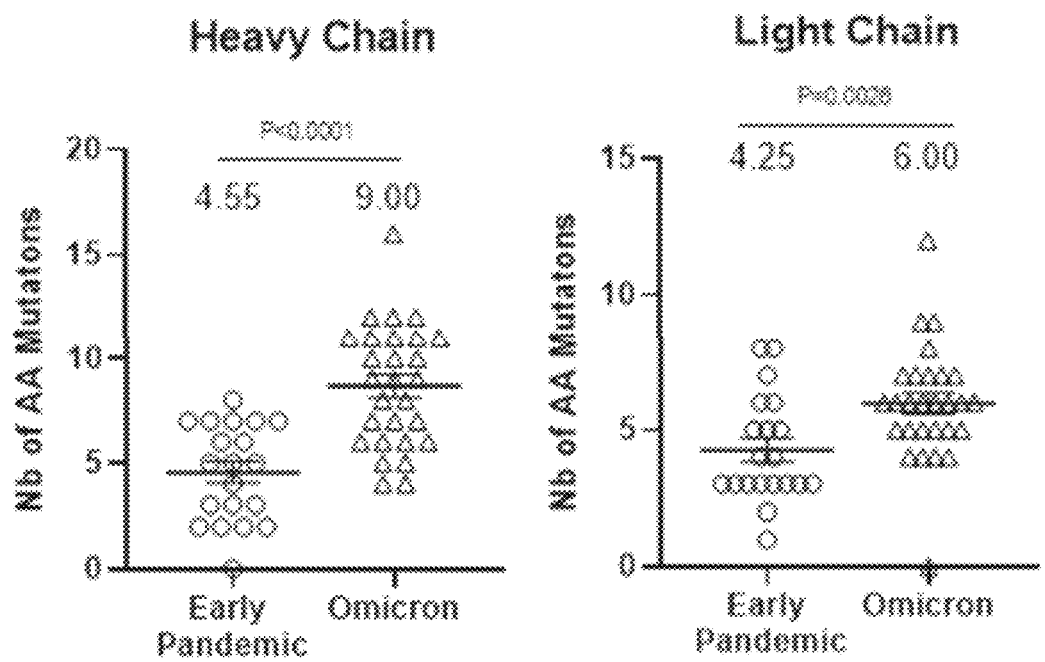

An antibody of the invention specifically binds to the spike protein of SAR-CoV-2.
In particular, it specifically binds to the S1 subunit of the spike protein, such as the receptor binding domain (RBD) or N-terminal domain (NTD).

An antibody of the invention may comprise at least three CDRs of an antibody in Table 3. The antibody may comprise at least four, five, or all six CDRs of an antibody in Table 3. The antibody may comprise a heavy chain variable domain comprising or consisting of an amino acid sequence having at least 80% sequence identity to the heavy chain variable domain of an antibody in Table 3. The antibody may comprise a light chain variable domain comprising or consisting of an amino acid sequence having at least 80% sequence identity to the light chain variable domain of an antibody in Table 3. The antibody may comprise a heavy chain variable domain and a light chain variable domain comprising or consisting of an amino acid sequence having at least 80% identity to the heavy chain variable domain and light chain domain, respectively, of an antibody in Table 3. The antibody may be any one of the antibodies in Table 3.

Table 3 lists 28 individual antibodies that were identified from recovered breakthrough Omicron SARS-CoV-2-infected patients, whom had already been received two doses of the Pfizer vaccine. Table 1 lists 42 individual antibodies that were previously identified from recovered COVID-19 patients [Dejnirattisai, Wanwisa, et al. "The antigenic anatomy of SARS-CoV-2 receptor binding domain." Cell 184(8) (2021): 2183-2200; Supasa, Piyada, et al. "Reduced neutralization of SARS-CoV-2 B. 1.1.7 variant by convalescent and vaccine sera." Cell 184(8) (2021): 2201-2211; Zhou, Daming, et al. "Evidence of escape of SARS-CoV-2 variant B.1.351 from natural and vaccine-induced sera." Cell 184(9) (2021): 2348-2361; Dejnirattisai, Wanwisa, et al. "Antibody evasion by the P.1 strain of SARS-CoV-2." Cell 184(11) (2021): 2939-2954; Liu, Chang, et al. "Reduced neutralization of SARS-CoV-2 B. 1.617 by vaccine and convalescent serum." Cell 184(16) (2021): 4220-4236.]. Table 2 lists 28 individual antibodies that were previously identified from recovered Beta SARS-CoV-2 infected patients [Liu, C et al. "The antibody response to SARS-CoV-2 Beta underscores the antigenic distance to other variants". Cell host & microbe 30(1)(2021): 53-68]. The antibodies in Table 1 are also referred to herein with a pre-fix "COVOX", e.g. COVOX-222. The antibodies in Table 2 are also referred to with a pre-fix "β", e.g. "β50". The antibodies in Table 3 are also referred to with a pre-fix "O", e.g. "O02". Tables 1 to 3 list the SEQ ID NOs for the heavy chain variable region and light chain variable region nucleotide and amino acid sequences, and the complementarity determining regions (CDRs) of the variable chains, of each of the antibodies.

The antibody in Table 3 may be selected from the group consisting of: Omi03, Omi12, Omi02, Omi39, Omi42, Omi16, Omi18, Omi20, Omi 23, Omi28, Omi08, Omi17, Omi29, Omi36 and Omi38. These antibodies were surprisingly found to retain strong neutralisation of the live SARS-CoV-2 variant strains Victoria, Alpha, Beta, Gamma, Delta and Omicron (e.g. an IC50 of ≤0.1 µg/ml against all live strains tested).

The antibody in Table 3 may be selected from the group consisting of: Omi03, Omi12, Omi02, Omi39, Omi42, Omi16, Omi18, Omi20, Omi 23, Omi28 and Omi 08. These antibodies were surprisingly found to retain strong neutralisation of the live SARS-CoV-2 variant strains Victoria, Alpha, Beta, Gamma, Delta and Omicron (e.g. an IC50 of ≤0.05 µg/ml against all live strains tested).

The antibody in Table 3 may be selected from the group consisting of: Omi03, Omi12, Omi02, Omi39 and Omi42. These antibodies were surprisingly found to retain strong neutralisation of the live SARS-CoV-2 variant strains Victoria, Alpha, Beta, Gamma, Delta and Omicron (e.g. an IC50 of ≤0.02 µg/ml against all live strains tested).

The antibody in Table 3 may be selected from the group consisting of: Omi03 and Omi12. These antibodies were surprisingly found to retain very strong neutralisation of the live SARS-CoV-2 variant strains Victoria, Alpha, Beta, Gamma, Delta and Omicron (e.g. an IC50 of ≤0.01 µg/ml against all live strains tested).

The antibody in Table 3 may be selected from the group consisting of: Omi02, Omi03, Omi12, Omi18, Omi28, Omi39 and Omi42. These antibodies were surprisingly found to retain very strong neutralisation of the live SARS-CoV-2 variant strains Victoria, Alpha, Beta, Gamma, Delta and Omicron.

Accordingly, in one embodiment, the antibody in Table 3 may be Omi03. Omi03 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 695, 696 and 697, respectively, a CDRL1 and CDRL3 having the amino acid sequences specified in SEQ ID NOs: 698 and 700, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi03 (i.e. SEQ ID NO: 692). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi03 (i.e. SEQ ID NO: 694). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi03 (i.e. SEQ ID NOs: 692 and 694, respectively).

The heavy chain domain of Omi03 is derived from a IGHV3-53 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi03, and not the light chain of Omi03. For example, the antibody may comprise a CDRH1, CDRH2 and CDRH3 having the amino acid sequences specified in SEQ ID NOs: 695, 696 and 697, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi03 (i.e. SEQ ID NO: 692). The antibody may comprise a heavy chain variable domain comprising or consisting of SEQ ID NO: 692.

Alternatively, in an embodiment of the invention, the antibody may comprise the light chain of Omi03, and not the heavy chain of Omi03. For example, the antibody may comprise a CDRL1 and CDRL3 having the amino acid sequences specified in SEQ ID NOs: 698 and 700, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi03 (i.e. SEQ ID NO: 694). The antibody may comprise a light chain variable domain comprising or consisting of SEQ ID NO: 694.

In one embodiment, the antibody in Table 3 may be Omi12. Omi12 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 735, 736 and 737, respectively, and a CDRL1 and CDRL3 having the amino acid sequences specified in SEQ ID NOs: 738 and 740, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi12 (i.e. SEQ ID NO: 732). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi12 (i.e. SEQ ID NO: 734). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi12 (i.e. SEQ ID NOs: 732 and 734, respectively).

The heavy chain domain of Omi12 is derived from a IGHV1-58 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi12, and not the light chain of Omi12. For example, the antibody may comprise a CDRH1, CDRH2 and CDRH3 having the amino acid sequences specified in SEQ ID NOs: 735, 736 and 737, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi12 (i.e. SEQ ID NO: 732). The antibody may comprise a heavy chain variable domain comprising or consisting of SEQ ID NO: 732.

Alternatively, in an embodiment of the invention, the antibody may comprise the light chain of Omi12, and not the heavy chain of Omi12. For example, the antibody may comprise a CDRL1 and CDRL3 having the amino acid sequences specified in SEQ ID NOs: 738 and 740, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi12 (i.e. SEQ ID NO: 734). The antibody may comprise a light chain variable domain comprising or consisting of SEQ ID NO: 734.

In one embodiment, the antibody in Table 3 may be Omi02. Omi02 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 685, 686 and 687, respectively, and a CDRL1 and CDRL3 having the amino acid sequences specified in SEQ ID NOs: 688 and 690, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi02 (i.e. SEQ ID NO: 682). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi02 (i.e. SEQ ID NO: 684). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi02 (i.e. SEQ ID NOs: 682 and 684, respectively).

The heavy chain domain of Omi02 is derived from a IGHV1-69 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi02, and not the light chain of Omi02. For example, the antibody may comprise a CDRH1, CDRH2 and CDRH3 having the amino acid sequences specified in SEQ ID NOs: 685, 686 and 687, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi02 (i.e. SEQ ID NO: 682). The antibody may comprise a heavy chain variable domain comprising or consisting of SEQ ID NO: 682.

Alternatively, in an embodiment of the invention, the antibody may comprise the light chain of Omi02, and not the heavy chain of Omi02. For example, the antibody may comprise a CDRL1 and CDRL3 having the amino acid sequences specified in SEQ ID NOs: 688 and 690, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi02 (i.e. SEQ ID NO: 684). The antibody may comprise a light chain variable domain comprising or consisting of SEQ ID NO: 684.

In one embodiment, the antibody in Table 3 may be Omi08. Omi08 was found to neutralise the live SARS-CoV-2 variant strains Victoria, Alpha, Beta, Gamma, Delta and Omicron, and the psuedoviral constructs of Victoria, Omicron BA.1 Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 715, 716 and 717, respectively, a CDRL1 and CDRL3 having the amino acid sequences specified in SEQ ID NOs: 718 and 720, respectively, and a CDRL2 having the amino acid sequence: GNT. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi08 (i.e. SEQ ID NO: 712). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi08 (i.e. SEQ ID NO: 714). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi08 (i.e. SEQ ID NOs: 712 and 714, respectively).

In one embodiment, the antibody in Table 3 may be Omi42. Omi42 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 955, 956 and 957, respectively, a CDRL1 and CDRL3 having the amino acid sequences specified in SEQ ID NOs: 958 and 960, respectively, and a CDRL2 having the amino acid sequence: EVS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi42 (i.e. SEQ ID NO: 952). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi42 (i.e. SEQ ID NO: 954). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi42 (i.e. SEQ ID NOs: 952 and 954, respectively).

The heavy chain domain of Omi42 is derived from a IGHV3-9 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi42, and not the light chain of Omi42. For example, the antibody may comprise a CDRH1, CDRH2 and CDRH3 having the amino acid sequences specified in SEQ ID NOs: 955, 956 and 957, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi42 (i.e. SEQ ID NO: 952). The antibody may comprise a heavy chain variable domain comprising or consisting of SEQ ID NO: 952.

Alternatively, in an embodiment of the invention, the antibody may comprise the light chain of Omi42, and not the heavy chain of Omi42. For example, the antibody may comprise a CDRL1 and CDRL3 having the amino acid sequences specified in SEQ ID NOs: 958 and 960, respectively, and a CDRL2 having the amino acid sequence: EVS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi42 (i.e. SEQ ID NO: 954). The antibody may comprise a light chain variable domain comprising or consisting of SEQ ID NO: 954.

In one embodiment, the antibody in Table 3 may be Omi16. Omi16 was found to neutralise the live SARS-CoV-2 variant strains Victoria, Alpha, Beta, Gamma, Delta and Omicron, and the psuedoviral constructs of Victoria, Omicron BA.1, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 745, 746 and 747, respectively, a CDRL1 and CDRL3 having the amino acid sequences specified in SEQ ID NOs: 748 and 750, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi16 (i.e. SEQ ID NO: 742). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi16 (i.e. SEQ ID NO: 744). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi16 (i.e. SEQ ID NOs: 742 and 744, respectively).

The heavy chain domain of Omi16 is derived from a IGHV3-66 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi16, and not the light chain of Omi16. For example, the antibody may comprise a CDRH1, CDRH2 and CDRH3 having the amino acid sequences specified in SEQ ID NOs: 745, 746 and 747, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi16 (i.e. SEQ ID NO: 742). The antibody may comprise a heavy chain variable domain comprising or consisting of SEQ ID NO: 742.

Alternatively, in an embodiment of the invention, the antibody may comprise the light chain of Omi16, and not the heavy chain of Omi16. For example, the antibody may comprise a CDRL1 and CDRL3 having the amino acid sequences specified in SEQ ID NOs: 748 and 750, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi16 (i.e. SEQ ID NO: 744). The antibody may comprise a light chain variable domain comprising or consisting of SEQ ID NO: 744.

In one embodiment, the antibody in Table 3 may be Omi18. Omi18 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 765, 766 and 767, respectively, a CDRL1 and CDRL3 having the amino acid sequences specified in SEQ ID NOs: 768 and 770, respectively, and a CDRL2 having the amino acid sequence: DDS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi18 (i.e. SEQ ID NO: 762). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi18 (i.e. SEQ ID NO: 764). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi18 (i.e. SEQ ID NOs: 762 and 764, respectively).

The heavy chain domain of Omi18 is derived from a IGHV3-53 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi18, and not the light chain of Omi18. For example, the antibody may comprise a CDRH1, CDRH2 and CDRH3 having the amino acid sequences specified in SEQ ID NOs: 765, 766 and 767, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi18 (i.e. SEQ ID NO: 762).

The antibody may comprise a heavy chain variable domain comprising or consisting of SEQ ID NO: 762.

Alternatively, in an embodiment of the invention, the antibody may comprise the light chain of Omi18, and not the heavy chain of Omi18. For example, the antibody may comprise a CDRL1 and CDRL3 having the amino acid sequences specified in SEQ ID NOs: 768 and 770, respectively, and a CDRL2 having the amino acid sequence: DDS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi18 (i.e. SEQ ID NO: 764). The antibody may comprise alight chain variable domain comprising or consisting of SEQ ID NO: 764.

In one embodiment, the antibody in Table 3 may be Omi20. Omi20 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 775, 776 and 777, respectively, a CDRL1 and CDRL3 having the amino acid sequences specified in SEQ ID NOs: 778 and 780, respectively, and a CDRL2 having the amino acid sequence: AAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi20 (i.e. SEQ ID NO: 772). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi20 (i.e. SEQ ID NO: 774). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi20 (i.e. SEQ ID NOs: 772 and 774, respectively).

The heavy chain domain of Omi20 is derived from a IGHV3-66 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi20, and not the light chain of Omi20. For example, the antibody may comprise a CDRH1, CDRH2 and CDRH3 having the amino acid sequences specified in SEQ ID NOs: 775, 776 and 777, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi20 (i.e. SEQ ID NO: 772). The antibody may comprise a heavy chain variable domain comprising or consisting of SEQ ID NO: 772.

Alternatively, in an embodiment of the invention, the antibody may comprise the light chain of Omi20, and not the heavy chain of Omi20. For example, the antibody may comprise a CDRL1 and CDRL3 having the amino acid sequences specified in SEQ ID NOs: 778 and 780, respectively, and a CDRL2 having the amino acid sequence: AAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi20 (i.e. SEQ ID NO: 774). The antibody may comprise alight chain variable domain comprising or consisting of SEQ ID NO: 774.

In one embodiment, the antibody in Table 3 may be Omi23. Omi23 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 785, 786 and 787, respectively, a CDRL1 and CDRL3 having the amino acid sequences specified in SEQ ID NOs: 788 and 790, respectively, and a CDRL2 having the amino acid sequence: AAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi23 (i.e. SEQ ID NO: 782). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi23 (i.e. SEQ ID NO: 784). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi23 (i.e. SEQ ID NOs: 782 and 784, respectively).

The heavy chain domain of Omi23 is derived from a IGHV4-31 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi23, and not the light chain of Omi23. For example, the antibody may comprise a CDRH1, CDRH2 and CDRH3 having the amino acid sequences specified in SEQ ID NOs: 785, 786 and 787, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi23 (i.e. SEQ ID NO: 782). The antibody may comprise a heavy chain variable domain comprising or consisting of SEQ ID NO: 782.

Alternatively, in an embodiment of the invention, the antibody may comprise the light chain of Omi23, and not the heavy chain of Omi23. For example, the antibody may comprise a CDRL1 and CDRL3 having the amino acid sequences specified in SEQ ID NOs: 788 and 790, respectively, and a CDRL2 having the amino acid sequence: AAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi23 (i.e. SEQ ID NO: 784). The antibody may comprise alight chain variable domain comprising or consisting of SEQ ID NO: 784.

In one embodiment, the antibody in Table 3 may be Omi28. Omi28 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 835, 836 and 837, respectively, a CDRL1 and CDRL3 having the amino acid sequences specified in SEQ ID NOs: 838 and 840, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi28 (i.e. SEQ ID NO: 832). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi28 (i.e. SEQ ID NO: 834). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi28 (i.e. SEQ ID NOs: 832 and 834, respectively). The heavy chain domain of Omi28 is derived from a IGHV3-66 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi28, and not the light chain of Omi28. For example, the antibody may comprise a CDRH1, CDRH2 and CDRH3 having the amino acid sequences specified in SEQ ID NOs: 835, 836 and 837, respectively. The antibody may comprise a heavy chain variable domain comprising or consisting of an amino acid sequence having ≥80%, ≥90%, ≥95%, ≥96%, ≥97%, ≥98%, ≥99% or 100% sequence 10 identity to the heavy chain variable domain of antibody Omi28 (i.e. SEQ ID NO: 832). The antibody may comprise a heavy chain variable domain comprising or consisting of SEQ ID NO: 832.

Alternatively, in an embodiment of the invention, the antibody may comprise the light chain of Omi28, and not the heavy chain of Omi28. For example, the antibody may comprise a CDRL1 and CDRL3 having the amino acid sequences specified in SEQ ID NOs: 838 and 840, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi28 (i.e. SEQ ID NO: 834). The antibody may comprise alight chain variable domain comprising or consisting of SEQ ID NO: 834.

In one embodiment, the antibody in Table 3 may be Omi39. Omi39 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 935, 936 and 937, respectively, a CDRL1 and CDRL3 having the amino acid sequences specified in SEQ ID NOs: 938 and 940, respectively, and a CDRL2 having the amino acid sequence: WAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi39 (i.e. SEQ ID NO: 932). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi39 (i.e. SEQ ID NO: 934). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi39 (i.e. SEQ ID NOs: 932 and 934, respectively).

In one embodiment, the antibody in Table 3 may be Omi17. Omi17 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 755, 756 and 757, respectively, a CDRL1 and CDRL3 having the amino acid sequences specified in SEQ ID NOs: 758 and 760, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi17 (i.e. SEQ ID NO: 752). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi17 (i.e. SEQ ID NO: 754). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi17 (i.e. SEQ ID NOs: 752 and 754, respectively).

The heavy chain domain of Omi17 is derived from a IGHV3-66 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi17, and not the light chain of Omi17. For example, the antibody may comprise a CDRH1, CDRH2 and CDRH3 having the amino acid sequences specified in SEQ ID NOs: 755, 756 and 757, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi17 (i.e. SEQ ID NO: 752). The antibody may comprise a heavy chain variable domain comprising or consisting of SEQ ID NO: 752.

Alternatively, in an embodiment of the invention, the antibody may comprise the light chain of Omi17, and not the heavy chain of Omi17. For example, the antibody may comprise a CDRL1 and CDRL3 having the amino acid sequences specified in SEQ ID NOs: 758 and 760, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi17 (i.e. SEQ ID NO: 754). The antibody may comprise alight chain variable domain comprising or consisting of SEQ ID NO: 754.

In one embodiment, the antibody in Table 3 may be Omi29. Omi29 was found to neutralise the live SARS-CoV-2 variant strains Victoria, Alpha, Beta, Gamma, Delta and Omicron, and the psuedoviral constructs of Victoria Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 845, 846 and 847, respectively, a CDRL1 and CDRL3 having the amino acid sequences specified in SEQ ID NOs: 848 and 850, respectively, and a CDRL2 having the amino acid sequence: DVS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi29 (i.e. SEQ ID NO: 842). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi29 (i.e. SEQ ID NO: 844). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi29 (i.e. SEQ ID NOs: 842 and 844, respectively).

The heavy chain domain of Omi29 is derived from a IGHV3-53 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi29, and not the light chain of Omi29. For example, the antibody may comprise a CDRH1, CDRH2 and CDRH3 having the amino acid sequences specified in SEQ ID NOs: 845, 846 and 847, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi29 (i.e. SEQ ID NO: 842). The antibody may comprise a heavy chain variable domain comprising or consisting of SEQ ID NO: 842.

Alternatively, in an embodiment of the invention, the antibody may comprise the light chain of Omi29, and not the heavy chain of Omi29. For example, the antibody may comprise a CDRL1 and CDRL3 having the amino acid sequences specified in SEQ ID NOs: 848 and 850, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi29 (i.e. SEQ ID NO: 844). The antibody may comprise a light chain variable domain comprising or consisting of SEQ ID NO: 844.

In one embodiment, the antibody in Table 3 may be Omi36. Omi36 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 915, 916 and 917, respectively, a CDRL1 and CDRL3 having the amino acid sequences specified in SEQ ID NOs: 918 and 920, respectively, and a CDRL2 having the amino acid sequence: GAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi36 (i.e. SEQ ID NO: 912). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi36 (i.e. SEQ ID NO: 914).

In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi36 (i.e. SEQ ID NOs: 912 and 914, respectively). The heavy chain domain of Omi36 is derived from a IGHV3-66 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi36, and not the light chain of Omi36. For example, the antibody may comprise a CDRH1, CDRH2 and CDRH3 having the amino acid sequences specified in SEQ ID NOs: 915, 916 and 917, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi36 (i.e. SEQ ID NO: 912). The antibody may comprise a heavy chain variable domain comprising or consisting of SEQ ID NO: 912.

Alternatively, in an embodiment of the invention, the antibody may comprise the light chain of Omi36, and not the heavy chain of Omi36. For example, the antibody may comprise a CDRL1 and CDRL3 having the amino acid sequences specified in SEQ ID NOs: 918 and 920, respectively, and a CDRL2 having the amino acid sequence: GAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi36 (i.e. SEQ ID NO: 914). The antibody may comprise a light chain variable domain comprising or consisting of SEQ ID NO: 914.

In one embodiment, the antibody in Table 3 may be Omi38. Omi38 was found to neutralise the live SARS-CoV-2 variant strains Victoria, Alpha, Beta, Gamma, Delta and Omicron, and the psuedoviral constructs of Victoria, Omicron BA.1, Omicron BA.1.1, Omicron BA.2 and Omicron BA.3 (see Tables 13 and 14, FIG. 2). In one embodiment, an antibody of the invention may comprise a CDRH1, CDRH2 and CDRH3 having the amino acid sequences specified in SEQ ID NOs: 925, 926 and 927, respectively, a CDRL1 and CDRL3 having the amino acid sequences specified in SEQ ID NOs: 928 and 930, respectively, and a CDRL2 having the amino acid sequence: DAS. In one embodiment, an antibody of the invention may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi38 (i.e. SEQ ID NO: 922). In one embodiment, an antibody of the invention may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Omi38 (i.e. SEQ ID NO: 924). In one embodiment, an antibody of the invention may comprise a heavy chain variable domain and a light chain variable domain comprising or consisting of an amino acid sequence having ≥80%, ≥90%, ≥95%, ≥96%, ≥97%, ≥98%, ≥99%, 100% sequence identity to the heavy chain variable domain and light chain variable domain, respectively, of antibody Omi38 (i.e. SEQ ID NOs: 922 and 924, respectively).

The heavy chain domain of Omi38 is derived from a IGHV1-69 v-region, and the inventors have previously demonstrated that switching of the heavy chains and light chains between antibodies derived from the same v-region results in an antibody that is particularly useful with the invention (explained further below). Hence, an antibody of the invention may comprise the heavy chain of Omi38, and not the light chain of Omi38. For example, the antibody may comprise a CDRH1, CDRH2 and CDRH3 having the amino acid sequences specified in SEQ ID NOs: 925, 926 and 927, respectively. The antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of antibody Omi38 (i.e. SEQ ID NO: 922). The antibody may comprise a heavy chain variable domain comprising or consisting of SEQ ID NO: 922.

Alternatively, in an embodiment of the invention, the antibody may comprise the light chain of Omi38, and not the heavy chain of Omi38. For example, the antibody may comprise a CDRL1 and CDRL3 having the amino acid sequences specified in SEQ ID NOs: 928 and 930, respectively, and a CDRL2 having the amino acid sequence: DAS. The antibody may comprise a light chain variable domain comprising or consisting of an amino acid sequence having ≥80%, ≥90%, ≥95%, ≥96%, ≥97%, ≥98%, ≥99% or 100% sequence identity to the light chain variable domain of antibody Om38 (i.e. SEQ ID NO: 924). The antibody may comprise a light chain variable domain comprising or consisting of SEQ ID NO: 924.

Mixed Chain Antibodies of the Invention

An antibody of the invention may comprise a light chain variable domain comprising CDRL1, CDRL2 and CDRL3 from a first antibody in Table 1, 2 or 3 and a heavy chain variable domain comprising CDRH1, CDRH2 and CDRH3 from a second antibody in Table 1, 2 or 3, with the proviso that the first and second antibodies are different. Such antibodies are referred to as mixed chain antibodies herein.

Examples of the mixed chain antibodies useful with the invention are provided in Tables 4 to 12. Table 4 shows examples of mixed chain antibodies generated from antibodies in Tables 1 to 3 that are derived from the same germline heavy chain IGHV 3-53. Table 5 shows examples of mixed chain antibodies generated from antibodies in Tables 1 to 3 that are derived from the same germline heavy chain IGHV 3-53 and IGHV3-66. Table 6 shows examples of mixed chain antibodies generated from antibodies in Tables 1 to 3 that are derived from the same germline heavy chain IGHV1-58. Table 7 shows examples of mixed chain antibodies generated from antibodies in Tables 2 and 3 that are derived from the same germline heavy chain IGHV1-69. Table 8 shows examples of mixed chain antibodies generated from antibodies in Tables 1 to 3 that are derived from the same germline heavy chain IGHV3-30. Table 9 shows examples of mixed chain antibodies generated from antibodies in Tables 2 and 3 that are derived from the same germline heavy chain IGHV3-33. Table 10 shows examples of mixed chain antibodies generated from antibodies in Tables 1 to 3 that are derived from the same germline heavy chain IGHV1-18. Table 11 shows examples of mixed chain antibodies generated from antibodies in Tables 1 and 3 that are derived from the same germline heavy chain IGHV3-9. Table 12 shows examples of mixed chain antibodies generated from antibodies in Tables 2 and 3 that are derived from the same germline heavy chain IGHV4-31. Examples of mixed chain antibodies that are derived from the same germline heavy chain IGHV1-69 are Omi02H/Beta-49L and Omi38H/Omi24L.

Hence, in one embodiment, an antibody of the invention comprises a heavy chain variable domain comprising CDRH1, CDRH2 and CDRH3 from a first antibody in Table 1, 2 or 3 and a light chain variable domain comprising CDRL1, CDRL2 and CDRL3 from a second antibody in Table 1, 2 or 3, with the proviso that the first and second antibodies are different. The antibody may comprise a heavy chain variable domain amino acid sequence having at least 80% sequence identity to the heavy chain variable domain from a first antibody in Table 1, 2 or 3, and a light chain variable domain amino acid sequence having at least 80% sequence identity to the light chain variable domain from a second antibody in Table 1, 2 or 3, with the proviso that the first and second antibodies are different. For example, the antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of an antibody in Table 1, 2 or 3, and a light chain variable domain comprising or consisting of an amino acid sequence having ≥80%, ≥90%, ≥95%, ≥96%, ≥97%, ≥98%, ≥99% or 100% sequence identity to the light chain variable domain of an antibody in Table 1, 2 or 3, with the proviso that the first and second antibodies are different.

The first antibody may be in Table 3 and the second antibody may be in Table 3.

The first antibody may be in Table 3 and the second antibody may be in Table 1. The first antibody may be in Table 3 and the second antibody may be in Table 2. The first antibody may be in Table 1 and the second antibody may be in Table 3. The first antibody may be in Table 2 and the second antibody may be in Table 3. The first antibody may be in Table 1 and the second antibody may be in Table 2. The first antibody may be in Table 2 and the second antibody may be in Table 1. The first antibody may be in Table 2 and the second antibody may be in Table 2. The first antibody may be in Table 1 and the second antibody may be in Table 1.

In one embodiment, at least one of the first and second antibodies is an antibody from Table 3.

In one embodiment, the first and second antibodies are not both in Table 1. In one embodiment, the first and second antibodies are not both in Table 2. In one embodiment, the first and second antibodies are not both selected from an antibody in Table 1 or 2.

In one embodiment, at least one of the heavy chain variable domain and the light chain variable domain are from Table 3.

The antibody in Table 3 may be selected from the group consisting of: Omi02, Omi03, Omi12, Omi18, Omi28, Omi39 and Omi42. The antibody in Table 3 may be selected from the group consisting of: Omi03, Omi12, Omi02, Omi39, Omi42, Omi16, Omi18, Omi20, Omi 23, Omi28, Omi08, Omi17, Omi29, Omi36 and Omi38. For example, the antibody in Table 3 may be selected from the group consisting of Omi03, Omi12, Omi02, Omi39, Omi42, Omi16, Omi18, Omi20, Omi 23, Omi28 and Omi08. The antibody in Table 3 may be selected from the group consisting of Omi03, Omi12, Omi02, Omi39, and Omi42. The antibody in Table 3 may be selected from the group consisting of Omi03 and Omi12.

In one embodiment, the first antibody and the second antibody are both selected from the group consisting of: Omi03, Omi18, Omi29, Beta-27, antibody 150, antibody 158, antibody 175, antibody 222 and antibody 269. The heavy chain variable domain of these antibodies are derived from IGHV3-53. The resulting mixed chain antibodies are set out in Table 4. Hence, the antibody of the invention may comprise all six CDRs (CDRH1-3 and CDRL1-3), and/or a heavy chain variable domain and a light chain variable domain, each comprising or consisting of an amino acid sequence having at least 80% sequence identity to the corresponding variable domain of any one of the mixed chain antibodies as set out in Table 4.

Antibodies derived from IGHV3-53 may be used to produce mixed-chain antibodies with antibodies from IGHV3-66 (e.g. antibodies 40 and 398 in Table 1) (see, e.g. Dejnirattisai, Wanwisa, et al. "The antigenic anatomy of SARS-CoV-2 receptor binding domain." Cell 184(8) (2021): 2183-2200; Supasa, Piyada, et al. "Reduced neutralization of SARS-CoV-2 B.1.1.7 variant by convalescent and vaccine sera." Cell 184(8) (2021): 2201-2211; Zhou, Daming, et al. "Evidence of escape of SARS-CoV-2 variant B.1.351 from natural and vaccine-induced sera." Cell 184(9) (2021): 2348-2361; Dejnirattisai, Wanwisa, et al. "Antibody evasion by the P.1 strain of SARS-CoV-2." Cell 184(11) (2021): 2939-2954; Liu, Chang, et al. "Reduced neutralization of SARS-CoV-2 B.1.617 by vaccine and convalescent serum." Cell 184(16) (2021): 4220-4236)). Accordingly, in one embodiment, the first antibody and the second antibody are both selected from the group consisting of: Omi03, Omi18, Omi29, Omi16, Omi17, Omi20, Omi27, Omi36, Beta-27, antibody 150, antibody 158, antibody 175, antibody 222, antibody 269, antibody 40 and antibody 398. The heavy chain variable domain of these antibodies are derived from IGHV3-53 and IGVH3-66. The resulting mixed chain antibodies are set out in Table 5. Hence, the antibody of the invention may comprise all six CDRs (CDRH1-3 and CDRL1-3), and/or a heavy chain variable domain and a light chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 5.

In one embodiment, the first antibody and the second antibody are both selected from the group consisting of: Omi12, Beta-47, Beta-25, antibody 55, antibody 165, antibody 253 and antibody 318. The heavy chain variable domain of these antibodies are derived from IGHV 1-58. The resulting mixed chain antibodies are set out in Table 6. Hence, the antibody of the invention may comprise all six CDRs (CDRH1-3 and CDRL1-3), and/or a heavy chain variable domain and a light chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 6.

In one embodiment, the first antibody and the second antibody are both selected from the group consisting of: Beta-49, Beta-50, Omi02, Omi24, Omi30, Omi31, Omi34 and Omi38. The heavy chain variable domain of these antibodies are derived from IGHV 1-69. The resulting mixed chain antibodies are set out in Table 7. Hence, the antibody of the invention may comprise all six CDRs (CDRH1-3 and CDRL1-3), and/or a heavy chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 7.

In one embodiment, the first antibody and the second antibody are both selected from the group consisting of: Beta-22, Beta-29, antibody 159, and Omi09. The heavy chain variable domain of these antibodies are derived from IGHV 3-30. The resulting mixed chain antibodies are set out in Table 8. Hence, the antibody of the invention may comprise all six CDRs (CDRH1-3 and CDRL1-3), and/or a heavy chain variable domain and a light chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 8.

In one embodiment, the first antibody and the second antibody are both selected from the group consisting of: Beta-20, Beta-43, Omi32 and Omi33. The heavy chain variable domain of these antibodies are derived from IGHV 3-33. The resulting mixed chain antibodies are set out in Table 9. Hence, the antibody of the invention may comprise all six CDRs (CDRH1-3 and CDRL1-3), and/or a heavy chain variable domain and alight chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 9. The CDRL1-3 of Omi32 and Omi33 are identical, meaning that they are, effectively, already exemplary mixed-chain antibodies of the invention.

In one embodiment, the first antibody and the second antibody are both selected from the group consisting of: antibody 278, Beta-44, Omi26 and Omi41. The heavy chain variable domain of these antibodies are derived from IGHV 1-18. The resulting mixed chain antibodies are set out in Table 10. Hence, the antibody of the invention may comprise all six CDRs (CDRH1-3 and CDRL1-3), and/or a heavy chain variable domain and a light chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 10.

In one embodiment, the first antibody and the second antibody are both selected from the group consisting of: antibody 58, Omi25, Omi35 and Omi42. The heavy chain variable domain of these antibodies are derived from IGHV 3-9. The resulting mixed chain antibodies are set out in Table 11. Hence, the antibody of the invention may comprise all six CDRs (CDRH1-3 and CDRL1-3), and/or a heavy chain variable domain and a light chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 11.

In one embodiment, the first antibody and the second antibody are both selected from the group consisting of: Beta-56 and Omi23. The heavy chain variable domain of these antibodies are derived from IGHV 4-31. The resulting mixed chain antibodies are set out in Table 12. Hence, the antibody of the invention may comprise all six CDRs (CDRH1-3 and CDRL1-3), and/or a heavy chain variable domain and a light chain variable domain, each comprising or consisting of an amino acid sequence having at least 80% (e.g. ≥80%, ≥90%, ≥95%, ≥96%, ≥97%, ≥98%, ≥99% or 100%) sequence identity to the corresponding variable domain of any one of the mixed chain antibodies as set out in Table 12.

The constant region domains of an antibody molecule of the invention, if present, may be selected having regard to the proposed function of the antibody molecule, and in particular the effector functions which may be required. For example, the constant region domains may be human IgA, IgD, IgE, IgG or IgM domains. Typically, the constant regions are of human origin. In particular, human IgG (i.e. IgG1, IgG2, IgG3 or IgG4) constant region domains may be used. Typically, the constant region is a human IgG1 constant region.

Certain Antibodies of the Invention

The invention also provides an antibody which is a full length antibody of any one of the antibodies in Tables 3, 4, 5, 6, 7, 8, 9, 10, 11 or 12. In other words, an antibody of the invention comprises a heavy chain variable domain and a light chain variable domain consisting of the heavy chain variable domain and light chain variable domain, respectively, of any one of the antibodies in Tables 3, 4, 5, 6, 7, 8, 9, 10, 11 or 12, and a IgG (e.g. IgG1) constant region.

For example, the antibody of the invention may be a full length Omi02, Omi03, Omi12, Omi18, Omi28, Omi39 or Omi42 antibody. The antibody of the invention may be a full length Omi03, Omi12, Omi02, Omi39, Omi42, Omi16, Omi18, Omi20, Omi 23, Omi28, Omi08, Omi17, Omi29, Omi36 or Omi38 antibody. These antibodies are all highly potent neutralising mAbs that have been shown to neutralise the Omicron variant of SARS-CoV-2 with an IC50 of ≤0.1 µg/ml. The antibodies also retain neutralisation of inter alia at least the Victoria, Alpha, Beta, Gamma and Delta strains of SARS-CoV-2 with an IC50 of ≤0.1 µg/ml.

The antibody may be derived from germline heavy chain IGHV1-58 and comprises proline at position 53 in the heavy chain variable region (according to absolute numbering). For example, the antibody may comprise a heavy chain variable domain comprising or consisting of an amino acid sequence having ≥80%, ≥90%, ≥95%, ≥96%, ≥97%, ≥98%, ≥99% or 100% sequence identity to the heavy chain variable domain of Omi-12 (SEQ ID NO: 731), Beta-47 (SEQ ID NO: 591), Beta-25 (SEQ ID NO: 461), antibody 55 (SEQ ID NO: 62), antibody 165 (SEQ ID NO: 182), antibody 253 (SEQ ID NO: 262), or antibody 318 (SEQ ID NO: 332), with the proviso that the amino acid at position 53 in the heavy chain variable region is proline (according to absolute numbering). For example, the antibody may comprise the heavy chain variable region and the light chain variable region of Beta-47 (SEQ ID NOs: 591 and 592, respectively), Beta-25 (SEQ ID NOs: 461 and 462, respectively), antibody 55 (SEQ ID NOs: 62 and 61, respectively), antibody 165 (SEQ ID NO: 182 and 181, respectively), antibody 253 (SEQ ID NOs: 262 and 261, respectively), or antibody 318 (SEQ ID NOs: 332 and 331, respectively), except with a V53P mutation in the heavy chain variable region. The inventors found that such antibodies are particularly effective against Omicron strains (e.g. see Example 5).

The position 53 in the heavy chain variable region of the IGHV1-58-derived antibodies Omi-12, Beta-47, Beta-25, antibody 55, antibody 165, antibody 253, and antibody 318 corresponds to position 58 according to IMGT numbering.

Accordingly, the invention also provides an antibody derived from germline heavy chain IGHV1-58, capable of binding to the spike protein of coronavirus SARS-CoV-2, wherein the amino acid at position 58 in the heavy chain variable region according to IMGT numbering is proline or is substituted with proline.

The antibody may comprise a heavy chain variable domain comprising an amino acid sequence having ≥80%, ≥90%, ≥95%, ≥96%, ≥97%, ≥98%, ≥99% or 100% sequence identity to the heavy chain variable domain of an antibody derived from germline heavy chain IGHV1-58, with the proviso that the amino acid at position 58 according to IMGT numbering is proline or is substituted with proline.

The antibody derived from germline heavy chain IGHV1-58 may be AZD8895, Omi-12, Beta-47, Beta-25, antibody 55, antibody 165, antibody 253, or antibody 318. The amino acid sequence of the heavy chain variable domain of Omi-12, Beta-47, Beta-25, antibody 55, antibody 165, antibody 253, or antibody 318 is described herein (e.g. see Tables 1 to 3). The amino acid sequence of the heavy chain variable domain of antibody AZD8895 is provided in SEQ ID NO: 963.

The IGHV1-58 germline V-gene sequence encodes the amino acid sequence:

(SEQ ID NO: 961)
MQLVQSGPEVKKPGTSVKVSCKASGFTFTSSAVQWVRQARGQRLEWIGWI

VVGSGNTNYAQKFQERVTITRDMSTSTAYMELSSLRSEDTAVYYCAA.

Hence, the invention also provides an antibody capable of binding to the spike protein of coronavirus SARS-CoV-2 comprising a heavy chain variable domain comprising an amino acid sequence having ≥60%, ≥70%, ≥80%, ≥90%, ≥95%, ≥96%, ≥97%, ≥98%, ≥99% or 100% sequence identity to SEQ ID NO: 961, with the proviso that the amino acid at position 58 according to IMGT numbering is proline or is substituted with proline.

The antibody may comprise a heavy chain variable domain comprising an amino acid sequence having ≥80%, ≥90%, ≥95%, ≥96%, ≥97%, ≥98%, ≥99% or 100% sequence identity to SEQ ID NO: 731, 591, 461, 62, 182, 262, 332 or 963, with the proviso that the amino acid at position 58 according to IMGT numbering is proline or is substituted with proline. The antibody may comprise a heavy chain variable domain comprising an amino acid sequence having SEQ ID NO: 591 461, 62, 182, 262, or 332, wherein the valine at position 58 according to IMGT numbering is substituted with proline.

The antibody may comprise a heavy chain variable domain comprising an amino acid sequence having SEQ ID NO: 963, wherein the isoleucine at position 58 according to IMGT numbering is substituted with proline.

In some embodiments, the antibody derived from germline heavy chain IGHV1-58, comprises a light chain variable domain derived from IGLV Kappa 3-20. The antibody may comprise a light chain variable domain comprising an amino acid sequence having ≥80%, ≥90%, ≥95%, ≥96%, ≥97%, ≥98%, ≥99% or 100% sequence identity to the light chain variable domain of an antibody derived from germline IGLV Kappa 3-20. The germline IGLV Kappa 3-20V sequence may encode the amino acid sequence:

(SEQ ID NO: 967)
EIVLTQSPGTLSLSPGERATLSCRASQSVSSSYLAWYQQKPGQAPRLLI
YGASSRATGIPDRFSGSGSGTDFTLTISRLEPEDFAVYYCQQYGSSP.

Hence, the antibody derived from germline heavy chain IGHV1-58 may comprise a light chain variable domain comprising an amino acid sequence having ≥60%, ≥70%, ≥80%, ≥90%, ≥95%, ≥96%, ≥97%, ≥98%, ≥99% or 100% sequence identity to SEQ ID NO: 967.

The invention also provides an antibody capable of binding to the spike protein of coronavirus SARS-CoV-2 comprising a heavy chain variable domain comprising an amino acid sequence that is a modified version of SEQ ID NO: 961, with the proviso that the amino acid at position 58 according to IMGT numbering is proline or is substituted with proline. The modified version of SEQ ID NO: 961 may comprise a modification as described herein, e.g. a substitution, deletion and/or addition. For example, the modification may comprise ≤50, ≤45, ≤40, ≤35, ≤30, ≤25, ≤20, ≤15, ≤10, ≤9, ≤8, ≤7, ≤6, ≤5, ≤4, ≤3, ≤2 or 1 amino acid substitutions and/or deletions from SEQ ID NO: 961. The modification may comprise ≤4, ≤3, ≤2, or 1 amino acid substitutions and/or deletions from SEQ ID NO: 961.

The antibody may comprise a heavy chain variable domain comprising an amino acid sequence that is a modified version of SEQ ID NO: 731, 591, 461, 62, 182, 262, 332 or 963 which comprises ≤10, ≤9, ≤8, ≤7, ≤6, ≤5, ≤4, ≤3, ≤2, or 1 modifications, with the proviso that the amino acid at position 58 according to IMGT numbering is proline or is substituted with proline. The modified version of SEQ ID NO: 731, 591, 461, 62, 182, 262, 332 or 963 may comprise a modification as described herein, e.g. a substitution, deletion and/or addition.

The antibody may comprise a IgG (e.g. IgG1) constant region.

The invention also provides a method of preparing such antibodies. For example, the method may comprise modifying an antibody derived from the germline heavy chain IGHV1-58, capable of binding to the spike protein of coronavirus SARS-CoV-2, by substituting the amino acid at position 58 in the heavy chain variable region (according to IMGT numbering) with proline. The antibody derived from the germline heavy chain IGHV1-58 may be AZD8895, Omi-12, Beta-47, Beta-25, antibody 55, antibody 165, antibody 253, or antibody 318. The amino acid sequence of the heavy chain variable domain of each these antibodies is described herein (e.g. see Tables 1 to 3 and SEQ ID NO: 963). The invention also provides an antibody obtainable or obtained by the method.

Properties of the Antibodies of the Invention

An antibody of the invention may be or may comprise a modification from the amino acid sequence of an antibody in Tables 1 to 12, whilst maintaining the activity and/or function of the antibody. The modification may a substitution, deletion and/or addition. For example, the modification may comprise 1, 2, 3, 4, 5, up to 10, up to 20, up to 30 or more amino acid substitutions and/or deletions from the amino acid sequence of an antibody in Tables 1 to 12. For example, the modification may comprise an amino acid substituted with an alternative amino acid having similar properties. Some properties of the 20 main amino acids, which can be used to select suitable substituents, are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

The modification may comprise a derivatised amino acid, e.g. a labelled or non-natural amino acid, providing the function of the antibody is not significantly adversely affected.

Modification of antibodies of the invention as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Antibodies of the invention may be modified (e.g. as described above) to improve the potency of said antibodies or to adapt said antibodies to new SARS-CoV-2 variants. The modifications may be amino acid substitutions to adapt the antibody to substitutions in a virus variant. For example, the known mode of binding of an antibody to the spike protein (e.g. by crystal structure determination, or modelling) may be used to identify the amino acids of the antibody that interact with the substitution in the virus variant. This information can then be used to identify possible substitutions of the antibody that will compensate for the change in the epitope characteristics. For example, a substitution of a hydrophobic amino acid in the spike protein to a negatively changes amino acid may be compensated by substituting the amino acid from the antibody that interacts with said amino acid in the spike protein to a positively charged amino acid. Methods for identifying residues of an antibody that may be substituted are encompassed by the present disclosure, for example, by determining the structure of antibody-antigen complexes as described herein.

The antibodies of the invention may contain one or more modifications to increase their cross-lineage neutralisation property. For example, E484 of the spike protein, which is a key residue that mediates the interaction with ACE2, is mutated in some SARS-CoV-2 strains (e.g. Victoria strain which contains E484, but P.1 and B.1.351 strains contain E484K) resulting in differing neutralisation effects of the antibodies. Thus, antibodies that bind to E484 can be modified to compensate for the changes in E484 of the spike protein. For example, E484 is mutated from a positively charge to negatively charged amino acid in SAR-CoV-2 strains of B.1.351 or P.1 lineage, when compared to the original strain. The amino acid residues of antibodies that bind to or near E484 may be mutated to compensate for the change in charge. Examples of such amino acid residues may be G104 and/or K108 in SEQ ID NO: 102 of antibody 88, or R52 in SEQ ID NO: 372 of antibody 384.

Antibodies of the invention may be isolated antibodies. An isolated antibody is an antibody which is substantially free of other antibodies having different antigenic specificities.

The term 'antibody' as used herein may relate to whole antibodies (i.e. comprising the elements of two heavy chains and two light chains inter-connected by disulphide bonds) as well as antigen-binding fragments thereof. Antibodies typically comprise immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Each heavy chain is comprised of a heavy chain variable region (abbreviated herein as HCVR or VH) and at least one heavy chain constant region. Each light chain is comprised of a light chain variable region (abbreviated herein as LCVR or VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR).

Antibodies may include, but are not limited to, polyclonal, monoclonal, chimeric, dAb (domain antibody), single chain, Fab, Fab' and F(ab')2 fragments, scFvs, and Fab expression libraries An antibody of the invention may be a monoclonal antibody. Monoclonal antibodies (mAbs) of the invention may be produced by a variety of techniques, including conventional monoclonal antibody methodology, for example those disclosed in "Monoclonal Antibodies: a manual of techniques" (Zola H, 1987, CRC Press) and in "Monoclonal Hybridoma Antibodies: techniques and applications" (Hurrell J G R, 1982 CRC Press). An antibody of the invention may be multispecific, such as bispecific. A bispecific antibody of the invention binds two different epitopes. The epitopes may be in the same protein (e.g. two epitopes in spike protein of SARS-CoV-2) or different proteins (e.g. one epitope in spike protein and one epitope in another protein (such as coat protein) of SARS-CoV-2).

In one embodiment, a bispecific antibody of the invention may bind to two separate epitopes on the spike protein of SARS-CoV-2. The bispecific antibody may bind to the NTD of the spike protein and to the RBD of the spike protein. The bispecific antibody may bind to two different epitopes in the RBD of the spike protein.

One or more (e.g. two) antibodies of the invention can be coupled to form a multispecific (e.g. bispecific) antibody. Methods to prepare multispecific, e.g. bispecific, antibodies are well known in the art.

An antibody may be selected from the group consisting of single chain antibodies, single chain variable fragments (scFvs), variable fragments (Fvs), fragment antigen-binding regions (Fabs), recombinant antibodies, monoclonal antibodies, fusion proteins comprising the antigen-binding domain of a native antibody or an aptamer, single-domain antibodies (sdAbs), also known as VHH antibodies, nanobodies (Camelid-derived single-domain antibodies), shark IgNAR-derived single-domain antibody fragments called VNAR, diabodies, triabodies, Anticalins, aptamers (DNA or RNA) and active components or fragments thereof.

The constant region domains of an antibody molecule of the invention, if present, may be selected having regard to the proposed function of the antibody molecule, and in particular the effector functions which may be required. For example, the constant region domains may be human IgA, IgD, IgE, IgG or IgM domains. Typically, the constant regions are of human origin. In particular, human IgG (i.e. IgG1, IgG2, IgG3 or IgG4) constant region domains may be used. Typically, the constant region is a human IgG1 constant region.

The light chain constant region may be either lambda or kappa.

Antibodies of the invention may be mono-specific or multi-specific (e.g. bi-specific). A multi-specific antibody comprises at least two different variable domains, wherein each variable domain is capable of binding to a separate antigen or to a different epitope on the same antigen.

An antibody of the invention may be a chimeric antibody, a CDR-grafted antibody, a nanobody, a human or humanised antibody. Typically, the antibody is a human antibody. Fully human antibodies are those antibodies in which the variable regions and the constant regions (where present) of both the heavy and the light chains are all of human origin, or substantially identical to sequences of human origin, but not necessarily from the same antibody.

The antibody of the invention may be a full-length antibody.

The antibody of the invention may be an antigen-binding fragment. An antigen-binding fragment of the invention binds to the same epitope of the parent antibody, i.e. the antibody from which the antigen-binding fragment is derived. An antigen-binding fragment of the invention typically retains the parts of the parent antibody that interact with the epitope. The antigen-binding fragment typically comprise the complementarity-determining regions (CDRs) that interact with the antigen, such as one, two, three, four, five or six CDRs. In some embodiments, the antigen-binding fragment further comprises the structural scaffold surrounding the CDRs of the parent antibody, such as the variable region domains of the heavy and/or light chains. Typically, the antigen-binding fragment retains the same or similar binding affinity to the antigen as the parent antibody.

An antigen-binding fragment does not necessarily have an identical sequence to the parent antibody. In one embodiment, the antigen-binding fragment may have ≥70%, ≥80%, ≥90%, ≥95%, ≥96%, ≥97%, ≥98%, ≥99%, 100% sequence identity with the respective CDRs of the parent antibody. In one embodiment, the antigen-binding fragment may have ≥70%, ≥80%, ≥90%, ≥95%, ≥96%, ≥97%, ≥98%, ≥99%, 100% sequence identity with the respective variable region domains of the parent antibody. Typically, the non-identical amino acids of a variable region are not in the CDRs.

The antigen-binding fragments of antibodies of the invention retain the ability to selectively bind to an antigen. Antigen-binding fragments of antibodies include single chain antibodies (i.e. a full-length heavy chain and light chain); Fab, modified Fab, Fab', modified Fab', F(ab')2, Fv, Fab-Fv, Fab-dsFv, single domain antibodies (e.g. VH or VL or VHH), scFv.

An antigen-binding function of an antibody can be performed by fragments of a full-length antibody. The methods for creating and manufacturing these antibody fragments are well known in the art (see for example Verma R et al., 1998, J. Immunol. Methods, 216, 165-181).

Methods for screening antibodies of the invention that do not share 100% amino acid sequence identity with one of the antibodies disclosed herein, that possess the desired specificity, affinity and functional activity include the methods described herein, e.g. enzyme linked immunosorbent assays, biacore, focus reduction neutralisation assay (FRNT), and other techniques known within the art.

With regards to function, an antibody of the invention may be able to neutralise at least one biological activity of SAR-CoV-2 (a neutralising antibody), particularly to neutralise virus infectivity.

Neutralisation may also be determined using IC50 or IC90 values. For example, the antibody may have an IC50 value of ≤0.1 μg/ml, ≤0.05 μg/ml, ≤0.01 μg/ml≤0.005 μg/ml or ≤0.002 μg/ml. In some instances an antibody of the invention may have an IC50 value of between 0.0001 μg/ml and 0.1 μg/ml, sometimes between 0.0001 μg/ml and 0.05 μg/ml or even between 0.0001 μg/ml and 0.001 μg/ml.

For example, the IC50 values of some of the antibodies of Tables 1 to 12 are provided in Tables 13 to 16.

The ability of an antibody to neutralise virus infectivity may be measured using an appropriate assay, particularly using a cell-based neutralisation assay, as shown in the Examples. For example, the neutralisation ability may be measured in a focus reduction neutralisation assay (FRNT) where the reduction in the number of cells (e.g. human cells) infected with the virus (e.g. for 2 hours at 37° C.) in the presence of the antibody is compared to a negative control in which no antibodies were added.

An antibody of the invention may block the interaction between the spike protein of SAR-CoV-2 with the cell surface receptor, angiotensin-converting enzyme 2 (ACE2), of the target cell, e.g. by direct blocking or by disrupting the pre-fusion conformation of the spike protein.

Blocking of the interaction between spike and ACE2 can be total or partial. For example, an antibody of the invention may reduce spike-ACE2 formation by ≥50%, ≥60%, ≥70%, ≥80%, ≥90%, ≥95%, ≥99% or 100%. Blocking of spike-ACE2 formation can be measured by any suitable means known in the art, for example, by ELISA.

Most antibodies showing neutralisation also showed blocking of the interaction between the spike protein and ACE2. Furthermore, a number of non-neutralising antibodies are good ACE2 blockers.

In terms of binding kinetics, an antibody of the invention may have an affinity constant ($K_D$) value for the spike protein of SARS-CoV-2 of ≤5 nM, ≤4 nM, ≤3 nM, ≤2 nM, ≤1 nM, ≤0.5 nM, ≤0.4 nM, ≤0.3 nM, ≤0.2 nM or ≤0.1 nM.

The KD value can be measured by any suitable means known in the art, for example, by ELISA or Surface Plasmon Resonance (Biacore) at 25° C.

Binding affinity ($K_D$) may be quantified by determining the dissociation constant ($K_d$) and association constant ($K_a$) for an antibody and its target. For example, the antibody may have an association constant ($K_a$) of ≥10000 $M^{-1}s^{-1}$, ≥50000 $M^{-1}s^{-1}$, ≥100000 $M^{-1}s^{-1}$, ≥200000 $M^{-1}s^{-1}$ or ≥500000 $M^{-1}s^{-1}$, and/or a dissociation constant ($K_d$) of ≤0.001 $s^{-1}$, ≤0.0005 $s^{-1}$, ≤0.004 $s^{-1}$, ≤0.003 $s^{-1}$, ≤0.002 $s^{-1}$ or ≤0.0001 $s^{-1}$.

An antibody of the invention is preferably able to provide in vivo protection in coronavirus (e.g. SARS-CoV-2) infected animals. For example, administration of an antibody of the invention to coronavirus (e.g. SARS-CoV-2) infected animals may result in a survival rate of ≥30%, ≥40%, ≥50%, ≥60%, ≥70%, ≥80%, ≥90%, ≥95% or 100%. Survival rates may be determined using routine methods.

Antibodies of the invention may have any combination of one or more of the above properties.

Antibodies of the invention may bind to the same epitope as, or compete for binding to SARS-CoV-2 spike protein with, any one of the antibodies described herein (i.e. in particular with antibodies with the heavy and light chain variable regions described above). Methods for identifying antibodies binding to the same epitope, or cross-competing with one another, are used in the Examples and discussed further below.

Fc Regions

An antibody of the invention may or may not comprise an Fc domain.

The antibodies of the invention may be modified in the Fc region in order to improve their stability. Such modifications are known in the art. Modifications may improve the stability of the antibody during storage of the antibody. The in vivo half-life of the antibody may be improved by modifications of the Fc-region. For example, cysteine residue(s) can be introduced into the Fc region, thereby allowing interchain disulphide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)).

Alternatively, an antibody can be engineered that has dual Fc regions and can thereby have enhanced complement lysis and ADCC capabilities. (See Stevenson et al., Anti-Cancer Drug Design, 3: 219-230 (1989)).

For example, an antibody of the invention may be modified to promote the interaction of the Fc domain with FcRn. The Fc domain may be modified to improve the stability of the antibody by affecting Fc and FcRn interaction at low pH, such as in the endosome. The M252Y/S254T/T256E (YTE) mutation may be used to improve the half-life of an IgG1 antibody.

The antibody may be modified to affect the interaction of the antibody with other receptors, such as FcγRI, FcγRIIA, FcγRIIB, FcγRIII, and FcαR. Such modifications may be used to affect the effector functions of the antibody.

In one embodiment, an antibody of the invention comprises an altered Fc domain as described herein below. In another preferred embodiment an antibody of the invention comprises an Fc domain, but the sequence of the Fc domain has been altered to modify one or more Fc effector functions.

In one embodiment, an antibody of the invention comprises a "silenced" Fc region. For example, in one embodiment an antibody of the invention does not display the effector function or functions associated with a normal Fc region. An Fc region of an antibody of the invention does not bind to one or more Fc receptors.

In one embodiment, an antibody of the invention does not comprise a $CH_2$ domain. In one embodiment, an antibody of the invention does not comprise a $CH_3$ domain. In one embodiment, an antibody of the invention comprises additional $CH_2$ and/or $CH_3$ domains.

In one embodiment, an antibody of the invention does not bind Fc receptors. In one embodiment, an antibody of the invention does not bind complement. In an alternative embodiment, an antibody of the invention does not bind FcγR, but does bind complement.

In one embodiment, an antibody of the invention in general may comprise modifications that alter serum half-life of the antibody. Hence, in another embodiment, an antibody of the invention has Fc region modification(s) that alter the half-life of the antibody. Such modifications may be present as well as those that alter Fc functions. In one preferred embodiment, an antibody of the invention has modification(s) that alter the serum half-life of the antibody.

In one embodiment, an antibody of the invention may comprise a human constant region, for instance IgA, IgD, IgE, IgG or IgM domains. In particular, human IgG constant region domains may be used, especially of the IgG1 and IgG3 isotypes when the antibody molecule is intended for therapeutic uses where antibody effector functions are required. Alternatively, IgG2 and IgG4 isotypes may be used when the antibody molecule is intended for therapeutic purposes and antibody effector functions are not required.

In one embodiment, the antibody heavy chain comprises a $CH_1$ domain and the antibody light chain comprises a CL domain, either kappa or lambda. In one embodiment, the antibody heavy chain comprises a $CH_1$ domain, a $CH_2$ domain and a $CH_3$ domain and the antibody light chain comprises a CL domain, either kappa or lambda.

The four human IgG isotypes bind the activating Fcγ receptors (FcγRI, FcγRIIa, FcγRIIc, FcγRIIIa), the inhibitory FcγRIIb receptor, and the first component of complement (C1q) with different affinities, yielding very different effector functions (Bruhns P. et al., 2009. Specificity and affinity of human Fcγ receptors and their polymorphic variants for human IgG subclasses. Blood. 113(16):3716-25), see also Jeffrey B. Stavenhagen, et al. *Cancer Research* 2007 Sep. 15; 67(18):8882-90. In one embodiment, an antibody of the invention does not bind to Fc receptors. In another embodiment of the invention, the antibody does bind to one or more type of Fc receptors.

In one embodiment the Fc region employed is mutated, in particular a mutation described herein. In one embodiment the Fc mutation is selected from the group comprising a mutation to remove or enhance binding of the Fc region to an Fc receptor, a mutation to increase or remove an effector function, a mutation to increase or decrease half-life of the antibody and a combination of the same. In one embodiment, where reference is made to the impact of a modification it may be demonstrated by comparison to the equivalent antibody but lacking the modification.

Some antibodies that selectively bind FcRn at pH 6.0, but not pH 7.4, exhibit a higher half-life in a variety of animal models. Several mutations located at the interface between the $CH_2$ and $CH_3$ domains, such as T250Q/M428L (Hinton P R. et al., 2004. Engineered human IgG antibodies with longer serum half-lives in primates. J Biol Chem. 279(8): 6213-6) and M252Y/S254T/T256E+H433K/N434F (Vaccaro C. et al., 2005. Engineering the Fc region of immunoglobulin G to modulate in vivo antibody levels. Nat Biotechnol. 23(10):1283-8), have been shown to increase the binding affinity to FcRn and the half-life of IgG1 in vivo. Hence, modifications may be present at M252/S254/T256+ H44/N434 that alter serum half-life and in particular M252Y/S254T/T256E+H433K/N434F may be present. In one embodiment, it is desired to increase half-life. In another embodiment, it may be actually desired to decrease serum half-life of the antibody and so modifications may be present that decrease serum half-life.

Numerous mutations have been made in the $CH_2$ domain of human IgG1 and their effect on ADCC and CDC tested in vitro (Idusogie E E. et al., 2001. Engineered antibodies with increased activity to recruit complement. J Immunol. 166 (4):2571-5). Notably, alanine substitution at position 333 was reported to increase both ADCC and CDC. Hence, in one embodiment a modification at position 333 may be present, and in particular one that alters ability to recruit complement. Lazar et al. described a triple mutant (S239D/ I332E/A330L) with a higher affinity for FcγRIIIa and a lower affinity for FcγRIIb resulting in enhanced ADCC (Lazar G A. et al., 2006). Hence, modifications at S239/ I332/A330 may be present, particularly those that alter affinity for Fc receptors and in particular S239D/I332E/ A330L. Engineered antibody Fc variants with enhanced effector function. PNAS 103(11): 4005-4010). The same mutations were used to generate an antibody with increased ADCC (Ryan M C. et al., 2007. Antibody targeting of B-cell maturation antigen on malignant plasma cells. Mol. Cancer Ther., 6: 3009-3018). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards J O et al 2008. Optimization of antibody binding to Fcgamma RIIa enhances macrophage phagocytosis of tumor cells. Mol Cancer Ther. 7(8):2517-27). In one embodiment, S239D/I332E/G236A modifications may be therefore present.

In another embodiment, an antibody of the invention may have a modified hinge region and/or CH1 region. Alternatively, the isotype employed may be chosen as it has a particular hinge regions.

Major Public V Regions

Public V-regions, also described as public V-genes herein, are the V regions of the germline heavy chain and light chain regions that are found in a large proportion of the antibody responses to SARS-CoV-2 found within the population. In this application, the V regions are specific responses to the Beta SARS-CoV-2 variant. That is to say, many individuals utilise the same v-regions from their germline v-region repertoire when generating an immune response to SARS-CoV-2 variants.

As used herein, an antibody "derived" from a specific v-region refers to antibodies that were generated by V(D)J recombination using that germline v-region sequence. For example, the germline IGHV3-53 v-region sequence may undergo somatic recombination and somatic mutation to arrive at an antibody that specifically binds to the spike protein of SARS-CoV-2. The nucleotide sequence encoding the antibody is unlikely to comprise a sequence identical to the IGHV3-53 germline sequence, nevertheless, the antibody is still derived from this v-region. An antibody of the invention typically comprises no more than non-silent mutations in the v-region, when compared to the germline sequence, such as no more than 15, 10, 9, 8, 7, 6, 5, 4, 3, 2 or 1 non-silent mutations. An antibody of the invention typically comprises no between 2-20 non-silent mutations in the v-region, when compared to the germline sequence, such as between 5-15, 6-13 and 7-12 non-silent mutations. Germline v-region sequences are well known in the art, and methods of identifying whether a certain region of an antibody is derived from a particular germline v-region sequence are also well known in the art.

In one embodiment, an antibody of the invention derives from a v-region selected from IGHV3-53, IGHV1-58, IGHV3-66, IGHV1-69, IGHV3-30, IGHV3-33, IGHV1-18, IGHV13-9 or IGHV4-31. The inventors found that the potent neutralising antibodies identified herein comprised relatively few mutations in the CDRs of these v-regions. Thus, in one embodiment, an antibody of the invention encoded by a v-region selected from IGHV3-53, IGHV1-58, IGHV3-66, IGHV1-69, IGHV3-30, IGHV3-33, IGHV1-18, IGHV13-9 or IGHV4-31 and having 2-20 non-silent nucleotide mutations, or 5-15 non-silent mutations, such as 15 or less, 14 or less, 13 or less, 12 or less, 11 or less, 10 or less, 9 or less, 8 or less, 7 or less, 6 or less, 5 or less, 4 or less 3 or less or 2 non-silent mutations when compared to the naturally occurring germline sequence. A silent mutation as defined herein is a change in the nucleotide sequence without a change in the amino acid sequence for which the nucleotide sequence encodes. A non-silent mutation is therefore a mutation that leads to a change in the amino acid sequence encoded by the nucleotide sequence.

The inventors have surprisingly found that the light chain variable region of two antibodies having the same heavy chain v-region may be exchanged to produce a mixed-chain antibody comprising the heavy chain variable region of a first antibody and the light chain variable region of a second antibody. For example, the two antibodies may both comprise a heavy chain variable region derived from IGHV3-53. Preferably, both antibodies also comprise a light chain variable region derived from the same light chain v-region, although this is not essential because, for example, the light chain of antibody 222 may be matched with any heavy chain variable region derived from IGHV3-53 and lead to a potent neutralising antibody. As described above, the two antibodies may comprise a heavy chain variable region derived from IGHV3-53 and/or IGHV3-66.

In one embodiment, an antibody of the invention comprises the CDRs of an heavy chain variable domain of an antibody derived from a major public v-region selected from IGHV3-53, IGHV1-58, IGHV3-66, IGHV4-39, IGHV3-30, IGHV5-51, IGHV1-02 or IGHV3-33, such as antibodies Omi03, Omi18, Omi29, Beta-27, antibody 150, antibody 158, antibody 175, antibody 222 and antibody 269 for IGHV3-53, antibodies Omi16, Omi17, Omi20, Omi27, Omi36, antibody 40 and antibody 398 for IGHV3-66, antibodies Omi12, Beta-47, Beta-25, antibody 55, antibody 165, antibody 253 for IGHV1-58, antibodies Beta-49, Beta-50, Omi02, Omi24, Omi30, Omi31, Omi34 and Omi38 for IGHV1-69, antibodies Beta-22, Beta-29, antibody 159 and Omi09 for IGHV3-30, antibodies Beta-20, Beta-43, Omi32 and Omi 33 for IGHV3-33, antibodies antibody 278, Beta-44, Omi26 and Omi41 for IGHV1-18, antibodies 58, Omi25, Omi35 and Omi42 for IGHV3-9, or antibodies Beta-56 and Omi23 for IGHV4-31. The SEQ ID NOs corresponding to the CDRs of each of these antibodies are shown in Tables 1, 2 and 3.

In one embodiment, an antibody of the invention comprises the heavy chain variable domain of an antibody derived from a major public v-region selected from IGHV3-53, IGHV1-58, IGHV3-66, IGHV4-39, IGHV3-30, IGHV5-51, IGHV1-02 or IGHV3-33, such as antibodies Omi03, Omi18, Omi29, Beta-27, antibody 150, antibody 158, antibody 175, antibody 222 and antibody 269 for IGHV3-53, antibodies Omi16, Omi17, Omi20, Omi27, Omi36, antibody 40 and antibody 398 for IGHV3-66, antibodies Omi12, Beta-47, Beta-25, antibody 55, antibody 165, antibody 253 for IGHV1-58, antibodies Beta-49, Beta-50, Omi02, Omi24, Omi30, Omi31, Omi34 and Omi38 for IGHV1-69, antibodies Beta-22, Beta-29, antibody 159 and Omi09 for IGHV3-30, antibodies Beta-20, Beta-43, Omi32 and Omi 33 for IGHV3-33, antibodies antibody 278, Beta-44, Omi26 and Omi41 for IGHV1-18, antibodies 58, Omi25, Omi35 and Omi42 for IGHV3-9, or antibodies Beta-56 and Omi23 for IGHV4-31. The SEQ ID NOs corresponding to the CDRs of each of these antibodies are shown in Tables 1, 2 and 3.

In one embodiment, the invention provides a method of generating an antibody that binds specifically to the spike protein of SARS-CoV-2 (e.g. a SARS-CoV-2 strain of the Alpha, Beta, Gamma, Delta and/or Omicron lineages), the method comprising identifying two or more antibodies derived from the same light chain and/or heavy chain v-regions, replacing the light chain of a first antibody with the light chain of a second antibody, to thereby generate a mixed-chain antibody comprising the heavy chain of the first antibody and the light chain of the second antibody. In one embodiment, the method further comprises determining the affinity for and/or neutralisation of SARS-CoV-2 of the mixed-chain antibody. The method may further comprise comparing the affinity of the mixed-chain antibody with that of the first and/or second antibodies. The method may further comprise selecting a mixed chain antibody that has the same or greater affinity than the first and/or second antibodies. In some embodiments, the heavy chain v-region is IGHV 1-58 and/or the light chain v-region is IGLV Kappa 3-20.

In another embodiment, the invention provides an antibody that specifically binds to the Omicron variant of SARS-CoV-2, wherein the antibody has a v-region derived from IGHV1-69. It has been surprisingly discovered that antibody responses to infection with the Omicron variant of SARS-CoV-2 is biased towards antibodies with a heavy chain variable region derived from IGHV1-69. In one embodiment, wherein the antibody heavy chain is derived from IGHV1-69, the antibody of the invention comprises the CDRH1, CDRH2 and CDRH3 from Beta-49, Beta-50, Omi02, Omi24, Omi30, Omi31, Omi34 and Omi38.

Antibody Conjugates

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Conjugates of the antibody and cytotoxic agent may be made using a variety of bifunctional protein-coupling agents known in the art.

An antibody, of the invention may be conjugated to a molecule that modulates or alters serum half-life. An antibody, of the invention may bind to albumin, for example in order to modulate the serum half-life. In one embodiment, an antibody of the invention will also include a binding region specific for albumin. In another embodiment, an antibody of the invention may include a peptide linker which is an albumin binding peptide. Examples of albumin binding peptides are included in WO2015/197772 and WO2007/106120 the entirety of which are incorporated by reference.

Polynucleotides, Vectors and Host Cells

The invention also provides one or more isolated polynucleotides (e.g. DNA) encoding the antibody of the invention. In one embodiment, the polynucleotide sequence is collectively present on more than one polynucleotide, but collectively together they are able to encode an antibody of the invention. For example, the polynucleotides may encode the heavy and/or light chain variable regions(s) of an antibody of the invention. The polynucleotides may encode the full heavy and/or light chain of an antibody of the invention. Typically, one polynucleotide would encode each of the heavy and light chains.

Polynucleotides which encode an antibody of the invention can be obtained by methods well known to those skilled in the art. For example, DNA sequences coding for part or all of the antibody heavy and light chains may be synthesised as desired from the corresponding amino acid sequences. General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing. A polynucleotide of the invention may be provided in the form of an expression cassette, which includes control sequences operably linked to the inserted sequence, thus allowing for expression of the antibody of the invention in vivo. Hence, the invention also provides one or more expression cassettes encoding the one or more polynucleotides that encoding an antibody of the invention. These expression cassettes, in turn, are typically provided within vectors (e.g. plasmids or recombinant viral vectors). Hence, in one embodiment, the invention provides a vector encoding an antibody of the invention. In another embodiment, the invention provides vectors which collectively encode an antibody of the invention. The vectors may be cloning vectors or expression vectors. A suitable vector may be any vector which is capable of carrying a sufficient amount of genetic information, and allowing expression of a polypeptide of the invention. The polynucleotides, expression cassettes or vectors of the invention are introduced into a host cell, e.g. by transfection. Hence, the invention also provides a host cell comprising the one or more polynucleotides, expression cassettes or vectors of the invention. The polynucleotides, expression cassettes or vectors of the invention may be introduced transiently or permanently into the host cell, allowing expression of an antibody from the one or more polynucleotides, expression cassettes or vectors. Such host cells include transient, or preferably stable higher eukaryotic cell lines, such as mammalian cells or insect cells, lower eukaryotic cells, such as yeast, or prokaryotic cells, such as bacteria cells. Particular examples of cells include mammalian HEK293, such as HEK293F, HEK293T, HEK293S or HEK Expi293F, CHO, HeLa, NSO and COS cells, or any other cell line used herein, such as the ones used in the Examples. Preferably the cell line selected will be one which is not only stable, but also allows for mature glycosylation.

The invention also provides a process for the production of an antibody of the invention, comprising culturing a host cell containing one or more vectors of the invention under conditions suitable for the expression of the antibody from the one or more polynucleotides of the invention, and isolating the antibody from said culture.

Combination of Antibodies

The inventors found that certain Table 3 antibodies are particularly effective when used in combination, and certain combinations of Table 3, Table 2, and Table 1 antibodies, e.g. to minimise loss of activity due to SARS-CoV-2 variants, maximise therapeutic effects and/or increase diagnostic power. Useful combinations include the antibodies that do not cross-compete with one another and/or bind to non-overlapping epitopes.

Thus, the invention provides a combination of the antibodies of the invention, wherein each antibody is capable of binding to the spike protein of coronavirus SARS-CoV-2, wherein at least one antibody comprises at least three CDRs of any one of the 28 antibodies in Table 3.

A combination of the antibodies of the invention may be useful as a therapeutic cocktail. Hence, the invention also provides a pharmaceutical composition comprising a combination of the antibodies of the invention, as explained further below.

A combination of the antibodies of the invention may be useful for diagnosis. Hence, the invention also provides a diagnostic kit comprising a combination of the antibodies of the invention. Also provided herein are methods of diagnosing a disease or complication associated with coronavirus infections in a subject, as explained further below. A fully cross-neutralising antibody, e.g. Omi03, may be used as a reference to confirm the presence and/or amount of any variants of concern (VoC) SARS-CoV-2 in the sample. An antibody that binds to a limited number of VoCs may be used to confirm the presence and/or amount of that VoC in the sample. For example, if Omi03 exhibits binding to the sample but Omi24 does not exhibit binding to the sample of SARS-CoV-2, then the spike protein may be the spike protein of the Delta VoC. This may be determined by any method known to the skilled person, such as via an immunoassay, e.g. an ELISA or an immunochromatographic assay. Reduced binding may be determined by comparison and/or normalisation to the reference, and/or by comparison to positive/negative control samples or data.

Pharmaceutical Composition

The invention provides a pharmaceutical composition comprising an antibody of the invention. The composition may comprise a combination (such as two, three or four) of the antibodies of the invention. The pharmaceutical composition may also comprise a pharmaceutically acceptable carrier.

The composition of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Suitable pharmaceutically acceptable carriers comprise aqueous carriers or diluents.

Examples of suitable aqueous carriers include water, buffered water and saline.

Other suitable pharmaceutically acceptable carriers include ethanol, polyols (such as glycerol, propylene glycol, polyethylene glycol, and the like), and suitable mixtures thereof, vegetable oils, such as olive oil, and injectable organic esters, such as ethyloleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional therapeutic agents, for example an anti-viral agent. The anti-viral agent may bind to coronavirus and inhibit viral activity. Alternatively, the anti-viral agent may not bind directly to coronavirus but still affect viral activity/infectivity. The anti-viral agent could be a further anti-coronavirus antibody, which binds somewhere on SARS-CoV-2 other than the spike protein. Examples of an anti-viral agent useful with the invention include Remdesivir, Lopinavir, ritonavir, APN01, and Favilavir.

The additional therapeutic agent may be an anti-inflammatory agent, such as a corticosteroid (e.g. Dexamethasone) or a non-steroidal anti-inflammatory drug (e.g. Tocilizumab).

The additional therapeutic agent may be an anti-coronavirus vaccine. The pharmaceutical composition may be administered subcutaneously, intravenously, intradermally, intramuscularly, intranasally or orally. Also within the scope of the invention are kits comprising antibodies or other compositions of the invention and instructions for use. The kit may further contain one or more additional reagents, such as an additional therapeutic or prophylactic agent as discussed herein.

Methods and Uses of the Invention

The invention further relates to the use of the antibodies, the combinations of the antibodies and the pharmaceutical compositions, described herein, e.g. in a method for treatment of the human or animal body by therapy, or in a diagnostic method. The method of treatment may be therapeutic or prophylactic.

For example, the invention relates to methods of treating coronavirus (e.g. SARS-CoV-2) infections, a disease or complication associated therewith, e.g. COVID-19. The method may comprise administering a therapeutically effective amount of an antibody, a combination of antibodies, or a pharmaceutical composition of the invention. The method may further comprise identifying the presence of coronavirus, or fragments thereof, in a sample, e.g. SARS-CoV-2, from the subject. The invention also relates to an antibody, a combination of antibodies, or a pharmaceutical composition according to the invention for use in a method of treating coronavirus (e.g. SARS-CoV-2) infections, a disease or complication associated therewith, e.g. COVID-19.

The invention also relates to a method of formulating a composition for treating coronavirus (e.g. SARS-CoV-2) infections, a disease or complication associated therewith, e.g. COVID-19, wherein said method comprises mixing an antibody, a combination of antibodies, or a pharmaceutical composition according to the invention with an acceptable carrier to prepare said composition.

The invention also relates to the use of an antibody, a combination of antibodies, or a pharmaceutical composition according to the invention for treating coronavirus (e.g. SARS-CoV-2) infections or a disease or complication associated therewith, e.g. COVID-19.

The invention also relates to the use of an antibody, a combination of antibodies, or a pharmaceutical composition according to the invention for the manufacture of a medicament for treating or preventing coronavirus (e.g. SARS-CoV-2) infections or a disease or complication associated therewith, e.g. COVID-19.

The invention also relates to preventing, treating or diagnosing coronavirus infection caused by any SARS-CoV-2 strain. The coronavirus infection may be caused by any SARS-CoV-2 strain.

The SARS-CoV-2 strain may be the earliest identified Wuhan strain (hCoV-19/Wuhan/WIV04/2019 (WIV04); GISAID accession no. EPI_ISL_402124), and variants thereof. For example, the SARS-CoV-2 strain may be a member of lineage A, A.1, A.2, A.3, A.5, B, B.1, B.1.1, B.2, B.3, B.4, B.1.1.7 (alpha), B.1.351 (beta), P.1 (gamma), delta, kappa, and/or lambda. The SARS-CoV-2 strain may be a member of lineage A.23.1, B.1.1.7 (alpha), B.1.351 (beta), B.1.258, B.1.526.2, B.1.616, B.1.617.1 (kappa), B.1.617.2 (delta), C36.3, C.37 (lambda), P.1 (gamma), B.1.1.529 (omicron), Omicron BA.1, Omicron BA.1.1, Omicron BA.2 and/or Omicron BA.3.

The SARS-CoV-2 strain may comprise one or more mutations, e.g. in the spike protein, relative to the hCoV-19/Wuhan/WIV04/2019 (WIV04) (GISAID accession no. EPI_ISL_402124). In other words, the SARS-CoV-2 strain may be a modified hCoV-19/Wuhan/WIV04/2019 (WIV04) strain comprising one or more modifications, e.g. in the spike protein.

The mutation may be the mutations (e.g. substitutions) observed in the Omicron strain of SARS-CoV-2.

Antibodies Omi02, Omi03, Omi12, Omi18, Omi28, Omi39 and Omi42 are particularly effective in neutralising the Omicron SARS-Cov-2 strain. Hence, the invention may relate to these antibodies for use in treating, prevent, treating or diagnosing coronavirus infection caused by a SARS-Cov-2 strain.

The methods and uses of the invention may comprise inhibiting the disease state (such as COVID-19), e.g. arresting its development; and/or relieving the disease state (such as COVID-19), e.g. causing regression of the disease state until a desired endpoint is reached.

The methods and uses of the invention may comprise the amelioration or the reduction of the severity, duration or frequency of a symptom of the disease state (such as COVID-19) (e.g. lessen the pain or discomfort), and such amelioration may or may not be directly affecting the disease. The symptoms or complications may be fever, headache, fatigue, loss of appetite, myalgia, diarrhoea, vomiting, abdominal pain, dehydration, respiratory tract infections, cytokine storm, acute respiratory distress syndrome (ARDS) sepsis, and/or organ failure (e.g. heart, kidneys, liver, GI, lungs).

The methods and uses of the invention may lead to a decrease in the viral load of coronavirus (e.g. SARS-CoV-2), e.g. by ≥10%, ≥20%, ≥30%, ≥40%, ≥50%, ≥60%, ≥70%, ≥80%, ≥90%, or 100% compared to pre-treatment. Methods of determining viral load are well known in the art, e.g. infection assays.

The methods and uses of the invention may comprise preventing the coronavirus infection from occurring in a subject (e.g. humans), in particular, when such subject is predisposed to complications associated with coronavirus infection.

The invention also relates to identifying subjects that have a coronavirus infection, such as by SARS-CoV-2. For example, the methods and uses of the invention may involve identifying the presence of coronavirus (e.g. SARS-CoV-2), or a protein or a fragment thereof, in a sample. The detection may be carried out in vitro or in vivo. In certain embodiments, the invention relates to population screening.

The invention relates to identifying any SARS-CoV-2 strain, as described herein. The invention may also relate to a method of identifying escape mutants of SARS-CoV-2, comprising contacting a sample with a combination of antibodies of the invention and identifying if each antibody binds to the virus. The term "escape mutants" refers to variants of SARS-CoV-2 comprising non-silent mutations that may affect the efficacy of existing treatments of SARS-CoV-2 infection. Typically, the non-silent mutations is on an epitope recognised by a prior art antibody and/or antibodies described herein that specifically binds to an epitope of SARS-CoV-2, e.g. on the spike protein of SARS-CoV-2. If the antibody does not bind to the target, it may indicate that the target comprises a mutation that may alter the efficacy of existing SARS-CoV-2 treatments.

The methods and uses of the invention may include contacting a sample with an antibody or a combination of the antibodies of the invention, and detecting the presence or absence of an antibody-antigen complex, wherein the presence of the antibody-antigen complex indicates that the subject is infected with SARS-CoV-2.

Methods of determining the presence of an antibody-antigen complex are known in the art. For example, in vitro detection techniques include enzyme linked immunosorbent assays (ELISAs), Western blots, immunoprecipitations, and immunofluorescence. In vivo techniques include introducing into a subject a labelled anti-analyte protein antibody. For example, the antibody can be labelled with a radioactive marker whose presence and location in a subject can be detected by standard imaging techniques. The detection techniques may provide a qualitative or a quantitative readout depending on the assay employed.

Typically, the invention relates to methods and uses for a human subject in need thereof. However, non-human animals such as rats, rabbits, sheep, pigs, cows, cats, or dogs is also contemplated. The subject may be at risk of exposure to coronavirus infection, such as a healthcare worker or a person who has come into contact with an infected individual. A subject may have visited or be planning to visit a country known or suspected of having a coronavirus outbreak. A subject may also be at greater risk, such as an immunocompromised individual, for example an individual receiving immunosuppressive therapy or an individual suffering from human immunodeficiency syndrome (HIV) or acquired immune deficiency syndrome (AIDS). The subject may be asymptomatic or pre-symptomatic.

The subject may be early, middle or late phase of the disease.

The subject may be in hospital or in the community at first presentation, and/or later times in hospital.

The subject may be male or female.

In certain embodiments, the subject is typically male. The subject may not have been infected with coronavirus, such as SARS-CoV-2. The subject may have a predisposition to the more severe symptoms or complications associated with coronavirus infections. The method or use of the invention may comprise a step of identifying whether or not a patient is at risk of developing the more severe symptoms or complications associated with coronavirus.

In embodiments of the invention relating to prevention or treatment, the subject may or may not have been diagnosed to be infected with coronavirus, such as SARS-CoV-2.

The invention relates to analysing samples from subjects. The sample may be tissues, cells and biological fluids isolated from a subject, as well as tissues, cells and fluids present within a subject. The sample may be blood and a fraction or component of blood including blood serum, blood plasma, or lymph. Typically, the sample is from a throat swab, nasal swab, or saliva.

The antibody-antigen complex detection assays may be performed in situ, in which case the sample is a tissue section (fixed and/or frozen) of the tissue obtained from biopsies or resections from a subject.

In the embodiments of the invention where the antibodies pharmaceutical compositions and combinations are administered, they may be administered subcutaneously, intravenously, intradermally, orally, intranasally, intramuscularly or intracranially. Typically, the antibodies pharmaceutical compositions and combinations are administered intravenously or subcutaneously.

The dose of an antibody may vary depending on the age and size of a subject, as well as on the disease, conditions and route of administration. Antibodies may be administered at a dose of about 0.1 mg/kg body weight to a dose of about 100 mg/kg body weight, such as at a dose of about 5 mg/kg to about 10 mg/kg. Antibodies may also be administered at a dose of about 50 mg/kg, 10 mg/kg or about 5 mg/kg body weight.

A combination of the invention may for example be administered at a dose of about 5 mg/kg to about 10 mg/kg for each antibody, or at a dose of about 10 mg/kg or about 5 mg/kg for each antibody. Alternatively, a combination may be administered at a dose of about 5 mg/kg total (e.g. a dose of 1.67 mg/kg of each antibody in a three antibody combination).

The antibody or combination of antibodies of the invention may be administered in a multiple dosage regimen. For example, the initial dose may be followed by administration of a second or plurality of subsequent doses. The second and subsequent doses may be separated by an appropriate time.

As discussed above, the antibodies of the invention are typically used in a single pharmaceutical composition/combination (co-formulated). However, the invention also generally includes the combined use of antibodies of the invention in separate preparations/compositions. The invention also includes combined use of the antibodies with additional therapeutic agents, as described above.

Combined administration of the two or more agents and/or antibodies may be achieved in a number of different ways. In one embodiment, all the components may be administered together in a single composition. In another embodiment, each component may be administered separately as part of a combined therapy.

For example, the antibody of the invention may be administered before, after or concurrently with another antibody, or binding fragment thereof, of the invention. The particularly useful combinations are described above for example.

For example, the antibody of the invention may be administered before, after or concurrently with an anti-viral agent or an anti-inflammatory agent.

In embodiments where the invention relates to detecting the presence of coronavirus, e.g. SARS-CoV-2, or a protein or a fragment thereof, in a sample, the antibody contains a detectable label. Methods of attaching a label to an antibody are known in the art, e.g. by direct labelling of the antibody by coupling (i.e., physically linking) a detectable substance to the antibody.

Alternatively, the antibody may be indirect labelled, e.g. by reactivity with another reagent that is directly labelled. Examples of indirect labelling include detection of a primary antibody using a fluorescently-labelled secondary antibody and end-labelling of a DNA probe with biotin such that it can be detected with fluorescently-labelled streptavidin.

The detection may further comprise: (i) an agent known to be useful for detecting the presence of coronavirus, e.g. SARS-CoV-2, or a protein or a fragment thereof, e.g. an antibody against other epitopes of the spike protein, or other proteins of the coronavirus, such as an anti-nucleocapsid antibody; and/or (ii) an agent known to not be capable of detecting the presence of coronavirus, e.g. SARS-CoV-2, or a fragment thereof, i.e. providing a negative control.

In certain embodiments, the antibody is modified to have increased stability.

Suitable modifications are explained above.

The invention also encompasses kits for detecting the presence of coronavirus, e.g. SARS-CoV-2, in a sample. For example, the kit may comprise: a labelled antibody or a combination of labelled antibodies of the invention; means for determining the amount of coronavirus, e.g. SARS-CoV-2, in a sample; and means for comparing the amount of coronavirus, e.g. SARS-CoV-2, in the sample with a standard. The labelled antibody or the combination of labelled antibodies can be packaged in a suitable container. The kit can further comprise instructions for using the kit to detect coronavirus, e.g. SARS-CoV-2, in a sample. The kit may further comprise other agents known to be useful for detecting the presence of coronavirus, as discussed above.

For example, the antibodies or combinations of antibodies of the invention are used in a lateral flow test. Typically, the lateral flow test kit is a hand-held device with an absorbent pad, which based on a series of capillary beds, such as pieces of porous paper, microstructured polymer, or sintered polymer. The test runs the liquid sample along the surface of the pad with reactive molecules that show a visual positive or negative result. The test may further comprise using other agents known to be useful for detecting the presence of coronavirus, e.g. SARS-CoV-2, or a fragment thereof, as discussed above, such as anti-an anti-nucleocapsid antibody.

It is to be understood that different applications of the disclosed antibodies combinations, or pharmaceutical compositions of the invention may be tailored to the specific needs in the art. It is also to be understood that the terminology used herein is for the purpose of describing particular embodiments of the invention only, and is not intended to be limiting. In addition as used in this specification and the appended claims, the singular forms "a", "an", and "the" include plural references unless the content clearly dictates otherwise. Thus, for example, reference to "an antibody" includes two or more "antibodies".

Furthermore, when referring to "≥x" herein, this means equal to or greater than x.

When referred to "≤x" herein, this means less than or equal to x.

For the purpose of this invention, in order to determine the percent identity of two sequences (such as two polynucleotide or two polypeptide sequences), the sequences are aligned for optimal comparison purposes (e.g. gaps can be introduced in a first sequence for optimal alignment with a second sequence). The nucleotide or amino acid residues at each position are then compared. When a position in the first sequence is occupied by the same nucleotide or amino acid as the corresponding position in the second sequence, then the nucleotides or amino acids are identical at that position. The percent identity between the two sequences is a function of the number of identical positions shared by the sequences (i.e., % identity=number of identical positions/total number of positions in the reference sequence×100). Typically the sequence comparison is carried out over the length of the reference sequence. For example, if the user wished to determine whether a given ("test") sequence is 95% identical to SEQ ID NO: 3, SEQ ID NO: 3 would be the reference sequence. To assess whether a sequence is at least 95% identical to SEQ ID NO: 3 (an example of a reference sequence), the skilled person would carry out an alignment over the length of SEQ ID NO: 3, and identify how many positions in the test sequence were identical to those of SEQ ID NO: 3. If at least 95% of the positions are identical, the test sequence is at least 95% identical to SEQ ID NO: 3. If the sequence is shorter than SEQ ID NO: 3, the gaps or missing positions should be considered to be non-identical positions. The skilled person is aware of different computer programs that are available to determine the homology or identity between two sequences. For instance, a comparison of sequences and determination of percent identity between two sequences can be accomplished using a mathematical algorithm. In an embodiment, the percent identity between two amino acid or nucleic acid sequences is determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

The CDRs of the heavy chain (CDRH) and light chain variable domain (CDRL) are located at residues 27-38 (CDR1), residues 56-65 (CDR2) and residues 105-117 (CDR3) of each chain according to the IMGT numbering system (http://www.imgt.org; Lefranc M P, 1997, *J, Immunol.* Today, 18, 509). This numbering system is used in the present specification except where otherwise indicated.

All publications, patents and patent applications cited herein, whether supra or infra, are hereby incorporated by reference in their entirety.

The following examples illustrate the invention.

EXAMPLES

Example 1. Generation of Antibodies Specific Against Early Pandemic SARS-CoV-2 and Beta SARS-CoV-2 Strains The antibodies in Table 1 relate to a set of mAbs generated against early pandemic strain of SARS-CoV-2. The antibodies in Table 2 relate to a set of mAbs generated against the Beta strain of SARS-CoV-2.

Further details of these antibodies may be found in international application no. PCT/GB2022/050306 & PCT/GB2022/050307. Further information on the generation and properties of these antibodies may be found in the following articles: Dejnirattisai, Wanwisa, et al. "The antigenic anatomy of SARS-CoV-2 receptor binding domain." *Cell* 184.8 (2021): 2183-2200. Supasa, Piyada, et al. "Reduced neutralization of SARS-CoV-2 B. 1.1. 7 variant by convalescent and vaccine sera." *Cell* 184.8 (2021): 2201-2211.

Liu, Chang, et al. "The antibody response to SARS-CoV-2 Beta underscores the antigenic distance to other variants." *Cell host & microbe* (2021).

Zhou, Daming, et al. "Evidence of escape of SARS-CoV-2 variant B. 1.351 from natural and vaccine-induced sera." *Cell* 184.9 (2021): 2348-2361.

Dejnirattisai, Wanwisa, et al. "Antibody evasion by the P. 1 strain of SARS-CoV-2." *Cell* 184.11 (2021): 2939-2954.

Liu, Chang, et al. "Reduced neutralization of SARS-CoV-2 B. 1.617 by vaccine and convalescent serum." *Cell* 184.16 (2021): 4220-4236.

Dejnirattisai, Wanwisa, et al. "SARS-CoV-2 Omicron-B. 1.1. 529 leads to widespread escape from neutralizing antibody responses." *Cell* (2022).

Example 2. Generation of Antibodies Specific Against the Omicron Strains of SARS-CoV-2

Omicron BA.2 Lineage

Omicron BA.2 was first reported from South Africa on the 17th November 2021, at a similar time that Omicron BA.1 was reported. BA.2 has been increasing relative to BA.1 in a number of countries such as Denmark, India and the UK and now accounts for the majority of Omicron infections in Denmark and evidence is accruing that BA.2 is more transmissible than BA.1, but there is no evidence for increased disease severity.

BA.2 is related to BA.1 sharing 21 amino acid substitutions spread throughout in S, however there are a number of differences BA.1, has an additional 6 amino acid deletions, 3 insertions and 9 substitutions compared to BA.2 and BA.2 has an additional 3 deletions and 7 substitutions compared to BA.1. In the RBD, BA.1 contains unique mutations S371L, G446S and G496S and in some isolates R346K (BA.1.1), while BA.2 carries S371F, T376A, D405N and R408S. All of these residues have the potential to differentially affect antibody binding and could modulate neutralization, particularly BA.1 G446S, G496S, BA.2 D405N, R408S which lie at the edge of the ACE2 binding footprint and for BA.1.1 the R346K change lies close to the N343 glycan and could modulate binding of potent antibodies to this region. BA.3 contains no unique mutations relative to BA.1 and BA.2 and appears to be a fusion of the two, being BA.1 like at the N terminus and switching to become BA.2 like at the C-terminus from the mutation G496S.

Omicron Lineages BA.4 and BA.5

In early April 2022 two new Omicron lineages were reported from Gauteng in South Africa and designated BA.4 and BA.5. The BA.4 and BA.5 S sequences are identical, and closely related to BA.2. Sequence diversity in Omicron S is shown in FIG. 9. Compared to BA.2, BA.4 has residues 69 and 70 deleted, and contains 2 additional substitutions in the RBD: L452R and F486V. Finally BA.4 lacks the Q493R change seen in BA.1 and BA.2, reverting to Q493 as in the Victoria/Wuhan strain.

The 2 additional mutations in the RBD are of most concern in terms of antibody escape: L452R is a chemically radical change and is one of the pair of changes in Delta RBD (the other, T478K, is already found in the Omicron lineage). Mutation F486L was found in sequences of SARS-CoV-2 isolated from Mink early in the pandemic and is also a site of escape mutations to several mAbs (Gobeil et al., 2021, "Effect of natural mutations of SARS-CoV-2 on spike structure, conformation, and antigenicity". Science 373, 6555). The change F486V in BA.4/5 is also a reduction in the bulk of the hydrophobic side-chain as in F486L, but more significant. Both residues 452 and 486 lie close to the edge of the ACE2 interaction surface (FIG. 9B) and both, together with the reversion to ancestral sequence Q493 which lies within the ACE2 footprint, have the potential to modulate ACE2 affinity as well as modulate the neutralizing capacity of vaccine or naturally acquired serum. The L452R and F486V mutations are likely to cause more antibody escape, while the reversion at 493 may reduce the escape from responses to earlier viruses.

The Omicron lineage BA.2.75

Figure 16:
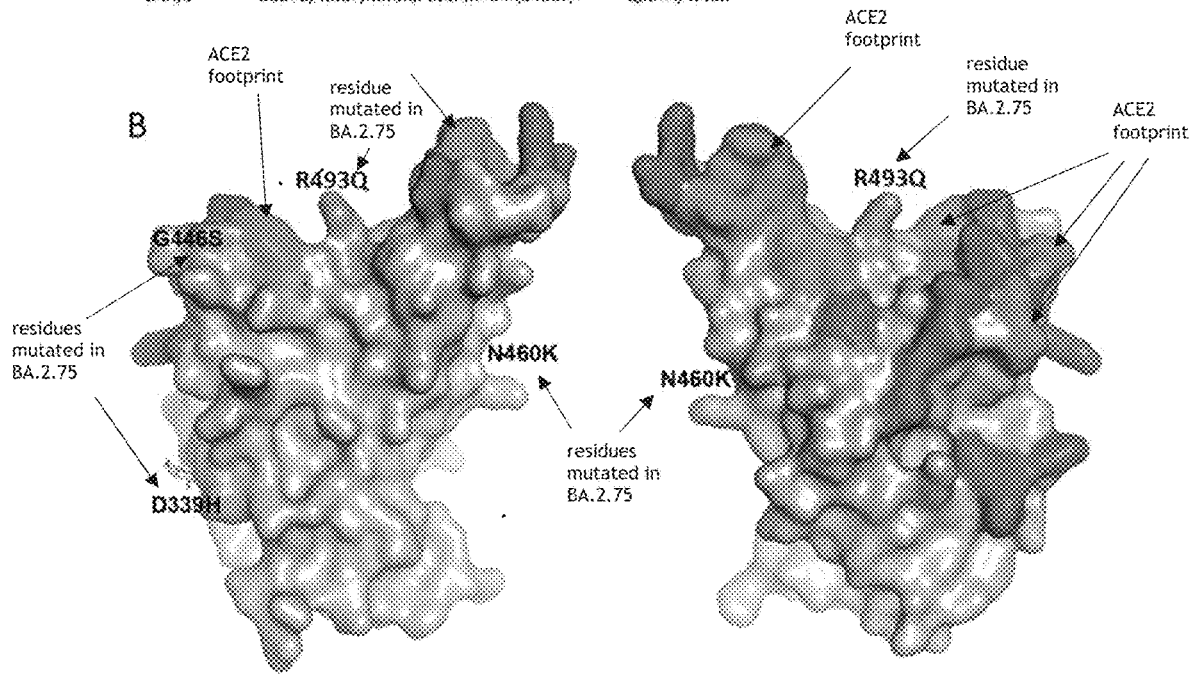
FIG. 16. Sequence changes in BA.2.75 compared to other Omicron sub-lineages. (A) Sequence alignments of BA.2.75 together with Omicron sublineages Omicron BA.1, BA.1.1, BA.2, BA.3 and BA.4/5. Boundaries of the NTD and RBD are marked. (B) Surface representation of mutated residues in BA.2.75 RBD in comparison to BA.2 RBD. Position of BA.2 RBD mutations (grey surface with the ACE2 footprint in dark green) are shown and residues mutated in BA.2.75 are shown in orange and labelled.

In early May 2022, a new Omicron BA.2 sublineage designated BA.2.75 was reported in India. It has spread to multiple countries, including the UK, US, Australia, Germany and Canada. BA.2.75 contains multiple mutational changes in the S protein compared to BA.2, including four substitutions in the NTD (W152R, F157L, 1210V and G257S) and four in the RBD: D339H, G446S, N460K and R493Q (FIG. 16). The RBD mutations impinge on major epitopes for neutralising antibodies and are likely to modulate ACE2 binding. D339H represents a further evolution of the G339D mutation found in all previous Omicron variants that has been found to impair the binding of certain 'right-flank' antibodies belonging to the IGHV1-69 family (e.g. Beta-49 and -50); it also falls in the binding footprint of certain Class 3 antibodies such as S309/sotrovimab (Dejnirattisai et al., 2022; "SARS-CoV-2 Omicron-B.1.1.529 leads to widespread escape from neutralizing antibody responses." Cell 185, 467-484 e415). G446S was found in BA.1, BA.1.1 and BA.3 but not in BA.2 and other BA.2 subvariants, and is also able to impair binding of certain Class 3 antibodies binding the right shoulder such as REGN10987/imdevimab (Dejnirattisai et al., 2022). The R493Q reversion was also found in BA.4/5, and may make the virus more sensitive to neutralization by a number of class 1 and 2 antibodies binding the neck/left shoulder. This reversion may also increase the affinity for ACE2 (see below).

N460K is a novel mutation not seen in previous VoC or Omicron sublineages, but it was found after in vitro (yeast display) evolution in RBD-62 which has an ultra-high ACE2 affinity (KD=16-18 pM) (Dejnirattisai et al., 2022; Zahradnik et al., 2021 "SARS-CoV-2 variant prediction and antiviral drug design are enabled by RBD in vitro evolution". Nat Microbiol 6, 1188-1198). Indeed N460K led to substantial increase in affinity for ACE2, second only to the effect of N501Y (Zahradnik et al., 2021). Furthermore, in silico analysis predicts that N460K may affect the binding of certain antibodies belonging to the IGHV3-53 family (e.g. Omi-3) which have been shown to be able to potently neutralise all VoC (Nutalai et al., 2022).

Using neutralization assays, Delta infection in isolation was show to provide no protection (no neutralization) against BA.2.75. The mutations in BA.2.75 lead to a reduction in neutralization titres of vaccine serum compared to BA.2. Individual BA.2.75 mutations can cause greater reduction in neutralization titres compared to the full BA.2.75 S sequence, but these are balanced by the R393Q reversion mutation, which may have been selected to increase affinity to ACE2 and increase the transmissibility of BA.2.75. It seems inevitable that further evolution of the Omicron lineage will occur and there are likely many possible trade-offs between antibody escape and ACE2 affinity, that can and will be made, leading to successive waves of infection.

Emerging BA.2, BA.4 and BA.5 Sublineages

A number of lineages are growing rapidly from within both the BA.2 and BA.5 branches. Most striking, is the large degree of convergent evolution, particularly at antigenic RBD positions such as 346, 444, 452, 460, 486, 490, 493 and 494. These lineages include examples from the BA.4/5 branches (which contain L452R, F486V and the reversion R493Q), such as BA.4.6 and BF.7 (R346T), BA.4.7 (R346S), BQ.1 (K444T, N460K) and BQ.1.1 (R346T, K444T, N460K); from the BA.2.75 branch (which contains G339H, G446S, N460K and the reversion R493Q), BA.2.75.2 (R346T and F486S and BA.2.75 mutations), BN.1 (aka BA.2.75.5.1 with R346T, K356T, F490S and BA.2.75 mutations), BM.1.1.1 (aka BA.2.75.3.1.1.1 with R346T, F486S, F490S and BA.2.75 mutations). There are also examples of several other second generation BA.2 variant lines such as BJ.1 (aka BA.2.10.1.1; G339H, R346T, L368I, V445P, G446S, V483A and F490V), BA.2.10.4 (G446S, F486P, S494P and the R493Q reversion), BS.1 (aka BA.2.3.2.1; R346T, L452R, N460K, G476S and the Q493R reversion), BA.2.3.20 (K444R, N450D, L452M, N460K, E484R and the Q493R reversion), and finally a BJ.1× BM.1.1.1 (aka BA.2.75.3.1.1.1) recombinant, XBB (which relative to BA.2 contains R346T, L368I, V445P, G446S, N460K, F486S, F490S and the Q493R reversion).

Outside the RBD the degree of convergent evolution is lesser but still present. Many of the second-generation BA.2 variant lineages contain deletions or mutations in the NTD, often similar to those seen in the VoCs, for example Δ~144 in BJ.1, BS.1, and BA.2.10.4 (previously seen in Alpha and BA.1) and NSP12 G671S in BJ.1, XBB and BA.2.10.4 (previously seen in Delta).

Potently Neutralizing Antibodies Isolated Following Omicron Infection

Five volunteers who had recovered from sequence confirmed Omicron infection were recruited and sampled them 10-14 days following symptom onset; all volunteers had received 2 doses of the Pfizer BioNtech vaccine before being infected with Omicron. First, neutralization assays were performed against Omicron BA.1 and Victoria (an early pandemic SARS-CoV-2 isolate containing only a single amino acid substitution in S NTD (S247R) compared to the sequence of the Wuhan stain used in all current vaccines). In all cases the focus reduction neutralization 50% titre (FRNT50) to Omicron was above 100, but at this early time point the titres were considerably below the titres to Victoria (FIG. 1A).

B cells from the five donors were stained with full length BA.1 trimer and single cells sorted by FACS (FIG. 1B). Following a degenerate RT-PCR reaction, heavy and light chain sequences were assembled into expression vectors using the Gibson reaction and the products transfected into 293T cells. Culture supernatants were screened for reactivity to full length BA.1 or wild type S (WT Wuhan) together with BA.1 RBD and NTD. In total 1,122 single cells were sorted and 545 mAb recovered.

All mAbs cross-reacted between WT and BA.1 S by ELISA, suggesting that they could have been generated from memory B cells induced by vaccination. In contrast to a previous panel of monoclonal antibodies were produced from naïve cases infected early during the pandemic (Dejnirattisai, Wanwisa, et al. "The antigenic anatomy of SARS-CoV-2 receptor binding domain." Cell 184.8 (2021): 2183-

2200), a higher proportion the omicron-specific mAbs were found to react to the RBD (56%) when compared to the early pandemic mAbs (21%, p<0.0001) (FIG. 1C). In addition 129 of the 545 isolated mAbs bound the BA.1 NTD.

Isolation of Potent Omicron mAb

Neutralization assays were performed on all ELISA positive mAb and those showing the highest activity were chosen for further study. The most potent 28 mAbs were selected for full characterization all of which showed BA.1 FRNT50 titres<100 ng/ml. 27/28 bound the RBD (one, Omi-41 bound the NTD) and none cross-reacted with SARS-CoV-1 S protein by ELISA.

Examination of gene usage (FIG. 1D, Table 17) revealed that 9/28 mAbs belong to the VH3-53 and the related VH3-66 gene families. VH3-53 and VH3-66 have been isolated repeatedly in SARS-CoV-2 infection, they form a public antibody response and bind to a site on the neck of the RBD and function to block ACE2 binding. It was previously observed that many VH3-53 and VH3-66 mAbs lose activity on VoCs containing the N501Y mutation, although some VH3-53 antibodies (mAb 222 and Beta-27) were fully resistant to the N501Y change found in Alpha, Beta and Gamma but suffered knock down of activity to Omicron BA.1 or BA.2.

Roughly one half of the gene families observed in the potent early pandemic antibodies (Table 1) are also represented in the Omicron set (FIG. 1C), perhaps the most notable difference is that VH1-69 does not feature in the early antibodies but is found in 6/28 of the potent Omicron set (2, 24, 30, 31, 34 and 38) and we also found it in 2 Beta antibodies, Beta 49 and 50, which bind to a site in proximity to the N343 glycan. Analysis of the Omicron mAb shows much longer CDR3 sequences suggesting a different mode of binding than Beta 49, 50. In the Beta set of mAb, expansion of a public response was found to be mediated through VH 4-39 (6/27 mAb), which bound an epitope around the 501Y mutation, most lost activity against BA.1 and it is noteworthy that none of the current set of Omicron mAb are encoded by VH4-39.

Compared to the early pandemic set of antibodies we found higher levels of somatic mutation in both heavy and light chains compared to the early pandemic set of mAb Omicron (mean of 9.00, 6.00 and early pandemic 4.55, 4.25 for VH and VL respectively). These results would be consistent with the evolution of increased Omicron affinity via somatic mutation of vaccine induced memory B cells.

Broad Neutralization of VoC by Omicron mAb

Figure 2A:
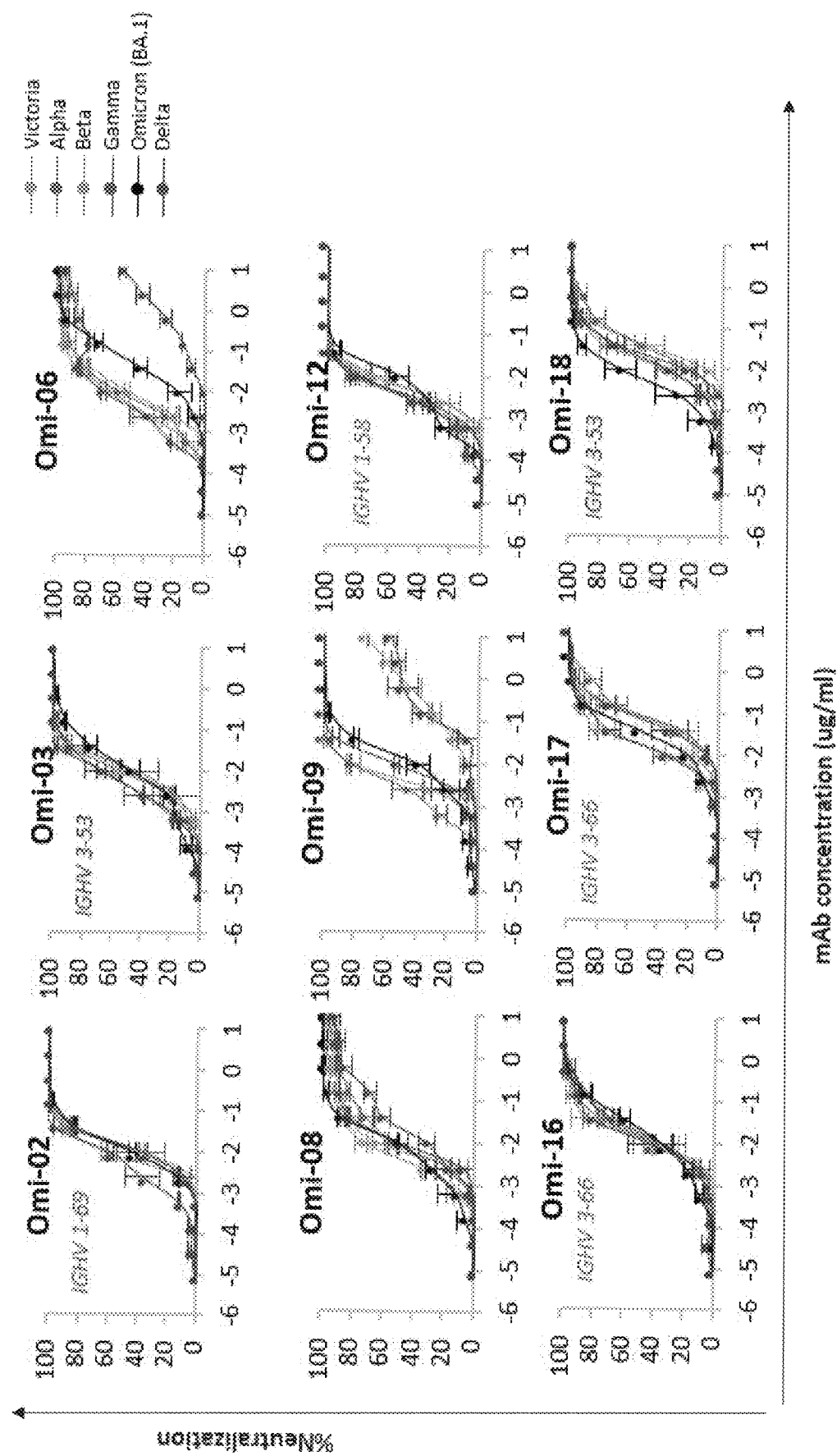
FIGS. 2A-2C. Neutralization curves using Omicron mAb. (2A) Victoria, Alpha, Beta, Gamma, Delta and Omicron BA.1 viruses. (2B) neutralization of Victoria, BA.1, BA.1.1, BA.2 and BA.3 pseudoviruses by Omicron mAb. (2C) neutralization of Victoria, BA.1, BA.1.1, BA.2 and BA.3 pseudoviruses by antibodies being developed for commercial use.
Figure 2A:
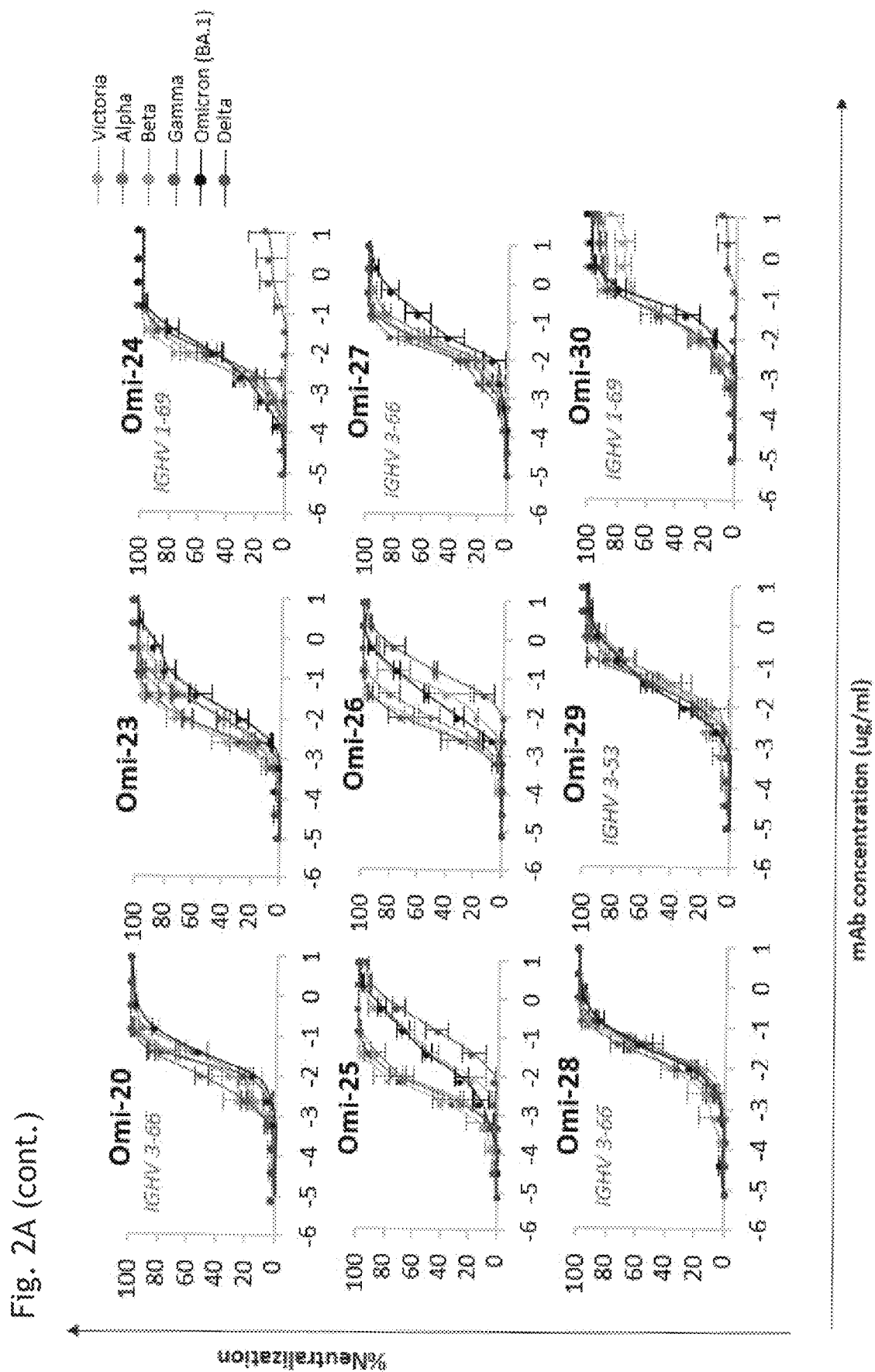
Figure 2A:
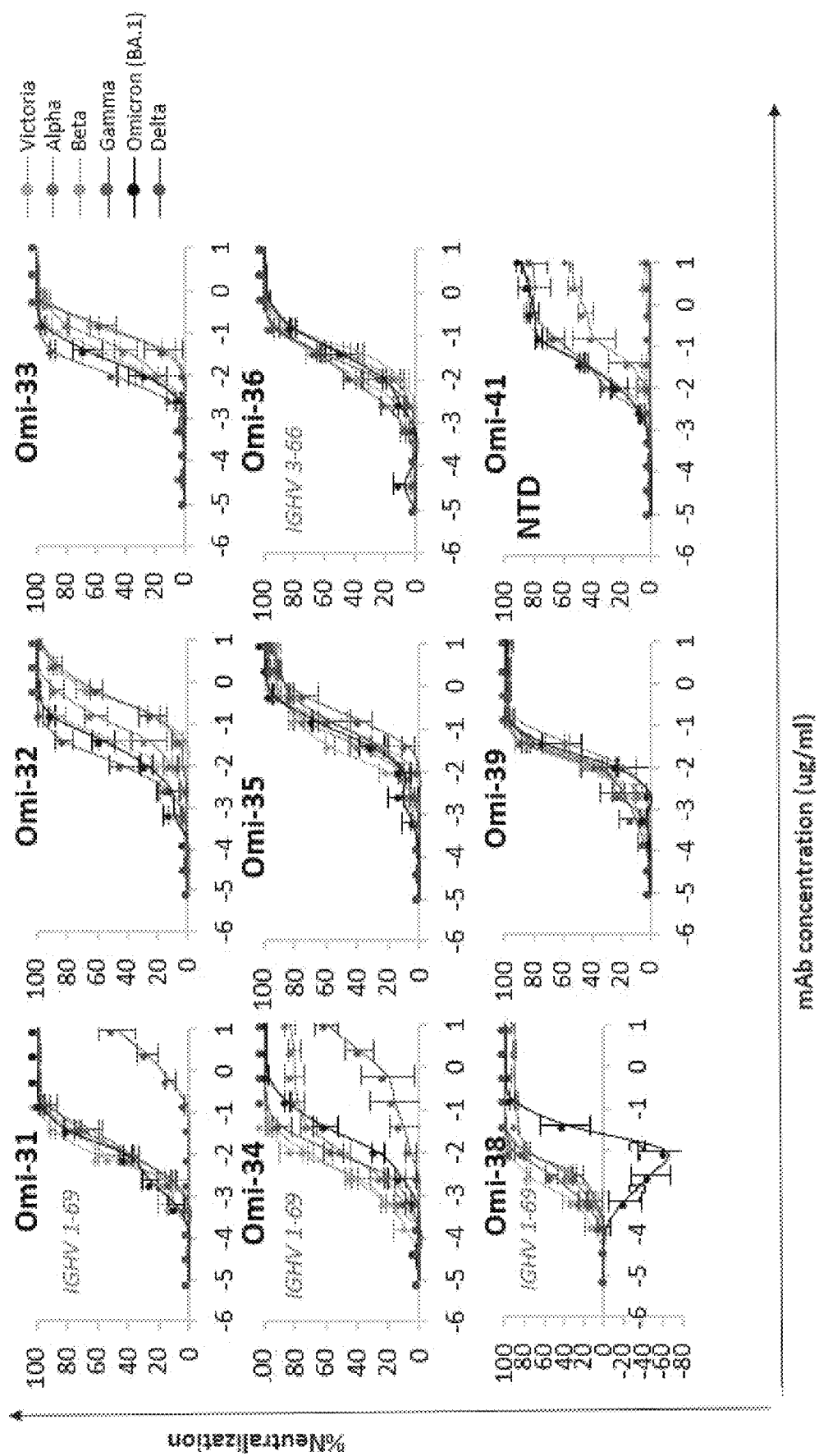
Figure 2A:
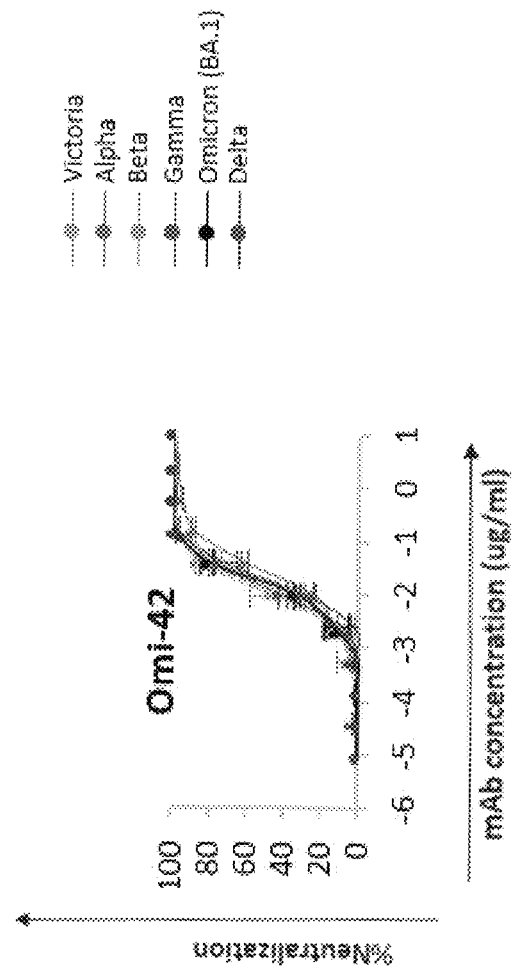
Figure 2B:
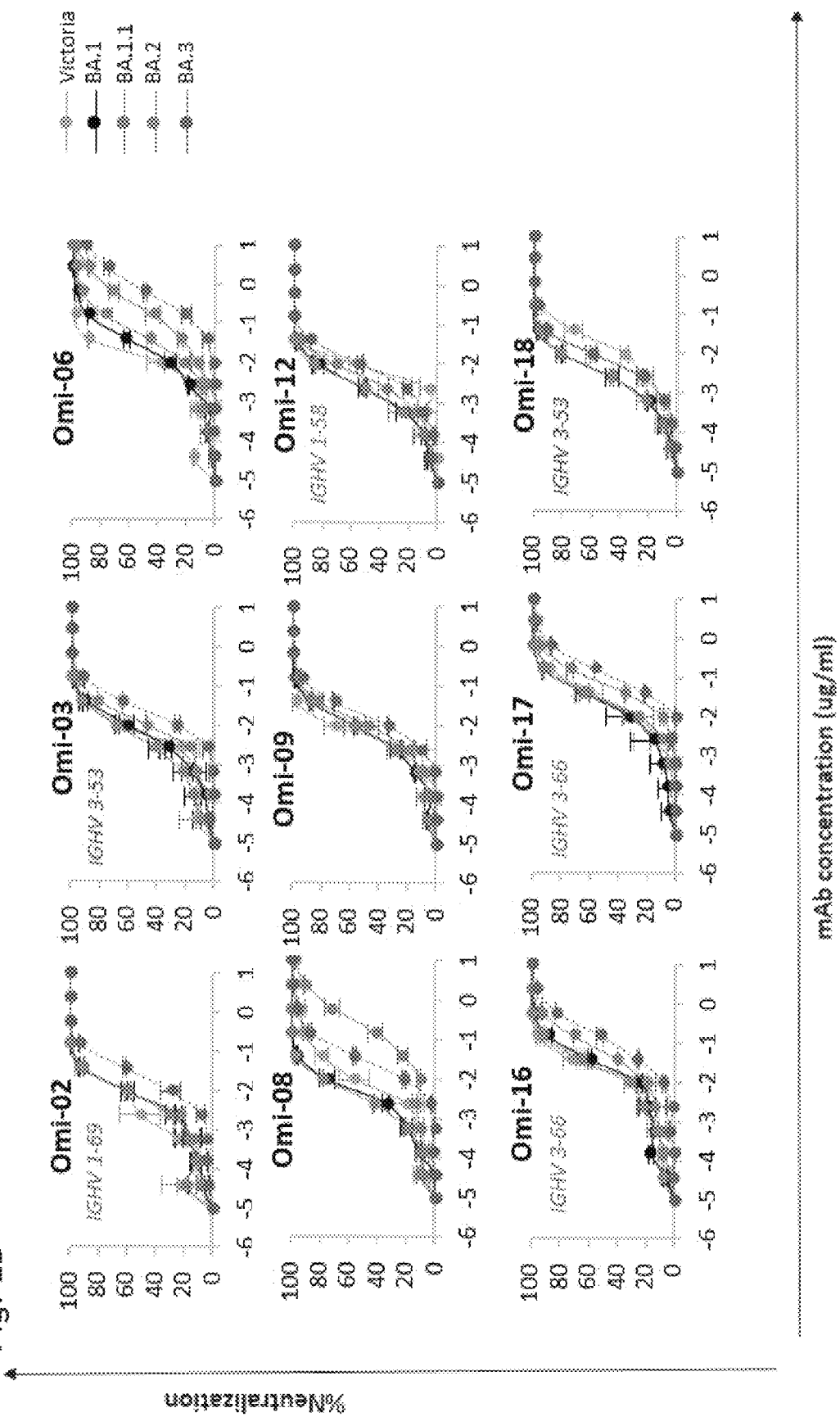
Figure 2B:
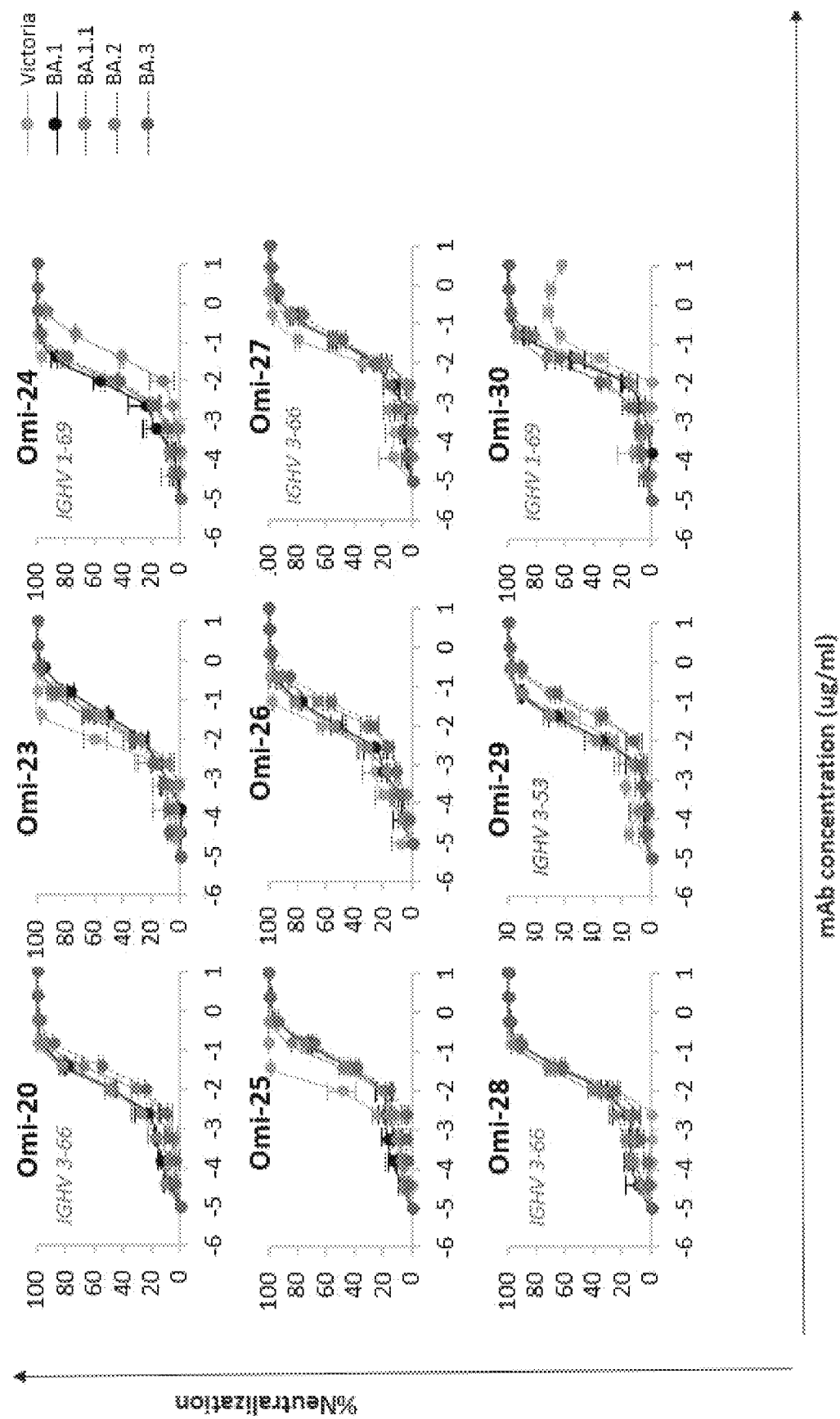
Figure 2B:
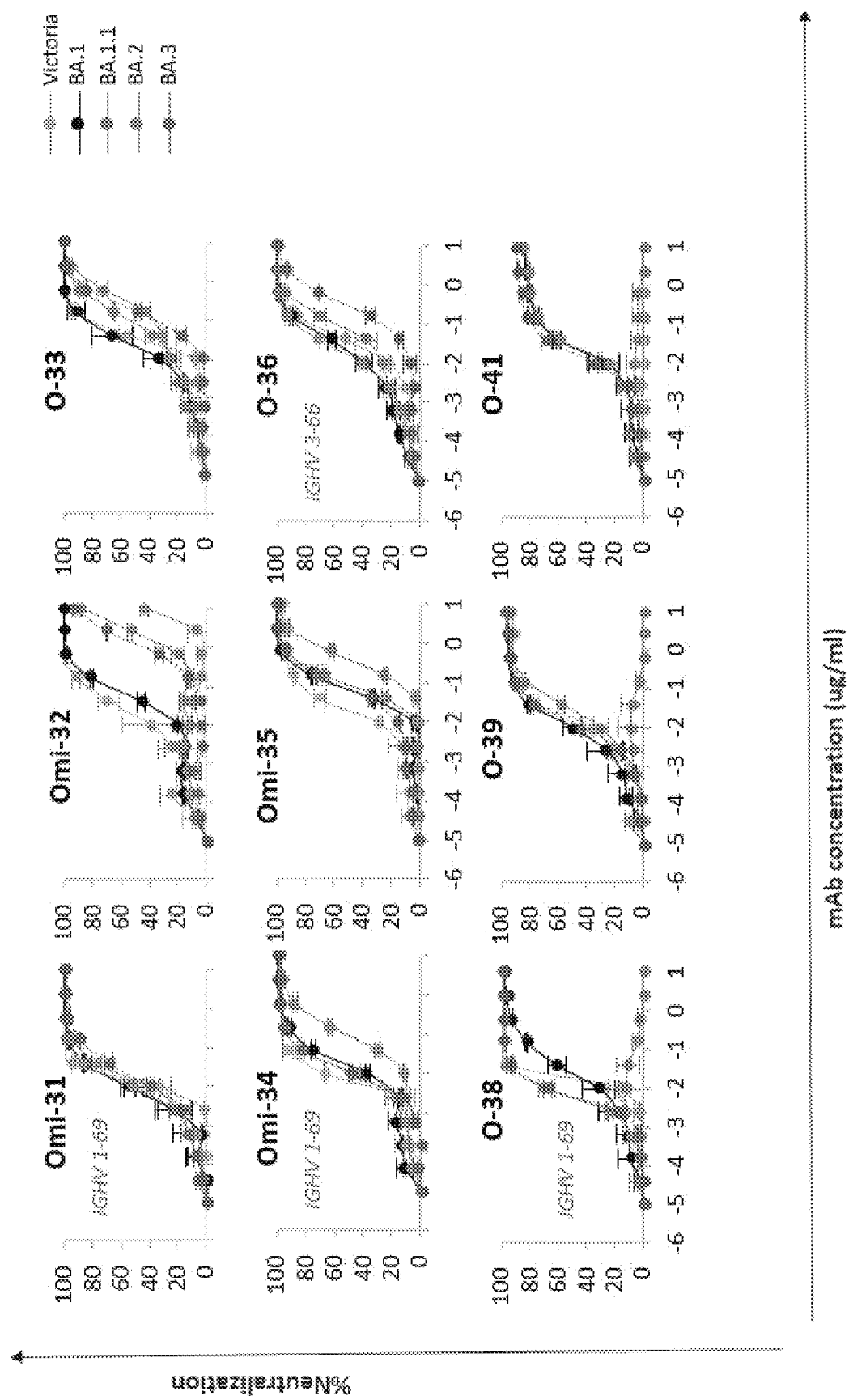
Figure 2B:
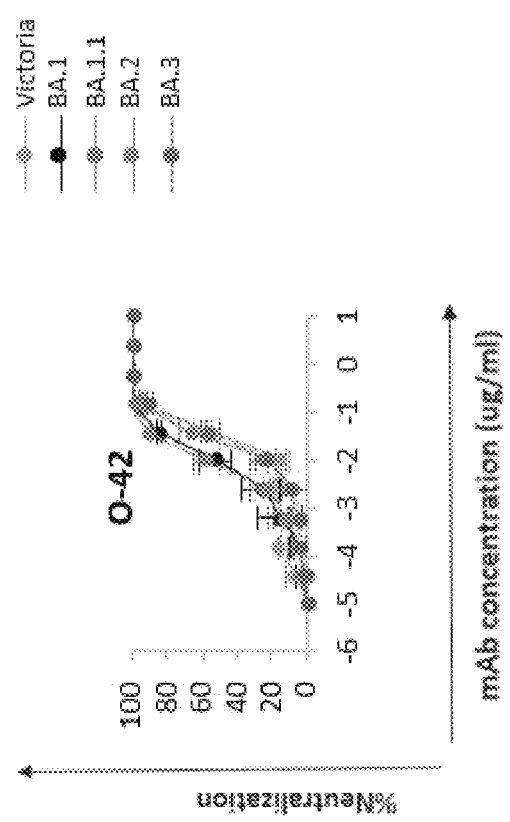
Figure 2C:
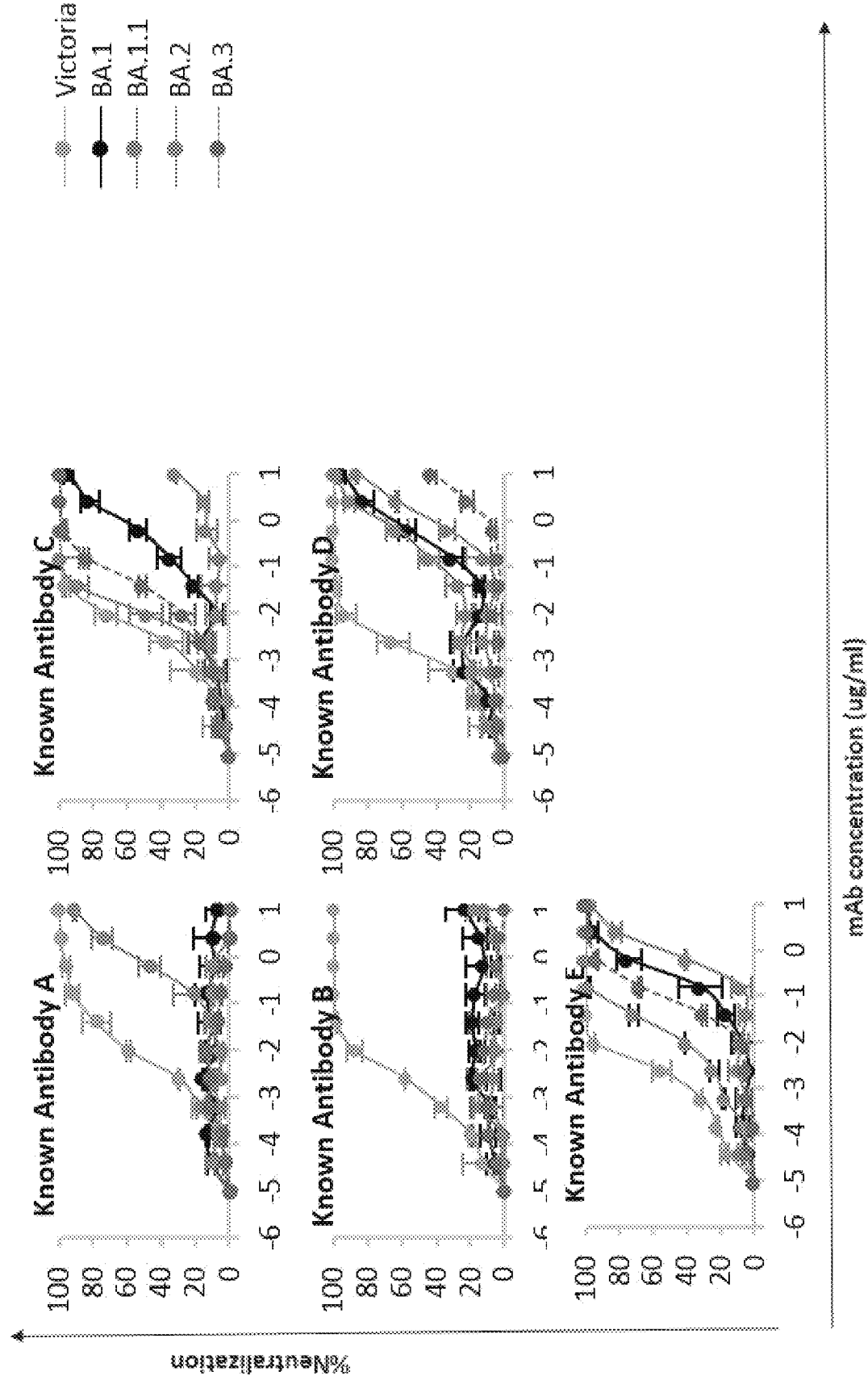

Neutralization assays were performed against Victoria and all variants of concern Alpha, Beta, Gamma, Delta and Omicron BA.1, for the panel of 28 potent mAbs (FIG. 2A-C, Tables 13 to 16 and 18). The likely origin of all of these antibodies from vaccine induced memory B cells is apparent in that in almost all cases, FRNT50 titres to Victoria are at the high end of all VoC tested for each mAb (FIG. 2A-C, Tables 13 to 16 and 18). Five of the mAbs neutralize BA.1 with FRNT50 titres<10 ng/ml, mAb Omi-3, 8, 12, 18 and 24 are the most potent with FRNT50 titres of 9, 8, 4, 6, 7 ng/ml and FRNT90 titres of 67, 42, 20, 18, 35 ng/ml respectively.

The data provided in Tables 13, 14 and 16 include some IC50 data obtained using pseudoviral constructs. The data in Table 18 consists of IC50 results obtained exclusively from authentic virus constructs.

17/28 antibodies are cross-reactive against all VoC with <10-fold difference in FRNT50 titres between all viruses. Omi-06, 24, 30, 31, 34 and 41 show reduced or absent activity against Delta, with 3/6 of these belonging to the VH1-69 family, and may have an epitope impinging on the L452R Delta mutation (Delta shares T478K with BA.1). Antibodies Omi-09 and 32 perform poorly on Beta and Gamma and may be sensitive to E484K found in Beta and Gamma, but may tolerate the E484A change in Omicron (Omicron shares N501Y and K417N with Beta whilst Gamma is N501Y, K417T). Finally, although 129 anti-NTD mAbs were isolated only one of these, Omi-41, showed FRNT50 titres<100 ng/ml, Omi-41 showed neutralizing activity against Victoria, Alpha, Beta and Gamma but no activity against Delta, presumably resulting from the unique spectrum of NTD changes found in Delta.

Neutralization of BA.1 Compared to BA.1.1, BA.2 and BA.3

Lentiviral based reporters were constructed pseudotyped with the S gene sequences for Victoria, BA.1, BA.1.1, BA.2 and BA.3. Neutralization assays against the Omicron mAb are shown in FIG. 2B, Tables 14 and 18, most antibodies show little difference in neutralization of BA.1, BA.1.1, BA.2 and BA.3. However, there were some notable exceptions; BA.2 neutralization was reduced 38, 3 and 158-fold compared to BA.1 for Omi-8, 29 and 32 respectively, while BA.1.1 neutralization was reduced 40.9, 10.8, 7.8 and 6.6-fold compared to BA.1 for Omi-6, 24, 34 and 35 respectively and knocked out for Omi-39 and 40. BA.3 neutralization by the Omi-mAb mirrored that found with BA.2 with the exception of Omi-06 and Omi-36 where BA.3 neutralization titres were considerably lower than either BA.1 or BA.2. For some reason the NTD binding mAb Omi-41 did not neutralize Victoria in the pseudoviral system but did neutralize live virus, this was also found with early pandemic mAb 159 which showed potent activity on live virus but no activity on pseudovirus.

Figure 4A:
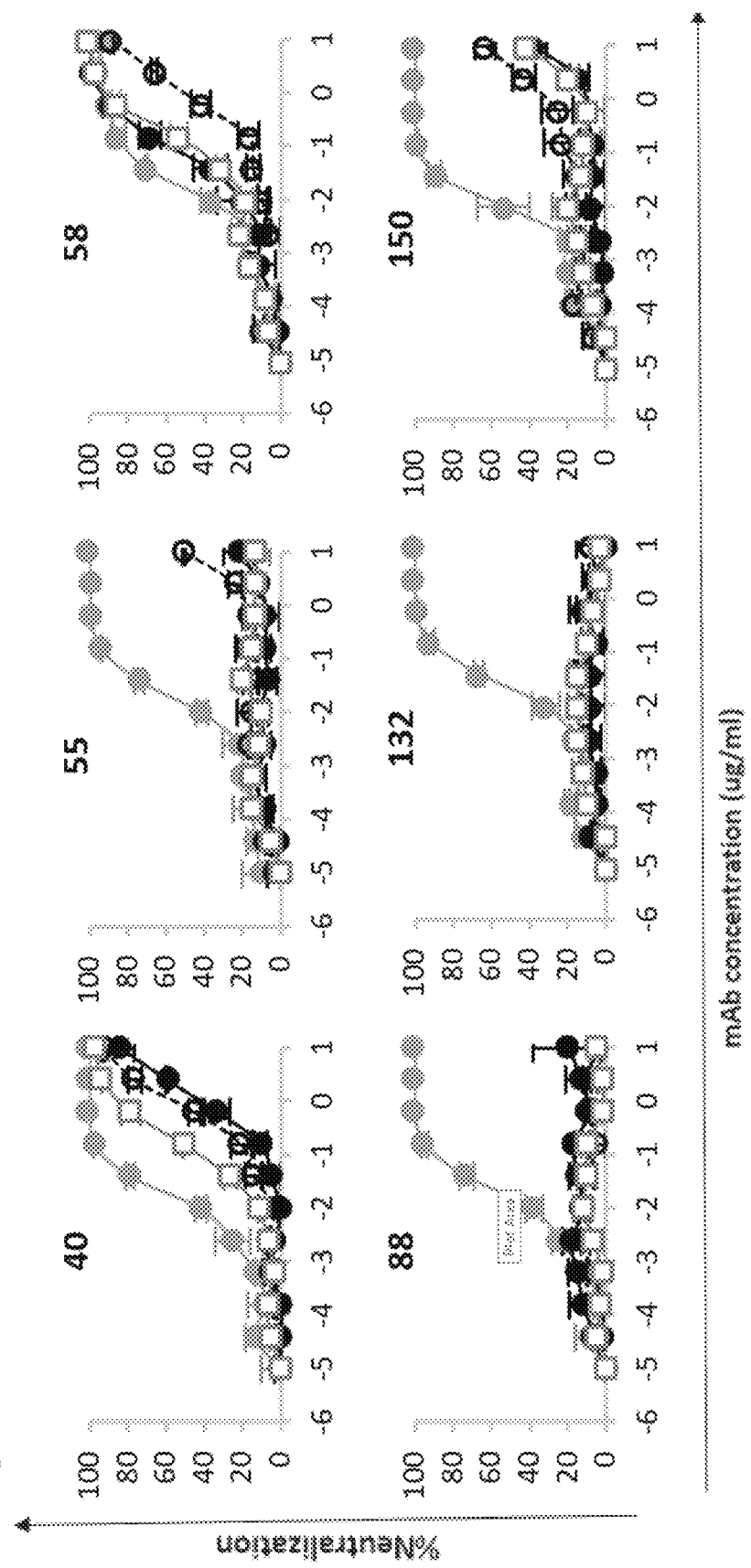
FIGS. 4A-4B. Pseudoviral neutralization curves. Pseudoviral neutralization curves for BA.1, BA.1.1, BA.2 and BA.3 on Early pandemic mAb (4B) Beta mAb.
Figure 4A:
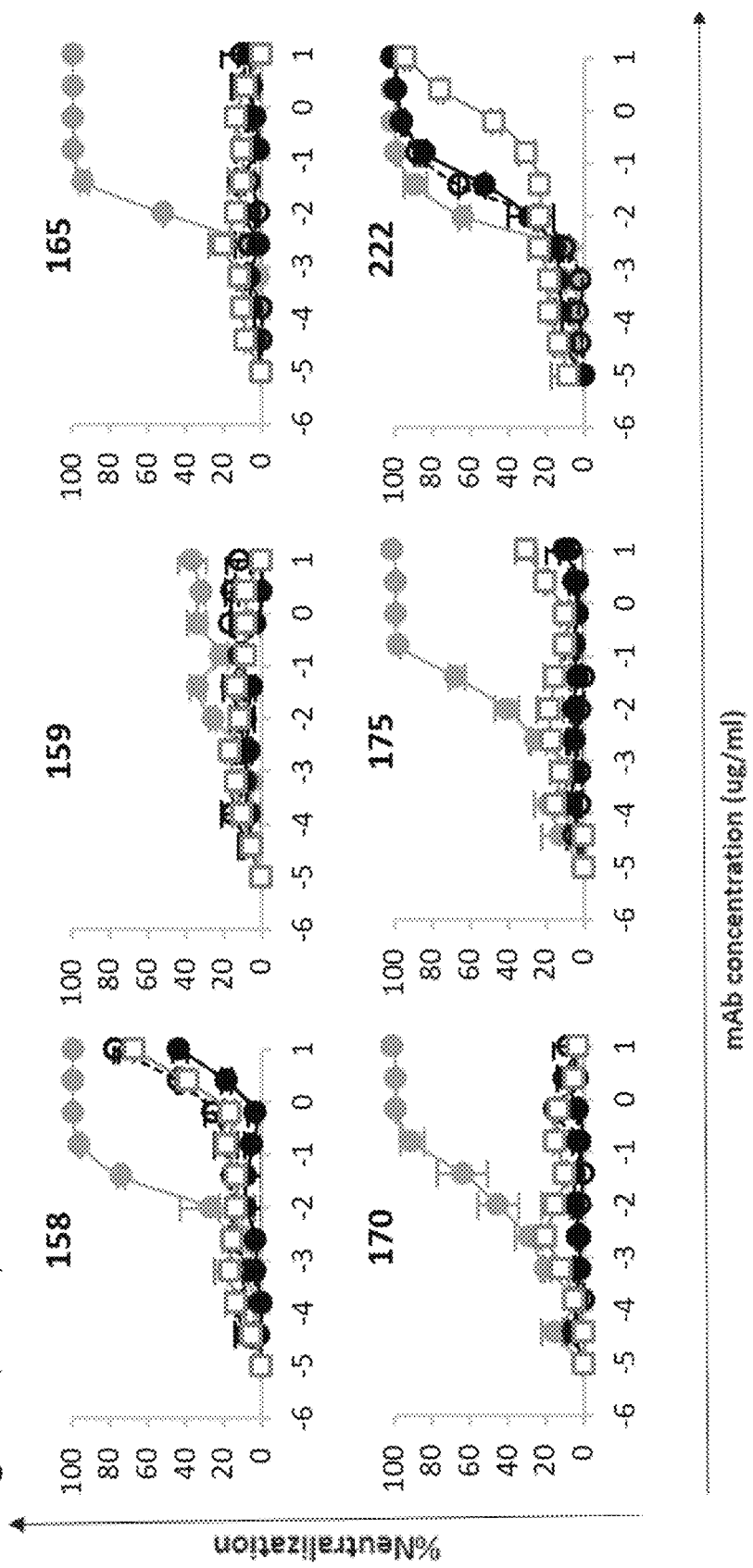
Figure 4A:
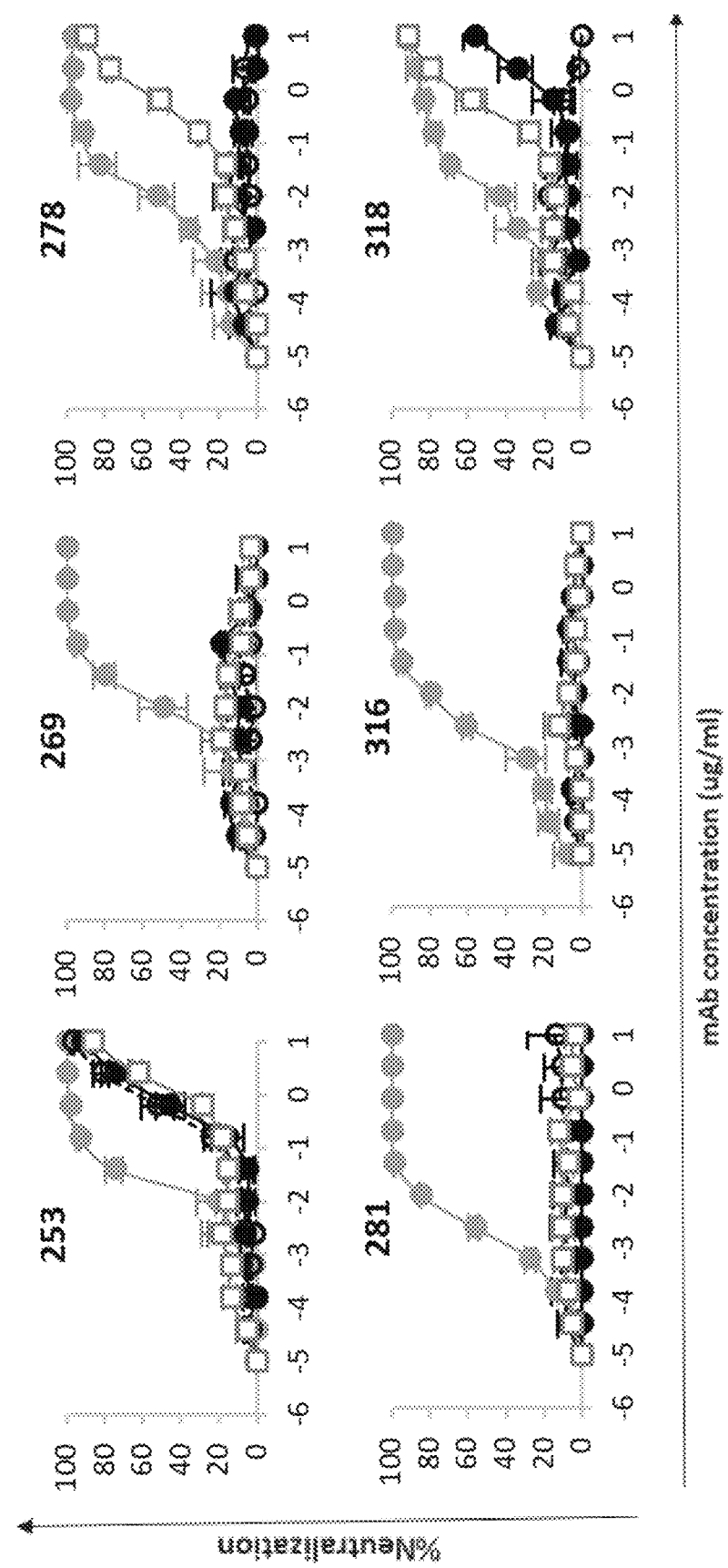
Figure 4A:
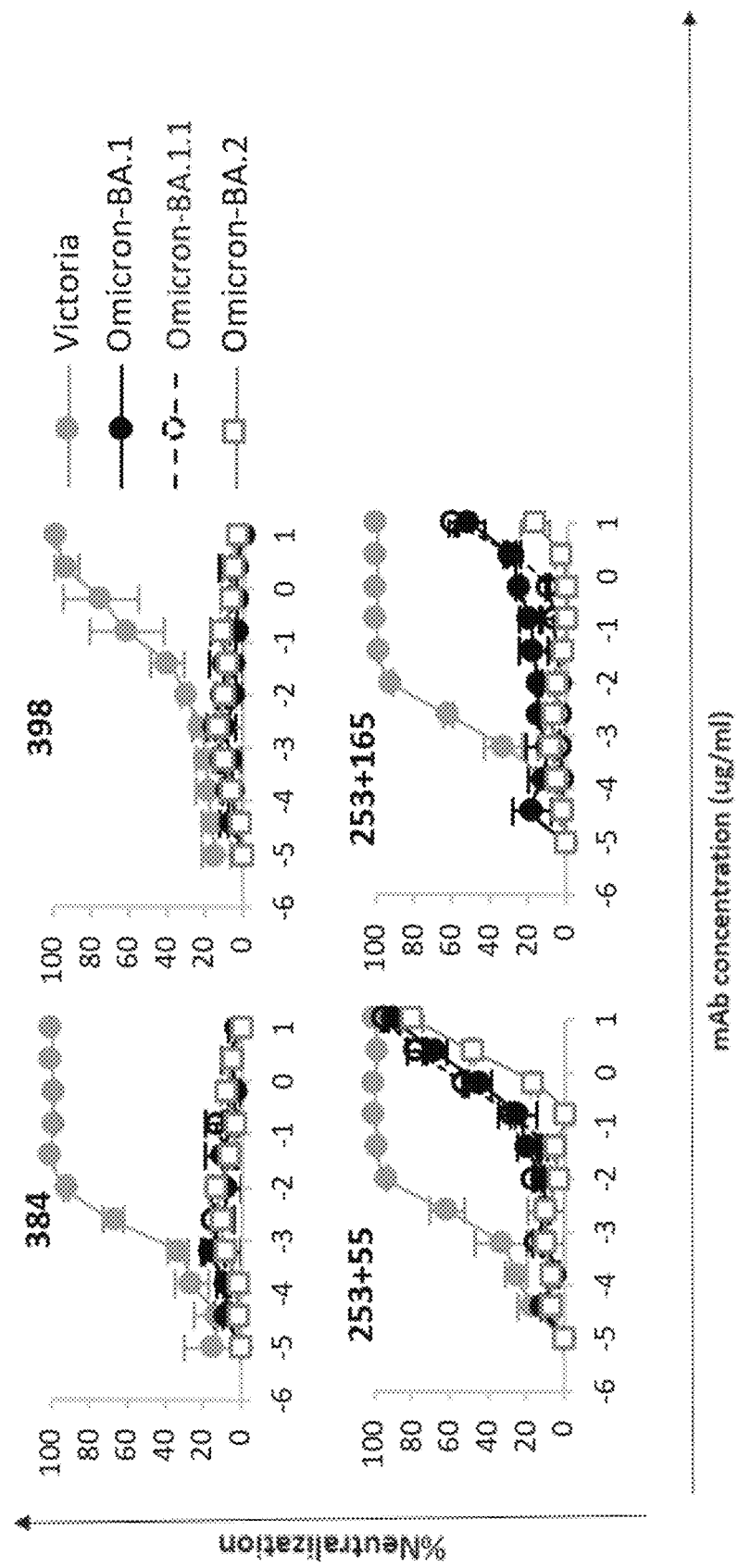
Figure 4B:
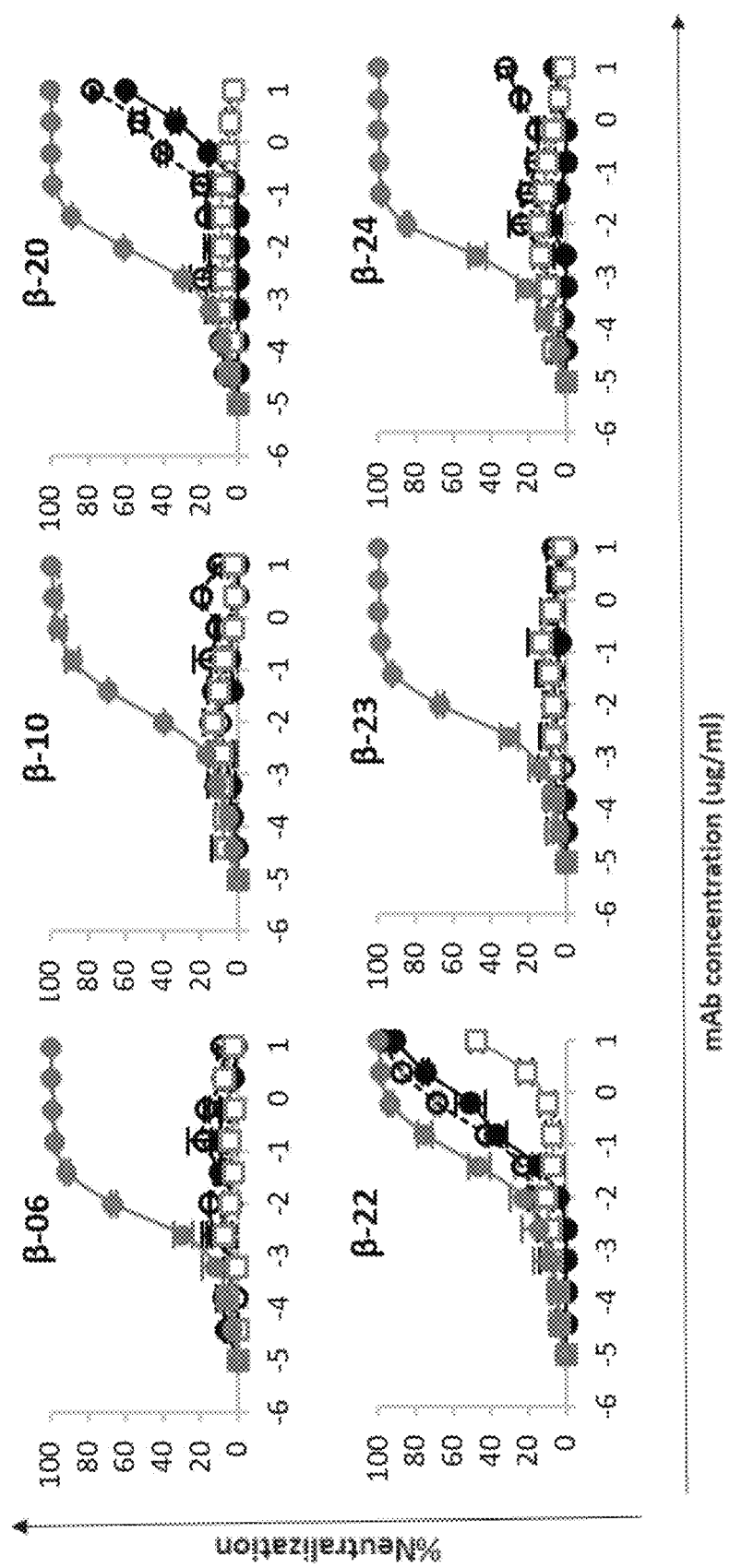
Figure 4B:
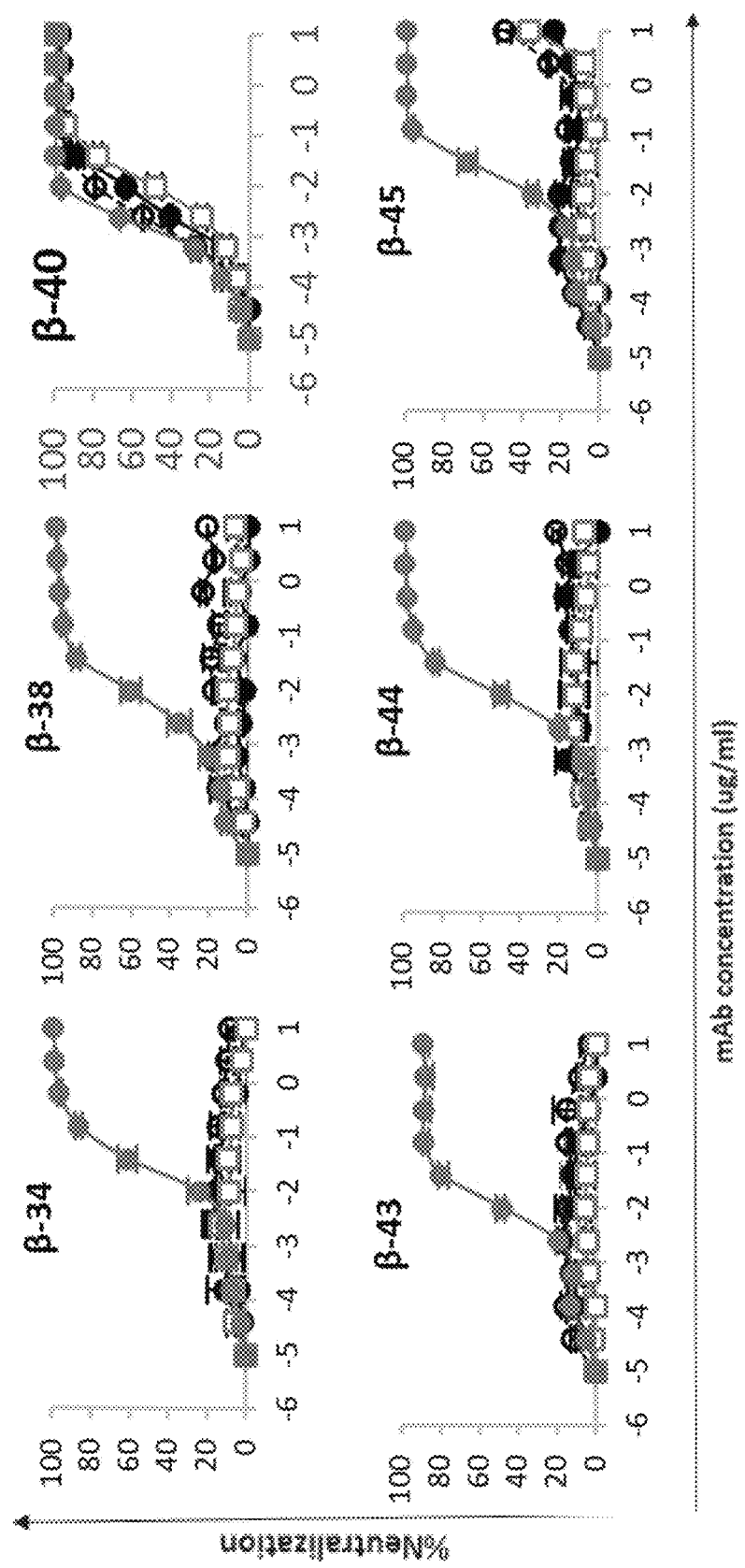
Figure 4B:
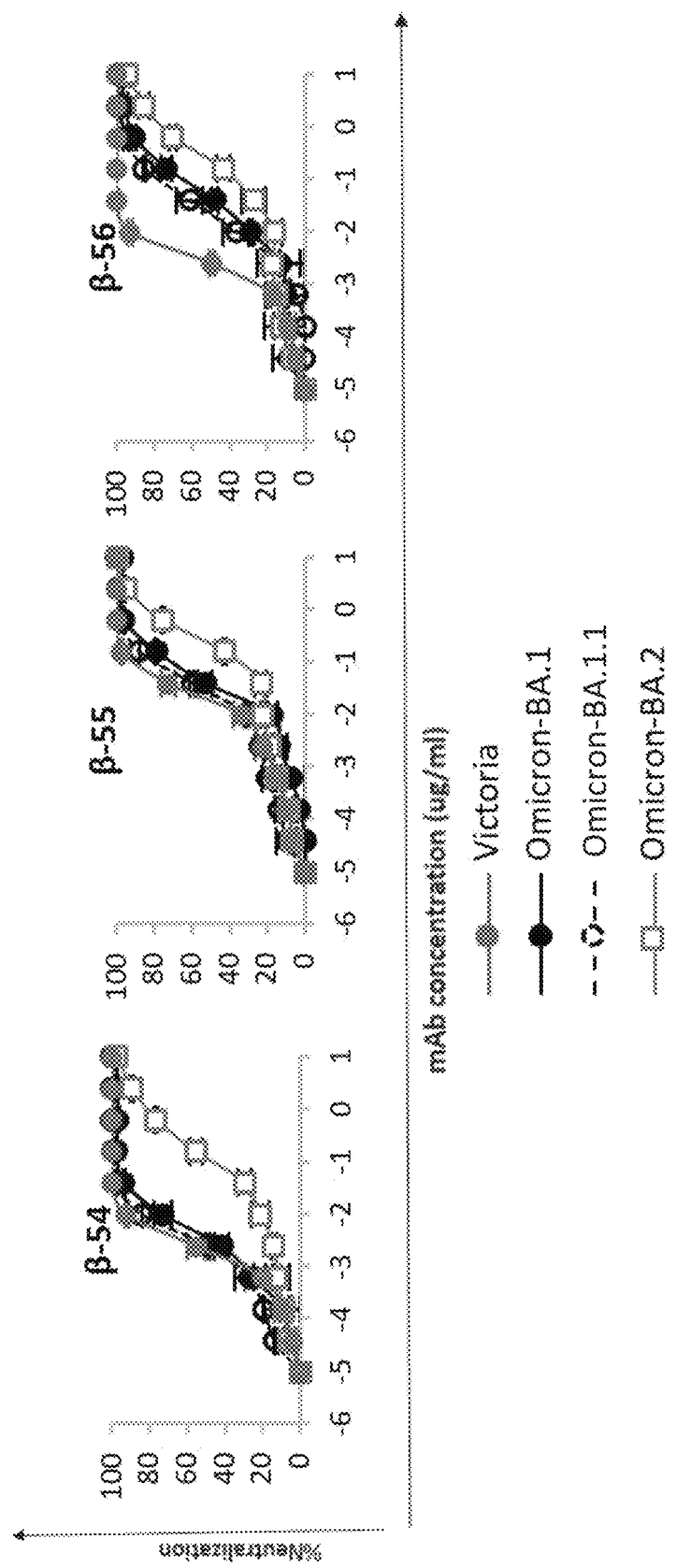

Pseudoviral neutralization curves for panels of mAb isolated from early pandemic cases together with mAb isolated from Beta cases is shown in FIGS. 4A, B, Table 15, in most cases, neutralization titres against BA.1, BA.1.1 and BA.2 are similar, but there are some differences, mAbs 40, 278 and 318 neutralize BA.2>BA.1, whereas 222, Beta 22, 29, 54, 55 and 56 neutralize BA.1 better than BA.2, whilst Beta-53 which binds close to the N343 glycan shows reduced neutralization of BA.1.1.

Neutralization by Antibodies Developed for Clinical Use.

Finally, neutralization of Victoria, BA.1, BA.1.1, BA.2 and BA.3 strains was tested using mAbs being developed for clinical use where a number of differences were found (FIG. 2C, Tables 16 and 18). Interestingly, activity of Known Antibody A (REGN 10987) was partially restored on BA.2 but still 308-fold reduced compared to Victoria, Activity of Known antibody C (AZD1061) was almost completely restored on BA.2, whilst Known antibody D (AZD8895) was 5.4-fold reduced on BA.2 vs BA.1 and the combination of both Known antibody D (AZD8895) and E, was only reduced 8-fold compared to Victoria. The activity of Known Antibody K (S309) was 6.8-fold reduced on BA.2 compared to BA.1, Finally the activity of Known Antibody G (ADG20) was completely lost on BA.2.

In summary, the neutralization of most Omicron monoclonal antibodies are not affected by the differences between BA.1, BA.1.1, BA.2 or BA.3 mutations. Some monoclonal antibodies do however show differences, in particular Known Antibody A (REGN 10987) and Known antibody C (AZD1061) which neutralize BA.2 more easily than BA.1 and Known Antibody K (S309) which shows reduced neutralization of BA.2 and this may encourage sub-lineage typing before use. The structural explanations for the differences between BA.1, BA.1.1, BA.2 and BA.3 neutralization will be discussed below.

Neutralization of BA.1, BA.1.1, BA.2 and BA3 by Immune Sera

Figure 3:
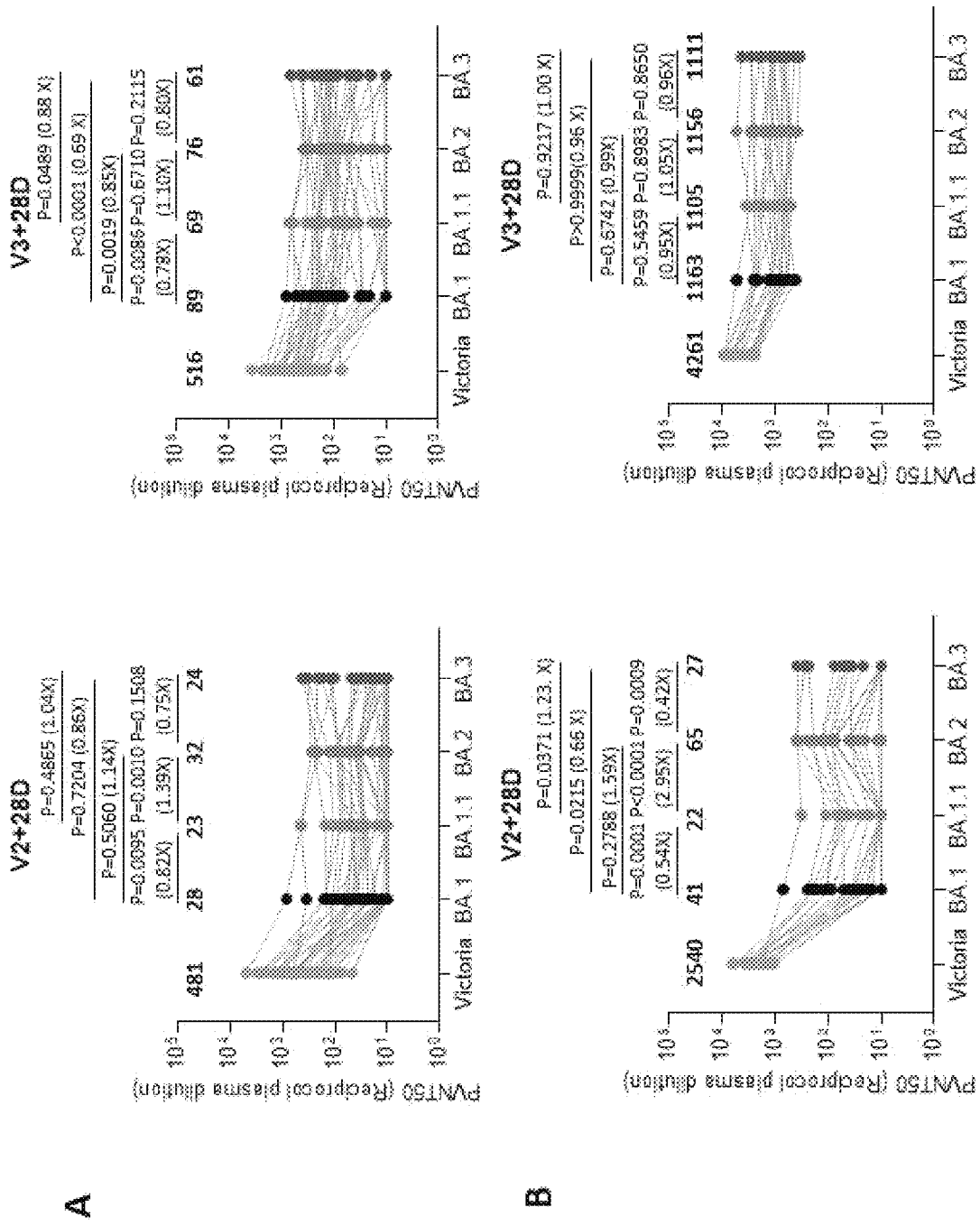
FIG. 3. Neutralization of Victoria, BA.1, BA.1.1, BA.2 and BA.3 pseudoviruses. Neutralization of Victoria, BA.1, BA.1.1, BA.2 and BA.3 pseudoviruses 28 days following the second and third doses of (A) AZD1222 (n=41), (B) BNT162b2 (n=20). (C) Live virus neutralization assays with Victoria, Alpha, Beta, Gamma, Delta and Omicron viruses using sera obtained <14 days and >21 days following symptom onset (D) Neutralization of Victoria, BA.1, BA.1.1, BA.2 and BA.3 pseudoviruses by early and late sera. Geometric mean titres are shown above each column. The Wilcoxon matched-pairs signed rank test (A and B) and Mann-Whitney test (C and D) were used for the analysis and two-tailed P values were calculated.
Figure 3:
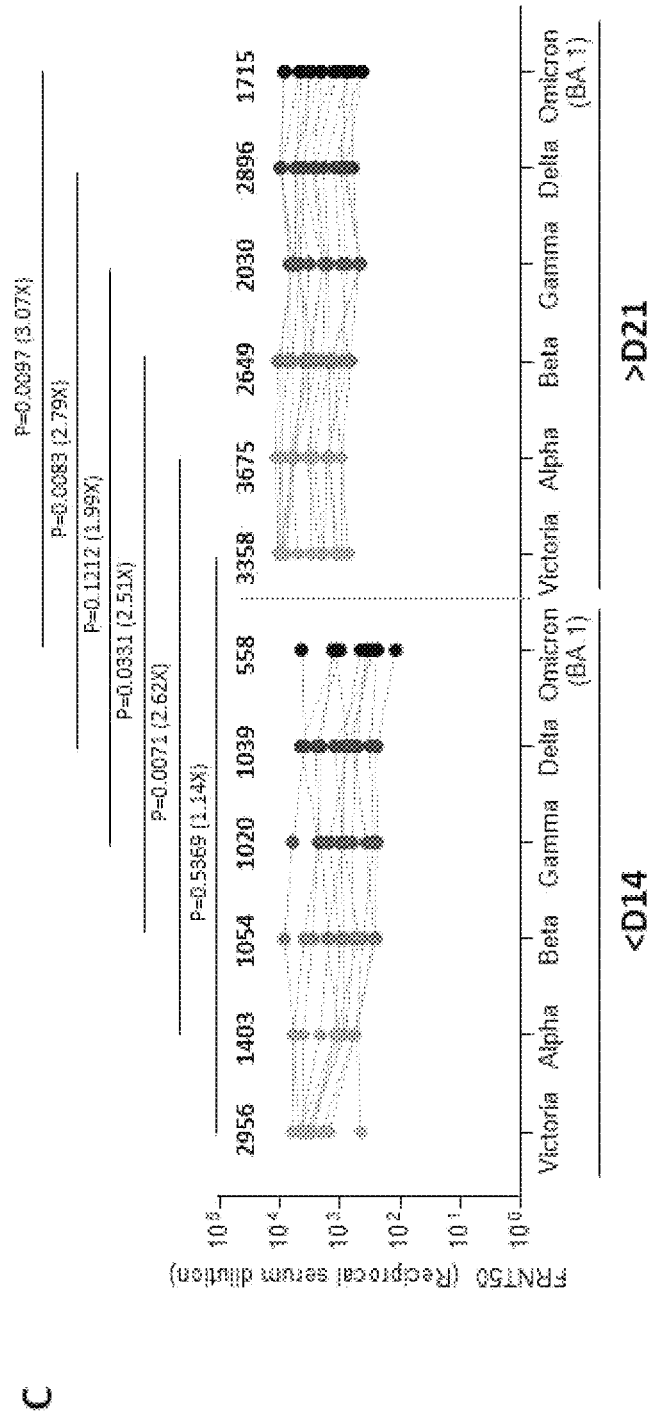
Figure 3:
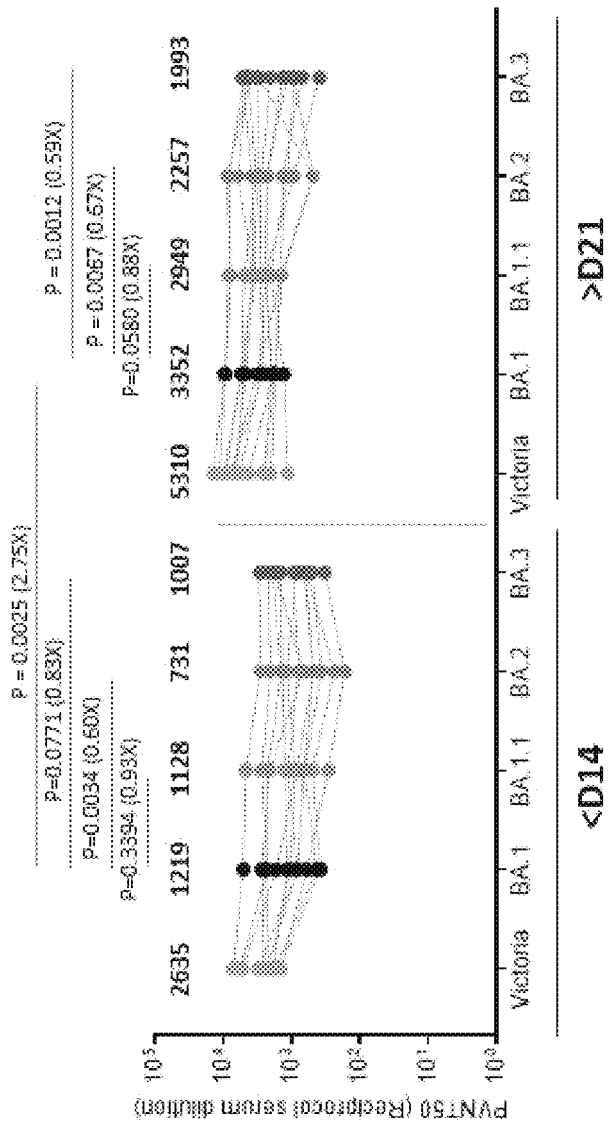

To determine whether the differences in transmissibility between BA.1 and BA.2 may be due to differential neutralization and also to determine whether there was a possibility that BA.2 could escape the BA.1 antibody response, neutralization assays were performed using sera from a variety of sources. First, neutralization assays were performed on Victoria, BA.1, BA.1.1, BA.2 and BA.3 using sera collected from vaccinees receiving the Oxford/AstraZeneca AZD1222 (n=41) or Pfizer/BioNtech BNT162b2 (n=20) vaccines (FIG. 3A, B).

Figure 5:
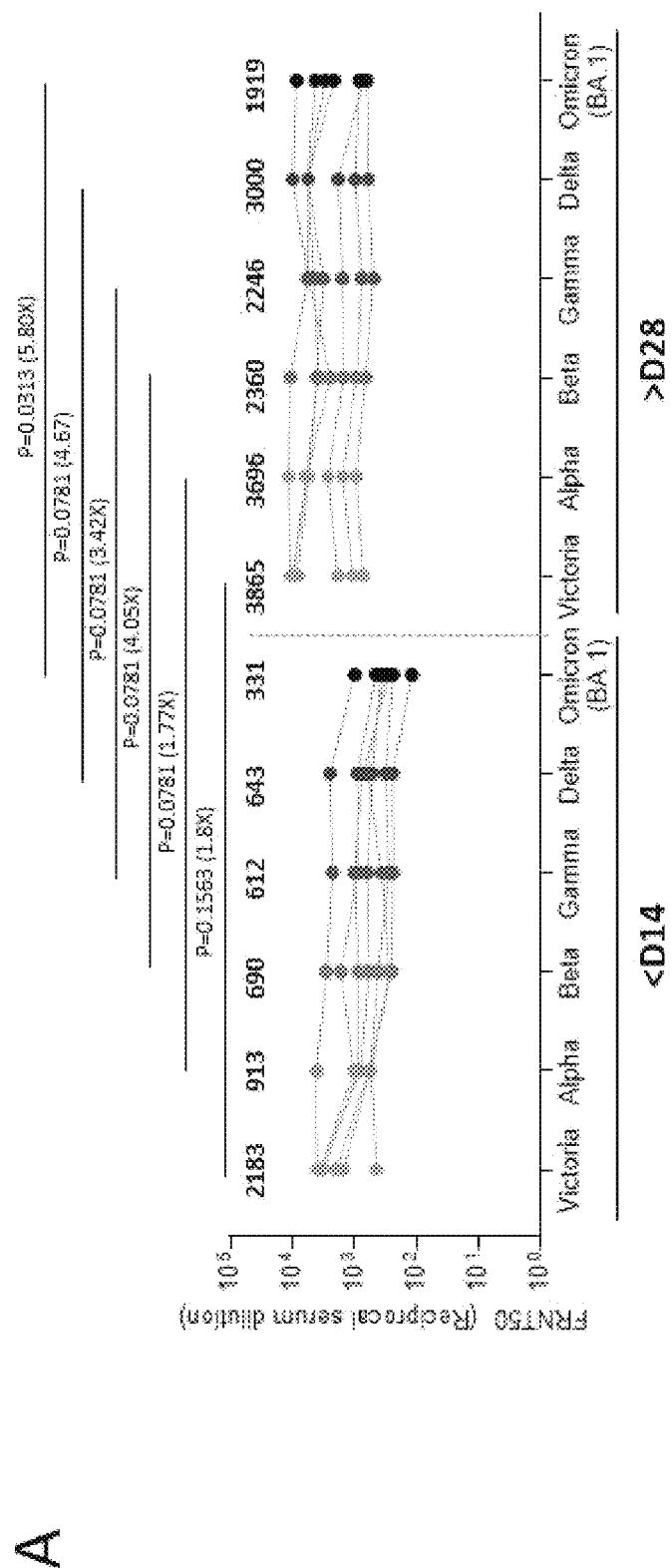
FIG. 5. Neutralization titres on the indicated viruses related to FIG. 3 (A) live viruses (B) pseudoviruses. Geometric mean titres are shown above each column. The Wilcoxon matched-pairs signed rank test was used for the analysis and two-tailed P values were calculated. (C) pseudovirus neutralization curves for selected VH1-58 mAb and control VH3-53 mAb 222 against Victoria and Iota (S477N).
Figure 5:
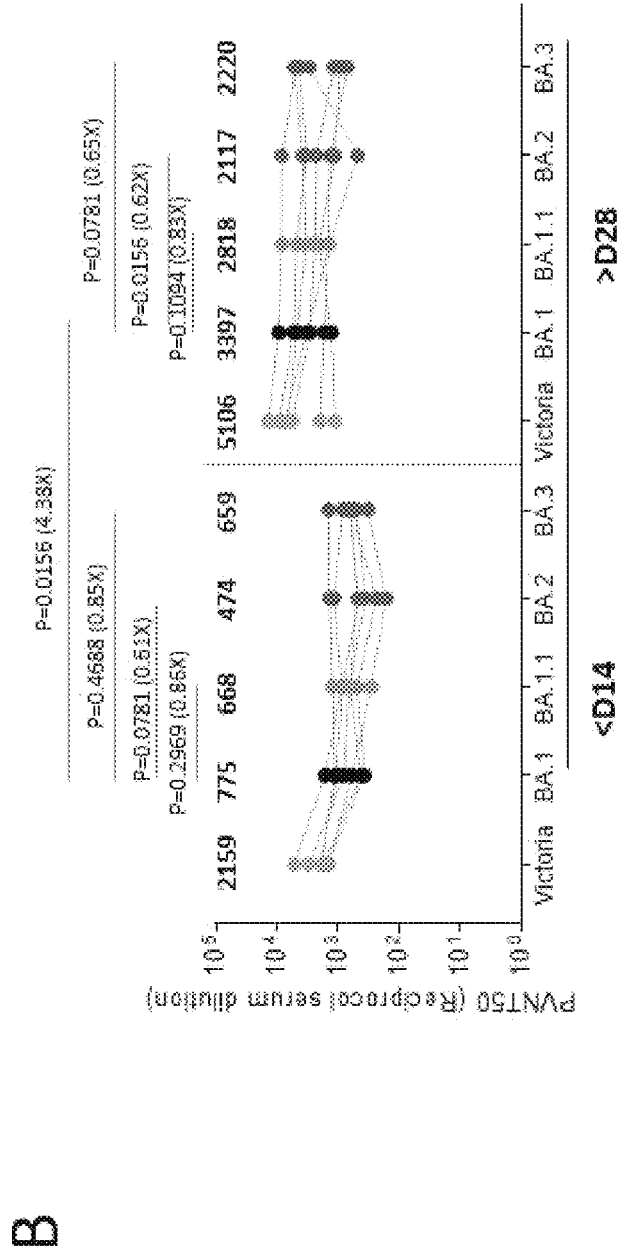
Figure 5:
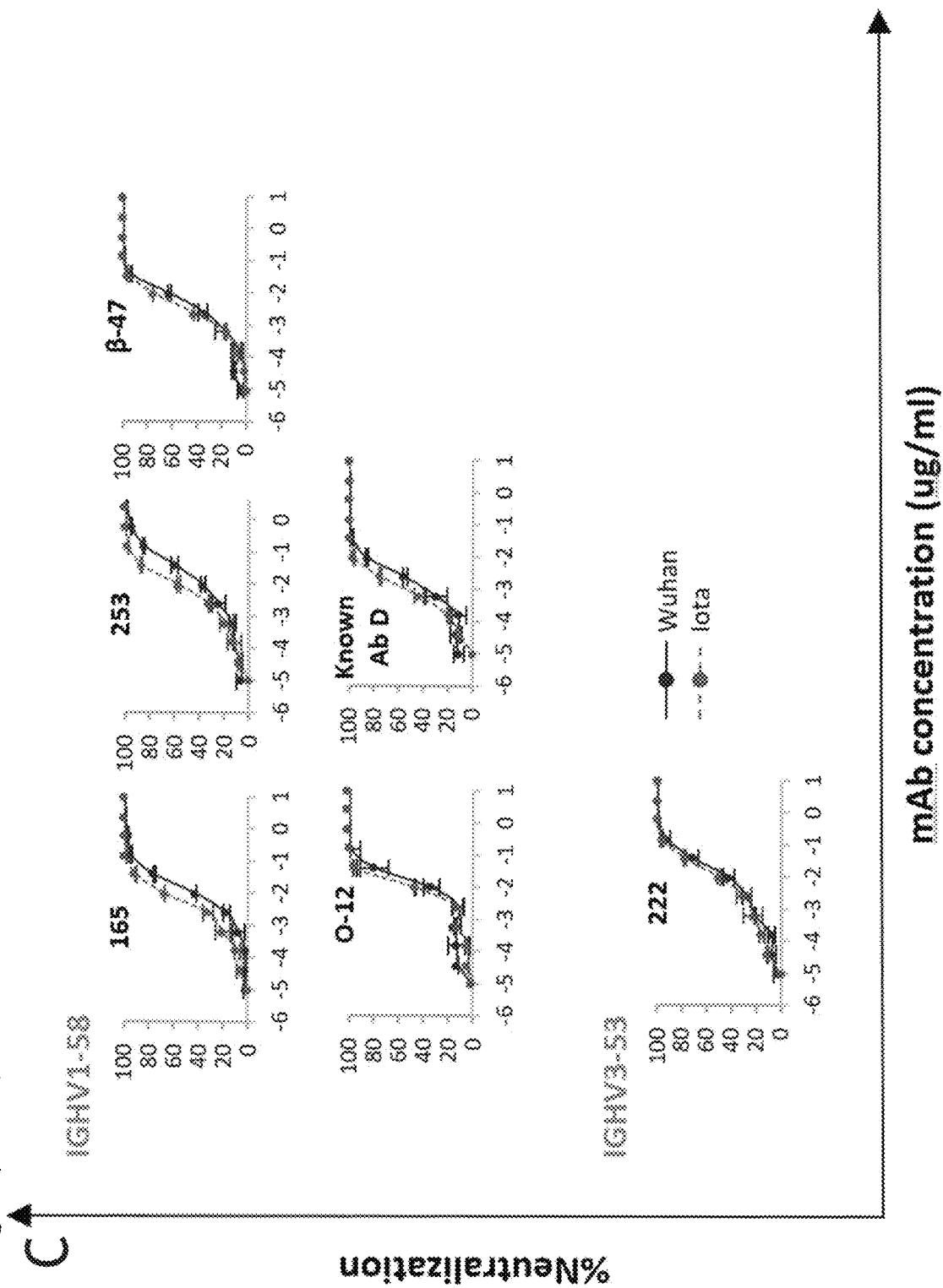

For AZD1222 samples were taken 4 weeks after the second and third doses of vaccine. Following the third dose of AZD1222 there were small but significant differences between pseudoviral neutralization with reductions of the titres against BA.2 vs BA.1 (1.17-fold p=0.0019) and BA.1.1 vs BA.1 (1.29-fold p=0.0086). For BNT162b2 samples were taken 4 weeks and 6 months following the second dose of vaccine, before the third dose and 4 weeks after the third dose. Following the third vaccine dose, titres against BA.1, BA.2 and BA.1.1 were similar with non-significant differences between them. Next, the neutralization profile of serum collected from cases infected with Omicron were determined. Early samples (n=12) were taken <14 days from symptom onset (median 13 days), later samples (n=17) were taken >21 days following symptom onset (median 38 days). All cases had received at least 2 doses of vaccine and a number of the late convalescent cases received a third dose of vaccine following Omicron infection. Neutralization against Victoria, Alpha, Beta, Gamma, Delta and Omicron was tested using live virus neutralization assays (FIG. 3C). At early time points, all vaccinated cases had high titres to Victoria with geometric mean FRNT50 close to 1/3000 and exhibited broad neutralization of VoC with FRNT50>1/1000 for all viruses except Omicron (FRNT50=558). At the later time point titres against Victoria were unchanged whilst there were increases in titres to the VoC and Omicron (3-fold p=0.0123). Pairwise comparison of early and late samples taken from the same individuals confirmed the broad boosting of the response following Omicron infection (FIG. 5A)

Neutralization of Victoria, BA.1, BA.1.1, BA.2 and BA.3 was assayed by pseudoviral neutralization. BA.1 neutralization titres were higher at later time points. However, all of the sera were obtained from BA.1 infected cases and there were small but significant reductions in the neutralization titres of BA.2 vs BA.1 (1.7 and 1.5-fold p=0.0034 and 0.0067 at <14 and >21 days respectively), the titres of BA.1.1 vs BA.1 were not significantly reduced while at >21 days the titre against BA.3 vs BA.1 was reduced 1.7-fold (p=0.0012) (FIG. 3D, 5B).

In summary, following three doses of vaccine, particularly BNT162b2, good neutralizing titres of antibody against Omicron BA.1 BA.1.1, BA.2 and BA.3 are induced, with only minor differences between the titre against BA.1 BA.1.1, BA.2 and BA.3. This may indicate that the increased transmissibility of BA.2 is not due to increased vaccine escape. Following break through Omicron infection, in previously vaccinated individuals, there is boosting of a broad antibody response to variants of concern and the generation of strong responses to Omicron. Since there are only small differences in the neutralization between BA.1 and BA.2, BA.2 superinfection of BA.1 exposed and vaccinated cases is unlikely, at least in the short term.

Neutralization of BA.4 Compared to BA.1, BA.1.1, BA.2 and BA.3

Neutralization of BA.4/5 was also assessed in comparison to Omicron sub-lineages BA.1, BA.1.1, BA.2, BA.3 and the early pandemic Victoria strain. BA.4/5 was shown to have a more extreme antibody escape phenotype than BA.1 and BA.2, and serum from triple vaccinated donors had ~2-3-fold reduction in neutralization titres compared to the neutralization of BA.1 and BA.2. Additionally, serum from breakthrough BA.1 infections in vaccinees showed ~2-3-fold reduction in neutralization titres to BA.4/5 compared to BA.1 and BA.2. This suggests that currently approved vaccines and mAbs may be less effective at preventing BA.4/5 transmission. New monoclonals and combinations may therefore be needed to plug the gap to protect the extremely vulnerable and those unable to mount adequate vaccine responses.

Neutralization of BA.4 by Vaccine Serum

A panel of pseudotyped lentiviruses (Di Genova et al., 2020, "Production, titration, neutralisation and storage of SARS-CoV-2 lentiviral pseudotypes". *Figshare preprint*) expressing the S gene from the Omicron sub-lineages BA.1, BA.1.1, BA.2, BA.3 and BA.4/5 was constructed, together with early pandemic Wuhan related strain, Victoria, used as a control.

Figure 7:
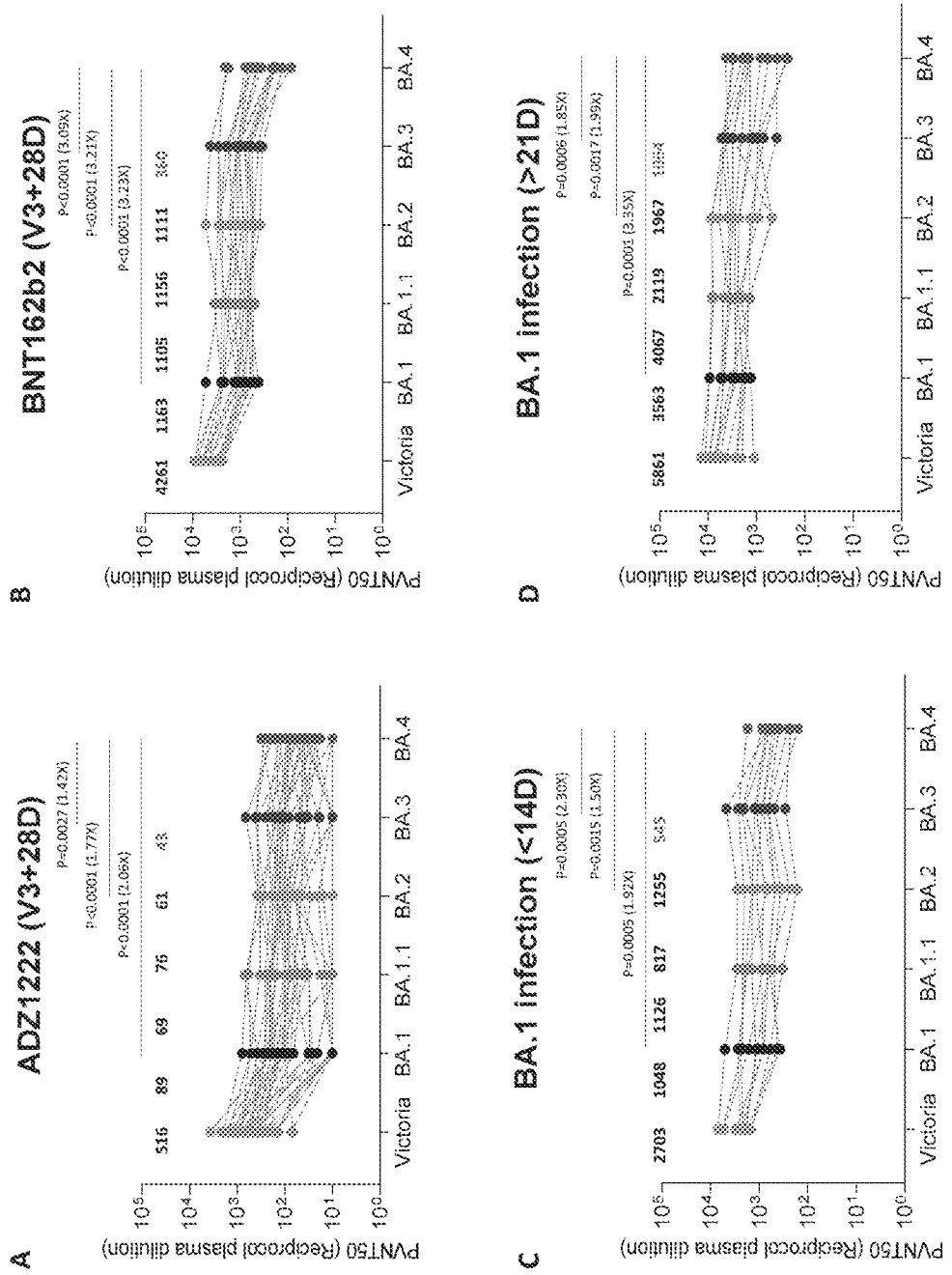
FIG. 7. Pseudoviral neutralization assays of BA.4/5 by vaccine and BA.1 immune serum. IC50 values for the indicated viruses using serum obtained from vaccinees 28 days following their third dose of vaccine (A) AstraZeneca AZD AZD1222 (n=41), (B) 4 weeks after the third dose of Pfizer BNT162b2 (n=20). Serum from volunteers suffering breakthrough BA.1 infection volunteer taken (C) early ≤1 14 (n=12) days from symptom onset (median 13 days) (D) late ≥21 days from symptom onset (median 38 days) n=16. Comparison is made with neutralization titres to Victoria (an early pandemic strain), BA.1, BA.1.1, BA.2 and BA.3. Geometric mean titres are shown above each column. The Wilcoxon matched-pairs signed rank test was used for the analysis and two-tailed P values were calculated.

Neutralization assays were performed using serum obtained 28 days following a third dose of the Oxford-AstraZeneca vaccine ADZ1222 (n=41)) (Flaxman et al, 2021, "Reactogenicity and immunogenicity after a late second dose or a third dose of ChAdOx1 nCoV-19 in the UK: a substudy of two randomised controlled trials (COV001 and COV002)". *Lancet* 398, 981-990) or the Pfizer-BioNtech vaccine BNT162b2) (Cele et al., 2021, "Omicron extensively but incompletely escapes Pfizer BNT162b2 neutralization". *Nature* 602, 654-666) (n=20) (FIG. 7 A,B). For AZD1222 neutralization titres for BA.4 were reduced 2.1-fold compared to BA.1 (p=0.0001) and 1.8-fold compared to BA.2 (p=0.0001). For BNT162b2 neutralization titres were reduced 3.2-fold (p=0.0001) and 3.1-fold (p=0.0001) compared to BA.1 and BA.2 respectively. These reductions in titre are likely to reduce vaccine effectiveness particularly at longer time points as antibody titres naturally wane.

Neutralization of BA.4/5 by Serum from Breakthrough BA.1 Infection

At the onset of the Omicron outbreak, vaccinated volunteers who had suffered breakthrough Omicron infections were recruited. Samples were first taken 14 days from symptom onset (median 13 days), while late samples were taken ≥21 days from symptom onset (median 38 days) n=16. Pseudoviral neutralization assays were performed against the panel of pseudoviruses representing variants of concern and the Omicron Sub-lineages (FIG. 7 C, D).

BA.1 infection following vaccination leads to a broad neutralizing response, with high titres to all the VoC, which is boosted at later time points (Nutalai et al. 2022, "Potent cross-reactive antibodies following Omicron breakthrough in vaccines". *Cell* (in press)). Neutralization titres against BA.4 were significantly less than BA.1 and BA.2, at the early time point BA.4/5 titres were reduced 1.9-fold (p=0.0001) and 1.5-fold (p=0.0015) compared to BA.1 and BA.2 respectively. At the later point BA.4/5 titres were reduced 3.4-fold (p=0.0001) and 2-fold (p=0.0017) compared to BA.1 and BA.2 respectively.

Thus, BA.4/5 shows a degree of immune escape from the vaccine/BA.1 response when compared with BA.1 and BA.2. These samples were all taken reasonably close to the time of infection meaning that further waning in the intervening months may render individuals susceptible to reinfection with BA.4/5.

Escape from Monoclonal Antibodies by BA.4/5

Figure 8:
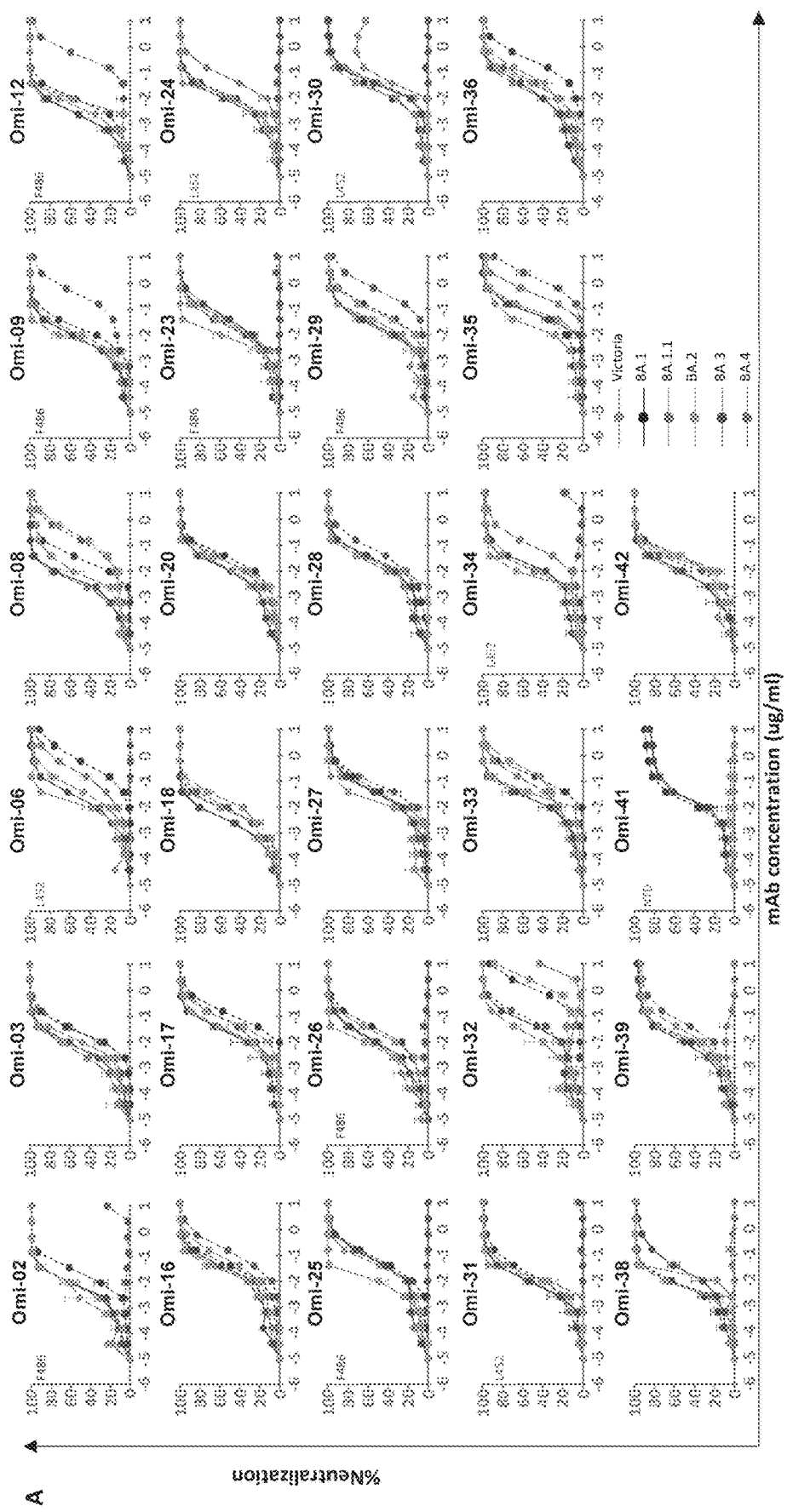
FIG. 8. Pseudoviral neutralization assays against Omicron and commercial monoclonal antibodies. Neutralization curve for a panel of 28 monoclonal antibodies made from samples taken from vaccinees infected with BA.1. Titration curves for BA.1 are compared with BA.1, BA.1.1, BA.2 and BA.3. mAb proposed to be affected by the L452R and F486L are indicated.
Figure 8:
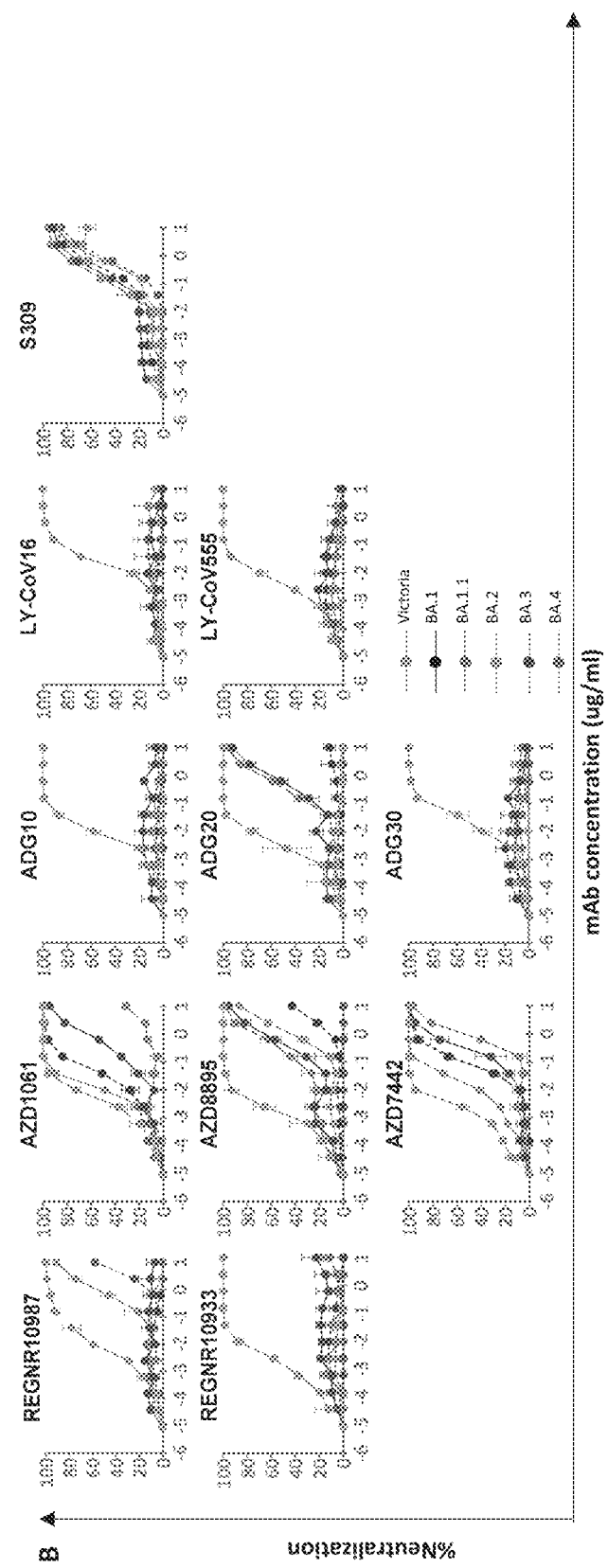

Sensitivity to L452R: It has previously been reported that Omi-24, 30, 31, 34 and 41 show complete knock out of neutralizing activity against Delta, with Omi-06 showing severe knock-down of activity (Nutalai et al., 2022). Since BA.1 and BA.2 harbour only one (T478K) of the 2 Delta RBD mutations, whilst BA.4/5 also harbour L452R, it is expected that all five of these L452 directed mAbs to be knocked out on BA.4/5. This is indeed observed (FIG. 8A, Table 20). Omi-41 also fails to neutralize, which is attributed to the differences in mutations in the NTD (FIG. 9A).

Figure 15:
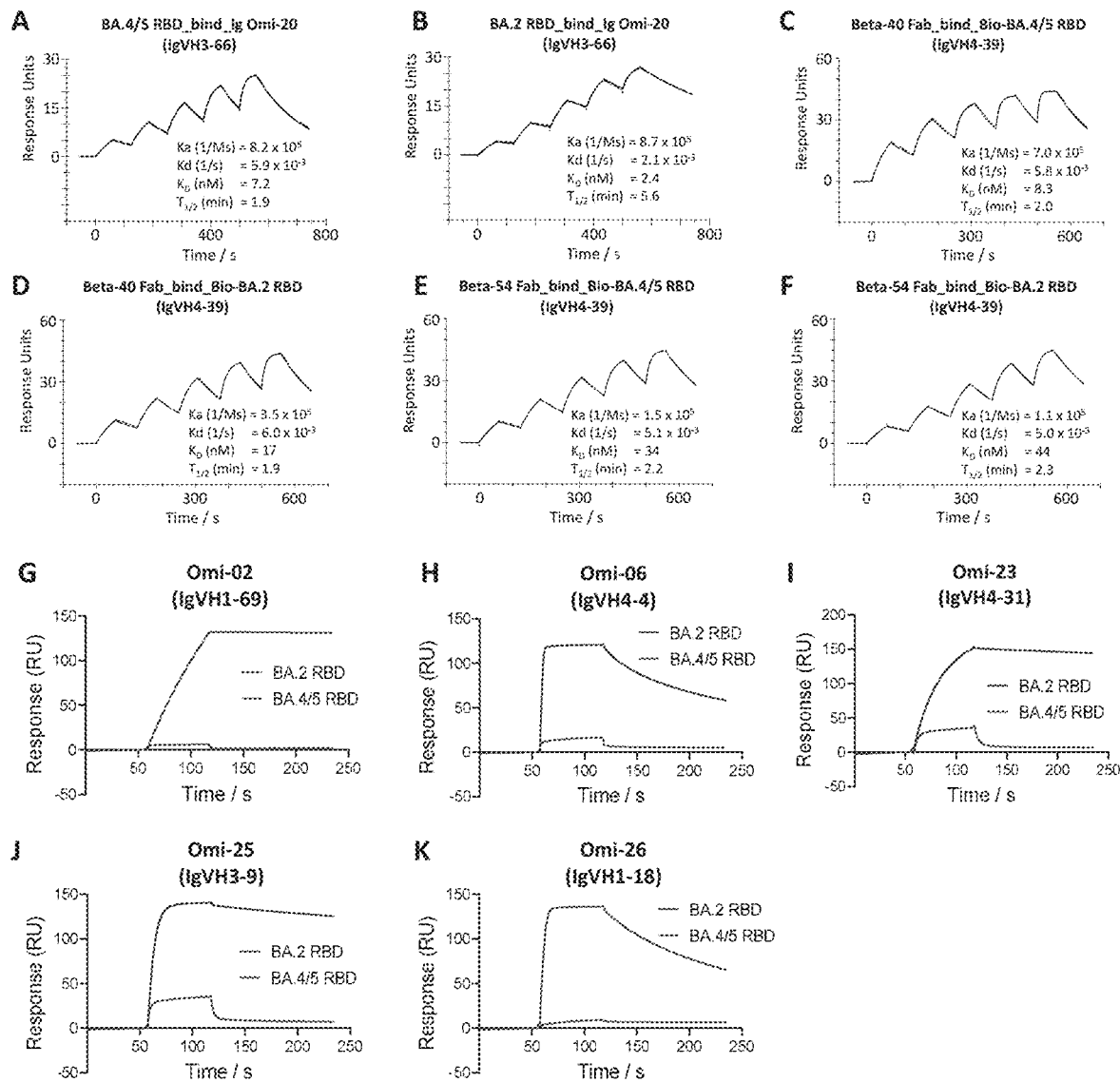
FIG. 15. Surface plasmon resonance (SPR) analysis of interaction between BA.2 or BA.4/5 RBD and selected mAbs. (A-F) Sensorgrams (Red: original binding curve; black: fitted curve) showing the interactions between BA.2 or BA.4/5 RBD and selected mAbs, with kinetics data shown. (G-K) Binding of BA.4/5 RBD is severely reduced compared to that of BA.2, so that the binding could not be accurately determined, as shown by a single-injection of 200 nM RBD over sample flow cells containing the mAb indicated.

To confirm that the neutralization effects observed are directly attributable to alterations in RBD interactions, binding analyses of selected antibodies to BA.4/5 and BA.2 RBDs by surface plasmon resonance (SPR) were also performed (FIGS. 10, 15). Omi-31 was chosen as representative of the set of L452R sensitive antibodies, and as expected the binding is severely affected.

Figure 11:
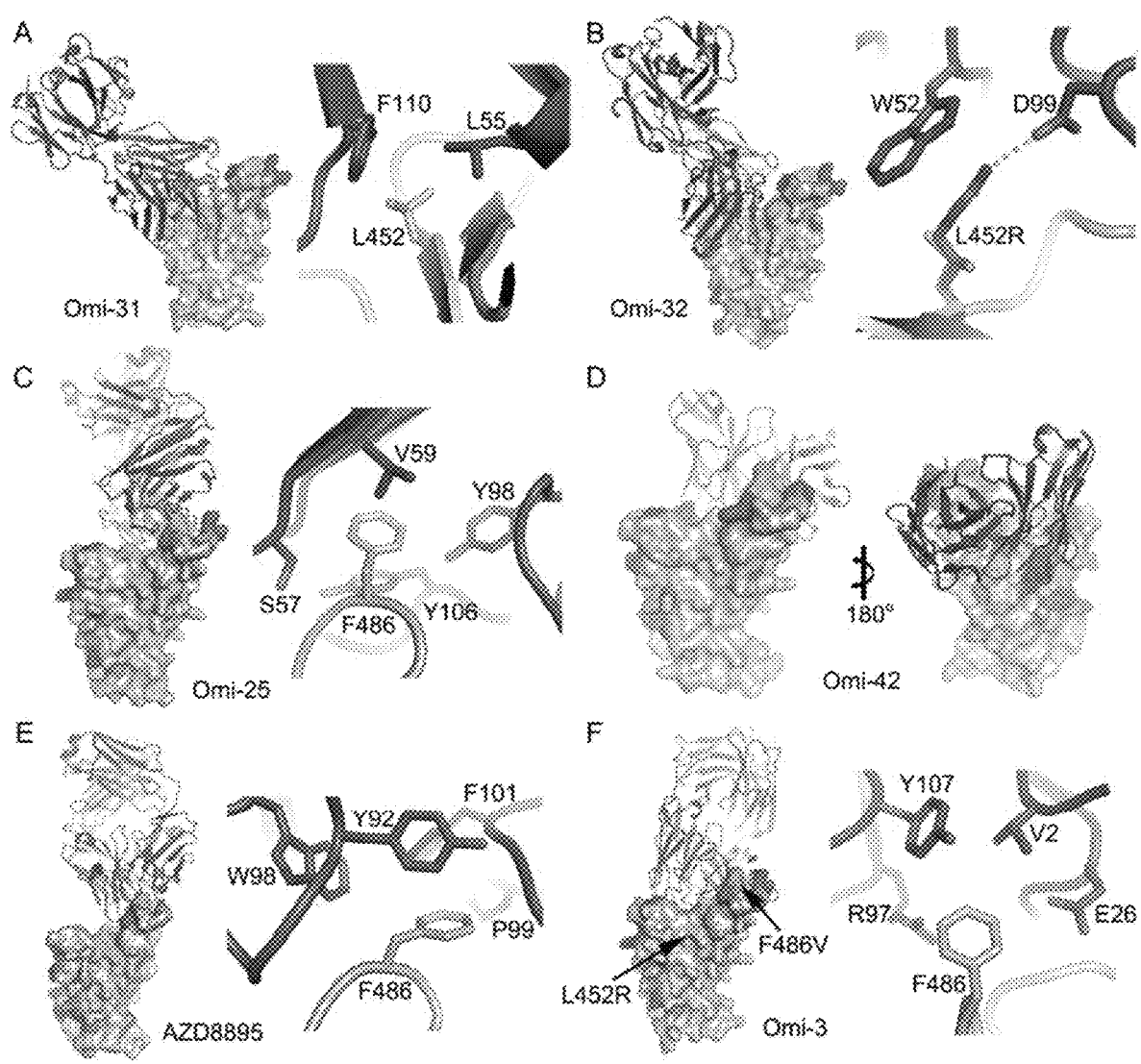
FIG. 11. Interactions between mAb and BA.4/5 mutation sites. Overall structure (left panel) and interactions (≤4 Å) with BA.4/5 mutation sites (right panel) for (A) BA.1-RBD/Omi-31 (PDB 7ZFB), (B) BA.1-RBD/Omi-32 (PDB 7ZFE), (C) BA.1-RBD/Omi-25 (PDB 7ZFD), (D) BA.1-RBD/Omi-42 (PDB7ZR7), (E) Wuhan-RBD/AZD8895 (PDB 7L7D) and (F) BA.1-RBD/Omi-3 (PDB 7ZF3) complexes. In the left panels RBD is shown as surface representation, with BA.4/5 mutation sites highlighted in magenta and the additional two mutation sites of BA.4/5 at 452 and 486 in cyan, and Fab LC as blue and HC as red ribbons. In the right panel, side chains of RBD, Fab HC and LC are drawn as grey, red and blue sticks, respectively. In (B) L452R (green sticks) are modelled to show a salt bridge to D99 of CDR-H3 may be formed (yellow broken sticks). (D) Beta-RBD/Omi-42 complex showing the Fab does not contact any of the two BA.4/5 mutation sites.

Since detailed information on the interaction of several Omicron responsive antibodies with the RBD is available, the BA.4/5 RBD mutations were modelled in the context of known structures for Omicron Fabs complexed with BA.1 or Delta RBDs (Dejnirattisai et al., 2022, "SARS-CoV-2 Omicron-B.1.1.529 leads to widespread escape from neutralizing antibody responses". Cell 185, 467-484 e415; Nutalai et al., 2022), (FIG. 11). The Omi-31 complex is shown in FIG. 11A and shows L452 tucked neatly into a hydrophobic pocket, which is unable to accommodate the larger positively charged arginine in BA.4/5 and Delta.

L452R enhancement of binding: Omi-32 shows 77-fold enhanced neutralization of BA.4/5 compared to BA.2. Kinetic analysis of Fab binding to the RBDs suggests that this is mainly achieved by a 5-fold increase in the on-rate of binding (FIG. 10A, B). This is largely explained by the favorable interaction of the arginine at 452 making a salt bridge to residue 99 of the heavy chain (HC) CDR3 (FIG. 11B), perhaps assisted by removal of slightly unfavourable charge interactions at residue 493. It is possible that these electrostatic changes enhance on-rate by electrostatic steering of the incoming antibody.

Sensitivity to F486V: Extending the logic used to understand Delta sensitivity, the remaining antibodies affected by BA.4/5>BA.2, but which retain activity against Delta, are likely sensitive to the F486V change, namely Omi-02, 09, 12, 23, 25, 26, 29. The binding sensitivity was confirmed by SPR analysis of Omi-12 (FIG. 10C, D) which showed an almost 1,000-fold reduction in affinity. An example of the structural basis of sensitivity is provided by the Omi-25 complex (FIG. 11C), which shows that the phenylalanine side chain acts as a binding hot-spot, nestled in a hydrophobic cavity making favorable ring-stacking interactions with Y106 of the HC CDR3.

Activity of Commercial Antibodies Against BA.4 and BA.5

A panel of antibodies that have been developed for therapeutic/prophylactic use was tested against BA.4/5 (FIG. 8B, Table 21). Many of these antibodies have already suffered severe reductions or knock out of activity against BA.1, BA.1.1 or BA.2. For AstraZeneca AZD1061, activity to BA.4/5 was similar to BA.2 (<2-fold reduction), whilst for AZD8895 residual activity against BA.2 was knocked out. The activity of the combination of both antibodies in AZD7442 (Dong et al., 2021, "Genetic and structural basis for recognition of SARS-CoV-2 spike protein by a two-antibody cocktail". Nature Microbiol. 6, 1233-1244) was reduced 8.1-fold compared with BA.2. The residual activity of REG10987 (Weinreich et al., 2021, "REGN-COV2, a Neutralizing Antibody Cocktail, in Outpatients with Covid-19". N Engl J Med 384, 238-251) against BA.2 was further reduced on BA.4/5, likewise residual BA.1 neutralizing activity was knocked out for ADG20 (Yuan et al., 2022, "A broad and potent neutralization epitope in SARS-related coronaviruses". bioRxiv. https://doi.org/10.1101/2022.03.13.484037) on BA.4/5. For S309 (VIR-7831/7832) (Sun and Ho, 2020, "Emerging antibody-based therapeutics against SARS-CoV-2 during the global pandemic". Antib Ther 3, 246-256), activity against BA.4/5 was 1.6 fold reduced compared to BA.2.

Figure 13:
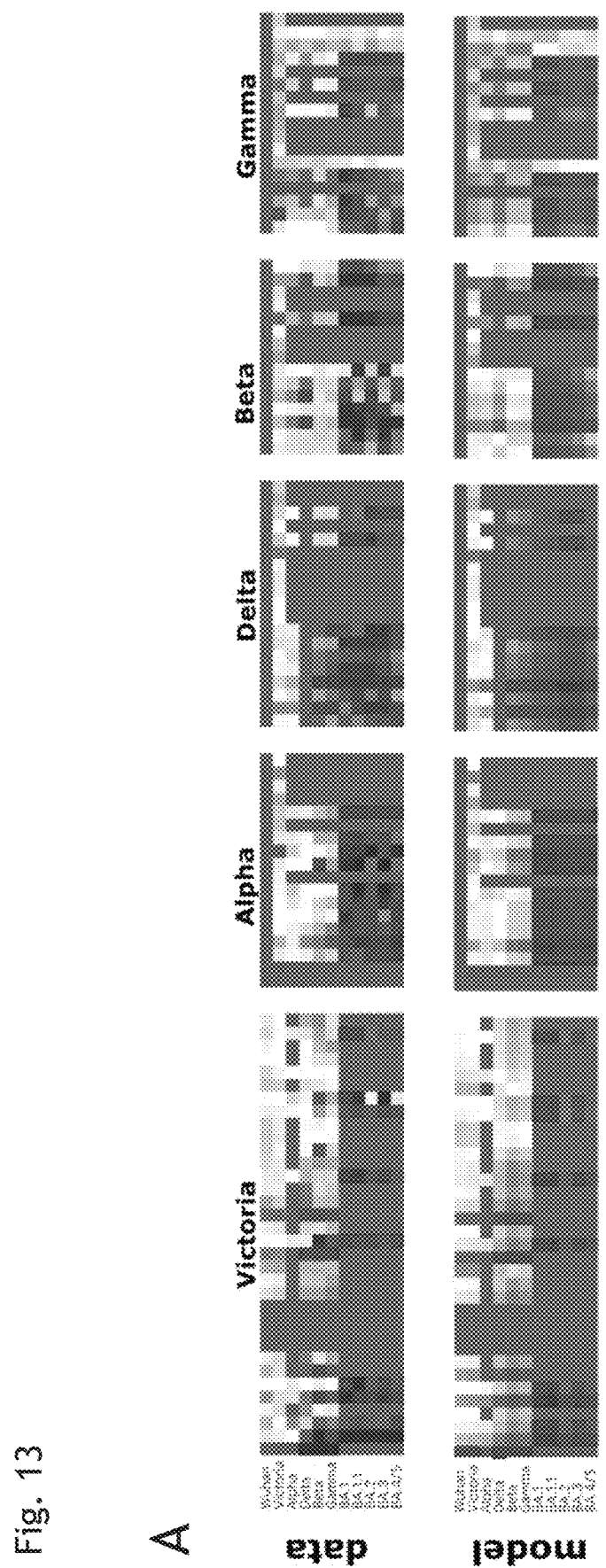
FIG. 13. Antigenic mapping. (A) Neutralization data and model (log titre values) used to calculate antigenic maps in (B). Columns represent sera collected from inoculated volunteers or infected patients. Rows are challenge strains: Victoria, Alpha, Delta, Beta, Gamma, BA.1, BA1.1, BA.2, BA.3 and BA.4/5 in order. Values are colored according to their deviation from the reference value; the reference value is calculated on a serum-type basis as the average of neutralization titres from the row which gives this the highest value. (B) Orthogonal views of the antigenic map showing BA.4/5 in the context of the positions of previous VoC and BA.1, BA.1.1, BA.1 and BA.2, calculated from pseudovirus neutralisation data. Distance between two positions is proportional to the reduction in neutralisation titre when one of the corresponding strains is challenged with serum derived by infection by the other.
Figure 13:
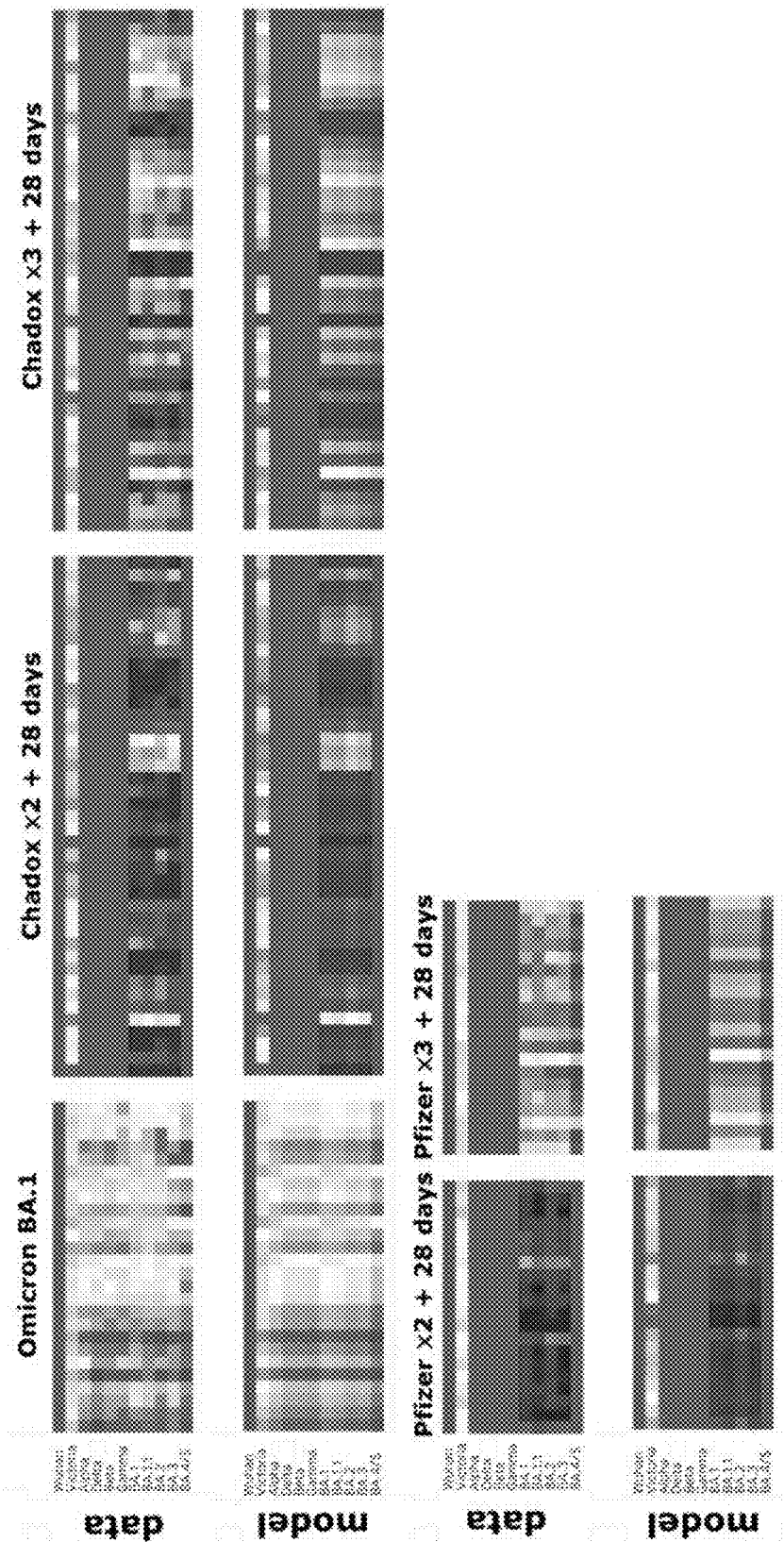
Figure 13:
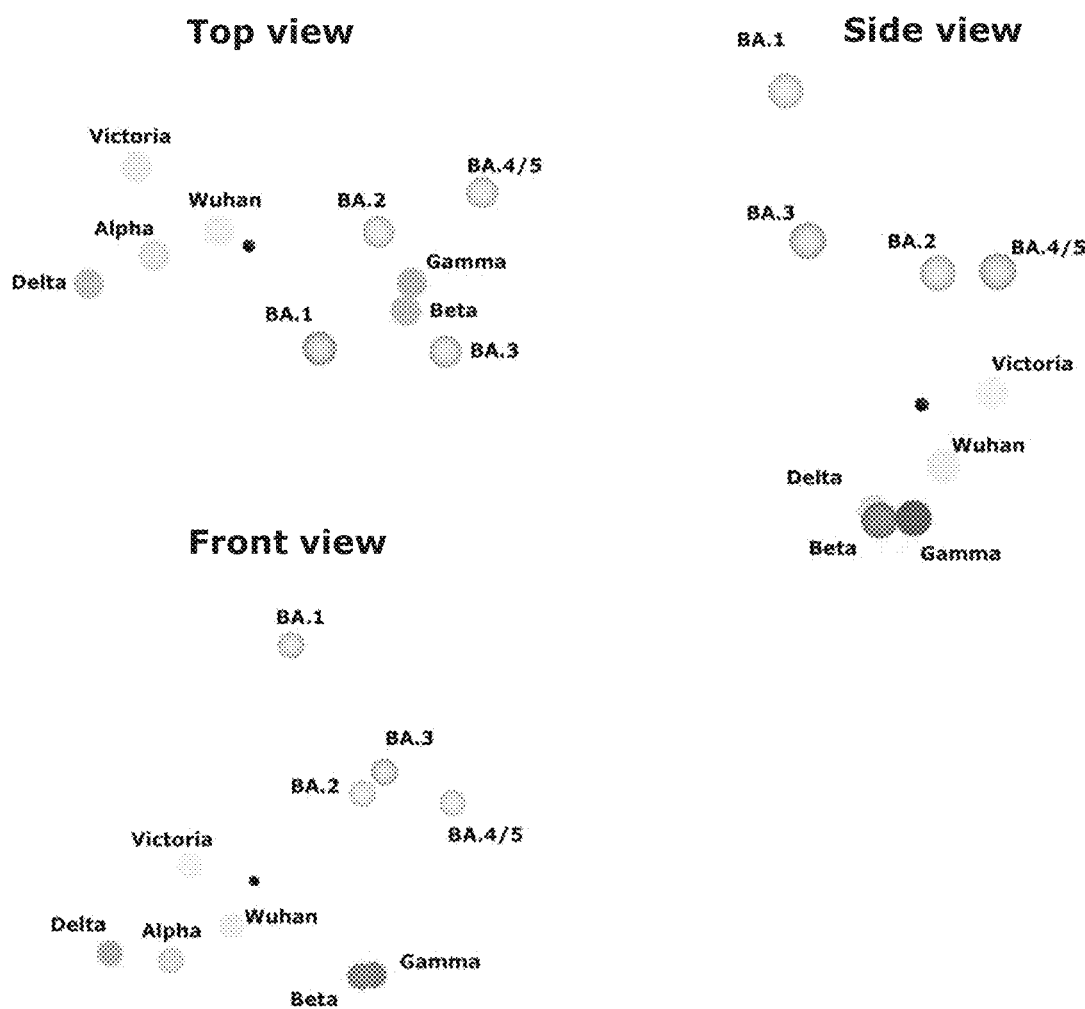
Figure 14:
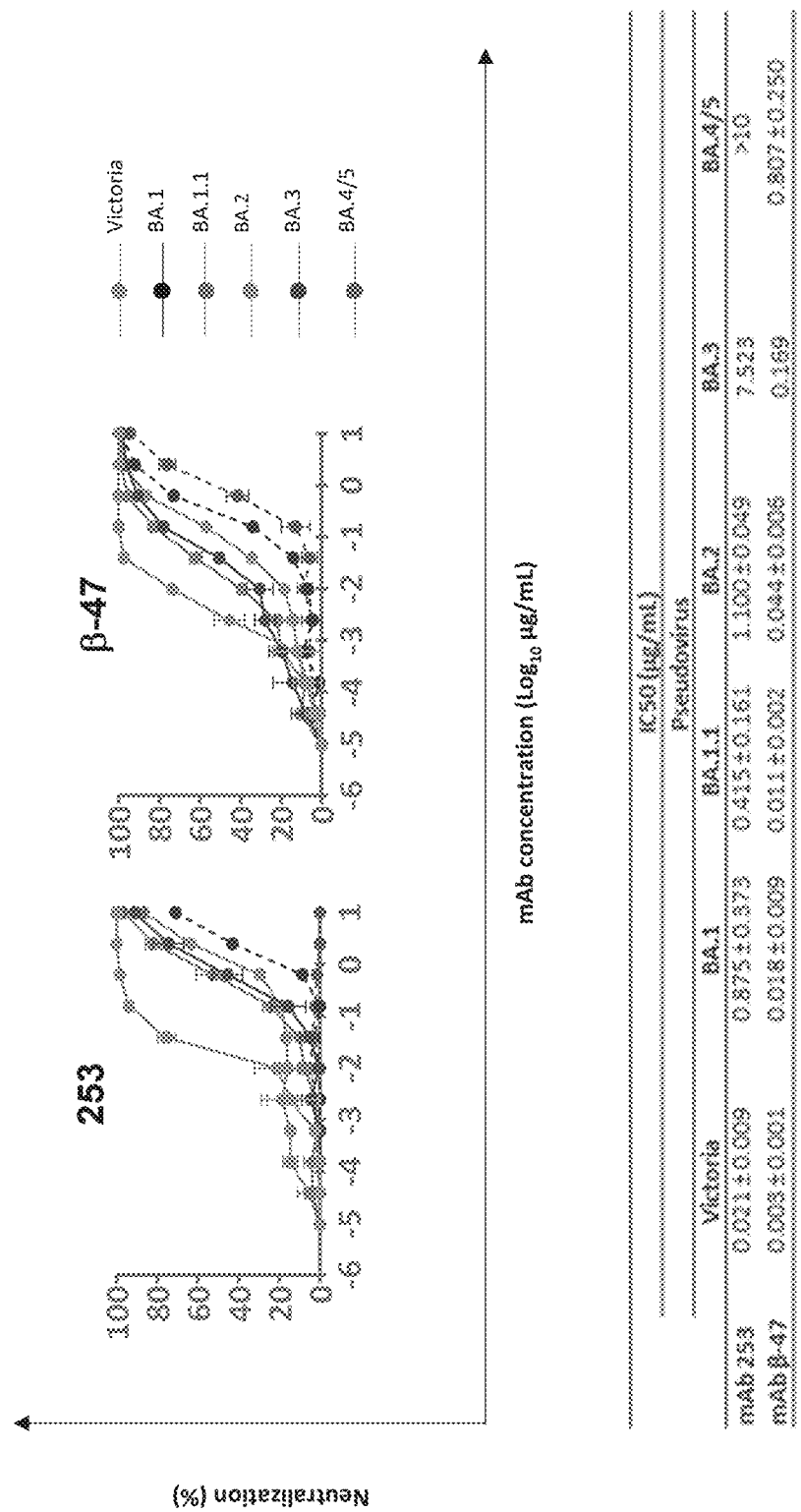

These effects can be rationalized by reference to the way the antibodies interact with the RBD, for instance in the case of AZD8895 (an IGHV1-58 genotype mAb, FIG. 11E), F486 forms a hydrophobic interaction hotspot which will be abrogated by the mutation to a much smaller valine sidechain. Antibody residues involved in the interactions with F486 are highly conserved among this genotype of mAbs, including Omi-12, 253 and Beta-47 (Nutalai et al., 2022, "Potent cross-reactive antibodies following Omicron breakthrough in vaccines". Cell (in press); Dejnirattisai et al., 2021, "The antigenic anatomy of SARS-CoV-2 receptor binding domain". Cell 184, 2183-2200 e2122; Liu et al., 2021, "The Beta mAb response underscores the antigenic distance to other SARS-CoV-2 variants". Cell, Host and Microbe 30, 53-68), explaining the severe effect of the F486V mutation on neutralization of these mAbs (FIGS. 8A, 13).

Neutralisation of BA.2.75 by Vaccine Serum

Figure 17:
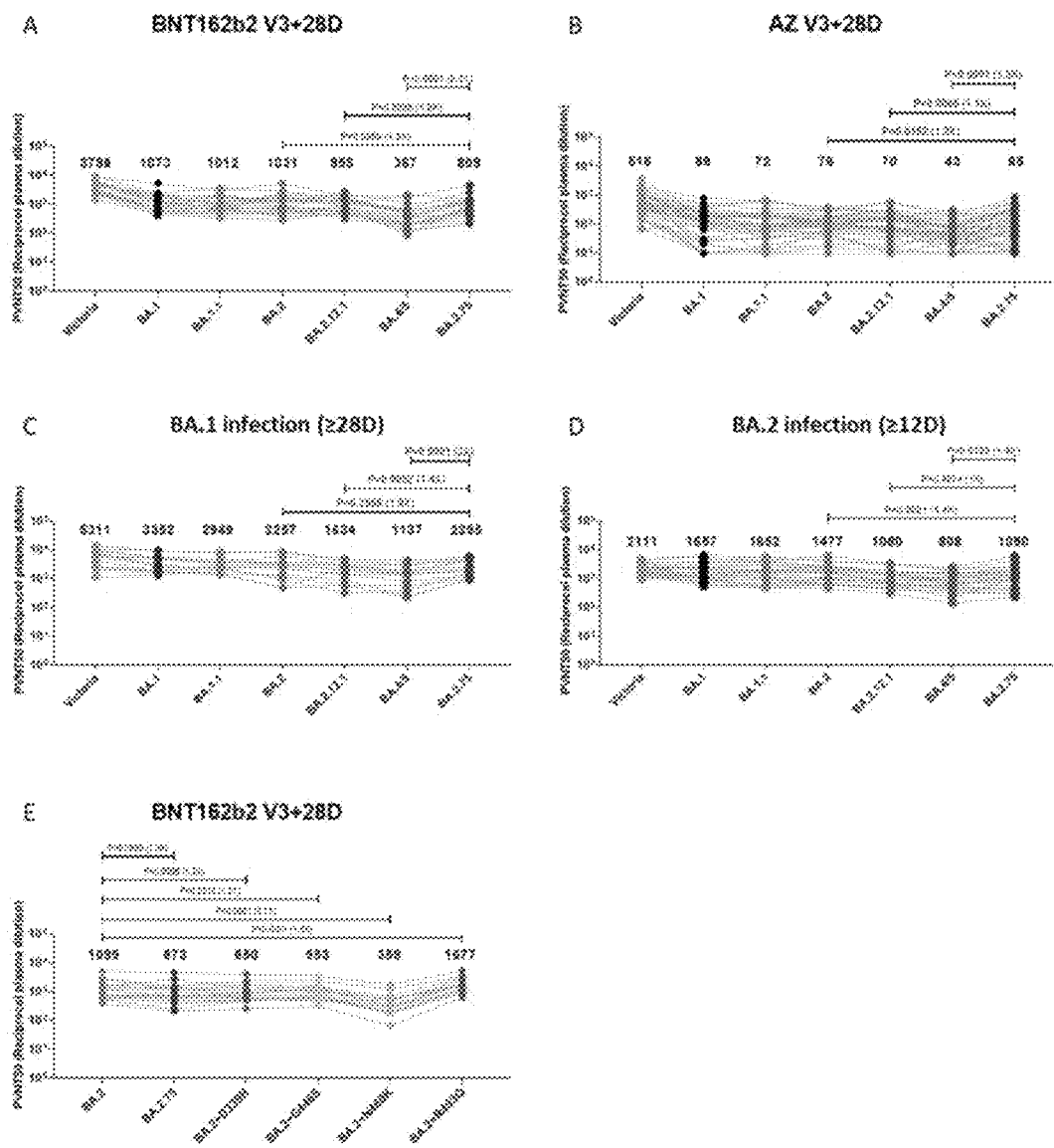
FIG. 17. Pseudoviral neutralization assays of BA.2.75 by vaccine and BA.1 and BA.2 immune serum. IC50 values for the indicated viruses using serum obtained from vaccinees 28 days following their third dose of vaccine (A) Pfizer BNT162b2 (n=22). (B) AstraZeneca AZD AZD1222 (n=41). (C, D) Serum from volunteers suffering vaccine breakthrough BA.1 (n=16) or BA.2 (n=23) infections. (EC) IC50 values for single RBD point mutations inserted into the BA.2 pseudovirus using Pfizer BNT162b2 serum (n=22) Geometric mean titres are shown above each column. The Wilcoxon matched-pairs signed rank test was used for the analysis and two-tailed P values were calculated.

A panel of pseudotyped lentiviruses was constructed as above (Di Genova et al., 2020) expressing the S gene from the Omicron sub-lineages BA.1, BA.1.1, BA.2, BA.2.12.1, BA.4/5, BA.2.75, together with Victoria, an early pandemic Wuhan related strain, used as a control. D339H, G446S, N460K and R493Q were also included as single mutations on the BA.2 background. Neutralization assays were performed using serum obtained 28 days following a third dose of the Oxford-AstraZeneca vaccine AZD1222 (n=41) (Flaxman et al., 2021 "Reactogenicity and immunogenicity after a late second dose or a third dose of ChAdOx1 nCoV-19 in the UK: a substudy of two randomised controlled trials (COV001 and COV002)." Lancet 398, 981-990) or of Pfizer-BioNtech vaccine BNT162b2 (n=22) (Cele et al., 2021; "Omicron extensively but incompletely escapes Pfizer BNT162b2 neutralization". Nature 602, 654-666e) (FIG. 17). For AZD1222, neutralization of BA.2.75 was reduced 1.2-fold compared to BA.2 (p=0.0182) and 1.1-fold compared to BA.2.12.1 (p=0.0065), but increased 1.5-fold compared to BA.4/5 (p<0.0001) (FIG. 17B). Overall, there are reductions in BA.2.75 neutralization titres of vaccine serum compared to BA.2 but not to the level seen with BA.4/5.

Neutralization of BA.2.75 by Serum from Vaccine Breakthrough BA.1 or BA.2 Infections Breakthrough BA.1 serum samples were taken from vaccinated volunteers 28 days from symptom onset (median 38 days; n=16). Pseudoviral neutralization assays were performed against the panel of pseudoviruses described above (FIG. 17C). Neutralisation titres for BA.2.75 were similar to BA.2, and 1.4-fold (p=0.0052) and 2.0-fold (p=0.0001) higher than BA.2.12.1 and BA.4/5 respectively, suggesting that BA.2.75 might be less likely to cause reinfections in individuals who have suffered BA.1 breakthrough infections than BA.2.12.1 or BA.4/5.

Breakthrough BA.2 serum samples were taken from vaccinated volunteers 12 days from symptom onset (median 29 days; n=23). Pseudoviral neutralization assays were performed against the panel of pseudoviruses Victoria, BA.1, BA.1.1, BA.2, BA.2.12.1, BA.4/5 and BA.2.75 (FIG. 17D).

Here, neutralization titres against BA.2.75 were significantly reduced compared to BA.2 (1.4-fold; P=0.0021), similar to BA.2.12.1, but still higher than BA.4/5 (1.4-fold; P=0.0123). Taken together, BA.2.75 shows a degree of escape from humoral response induced by BA.2 breakthrough infection but not BA.1 infection.

Individual BA.2.75 Mutation have Differential Effects on Neutralization

To understand the effects of the individual mutations in the BA.2.75 RBD, these mutations were introduced individually into the pseudovirus BA.2 background and their neutralization was assayed using triple vaccinated Pfizer BNT162b2 serum (FIG. 17E). Neutralization titres for BA.2 were reduced for 3/4 single mutation variants of BA.2, with the greatest decrease for N460K (3.1-fold, p<0.0001), followed by D339H (1.3-fold, p=0.0006), then by G446S (1.2-fold, p=0.2312), however neutralization titres were increased 1.5-fold by the R493Q reversion mutation (p<0.0001). Q493 is present in all vaccines thus explaining the increase in activity of vaccine serum to this reversion mutation.

Escape from Monoclonal Antibodies by BA.2.75

Figure 19:
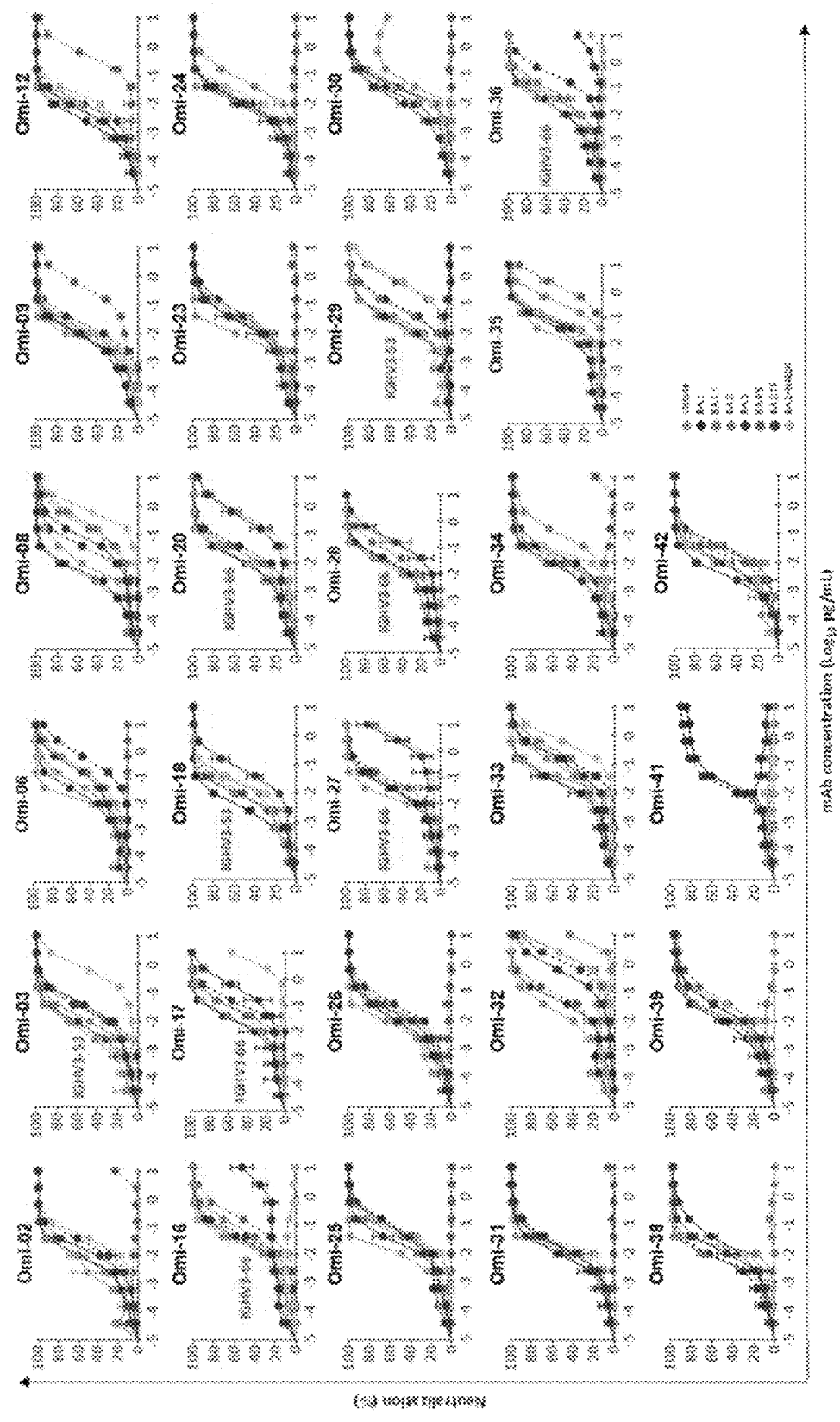
FIG. 19. Pseudoviral neutralization assays against monoclonal antibodies. (A) Neutralization curves for a panel of 28 mAb made from samples taken from vaccinees infected with BA.1. Titration curves for BA.2.75 are compared with Victoria, BA.1, BA.1.1, BA.2 and BA.4/5. IC50 titres are shown in Table 22. (B) Pseudoviral neutralization assays with mAbs developed for human use. IC50 titres are shown in Table 23. Data for Victoria, BA.1, BA.1.1 and BA.2 and BA.4/5 are used for comparison and taken from Tuekprakhon et al., 2022
Figure 19:
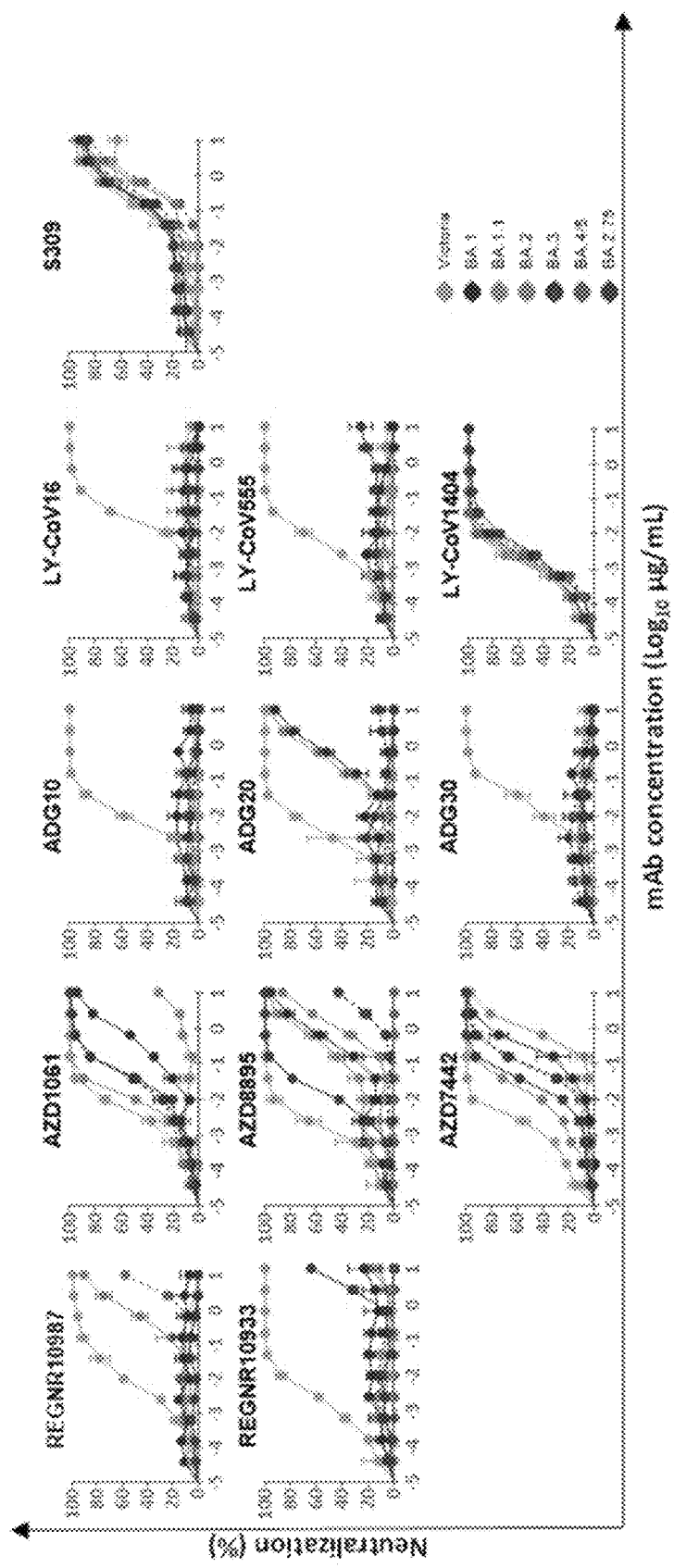

To dissect how BA.2.75 might affect neutralising antibody activity, pseudoviral assays were used to test a recently reported panel of potent human mAbs generated from cases of Omicron breakthrough infection (BA.1 IC50 titres<0.1 µg/ml) (Nutalai et al., 2022) (FIG. 19A, Table 22). Among the 27 RBD-specific mAbs, those belonging to the IGHV3-53/66 families are most severely affected. Three (Omi-16, Omi-29 and Omi-36) showed a complete knock out of BA.2.75 neutralization; an additional four (Omi-18, Omi-20, Omi-27 and Omi-28) showed >5-fold reduction compared to BA.2, which is in line with the observation that N460 interacts with highly conserved GGS/T motif of CDR-H2 in the structures of RBD/IGHV-3/66 complexes (FIG. 21B) (Dejnirattisai et al. 2021, Liu et al. 2021, Nutalai et al. 2022).

Like BA.2 and BA.4/5, BA.2.75 is not neutralised by the anti-NTD mAb Omi-41, which only interacts with the NTD of BA.1, BA.1.1 and BA.3.

Figure 23:
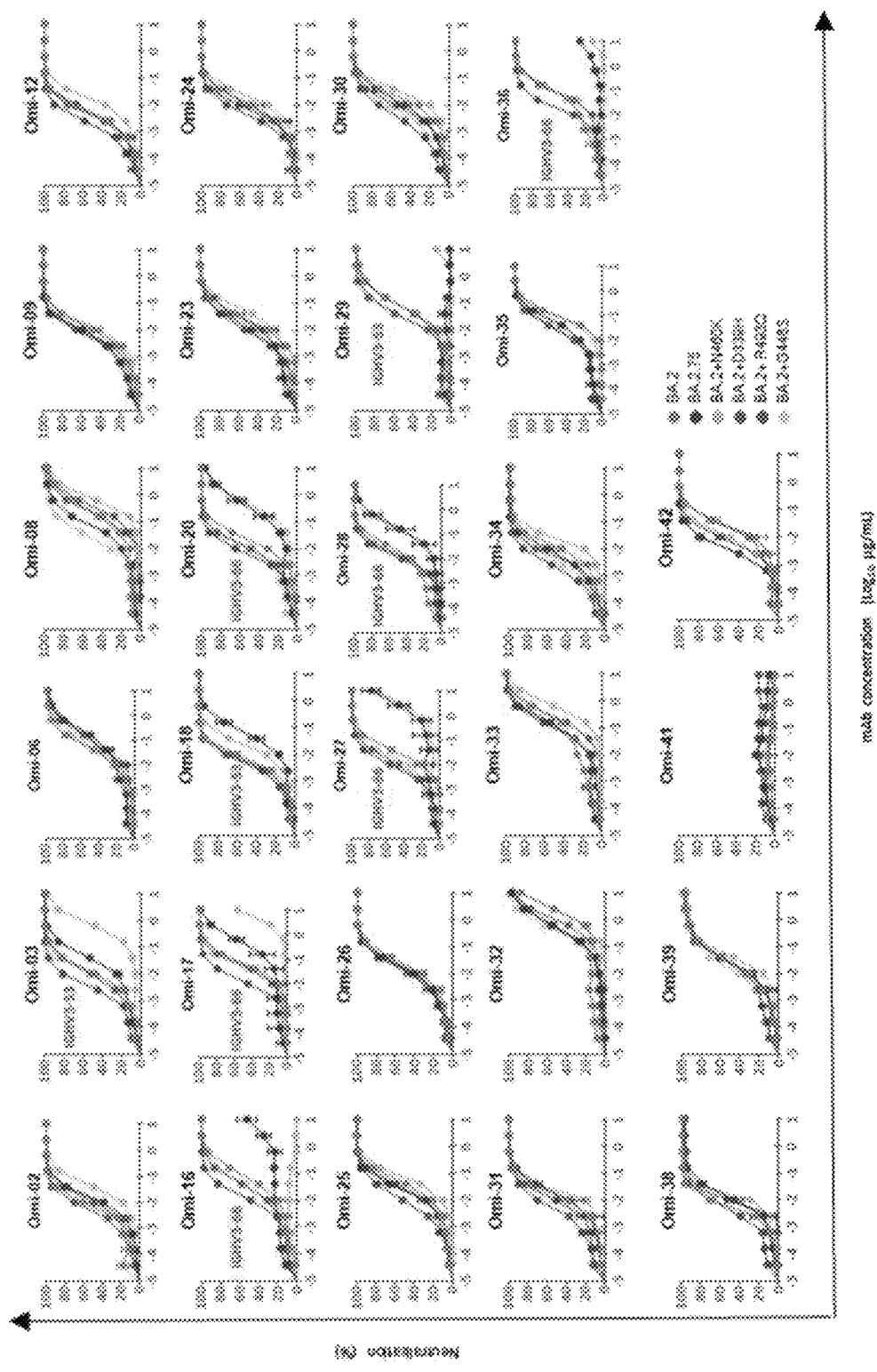
FIG. 23. Pseudoviral neutralization assays against monoclonal antibodies. (A) Neutralization curves for a panel of 28 monoclonal antibodies made from samples taken from vaccinees infected with BA.1. Titration curves for single mutations of BA.2.75 in the BA.2 backbone are compared with BA.2 and BA.2.75. IC50 titres are shown in Table 24.

The Omi mAbs were also tested against the pseudoviruses encoding single point mutations in the BA.2 RBD described above (FIG. 23, Table 24). The VH3-53/66 mAbs that lost neutralization to BA.2.75 were also impacted by the N460K mutation, confirming the prediction that this residue was critical for the binding of a number of members of this public gene family. Interestingly, The BA.2+N460K mutation in isolation shows a larger impact than BA.2.75 on the activity of several mAbs: the neutralisation titre of Omi-03 (IGHV3-53) was reduced 50-fold for BA.2+N460K but only 2-fold for BA.2.75; Omi-17 (IGHV3-66) was completely knocked out on BA.2+N460K but only reduced 4-fold for BA.2.75; and Omi-33 (IGHV3-33) was reduced 7-fold for BA.2+N460K but there was no change observed for BA.2.75. Thus, other mutations in BA.2.75 might have mitigated the effect of the N460K mutation, particularly the R493Q mutation.

Interestingly, BA.2.75 is more sensitive to Omi-32 (IGHV-3-33) than BA.2, with an 8-fold increase in neutralisation titre. The enhancement in activity by Omi-32 is likely due to a stronger interaction of the antibody with the RBD through the G446S mutation (FIG. 19A, Table 22).

Figure 24:
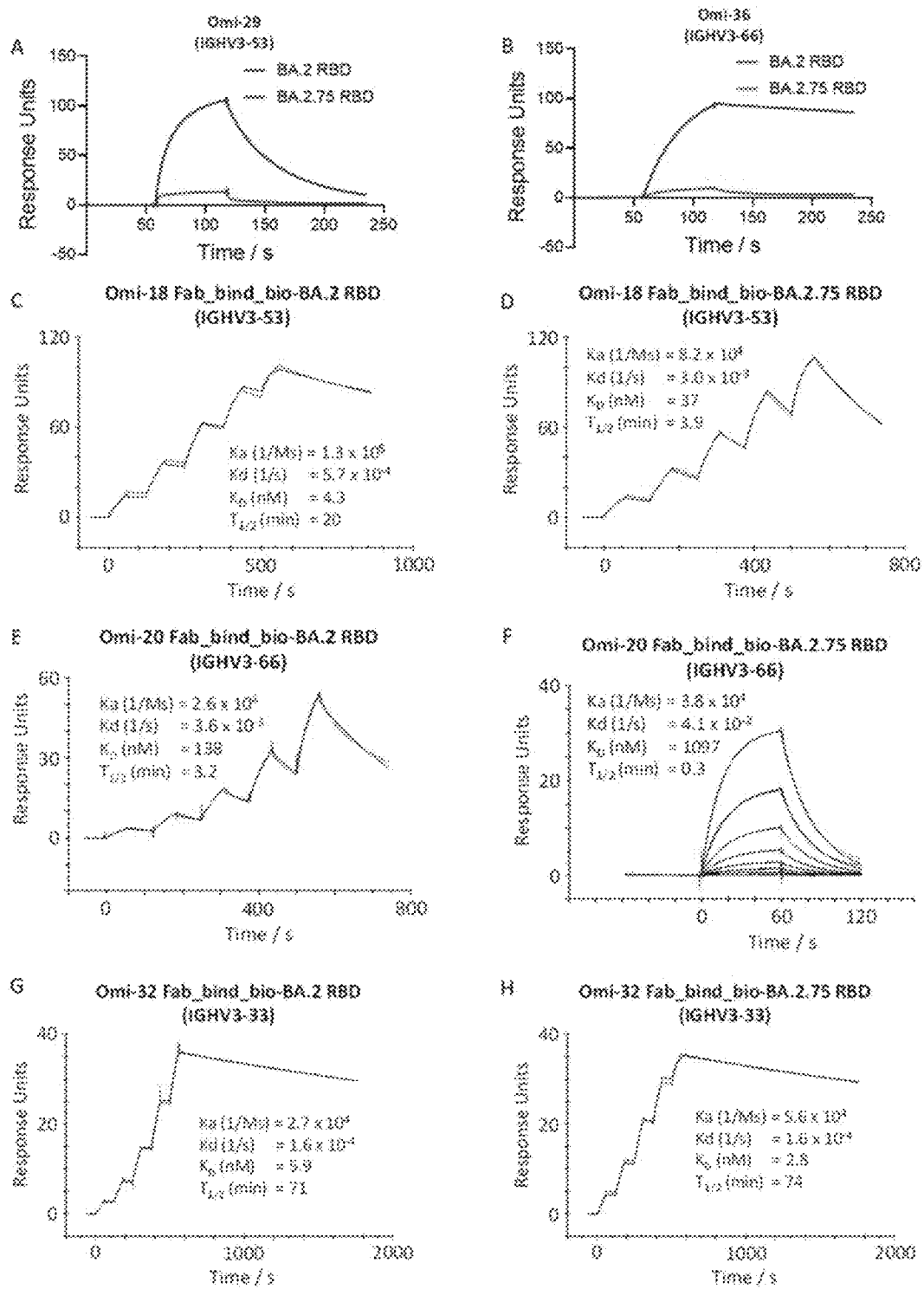
FIG. 24. Surface plasmon resonance (SPR) analysis of interaction between BA.2 or BA.2.75 RBD and selected mAbs. (A) Binding of Omi-29 (IGHV3-53) to BA.2.75 RBD is severely reduced compared to that of BA.2, as shown by a single-injection of 1 µM Omi-29 Fab over sample flow cells containing biotinylated BA.2 or BA.2.75 RBD. (B) Binding of Omi-36 (IGHV3-66) to BA.2.75 RBD is severely reduced compared to that of BA.2, as shown by a single-injection of 0.2 µM BA.2 or BA.2.75 RBD over sample flow cells containing Omi-36 in the IgG form. (C-H) Sensorgrams (Red/Coloured: original binding curve; black: fitted curve) showing the interactions between BA.2 or BA.4/5 RBD and selected mAbs, with kinetics data shown.

To confirm that the change in neutralising activities observed are associated with alterations in RBD interaction, binding analyses of selected antibodies to BA.2.75 and BA.2 RBDs were performed by surface plasmon resonance (SPR) (FIG. 24). Binding of Omi-29 (IGHV3-53) and Omi-36 (IGHV3-66) to BA.2.75 was severely impaired, and Omi-18 and Omi-20 showed 8-fold reductions compared to BA.2. On the other hand, a 2-fold increase in binding affinity of Omi-32 was seen for BA.2.75 in comparison with BA.2, in line with the enhanced neutralisation titre observed.

Escape from Commercial Monoclonals Against BA.2.75

Figure 21:
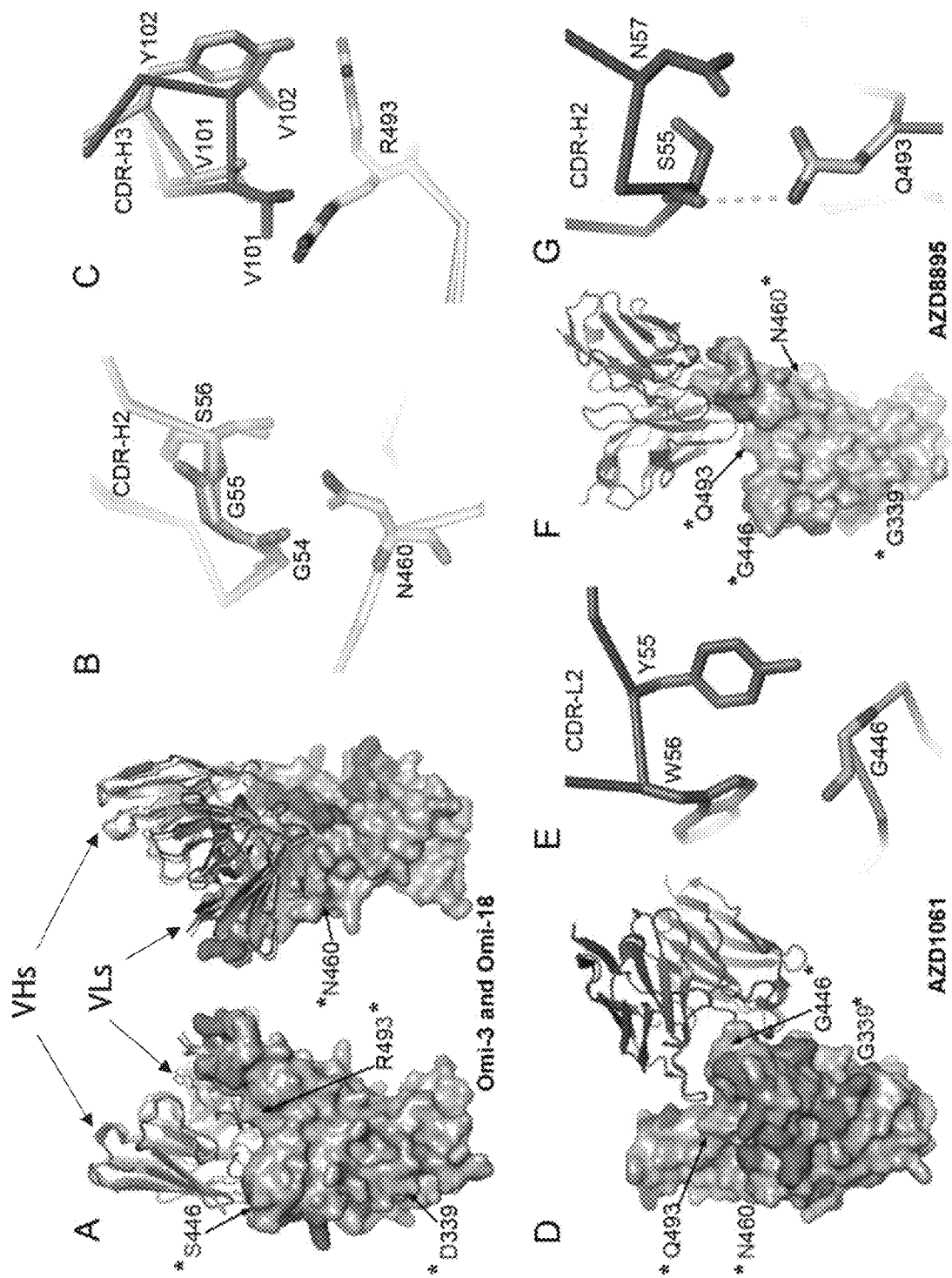
FIG. 21 Interactions between mAb and BA.75 mutation sites. (A) Front and back views of the binding modes of Omi-3 (PDB, 7ZF3) and Omi-18 (PDB, 7ZFC) complexed with omicron BA.1 RBD by overlapping the RBD. The RBD is shown as grey surface representation with mutations common to both BA.2 and BA.2.75 coloured in magenta, and the four mutations different between the two in cyan. VHs and VLs are shown as ribbons and coloured in red and blue for Omi-3, and light blue and salmon for Omi-18, respectively. (B) Interactions between N460 of the RBD and CDR-H2 of the Fabs. (C) Contacts between R493 of the RBD and CDR-H3 of the Fabs. In (B) and (C) The RBD associated with Omi-3 is in grey and Omi-18 in cyan, and the colours of the Fabs are as in (A). (D) AZD1061 bound with the ancestral SARS-CoV-2 RBD (PDB, 7L7E) and (E) contacts between G446 of the RBD and CDR-L2 of the Fab. (E) AZD8895 bound with the ancestral SARS-CoV-2 spike RBD (PDB, 7L7E) and (F) contacts between Q493 of the RBD and CDR-H2 of the Fab. In (D)-(F), RBD is drawn and coloured as in (A), HC is in red and LC in blue.

The sensitivity of a panel of mAbs that have been developed as therapeutics against BA.2.75 (FIG. 19B, Table 23) was evaluated. The neutralisation profiles are in general similar between BA.2.75 and BA.2; however, further to the 6/12 mAbs (REGN10933, ADG10, ADG20, ADG30, Ly-CoV555, Ly-CoV16) which have already suffered complete loss of neutralising activity for BA.2, the residual activity of REG10987 (Weinreich et al., 2021, "REGN-COV2, a Neutralizing Antibody Cocktail, in Outpatients with Covid-19." *N Engl J Med* 384, 238-251) against BA.2 was further knocked out for BA.2.75 due to the G446S mutation (Dejnirattisai et al, 2022). For AstraZeneca AZD1061, activity against BA.2.75 was similar to that against BA.2 (<3-fold reduction); whilst the AZD8895 titre was restored to 0.008 µg/ml for BA.2.75 from 1.333 µg/ml for BA.2, a 167-fold increase in activity. As a result, AZD7442 (a combination of AZD8895 and AZD1061) (Dong et al., 2021, "Genetic and structural basis for recognition of SARS-CoV-2 spike protein by a two-antibody cocktail". *Nature Microbiol.* 6, 1233-1244) showed similar activity against BA.2.75 and BA.2 (2-fold reduction). The results can be explained by the structure of the ternary complex of the ancestral SARS-CoV-2 RBD/AZD1061/AZD8895 (Dong et al., 2021). G446 has contacts with CDR-L2 Y55 and W56 of AZD1061, G446S mutation will induce steric clashes (FIGS. 21D, E). While CDR-H2 of AZD8895 sits above and makes a hydrogen bond to Q493 of the RBD, an arginine at 493 will severely clash with CDR-H2 of the mAb (FIGS. 21F, G). The activity of S309 (Sun and Ho, 2020, "Emerging antibody-based therapeutics against SARS-CoV-2 during the global pandemic." *Antib Ther* 3, 246-256) is increased 3-fold for BA.2.75 compared to BA.2, suggesting that the D339H mutation in BA.2.75 reduces the impact of the preceding G339D mutation in BA.2 on the activity of S309. LY-CoV 1404 (bebtelovimab) (Westendorf et al., 2022, "*LY-CoV*1404 (*bebtelovimab*) *potently neutralizes SARS-CoV-2 variants*." Cell Rep 39, 110812) is the only mAb where neutralization is fully retained on all Omicron sub-lineages.

Escape from Monoclonal Antibodies by BA.2, BA.4 and BA.5 Sublineages

Figure 34:
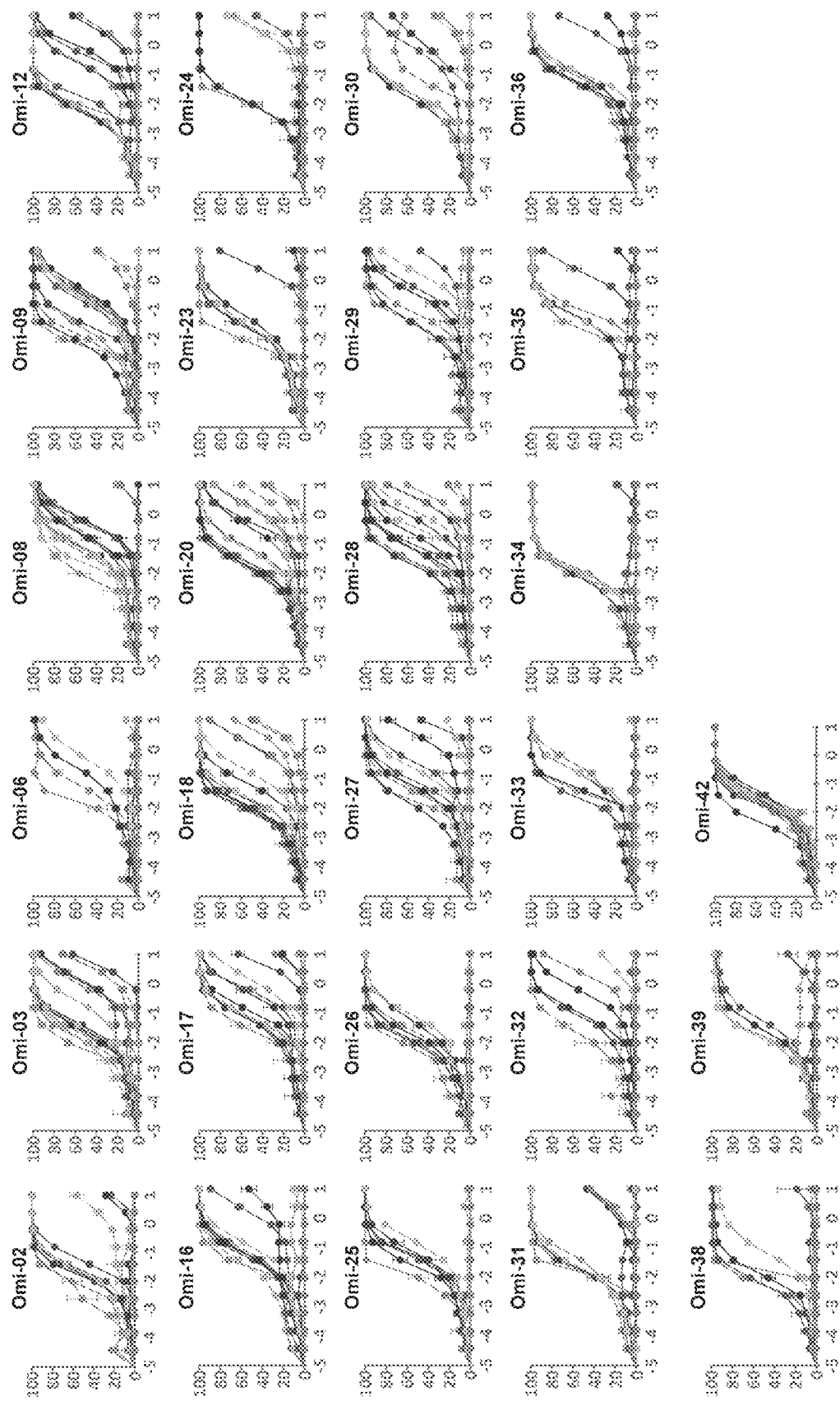
FIG. 34. Neutralization assays. Neutralization curves using lentivirus pseudotyped with the S gene of the indicated BA.2 sub-lineages.

Attrition of mAb activity was also observed with the new BA.2, BA.4 and BA.5 sublineages (including BA.4.6, BA.2.75, BA.2.75.2, BA.2.3.20, BJ.1, BQ.1, BQ.1.1, XBB, XBB.1 and XBB.1.5) (FIG. 34), with XBB leading to the most extreme escape. Activity of all 9 IGHV3-53/66 mAbs was reduced >100-fold with complete knock out of activity in 5/9 by BA.2.75.2. Only a single mAb, Omi-42 was unaffected by all variants. Omi-42 is unusual as it binds at the back of the left shoulder of the RBD (Nutalai et al., 2022) in a region that has not yet been targeted for mutation by the set of newly emerging BA.2 variants, perhaps because of the relative rarity of antibodies binding in this region.

Further data can be found in Nutalai, et al. (2022) "Potent cross-reactive antibodies following Omicron breakthrough in vaccinees", *Cell* 185(12), 2116-2131; Huo et al. (2022) "Humoral responses against SARS-CoV-2 Omicron BA.2.11, BA.2.12.1 and BA.2.13 from vaccine and BA.1 serum", Cell discovery 8, 119; and Huo, et al. (2022) "A delicate balance between antibody evasion and ACE2 affinity for Omicron BA.2.75" Cell Reports, 42(1). 2023.

Neutralisation of BA.2 Subvariants BA.2.11, BA.2.12 and BA.2.13 by Vaccine Serum The receptor binding capacity of the BA.2 subvariants BA.2.11, BA.2.12 and BA.2.13 was also evaluated. A high-resolution crystal structure of BA.2.12.1 RBD was generated, showing differential sensitivity of new BA.2 subvariants BA.2.11, BA.2.12 and BA.2.13 to serum samples and monoclonal antibodies (mAbs) compared to BA.2.

Considering the physico-chemical properties of the side chain of residue 452, BA.2.13 would be expected to be a relatively modest change; L to M will increase the size of the side chain but it remains hydrophobic. L to Q in BA.2.12.1 introduces some polar character, whilst BA.2.11 is the most radical with L to R introducing a large basic amino acid.

Neutralisation of BA.2 Subvariants BA.2.11, BA.2.12 and BA.2.13 by Vaccine Serum To evaluate the susceptibility of the BA.2 subvariants to neutralisation by immune sera, neutralization assays were performed on pseudotyped lentiviruses expressing the Spike gene of BA.2.11, BA.2.12 and BA.2.13, using a series of serum samples.

Figure 27:
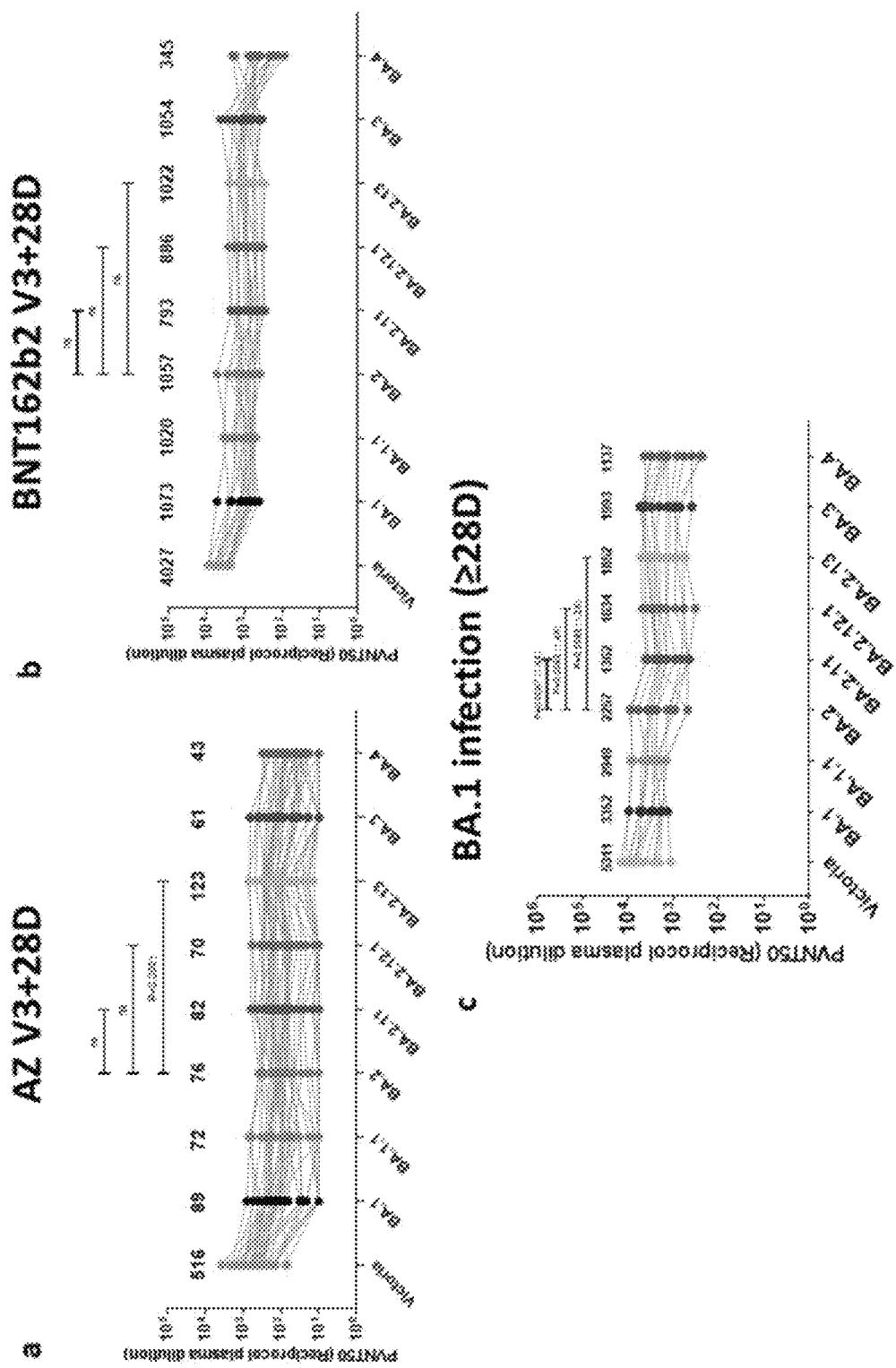
FIG. 27. Characterisation of BA.2.11, BA.2.12.1 and BA.2.13 by pseudoviral neutralization assays, surface plasmon resonance and structural analysis. (a), (b) IC50 values for the indicated viruses using serum obtained 4 weeks after a third dose of vaccine (a) AstraZeneca AZD1222 (n=41), (b) Pfizer BNT162b2 (n=18). (c) Neutralization titres of serum from vaccinated volunteers suffering breakthrough BA.1 infection were taken. Comparison is made with neutralization titers to Victoria, BA.1, BA.1.1, BA.2 and BA.4/5 previously reported in Tuekprakhon et al. (2022). Geometric mean titers are shown above each column. The Wilcoxon matched-pairs signed-rank test was used for the analysis, and two-tailed p values were calculated. (d-g) SPR sensorgrams (red: experimental binding curve; black: fitted curve) showing ACE2 binding of the RBD of BA.2.11 (e), BA.2.12.1 (f), BA.2.13 (g) in comparison with binding to BA.2 RBD (h), with kinetics data shown. The data for BA.2 RBD were reported in Nutalai et al. (2022). (h-m) Crystal structure of BA.2.12.1 RBD/Beta-27/NbC1 complex. (h) Overall structure shown as Cα traces with RBD (grey), Beta-27 HC (red) and LC (blue), and NbC1 (yellow). Cαs of residues L452Q, F486 and Q493R (L, F and R in BA.2, R, V and Q in BA.4/5) are shown as spheres. (i) Comparison of Beta-27 binding modes in the BA.2.12.1 RBD/Beta-27/NbC1 (RBD as surface representation, HC in red and LC in blue), BA.4/5 RBD/Beta-27/NbC1 (cyan, PDB 7ZXU) and Beta RBD/Beta-27 (green, PDB 7PS1) complexes by overlapping the RBDs. Apart from the flexible N- and C-terminal regions of RBD, significant differences occur at N-terminus and CDR-H1 of the Fab HC, α2 helix, 371-375 loop and G446 loop of the RBD. CDR-L3 has double conformations in the BA.4/5 RBD complex, and a single conformation in other two complexes (i). The HC N-terminus and CDR-H1 which contacts residue 486 of the RBD differs to those in both Beta and BA.4/5 RBD complexes, the latter contains F486V mutation. The differences are likely caused by contacts from a symmetry related C1 nanobody shown as grey bonds in (j). (k) The structural difference at G446 loop in the BA.4/5 RBD is also induced by crystal contact. (l) 371-375 loop that carries S371F, S373P and S375F mutations in BA.2.12.1 and BA.4/5 RBDs is stabilized by interactions with CDR-H3 of NbC1. (m) Superimposition of BA.2.12.1 (grey), BA.2 (green, PDB 7ZF9) and BA.4/5 (cyan) RBDs. (n) Mutations at 452 do not introduce significant local structural changes. R452 in BA.4/5 has a double conformation.
Figure 27:
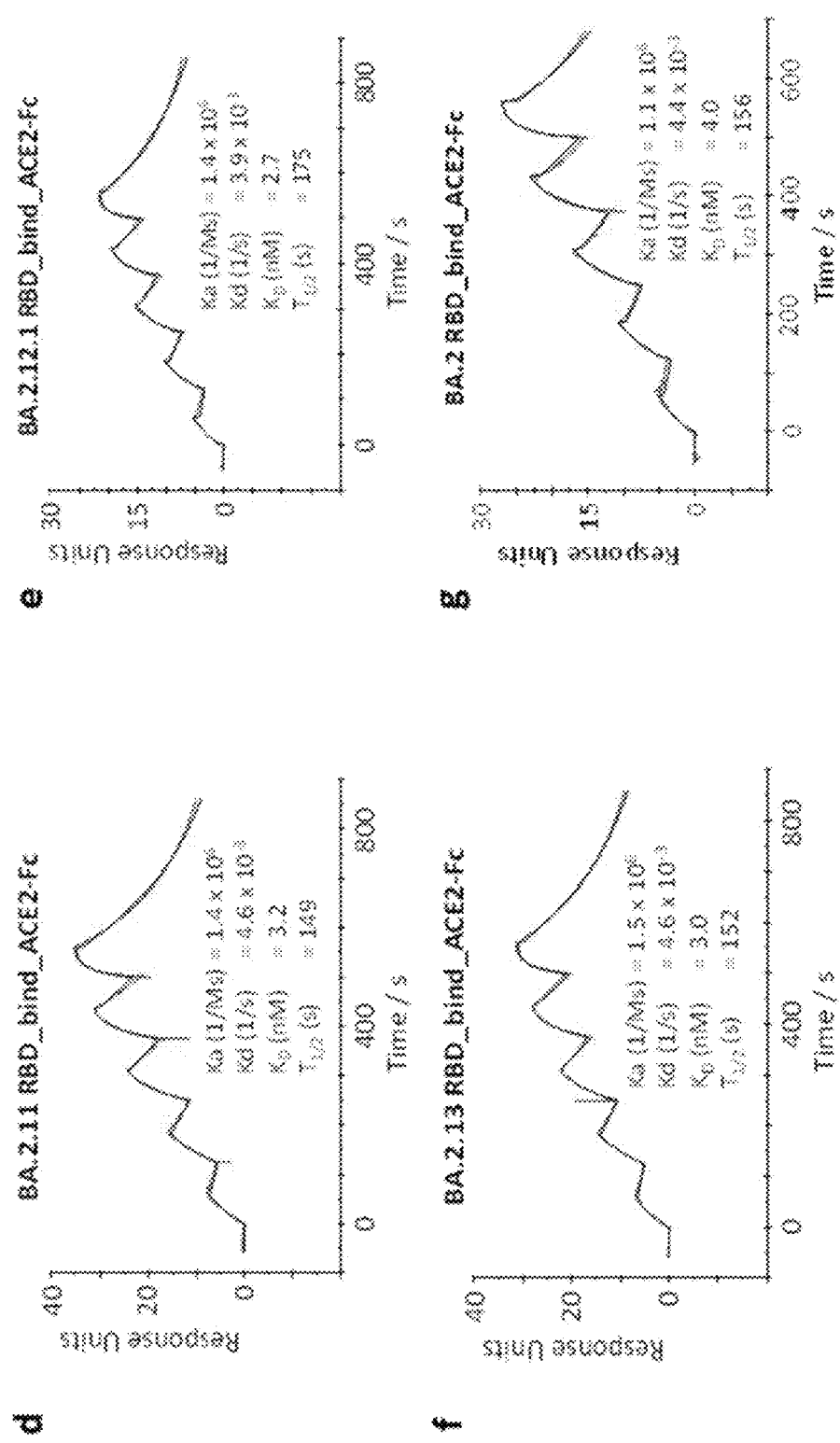
Figure 27:
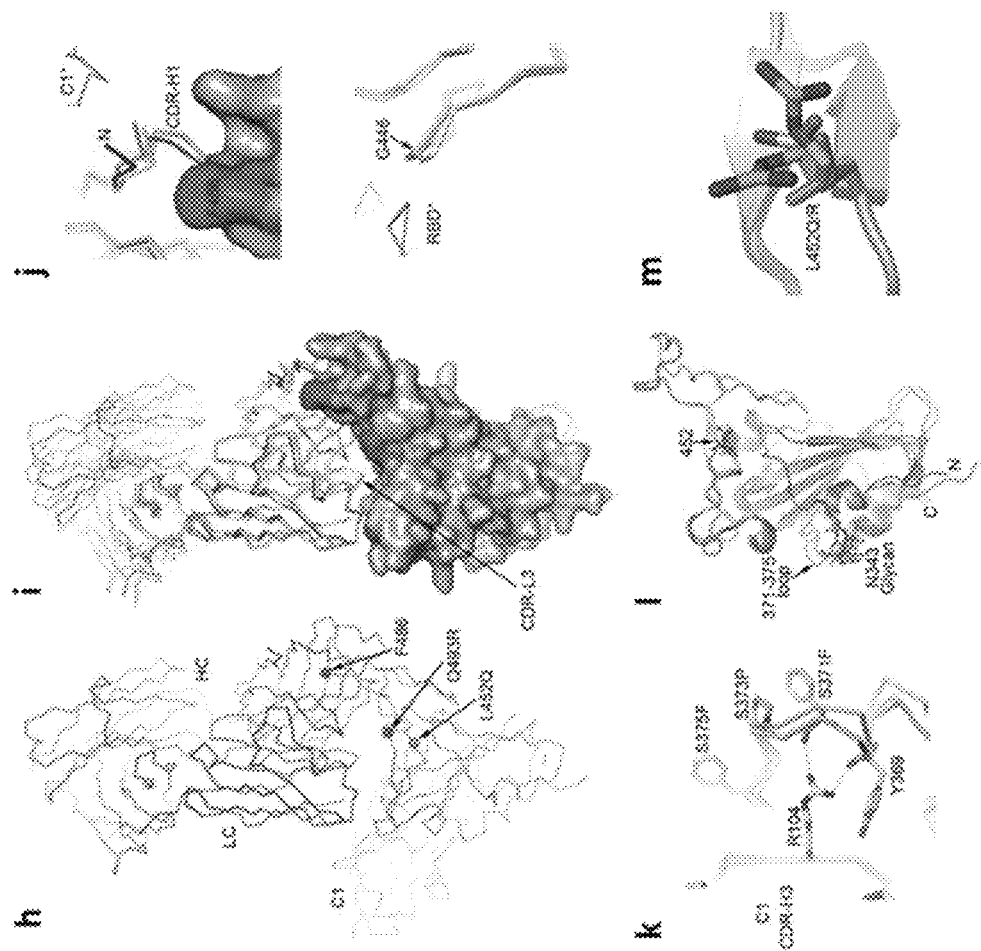

Firstly, the neutralisation profile with sera collected 4 weeks following a third dose of the Oxford-AstraZeneca vaccine AZD1222 (n=41) or Pfizer-BioNtech vaccine BNT162b2 (n=18) was observed. No significant loss in neutralisation titre was seen compared to BA.2. In fact, BA.2.13 showed a significant increase (1.6-fold, p<0.0001) for AZD1222 vaccinees (FIG. 27a, b). This contrasts with a recent report (Cao, Y., et al., "BA.2.12.1, BA.4 and BA.5 escape antibodies elicited by Omicron infection". Nature, 2022), where sera collected from triple-dose vaccinees (4 weeks following a third dose of the inactivated vaccine CoronaVac or a ZF2001 booster after two doses of CoronaVac) showed significant reductions in neutralisation titre for both BA.2.12.1 and BA.2.13 (BA.2.11 was not tested).

Neutralisation of BA.2 Subvariants BA.2.11, BA.2.12 and BA.2.13 by Serum from Vaccine Breakthrough BA.1 or BA.2 Infections Next, the neutralisation profile for serum samples collected from vaccinees infected with BA.1 were examined. Samples (n=14) were taken ≥28 days following symptom onset (median 38 days); all convalescent individuals had received at least 2 doses of vaccine, 3 of them received a third dose of vaccine following Omicron infection. There were significant reductions in neutralisation titre for all three variants compared to BA.2, with the greatest decrease for BA.2.11 (1.6-fold, P=0.0067), followed by BA.2.12.1 (1.4-fold, P=0.0085) and BA.2.13 (1.2-fold, P=0.0085) (FIG. 27c). Together, these observations suggest that, in comparison with BA.2, its subvariants are not showing stronger humoral immune escape in individuals vaccinated with three doses of AZD1222 or BNT162b2. However, for vaccinees who had a BA.1 breakthrough infection, regardless of the type of vaccine they had received, the BA.2 variants are more capable of evading the humoral response, although a broad neutralizing antibody response, with high titres to all the variants of concern, is induced (Nutalai, R., et al., "Potent cross-reactive antibodies following Omicron breakthrough in vaccines". Cell, 2022. 185(12): p. 2116-2131 e18). This may indicate the different selective pressure on BA.2 and its subvariants on a high background of breakthrough infection. As antibody titres naturally wane at longer time points, people with BA.1 breakthrough infections are expected to be more susceptible to reinfection with the BA.2 subvariants.

Figure 29:
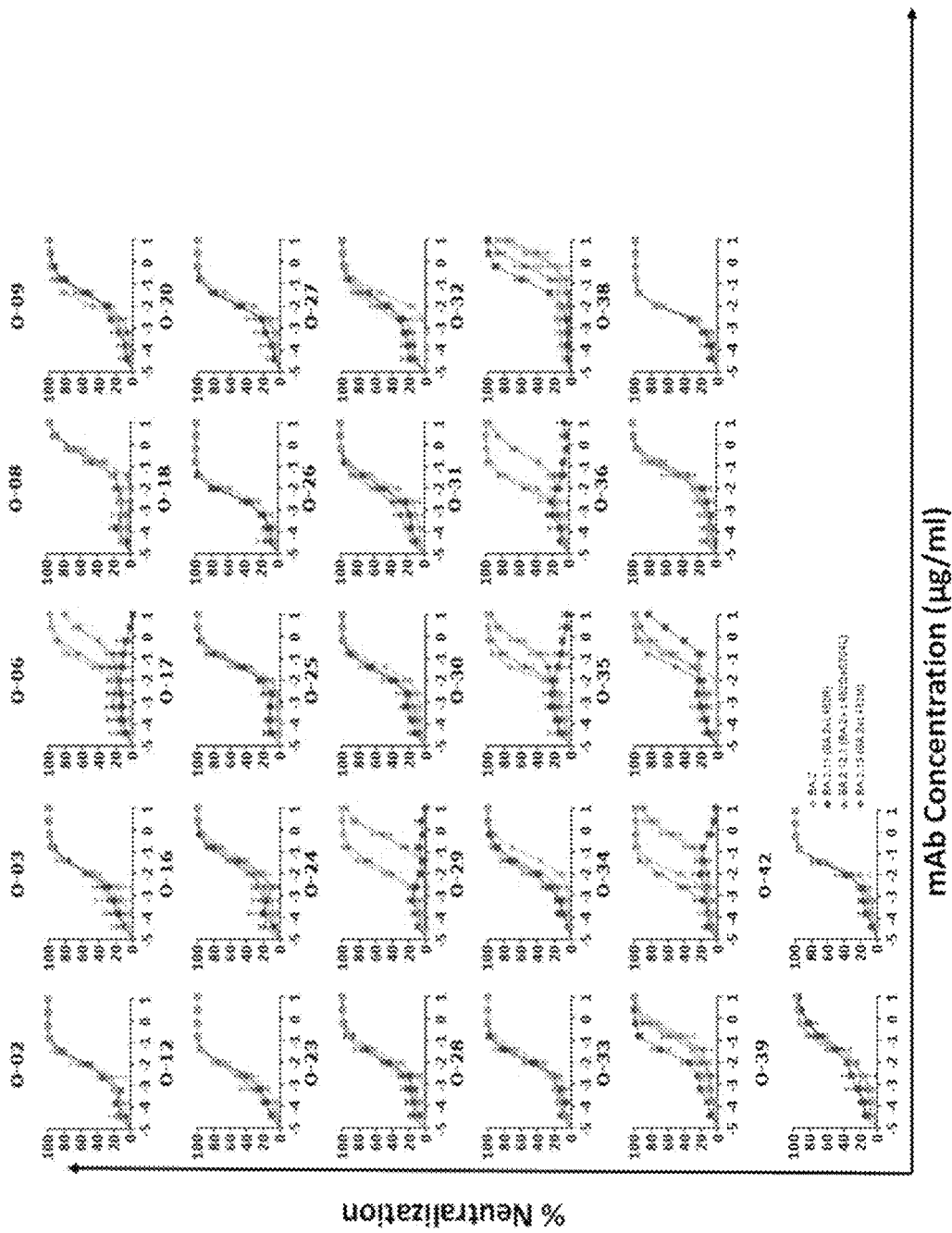
FIG. 29. Pseudoviral neutralization assays. Pseudoviral neutralization assays against Omicron monoclonal antibodies, related to Table 26 where IC50 titers are shown. Neutralization curves for a panel of 27 monoclonal antibodies made from samples taken from vaccinees infected with BA.1. Titration curves for BA.2.11, BA.2.12.1 and BA.2.13 are compared with BA.2.
Figure 30:
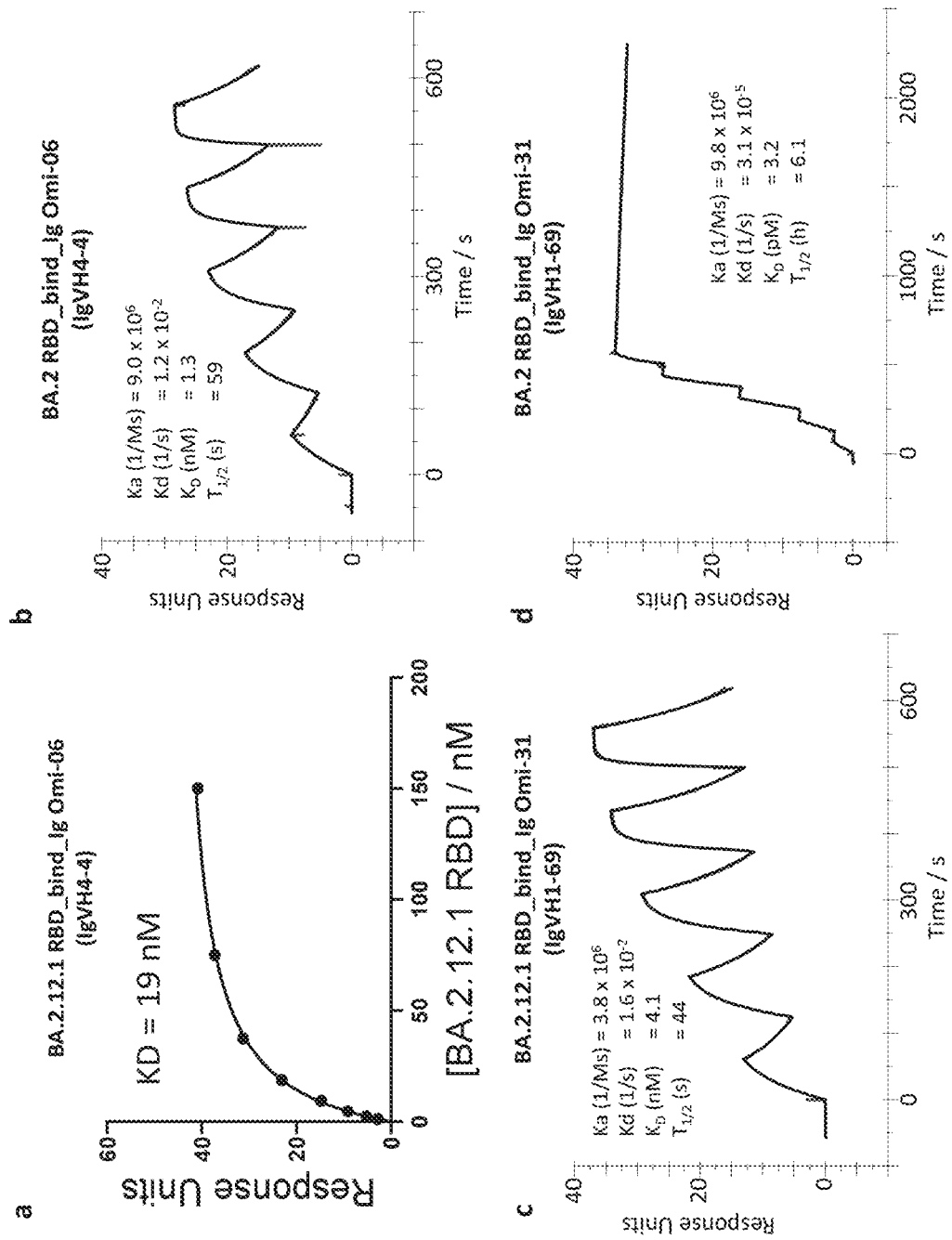
FIG. 30. Surface plasmon resonance (SPR) analysis of the interaction between BA.2.12.1 or BA.2 RBD and selected mAbs (Omi-6 and Omi-31). (a) Determination of the affinity of BA.2.12.1 RBD to Omi-6 using a 1:1 binding equilibrium analysis. (b), (c), (d) Sensorgrams (red: original binding curve; black: fitted curve) showing the interactions between BA.2.12.1 or BA.2 RBD and selected mAbs, with kinetics data shown.
Figure 31:
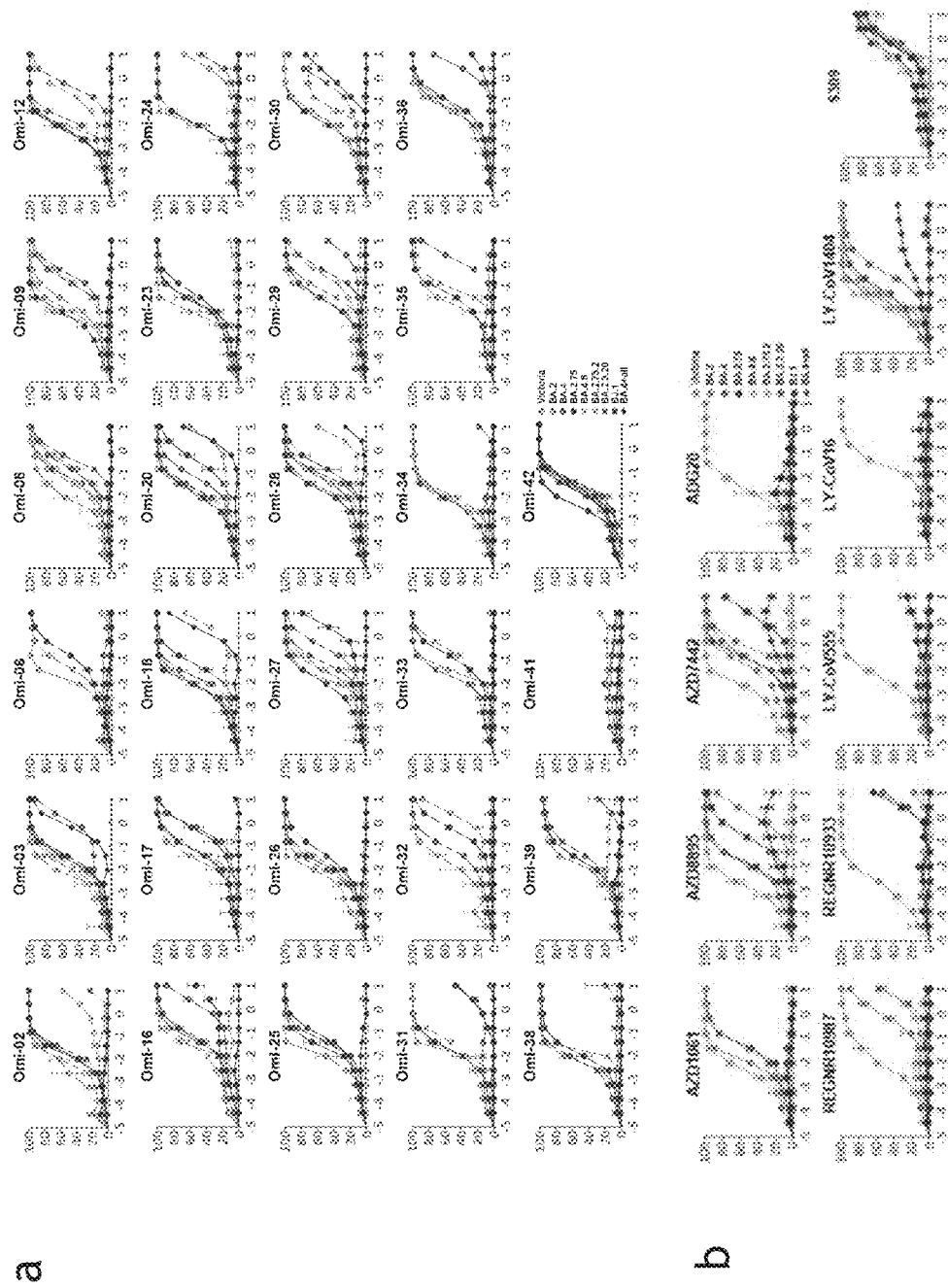
FIG. 31. Neutralization assays. Neutralization curves using lentivirus pseudotyped with the S gene of indicated BA.2 sub-lineages (A) Omi-mAb, (B) Commercial mAb. See also Table 32. The "BA.4+all" variant is a synthetic variant, designed following the assessment of different mutations that occur in the SARS-CoV-2 Omicron S gene. These mutations were combined and incorporated into an Omicron BA.4 S gene to produce the artificial S gene called "BA.4+all". This variant was created solely as an experimental tool and does not exist in nature, nor corresponds to the S gene of any circulating SARs-Cov-2 variant.
Figure 32:
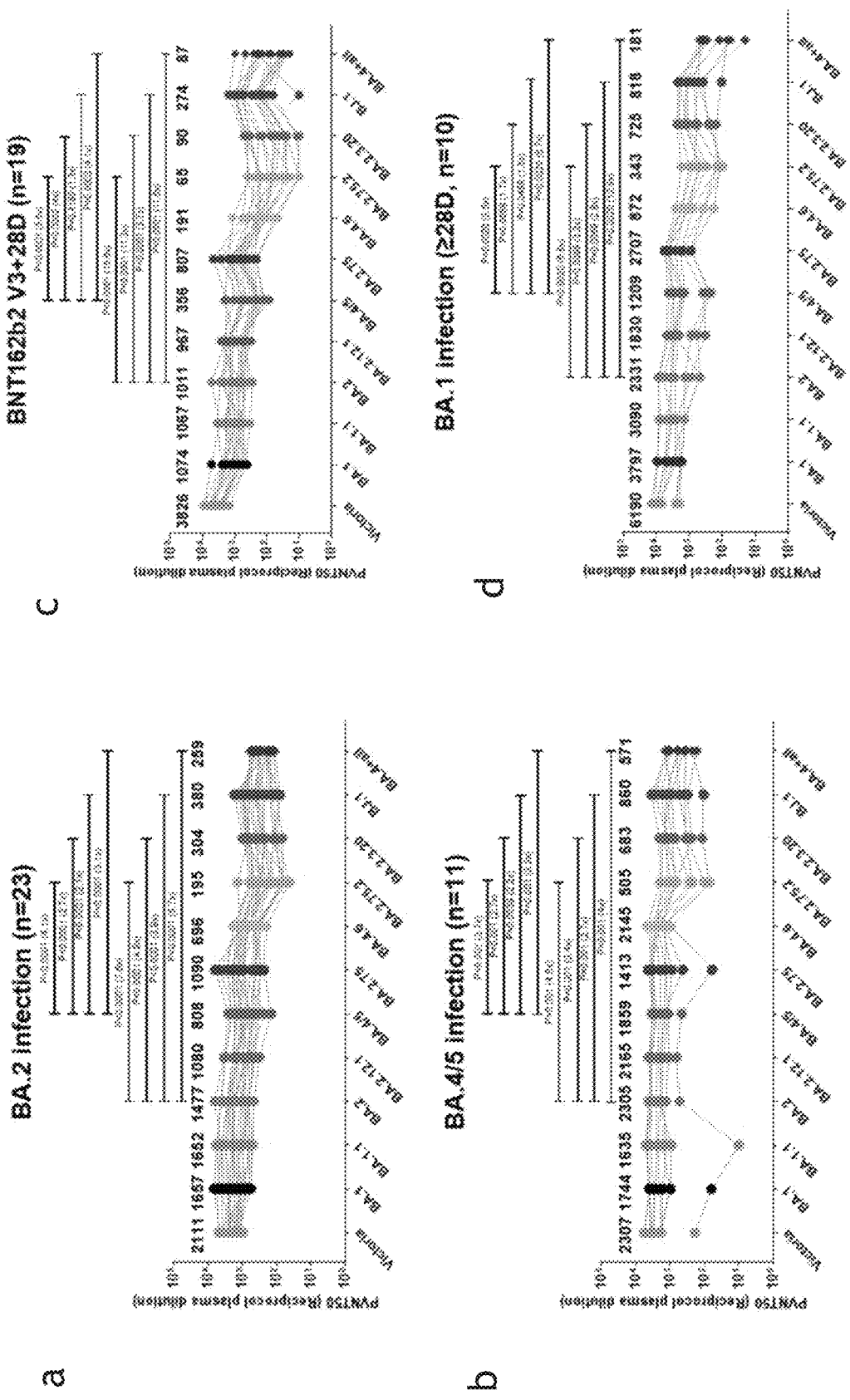
FIG. 32. Serum neutralization IC50 titres (fold dilution) of lentivirus pseudotyped with the S gene of the indicated BA.2 sub-lineages. (A) Serum obtained 28 days following the third dose of BNT162b2 vaccine or following infection with (B) BA.1 (C) BA.2 or (D) BA.4/5. Geometric mean titres are shown above each column. The Wilcoxon matched-pairs signed rank test (C and D) and Mann-Whitney test (E) were used and two-tailed P values calculated.
Figure 33:
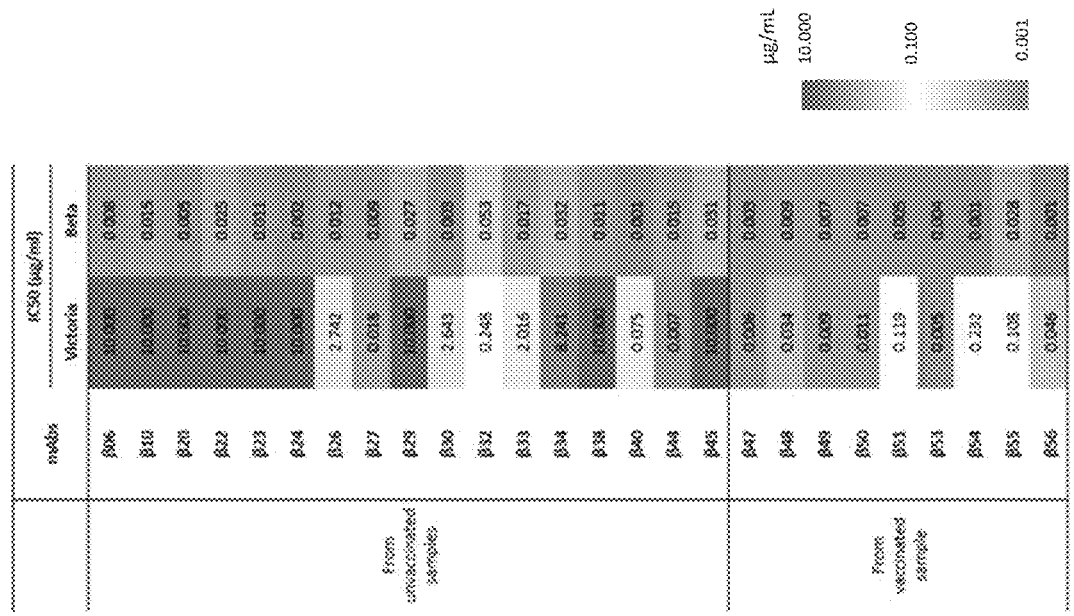
FIG. 33. Heatmaps of antibody binding. Heatmap showing the IC50 (µg/ml) of various antibodies against the Victoria and Beta strains in both vaccinated and unvaccinated samples.

To further elucidate the differential responses between BA.2 and its subvariants, pseudoviral assays were performed on a panel of potent human monoclonal antibodies (mAbs) generated from cases of BA.1 breakthrough infection (Nutalai, et al., 2022). (FIG. 29). In line with the structural observation and neutralisation results, the greatest reduction of neutralisation titre was seen for BA.2.11, followed by BA.2.12.1 and BA.2.13, neutralization of BA.2.11 was completely knocked out for 5/27 mAbs (Omi-06, Omi-24, Omi-30, Omi-31 and Omi-34). The neutralising activity against BA.2.12.1 was also reduced to varying degrees for the same set of mAbs, whilst the profiles were largely unchanged against BA.2.13. Among them, Omi-06 belongs to the IGVH4-4 family, and the other four mAbs belong to the IGVH1-69 family. Indeed, previous structural studies predicted Omi-06 and Omi-31 to be sensitive to the L452R mutation in Delta (Nutalai, et al., 2022). To confirm that the differential neutralization effects observed are directly attributable to the changes in RBD binding, surface plasmon resonance (SPR) was used to compare the binding behaviour of BA.2 and BA.2.12.1 RBD, using Omi-06 and Omi-31 as examples. As expected the affinities were reduced, for Omi-06, BA.2.12.1 RBD was 15-fold weaker binding than BA.2 and, strikingly, the binding of BA.2.12.1 RBD to Omi-31 was about 1300-fold weaker (FIG. 30).

The spike mutations in the BA.2.11, BA.2.12 and BA.2.13 variants could render it slightly more transmissible than BA.2. However, compared to BA.2, they do not appear to have acquired greater humoral immune escape in healthy vaccinees who have received three doses of the Oxford-AstraZeneca or Pfizer-BioNtech BNT162b2 vaccine. This result differs from that of vaccinees who have received the triple-dose CoronaVac vaccine, for whom significant reductions in neutralisation titres were observed (Cao, Y., et al., BA.2.12.1, BA.4 and BA.5 escape antibodies elicited by Omicron infection. Nature, 2022). Nevertheless, significant reductions in neutralisation titres were seen in vaccinees who had experienced BA.1 breakthrough infections, no matter which type of vaccine was received, perhaps partly due to partial or complete knock-out of neutralising activity of antibodies belonging to the IGVH1-69 family, many of which are sensitive the mutation at leucine 452 of the Spike RBD. This suggests that the continuously evolving Omicron sublineages are able to gain evasion from the humoral immune responses mounted by BA.1, thus implying that BA.1 Spike or RBD might not be a substantially better immunogen than that of the ancestral Wuhan strain for the development of the next-generation SARS-CoV-2 vaccine.

BA.2.12.1 Crystal Structures

The crystal structure of BA.2.12.1 RBD was determined at 2.38 Å as a ternary complex with a neutralizing Fab and nanobody (FIG. 27h-m), demonstrating that structural differences are essentially restricted to the side-chain of residue 452.

Neutralisation of BA.2.75.2 by mAbs Made Following BA.1 Infection

Neutralisation of BA.2.75.2 by a panel of mAbs made following BA.1 infection (Nutalai et al., 2022) was investigated. Attrition of mAb activity was observed against BA.2.75.2 (Table 32a). Activity of all 9 IGVH3-53/66 mAbs was reduced >100-fold with complete knock out of activity in 4/9 by BA.2.75.2. Only a single mAb, Omi-42 was unaffected by all variants showing neutralization of the BA.4+14 mutations described with IC50 of 11 ng/ml. Omi-42 is unusual as it binds at the back of the left shoulder of the RBD (Nutalai et al., 2022) in a region that has not yet been targeted for mutation, perhaps because of the relative rarity of antibodies binding in this region.

A panel of mAb that have been developed for clinical use was also tested (Dong et al., 2021; Sun and Ho, 2020; Weinreich et al., 2021; Yuan et al., 2022). Many of these were severely impacted by a number of variants. Activity of all mAbs apart from S309 was knocked out by one or more variants including Ly-CoV1404 (Westendorf et al., 2022) (see Table 32b).

Pfizer BNT162b2 Vaccine Serum Neutralization Titres for BA.2.75.2 and BA.2.3.20.

Neutralization on serum collected 28 days following a third dose of Pfizer BNT162b2 vaccine (Polack et al., 2020) and in cases infected with BA.1, BA.2 of BA.4/5 the characteristics of these subjects are described in the methods.

Using serum obtained 28 days following BNT162b, infection titres to BA.2.75.2 showed large reductions compared to BA.2 and BA.4, and were the lowest of all variants tested compared to the ancestral strain Victoria. The reduction in titres to BA.2.75.2 were in contrast to BA.2.75 which showed only a modest reduction compared to BA.2. There were also large reductions in titres to BA.2.3.20.

Using serum obtained following BA.1, BA.2 and BA.4/5 infection, there were similar large reductions in the neutralization titres of BA.2.75.2 and BA.2.3.20 compared to BA.4/5. Neutralization of the BA.4+14 RBD mutations described above were also reduced compared to BA.2 and BA.4/5 but not a great deal more than BA.2.75.2 indicating a dominant effect of mutations in BA.2.75.2

Neutralisation of BA4.6 by Serum from Vaccine Breakthrough BA.1 or BA.2 Infections Here, we study the neutralisation profile of BA.4.6 using: Pfizer-BioNtech vaccine serum, BA.1, BA.2 and BA.4/5 vaccine breakthrough immune serum, as well as panels of monoclonal antibodies. Remarkably, we show further antibody evasion of BA.4.6, providing guidance for vaccine design and the use of therapeutic monoclonals.

To evaluate the antibody evasion capacity of BA.4.6, we constructed a panel of pseudotyped lentiviruses (Di Genova, C., et al., Production, titration, neutralisation and storage of SARS-CoV-2 lentiviral pseudotypes. figshare, 2020) expressing the S gene from BA.4.6 and other SARS-CoV-2 variants together with early pandemic Wuhan related strain, Victoria, used as a control. Firstly, the neutralisation profile was examined with sera collected 4 weeks following a third dose of the Pfizer-BioNtech vaccine BNT162b2 (n=22). Compared to BA.4/5, neutralisation titres against BA.4.6 were reduced 2-fold (p<0.0001) for BNT162b2 sera (FIG. 28*a*).

The neutralisation profile for serum samples collected from vaccinees infected with BA.1 were assated. Samples (n=16) were taken ≥28 days following symptom onset. BA.2 samples (n=23) were taken ≥12 days following symptom onset or BA.4/5. Samples (n=11; all but one vaccinated) were taken >23 days following symptom onset (FIG. 28*b-d*). Neutralization titres against BA.4.6 were significantly reduced compared to BA.4/5 for both breakthrough BA.1 (1.5-fold; P=0.0006) and BA.2 (1.2-fold; P=0.0384) serum samples. Notably, BA.4.6 was able to effectively escape neutralisation by serum samples from BA.1 breakthrough infections, showing substantial reduction in titres compared to BA.1 (4.4-fold; p=0.0001), BA.2 (3-fold; p=0.0009) and BA.4/5 (1.5-fold; p=0.0006). A small non-significant increase in neutralisation titres against BA.4.6 was observed in the BA.4/5 breakthrough cohort compared to BA.4/5.

Figure 28:
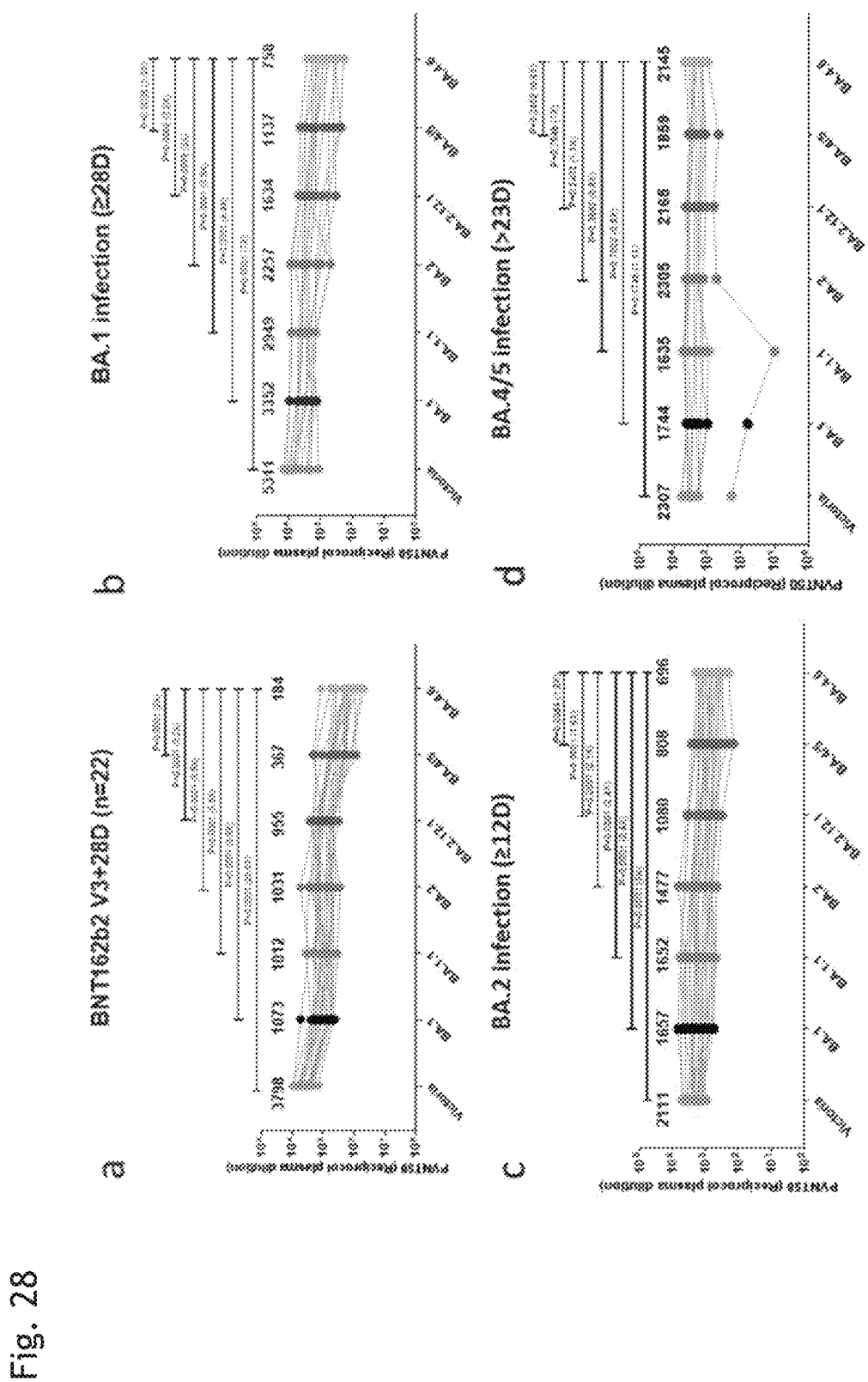
FIG. 28. Pseudoviral neutralization assays of BA.4.6 by vaccine. BA.1, BA.2, BA.4.5 immune serum (a-d) and monoclonal antibodies (e-f). IC50 values for the indicated viruses using serum obtained from vaccinees 28 days following their third dose of Pfizer BNT162b2 vaccine (n=22, a). IC50 values for the indicated viruses against serum from volunteers suffering vaccine breakthrough BA.1 (n=14, b), BA.2 (n=23, c) and BA.4/5 (n=11, d) infections. Geometric mean titres are shown above each column. The Wilcoxon matched-pairs signed rank test was used for the analysis and two-tailed P values were calculated. Neutralization curves for a panel of 28 monoclonal antibodies made from samples taken from vaccinees infected with BA.1 (e) against BA.4.6 were compared with Victoria, BA.1, BA.1.1, BA.2, BA.4/5 and BA.2.75 variants. Neutralization curves for a panel of 14 commercial monoclonal antibodies against same variants (e). IC50 values are shown in Table 29A and 29B.

To further characterise the antigenic escape properties of BA.4.6, pseudoviral assays were performed on a panel of potent human mAbs generated from BA.1 breakthrough convalescents (Nutalai et al., 2022) (FIG. 28*e*). In general, the neutralisation profiles of BA.4.6 were similar to those of BA.4/5. However, the residual activity of Omi-35 (IC50=1.687 µg/mL) was further knocked out for BA.4.6, and the potency of Omi-32 and Omi-33 against BA.4/5 (IC50=0.035 and 0.013 µg/mL, respectively) was completely impaired for BA.4.6. The loss in activity of Omi-32 could be explained by the disrupted interaction between H1 and R346 as illustrated by previous structural analysis (Nutalai et al., 2022).

Neutralisation of BA.4.6, by mAbs in Clinical Use

Finally, neutralisation activities of a number of mAbs in clinical use was evaluated (FIG. 28*f*). The potency of AZ1061/cilgavimab against BA.4/5 was completely knocked out against BA.4.6, leading to a total loss in activity of AZ7742/Evusheld (a combination of AZ1061/cilgavimab and AZ8895/tixagevimab which is already inactive against BA.4/5). The activity of S309/sotrovimab (no longer authorized by the U.S. food and drug administration FDA for COVID-19 treatment since April 2022 due to its inefficacy against BA.2) was further reduced compared to BA.2 and BA.4/5. This therefore leaves Ly-Cov1404/bebtelovimab the only option for treatment of BA.4.6.

In summary, BA.4.6 showed further reduction in neutralisation by serum from triple dose Pfizer vaccinees, as well as from BA.1 and BA.2 vaccine breakthrough convalescents compared to BA.4/5. Notably, BA.4.6 does not seem to more resistant to neutralisation by serum from BA.4/5 breakthrough infection compared to other variants. This altogether suggests that there is a strong likelihood of infection or breakthrough infection by BA.4.6 unless one has been triply vaccinated and recovered from BA.4/5 infections, which seems to provide some protection against BA.4.6.

As of September 2022, bivalent booster vaccination, combining the ancestral strain with Omicron BA.1 is being rolled out in the UK, and has been recently authorised by FDA. It remains to be seen how effective these bivalent boosters are at preventing BA.4.6 infection. Finally, BA.4.6 has further impaired the activity of Evusheld which remained active against BA.4/5; as a result, now only LY-CoV1404/bebtelovimab retains potency against all circulating SARS-CoV-2 variants.

Systematic Themes in mAb Interactions

Both Omi-3 (a representative of the IGVH3-53 gene family) and AZD8895 (IGVH1-58) make contacts with F486. Whilst the F486V mutation has little effect on Omi-3 (FIG. 10E, F, 11F), it seriously reduces the neutralization of AZD8895 and other IGVH1-58 mAbs e.g. Omi-12 (FIG. 10C, D, 11E). It is notable that whereas the numerous Omi series antibodies belonging to the closely related IGVH3-53 and IGVH3-66 gene families (9/28 in total FIG. 8A Table 21) are almost entirely resilient to the BA.4/5 changes, the large majority of antibodies from these gene families elicited against earlier variants are knocked out on BA.1 and BA.2 (Nutalai et al., 2022), consistent with selection of a subset of antibodies by breakthrough Omicron infection that are insensitive to the further BA.4/5 mutations.

The effects on antibodies with broadly similar epitopes can vary dramatically, and this is equally true for antibodies which have 452 or 486 central to their binding footprint. Thus Omi-31 (IGVH1-69) and Omi-32 (IGVH3-33), both bind in front of the right shoulder with their CDR-H3 positioned close to 452, whilst the activity of Omi-31 is abolished by L452R (as detailed above), Omi-32 is markedly enhanced (FIG. 8A, 11A, B). Similarly, Omi-25 and Omi-42 both belong to the IGVH3-9 gene family and their footprints are in the 486 region (FIG. 11C, D). Omi-25 contacts F486 thus neutralization of BA.4/5 is abolished. In contrast Omi-42 does not contact either of the mutation sites and neutralization is fully retained for BA.4/5 (FIG. 10G, H, 11D).

Fine Mapping of RBD Antibody Binding Using Competition Measurements.

A matrix of pairwise BLI measurements were used to map the potent RBD binding Omicron mAbs and several pre-pandemic mAbs of known binding position.

The method yielded a consistent prediction. The mAbs segregate into a restricted set of epitopes, which appear to be subset of the epitopes observed for the early pandemic virus, and are quite distinct from the focus seen for Beta. Essentially the antibodies cluster in two regions, one which includes the VH3-53 and VH3-66 type antibodies is towards the back of the neck/left shoulder, extending up to the top of the left shoulder, whilst the other is on the front of the neck right shoulder region, spilling towards the S309 known antibody binding site. This region is occupied by the VH1-69 family antibodies, with the exception of Omi-2 which is sited within the other cluster. mAb Omi-09 which shows reduced neutralization of Beta and Gamma positions close to residue 484 which is mutated from Glu to Lys in Beta/Gamma and Ala in Omicron. VH1-69 mAb Omi-24, 30, 31 and 34, which show reduced neutralization of Delta are placed close to residue 452 which is mutated from Leu to Arg in Delta.

Structures of Anti-Omicron Fab RBD Complexes

Structural analyses of selected potent Omicron mAbs were performed. Crystal structures were determined for complexes of Omicron BA.1 RBD with 3 different Fabs: Omi-3, 9 and 12. The complex of Omi-12 was at low resolution (5.5 Å) and so the structure of the Fab alone was determined at high resolution and rigid-body fitted to obtain the complex structure.

Omi-3 belongs to the VH3-53 gene family and demonstrates how this gene family can be adapted to be broadly neutralising against all major SARS-CoV-2 variants (but, like all the potent Omicron antibodies it does not bind SARS-CoV-1 RBD). A fundamental problem for these antibodies is that most VoC harbour mutation N501Y, which introduces a steric clash with the LC CDR1 (L1) capable of abrogating the binding of the large majority of VH3-53 containing antibodies. However, two mechanisms for displacing L1 to avoid this clash have been previously reported (Dejnirattisai et al., 2021b; Liu et al., 2021b). In mAb-222, isolated from individuals infected with early pandemic strains, a proline is inserted at residue 30 which can pack against Tyr-501 without clashes (Dejnirattisai et al., 2021b), allowing it to effectively neutralize Alpha, Beta and Gamma variants. Beta-27 uses an alternative mechanism, lengthening the HC CDR3 (H3) loop to 11 residues from the usual 9, displacing L1 to produce enough space to allow 501Y to be stabilised by main chain interactions conferring similar cross-reactivity (Liu et al., 2021b).

Omi-3 uses the same mechanism as Beta-27 for accommodating the N501Y mutation, although the Omi-3 H3 is one residue longer again. Other VH3-53 Omicron antibodies (Omi-18 and Omi-29) have H3s very similar to Beta-27 and presumably use the same mechanism. This L1 configuration is also compatible with the Y505H mutation in Omicron. However, neither 222 nor Beta-27 can effectively neutralize Omicron and this may be due to specific features of the H3 loop which makes close contact with the Q493R Omicron mutation.

Omi-9 is a one of three VH3-30 mAbs and binds across the left shoulder of the RBD. Omi-9 shows relatively weak neutralization of Beta and Gamma (FIG. 2). Other antibodies with a high degree of sequence similarity bind similarly, with H3 contacting residue 484. Although the Omi-9/BA.1 complex is lower resolution (4.2 Å), it is clear that H3 contacts residue 484 explaining the sensitivity to E484K in Beta and Gamma whilst E484A in Omicron is tolerated.

Omi-12 belongs to the VH1-58 gene family (it is the only member of this family amongst the 28 potent Omicron antibodies). Like Omi-12, several members of this gene family have a glycosylation site at residue 102 of the heavy chain CDR3, the role of which is unclear. VH1-58 antibodies elicited during early pandemic or beta virus infection show reduced ability to neutralize Omicron e.g. mAb 253, Beta-47 and Known antibody D (AZD8895) show a reduction in activity of Omicron BA.1 vs Victoria respectively.

In contrast, Omi-12 has adapted and can potently neutralize Omicron and all VoCs (FIG. 2 A, B). VH1-58 antibodies bind a left shoulder epitope, H3 contacts S477N but a mutation at this position in Iota had no effect on VH1-58 mAb neutralization using a pseudovirus assay. Additionally, mAb 253 is still able to neutralize Delta despite the T478K mutation. BA.2 with early pandemic mAb 150 (VH3-53). Detectable residual activity was observed with BA.1, BA.1.1 and BA.2 (BA.3 not tested). Two complex structures were obtained in different space groups which were very similar and provided 3 independent views of the complex. mAb 150 binds in a pose similar to that observed previously for early pandemic virus however it is translated and forms looser interactions, consistent with almost complete loss of neutralization activity. This shows the dramatic impact of the accommodating mutations found in Omi-3.

Interestingly, in BA.2 the three serine residues mutated in BA.1 RBD: S371L, S373P and S375F in the loop adjacent to the lipid binding pocket are also muted in BA.2 but the mutation at 371 is to a Phe, which means that this is likely a single point mutation from early pandemic, whereas the S317L mutation in BA.1 requires two mutations. BA.2 may therefore have features common to earlier versions of the Omicron lineage. In addition, the various views provided of this part of the structure show that it adopts a range of different conformations. This is likely due to different crystal contacts and reflects flexibility in this loop region. This is likely to have a biological function since the Ser mutation required a double codon change and may possibly affect the presentation of the RBDs. Since we have multiple views of this loop in early pandemic virus, VoC, Omicron BA.1 and BA.2 we can see that flexibility is maintained across all variants.

Modelling of Effects on Selected Commercial Known Antibodies, Early Pandemic and Beta mAb for BA.1, BA.1.1 and BA.2 Changes Known Antibody A (REGN 10987) and B (10933): Known Antibody B (REGN 10933) binds the back of the left shoulder and REGN 10987 the right shoulder. Activity of both is knocked out by the Omicron lineage apart from Known Antibody A (REGN 10987) with BA.2. Known Antibody B (REGN 10933) H2 contacts residue 493 and since Q493R is present in all Omicron strains, neutralizing activity to Omicron is universally lost. Known Antibody A (REGN 10987) H2 contacts residue 446. BA.2 uniquely lacks the G446S mutation thus regn10987 retains some neutralization capability.

Known Antibody C (AZD1061) & D (AZD8895): Known antibody C (AZD1061) and D (AZD8895) bind the back of the left shoulder and the front of the right shoulder respectively both show reduced neutralization. Known antibody C (AZD1061) is still able to neutralize BA.2 and BA.3 (~10-fold reduction) but neutralization of BA.1 is reduced >100-fold compared to Victoria and BA.1.1>1000-fold compared to Victoria. Known antibody C (AZD1061) is affected due to contacts with G446S (absent in BA.2 and BA.3) and R346K (BA.1.1) mutations (contacted by L2 and H3). Known antibody D (AZD8895) is a VH1-58 antibody and contacts residues 477 (H3) & 493 (H2) and is compromised by the S477N and Q493R mutations universally present in the Omicron lineage. Known Antibody E (AZD7442) (a combination of C and D) maintains some neutralizing activity against Omicron strains as the sum of its components.

Known Antibodies F, G and H: All of Known Antibodies F, G and H suffer considerable loss of activity against Omicron. Activity of Known Antibodies F and H are completely lost whilst the activity of Known Antibody G (ADG20) on Omicron is reduced 276-fold Known Antibodies I and J: Activity of both antibodies on the entire Omicron lineage is knocked out. Known Antibody J (Ly-CoV16) (VH3-53) makes extensive interactions with N501 and Y505 via L1 and L3 making it sensitive to mutations at these residues. Known Antibody I (Ly-CoV-555) is vulnerable to the E484K mutation in delta but likely tolerates E484A however, it also contacts residue 493, thus the universal
Omicron Q493R mutation will abrogate binding across the board.

Known Antibody K (S309): Known Antibody K (S309) retains reasonable activity across the Omicron lineage. S309 binds on the right flank with H3 contacting G339 and N343 glycans the latter close to the Serine 371, 373 and 375 mutations. The S371F mutation in BA.2 as opposed to S371L) may affect binding resulting in the slightly weaker activity with this virus.

Structure of BA.2 RBD and ACE2 Affinity

The affinity of Omicron BA.1, BA.1.1, BA.2 and BA.3 RBDs for ACE2 was measured by SPR and BLI. The affinity of BA.1 was on a par with that of the early virus, 8 nM and 7 nM respectively (binding affinities for Omicron RBDs shown in Tables 14 and 18), implying that the increased affinity imparted by S477N, Q498R and N501Y is counter balanced by other mutations in the ACE2 footprint. The affinity of BA.2 was slightly increased compared to early virus (~1.5-fold x and Y nM respectively). On the basis of earlier measurements of the contributions of individual mutations to binding affinity G496S and the triple-mutation S371L, S373P and S375F reduce binding by 2-fold and 2.2-fold respectively whereas BA.2 lacks G496S and has S371F. This may account for some of the difference but more likely the mutations in BA.2 on the edge of the ACE2 footprint may enhance binding. This is confirmed by the structure of the BA.2/ACE2.

BA.4/5 RBD and ACE2 Affinity

The affinity of BA.4/5 RBD for ACE2 was also measured by SPR (FIG. 12A-D). The affinity of BA.4/5 RBD was increased compared to the ancestral virus (Wuhan), BA.1 and BA.2 (approximately 3-fold, 3-fold and 2-fold, respectively (BA.4/5/ACE2 KD=2.4 nM) (Dejnirattisai et al., 2022; Nutalai et al., 2022), which is mainly attributed to an increase in binding half-life. Modelling of the ACE2/RBD complex suggests that the bulk of this effect comes from the electrostatic complementary between ACE2 and the RBD contributed by the L452R mutation (FIG. 12E-G).

BA.2.75 RBD and ACE2 Affinity

Figure 18:
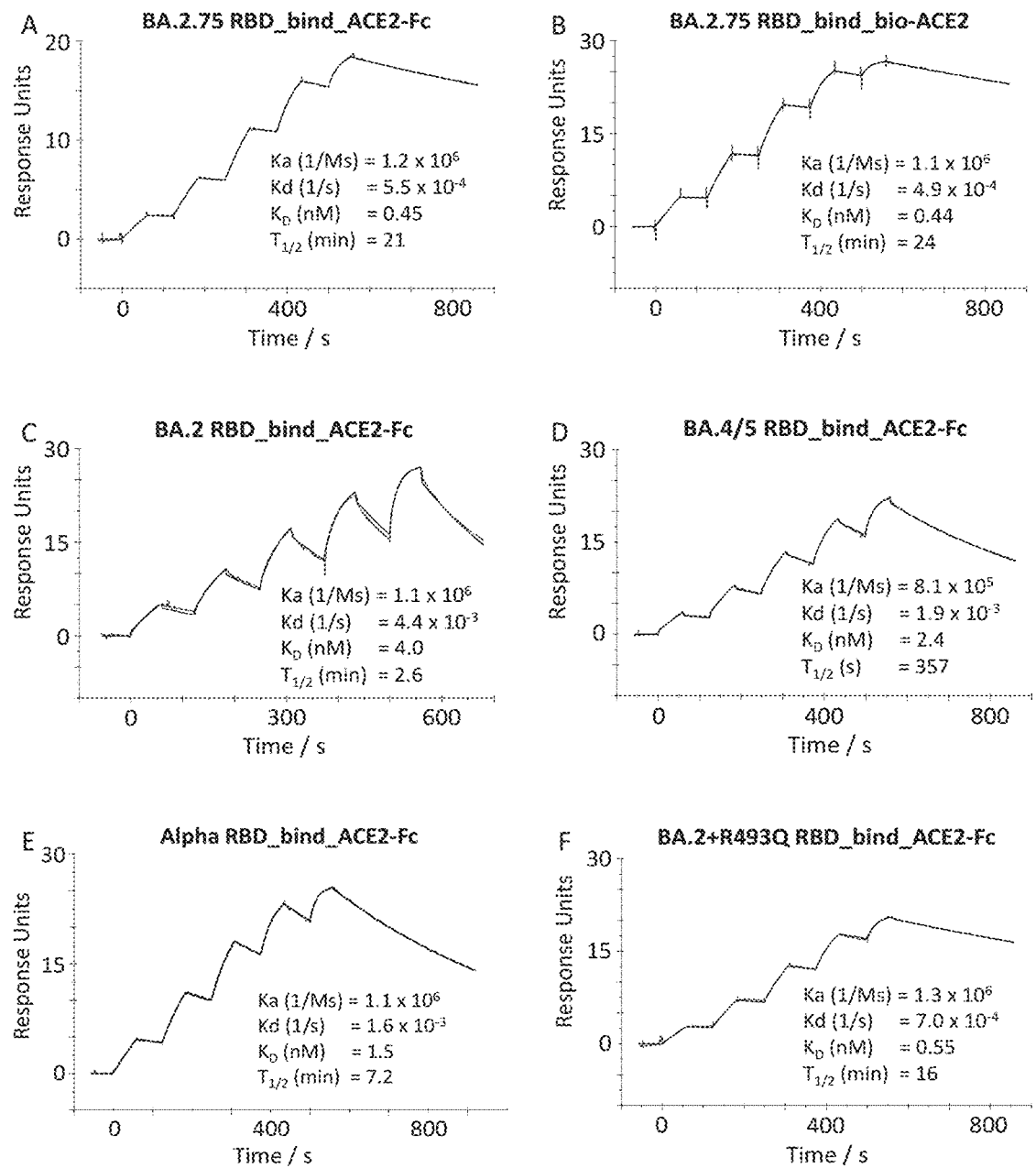
FIG. 18. ACE2/RBD affinity. SPR sensorgrams showing ACE2 binding of BA.2.75 RBD using ACE2-Fc (A) or biotinylated ACE2 as ligand (B) in comparison to binding to the RBD of BA.2 (C), BA.4/5 (D), Alpha (E) and BA.2+ R493Q (F). The data for BA.2, BA.4/5 and Alpha have been reported previously in Nutalai et al., 2022, Tuekprakhon et al., 2022 and Dejnirattisai et al., 2022, respectively.

Surface plasmon resonance (SPR) was also used to characterise the interaction between ACE2 and the BA.2.75 RBD. The off-rate was very slow, leading to a sub-nanomolar affinity (BA.2.75/ACE2 KD=0.45 nM) (FIGS. 18A, B). This represents a considerable increase in affinity compared to BA.2 (9-fold) (FIG. 18C), and even tighter than BA.4/5 (5-fold) (FIG. 18D), which binds to ACE2 with higher affinity than BA.2 (Tuekprakhon et al., 2022). BA.2.75 was found to be the strongest ACE2 binder amongst all SARS-CoV-2 VoC, including Alpha (Alpha/ACE2 KD=1.5 nM; FIG. 18E), and the first SARS-CoV-2 VoC to have a sub-nanomolar affinity.

BA.2+N460K RBD could not be expressed, but the binding affinity of BA.2+R493Q RBD to ACE2 (FIG. 18F) was also measured (KD=0.55 nM). This confirms that the R493Q reversion mutation contributes to the high affinity of BA.2.75 RBD.

Impact of Mutations in BA.2.75

The constellation of mutations in BA.2.75 compared to BA.2 have opposing effects on neutralization. The reversion mutation R493Q makes the virus easier to neutralize using vaccine serum (the vaccine contains Q493), whilst N460K reduces neutralization titres to a greater extent when expressed in isolation compared to the combination of mutations seen in BA.2.75. N460K is a novel substitution that has not appeared in preceding variants of SARS-CoV-2. This mutation was introduced into the BA.2 backbone and its impact on neutralisation by BNT162b2 serum was evaluated. Strikingly, BA.2+N460K titres were reduced 3.1-fold compared to BA.2, greater than the reduction seen with BA.2.75, and on a par with the reduction seen for BA.4/5.

Using a panel of potent mAbs derived from vaccinated individuals who suffered BA.1 vaccine breakthrough infection, it was shown that the activity of a number of mAbs belonging to the IGHV3-53/66 family are reduced or knocked out against BA.2.75. IGHV3-53/66 are the most frequently isolated mAbs in SARS-CoV-2, and bind an epitope on the 'neck'. IGHV53/66 thus forms a major public antibody response and it is no surprise that the virus has evolved to escape this response.

Although BA.2+N460K RBD could not be expressed, a previous study using yeast display showed N460K can enhance RBD binding for ACE2, an effect similar to that seen with the N501Y mutation first described in Alpha (Zahradnik et al., 2021). Thus, N460K can both enhance antibody escape and increase receptor binding affinity.

Interestingly, BA.2.75 has also acquired the R493Q reversion (Q493R was acquired in BA.1 and present in all other Omicron sublineages except BA.4/5). BA.2.75 RBD was able to bind ACE2 with 9-fold higher affinity than BA.2 and more tightly than BA.4/5 (Dejnirattisai et al., 2022; Tuekprakhon et al., 2022). This is partly contributed by the R493Q mutation. BA.2.75 RBD has the highest receptor binding affinity among all SARS-CoV-2 variants measured to date.

These data suggest there may be a fine balance between antibody escape and ACE2 receptor affinity. Mutations in BA.2.75 lead to a reduction in neutralization titres of vaccine serum compared to BA.2. Individual BA.2.75 mutations can cause greater reduction in neutralization titres compared to the full BA.2.75 S sequence, but these are balanced by the R393Q reversion mutation, which may have been selected to increase affinity to ACE2 and increase the transmissibility of BA.2.75.

BA.2.11, BA.2.12 and BA.2.13 RBD and ACE2 Affinity

To evaluate the possible change in transmissibility of the BA.2 subvariants SPR experiments were performed to analyse their RBD binding to ACE2 (FIG. 27d-g). The three RBD variants have an affinity of approximately 3 nM for ACE2, slightly higher than that of BA.2 RBD (KD=4 nM)

as previously reported (Nutalai et al., 2022). Modelling of the ACE2/RBD complex suggests that this increase in affinity may result from slightly improved complementarity between ACE2 and the RBD contributed by the mutation at leucine 452. Therefore, these variants might have a subtle advantage in transmission over BA.2.

Antigenic Cartography of BA.3 and BA.4/5

The neutralization data above has been used to place BA.3 and BA.4/5 on an antigenic map. The method used for analysis of the Delta and Omicron variants was repeated (Liu et al., 2021, "Reduced neutralization of SARS-CoV-2 B.1.617 by vaccine and convalescent serum". *Cell* 184, 4220-4236 e4213), where individual viruses were independently modelled allowing for serum specific scaling of the responses. The measured and modelled responses are shown in FIG. 13A (with 1551 observations and 340 parameters the residual error is 23%). The results are best visualized in three dimensions (see 2D projections in FIG. 13B). This shows, as expected, that the Omicron sub-lineages are clustered together but well separated from early pandemic virus and earlier VoC. Amongst the Omicron cluster BA.4/5 is the most distant from the pre-Omicron viruses.

Antigenic Cartography of BA.2.75

Figure 25:
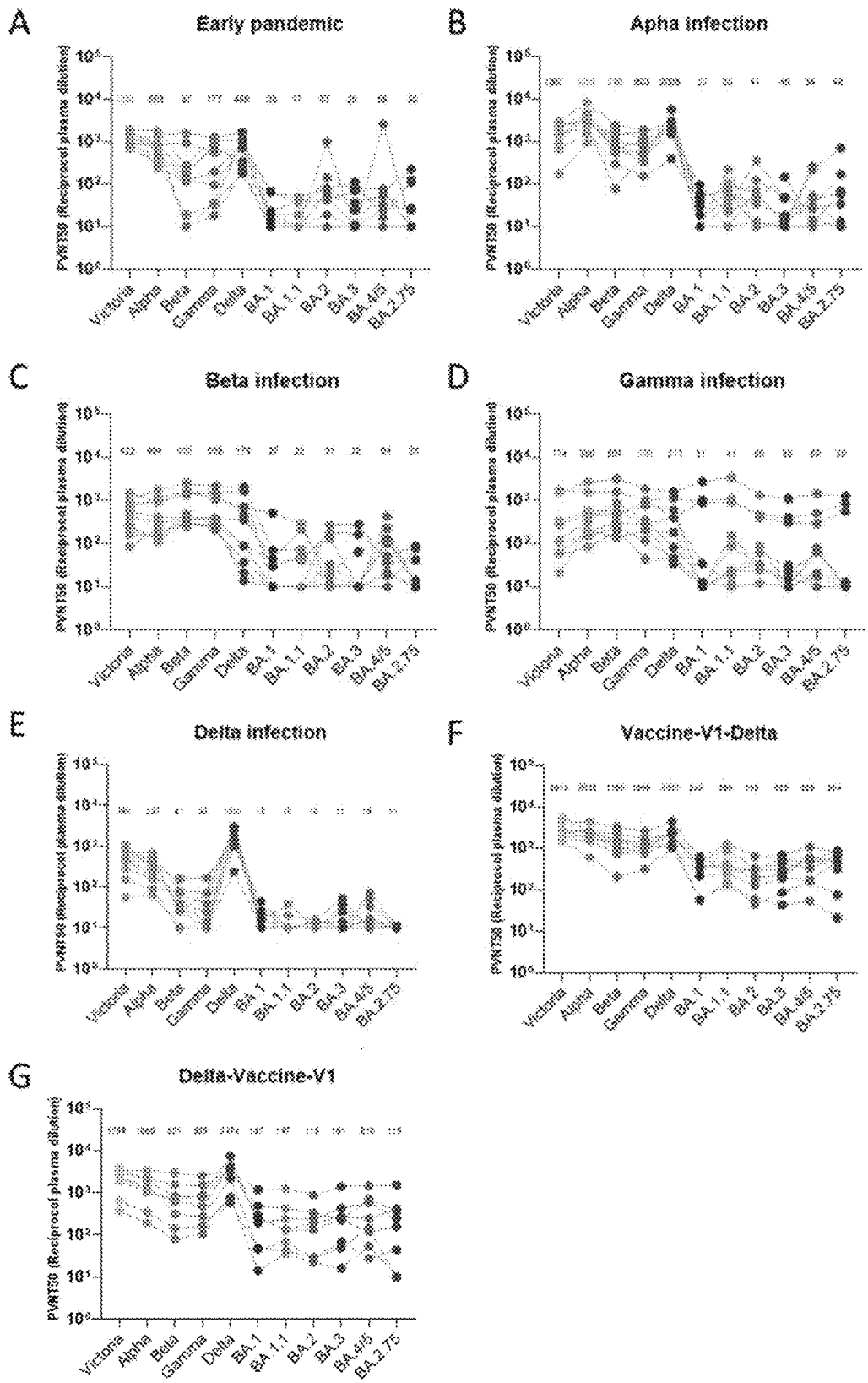
FIG. 25. Neutralization of BA.2.75 by panels of convalescent serum collected from infection with historic variants. Neutralization titres of the indicated sera against BA.2.75 and the indicated pseudoviruses. Data apart from BA.2.75 has been taken from Tuekprakhon et al., 2022.

Neutralization of BA.2.75 was tested using serum from individuals previously infected during the course of the pandemic. These included serum obtained early in the pandemic (before the emergence of Alpha) together with serum obtained following Alpha, Beta, Gamma, Delta, BA.1 and BA.2 infection (FIG. 25). As expected, BA.2.75 neutralization titres were lower than the homologous infecting strain (e.g. Alpha serum on Alpha virus). Most striking however was the complete loss of BA.2.75 neutralization using Delta serum (zero samples achieved 50% neutralization at 1/20 dilution). However, titres to BA.2.75 were much higher in cases who had been vaccinated before or after Delta infection.

Figure 22:
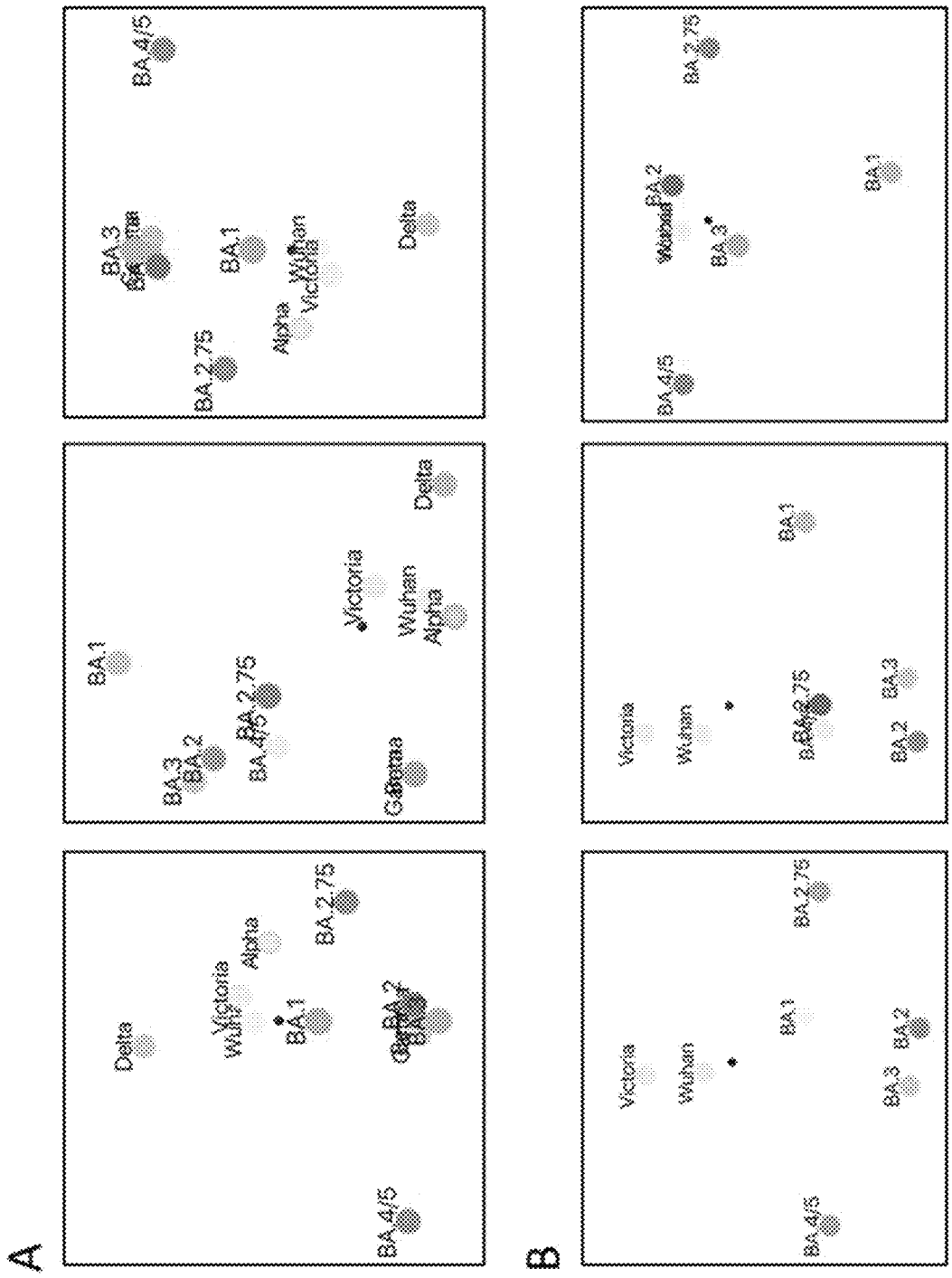
FIG. 22. Antigenic mapping. (A) Orthogonal views of the antigenic map showing BA.2.75 in the context of the positions of previous VoC and BA.1, BA.1.1, BA.1 and BA.2, calculated from pseudovirus neutralisation data. Distance between two positions is proportional to the reduction in neutralisation titre when one of the corresponding strains is challenged with serum derived by infection by the other. No scale is provided since the figures are projections of a three-dimensional distribution, however the variation can be calibrated by comparison with (i) BA.1 to BA.2 which is 2.93× reduced and (ii) BA.2 to BA.4/5 which is 3.03× reduced. (B) As (A) but including only Omicron sublineages and early pandemic viruses to allow more accurate projection of this subset into three-dimensions. Note that responses of these viruses against all sera were included in the calculations.

These data were used to place BA.2.75 onto a three dimensional antigenic map using the method previously reported in Tuekprakhon et al., 2022 (FIGS. 22A, B). Initially all VoC were included (FIG. 22A); this showed that BA.2.75 was grouped with the other Omicron viruses, which segregated into one hemisphere of the 3D plot. BA.2.75 appeared well separated from other Omicron sub-lineages and especially from BA.4/5. It is also notable that BA.2.75 and Delta are diametrically opposed in the diagram, emphasizing the antigenic distance between these two viruses. Since the data are higher dimensional, the 3D projection is likely to distort the true distances and so were calculated for only the Omicron and early pandemic viruses (but retaining the full serology information for each of these). The results are shown in FIG. 22B and recapitulate the major features of the full plot, but allow the Omicron sublineages to distribute more broadly in 3D space. Remarkably, if the clustered early pandemic and BA.2/BA.3 pairs are merged then the points are distributed as a trigonal bi-pyramid maximising their separation, consistent with antigenic escape being a significant factor in their evolution.

Example 3. Examples of Antibodies that May be Created by Swapping the Light Chain Between Antibodies Derived from the Same Heavy Chain V-Gene As discussed in the detailed description above, antibodies derived from the same heavy chain V-gene may swap light chains to result in an antibody comprising the heavy chain variable region of a first antibody and a light chain variable region of a second antibody, and such new antibodies may have improved neutralisation and/or other characteristics when compared to the 'parent' antibodies.

Tables 4 to 12 provide examples of such antibodies that may be creased by swapping the light chain between antibodies derived from the same heavy chain V-gene. Table 17 provides information as to the heavy chain and light chain V-genes from which the 28 Omicron-specific mAbs are derived, together with their specificity to the RBD or NTD of the spike protein of SARS-CoV-2.

Example 4. Materials and Methods

Viral Stocks

SARS-CoV-2/human/AUS/VIC01/2020 (Caly et al, 2020), Alpha and Beta were provided by Public Health England, Gamma cultured from a throat swab from Brazil, Delta was a gift from Wendy Barclay and Thushan de Silva, from the UK G2P genotype to phenotype consortium and Omicron was grown from a positive throat swab (IRAS Project ID: 269573, Ethics Ref: 19/NW/0730. Briefly, VeroE6/TMPRSS2 cells (NIBSC) were maintained in Dulbecco's Modified Eagle Medium (DMEM) high glucose supplemented with 1% fetal bovine serum, 2 mM Glutamax, 100 IU/ml penicillin-streptomycin and 2.5 ug/ml amphotericin B, at 37° C. in the presence of 5% CO2 before inoculation with 200 ul of swab fluid. Cells were further maintained at 37° C. with daily observations for cytopathic effect (CPE). Virus containing supernatant were clarified at 80% CPE by centrifugation at 3,000 r.p.m. at 4° C. before being stored at −80° C. in single-use aliquots. Viral titres were determined by a focus-forming assay on Vero CCL-81 cells (ATCC).

Sequencing of the Omicron isolate shows the expected consensus S gene changes (A67V, Δ69-70, T95I, G142D/Δ143-145, Δ211/L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F), an intact furin cleavage site and a single additional mutation A701V.

Cells were infected with the SARS-CoV-2 virus using an MOI of 0.0001.

Virus containing supernatant were harvested at 80% CPE and spun at 3000 rpm at 4° C. before storage at −80° C. Viral titres were determined by a focus-forming assay on Vero cells. Victoria passage 5, Alpha passage 2 and Beta passage 4 stocks Gamma passage 1, Delta passage 3 and Omicron passage 1 were sequenced to verify that they contained the expected spike protein sequence and no changes to the furin cleavage sites.

Bacterial Strains and Cell Culture

Vero (ATCC CCL-81) and VeroE6/TMPRSS2 cells were cultured at 37° C. in Dulbecco's Modified Eagle medium (DMEM) high glucose (Sigma-Aldrich) supplemented with 10% fetal bovine serum (FBS), 2 mM GlutaMAX (Gibco, 35050061) and 100 U/ml of penicillin-streptomycin. Human mAbs were expressed in HEK293T cells cultured in Ultra-DOMA PF Protein-free Medium (Cat #12-727F, LONZA) at 37° C. with 5% $CO_2$. HEK293T (ATCC CRL-11268) cells were cultured in DMEM high glucose (Sigma-Aldrich) supplemented with 10% FBS, 1% 100× Mem Neaa (Gibco) and 1% 100× L-Glutamine (Gibco) at 37° C. with 5% $CO_2$. To express RBD, RBD variants and ACE2, HEK293T cells were cultured in DMEM high glucose (Sigma) supplemented with 2% FBS, 1% 100× Mem Neaa and 1% 100× L-Glutamine at 37° C. for transfection. Omicron RBD and human mAbs were also expressed in HEK293T (ATCC CRL-11268) cells cultured in FreeStyle 293 Expression Medium (ThermoFisher, 12338018) at 37° C. with 5% $CO_2$. E. coli DH5a bacteria were used for transformation and large-scale preparation of plasmids. A single colony was picked and cultured in LB broth at 37° C. at 200 rpm in a shaker overnight.

Sera from Pfizer Vaccinees

Pfizer vaccine serum was obtained from volunteers who had received either one or two doses of the BNT162b2 vaccine. Vaccinees were Health Care Workers, based at Oxford University Hospitals NHS Foundation Trust, not known to have prior infection with SARS-CoV-2 and were enrolled in the OPTIC Study as part of the Oxford Translational Gastrointestinal Unit GI Biobank Study 16/YH/0247 [research ethics committee (REC) at Yorkshire & The Humber—Sheffield] which has been amended for this purpose on 8 Jun. 2020. The study was conducted according to the principles of the Declaration of Helsinki (2008) and the International Conference on Harmonization (ICH) Good Clinical Practice (GCP) guidelines. Written informed consent was obtained for all participants enrolled in the study. Participants were studied after receiving two doses of, and were sampled approximately 28 days (range 25-38), 180 days (range 178-221) and 270 days (range 243-273) after receiving two doses of Pfizer/BioNtech BNT162b2 mRNA Vaccine, 30 micrograms, administered intramuscularly after dilution (0.3 mL each), 17-28 days apart, then approximately 28 days (range 25-56) after receiving a third "booster dose of BNT162B2 vaccine. The mean age of vaccinees was 37 years (range 22-66), 21 male and 35 female.

Plasma from Early Pandemic and Alpha Cases

Participants from the first wave of SARS-CoV2 in the U.K. and those sequence confirmed with B.1.1.7 lineage in December 2020 and February 2021 were recruited through three studies: Sepsis Immunomics [Oxford REC C, reference: 19/SC/0296]), ISARIC/WHO Clinical Characterisation Protocol for Severe Emerging Infections [Oxford REC C, reference 13/SC/0149] and the Gastro-intestinal illness in Oxford: COVID sub study [Sheffield R E C, reference: 16/YH/0247]. Diagnosis was confirmed through reporting of symptoms consistent with COVID-19 and a test positive for SARS-CoV-2 using reverse transcriptase polymerase chain reaction (RT-PCR) from an upper respiratory tract (nose/throat) swab tested in accredited laboratories. A blood sample was taken following consent at least 14 days after symptom onset. Clinical information including severity of disease (mild, severe or critical infection according to recommendations from the World Health Organisation) and times between symptom onset and sampling and age of participant was captured for all individuals at the time of sampling. Following heat inactivation of plasma/serum samples they were aliquoted so that no more than 3 freeze thaw cycles were performed for data generation.

Sera from Beta, Gamma and Delta and BA.1 Infected Cases

Beta and Delta samples from UK infected cases were collected under the "Innate and adaptive immunity against SARS-CoV-2 in healthcare worker family and household members" protocol affiliated to the Gastro-intestinal illness in Oxford: COVID sub study discussed above and approved by the University of Oxford Central University Research Ethics Committee. All individuals had sequence confirmed Beta/Delta infection or PCR-confirmed symptomatic disease occurring whilst in isolation and in direct contact with Beta/Delta sequence-confirmed cases. Additional Beta infected serum (sequence confirmed) was obtained from South Africa. At the time of swab collection patients signed an informed consent to consent for the collection of data and serial blood samples. The study was approved by the Human Research Ethics Committee of the University of the Witwatersrand (reference number 200313) and conducted in accordance with Good Clinical Practice guidelines. Gamma samples were provided by the International Reference Laboratory for Coronavirus at FIOCRUZ (WHO) as part of the national surveillance for coronavirus and had the approval of the FIOCRUZ ethical committee (CEP 4.128.241) to continuously receive and analyse samples of COVID-19 suspected cases for virological surveillance. Clinical samples were shared with Oxford University, UK under the MTA IOC FIOCRUZ 21-02.

Sera from BA.1 Infected Cases, Study Subjects

Following informed consent, individuals with omicron BA.1 were co-enrolled into the ISARIC/WHO Clinical Characterisation Protocol for Severe Emerging Infections [Oxford REC C, reference 13/SC/0149] and the "Innate and adaptive immunity against SARS-CoV-2 in healthcare worker family and household members" protocol affiliated to the Gastro-intestinal illness in Oxford: COVID sub study [Sheffield R E C, reference: 16/YH/0247] further approved by the University of Oxford Central University Research Ethics Committee. Diagnosis was confirmed through reporting of symptoms consistent with COVID-19 or a positive contact of a known Omicron case, and a test positive for SARS-CoV-2 using reverse transcriptase polymerase chain reaction (RT-PCR) from an upper respiratory tract (nose/throat) swab tested in accredited laboratories and lineage sequence confirmed through national reference laboratories. A blood sample was taken following consent at least 10 days after PCR test confirmation. Clinical information including severity of disease (mild, severe or critical infection according to recommendations from the World Health Organisation) and times between symptom onset and sampling and age of participant was captured for all individuals at the time of sampling.

AstraZeneca-Oxford Vaccine Study Procedures and Sample Processing

Full details of the randomized controlled trial of ChAdOx1 nCoV-19(AZD1222), were previously published (PMID: 33220855/PMID: 32702298). These studies were registered at ISRCTN (15281137 and 89951424) and ClinicalTrials.gov (NCT04324606 and NCT04400838). A copy of the protocols was included in previous publications (Folegatti et al., 2020, Lancet 396, 467-478).

Data from vaccinated volunteers who received two vaccinations are included in the Examples. Vaccine doses were either $5\times10^{10}$ viral particles (standard dose; SD/SD cohort n=21) or half dose as their first dose (low dose) and a standard dose as their second dose (LD/SD cohort n=4). The interval between first and second dose was in the range of 8-14 weeks. Blood samples were collected and serum separated on the day of vaccination and on pre-specified days after vaccination e.g. 14 and 28 days after boost.

Focus Reduction Neutralization Assay (FRNT)

The neutralization potential of Ab was measured using a Focus Reduction Neutralization Test (FRNT), where the reduction in the number of the infected foci is compared to a negative control well without antibody. Briefly, serially diluted Ab or plasma was mixed with SARS-CoV-2 strains and incubated for 1 hr at 37° C. The mixtures were then transferred to 96-well, cell culture-treated, flat-bottom microplates containing confluent Vero cell monolayers in duplicate and incubated for a further 2 hrs followed by the addition of 1.5% semi-solid carboxymethyl cellulose (CMC) overlay medium to each well to limit virus diffusion. A focus forming assay was then performed by staining Vero cells with human anti-NP mAb (mAb206) followed by peroxidase-conjugated goat anti-human IgG (A0170; Sigma). Finally, the foci (infected cells) approximately 100 per well in the absence of antibodies, were visualized by adding TrueBlue Peroxidase Substrate. Virus-infected cell foci were counted on the classic AID EliSpot reader using AID ELISpot software. The percentage of focus reduction was calculated and IC50 was determined using the probit program from the SPSS package.

Plasmid Construction and Pseudotyped Lentiviral Particles Production

Pseudotyped lentivirus expressing SARS-CoV-2 S proteins from ancestral strain (Victoria, S247R), BA.1, BA.1.1, and BA.2 were constructed as described before (Nie, Jianhui, et al. "Establishment and validation of a pseudovirus neutralization assay for SARS-CoV-2." *Emerging microbes & infections* 9.1 (2020):680-686. Liu, Chang, et al. "Reduced neutralization of SARS-CoV-2 B. 1.617 by vaccine and convalescent serum." *Cell* 184.16 (2021): 4220-4236), with some modifications. Briefly, synthetic codon-optimized SARS-CoV-2 BA.1 and BA.2 were custom synthesized by GeneArt (Thermo Fisher Scientific GENEART). The insert fragments and pcDNA3.1 vector were cloned by using Gibson assembly. Victoria (S247R) construct is as previously described in Liu, Chang, et al. "Reduced neutralization of SARS-CoV-2 B. 1.617 by vaccine and convalescent serum." *Cell* 184.16 (2021): 4220-4236. To construct BA.1.1, mutagenic primers of R346K (R346K_F 5'-GTGTTCAATGCCACCAAAT-TCGCCAGCGTGTAC-3' and R346K_R5'-GTACACGCTGGCGAATTTGGTGGCATTGAACAC-3') were PCR amplified by using BA.1 construct as a template, together with two primers of pcDNA3.1 vector (pcDNA3.1_BamHI_F 5'-GGATCCATGTTCCTGCTGAC-CACCAAGAG-3' and pcDNA3.1_Tag_S_EcoRI_R5'-GAATTCTCACTTCTCGAACTGAGGGTGGC-3'), purified by using QIAquick Gel Extraction Kit (QIAGEN) and followed by Gibson assembly. All constructs were verified by Sanger sequencing after plasmid isolation using QIAGEN Miniprep kit (QIAGEN).

A similar strategy was applied for BA.3 and BA.4/5, briefly, BA.3 mutations were constructed using the combination fragments from BA.1 and BA.2. The resulting mutations are as follows. The resulting mutations are as follows, A67V, Δ69-70, T95I, G142D, Δ143-145, Δ211/L212I, G339D, S371F, S373P, S375F, D405N, K417N, N440K, G446S, S477N, T478K, E484A, Q493R, Q498R, N501Y, Y505H, D614G, H655Y, N679K, P681H, N764K, D796Y, Q954H, and N969K. Although BA.4/5 S protein shared some amino acid mutations with BA.2 (Nutalai et al., 2022), to generate BA.4/5 mutations were added Δ69-70, L452R, F486V, and R498Q. The resulting S gene-carrying pcDNA3.1 was used for generating pseudoviral particles together with the lentiviral packaging vector and transfer vector encoding luciferase reporter. Integrity of constructs was sequence confirmed.

The same method was also used to construct BA.2.12.1, and BA.2.75, by adding more mutations into the BA.2 construct. To generate BA.2.75, K147E, W152R, F157L, I210V, G275S, G446S and N460K were added into a BA.2 backbone. 339D was also changed in BA.2 S into 339H, and 493R was reversed in BA.2 to 493Q as in the ancestral strain. To test single mutation impact, D339H, G446S, N460K and R493Q were introduced individually into a BA.2 backbone. The resulting pcDNA3.1 plasmid carrying S gene was used for generating pseudoviral particles together with the lentiviral packaging vector and transfer vector encoding a Pseudoviral Neutralization Test The details of pseudoviral neutralization test were described previously (Liu, Chang, et al. "Reduced neutralization of SARS-CoV-2 B. 1.617 by vaccine and convalescent serum." *Cell* 184.16 (2021): 4220-4236) with some modifications. Briefly, the neutralizing activity of potent monoclonal antibodies (mAbs) generated from donors who had recovered from Omicron- and Beta-infection as well as those who were infected during the early pandemic in UK were performed against Victoria, Omicron-BA.1, BA.1.1, BA.2, BA.2.11, BA.2.12.1, BA.2.13, BA.3, BA.4.6, BA.4/5, BA.2.75 and BA.2+N460K. A four-fold serial dilution of each mAb was incubated with pseudoviral particles at 37° C., 5% $CO_2$ for 1 hr. The stable HEK293T/17 cells expressing human ACE2 were then added to the mixture at $1.5 \times 10^4$ cells/well. At 48 hr. post transduction, culture supernatants were removed and 50 µL of 1:2 Bright-Glo™ Luciferase assay system (Promega, USA) in 1×PBS was added to each well. The reaction was incubated at room temperature for 5 mins and the firefly luciferase activity was measured using CLARIOstar® (BMG Labtech, Ortenberg, Germany). The percentage of mAb neutralization was calculated relative to the control. Probit analysis was used to estimate the value of dilution that inhibits half of the maximum pseudotyped lentivirus infection (PVNT50).

To determine the neutralizing activity of convalescent plasma/serum samples or vaccine sera, 3-fold serial dilutions of samples were incubated with the pseudoviral particles for 1 hr and the same strategy as mAb was applied.

DNA Manipulations

Cloning was done by using a restriction-free approach (Peleg and Unger, 2014). Mutagenic megaprimers were PCR amplified (KAPA HiFi HotStart ReadyMix, Roche, Switzerland, cat. KK3605), purified by using NucleoSpin® Gel and PCR Clean-up kit (Nacherey-Nagel, Germany, REF 740609.50) and cloned into pJYDC1 (Addgene ID: 162458) (Zahradnik et al., 2021a). Parental pJYDC1 molecules were cleaved by DpnI treatment (1 h, NEB, USA, cat. R0176) and the reaction mixture was electroporated into *E. coli* Cloni® 10G cells (Lucigen, USA). The correctness of mutagenesis was verified by sequencing.

Cloning of Spike and RBD

Expression plasmids of wild-type and Omicron BA.1 spike and RBD of BA.1 and BA.2 were constructed encoding for human codon-optimized sequences from BA.1 (EPI_ISL_6640917) and BA.2 (EPI_ISL_6795834.2). The constructs of Wild-type and BA.1 Spike and RBD plasmids are the same as previously described (Dejnirattisai, Wanwisa, et al. "The antigenic anatomy of SARS-CoV-2 receptor binding domain." *Cell* 184.8 (2021): 2183-2200). A synthetic codon-optimized RBD fragment of BA.2 was used as a template and construct was amplified by PCR and cloned into pNEO vector as previously described (Dejnirattisai et al., 2021a; Supasa et al., 2021; Zhou et al., 2021). The construct was verified by Sanger sequencing.

To generate His-tagged constructs of BA.4/5 RBD, site-directed PCR mutagenesis was performed using the BA.2 RBD construct as the template (Nutalai et al., 2022), with the introduction of L452R, F486V and R493Q mutations. The gene fragment was amplified with pNeoRBD333OmiIF (5'-CGTTGCGTAGCTGAAACCGGTCATCACCATCAC-CATCACACC AATCTGTGCCCITTCGAC-3') and pNeoRBD333_R (5'-GTGATGGTGGTGCTTGGTACCT TATTACTTCT TGCCGCACACGGTAGC-3'), and cloned into the pNeo vector (Supasa et al., 2021, "Reduced neutralization of SARS-CoV-2 B.1.1.7 variant by convalescent and vaccine sera", *Cell* 184, 2201-2211 e2207). To generate the BA.4/5 RBD construct containing a BAP-His tag, the gene fragment was amplified with RBD333_F (5'-GCGTAGCTGAAACCGGCACCAATCTGTGC CCTTTCGAC-3') and RBD333_BAP_R (5'-GTCAT-TCAGCAAGCCTCTTCTGCCGCACACGG TAGC-3'), and cloned into the pOPINTTGneo-BAP vector (Huo et al., 2020, "Neutralizing nanobodies bind SARS-CoV-2 spike RBD and block interaction with ACE2". *Nature structural & molecular biology* 27, 846-854). Cloning was performed using the ClonExpress II One Step Cloning Kit (Vazyme). The Constructs %% ere verified by Sanger sequencing after plasmid isolation using QIAGEN Miniprep kit (QIAGEN).

To generate the BA.2.75 RBD construct, site-directed PCR mutagenesis was performed using the BA.2 Spike construct as the template (Nutalai et al., 2022), with the introduction of D339H, G446S, N460K and R493Q mutations suing primers listed in FIG. 26; the gene fragment was amplified with D339H_pNeoF and RBD333_BAP_R (FIG. 26), and cloned into the pOPINITGneo-BAP vector (Huo et al., 2020 "Neutralizing nanobodies bind SARS-CoV-2 spike RBD and block interaction with ACE2." *Nature structural & molecular biology* 27, 846-854). To generate the BA.2+ R493Q RBD construct, site-directed PCR mutagenesis was performed using the BA.2 Spike construct as the template, with the introduction of the R493Q mutation using primers listed in FIG. 26; the gene fragment was amplified with pNeoRBD3330mi_F and BD333_BAP_R, and cloned into the pNeo vector (Supasa et al., 2021 "Reduced neutralization of SARS-CoV-2 B.1.1.7 variant by convalescent and vaccine sera." *Cell* 184, 2201-2211 e2207). Cloning was performed using the ClonExpress II One Step Cloning Kit (Vazyme). The Constructs were verified by Sanger sequencing after plasmid isolation using QIAGEN Miniprep kit (QIAGEN).

Production of RBDs

Plasmids encoding RBDs were transfected into Expi293F™ Cells (ThermoFisher) by PEI, cultured in FreeStyle™ 293 Expression Medium (ThermoFisher) at 30° C. with 8% CO2 for 4 days. To express biotinylated RBDs, the RBD-BAP plasmid was co-transfected with pDisplay-BirA-ER (Addgene plasmid 20856; coding for an ER-localized biotin ligase), in the presence of 0.8 mM D-biotin (Sigma-Aldrich).

Production of BA.2.75 RBDs

Plasmids encoding RBDs were transfected into Expi293F™ Cells (ThermoFisher) by PEI, cultured in FreeStyle™ 293 Expression Medium (ThermoFisher) at 37° C. for 1 day followed by 30° C. for 3 days with 8% CO2. To express biotinylated RBDs, the RBD-BAP plasmid was co-transfected with pDisplay-BirA-ER (Addgene plasmid 20856; coding for an ER-localized biotin ligase), in the presence of 0.8 mM D-biotin (Sigma-Aldrich). The conditioned medium was diluted 1:2 into binding buffer (50 mM sodium phosphate, 500 mM sodium chloride, pH 8.0). RBDs were purified with a 5 mL HisTrap nickel column (GE Healthcare) through His-tag binding, followed by a Superdex 75 10/300 GL gel filtration column (GE Healthcare) in 10 mM HEPES and 150 mM sodium chloride.

Protein Production

Protein expression and purification were conducted as described previously (Dejnirattisai et al., 2021a; Zhou et al., 2020). Briefly, plasmids encoding proteins were transiently expressed in HEK293T (ATCC CRL-11268) cells. The conditioned medium was concentrated using a QuixStand benchtop system. His-tagged Omicron RBD were purified with a 5 mL HisTrap nickel column (GE Healthcare) and further polished using a Superdex 75 HiLoad 16/60 gel filtration column (GE Healthcare). Twin-strep tagged Omicron spike was purified with Strep-Tactin XT resin (IBA lifesciences). ~4 mg of ACE2 was mixed with homemade His-tagged 3C protease and DTT (final concentration 1 mM). After incubated at 4° C. for one day, the sample was flown through a 5 mL HisTrap nickel column (GE Healthcare). His-tagged proteins were removed by the nickel column and purified ACE2 was harvested and concentrated.

IgG mAbs and Fab Purification

To purify full length IgG mAbs, supernatants of mAb expression were collected and filtered by a vacuum filter system and loaded on protein A/G beads over night at 4° C. Beads were washed with PBS three times and 0.1 M glycine pH 2.7 was used to elute IgG. The eluate was neutralized with Tris-HCl pH 8 buffer to make the final pH=7. The IgG concentration was determined by spectro-photometry and buffered exchanged into PBS. To express and purify Fabs 158 and EY6A, heavy chain and light chain expression plasmids of Fab were co-transfected into HEK293T cells by PEI. After cells cultured for 5 days at 37° C. with 5% CO2, culture supernatant was harvested and filtered using a 0.22 mm polyethersulfone filter. Fab 158 was purified using Strep-Tactin XT resin (IBA lifesciences) and Fab EY6A was purified with Ni-NTA column (GE HealthCare) and a Superdex 75 HiLoad 16/60 gel filtration column (GE Healthcare). AstraZeneca and Regeneron antibodies were provided by AstraZeneca, Vir, Lilly and Adagio antibodies were provided by Adagio. For the antibodies heavy and light chains of the indicated antibodies were transiently transfected into 293Y cells and antibody purified from supernatant on protein A. Fab fragments of 58 and beta-55 were digested from purified IgGs with papain using a Pierce Fab Preparation Kit (Thermo Fisher), following the manufacturer's protocol.

Surface Plasmon Resonance

The surface plasmon resonance experiments were performed using a Biacore T200 (GE Healthcare). All assays were performed with a running buffer of HBS-EP (Cytiva) at 25° C.

To determine the binding kinetics between the SARS-CoV-2 RBDs and ACE2/monoclonal antibody (mAb), a Protein A sensor chip (Cytiva) was used. ACE2-Fc or mAb was immobilised onto the sample flow cell of the sensor chip. The reference flow cell was left blank. RBD was injected over the two flow cells at a range of five concentrations prepared by serial twofold dilutions, at a flow rate of 30 μl min$^{-1}$ using a single-cycle kinetics programme. Running buffer was also injected using the same programme for background subtraction. All data were fitted to a 1:1 binding model using Biacore T200 Evaluation Software 3.1.

To determine the binding kinetics between the SARS-CoV-2 Spikes and ACE2, a CM5 sensor chip was used. The sensor chip was firstly activated by an injection of equal volume mix of EDC and NHS (Cytiva) at 20 uL/min for 300 s, followed by an injection of Spike sample at 20 ug/mL in 10 mM sodium acetate pH 5.0 (Cytiva) onto the sample flow cell of the sensor chip at 10 uL/min, and finally with an injection of 1.0 M Ethanolamine-HCl, pH 8.5 (Cytiva) at 20 uL/min for 180 s. The reference flow cell was left blank. ACE2 was injected over the two flow cells at a range of five concentrations prepared by serial twofold dilutions, at a flow rate of 30 μl min$^{-1}$ using a single-cycle kinetics programme. Running buffer was also injected using the same programme for background subtraction.

All data were fitted to a 1:1 binding model using Biacore T200 Evaluation Software 3.1. To determine the binding kinetics between the RBDs and mAb Omi-32/Omi-42, a Biotin CAPture Kit (Cytiva) was used. Biotinylated RBD was immobilised onto the sample flow cell of the sensor chip. The reference flow cell was left blank. The mAb Fab was injected over the two flow cells at a range of five concentrations prepared by serial two-fold dilutions, at a flow rate of 30 µl min-1 using a single-cycle kinetics programme. Running buffer was also injected using the same programme for background subtraction. All data were fitted to a 1:1 binding model using Biacore T200 Evaluation Software 3.1.

To determine the binding affinity of BA.4/5 RBD and mAb Omi-12, a Protein A sensor chip (Cytiva) was used. The Ig Omi-12 was immobilised onto the sample flow cell of the sensor chip. The reference flow cell was left blank. RBD was injected over the two flow cells at a range of seven concentrations prepared by serial twofold dilutions, at a flow rate of 30 µl min-1. Running buffer was also injected using the same programme for background subtraction. All data were fitted to a 1:1 binding model using Prism9 (GraphPad).

To compare the binding profiles between BA.2 and BA.4/5 RBD for mAb Omi-06/Omi-25/Omi-26, a Protein A sensor chip (Cytiva) was used. mAb in the IgG form was immobilised onto the sample flow cell of the sensor chip to a similar level (~350 RU). The reference flow cell was left blank. A single injection of RBD was performed over the two flow cells at 200 nM, at a flow rate of 30 µl min-1. Running buffer was also injected using the same programme for background subtraction. The sensorgrams were plotted using Prism9 (GraphPad).

To compare the binding profiles between BA.2 and BA.4/5 RBD for mAb Omi-02/Omi-23/Omi-31, a Biotin CAPture Kit (Cytiva) was used. Biotinylated BA.2 and BA.4/5 RBD was immobilised onto the sample flow cell of the sensor chip to a similar level (~120 RU). The reference flow cell was left blank. A single injection of mAb Fab was performed over the two flow cells at 200 nM, at a flow rate of 30 d min-1. Running buffer was also injected using the same programme for background subtraction. The sensorgrams were plotted using Prism9 (GraphPad).

To determine the binding kinetics between BA.2.75 or BA.2+R493Q RBD and ACE2, a Protein A sensor chip (Cytiva) was used. ACE2-Fc was immobilised onto the sample flow cell of the sensor chip. The reference flow cell was left blank. RBD was injected over the two flow cells at a range of five concentrations prepared by serial two-fold dilutions, at a flow rate of 30 µl min-1 using a single-cycle kinetics programme. Running buffer was also injected using the same programme for background subtraction. All data were fitted to a 1:1 binding model using Biacore T200 Evaluation Software 3.1.

To confirm the binding kinetics between the BA.2.75 RBD and ACE2, a Biotin CAPture Kit (Cytiva) was used. Biotinylated ACE2 (bio-ACE2) was immobilised onto the sample flow cell of the sensor chip. The reference flow cell was left blank. The BA.2.75 RBD was injected over the two flow cells at a range of five concentrations prepared by serial two-fold dilutions, at a flow rate of 30 µl min$^{-1}$ using a single-cycle kinetics programme. Running buffer was also injected using the same programme for background subtraction. All data were fitted to a 1:1 binding model using Biacore T200 Evaluation Software 3.1.

To determine the binding kinetics between the BA.2.75 or BA.2 RBD and mAbs, a Biotin CAPture Kit (Cytiva) was used. Biotinylated RBD was immobilised onto the sample flow cell of the sensor chip. The reference flow cell was left blank. The Fab of Omi-18 or Omi-32 was injected over the two flow cells at a range of five concentrations prepared by serial two-fold dilutions, at a flow rate of 30 µl min$^{-1}$ using a single-cycle kinetics programme. For the binding of Omi-20 for bio-BA.2 RBD, the Fab of Omi-20 was injected over the two flow cells at a range of five concentrations prepared by serial two-fold dilutions, at a flow rate of 30 µl min$^{-1}$ using a single-cycle kinetics programme. For the binding of Omi-20 for bio-BA.2.75 RBD, the Fab of Omi-20 was injected over the two flow cells at a range of eight concentrations prepared by serial twofold dilutions, at a flow rate of 30 µl min$^{-1}$. Running buffer was also injected using the same programme for background subtraction. All data were fitted to a 1:1 binding model using Biacore T200 Evaluation Software 3.1.

To compare the binding profiles between BA.2 and BA.2.75 RBD for mAb Omi-29, a Biotin CAPture Kit (Cytiva) was used. Biotinylated BA.2 and BA.2.75 RBD was immobilised onto the sample flow cell of the sensor chip to a similar level (~110 RU). The reference flow cell was left blank. A single injection of mAb Fab was performed over the two flow cells at 1 µM, at a flow rate of 30 µl min$^{-1}$. Running buffer was also injected using the same programme for background subtraction. The sensorgrams were plotted using Prism9 (GraphPad).

To compare the binding profiles between BA.2 and BA.2.75 RBD for mAb Omi-36, a sensor chip Protein A (Cytiva) was used. mAb Omi-36 in the IgG form was immobilised onto the sample flow cell of the sensor chip. The reference flow cell was left blank. A single injection of RBD was performed over the two flow cells at 200 nM, at a flow rate of 30 µl min$^{-1}$. Running buffer was also injected using the same programme for background subtraction. The sensorgrams were plotted using Prism9 (GraphPad).

IgG mAbs and Fabs Production

AstraZeneca and Regeneron antibodies were provided by AstraZeneca, Vir, Lilly and Adagio antibodies were provided by Adagio, LY-CoV1404 was provided by LifeArc. For the in-house antibodies, heavy and light chains of the indicated antibodies were transiently transfected into 293Y or 293T cells and antibody purified from supernatant on protein A as previously described (Nutalai et al., 2022). Fabs were digested from purified IgGs with papain using a Pierce Fab Preparation Kit (Thermo Fisher), following the manufacturer's protocol.

Quantification and Statistical Analysis

Statistical analyses are reported in the results and figure legends. Neutralization was measured by FRNT. The percentage of focus reduction was calculated and IC50 (FRNT50) was determined using the probit program from the SPSS package. The Wilcoxon matched-pairs signed rank test was used for the analysis and two-tailed P values were calculated on geometric mean values.

Crystallization

RBD proteins were deglycosylated with Endoglycosidase F1 before used for crystallization. Omicron BA.1-RBD was mixed with Omi-12 and beta-54 Fabs, separately, in a 1:1:1 molar ratio, with a final concentration of 7 mg ml-1. These complexes were separately incubated at room temperature for 30 min. Initial screening of crystals was set up in Crystalquick 96-well X plates (Greiner Bio-One) with a Cartesian Robot using the nanoliter sitting-drop vapor-diffusion method, with 100 nL of protein plus 100 nL of reservoir in each drop, as previously described (Walter et al., 2003, Journal of Applied Crystallography 36, 308-314).

Crystals of BA.1-RBD/Omi-12/beta-54 were formed in Hampton Research PEGRx condition 1-46, containing 0.1 M Sodium citrate tribasic dihydrate pH 5.0 and 18% (w/v) PEG 20000. Complex of BA.1-RBD/Omi-12/beta-54 was screen in Hampton Research Ammonium sulphate screen C2, containing 2.4 M $(NH_4)_2SO_4$ and 0.1 M citric acid pH 5.0, but only crystals of Fab Omi-12 alone were formed in this condition.

Crystallization of BA.2.75 RBD

Purified BA.2.75 RBD was deglycosylated with Endoglycosidase H1 and mixed with ACE2 in a 1:1 molar ratio, with a final concentration of 13.0 mg ml-1. Initial screening of crystals was set up in Crystalquick 96-well X plates (Greiner Bio-One) with a Cartesian Robot using the nano-liter sitting-drop vapor-diffusion method, with 100 nL of protein plus 100 nL of reservoir in each drop, as previously described (Walter et al., 2003). Crystals of BA.2.75 RBD-ACE2 complex were formed in Hampton Research PEGRx condition 2-25, containing 0.1% (w/v) n-Octyl-b-D-glucoside, 0.1 M Sodium citrate tribasic dihydrate pH 5.5 and 22% (w/v) PEG 3350. Diffraction data were collected at 100 K at beamline I03 of Diamond Light Source, UK, using the automated queue system that allows unattended automated data collection (https://www.diamond.ac.uk/Instruments/Mx/I03/I03-Manual/Unattended-Data-Collections.html).

X-Ray Data Collection, Structure Determination and Refinement

Diffraction data were collected at 100 K at beamline I03 of Diamond Light Source, UK. All data were collected as part of an automated queue system allowing unattended automated data collection (https://www.diamond.ac.uk/Instruments/Mx/I03/I03-Manual/Unattended-Data-Collections.html). Crystals were pre-frozen by mounting in loops and soaked for a second in cryo-protectant containing 25% glycerol and 75% mother liquor. Diffraction images of 0.1° rotation were recorded on an Eiger2 XE 16M detector (exposure time from 0.018 s per image, beam size 80×20 µm, 10% beam transmission and wavelength of 0.9762 Å). Data were indexed, integrated and scaled with the automated data processing program Xia2-dials (Winter, 2010, Journal of applied crystallography 43, 186-190; Winter et al., 2018, Acta Crystallogr D Struct Biol 74, 85-97). 360° of data was collected from a single crystal for each of the data sets.

Structures were determined by molecular replacement with PHASER (McCoy et al., 2007, J Appl Crystallogr 40, 658-674). VhVl and ChCl domains which have the most sequence similarity to previously determined SARS-CoV-2 RBD/Fab structures (Dejnirattisai et al., 2021, Cell 184, 2183-2200 e2122; Dejnirattisai et al., 2021, Cell 184, 2939-2954 e2939; Huo et al., 2020, Cell Host Microbe 28, 445-454; Liu et al., 2021, Cell 184, 4220-4236 e4213; Supasa et al., 2021, Cell 184, 2201-2211 e2207; Zhou et al., 2021, Cell 184, 2348-2361 e2346; Zhou et al., 2020, Nature structural & molecular biology 27, 950-958) were used as search models for each of the current structure determination.

Model rebuilding with COOT (Emsley et al., 2010, Biological Crystallography 66, 486-501) and refinement with Phenix (Liebschner et al., 2019, Acta Crystallogr D Struct Biol 75, 861-877) were used for all the structures. Due to the lower resolution, only rigid-body and group B-factor refinement were performed for structures of BA.1-RBD/O-12/Beta-54 complex.

Data collection and structure refinement statistics are given in Tables 19 and 25. Structural comparisons used SHP (Stuart et al., 1979, J Mol Biol 134, 109-142), residues forming the RBD/Fab interface were identified with PISA (Krissinel and Henrick, 2007, J Mol Biol 372, 774-797) and figures were prepared with PyMOL (The PyMOL Molecular Graphics System, Version 1.2r3pre, Schrödinger, LLC).

Example 5

Antibody Structure

Figure 6:
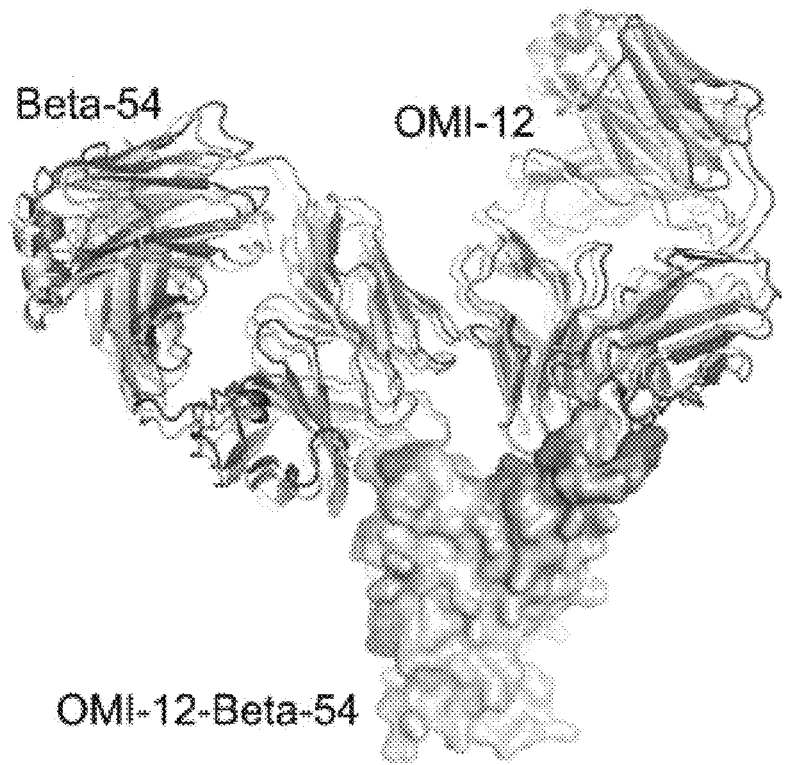
FIG. 6. Structure of BA.1 RBD with Omi-12 Fab. (A) Two ternary complexes of Omi-12 and Beta-54 Fabs with BA.1 (produced by fitting the high-resolution structures of BA.1 RBD, Omi-12 and Beta-54 to the lower-resolution ternary complex density) in the crystal asymmetric unit are compared by overlapping the RBD. Fabs in one complex are in bright colours (cartoon depiction HC red, LC blue) and the other in pale colours. (B) The binding mode of Omi-12. (C) Close-up of the binding differences of Omi-12 with Fab 253 complexed with early pandemic RBD (pale blue) and Beta-47 with Beta RBD (pale cyan). (D) The somatic mutation V53P contributes to re-folding of the H3 loop so that Q493R can be accommodated in Omi-12.

The structure of the BA.1 RBD/Fab Omi-12/Fab Beta-54 ternary complex was determined to 5.5 Å resolution (Table 19, FIG. 6A). A slight clash was observed between the two Fabs despite the BLI experiment showing no significant competition for binding between them. A high-resolution structure of un-complexed Omi-12 fab (2.1 Å resolution, Table 19) has been modelled into the electron density for the complex (FIG. 6B, 6C). Superimposing Fab 253 onto Fab Omi-12 suggests that Q493R would clash with the H2 loop of Fab 253, whereas in Omi-12, H2 adopts a slightly flattened structure. This structural change is attributable to antibody maturation via the somatic mutation V53P in the heavy chain variable region of Omi-12 which forms a stacking interaction with Y489 (FIG. 6D).

Omi-12 and Antibody 253 are both derived from the germline heavy chain IGHV1-58. Interestingly, similar to antibody 253, other antibodies derived from the germline heavy chain IGHV1-58 described herein, i.e. Beta-47, Beta-25, antibody 55, antibody 165 and antibody 318, also has a valine (V) at position 53 in the heavy chain variable region, i.e. valine (V) at position 53 in SEQ ID NO: 262 (antibody 253), SEQ ID NO: 591 (Beta-47), SEQ ID NO: 461 (Beta-25), SEQ ID NO: 62 (antibody 55), SEQ ID NO: 182 (antibody 165) and SEQ ID NO: 332 (antibody 318). Position 53 in these sequences corresponds to position 58 according to IMGT numbering. Based on the data, modification of any of these antibodies by substitution of valine at position 53 with proline (i.e. V53P absolute numbering, or V58P according to IMGT numbering) would result in an antibody that would be effective against Omicron.

Furthermore, antibody AZD8895 (heavy chain variable region amino acid sequences provided in SEQ ID NO: 963 and light chain variable region amino acid sequence provided in SEQ ID NO: 965) is also derived from the germline heavy chain IGHV1-58 (e.g. see Dong et al. Nat Microbiol 6, 1233-1244 (2021)). AZD8895 has an isoleucine (I) at position 53 in the heavy chain variable region, which corresponds to position 58 according to IMGT numbering. Based on the data herein, modification of the heavy chain variable region AZD8895 (SEQ ID NO: 963) by substitution of isoleucine at position 53 with proline (i.e. I53P) using absolute numbering, or I58P using IMGT numbering, would result in an antibody that would be effective against Omicron.

Hence, the data indicate that the modification of VH1-58 antibodies such that a proline is present at position 53 (corresponding to position 58 according to IMGT numbering) in the heavy chain variable region would make them particularly effective against Omicron.

ACE2/BA.2.75 RBD Structure

Figure 20:
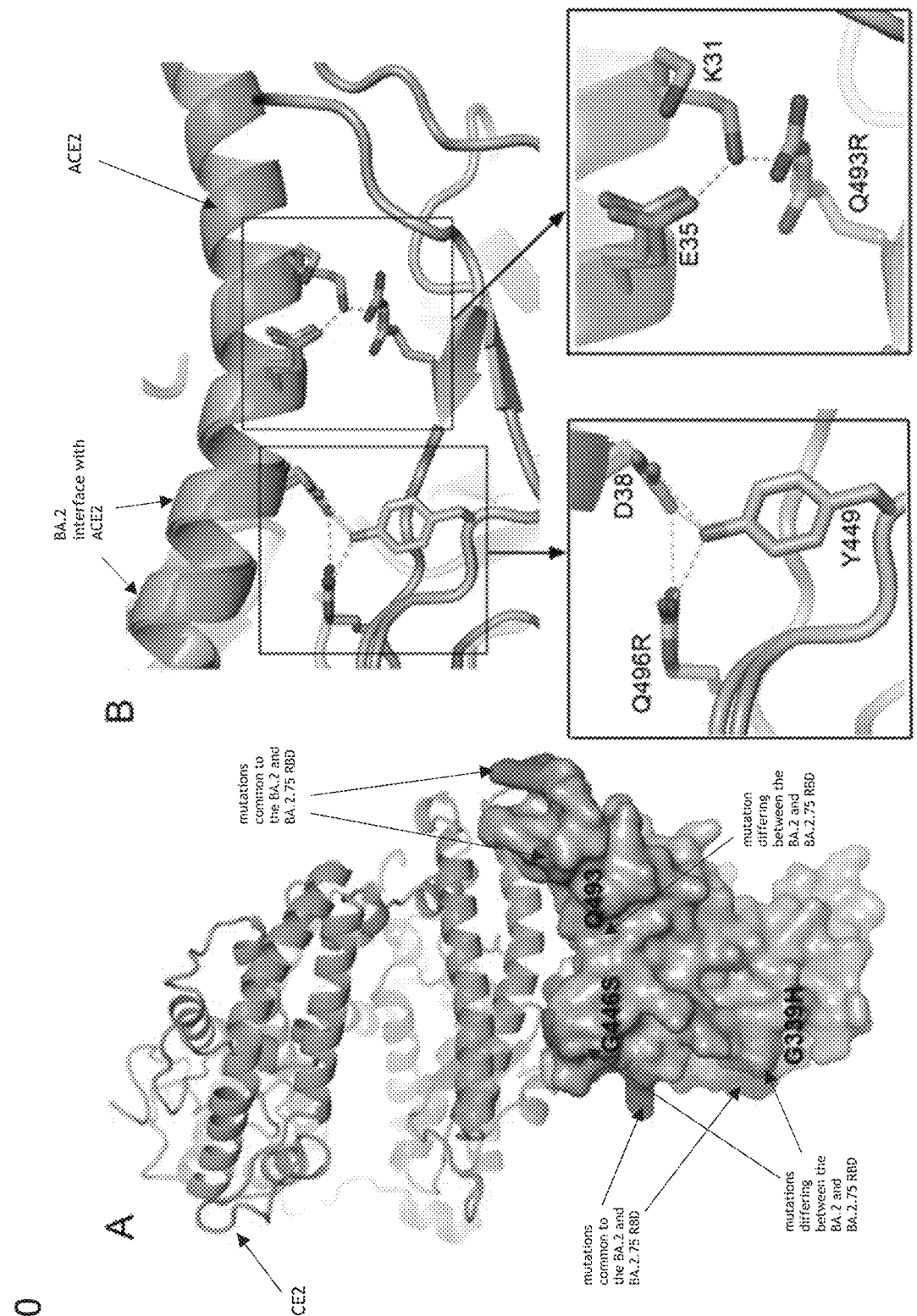
FIG. 20. The Structure of BA.2.75 RBD/ACE2 complex. (A) The overall structure of the BA.2.75 RBD/ACE2 complex. ACE2 is shown as green ribbons and the RBD as surface with mutations common to BA.2 highlighted in magenta and different in orange. (B) BA.2.75 RBD (grey) and ACE2 (green) interface compared with that of BA.2 and ACE2 (both in salmon). Closeups show interactions of Q496R and Q493 (R493 in BA.2) with ACE2.

To elucidate the molecular mechanism for high affinity, the structure of the BA.2.75 RBD with ACE2 was determined by crystallography (according to the methods described in Example 4). As expected the binding mode was essentially indistinguishable from that observed before (FIG. 20A), although there were significant rearrangements outside of the ACE2 footprint, with the flexible RBD 371-375 loop re-arranging and part of the C-terminal 6×His tag becoming ordered. FIG. 20B shows a close-up of the binding interface, compared with the ACE2/BA.2 RBD complex. In other complexes (with either R or Q at RBD 493) K31 of ACE2 tends to be disordered, whereas it is well ordered in the BA.2.75 complex, allowing K31 to form a potential hydrogen bond with the glutamine sidechain possibly increasing the affinity of ACE2.

Tables

TABLE 1

SEQ ID NOs of antibodies raised against early pandemic strains

| Antibody number | Heavy Chain protein sequence | Heavy Chain nucleotide | Light Chain sequence protein | Light Chain nucleotid | CDRH1 | CDRH2 | CDRH3 | CDRL1 | CDRL2 | CDRL3 |
|---|---|---|---|---|---|---|---|---|---|---|
| 2 | 2 | 1 | 4 | 3 | 5 | 6 | 7 | 8 | 9 | 10 |
| 22 | 12 | 11 | 14 | 13 | 15 | 16 | 17 | 18 | 19 | 20 |
| 40 | 22 | 21 | 24 | 23 | 25 | 26 | 27 | 28 | 29 | 30 |
| 44 | 32 | 31 | 34 | 33 | 35 | 36 | 37 | 38 | 39 | 40 |
| 45 | 42 | 41 | 44 | 43 | 45 | 46 | 47 | 48 | 49 | 50 |
| 54 | 52 | 51 | 54 | 53 | 55 | 56 | 57 | 58 | 8 | 60 |
| 55 | 62 | 61 | 64 | 63 | 65 | 66 | 67 | 68 | 69 | 70 |
| 58 | 72 | 71 | 74 | 73 | 75 | 76 | 77 | 78 | 79 | 80 |
| 61 | 82 | 81 | 84 | 83 | 85 | 86 | 87 | 88 | 89 | 90 |
| 75 | 92 | 91 | 94 | 93 | 95 | 96 | 97 | 98 | 99 | 100 |
| 88 | 102 | 101 | 104 | 103 | 105 | 106 | 107 | 108 | 109 | 110 |
| 111 | 112 | 111 | 14 | 113 | 115 | 116 | 117 | 118 | 119 | 120 |
| 132 | 122 | 121 | 124 | 123 | 125 | 126 | 127 | 128 | 129 | 130 |
| 140 | 132 | 131 | 134 | 133 | 135 | 136 | 137 | 138 | 139 | 140 |
| 148 | 142 | 141 | 144 | 143 | 145 | 146 | 147 | 148 | 149 | 150 |
| 150 | 152 | 151 | 154 | 153 | 155 | 156 | 157 | 158 | 159 | 160 |
| 158 | 162 | 161 | 164 | 163 | 165 | 166 | 167 | 168 | 169 | 170 |
| 159 | 172 | 171 | 174 | 173 | 175 | 176 | 177 | 178 | 179 | 180 |
| 165 | 182 | 181 | 184 | 183 | 185 | 186 | 187 | 188 | 189 | 190 |
| 170 | 192 | 191 | 194 | 193 | 195 | 196 | 197 | 198 | 199 | 200 |
| 175 | 202 | 201 | 204 | 203 | 205 | 206 | 207 | 208 | 209 | 210 |
| 177 | 212 | 211 | 214 | 213 | 215 | 216 | 217 | 218 | 219 | 220 |
| 181 | 222 | 221 | 224 | 223 | 225 | 226 | 227 | 228 | 229 | 230 |
| 182 | 232 | 231 | 234 | 233 | 235 | 236 | 237 | 238 | 239 | 240 |
| 183 | 242 | 241 | 244 | 243 | 245 | 246 | 247 | 248 | 249 | 250 |
| 222 | 252 | 251 | 254 | 253 | 255 | 256 | 257 | 258 | 259 | 260 |
| 253 | 262 | 261 | 264 | 263 | 265 | 266 | 267 | 268 | 269 | 270 |
| 253H55L | 262 | 261 | 64 | 63 | 265 | 266 | 267 | 68 | 69 | 70 |
| 253H165I | 262 | 261 | 184 | 183 | 265 | 266 | 267 | 188 | 189 | 190 |
| 269 | 272 | 271 | 274 | 273 | 275 | 276 | 277 | 278 | 279 | 280 |
| 278 | 282 | 281 | 284 | 283 | 285 | 286 | 287 | 288 | 289 | 290 |
| 281 | 292 | 291 | 294 | 293 | 295 | 296 | 297 | 298 | 299 | 300 |
| 282 | 302 | 301 | 304 | 303 | 305 | 306 | 307 | 308 | 309 | 310 |
| 285 | 312 | 311 | 314 | 313 | 315 | 316 | 317 | 318 | 319 | 320 |
| 316 | 322 | 321 | 324 | 323 | 325 | 326 | 327 | 328 | 329 | 330 |
| 318 | 332 | 331 | 334 | 333 | 335 | 336 | 337 | 338 | 339 | 340 |
| 334 | 342 | 341 | 344 | 343 | 345 | 346 | 347 | 348 | 349 | 350 |
| 361 | 352 | 351 | 354 | 353 | 355 | 356 | 357 | 358 | 359 | 360 |
| 382 | 362 | 361 | 364 | 363 | 365 | 366 | 367 | 368 | 369 | 370 |
| 384 | 372 | 371 | 374 | 373 | 375 | 376 | 377 | 378 | 379 | 380 |
| 394 | 382 | 381 | 384 | 383 | 385 | 386 | 387 | 388 | 389 | 390 |
| 398 | 392 | 391 | 394 | 393 | 395 | 396 | 397 | 398 | 399 | 400 |

TABLE 2

SEQ ID NOs of antibodies raised against the Beta strain

| Antibody number | Heavy Chain nucleotide sequence | Heavy Chain protein sequence | Light Chain nucleotide sequence | Light Chain protein sequence | CDRH1 | CDRH2 | CDRH3 | CDRL1 | CDRL2 | CDRL3 |
|---|---|---|---|---|---|---|---|---|---|---|
| Beta-06 | 401 | 402 | 403 | 404 | 405 | 406 | 407 | 408 | 409 | 410 |
| Beta-10 | 411 | 412 | 413 | 414 | 415 | 416 | 417 | 418 | 419 | 420 |
| Beta-20 | 421 | 422 | 423 | 424 | 425 | 426 | 427 | 428 | 429 | 430 |
| Beta-22 | 431 | 432 | 433 | 434 | 435 | 436 | 437 | 438 | 439 | 440 |
| Beta-23 | 441 | 442 | 443 | 444 | 445 | 446 | 447 | 448 | 449 | 450 |
| Beta-24 | 451 | 452 | 453 | 454 | 455 | 456 | 457 | 458 | 459 | 460 |
| Beta-25 | 461 | 462 | 463 | 464 | 465 | 466 | 467 | 468 | 469 | 470 |
| Beta-26 | 471 | 472 | 473 | 474 | 475 | 476 | 477 | 478 | 479 | 480 |
| Beta-27 | 481 | 482 | 483 | 484 | 485 | 486 | 487 | 488 | 489 | 490 |
| Beta-29 | 491 | 492 | 493 | 494 | 495 | 496 | 497 | 498 | 499 | 500 |
| Beta-30 | 501 | 502 | 503 | 504 | 505 | 506 | 507 | 508 | 509 | 510 |
| Beta-32 | 511 | 512 | 513 | 514 | 515 | 516 | 517 | 518 | 519 | 520 |
| Beta-33 | 521 | 522 | 523 | 524 | 525 | 526 | 527 | 528 | 529 | 530 |
| Beta-34 | 531 | 532 | 533 | 534 | 535 | 536 | 537 | 538 | 539 | 540 |
| Beta-38 | 541 | 542 | 543 | 544 | 545 | 546 | 547 | 548 | 549 | 550 |

TABLE 2-continued

SEQ ID NOs of antibodies raised against the Beta strain

| Antibody number | Heavy Chain nucleotide sequence | Heavy Chain protein sequence | Light Chain nucleotide sequence | Light Chain protein sequence | CDRH1 | CDRH2 | CDRH3 | CDRL1 | CDRL2 | CDRL3 |
|---|---|---|---|---|---|---|---|---|---|---|
| Beta-40 | 551 | 552 | 553 | 554 | 555 | 556 | 557 | 558 | 559 | 560 |
| Beta-43 | 561 | 562 | 563 | 564 | 565 | 566 | 567 | 568 | 569 | 570 |
| Beta-44 | 571 | 572 | 573 | 574 | 575 | 576 | 577 | 578 | 579 | 580 |
| Beta-45 | 581 | 582 | 583 | 584 | 585 | 586 | 587 | 588 | 589 | 590 |
| Beta-47 | 591 | 592 | 593 | 594 | 595 | 596 | 597 | 598 | 599 | 600 |
| Beta-48 | 601 | 602 | 603 | 604 | 605 | 606 | 607 | 608 | 609 | 610 |
| Beta-49 | 611 | 612 | 613 | 614 | 615 | 616 | 617 | 618 | 619 | 620 |
| Beta-50 | 621 | 622 | 623 | 624 | 625 | 626 | 627 | 628 | 629 | 630 |
| Beta-51 | 631 | 632 | 633 | 634 | 635 | 636 | 637 | 638 | 639 | 640 |
| Beta-53 | 641 | 642 | 643 | 644 | 645 | 646 | 647 | 648 | 649 | 650 |
| Beta-54 | 651 | 652 | 653 | 654 | 655 | 656 | 657 | 658 | 659 | 660 |
| Beta-55 | 661 | 662 | 663 | 664 | 665 | 666 | 667 | 668 | 669 | 670 |
| Beta-56 | 671 | 672 | 673 | 674 | 675 | 676 | 677 | 678 | 679 | 680 |

TABLE 3

SEQ ID NOs of antibodies raised against the Omicron strain

| Antibody number | Heavy Chain nucleotide | Heavy Chain protein sequence | Light Chain nucleotide | Light Chain protein sequence | CDRH1 | CDRH2 | CDRH3 | CDRL1 | CDRL2 | CDRL3 |
|---|---|---|---|---|---|---|---|---|---|---|
| Omi02 | 681 | 682 | 683 | 684 | 685 | 686 | 687 | 688 | 689 | 690 |
| Omi03 | 691 | 692 | 693 | 694 | 695 | 696 | 697 | 698 | 699 | 700 |
| Omi06 | 701 | 702 | 703 | 704 | 705 | 706 | 707 | 708 | 709 | 710 |
| Omi08 | 711 | 712 | 713 | 714 | 715 | 716 | 717 | 718 | 719 | 720 |
| Omi09 | 721 | 722 | 723 | 724 | 725 | 726 | 727 | 728 | 729 | 730 |
| Omi12 | 731 | 732 | 733 | 734 | 735 | 736 | 737 | 738 | 739 | 740 |
| Omi16 | 741 | 742 | 743 | 744 | 745 | 746 | 747 | 748 | 749 | 750 |
| Omi17 | 751 | 752 | 753 | 754 | 755 | 756 | 757 | 758 | 759 | 760 |
| Omi18 | 761 | 762 | 763 | 764 | 765 | 766 | 767 | 768 | 769 | 770 |
| Omi20 | 771 | 772 | 773 | 774 | 775 | 776 | 777 | 778 | 779 | 780 |
| Omi23 | 781 | 782 | 783 | 784 | 785 | 786 | 787 | 788 | 789 | 790 |
| Omi24 | 791 | 792 | 793 | 794 | 795 | 796 | 797 | 798 | 799 | 800 |
| Omi25 | 801 | 802 | 803 | 804 | 805 | 806 | 807 | 808 | 809 | 810 |
| Omi26 | 811 | 812 | 813 | 814 | 815 | 816 | 817 | 818 | 819 | 820 |
| Omi27 | 821 | 822 | 823 | 824 | 825 | 826 | 827 | 828 | 829 | 830 |
| Omi28 | 831 | 832 | 833 | 834 | 835 | 836 | 837 | 838 | 839 | 840 |
| Omi29 | 841 | 842 | 843 | 844 | 845 | 846 | 847 | 848 | 849 | 850 |
| Omi30 | 851 | 852 | 853 | 854 | 855 | 856 | 857 | 858 | 859 | 860 |
| Omi31 | 861 | 862 | 863 | 864 | 865 | 866 | 867 | 868 | 869 | 870 |
| Omi32 | 871 | 872 | 873 | 874 | 875 | 876 | 877 | 878 | 879 | 880 |
| Omi33 | 881 | 882 | 883 | 884 | 885 | 886 | 887 | 888 | 889 | 890 |
| Omi34 | 891 | 892 | 893 | 894 | 895 | 896 | 897 | 898 | 899 | 900 |
| Omi35 | 901 | 902 | 903 | 904 | 905 | 906 | 907 | 908 | 909 | 910 |
| Omi36 | 911 | 912 | 913 | 914 | 915 | 916 | 917 | 918 | 919 | 920 |
| Omi38 | 921 | 922 | 923 | 924 | 925 | 926 | 927 | 928 | 929 | 930 |
| Omi39 | 931 | 932 | 933 | 934 | 935 | 936 | 937 | 938 | 939 | 940 |
| Omi41 | 941 | 942 | 943 | 944 | 945 | 946 | 947 | 948 | 949 | 950 |
| Omi42 | 951 | 952 | 953 | 954 | 955 | 956 | 957 | 958 | 959 | 960 |

TABLE 4

Examples of the mixed chain antibodies generated from antibodies derived from the same germline heavy chain IGHV3-53

| Heavy chain (H)/light chain (L) of antibody | Omi03H | Omi18H | Omi29H | Beta-27H | 150H | 158H | 175H | 222H | 269H |
|---|---|---|---|---|---|---|---|---|---|
| Omi03L | — | Omi18H Omi03L | Omi29H Omi03L | Beta-27H Omi03L | 150H Omi03L | 158H Omi03L | 175H Omi03L | 222H Omi03L | 269H Omi03L |

TABLE 4-continued

Examples of the mixed chain antibodies generated from antibodies derived from the same germline heavy chain IGHV3-53

| Heavy chain (H)/light chain (L) of antibody | Omi03H | Omi18H | Omi29H | Beta-27H | 150H | 158H | 175H | 222H | 269H |
|---|---|---|---|---|---|---|---|---|---|
| Omi18L | Omi03H Omi18L | — | Omi29H Omi18L | Beta-27H Omi18L | 150H Omi18L | 158H Omi18L | 175H Omi18L | 222H Omi18L | 269H Omi18L |
| Omi29L | Omi03H Omi29L | Omi18H Omi29L | — | Beta-27H Omi29L | 150H Omi29L | 158H Omi29L | 175H Omi29L | 222H Omi29L | 269H Omi29L |
| Beta-27L | Omi03 HBeta-27L | Omi18 HBeta-27L | Omi29 HBeta-27L | — | 150H Beta-27L | 158H Beta-27L | 175H Beta-27L | 222H Beta-27L | 269H Beta-27L |
| 150L | Omi03 H150L | Omi18 H150L | Omi29 H150L | Beta-27H 150L | — | 158H 150L | 175H 150L | 222H 150L | 269H 150L |
| 158L | Omi03 H158L | Omi18 H158L | Omi29 H158L | Beta-27H 158L | 150H 158L | — | 175H 158L | 222H 158L | 269H 158L |
| 175L | Omi03 H175L | Omi18 H175L | Omi29 H175L | Beta-27H 175L | 150H 175L | 158H 175L | — | 222H 175L | 269H 175L |
| 222L | Omi03 H222L | Omi18 H222L | Omi29 H222L | Beta-27H 222L | 150H 222L | 158H 222L | 175H 222L | — | 269H 222L |
| 269L | Omi03 H269L | Omi18 H269L | Omi29 H269L | Beta-27H 269L | 150H 269L | 158H 269L | 175H 269L | 222H 269L | — |

TABLE 5

Examples of the mixed chain antibodies generated from antibodies derived from the same germline heavy chain IGHV3-53 + IGHV3-66

| Heavy chain (H)/light chain (L) of antibody | Omi03H | Omi18H | Omi29H | Omi16H | Omi17H | Omi20H | Omi27H | Omi28H | Omi36H | Beta-27H | 150H | 158H | 175H | 222H | 269H | 40H | 398H |
|---|---|---|---|---|---|---|---|---|---|---|---|---|---|---|---|---|---|
| Omi03L | — | Omi18H Omi03L | Omi29H Omi03L | Omi16H Omi03L | Omi17H Omi03L | Omi20H Omi03L | Omi27H Omi03L | Omi28H Omi03L | Omi36H Omi03L | Beta-27H Omi03L | 150H Omi03L | 158H Omi03L | 175H Omi03L | 222H Omi03L | 269H Omi03L | 40H Omi03L | 398H Omi03L |
| Omi18L | Omi03H Omi18L | — | Omi29H Omi18L | Omi16H Omi18L | Omi17H Omi18L | Omi20H Omi18L | Omi27H Omi18L | Omi28H Omi18L | Omi36H Omi18L | Beta-27H Omi18L | 150H Omi18L | 158H Omi18L | 175H Omi18L | 222H Omi18L | 269H Omi18L | 40H Omi18L | 398H Omi18L |
| Omi29L | Omi03H Omi29L | Omi18H Omi29L | — | Omi16H Omi29L | Omi17H Omi29L | Omi20H Omi29L | Omi27H Omi29L | Omi28H Omi29L | Omi36H Omi29L | Beta-27H Omi29L | 150H Omi29L | 158H Omi29L | 175H Omi29L | 222H Omi29L | 269H Omi29L | 40H Omi29L | 398H Omi29L |
| Omi16L | Omi03H Omi16L | Omi18H Omi16L | Omi29H Omi16L | — | Omi17 Omi 16L | Omi20H Omi16L | Omi27H Omi16L | Omi28H Omi16L | Omi36H Omi16L | Beta-27H Omi16L | 150H Omi16L | 158H Omi16L | 175H Omi16L | 222H Omi16L | 269H Omi16L | 40H Omi16L | 398H Omi16L |
| Omi17H | Omi03H Omi17L | Omi18H Omi17L | Omi29H Omi17L | Omi16H Omi17L | — | Omi20H Omi17L | Omi27H Omi17L | Omi28H Omi17L | Omi36H Omi17L | Beta-27H Omi17L | 150H Omi17L | 158H Omi17L | 175H Omi17L | 222H Omi17L | 269H Omi17L | 40H Omi17L | 398H Omi17L |
| Omi20H | Omi03H Omi20L | Omi18H Omi20L | Omi29H Omi20L | Omi16H Omi20L | Omi17H Omi20L | — | Omi27H Omi20L | Omi28H Omi20L | Omi36H Omi20L | Beta-27H Omi20L | 150H Omi20L | 158H Omi20L | 175H Omi20L | 222H Omi20L | 269H Omi20L | 40H Omi20L | 398H Omi20L |
| Omi27H | Omi03H Omi27L | Omi18H Omi27L | Omi29H Omi27L | Omi16H Omi27L | Omi17H Omi27L | Omi20H Omi27L | — | Omi28H Omi27L | Omi36H Omi27L | Beta-27H Omi27L | 150H Omi27L | 158H Omi27L | 175H Omi27L | 222H Omi27L | 269H Omi27L | 40H Omi27L | 398H Omi27L |
| Omi28H | Omi03H Omi28L | Omi18H Omi28L | Omi29H Omi28L | Omi16H Omi28L | Omi17H Omi28L | Omi20H Omi28L | Omi27H Omi28L | — | Omi36H Omi28L | Beta-27H Omi28L | 150H Omi28L | 158H Omi28L | 175H Omi28L | 222H Omi28L | 269H Omi28L | 40H Omi28L | 398H Omi28L |
| Omi36H | Omi03H Omi36L | Omi18H Omi36L | Omi29H Omi36L | Omi16H Omi36L | Omi17H Omi36L | Omi20H Omi36L | Omi27H Omi36L | Omi28H Omi36L | — | Beta-27H Omi36L | 150H Omi36L | 158H Omi36L | 175H Omi36L | 222H Omi36L | 269H Omi36L | 40H Omi36L | 398H Omi36L |
| Beta-27L | Omi03H Beta-27L | Omi18H Beta-27L | Omi29H Beta-27L | Omi16H Beta-27L | Omi17H Beta-27L | Omi20H Beta-27L | Omi27H Beta-27L | Omi28H Beta-27L | Omi36H Beta-27L | — | 150H Beta-27L | 158H Beta-27L | 175H Beta-27L | 222H Beta-27L | 269H Beta-27L | 40H Beta-27L | 398H Beta-27L |
| 150L | Omi03 H150L | Omi18 H150L | Omi29 H150L | Omi16 H150L | Omi17 H150L | Omi20 H150L | Omi27 H150L | Omi28 H150L | Omi36 H150L | Beta-27 150H | — | 158H 150L | 175H 150L | 222H 150L | 269H 150L | 40H 150L | 398H 150L |
| 158L | Omi03 H158L | Omi18 H158L | Omi29 H158L | Omi16 H158L | Omi17 H158L | Omi20 H158L | Omi27 H158L | Omi28 H158L | Omi36 H158L | — | 150H 158L | — | 175H 158L | 222H 158L | 269H 158L | 40H 158L | 398H 158L |
| 175L | Omi03 H175L | Omi18 H175L | Omi29 H175L | Omi16 H175L | Omi17 H175L | Omi20 H175L | Omi27 H175L | Omi28 H175L | Omi36 H175L | Beta-27 175L | 150H 175L | 158H — | — | 222H 175L | 269H 175L | 40H 175L | 398H 175L |
| 222L | Omi03 H222L | Omi18 H222L | Omi29 H222L | Omi16 H222L | Omi17 H222L | Omi20 H222L | Omi27 H222L | Omi28 H222L | Omi36 H222L | Beta-27 222L | 150H 222L | 158L 222L | 175L 222L | — | 269L 222L | 40H 222L | 398H 222L |
| 269L | Omi03 H269L | Omi18 H269L | Omi29 H269L | Omi16 H269L | Omi17 H269L | Omi20 H269L | Omi27 H269L | Omi28 H269L | Omi36 H269L | Beta-27 269L | 150H 269L | 158H 269L | 175H 269L | 222H 269L | — | 40H 269L | 398H 269L |
| 40L | Omi03 H40L | Omi18 H40L | Omi29 H40L | Omi16 H40L | Omi17 H40L | Omi20 H40L | Omi27 H40L | Omi28 H40L | Omi36 H40L | Beta-27 40L | 150H 40L | 158L 40L | 175L 40L | 222L 40L | 269H 40L | — | 40H 398H |
| 398L | Omi03 H398L | Omi18 H398L | Omi29 H398L | Omi16 H398L | Omi17 H398L | Omi20 H398L | Omi27 H398L | Omi28 H398L | Omi36 H398L | Beta-27 398L | 150H 398L | 158L 398L | 175L 398L | 222L 398L | 269H 398L | 40H 398L | — |

TABLE 6

Examples of the mixed chain antibodies generated from antibodies derived from the same germline heavy chain IGHV1-58

| Heavy chain (H)/light chain (L) of antibody | Omi12H | Beta-47H | Beta-25H | 55H | 165H | 253H | 318H |
|---|---|---|---|---|---|---|---|
| Omi12L | — | Beta-47H Omi12L | Beta-25H Omi12L | 55H Omi12L | 165H Omi12L | 253H Omi12L | 318H Omi12L |
| Beta-47L | Omi12H Beta-47L | — | Beta 25H Beta-47L | 55H Beta-47L | 165H Beta-47L | 253H Beta-47L | 318H Beta-47L |
| Beta-25L | Omi12H Beta-25L | Beta-47H Beta-25L | — | 55H Beta 25L | 165H Beta 25L | 253H Beta 25L | 318H Beta 25L |
| 55L | Omi12H 55L | Beta-47H 55L | Beta-25H 55L | — | 165H 55L | 253H 55L | 318H 55L |
| 165L | Omi12 H165L | Beta-47H 165L | Beta-25H 165L | 55H 165L | — | 253H 165L | 318H 165L |
| 253L | Omi12 H253L | Beta-47H 253L | Beta-25H 253L | 55H 253L | 165H 253L | — | 318H 253L |
| 318L | Omi12 H318L | Beta-47H 318L | Beta-25H 318L | 55H 318L | 165H 318L | 253H 318L | — |

TABLE 7

Examples of the mixed chain antibodies generated from antibodies derived from the same germline heavy chain IGHV1-69

| Heavy chain (H) /light chain (L) of antibody | Beta-49H | Beta-50H | Omi02H | Omi24H | Omi30H | Omi31H | Omi34H | Omi38H |
|---|---|---|---|---|---|---|---|---|
| Beta-49L | — | Beta-50H Beta-49L | Omi02H Beta-49L | Omi24H Beta-49L | Omi30H Beta-49L | Omi31H Beta-49L | Omi34H Beta-49L | Omi38H Beta-49L |
| Beta-50L | Beta-49H Beta-50L | — | Omi02H Beta-50L | Omi24H Beta-50L | Omi30H Beta-50L | Omi31H Beta-50L | Omi34H Beta-50L | Omi38H Beta-50L |
| Omi02L | Beta-49H Omi02L | Beta-50H Omi02L | — | Omi24H Omi02L | Omi30H Omi02L | Omi31H Omi02L | Omi34H Omi02L | Omi38H Omi02L |
| Omi24L | Beta-49H Omi24L | Beta-50H Omi24L | Omi02H Omi24L | — | Omi30H Omi24L | Omi31H Omi24L | Omi34H Omi24L | Omi38H Omi24L |
| Omi30L | Beta-49H Omi30L | Beta-50H Omi30L | Omi02H Omi30L | Omi24H Omi30L | — | Omi31H Omi30L | Omi34H Omi30L | Omi38H Omi30L |
| Omi31L | Beta-49H Omi31L | Beta-50H Omi31L | Omi02H Omi31L | Omi24H Omi31L | Omi30H Omi31L | — | Omi34H Omi31L | Omi38H Omi31L |
| Omi34H | Beta-49H Omi34L | Beta-50H Omi34L | Omi02H Omi34L | Omi24H Omi34L | Omi30H Omi34L | Omi31H Omi34L | — | Omi38H Omi34L |
| Omi38H | Beta-49H Omi38L | Beta-50H Omi38L | Omi02H Omi38L | Omi24H Omi38L | Omi30H Omi38L | Omi31H Omi38L | Omi34H Omi38L | — |

TABLE 8

Examples of the mixed chain antibodies generated from antibodies derived from the same germline heavy chain IGHV3-30

| Heavy chain (H)/light chain (L) of antibody | Beta-22H | Beta-29H | 159H | Omi09H |
|---|---|---|---|---|
| Beta-22L | — | Beta-29H Beta-22L | 159H Beta-22L | Omi09H Beta-22L |
| Beta-29L | Beta-22H Beta 29L | — | 159H Beta-29L | Omi09H Beta 29L |
| 159L | Beta-22H 159L | Beta-29H 159L | — | Omi09 H159L |
| Omi09L | Beta-22H Omi09L | Beta-29H Omi09L | 159H Omi09L | — |

TABLE 9

Examples of the mixed chain antibodies generated from antibodies derived from the same germline heavy chain IGHV3-33

| Heavy chain (H)/light chain (L) of antibody | Beta-20H | Beta-43H | Omi32H | Omi33H |
|---|---|---|---|---|
| Beta-20L | — | Beta-43H Beta-20L | Omi32H Beta-20L | Omi33H Beta-20L |
| Beta-43L | Beta-20H Beta-43L | — | Omi32H Beta-43L | Omi33H Beta-43L |
| Omi32L | Beta-20H Omi32L | Beta-43H Omi32L | — | Omi33H Omi32L |
| Omi33L | Beta-20H Omi33L | Beta-43H Omi33L | Omi32H Omi33L | — |

TABLE 10

Examples of the mixed chain antibodies generated from antibodies derived from the same germline heavy chain IGHV 1-18

| Heavy chain (H)/lightchain (L) of antibody | 278H | Beta-44H | Omi26H | Omi41H |
|---|---|---|---|---|
| 278L | — | Beta-44H 278L | Omi26 H278L | Omi41 H278L |
| Beta-44L | 278H Beta- 44L | — | Omi26H Beta-44L | Omi41H Beta-44L |
| Omi26L | 278H Omi26L | Beta-44H Omi26L | — | Omi41H Omi26L |
| Omi41L | 278H Omi41L | Beta-44H Omi41L | Omi26H Omi41L | — |

TABLE 11

Examples of the mixed chain antibodies generated from antibodies derived from the same germline heavy chain IGHV3-9

| Heavy chain (H)/light chain (L) of antibody | 58H | Omi25H | Omi35H | Omi42H |
|---|---|---|---|---|
| 58L | — | Omi25 H58L | Omi35 H58L | Omi42 H58L |
| Omi25L | 58H Omi25L | — | Omi35H Omi25L | Omi42H Omi25L |
| Omi35L | 58H Omi35L | Omi25H Omi35L | — | Omi42H Omi35L |
| Omi42L | 58H Omi42L | Omi25H Omi42L | Omi35H Omi42L | — |

TABLE 12

Examples of the mixed chain antibodies generated from antibodies derived from the same germline heavy chain IGHV4-31

| Heavy chain (H)/light chain (L) of antibody | Beta-56H | Omi23H |
|---|---|---|
| Beta-56L | — | Omi23H Beta-56L |
| Omi23L | Beta-56HOmi23L | — |

TABLE 13

IC50 titres of 22 Omicron SARS-CoV-2-specific human mAbs against live virus strains Victoria, Alpha, Beta, Gamma, Delta and Omicron (BA.1).

| | Authentic virus - IC50 (µg/ml) | | | | | |
|---|---|---|---|---|---|---|
| | Victoria | Alpha | Beta | Gamma | Delta | Omicron (BA.1) |
| Omi-02 | 0.015 ± 0.001 | 0.014 ± 0.005 | 0.009 ± 0.000 | 0.004 ± 0.000 | 0.014 ± 0.003 | 0.013 ± 0.001 |
| Omi-03 | 0.007 ± 0.000 | 0.012 ± 0.007 | 0.009 ± 0.001 | 0.004 ± 0.000 | 0.004 ± 0.000 | 0.009 ± 0.002 |
| Omi-06 | 0.007 ± 0.001 | 0.011 ± 0.002 | 0.012 ± 0.000 | 0.010 ± 0.003 | 5.040 ± 0.747 | 0.054 ± 0.005 |
| Omi-08 | 0.014 ± 0.007 | 0.022 ± 0.002 | 0.007 ± 0.000 | 0.024 ± 0.007 | 0.048 ± 0.012 | 0.008 ± 0.004 |
| Omi-09 | 0.004 ± 0.001 | 0.002 ± 0.000 | 1.218 ± 0.324 | 2.373 ± 1.008 | 0.008 ± 0.002 | 0.011 ± 0.005 |
| Omi-12 | 0.005 ± 0.000 | 0.003 ± 0.001 | 0.006 ± 0.001 | 0.003 ± 0.000 | 0.003 ± 0.000 | 0.004 ± 0.001 |
| Omi-16 | 0.016 ± 0.002 | 0.022 ± 0.009 | 0.018 ± 0.004 | 0.022 ± 0.007 | 0.016 ± 0.002 | 0.019 ± 0.003 |
| Omi-17 | 0.066 ± 0.015 | 0.098 ± 0.027 | 0.021 ± 0.007 | 0.021 ± 0.007 | 0.074 ± 0.019 | 0.028 ± 0.005 |
| Omi-18 | 0.041 ± 0.005 | 0.038 ± 0.008 | 0.018 ± 0.006 | 0.016 ± 0.004 | 0.025 ± 0.000 | 0.006 ± 0.003 |
| Omi-20 | 0.012 ± 0.002 | 0.023 ± 0.004 | 0.019 ± 0.009 | 0.019 ± 0.006 | 0.008 ± 0.001 | 0.043 ± 0.012 |
| Omi-23 | 0.005 ± 0.002 | 0.009 ± 0.004 | 0.020 ± 0.005 | 0.018 ± 0.006 | 0.006 ± 0.002 | 0.044 ± 0.013 |
| Omi-24 | 0.005 ± 0.001 | 0.008 ± 0.003 | 0.006 ± 0.001 | 0.010 ± 0.005 | >10 | 0.007 ± 0.001 |
| Omi-25 | 0.003 ± 0.001 | 0.007 ± 0.001 | 0.059 ± 0.007 | 0.257 ± 0.079 | 0.006 ± 0.002 | 0.046 ± 0.015 |
| Omi-26 | 0.005 ± 0.000 | 0.010 ± 0.003 | 0.055 ± 0.020 | 0.214 ± 0.046 | 0.005 ± 0.001 | 0.034 ± 0.000 |
| Omi-27 | 0.026 ± 0.001 | 0.032 ± 0.012 | 0.019 ± 0.006 | 0.017 ± 0.006 | 0.010 ± 0.001 | 0.091 ± 0.050 |
| Omi-28 | 0.028 ± 0.004 | 0.028 ± 0.001 | 0.019 ± 0.010 | 0.033 ± 0.008 | 0.018 ± 0.002 | 0.032 ± 0.009 |
| Omi-29 | 0.044 ± 0.002 | 0.066 ± 0.034 | 0.048 ± 0.020 | 0.040 ± 0.007 | 0.029 ± 0.004 | 0.036 ± 0.003 |
| Omi-30 | 0.109 ± 0.035 | 0.043 ± 0.016 | 0.028 ± 0.009 | 0.038 ± 0.004 | >10 | 0.058 ± 0.008 |
| Omi-31 | 0.007 ± 0.001 | 0.020 ± 0.003 | 0.011 ± 0.005 | 0.017 ± 0.006 | >10 | 0.010 ± 0.002 |
| Omi-32 | 0.032 ± 0.016 | 0.102 ± 0.041 | 0.460 ± 0.092 | 0.430 ± 0.012 | 0.012 ± 0.002 | 0.024 ± 0.011 |
| Omi-33 | 0.028 ± 0.005 | 0.057 ± 0.017 | 0.136 ± 0.002 | 0.132 ± 0.037 | 0.011 ± 0.001 | 0.026 ± 0.008 |
| Omi-34 | 0.003 ± 0.001 | 0.041 ± 0.027 | 0.003 ± 0.000 | 0.008 ± 0.002 | >10 | 0.028 ± 0.009 |
| Omi-35 | 0.057 ± 0.003 | 0.080 ± 0.030 | 0.128 ± 0.058 | 0.136 ± 0.024 | 0.280 ± 0.059 | 0.069 ± 0.032 |
| Omi-36 | 0.056 ± 0.008 | 0.047 ± 0.009 | 0.018 ± 0.001 | 0.015 ± 0.000 | 0.026 ± 0.003 | 0.038 ± 0.006 |
| Omi-38 | 0.001 ± 0.000 | 0.009 ± 0.001 | 0.004 ± 0.000 | 0.002 ± 0.000 | 0.004 ± 0.001 | 0.054 ± 0.028 |
| Omi-39 | 0.015 ± 0.006 | 0.039 ± 0.007 | 0.009 ± 0.000 | 0.014 ± 0.001 | 0.012 ± 0.007 | 0.025 ± 0.004 |
| Omi-41 | 0.090 ± 0.013 | 2.262 ± 1.199 | >10 | 0.126 ± 0.059 | >10 | 0.081 ± 0.004 |
| Omi-42 | 0.016 ± 0.003 | 0.024 ± 0.001 | 0.011 ± 0.004 | 0.013 ± 0.003 | 0.019 ± 0.001 | 0.014 ± 0.002 |

TABLE 14

IC50 titres of 22 Omicron SARS-COV-2-specific human mAbs against pseudovirus strains Victoria, Omicron BA.1, Omicron BA.1.1, Omicron BA.2 and Omicron BA.3.

| | Pseudovirus - IC50 (µg/ml) | | | | |
|---|---|---|---|---|---|
| | Victoria | OmicronBA.1 | OmicronBA.1.1 | OmicronBA.2 | OmicronBA.3 |
| Omi-02 | 0.002 ± 0.001 | 0.004 ± 0.001 | 0.004 ± 0.001 | 0.003 ± 0.001 | 0.019 ± 0.007 |
| Omi-03 | 0.003 ± 0.000 | 0.005 ± 0.002 | 0.003 ± 0.001 | 0.008 ± 0.001 | 0.022 ± 0.003 |
| Omi-06 | 0.007 ± 0.000 | 0.017 ± 0.003 | 0.139 ± 0.033 | 0.039 ± 0.008 | 0.696 ± 0.106 |
| Omi-08 | 0.008 ± 0.004 | 0.003 ± 0.000 | 0.002 ± 0.000 | 0.114 ± 0.045 | 0.032 ± 0.001 |
| Omi-09 | 0.006 ± 0.002 | 0.005 ± 0.000 | 0.005 ± 0.002 | 0.008 ± 0.002 | 0.017 ± 0.002 |
| Omi-12 | 0.006 ± 0.002 | 0.002 ± 0.000 | 0.002 ± 0.001 | 0.003 ± 0.001 | 0.006 ± 0.001 |
| Omi-16 | 0.014 ± 0.003 | 0.012 ± 0.002 | 0.011 ± 0.003 | 0.034 ± 0.012 | 0.111 ± 0.008 |
| Omi-17 | 0.023 ± 0.011 | 0.018 ± 0.012 | 0.022 ± 0.009 | 0.060 ± 0.004 | 0.123 ± 0.002 |
| Omi-18 | 0.008 ± 0.003 | 0.002 ± 0.000 | 0.002 ± 0.000 | 0.005 ± 0.000 | 0.006 ± 0.002 |
| Omi-20 | 0.009 ± 0.002 | 0.006 ± 0.001 | 0.005 ± 0.001 | 0.015 ± 0.003 | 0.020 ± 0.004 |
| Omi-23 | 0.005 ± 0.002 | 0.029 ± 0.006 | 0.023 ± 0.12 | 0.019 ± 0.005 | 0.011 ± 0.000 |
| Omi-24 | 0.005 ± 0.000 | 0.006 ± 0.002 | 0.054 ± 0.015 | 0.007 ± 0.001 | 0.009 ± 0.002 |
| Omi-25 | 0.005 ± 0.001 | 0.023 ± 0.005 | 0.027 ± 0.005 | 0.024 ± 0.004 | 0.050 ± 0.004 |
| Omi-26 | 0.002 ± 0.001 | 0.006 ± 0.002 | 0.005 ± 0.001 | 0.013 ± 0.001 | 0.018 ± 0.002 |
| Omi-27 | 0.008 ± 0.003 | 0.026 ± 0.006 | 0.034 ± 0.009 | 0.034 ± 0.005 | 0.026 ± 0.007 |
| Omi-28 | 0.022 ± 0.000 | 0.011 ± 0.004 | 0.009 ± 0.002 | 0.008 ± 0.000 | 0.019 ± 0.000 |
| Omi-29 | 0.014 ± 0.006 | 0.017 ± 0.003 | 0.016 ± 0.009 | 0.056 ± 0.014 | 0.064 ± 0.017 |
| Omi-30 | 0.012 ± 0.002 | 0.008 ± 0.003 | 0.008 ± 0.004 | 0.011 ± 0.002 | 0.015 ± 0.003 |
| Omi-31 | 0.376 ± 0.090 | 0.029 ± 0.002 | 0.031 ± 0.012 | 0.013 ± 0.002 | 0.013 ± 0.004 |
| Omi-32 | 0.010 ± 0.006 | 0.017 ± 0.000 | >10 | 2.682 ± 0.553 | 1.018 ± 0.139 |
| Omi-33 | 0.027 ± 0.011 | 0.014 ± 0.005 | 0.042 ± 0.018 | 0.068 ± 0.022 | 0.133 ± 0.021 |
| Omi-34 | 0.007 ± 0.004 | 0.008 ± 0.001 | 0.062 ± 0.004 | 0.009 ± 0.003 | 0.014 ± 0.000 |
| Omi-35 | 0.018 ± 0.004 | 0.058 ± 0.009 | 0.381 ± 0.086 | 0.093 ± 0.005 | 0.044 ± 0.018 |
| Omi-36 | 0.022 ± 0.004 | 0.009 ± 0.003 | 0.009 ± 0.003 | 0.030 ± 0.014 | 0.178 ± 0.048 |
| Omi-38 | 0.015 ± 0.004 | 0.024 ± 0.015 | >10 | 0.005 ± 0.000 | 0.008 ± 0.002 |
| Omi-39 | 0.014 ± 0.002 | 0.009 ± 0.004 | >10 | 0.026 ± 0.011 | 0.014 ± 0.001 |
| Omi-41 | >10 | 0.053 ± 0.028 | 0.037 ± 0.002 | >10 | 0.032 ± 0.007 |
| Omi-42 | 0.013 ± 0.004 | 0.007 ± 0.004 | 0.006 ± 0.002 | 0.021 ± 0.011 | 0.025 ± 0.012 |

TABLE 15

IC50 titres of early pandemic SARS-COV-2-specific human mAbs and Beta SARS-CoV-2 specific human mAbs against pseudovirus strains Victoria, Omicron BA.1, Omicron BA.1.1 and Omicron BA.2.

| Early mAbs pandemic | IC50 (ug/ml) | | | |
|---|---|---|---|---|
| | Victoria | Omicron BA.1 | Omicron BA.1.1 | Omicron BA.2 |
| 40 | 0.006 ± 0.002 | 1.705 ± 0.840 | 0.544 ± 0.007 | 0.100 ± 0.007 |
| 55 | 0.006 ± 0.002 | >10 | >10 | >10 |
| 58 | 0.019 ± 0.004 | 0.060 ± 0.041 | 0.876 ± 0.135 | 0.043 ± 0.007 |
| 88 | 0.005 ± 0.002 | >10 | >10 | >10 |
| 132 | 0.012 ± 0.004 | >10 | >10 | >10 |
| 150 | 0.008 ± 0.004 | >10 | 3.500 ± 0.712 | >10 |
| 158 | 0.021 ± 0.006 | >10 | 2.843 ± 0.733 | 4.249 ± 0.694 |
| 159 | >10 | >10 | >10 | >10 |
| 165 | 0.007 ± 0.005 | >10 | >10 | >10 |
| 170 | 0.006 ± 0.001 | >10 | >10 | >10 |
| 175 | 0.012 ± 0.004 | >10 | >10 | >10 |
| 222 | 0.006 ± 0.000 | 0.021 ± 0.002 | 0.023 ± 0.001 | 0.249 ± 0.082 |
| 253 | 0.021 ± 0.009 | 0.875 ± 0.373 | 0.415+ 0.161 | 1.100 ± 0.049 |
| 269 | 0.008 ± 0.004 | >10 | >10 | >10 |
| 278 | 0.001 ± 0.000 | >10 | >10 | 0.326 ± 0.011 |
| 281 | 0.001 ± 0.000 | >10 | >10 | >10 |
| 316 | 0.001 ± 0.000 | >10 | >10 | >10 |
| 318 | 0.012 ± 0.003 | 9.490 ± 4.540 | >10 | 0.303 ± 0.190 |
| 384 | 0.001 ± 0.000 | >10 | >10 | >10 |
| 398 | 0.072 ± 0.065 | >10 | >10 | >10 |
| 253 + 55 | 0.001 ± 0.000 | 0.638 ± 0.315 | 0.451 ± 0.014 | >10 |
| 253 + 165 | 0.001 ± 0.000 | >10 | 6.591 ± 0.799 | >10 |

TABLE 15-continued

IC50 titres of early pandemic SARS-COV-2-specific human mAbs and Beta SARS-CoV-2 specific human mAbs against pseudovirus strains Victoria, Omicron BA.1, Omicron BA.1.1 and Omicron BA.2.

| | IC50 (ug/ml) | | | |
|---|---|---|---|---|
| Beta mAbs | Beta | Omicron BA.1 | Omicron BA.1.1 | Omicron BA.2 |
| β06 | 0.005 ± 0.001 | >10 | >10 | >10 |
| β10 | 0.021 ± 0.008 | >10 | >10 | >10 |
| β20 | 0.006 ± 0.002 | 5.679 ± 0.452 | 1.836 ± 0.780 | >10 |
| β22 | 0.041 ± 0.014 | 0.479 ± 0.029 | 0.130 ± 0.005 | >10 |
| β23 | 0.005 ± 0.001 | >10 | >10 | >10 |
| β24 | 0.002 ± 0.000 | >10 | >10 | >10 |
| β26 | 0.004 ± 0.001 | >10 | >10 | >10 |
| β27 | 0.003 ± 0.001 | 0.766 ± 0.043 | 0.274 ± 0.095 | 0.348 ± 0.030 |
| β29 | 0.009 ± 0.000 | 0.095 ± 0.029 | 0.066 ± 0.002 | 4.029 ± 0.402 |
| β30 | 0.002 ± 0.000 | >10 | >10 | >10 |
| β32 | 0.023 ± 0.001 | >10 | >10 | >10 |
| β33 | 0.020 ± 0.002 | >10 | >10 | >10 |
| β34 | 0.030 ± 0.004 | >10 | >10 | >10 |
| β38 | 0.004 ± 0.001 | >10 | >10 | >10 |
| β40 | 0.001 ± 0.000 | 0.005 ± 0.001 | 0.002 ± 0.000 | 0.008 ± 0.002 |
| β43 | 0.014 ± 0.003 | >10 | >10 | >10 |
| β44 | 0.008 ± 0.001 | >10 | >10 | >10 |
| β45 | 0.010 ± 0.001 | >10 | >10 | >10 |
| β47 | 0.002 ± 0.000 | 0.018 ± 0.009 | 0.011 ± 0.002 | 0.044 ± 0.006 |
| β48 | 0.003 ± 0.001 | 5.706 ± 0.676 | 0.752 ± 0.052 | 5.042 ± 0.650 |
| β49 | 0.014 ± 0.004 | >10 | >10 | >10 |
| β50 | 0.008 ± 0.001 | >10 | >10 | >10 |
| β51 | 0.003 ± 0.000 | >10 | >10 | >10 |
| β53 | 0.007 ± 0.001 | 0.141 ± 0.026 | 5.849 ± 0.036 | 0.170 ± 0.073 |
| β54 | 0.002 ± 0.000 | 0.003 ± 0.001 | 0.001 ± 0.000 | 0.076 ± 0.029 |
| β55 | 0.009 ± 0.002 | 0.033 ± 0.008 | 0.009 ± 0.001 | 0.069 ± 0.008 |

TABLE 16

IC50 titres of commercial mAbs against pseudovirus strains Victoria, Omicron BA.1, Omicron BA.1.1, Omicron BA.2 and Omicron BA.3.

| | IC50 (ug/ml) | | | | |
|---|---|---|---|---|---|
| Commercial mAbs | Victoria | Omicron BA.1 | Omicron BA.1.1 | Omicron BA.2 | Omicron BA.3 |
| Known Antibody A (REGN 10987) | 0.002 ± 0.001 | >10 | >10 | 0.616 ± 0.347 | >10 |
| Known Antibody B (REGN 10933) | 0.001 ± 0.002 | >10 | >10 | >10 | >10 |
| Known Antibody C (AZD1061) | 0.002 ± 0.001 | 0.308 ± 0.058 | >10 | 0.008 ± 0.003 | 0.019 |
| Known Antibody D (AZD8895) | 0.001 ± 0.000 | 0.246 ± 0.027 | 0.100 ± 0.053 | 1.333 ± 0.317 | >10 |
| Known Antibody E (AZD7442) | 0.001 ± 0.000 | 0.232 ± 0.113 | 0.806 ± 0.093 | 0.008 ± 0.001 | 0.065 ± 0.011 |
| Known Antibody F (ADG10) | 0.007 ± 0.002 | >10 | >10 | >10 | >10 |
| Known Antibody G (ADG20) | 0.003 ± 0.002 | 0.348 ± 0.169 | 0.253 ± 0.070 | >10 | >10 |
| Known Antibody H (ADG30) | 0.014 ± 0.006 | >10 | >10 | >10 | >10 |
| Known Antibody I (Ly-CoV-555) | 0.002 ± 0.000 | >10 | >10 | >10 | >10 |
| Known Antibody J (Ly-CoV16) | 0.014 ± 0.010 | >10 | >10 | >10 | >10 |
| Known Antibody K (S309) | 0.587 ± 0.286 | 0.094 ± 0.008 | 0.138 ± 0.020 | 0.638 ± 0.107 | 0.228 ± 0.009 |

TABLE 17

Properties of omicron antibodies

| | Heavy Chain | | | |
|---|---|---|---|---|
| mAbs | V-GENE | J-GENE | D-GENE | #Amino acid substitutions |
| Omi-02 | 1-69*01, or 1-69D*01 | 2*01 | 2-21*02 | 7 |
| Omi-03 | 3-53*01 | 4*02 | 1-26*01 | 5 |
| Omi-06 | 4-4*07 | 3*02 | 3-16*02 | 4 |
| Omi-08 | 1-46*01, or 1-46*03 | 4*02 | 6-13*01 | 12 |
| Omi-09 | 3-30*01 | 3*02 | 4-17*01 | 6 |
| Omi-12 | 1-58*02 | 3*02 | 2-2*01 | 12 |
| Omi-16 | 3-66*02 | 4*02 | 2-15*01 | 9 |
| Omi-17 | 3-66*02 | 4*02 | 6-19*01 | 7 |
| Omi-18 | 3-53*01 | 6*02 | 4-11*01 | 11 |
| Omi-20 | 3-66*02 | 6*02 | 5-12*01 | 11 |
| Omi-23 | 4-31*03 | 4*02 | 3-22*01 | 6 |
| Omi-24 | 1-69*06 | 4*02 | 3-16*01 | 9 |
| Omi-25 | 3-9*01 | 6*02 | 3-16*01 | 6 |
| Omi-26 | 1-18*01 | 4*02 | 1-26*01 | 12 |
| Omi-27 | 3-66*01, or 3-66*04 | 6*02 | 6-19*01 | 8 |
| Omi-28 | 3-66*01, or 3-66*04 | 4*02 | 3-16*01 | 4 |
| Omi-29 | 3-53*04 | 6*02 | 2-15*01 | 11 |
| Omi-30 | 1-69*06 | 6*02 | 2-15*01 | 10 |
| Omi-31 | 1-69*06 | 6*02 | 3-16*01 | 11 |
| Omi-32 | 3-33*01, or 3-33*06 | 4*02 | 2-21*02 | 6 |
| Omi-33 | 3-33*01, or 3-33*06 | 4*02 | 2-21*02 | 10 |
| Omi-34 | 1-69*06, or 1-69*14 | 4*02 | 2-2*01 | 10 |
| Omi-35 | 3-9*01 | 6*02 | 2-2*02 | 5 |
| Omi-36 | 3-66*02 | 4*02 | 2-15*01 | 9 |
| Omi-38 | 1-69*09 | 3*01 | 1-26*01 | 16 |
| Omi-39 | 3-43*01 | 6*03 | 2-2*01 | 8 |
| Omi-41 | 1-18*04 | 4*02 | 3-9*01 | 11 |
| Omi-42 | 3-9*01 | 6*02 | 6-19*01 | 7 |

TABLE 17-continued

Properties of omicron antibodies

| | Light Chain | | | |
|---|---|---|---|---|
| mAbs | K/λ | V-GENE | J-GENE | #Amino acid substitutions |
| Omi-02 | K | 3-20*01 | 5*01 | 9 |
| Omi-03 | K | 3-20*01 | 2*01 | 10 |
| Omi-06 | K | 1-39*01, or 1D-39*01 | 4*01 | 9 |
| Omi-08 | λ | 1-40*02 | 1*01 | 13 |
| Omi-09 | λ | 3-25*02 | 2*01, or 3*01 | 14 |
| Omi-12 | K | 3-20*01 | 1*01 | 9 |
| Omi-16 | K | 3-20*01 | 2*01 | 10 |
| Omi-17 | K | 3-20*01 | 2*01 | 10 |
| Omi-18 | λ | 3-21*02 | 1*01 | 10 |
| Omi-20 | K | 1-9*01 | 4*02 ( ) | 9 |
| Omi-23 | K | 1-NL1*01 | 1*01 | 10 |
| Omi-24 | K | 3-15*01 | 1*01 | 10 |
| Omi-25 | K | 1-39*01, or 1D-39*01 | 2*01 | 9 |
| Omi-26 | λ | 1-36*01 | 3*02 | 11 |
| Omi-27 | K | 1-6*01 | 2*01 | 9 |
| Omi-28 | K | 3-20*01 | 1*01 | 9 |
| Omi-29 | | 2-14*01, or 2-14*03 | 3*02 | 10 |
| Omi-30 | λ | 1-44*01 | 3*02 | 11 |
| Omi-31 | λ | 1-44*01 | 3*02 | 11 |
| Omi-32 | K | 3-20*01 | 4*01 | 10 |
| Omi-33 | K | 3-20*01 | 4*01 | 4 |
| Omi-34 | λ | 1-40*01 | 1*01 | 12 |
| Omi-35 | λ | 3-21*02 | 2*01, or 3*01 | 11 |
| Omi-36 | K | 3-20*01 | 2*01 | 5 |
| Omi-38 | K | 1-5*01 | 5*01 | 6 |
| Omi-39 | K | 4-1*01 | 3*01 | 5 |
| Omi-41 | K | 4-1*01 | 2*02 ( ) | 5 |
| Omi-42 | λ | 2-8*01 | 2*01, or 3*01 or 3*02 | 8 |

TABLE 18

IC50 titres of 22 Omicron SARS-CoV-2-specific human mAbs or commercial mAbs against various SARS-CoV-2 strains.

| | IC50 (ug/ml) | | | | | | | |
|---|---|---|---|---|---|---|---|---|
| mAbs | Victoria | Alpha | Beta | Gamma | Delta | BA.1 | BA.1.1 | BA.2 |
| Omi-02 | 0.015 ± 0.001 | 0.014 ± 0.005 | 0.009 ± 0.000 | 0.004 ± 0.000 | 0.014 ± 0.003 | 0.013 ± 0.001 | 0.015 ± 0.001 | 0.040 ± 0.021 |
| Omi-03 | 0.007 ± 0.000 | 0.012 ± 0.007 | 0.009 ± 0.001 | 0.004 ± 0.000 | 0.004 ± 0.000 | 0.009 ± 0.002 | 0.015 ± 0.000 | 0.028 ± 0.002 |
| Omi-06 | 0.007 ± 0.001 | 0.011 ± 0.002 | 0.012 ± 0.000 | 0.010 ± 0.003 | 5.040 ± 0.747 | 0.054 ± 0.005 | 1.505 ± 0.341 | 0.238 ± 0.007 |
| Omi-08 | 0.014 ± 0.007 | 0.022 ± 0.002 | 0.007 ± 0.000 | 0.024 ± 0.007 | 0.048 ± 0.012 | 0.008 ± 0.004 | 0.007 ± 0.001 | 1.510 ± 0.683 |
| Omi-09 | 0.004 ± 0.001 | 0.002 ± 0.000 | 1.218 ± 0.324 | 2.373 ± 1.008 | 0.008 ± 0.002 | 0.011 ± 0.005 | 0.017 ± 0.003 | 0.034 ± 0.010 |
| Omi-12 | 0.005 ± 0.000 | 0.003 ± 0.001 | 0.006 ± 0.001 | 0.003 ± 0.000 | 0.003 ± 0.000 | 0.004 ± 0.001 | 0.009 ± 0.001 | 0.010 ± 0.001 |
| Omi-16 | 0.016 ± 0.002 | 0.022 ± 0.009 | 0.018 ± 0.004 | 0.022 ± 0.007 | 0.016 ± 0.002 | 0.019 ± 0.003 | 0.027 ± 0.007 | 0.067 ± 0.021 |
| Omi-17 | 0.066 ± 0.015 | 0.098 ± 0.027 | 0.021 ± 0.007 | 0.021 ± 0.007 | 0.074 ± 0.019 | 0.028 ± 0.005 | 0.026 ± 0.001 | 0.095 ± 0.008 |
| Omi-18 | 0.041 ± 0.005 | 0.038 ± 0.008 | 0.018 ± 0.006 | 0.016 ± 0.004 | 0.025 ± 0.000 | 0.006 ± 0.003 | 0.006 ± 0.001 | 0.007 ± 0.001 |
| Omi-20 | 0.012 ± 0.002 | 0.023 ± 0.004 | 0.019 ± 0.009 | 0.019 ± 0.006 | 0.008 ± 0.001 | 0.043 ± 0.012 | 0.032 ± 0.002 | 0.022 ± 0.005 |
| 0mi-23 | 0.005 ± 0.002 | 0.009 ± 0.004 | 0.020 ± 0.005 | 0.018 ± 0.006 | 0.006 ± 0.002 | 0.044 ± 0.013 | 0.03 ± 0.001 | 0.028 ± 0.001 |
| Omi-24 | 0.005 ± 0.001 | 0.008 ± 0.003 | 0.006 ± 0.001 | 0.010 ± 0.005 | >10 | 0.007 ± 0.001 | 0.035 ± 0.010 | 0.008 ± 0002 |

TABLE 18-continued

IC50 titres of 22 Omicron SARS-CoV-2-specific human mAbs or commercial mAbs against various SARS-CoV-2 strains.

| mAbs | IC50 (ug/ml) | | | | | | | |
|---|---|---|---|---|---|---|---|---|
| | Victoria | Alpha | Beta | Gamma | Delta | BA.1 | BA.1.1 | BA.2 |
| Omi-25 | 0.003 ± 0.001 | 0.007 ± 0.001 | 0.059 ± 0.007 | 0.257 ± 0.079 | 0.006 ± 0.002 | 0.046 ± 0.015 | 0.138 ± 0.046 | 0.056 ± 0.030 |
| Omi-26 | 0.005 ± 0.000 | 0.010 ± 0.003 | 0.055 ± 0.020 | 0.214 ± 0.046 | 0.005 ± 0.001 | 0.034 ± 0.000 | 0.055 ± 0.030 | 0.03 ± 0.011 |
| Omi-27 | 0.026 ± 0.001 | 0.032 ± 0.012 | 0.019 ± 0.006 | 0.017 ± 0.006 | 0.010 ± 0.001 | 0.091 ± 0.050 | 0.239 ± 0.052 | 0.039 ± 0.006 |
| Omi-28 | 0.028 ± 0.004 | 0.028 ± 0.001 | 0.019 ± 0.010 | 0.033 ± 0.008 | 0.018 ± 0.002 | 0.032 ± 0.009 | 0.075 ± 0.032 | 0.047 ± 0.010 |
| Omi-29 | 0.044 ± 0.002 | 0.066 ± 0.034 | 0.048 ± 0.020 | 0.040 ± 0.007 | 0.029 ± 0.004 | 0.036 ± 0.003 | 0.052 ± 0.004 | 0.192 ± 0.021 |
| Omi-30 | 0.109 ± 0.035 | 0.043 ± 0.016 | 0.028 ± 0.009 | 0.038 ± 0.004 | >10 | 0.058 ± 0.008 | 0.084 ± 0.021 | 0.045 ± 0.010 |
| Omi-31 | 0.007 ± 0.001 | 0.020 ± 0.003 | 0.011 ± 0.005 | 0.017 ± 0.006 | >10 | 0.010 ± 0.002 | 0.017 ± 0.009 | 0.083 ± 0.040 |
| Omi-32 | 0.032 ± 0.016 | 0.102 ± 0.041 | 0.460 ± 0.092 | 0.430 ± 0.012 | 0.012 ± 0.002 | 0.024 ± 0.011 | 4.642 ± 0.283 | 1.899 ± 0.280 |
| Omi-33 | 0.028 ± 0.005 | 0.057 ± 0.017 | 0.136 ± 0.002 | 0.132 ± 0.037 | 0.011 ± 0.001 | 0.026 ± 0.008 | 0.113 ± 0.035 | 0.681 ± 0.0170 |
| Omi-34 | 0.003 ± 0.001 | 0.041 ± 0.027 | 0.003 ± 0.000 | 0.008 ± 0.002 | >10 | 0.028 ± 0.009 | 0.074 ± 0.016 | 0.014 ± 0.003 |
| Omi-35 | 0.057 ± 0.003 | 0.080 ± 0.030 | 0.128 ± 0.058 | 0.136 ± 0.024 | 0.280 ± 0.059 | 0.069 ± 0.032 | 0.262 ± 0.086 | 0.082 ± 0.043 |
| Omi-36 | 0.056 ± 0.008 | 0.047 ± 0.009 | 0.018 ± 0.001 | 0.015 ± 0.000 | 0.026 ± 0.003 | 0.038 ± 0.006 | 0.053 ± 0.022 | 0.105 ± 0.023 |
| Omi-38 | 0.001 ± 0.000 | 0.009 ± 0.001 | 0.004 ± 0.000 | 0.002 ± 0.000 | 0.004 ± 0.001 | 0.054 ± 0.028 | >10 | 0.027 ± 0.001 |
| Omi-39 | 0.015 ± 0.006 | 0.039 ± 0.007 | 0.009 ± 0.000 | 0.014 ± 0.001 | 0.012 ± 0.007 | 0.025 ± 0.004 | >10 | 0.073 ± 0.014 |
| Omi-41 | 0.090 ± 0.013 | 2.262 ± 1.199 | >10 | 0.126 ± 0.059 | >10 | 0.081 ± 0.004 | 0.191 ± 0.014 | >10 |
| Omi-42 | 0.016 ± 0.003 | 0.024 ± 0.001 | 0.011 ± 0.004 | 0.013 ± 0.003 | 0.019 ± 0.001 | 0.014 ± 0.002 | 0.017 ± 0.004 | 0.031 ± 0.008 |
| REGN10987 | 0.032 ± 0.007 | 0.028 ± 0.003 | 0.007 ± 0.001 | 0.013 ± 0.002 | 0.017 ± 0.009 | >10 | >10 | 1.847 ± 1.231 |
| REGN10933 | 0.004 ± 0.002 | 0.014 ± 0.002 | 3.284 ± 2.014 | 6.177 ± 1.914 | 0.003 ± 0.001 | >10 | >10 | >10 |
| AZD1061 | 0.013 ± 0.003 | 0.012 ± 0.002 | 0.014 ± 0.002 | 0.007 ± 0.002 | 0.038 ± 0.006 | 3.488 ± 2.085 | >10 | 0.028 ± 0.014 |
| AZD8895 | 0.005 ± 0.001 | 0.011 ± 0.002 | 0.046 ± 0.031 | 0.046 + 0.016 | 0.003 ± 0.000 | 1.152 ± 0.170 | 6.078 ± 1.558 | 7.702 ± 2.224 |
| AZD7442 | 0.009 ± 0.000 | 0.007 ± 0.001 | 0.012 ± 0.001 | 0.006 ± 0.003 | 0.005 ± 0.000 | 0.273 ± 0.062 | 3.816 ± 0.138 | 0.052 ± 0.004 |
| ADG10 | 0.006 ± 0.000 | 0.010 ± 0.001 | 0.011 ± 0.001 | 0.003 ± 0.000 | 0.026 ± 0.005 | >10 | >10 | >10 |
| ADG20 | 0.004 ± 0.001 | 0.006 ± 0.000 | 0.01 ± 0.001 | 0.009 ± 0.000 | 0.006 ± 0.001 | 1.104 ± 0.509 | 1.269 ± 0.223 | >10 |
| ADG30 | 0.007 ± 0.002 | 0.016 ± 0.001 | 0.029 ± 0.003 | 0.002 ± 0.001 | 0.033 ± 0.007 | >10 | >10 | >10 |
| Ly-CoV-555 | 0.006 ± 0.002 | 0.009 ± 0.000 | >10 | >10 | 8.311 ± 4.059 | >10 | >10 | >10 |
| Ly-CoV16 | 0.034 ± 0.007 | 3.225 ± 1.030 | >10 | >10 | 0.012 ± 0.002 | >10 | >10 | >10 |
| S309 | 0.040 ± 0.005 | 0.078 ± 0.069 | 0.082 ± 0.002 | 0.076 ± 0,014 | 0.113 ± 0.028 | 0.256 ± 0.034 | 1.119 ± 0.119 | 5.035 ± 0.244 |

TABLE 19

X-ray data collection and structure refinement statistics for BA.1 RBD/Omi-12-Beta54 and Omi-12 Fab

| Structure | BA.1 RBD/Omi-12-Beta54[a] | Omi-12 Fab[a] |
|---|---|---|
| Data collection | | |
| Space group | P2$_1$ | C222$_1$ |
| Cell dimensions | | |
| a, b, c (Å) | 95.7, 156.3, 122.4 | 65.0, 210.1, 85.9 |
| α, β, γ (°) | 90, 90.3, 90 | 90, 90, 90 |
| Resolution (Å) | 78-5.50 (5.60-5.50) | 33-2.08 (2.12-2.08) |
| R$^{merge}$ | 0.641 (—) | 0.179 (—) |
| R$^{pim}$ | 0.259 (0.919) | 0.052 (1.151) |
| I/σ(I) | 2.1 (0.4) | 6.2 (0.2) |
| CC$^{1/2}$ | 0.849 (0.332) | 0.994 (0.255) |
| Completeness (%) | 100 (98.2) | 93.3 (62.9) |
| Redundancy | 7.1 (7.4) | 12.1 (6.8) |

TABLE 19-continued

X-ray data collection and structure refinement statistics for BA.1 RBD/Omi-12-Beta54 and Omi-12 Fab

| Structure | BA.1 RBD/Omi-12-Beta54[a] | Omi-12 Fab[a] |
|---|---|---|
| Refinement | | |
| Resolution (Å) | 78-5.50[c] | 53-2.08 |
| No. reflections | 11051/615 | 29710/1547 |
| $R^{work}/R^{free}$ | 0.285/0.285 | 0.241/0.267 |
| No. atoms | | |
| Protein | 16328 | 3320 |
| Ligand/ion/water | | 133 |
| B factors (Å$^2$) | | |
| Protein | 248 | 59 |
| Ligand/ion/water | | 74 |
| r.m.s. deviations | | |
| Bond lengths (Å) | 0.010 | 0.002 |
| Bond angles (°) | 0.7 | 0.6 |

[a]Omi12 is glycosylated at N102 of the heavy chain.
[b]Values in parentheses are for highest-resolution shell.
[c]Rigid body and group B-factor refinement only.

TABLE 20

Pseudoviral assays comparing BA.4 neutralization with neutralization of BA.1, BA.1.1, BA.2 and BA.3

| | IC50 (μg/mL) Pseudovirus | | | | | |
|---|---|---|---|---|---|---|
| | Victoria | BA.1 | BA.1.1 | BA.2 | BA.3 | BA.4 |
| Omi-02 | 0.002 ± 0.001 | 0.004 ± 0.001 | 0.004 ± 0.001 | 0.003 ± 0.001 | 0.019 ± 0.007 | >10 |
| Omi-03 | 0.003 ± 0.000 | 0.005 ± 0.002 | 0.003 ± 0.001 | 0.008 ± 0.001 | 0.022 ± 0.003 | 0.017 ± 0.005 |
| Omi-06 | 0.007 ± 0.000 | 0.017 ± 0.003 | 0.139 ± 0.033 | 0.039 ± 0.008 | 0.696 ± 0.106 | >10 |
| Omi-08 | 0.008 ± 0.004 | 0.003 ± 0.000 | 0.002 ± 0.000 | 0.114 ± 0.045 | 0.032 ± 0.001 | 0.086 ± 0.005 |
| Omi-09 | 0.006 ± 0.002 | 0.005 ± 0.000 | 0.005 ± 0.002 | 0.008 ± 0.002 | 0.017 ± 0.002 | 0.166 ± 0.007 |
| Omi-12 | 0.006 ± 0.002 | 0.002 ± 0.000 | 0.002 ± 0.001 | 0.003 ± 0.001 | 0.006 ± 0.001 | 0.429 ± 0.060 |
| Omi-16 | 0.014 ± 0.003 | 0.012 ± 0.002 | 0.011 ± 0.003 | 0.034 ± 0.012 | 0.111 ± 0.008 | 0.029 ± 0.007 |
| Omi-17 | 0.023 ± 0.011 | 0.018 ± 0.012 | 0.022 ± 0.009 | 0.060 ± 0.004 | 0.123 ± 0.002 | 0.028 ± 0.001 |
| Omi-18 | 0.008 ± 0.003 | 0.002 ± 0.000 | 0.002 ± 0.000 | 0.005 ± 0.000 | 0.006 ± 0.002 | 0.005 ± 0.001 |
| Omi-20 | 0.009 ± 0.002 | 0.006 ± 0.001 | 0.005 ± 0.001 | 0.015 ± 0.003 | 0.020 ± 0.004 | 0.014 ± 0.006 |
| Omi-23 | 0.005 ± 0.002 | 0.029 ± 0.006 | 0.023 ± 0.12 | 0.019 ± 0.005 | 0.011 ± 0.000 | >10 |
| Omi-24 | 0.005 ± 0.000 | 0.006 ± 0.002 | 0.054 ± 0.015 | 0.007 ± 0.001 | 0.009 ± 0.002 | >10 |
| Omi-25 | 0.005 ± 0.001 | 0.023 ± 0.005 | 0.027 ± 0.005 | 0.024 ± 0.004 | 0.050 ± 0.004 | >10 |
| Omi-26 | 0.002 ± 0.001 | 0.006 ± 0.002 | 0.005 ± 0.001 | 0.013 ± 0.001 | 0.018 ± 0.002 | >10 |
| Omi-27 | 0.008 ± 0.003 | 0.026 ± 0.006 | 0.034 ± 0.009 | 0.034 ± 0.005 | 0.026 ± 0.007 | 0.069 ± 0.023 |
| Omi-28 | 0.022 ± 0.000 | 0.011 ± 0.004 | 0.009 ± 0.002 | 0.008 ± 0.000 | 0.019 ± 0.000 | 0.028 ± 0.009 |
| Omi-29 | 0.014 ± 0.006 | 0.017 ± 0.003 | 0.016 ± 0.009 | 0.056 ± 0.014 | 0.064 ± 0.017 | 0.396 ± 0.007 |
| Omi-30 | 0.053 ± 0.010 | 0.029 ± 0.002 | 0.031 ± 0.012 | 0.013 ± 0.002 | 0.015 ± 0.003 | >10 |
| Omi-31 | 0.012 ± 0.002 | 0.008 ± 0.003 | 0.008 ± 0.004 | 0.011 ± 0.002 | 0.013 ± 0.004 | >10 |
| Omi-32 | 0.010 ± 0.006 | 0.017 ± 0.000 | >10 | 2.682 ± 0.553 | 1.018 ± 0.139 | 0.035 ± 0.016 |
| Omi-33 | 0.027 ± 0.011 | 0.014 ± 0.005 | 0.042 ± 0.018 | 0.068 ± 0.022 | 0.133 ± 0.021 | 0.013 ± 0.004 |
| Omi-34 | 0.007 ± 0.004 | 0.008 ± 0.001 | 0.062 ± 0.004 | 0.009 ± 0.003 | 0.014 ± 0.000 | >10 |
| Omi-35 | 0.021 ± 0.003 | 0.058 ± 0.006 | 0.381 ± 0.061 | 0.094 ± 0.004 | 0.044 ± 0.018 | 1.687 ± 0.441 |
| Omi-36 | 0.022 ± 0.004 | 0.009 ± 0.003 | 0.009 ± 0.003 | 0.030 ± 0.014 | 0.178 ± 0.048 | 0.024 ± 0.006 |
| Omi-38 | 0.015 ± 0.004 | 0.024 ± 0.015 | >10 | 0.005 ± 0.000 | 0.008 ± 0.002 | 0.005 ± 0.001 |
| Omi-39 | 0.014 ± 0.002 | 0.009 ± 0.004 | >10 | 0.026 ± 0.011 | 0.014 ± 0.001 | 0.035 ± 0.003 |
| Omi-41 | >10 | 0.053 ± 0.028 | 0.037 ± 0.002 | >10 | 0.032 ± 0.007 | >10 |
| Omi-42 | 0.013 ± 0.004 | 0.007 ± 0.004 | 0.006 ± 0.002 | 0.021 ± 0.011 | 0.025 ± 0.012 | 0.013 ± 0.001 |

TABLE 21

Activity of commercial antibodies against BA.4 and BA.5
IC50 (μg/mL)
Pseudovirus

| | Victoria | BA.1 | BA.1.1 | BA.2 | BA.3 | BA.4 |
|---|---|---|---|---|---|---|
| REGN10987 | 0.002 ± 0.001 | >10 | >10 | 0.616 ± 0.347 | >10 | >10 |
| REGN10933 | 0.001 ± 0.002 | >10 | >10 | >10 | >10 | >10 |
| AZD1061 | 0.002 ± 0.001 | 0.308 ± 0.058 | >10 | 0.008 ± 0.003 | 0.019 ± 0.007 | 0.015 ± 0.004 |
| AZD8895 | 0.001 ± 0.000 | 0.246 ± 0.027 | 0.100 ± 0.053 | 1.333 ± 0.317 | >10 | >10 |
| AZD7442 | 0.001 ± 0.000 | 0.232 ± 0.113 | 0.806 ± 0.093 | 0.008 ± 0.001 | 0.065 ± 0.011 | 0.065 ± 0.007 |
| ADG10 | 0.007 ± 0.002 | >10 | >10 | >10 | >10 | >10 |
| ADG20 | 0.003 ± 0.002 | 0.348 ± 0.169 | 0.253 ± 0.070 | >10 | >10 | >10 |
| ADG30 | 0.014 ± 0.006 | >10 | >10 | >10 | >10 | >10 |
| Ly-CoV-555 | 0.002 ± 0.000 | >10 | >10 | >10 | >10 | >10 |
| Ly-CoV16 | 0.014 ± 0.010 | >10 | >10 | >10 | >10 | >10 |
| S309 | 0.130 ± 0.030 | 0.094 ± 0.008 | 0.138 ± 0.020 | 0.638 ± 0.107 | 0.228 ± 0.009 | 1.041 ± 0.072 |

TABLE 22

IC50 of BA.1 mAbs against PV BA.2.75 and BA.2 + N460K

| mAbs | Victoria | BA.1 | BA.1.1 | BA.2 | BA.3 | BA.4/5 | BA.2.75 | BA.2 + N460K |
|---|---|---|---|---|---|---|---|---|
| Omi-02 | 0.002 ± 0.001 | 0.004 ± 0.001 | 0.004 ± 0.001 | 0.003 ± 0.001 | 0.019 ± 0.007 | >10 | 0.009 ± 0.002 | 0.025 ± 0.003 |
| Omi-03 (3-53) | 0.003 ± 0.000 | 0.005 ± 0.002 | 0.003 ± 0.001 | 0.008 ± 0.001 | 0.022 ± 0.003 | 0.037 ± 0.005 | 0.017 ± 0.000 | 0.401 ± 0.026 |
| Omi-06 | 0.007 ± 0.000 | 0.017 ± 0.003 | 0.139 ± 0.033 | 0.039 ± 0.008 | 0.696 ± 0.306 | >10 | 0.063 ± 0.005 | 0.026 ± 0.002 |
| Omi-08 | 0.008 ± 0.004 | 0.003 ± 0.000 | 0.002 ± 0.000 | 0.314 ± 0.045 | 0.032 ± 0.001 | 0.086 ± 0.005 | 0.030 ± 0.002 | 0.552 ± 0.090 |
| Omi-09 | 0.005 ± 0.002 | 0.005 ± 0.000 | 0.005 ± 0.002 | 0.008 ± 0.002 | 0.017 ± 0.002 | 0.166 ± 0.007 | 0.003 ± 0.000 | 0.020 ± 0.002 |
| Omi-12 | 0.006 ± 0.002 | 0.002 ± 0.000 | 0.002 ± 0.001 | 0.003 ± 0.001 | 0.006 ± 0.001 | 0.429 ± 0.060 | 0.003 ± 0.001 | 0.011 ± 0.002 |
| Omi-16 | 0.014 ± 0.003 | 0.012 ± 0.002 | 0.011 ± 0.003 | 0.034 ± 0.012 | 0.111 ± 0.008 | 0.029 ± 0.007 | >10 | >10 |
| Omi-17 (3-56) | 0.022 ± 0.011 | 0.018 ± 0.012 | 0.022 ± 0.005 | 0.060 ± 0.004 | 0.123 ± 0.002 | 0.028 ± 0.001 | 0.255 ± 0.169 | >10 |
| Omi-18 (3-53) | 0.008 ± 0.003 | 0.002 ± 0.000 | 0.002 ± 0.000 | 0.005 ± 0.000 | 0.006 ± 0.002 | 0.005 ± 0.001 | 0.035 ± 0.007 | 0.014 ± 0.002 |
| Omi-20 (3-56) | 0.009 ± 0.002 | 0.006 ± 0.001 | 0.005 ± 0.001 | 0.015 ± 0.003 | 0.020 ± 0.004 | 0.014 ± 0.006 | 0.178 ± 0.075 | 0.315 ± 0.142 |
| Omi-23 | 0.005 ± 0.002 | 0.029 ± 0.005 | 0.023 ± 0.12 | 0.019 ± 0.005 | 0.011 ± 0.000 | >10 | 0.011 ± 0.006 | 0.022 ± 0.005 |
| Omi-24 | 0.005 ± 0.003 | 0.005 ± 0.002 | 0.054 ± 0.015 | 0.007 ± 0.001 | 0.009 ± 0.002 | >10 | 0.008 ± 0.004 | 0.014 ± 0.000 |
| Omi-25 | 0.005 ± 0.001 | 0.023 ± 0.005 | 0.027 ± 0.005 | 0.024 ± 0.004 | 0.050 ± 0.004 | >10 | 0.014 ± 0.005 | 0.050 ± 0.010 |
| Omi-26 | 0.002 ± 0.001 | 0.005 ± 0.002 | 0.005 ± 0.001 | 0.013 ± 0.001 | 0.018 ± 0.002 | >10 | 0.010 ± 0.004 | 0.010 ± 0.000 |
| Omi-27 (3-56) | 0.008 ± 0.003 | 0.026 ± 0.006 | 0.034 ± 0.009 | 0.034 ± 0.035 | 0.025 ± 0.007 | 0.069 ± 0.023 | 6.672 ± 4.465 | >10 |
| Omi-28 (3-56) | 0.022 ± 0.000 | 0.011 ± 0.004 | 0.009 ± 0.002 | 0.008 ± 0.000 | 0.019 ± 0.000 | 0.028 ± 0.009 | 0.133 ± 0.082 | 0.103 ± 0.048 |
| Omi-29 (3-53) | 0.014 ± 0.006 | 0.017 ± 0.003 | 0.018 ± 0.009 | 0.056 ± 0.014 | 0.064 ± 0.017 | 0.396 ± 0.007 | >10 | >10 |
| Omi-30 | 0.012 ± 0.002 | 0.008 ± 0.003 | 0.006 ± 0.004 | 0.011 ± 0.002 | 0.015 ± 0.003 | >10 | 0.008 ± 0.002 | 0.018 ± 0.001 |
| Omi-31 | 0.376 ± 0.090 | 0.029 ± 0.002 | 0.031 ± 0.012 | 0.013 ± 0.002 | 0.018 ± 0.004 | >10 | 0.014 ± 0.008 | 0.015 ± 0.001 |
| Omi-32 | 0.010 ± 0.005 | 0.017 ± 0.000 | >10 | 2.682 ± 0.553 | 1.018 ± 0.139 | 0.035 ± 0.016 | 0.354 ± 0.064 | 2.341 ± 0.282 |
| Omi-33 | 0.027 ± 0.011 | 0.014 ± 0.005 | 0.042 ± 0.018 | 0.058 ± 0.022 | 0.133 ± 0.021 | 0.013 ± 0.004 | 0.053 ± 0.005 | 0.490 ± 0.156 |
| Omi-34 | 0.007 ± 0.004 | 0.008 ± 0.001 | 0.062 ± 0.004 | 0.009 ± 0.003 | 0.014 ± 0.000 | >10 | 0.005 ± 0.000 | 0.020 ± 0.001 |
| Omi-35 | 0.018 ± 0.004 | 0.058 ± 0.005 | 0.381 ± 0.051 | 0.054 ± 0.004 | 0.044 ± 0.018 | 1.657 ± 0.441 | 0.020 ± 0.000 | 0.056 ± 0.012 |
| Omi-36 (3-66) | 0.022 ± 0.004 | 0.009 ± 0.003 | 0.009 ± 0.003 | 0.030 ± 0.014 | 0.178 ± 0.048 | 0.024 ± 0.006 | >10 | >10 |
| Omi-38 | 0.015 ± 0.004 | 0.024 ± 0.015 | >10 | 0.005 ± 0.000 | 0.008 ± 0.002 | 0.005 ± 0.001 | 0.011 ± 0.005 | 0.010 ± 0.001 |
| Omi-39 | 0.015 ± 0.002 | 0.009 ± 0.004 | >10 | 0.026 ± 0.011 | 0.014 ± 0.001 | 0.035 ± 0.003 | 0.027 ± 0.009 | 0.045 ± 0.017 |
| Omi-41 | >10 | 0.053 ± 0.028 | 0.037 ± 0.002 | >10 | 0.032 ± 0.007 | >10 | >10 | >10 |
| Omi-42 | 0.013 ± 0.004 | 0.007 ± 0.004 | 0.006 ± 0.002 | 0.021 ± 0.011 | 0.025 ± 0.012 | 0.013 ± 0.001 | 0.003 ± 0.000 | 0.007 ± 0.002 |

TABLE 23

IC50 of commercial mAbs against PV BA.2.75

| | IC50 (μg/mL) Pseudovisus | | | | | | |
|---|---|---|---|---|---|---|---|
| | Victoria | BA.1 | BA.1.1 | BA.2 | BA.3 | BA.4/5 | BA.2.75 |
| REGN10993 | 0.002 ± 0.001 | >10 | >10 | 0.616 ± 0.347 | >10 | >10 | >10 |
| REGN11093 | 0.001 ± 0.002 | >10 | >10 | >10 | >10 | >10 | >10 |
| AZD1061 | 0.002 ± 0.001 | 0.308 ± 0.058 | >10 | 0.008 ± 0.003 | 0.019 ± 0.007 | 0.015 ± 0.004 | 0.021 ± 0.002 |
| AZD8895 | 0.001 ± 0.003 | 0.246 ± 0.027 | 0.100 ± 0.317 | 1.335 ± 0.317 | >10 | >10 | 0.008 ± 0.080 |
| AZD7442 | 0.001 ± 0.000 | 0.252 ± 0.115 | 0.805 ± 0.095 | 0.008 ± 0.001 | 0.065 ± 0.011 | 0.065 ± 0.007 | 0.017 ± 0.003 |
| ADG10 | 0.007 ± 0.002 | >10 | >10 | >10 | >10 | >10 | >10 |
| ADG20 | 0.008 ± 0.002 | 0.348 ± 0.159 | 0.253 ± 0.070 | >10 | >10 | >10 | >10 |
| ADG30 | 0.014 ± 0.006 | >10 | >10 | >10 | >10 | >10 | >10 |
| Ly-CoV555 | 0.002 ± 0.000 | >10 | >10 | >10 | >10 | >10 | >10 |
| Ly-CoV16 | 0.014 ± 0.010 | >10 | >10 | >10 | >10 | >10 | >10 |
| Ly-CoV1404 | 0.001 ± 0.000 | 0.002 ± 0.000 | 0.001 ± 0.000 | 0.002 ± 0.000 | 0.002 ± 0.000 | 0.002 ± 0.000 | 0.002 ± 0.000 |
| 5309 | 0.079 ± 0.027 | 0.113 ± 0.006 | 0.142 ± 0.012 | 0.538 ± 0.154 | 0.311 ± 0.023 | 0.689 ± 0.041 | 0.202 ± 0.017 |

TABLE 24

| | IC50 (μg/ml) | | | | | |
|---|---|---|---|---|---|---|
| mAbs | BA.2 | BA.2 + D339H | BA.2 + R493Q | BA.2 + G446S | BA.2. + N460K | BA.2.75 |
| Omi02 | 0.003 ± 0.000 | 0.007 ± 0.003 | 0.003 ± 0.000 | 0.007 ± 0.002 | 0.025 ± 0.003 | 0.009 ± 0.002 |
| Omi03 | 0.008 ± 0.001 | 0.006 ± 0.000 | 0.002 ± 0.001 | 0.005 ± 0.001 | 0.401 ± 0.026 | 0.017 ± 0.000 |
| Omi06 | 0.039 ± 0.008 | 0.012 ± 0.002 | 0.023 ± 0.010 | 0.087 ± 0.002 | 0.026 ± 0.002 | 0.063 ± 0.005 |
| Omi08 | 0.114 ± 0.045 | 0.250 ± 0.009 | 0.194 ± 0.020 | 0.017 ± 0.001 | 0.552 ± 0.090 | 0.036 ± 0.002 |
| Omi09 | 0.008 ± 0.002 | 0.005 ± 0.001 | 0.003 ± 0.000 | 0.006 ± 0.001 | 0.010 ± 0.002 | 0.003 ± 0.000 |
| Omi12 | 0.003 ± 0.001 | 0.003 ± 0.001 | 0.001 ± 0.000 | 0.003 ± 0.001 | 0.011 ± 0.002 | 0.003 ± 0.001 |
| Omi16 | 0.034 ± 0.012 | 0.014 ± 0.004 | 0.008 ± 0.003 | 0.018 ± 0.004 | >10 | >10 |
| Omi17 | 0.060 ± 0.004 | 0.036 ± 0.015 | 0.013 ± 0.001 | 0.038 ± 0.002 | >10 | 0.255 ± 0.169 |
| Omi18 | 0.005 ± 0.000 | 0.003 ± 0.000 | 0.004 ± 0.000 | 0.003 ± 0.000 | 0.014 ± 0.002 | 0.035 ± 0.007 |
| Omi20 | 0.015 ± 0.003 | 0.007 ± 0.000 | 0.005 ± 0.001 | 0.005 ± 0.001 | 0.315 ± 0.142 | 0.178 ± 0.075 |
| Omi23 | 0.019 ± 0.005 | 0.006 ± 0.000 | 0.007 ± 0.000 | 0.010 ± 0.002 | 0.022 ± 0.005 | 0.011 ± 0.006 |
| Omi24 | 0.007 ± 0.001 | 0.005 ± 0.001 | 0.004 ± 0.000 | 0.005 ± 0.000 | 0.014 ± 0.000 | 0.008 ± 0.004 |
| Omi25 | 0.024 ± 0.004 | 0.016 ± 0.003 | 0.007 ± 0.002 | 0.022 ± 0.000 | 0.050 ± 0.010 | 0.014 ± 0.005 |
| Omi26 | 0.013 ± 0.001 | 0.007 ± 0.002 | 0.008 ± 0.001 | 0.008 ± 0.002 | 0.010 ± 0.000 | 0.010 ± 0.004 |
| Omi27 | 0.034 ± 0.006 | 0.007 ± 0.001 | 0.007 ± 0.001 | 0.011 ± 0.001 | >10 | 6.672 ± 4.466 |
| Omi28 | 0.008 ± 0.000 | 0.009 ± 0.001 | 0.010 ± 0.001 | 0.014 ± 0.000 | 0.103 ± 0.048 | 0.133 ± 0.082 |
| Omi29 | 0.056 ± 0.014 | 0.018 ± 0.006 | 0.042 ± 0.012 | 0.024 ± 0.002 | >10 | >10 |
| Omi30 | 0.013 ± 0.002 | 0.006 ± 0.001 | 0.002 ± 0.000 | 0.003 ± 0.000 | 0.018 ± 0.001 | 0.008 ± 0.002 |
| Omi31 | 0.011 ± 0.002 | 0.005 ± 0.001 | 0.003 ± 0.000 | 0.005 ± 0.001 | 0.015 ± 0.001 | 0.014 ± 0.008 |
| Omi32 | 2.614 ± 0.533 | 0.683 ± 0.179 | 0.312 ± 0.008 | 0.330 ± 0.010 | 2.341 ± 0.282 | 0.354 ± 0.064 |
| Omi33 | 0.070 ± 0.024 | 0.177 ± 0.035 | 0.063 ± 0.008 | 0.043 ± 0.016 | 0.490 ± 0.156 | 0.053 ± 0.006 |
| Omi34 | 0.009 ± 0.003 | 0.004 ± 0.000 | 0.002 ± 0.000 | 0.002 ± 0.000 | 0.020 ± 0.001 | 0.005 ± 0.000 |
| Omi35 | 0.092 ± 0.004 | 0.012 ± 0.003 | 0.017 ± 0.011 | 0.014 ± 0.006 | 0.056 ± 0.012 | 0.020 ± 0.000 |
| Omi36 | 0.030 ± 0.014 | 0.036 ± 0.002 | 0.013 ± 0.003 | 0.067 ± 0.015 | >10 | >10 |
| Omi38 | 0.005 ± 0.000 | 0.011 ± 0.000 | 0.003 ± 0.001 | 0.010 ± 0.000 | 0.010 ± 0.001 | 0.011 ± 0.005 |
| Omi39 | 0.026 ± 0.011 | 0.012 ± 0.002 | 0.021 ± 0.007 | 0.009 ± 0.002 | 0.045 ± 0.017 | 0.027 ± 0.009 |
| Omi41 | >10 | >10 | >10 | >10 | >10 | >10 |
| Omi42 | 0.021 ± 0.011 | 0.011 ± 0.002 | 0.006 ± 0.001 | 0.016 ± 0.002 | 0.007 ± 0.002 | 0.003 ± 0.000 |

TABLE 25

X-ray data collection and structure refinement statistics for BA.2.75 RBD/ACE2

| Structure | BA.2.75 RBD/ACE2 |
|---|---|
| Data collection | |
| Space group | $P4_12_12$ |
| Cell dimensions | |
| a, b, c (Å) | 105.3, 105.3, 220.8 |
| a, b, g (°) | 90, 90, 90 |
| Resolution (Å) | 76-2.85 (2.80-2.85)[a] |
| $R_{merge}$ | 0.443 (—) |
| $R_{pim}$ | 0.086 (1.401) |
| I/s(I) | 7.6 (0.4) |
| $CC_{1/2}$ | 0.971 (0.279) |
| Completeness (%) | 99.8 (96.9) |
| Redundancy | 26.8 (25.7) |
| Refinement | |
| Resolution (Å) | 76-2.85 |
| No. reflections | 2089/1439 |
| $R_{work}/R_{free}$ | 0.217/0.265 |
| No. atoms | |
| Protein | 6464 |
| Ligand/ion/water | 167 |
| B factors (Å$^2$) | |
| Protein | 86 |
| Ligand/ion/water | 108 |
| r.m.s. deviations | |
| Bond lengths (Å) | 0.002 |
| Bond angles (°) | 0.4 |

[a] Values in parentheses are for highest-resolution shell.

TABLE 26

IC50 values for Omicron mAbs

| | IC50 (µg/ml) | | | |
|---|---|---|---|---|
| mAbs | BA.2 | BA.2.11 | BA.2.12.1 | BA.2.13 |
| Omi02 | 0.003 ± 0.000 | 0.004 ± 0.001 | 0.005 ± 0.001 | 0.004 ± 0.000 |
| Omi03 | 0.008 ± 0.001 | 0.005 ± 0.002 | 0.003 ± 0.001 | 0.007 ± 0.005 |
| Omi06 | 0.039 ± 0.008 | 0.000 ± 0.000 | 0.616 ± 0.123 | 0.046 ± 0.024 |
| Omi08 | 0.114 ± 0.045 | 0.099 ± 0.020 | 0.358 ± 0.076 | 0.117 ± 0.009 |
| Omi09 | 0.008 ± 0.002 | 0.016 ± 0.005 | 0.015 ± 0.003 | 0.022 ± 0.002 |
| Omi12 | 0.003 ± 0.001 | 0.002 ± 0.000 | 0.001 ± 0.000 | 0.003 ± 0.000 |
| Omi16 | 0.034 ± 0.012 | 0.017 ± 0.004 | 0.011 ± 0.005 | 0.008 ± 0.000 |
| Omi17 | 0.060 ± 0.004 | 0.022 ± 0.008 | 0.034 ± 0.001 | 0.016 ± 0.001 |
| Omi18 | 0.005 ± 0.000 | 0.002 ± 0.000 | 0.002 ± 0.000 | 0.002 ± 0.001 |
| Omi20 | 0.015 ± 0.003 | 0.007 ± 0.004 | 0.007 ± 0.000 | 0.006 ± 0.000 |
| Omi23 | 0.019 ± 0.005 | 0.009 ± 0.003 | 0.006 ± 0.002 | 0.005 ± 0.001 |
| Omi24 | 0.007 ± 0.001 | 0.000 ± 0.000 | 0.450 ± 0.140 | 0.008 ± 0.000 |
| Omi25 | 0.024 ± 0.004 | 0.007 ± 0.001 | 0.009 ± 0.002 | 0.010 ± 0.000 |
| Omi26 | 0.013 ± 0.001 | 0.007 ± 0.003 | 0.002 ± 0.000 | 0.006 ± 0.000 |
| Omi27 | 0.034 ± 0.006 | 0.005 ± 0.001 | 0.003 ± 0.001 | 0.006 ± 0.000 |
| Omi28 | 0.008 ± 0.000 | 0.007 ± 0.000 | 0.005 ± 0.000 | 0.009 ± 0.001 |
| Omi29 | 0.056 ± 0.014 | 0.011 ± 0.001 | 0.007 ± 0.001 | 0.012 ± 0.001 |
| Omi30 | 0.013 ± 0.002 | 10 | 0.086 ± 0.026 | 0.020 ± 0.002 |
| Omi31 | 0.011 ± 0.002 | 10 | 0.089 ± 0.035 | 0.008 ± 0.004 |
| Omi32 | 2.614 ± 0.53 | 0.070 ± 0.008 | 10 | 0.503 ± 0.080 |
| Omi33 | 0.070 ± 0.024 | 0.008 ± 0.002 | 0.086 ± 0.045 | 0.055 ± 0.007 |
| Omi34 | 0.009 ± 0.003 | 10 | 0.408 ± 0.140 | 0.003 ± 0.001 |
| Omi35 | 0.092 ± 0.003 | 0.667 ± 0.104 | 0.188 ± 0.074 | 0.016 ± 0.004 |
| Omi36 | 0.030 ± 0.014 | 0.051 ± 0.027 | 0.026 ± 0.011 | 0.020 ± 0.004 |
| Omi38 | 0.005 ± 0.000 | 0.004 ± 0.001 | 0.003 ± 0.000 | 0.003 ± 0.001 |
| Omi39 | 0.026 ± 0.011 | 0.018 ± 0.003 | 0.068 ± 0.008 | 0.025 ± 0.007 |
| Omi42 | 0.021 ± 0.011 | 0.009 ± 0.003 | 0.012 ± 0.001 | 0.009 ± 0.001 |

TABLE 27

Primer sequences used to generate pseudoviruses. Related to Plasmid construction and pseudotyped lentiviral particles production.

| Primer | Sequence (5' to 3') |
|---|---|
| BA.2.11 | |
| LA52R_F | GGAGGCAATTACAATTACC GGTACAGACTGTTCAGAAAG |
| L452R_R | CTTTCTGAACAGTCTGTACC GGTAATTGTAATTGCCTCC |
| BA.2.12.1 | |
| LA52Q_R | CTTTCTGAACAGTCTGTAC TGGTAATTGTAATTGCCTCC |
| L452Q_F | GGAGGCAATTACAATTACCA GTACAGACTGTTCAGAAAG |
| S704L_F | GAGCCTGGGGGCCGAGAATC TAGTGGCCTACAGCAATAAT AG |
| S704L_R | CTATTATTGCTGTAGGCCAC TAGATTCTCGGCGCCCAGGC TC |
| BA.2.13 | |
| L452M_F | GTTGGAGGCAATTACAATTAC ATGTACAGACTGTTCAGAAAGA |
| L452M_R | TCTTTCTGAACAGTCTGTACA TGTAATTGTAATTGCCTCCAAC |

TABLE 28

X-ray data collection and structure refinement statistics a Values in parentheses are for highest-resolution shell.

| Structure | BA.2.12.1 RBD/Beta-27/NbCl |
|---|---|
| Data collection | |
| Space group | C2 |
| Cell dimensions | |
| a, b, c (Å) | 186.8, 100.0, 56.5 |
| α, β, γ (°) | 90, 104.1, 90 |
| Resolution (Å) | 55-2.38 (2.42-2.38)[a] |
| $R_{merge}$ | 0.240 (—) |
| $R_{pim}$ | 0.071 (1.366) |
| I/σ(I) | 6.3 (0.3) |
| $CC_{1/2}$ | 0.988 (0.13) |
| Completeness (%) | 94.8 (67.7) |
| Redundancy | 11.2 (4.4) |
| Refinement | |
| Resolution (Å) | 55-2.38 |
| No. reflections | 35221/1842 |
| $R_{work}/R_{free}$ | 0.186/0.233 |
| No. atoms | |
| Protein | 5723 |
| Ligand/ion/water | 259 |
| B factors (Å$^2$) | |
| Protein | 58 |
| Ligand/ion/water | 60 |
| r.m.s. deviations | |
| Bond lengths (Å) | 0.002 |
| Bond angles (°) | 0.5 |

TABLE 29

IC50 values for Omicron mAbs and commercial monoclonals a

| mAbs | Victoria | BA.1 | BA.1.1 | BA.2 | BA.4/5 | BA.4.6 |
|---|---|---|---|---|---|---|
| Omi-02 | 0.002 ± 0.001 | 0.004 ± 0.001 | 0.004 ± 0.001 | 0.003 ± 0.001 | >10 | >10 |
| Omi-03 (3-53) | 0.003 ± 0.000 | 0.005 ± 0.002 | 0.003 ± 0.001 | 0.008 ± 0.001 | 0.017 ± 0.005 | 0.006 ± 0.002 |
| Omi-06 | 0.007 ± 0.000 | 0.017 ± 0.003 | 0.139 ± 0.033 | 0.039 ± 0.008 | >10 | >10 |
| Omi-08 | 0.008 ± 0.004 | 0.003 ± 0.000 | 0.002 ± 0.000 | 0.114 ± 0.045 | 0.086 ± 0.005 | 0.033 ± 0.002 |
| Omi-09 | 0.006 ± 0.002 | 0.005 ± 0.000 | 0.005 ± 0.002 | 0.008 ± 0.002 | 0.166 ± 0.007 | 0.108 ± 0.009 |
| Omi-12 | 0.006 ± 0.002 | 0.002 ± 0.000 | 0.002 ± 0.001 | 0.003 ± 0.001 | 0.429 ± 0.060 | 0.074 ± 0.018 |
| Omi-16 (3-66) | 0.014 ± 0.003 | 0.012 ± 0.002 | 0.011 ± 0.003 | 0.034 ± 0.012 | 0.029 ± 0.007 | 0.007 ± 0.001 |
| Omi-17 (3-66) | 0.023 ± 0.011 | 0.018 ± 0.012 | 0.022 ± 0.009 | 0.060 ± 0.004 | 0.028 ± 0.001 | 0.039 ± 0.008 |
| Omi-18 (3-53) | 0.008 ± 0.003 | 0.002 ± 0.000 | 0.002 ± 0.000 | 0.005 ± 0.000 | 0.005 ± 0.001 | 0.006 ± 0.001 |
| Omi-20 (3-66) | 0.009 ± 0.002 | 0.006 ± 0.001 | 0.005 ± 0.001 | 0.015 ± 0.003 | 0.014 ± 0.006 | 0.008 ± 0.003 |
| Omi-23 | 0.005 ± 0.002 | 0.029 ± 0.006 | 0.023 ± 0.12 | 0.019 ± 0.005 | >10 | >10 |
| Omi-24 | 0.005 ± 0.000 | 0.005 ± 0.002 | 0.054 ± 0.015 | 0.007 ± 0.001 | >10 | >10 |
| Omi-25 | 0.005 ± 0.001 | 0.023 ± 0.005 | 0.027 ± 0.005 | 0.024 ± 0.004 | >10 | >10 |
| Omi-26 | 0.002 ± 0.001 | 0.006 ± 0.002 | 0.005 ± 0.001 | 0.013 ± 0.001 | >10 | >10 |
| Omi-27 (3-66) | 0.008 ± 0.003 | 0.026 ± 0.006 | 0.034 ± 0.009 | 0.034 ± 0.005 | 0.069 ± 0.023 | 0.023 ± 0.002 |
| Omi-28 (3-66) | 0.022 ± 0.005 | 0.011 ± 0.004 | 0.009 ± 0.002 | 0.008 ± 0.002 | 0.028 ± 0.009 | 0.035 ± 0.011 |
| Omi-29 (3-53) | 0.014 ± 0.006 | 0.017 ± 0.003 | 0.016 ± 0.009 | 0.056 ± 0.014 | 0.396 ± 0.007 | 0.170 ± 0.030 |
| Omi-30 | 0.012 ± 0.002 | 0.008 ± 0.003 | 0.008 ± 0.004 | 0.011 ± 0.002 | >10 | >10 |
| Omi-31 | 0.376 ± 0.090 | 0.029 ± 0.002 | 0.031 ± 0.012 | 0.013 ± 0.002 | >10 | >10 |
| Omi-32 | 0.010 ± 0.006 | 0.017 ± 0.000 | >10 | 2.682 ± 0.553 | 0.035 ± 0.016 | >10 |
| Omi-33 | 0.027 ± 0.011 | 0.014 ± 0.005 | 0.042 ± 0.018 | 0.068 ± 0.022 | 0.013 ± 0.004 | >10 |
| Omi-34 | 0.007 ± 0.004 | 0.008 ± 0.001 | 0.062 ± 0.004 | 0.009 ± 0.003 | >10 | >10 |
| Omi-35 | 0.016 ± 0.004 | 0.058 ± 0.006 | 0.381 ± 0.051 | 0.094 ± 0.004 | 1.587 ± 0.441 | >10 |
| Omi-36 (3-66) | 0.022 ± 0.005 | 0.009 ± 0.003 | 0.009 ± 0.003 | 0.090 ± 0.014 | 0.024 ± 0.006 | 0.029 ± 0.001 |
| Omi-38 | 0.015 ± 0.004 | 0.024 ± 0.015 | >10 | 0.005 ± 0.000 | 0.005 ± 0.001 | >10 |
| Omi-39 | 0.014 ± 0.002 | 0.009 ± 0.004 | >10 | 0.026 ± 0.011 | 0.035 ± 0.003 | >10 |
| Omi-41 | >10 | 0.053 ± 0.028 | 0.037 ± 0.002 | >10 | >10 | >10 |
| Omi-42 | 0.013 ± 0.004 | 0.007 ± 0.004 | 0.006 ± 0.002 | 0.021 ± 0.011 | 0.013 ± 0.001 | 0.010 ± 0.001 | b

| | IC50 (µg/mL) Pseudovirus | | | | | | |
|---|---|---|---|---|---|---|---|
| | Victoria | BA.1 | BA.1.1 | BA.2 | BA.3 | BA.4 | BA.4.6 |
| AZD1061 | 0.002 ± 0.003 | 0.308 ± 0.058 | >10 | 0.008 ± 0.008 | 0.019 ± 0.007 | 0.015 ± 0.004 | >10 |
| AZD8895 | 0.001 ± 0.000 | 0.246 ± 0.027 | 0.100 ± 0.053 | 1.333 ± 0.317 | >10 | >10 | >10 |
| AZD7442 | 0.001 ± 0.000 | 0.232 ± 0.113 | 0.806 ± 0.093 | 0.008 ± 0.001 | 0.065 ± 0.011 | 0.065 ± 0.007 | >10 |
| REGN10987 | 0.002 ± 0.001 | >10 | >10 | 0.516 ± 0.347 | >10 | >10 | >10 |
| REGN10933 | 0.001 ± 0.002 | >10 | >10 | >10 | >10 | >10 | >10 |
| ADG10 | 0.007 ± 0.002 | >10 | >10 | >10 | >10 | >10 | >10 |
| ADG20 | 0.003 ± 0.002 | 0.348 ± 0.159 | 0.253 ± 0.070 | >10 | >10 | >10 | >10 |
| ADG30 | 0.014 ± 0.005 | >10 | >10 | >10 | >10 | >10 | >10 |
| Ly-CoV555 | 0.002 ± 0.000 | >10 | >10 | >10 | >10 | >10 | >10 |
| Ly-Cov16 | 0.014 ± 0.010 | >10 | >10 | >10 | >10 | >10 | >10 |
| Ly-CoV1404 | 0.001 ± 0.000 | 0.002 ± 0.000 | 0.001 ± 0.000 | 0.001 ± 0.000 | 0.002 ± 0.000 | 0.002 ± 0.000 | 0.001 ± 0.000 |
| S309 | 0.079 ± 0.027 | 0.313 ± 0.006 | 0.142 ± 0.012 | 0.638 ± 0.154 | 0.311 ± 0.023 | 0.589 ± 0.041 | 1.029 ± 0.098 |

TABLE 30

Primer sequences used to generate pseudoviruses. Related to Plasmid construction and pseudotyped lentiviral particle production.

| Primer | Sequence (5' to 3') |
|---|---|
| pcDNA3.1_BamHI_F | GGATCCATGTTCCTGCTGACCACCAAGAG |
| pcDNA3.1_Tag_S_EcoRI_R | GAATTCTCACTTCTCGAACTGAGGGTGGC |
| pcDNA3.1_Tag_S_EcoRI_F | GCCACCCTGAGTTCGAGAAGTGAGAGTTC |
| pcDNA3.1_BamHI_R | CTCTTGGTGGTCAGCAGGAACATGGATCC |
| BA 4 + R346T_F | GTGTTCAATGCCACCACGTTCGCCAGCGTGTACG |
| BA.4 + R345T_R | CGTACACGCTGGCGAACGTGGTGGCATTGAACAG |
| BA.4 + N6S58S_F | CGGCGCCGAGTACGTGAATAGTAGCTACGAGTGCG |
| BA.4 + N6S58S_R | CGCACTCGTAGCTACTATTCACGTACTCGGCGCCG |

TABLE 31

Table of SARS-CoV-2 lineages and genomic mutations

| Lineage | Defining RBD mutations | Example early genome | Submitting scientist, laboratory | Country/Region of earliest sequences | Date of earliest sequences | Pango issue, contributor |
|---|---|---|---|---|---|---|
| BA.A.6 | BA.4/5 + R3467 | EPI_ISL_32475382 | Oliveratal, HOSPITAL UNIVERSITARIO SON ESPASES | Europe/South Africa | April 2022 | #741, ryhisner |
| BA.A.7 | BA.4/5 + R3457 | EPI_ISL_32644817 | Iranzauen et al. NHLS/UCT | South Africa/Israel | April 2022 | #777, FedaGuell |
| BA.7(BA.5.2.3.7) | BA.4/5 R3467 | EPI_ISL_32810243 | Coppens et al., Labo Kinische Biologie, 2A | Belgium | May 2022 | #827, ryhisner |
| BO.1(BA.5.3.1.1.3.1.5) | BA.4/5 K444T, N450K | EPI_ISL_34294805 | Howardetal, Centers for Disease Control and Prevention Division of Viral Diseases, Pathogen Discovery | Nigeria | July 2022 | #998, FedaGuell |
| BO.1.3(BA.5 5.3.1.1.3.1.1) | BO.1 + R346T | EPI_ISL_14752457 | Christensen et al., Houston Methodis Hospital | USA | August 2022 | #993, FedaGuell |
| BA.2.7.5 | BA.2 + G4465, N450K, R498Q* | EPI_ISL_33802209 | Rhaimaratal, CSIR-NEER, Nego/Covid-19 Testing lab | India | April 2022 | #773, Siten |
| BA.2.75.2 | BA.2.75 + R3451, FA86S | EPI_ISL_24250506 | Gupta et al. IL85/INSAOOG | India | July 2022 | #965, agamediate |
| BN.1(BA.2.75.5.2) | BA.2.75 + R345T, K356T, FA908 | EPI_ISL_24801544 | Sima et al., Lifebrain CovidLabor Gmiss | India | July 2022 | #994, cornetiusenemer |
| BA.1(BA.2.10.1.1) | BA.2 + R345T, L3681, V4459, G448S, V483A, F480V | EPI_ISL_14366803 | Maitraetal National institute of Biomedical Genomics-INSACOG | India | June 2022 | #935, Sikn |
| BA.2.10.A | BA.2 +G4485, F485P, R498Q*, 5494P | EPI_ISL_18929780 | et al., Center for Genomics, Department of Microbiology, BJ Government Medical College and Gaesoon Hospitals | India | June 2022 | #898, Sikn |
| BS.1(BA.2.3.2.3) | BA.2 + R345T, L452H, N450K, G475S | EPI_ISL_34565710 | Sekuzuka et al, Pathogen Genomics Center, National Institute of Infectious Diseases | Japan ex Vietnam | August 2022 | #1052, TakaKeng |
| BA.2.3.20 | K44N, N450D, L452M, N450K, E484R, R493Q* | EPI_ISL_34725265 | Setway et al, SA Pathology | USA/Singapore/Australia | August 2022 | #1053, ryhisner |
| X55 | BA.2 + R3457, L368I, V445P, G446S, N460K, F4565, F450S | EPI_ISL_24917701 | Nigan et al, National Public Health Laboratory, National Centre for Infectious Diseases | India | August 2022 | #1058, cornetiusnemer |

TABLE 32

IC50 values for BA.1 mAbs and commercial mAbs

| mAbs | Victoria | BA.2 | BA.4/5 | BA.4.5 | BA.2.75 | BA.2.75.2 | BA.2.3.20 | BA.1 | BA.4 + all |
|---|---|---|---|---|---|---|---|---|---|
| Omi-02 | 0.002 ± 0.001 | 0.003 ± 0.001 | >10 | >10 | 0.009 ± 0.002 | >10 | 0.013 ± 0.001 | 0.011 ± 0.001 | >10 |
| Omi-03 (3-53) | 0.003 ± 0.000 | 0.008 ± 0.001 | 0.017 ± 0.005 | 0.006 ± 0.002 | 0.017 ± 0.000 | 0.546 ± 0.166 | 0.020 ± 0.007 | 0.014 ± 0.000 | 0.432 ± 0.106 |
| Omi-06 | 0.007 ± 0.000 | 0.039 ± 0.008 | >10 | >10 | 0.063 ± 0.005 | >10 | >10 | >10 | >10 |
| Omi-08 | 0.008 ± 0.004 | 0.114 ± 0.045 | 0.086 ± 0.005 | 0.033 ± 0.002 | 0.035 ± 0.002 | 0.027 ± 0.012 | 0.426 ± 0.024 | >10 | >10 |
| Omi-09 | 0.006 ± 0.002 | 0.008 ± 0.002 | 0.166 ± 0.007 | 0.108 ± 0.009 | 0.003 ± 0.000 | 0.012 ± 0.000 | 0.133 ± 0.003 | >10 | >10 |
| Omi-12 | 0.006 ± 0.002 | 0.003 ± 0.001 | 0.429 ± 0.060 | 0.074 ± 0.018 | 0.003 ± 0.001 | >10 | 0.008 ± 0.001 | 0.004 ± 0.000 | >10 |
| Omi-16 (3-66) | 0.014 ± 0.003 | 0.034 ± 0.012 | 0.029 ± 0.007 | 0.007 ± 0.001 | 8.666 ± 4.596 | >10 | 1.075 ± 0.241 | 0.025 ± 0.000 | >10 |
| Omi-17 (3-66) | 0.023 ± 0.011 | 0.060 ± 0.004 | 0.028 ± 0.001 | 0.039 ± 0.008 | 0.255 ± 0.169 | >10 | 0.347 ± 0.123 | 0.030 ± 0.006 | >10 |
| Omi-18 (3-53) | 0.008 ± 0.003 | 0.005 ± 0.000 | 0.005 ± 0.001 | 0.006 ± 0.001 | 0.035 ± 0.007 | 4.800 ± 0.568 | 0.011 ± 0.001 | 0.005 ± 0.002 | 3.607 ± 0.807 |
| Omi-20 (3-66) | 0.009 ± 0.002 | 0.015 ± 0.003 | 0.014 ± 0.006 | 0.008 ± 0.003 | 0.178 ± 0.075 | 8.948 ± 3.561 | 0.030 ± 0.005 | 0.009 ± 0.002 | >10 |
| Omi-23 | 0.005 ± 0.002 | 0.019 ± 0.005 | >10 | >10 | 0.011 ± 0.006 | >10 | 0.009 ± 0.003 | 0.024 ± 0.001 | >10 |
| Omi-24 | 0.005 ± 0.000 | 0.007 ± 0.001 | >10 | >10 | 0.008 ± 0.004 | 4.681 ± 1.859 | >10 | >10 | >10 |
| Omi-25 | 0.005 ± 0.001 | 0.024 ± 0.004 | >10 | >10 | 0.014 ± 0.005 | >10 | 0.025 ± 0.004 | 0.041 ± 0.028 | >10 |
| Omi-26 | 0.002 ± 0.001 | 0.013 ± 0.001 | >10 | >10 | 0.010 ± 0.004 | >10 | 0.006 ± 0.001 | 0.031 ± 0.015 | >10 |
| Omi-27 (3-66) | 0.008 ± 0.003 | 0.034 ± 0.005 | 0.069 ± 0.023 | 0.023 ± 0.002 | 6.672 ± 4.466 | >10 | 0.215 ± 0.111 | 0.007 ± 0.000 | >10 |
| Omi-28 (3-66) | 0.022 ± 0.000 | 0.008 ± 0.009 | 0.028 ± 0.009 | 0.035 ± 0.011 | 0.133 ± 0.082 | 7.592 ± 0.028 | 0.053 ± 0.013 | 0.010 ± 0.013 | >10 |

TABLE 32-continued

IC50 values for BA.1 mAbs and commercial mAbs

| mAbs | Victoria | BA.2 | BA.4/5 | BA.4.5 | BA.2.75 | BA.2.75.2 | BA.2.3.20 | BA.1 | BA.4 + all |
|---|---|---|---|---|---|---|---|---|---|
| Omi-29 (3-53) | 0.014 ± 0.005 | 0.056 ± 0.014 | 0.396 ± 0.007 | 0.170 ± 0.030 | >10 | >10 | >10 | 0.025 ± 0.012 | >10 |
| Omi-30 | 0.085 ± 0.008 | 0.011 ± 0.002 | >10 | >10 | 0.008 ± 0.002 | 0.009 ± 0.001 | 0.343 ± 0.023 | 1.827 ± 0.436 | >10 |
| Omi-31 | 0.014 ± 0.001 | 0.013 ± 0.002 | >10 | >10 | 0.014 ± 0.008 | 0.012 ± 0.001 | >10 | >10 | >10 |
| Omi-32 | 0.010 ± 0.006 | 2.682 ± 0.553 | 0.035 ± 0.016 | >10 | 0.354 ± 0.064 | >10 | >10 | >10 | >10 |
| Omi-33 | 0.027 ± 0.011 | 0.068 ± 0.022 | 0.013 ± 0.004 | >10 | 0.053 ± 0.006 | >10 | >10 | > | 10 |
| Omi-34 | 0.007 ± 0.004 | 0.009 ± 0.003 | >10 | >10 | 0.005 ± 0.000 | 0.005 ± 0.001 | >10 | >10 | >10 |
| Omi-35 | 0.018 ± 0.004 | 0.094 ± 0.004 | 1.687 ± 0.441 | >10 | | | | | |
| Omi-36 (3-66) | 0.022 ± 0.004 | 0.030 ± 0.014 | 0.024 ± 0.006 | 0.009 ± 0.001 | >10 | 3.815 ± 0.054 | >10 | 0.045 ± 0.005 | >10 |
| Omi-38 | 0.015 ± 0.004 | 0.005 ± 0.000 | 0.005 ± 0.001 | >10 | 0.011 ± 0.005 | >10 | >10 | >10 | >10 |
| Omi-39 | 0.014 ± 0.002 | 0.026 ± 0.011 | 0.035 ± 0.003 | >10 | 0.027 ± 0.009 | >10 | >10 | >10 | >10 |
| Omi-41 | >10 | >10 | >10 | >10 | >10 | >10 | >10 | >10 | 0.0008 ± 0.001 |
| Omi-42 | 0.033 ± 0.004 | 0.021 ± 0.011 | 0.013 ± 0.001 | 0.010 ± 0.001 | 0.003 ± 0.000 | 0.011 ± 0.005 | 0.028 ± 0.001 | 0.010 ± 0.001 | 0.008 ± 0.001 | b

| | Victoria | BA.2 | BA.4/5 | BA.2.75 | BA.4.6 | BA2.75.2 | BA.2.3.20 | BA.1 | BA.4 + all |
|---|---|---|---|---|---|---|---|---|---|
| AZD1063 | 0.052 ± 0.055 | 0.003 ± 0.003 | 0.015 ± 0.054 | 0.021 ± 0.000 | >10 | >10 | >10 | >10 | >10 |
| AZD8895 | 0.001 ± 0.000 | 2.353 ± 0.317 | >10 | 0.008 ± 0.000 | >10 | >10 | 0.007 ± 0.001 | 5.114 ± 0.015 | >10 |
| AZD7442 | 0.001 ± 0.000 | 0.003 ± 0.001 | 0.065 ± 0.007 | 0.017 ± 0.003 | >10 | >10 | 0.026 ± 0.001 | 2.735 ± 0.537 | >10 |
| REGN10987 | 0.002 ± 0.001 | 0.616 ± 0.347 | >10 | >10 | >10 | >10 | >10 | >10 | >10 |
| REGN10933 | 0.001 ± 0.002 | >10 | >10 | >10 | >10 | >10 | 5.654 ± 0.019 | >10 | >10 |
| ADG20 | 0.005 ± 0.002 | >10 | >10 | >10 | >10 | >10 | >10 | >10 | >10 |
| Ly-CoV555 | 0.022 ± 0.000 | >10 | >10 | >10 | >10 | >10 | >10 | >10 | >10 |
| Ly-CoV16 | 0.014 ± 0.000 | >10 | >10 | >10 | >10 | >10 | >10 | >10 | >10 |
| Ly-CoV1404 | 0.001 ± 0.000 | 0.001 ± 0.000 | 0.001 ± 0.000 | 0.022 ± 0.000 | 0.001 ± 0.000 | 0.001 ± 0.001 | 0.013 ± 0.005 | >10 | >10 |
| 5309 | 0.078 ± 0.027 | 0.558 ± 0.154 | 0.889 ± 0.041 | 0.202 ± 0.041 | 1.029 ± 0.097 | 0.498 ± 0.538 | 0.977 ± 0.107 | 0.436 ± 0.010 | 0.582 ± 0.072 |

Sequence Listing
Amino Acid Sequence of Heavy Chain and Light Chain
Variable Regions of Selected Antibodies

| Antibody number: | Amino acid sequence | SEQ ID NO: | Amino acid sequence | SEQ ID NO: |
|---|---|---|---|---|
| 2 | EVQLVQSGAEVKKPGSSVK VSCKASGGTFSNYAISWVR QAPGQGLEWMGGIIPIFGTA NYAQNFQGRVTITADESMS TAYMELSSLRSEDTAVYYC AGGGRYCSGGRCHSAYSAY WGQGTLVTSS | 2 | AIQLTQSPGTLSLPPGERATL SCRASQSVSSSYLAWYQQK PGQAPRLLIYGASSRATGIP DRFSGSGSGTDFTLTISRLD PEDFAVYYCQQYGSSLTFG GGTKVDIK | 4 |
| 22 | QVQLVESGGGLVHPGGSLR LSCSASGFTFSNYAMHWVR QAPGKGLEYVSAISSSGDITY YADSVKGRFTISRDNSKNSL YLQMNSLRAEDTAVYYCV KDVTRTYYVVFDYWGQGT LVTVSS | 12 | AIQLTQSPSSLSASVGDRVT ITCRASQSISSYLNWYQQEP GKAPKLLIYAASSLQGGVP SRFSGSGSGTDFTLTISSLQP EDFATYYCQQSYTTPYTFG QGTKVDIK | 14 |
| 40 | QVQLVESGGGLVQPGGSLR LSCAVSGFTVSRNYMSWVR QAPGKGLEWVSLIYSGGSTF YADSVKGRFTISRDNSKNTL YLQMNSLRAEDTAVYYCA RDLFHRSGYHDYWGQGTL VTVSS | 22 | VIWMTQSPSSLSASVGDRV TITCQASQDINNYLNWYQQ KPGKAPKLLIFDASNLETGV PSRFSGSGSGTDFTFTISSLQ PEDIATYYCQQYDNLPAFG GGTKVDIK | 24 |
| 44 | EVQLVESGGGVVQPGRSLR LSCAASGFTFSNYGMHWVR QAPGKGLEWVAVVWYDGS KKYYADSVKGRFTISRDNS KNTLYLQMNSLRVEDTAV YYCARDFAVGEEIADSWGQ GTLVTVSS | 32 | SYELTQPPSVSVSPGQTARI TCSGDALPKKYAYWYQQK SGQAPVLVIYEDSKRPSGIP ERFSGSSSGTMATLTISGAQ VEDEGDYYCYSRDSSGDH WVFGAGTKLTVL | 34 |
| 45 | QVQLVESGGGVVQPGRSLR LSCAASGFTFSTYAMHWVR | 42 | DIQLTQSPSSLSASVGDRVTI TCQASQDISNYLNWYQQKP | 44 |

| Antibody number: | Amino acid sequence | SEQ ID NO: | Amino acid sequence | SEQ ID NO: |
|---|---|---|---|---|
| | QAPGKGLEWVAVLSYDGSN KYYADSVKGRFTISRDNSK NTLYLQMNSLRAEDTAVY YCAKGGSYAYYYYMDVW GKGTTVTVSS | | GKAPKLLIYDASNLETGVPS RFSGGGSGTDFTFTITSLQPE DIATYYCQQYDNLPLTFGG GTKVDIK | |
| 54 | VQLVQESGPGLVKPSETLSL TCTVSGGSVSSGSYYWSWI RQPPGKGLEWIGYMYFSGS TNYNPSLKSRVTISLATSKN QFSLKLSSVTAADTAVYYC ARGDYDFWSGPPGRVDVW GKGTTVTVSS | 52 | EIVMTQSPGTLSLSPGERATL SCRASQSVSSSYLAWYQQKP GQAPRLLIYGASSRATGIPDR FSGSGSGTDFTLTISRLEPED FAVYYCQHYGSSPVTFGQGT KVDIK | 54 |
| 55 | QVQLVQSGPEVKKPGTSVK VSCKASGFTFTSSAVQWVR QARGQRLEWIGWIVVGSGN TNYAQKFQERVTITRDMST STAYMEMSSLRSEDTAVYY CAAPACGTSCSDAFDIWGQG TMVTVSS | 62 | DIQMTQSPGTLSLSPGERAT LSCRASQSVSSSYLAWYQQK PGQAPRLLIYGASSRATGIP DRFSGSGSGTDFTLTISRLEP EDFGVYYCQQYGSSPWTFG QGTKVEIK | 64 |
| 58 | QVQLVESGGGLVQPGRSL RLSCAASGFTFDDYAMHW VRQPPGKGLEWVSGVSWN SGTIGYADSVKGRFIISRDN AKNSLYLQMNSLKAEDTA LYYCAREVGGTFGVLISRE GGLDYWGQGTLVTVSS | 72 | SYELTQPPSVSVAPGQTARIT CGGNTIGSKSVHWYQQRPGQ APVLVVYDDSDRPSGIPERFS GSNSGNTATLTISRVEAGDE ADYYCQVWDSSSDRVVFGG GTKLTVL | 74 |
| 61 | QVQLQESGPGLVKPSETLS LICTVSGGSVSSGNFYWSW IRQPPGKGLEWIGSIYYTG SPNYNPSLKSRVTISLDTS KNQFSLKLSSVTAADTAVY YCAREIYYYDRSGSYNSDA FDIWGQGTMVTVSS | 82 | DIVMTQSPATLSVSPGERGT LSCRASQSVSSNLAWYQQK PGQAPRLLIYGASTRATGIP ARFSGSGSGTEFTLTISSLQS EDFAVYYCQQYNNWPPLT FGGGTKVDIK | 84 |
| 75 | QVQLVESGGGVVQPGRSL RLSCAASGFTFNNYPLHW VRQAPGKGPEWVAVISQD GGNKYYVDSVKGRFTISRD NSKNTLYLQMNNLRAEDT ALYYCARDVVVVVAARN HYYNGMDVWGQGTTVTV SS | 92 | DIQLTQSPSSVSASVGDRVT ITCRASQGISSWLAWYQQK PGKAPKLLIYAVSSLQSGVP SRFSGSGSGTDFTLTISSLQP EDFATYYCQQAKSFPPTFG PGTKVEIK | 94 |
| 88 | QLQLQESGPGLVKPSQTLSL TCTVSGGSISSGSYNWTWIR QPAGKGLEWIGRIYNSGSTN YNPSLKSRVTISVDTSKNQLS LKVRSVTAADTAVYYCAR HCSGGTCYPKYYYGMDVW GQGTTVTVSS | 102 | QSALTQPPSVSEAPRQRVTIS CSGSSSNIGNNAVNWYQQFP GKAPKLLIYYDDLLPSGVSD RFSGSKSGTSASLAISGVQSE DEADYYCAAWDDSLNVVVF GGGTKLTVL | 104 |
| 111 | QVQLVESGPGLVKPSETLSL TCTVSGGSISSNSYFWGWIR QPPGTGLEWIGNIYYTGSTY YNPSFESRVTMSVDTSKNQ FSLRLSSVTAADTAVYYCAR HVRAYDYDAPFDIWGQGT MVTVSS | 112 | VIWMTQSPSSLSASVGDRVTI TCRASQGIRNDLGWYQQKPG KAPKRLIYAASSLQSGVPSRF SGSGSGTQFTLTISSLQPEDF ATYYCLQINSYPLTFGGGTK VEIK | 114 |
| 132 | QVQLQQWGAGLLKPSETL SLTCAVYGGSFSGYYWSW IRQPPGKGLEWIGEINHSGS TNYNPSLKSRVTISVDTSK NQFSLKLSSVTAADTAVY YCARTDYYDSIDWGQGTL VTVSS | 122 | QSVLTQEPSLTVSPGGTVTLT CGSSTGAVTSGHYPYWFQQ KPGQVPRTLIYDTRNKHSWT PARFSGSLLGGKAALTLSGA QPEDEAEYYCLLSSSGARVF GGGTKLTVL | 124 |
| 140 | EVQLVESGGGLVQPGGSLR LSCAASGFTFSTYDIHWVR QATGKGLEWVSAIGTAGDT YYSGSVKGRFTISRENAKNS | 132 | DIVMTQSPSSLSASVGDRITI TCRASQSINNYLNWYQQKP GKAPKLLIYAASRLQTGVPS RFSGSGSGTDSTLTINTLQPE | 134 |

-continued

| Antibody number: | Amino acid sequence | SEQ ID NO: | Amino acid sequence | SEQ ID NO: |
|---|---|---|---|---|
| | LYLQMNSLRAGDTAVYYC ARGSGTYFYYFDYWGQGT LVTVSS | | DFATYYCQQSYSAPPWTFG QGTKVDIK | |
| 148 | QVQLVESGPGLVKPSETLS LTCTVSGGSISSSYYWGWI RQPPGKGLEWIGSVYYSGS TYYNPSLKSRVTISVDTSK NQFSLRLSSVTAADTAVYY CARLMTTEDYYSGMDVW GQGTTVTVSS | 148 | AIQMTQSPSSLSASVGDRV TITCRASQGISDYLAWFQQ KPGKAPKSLIYAASSLQSG VPSKFSGGGSGTDFTLTISS LQPEDFATYYCQQYHSYPI TFGQGTRLEIK | 144 |
| 150 | QVQLVESGGGLIQPGGSLR LSCAASGVTVSSNYMSWV RQAPGKGLEWVSIIYSGGT TYYADSVKGRFTISRDSSM NTLYLQMNSLRAEDTAVY YCARDLMVYGIDVWGQG TTVTVSS | 152 | EIVMTQSPSSLSASVGDRVT ITCRASQGISSYLAWYQQK PGKAPKLLIYAASTLQSGVP SRFSGSGSGTDFTLTISSLQP EDFATYYCQQLDSYPPGYT FGQGTKVDIK | 154 |
| 158 | EVQLLESGGDLIQPGGSLRL SCAASGVTVSSNYMSWVR QAPGKGLEWVSIIYPGGSTF YADSVKGRFTISRDNSKNTL YLQMHSLRAEDTAVYYCA RDLGSGDMDVWGKGTTVT VSS | 162 | DIVMTQSPSFLSASVGDRV TITCRASQGISSYLAWYQQ KPGKAPKLLIQAASTLQSG VPSRFSGSGSGTEFTLTISSL QPEDFATYYCQQLNSYRYT FGQGTKVEIK | 164 |
| 159 | EVQLVESGGGVVQPGRSL RLSCAASGFTFSSYGMHW VRQAPGKGLEWVALISYD GGNRYYADSVKGRFTISRD NSKNTLYLQMNRLRAEDT AMYYCAKDRDDGWDWY YFMDVWGKGTTVTVSS | 172 | DIQLTQSPGTLSLSPGERAT LSCRASQSISGNYLAWYQH KPGQAPRLLIYGASTRATGI PDRFSGSGSGTDFTLTISRLE PEDFAVYYCQQYGSSYTFG QGTKVEIK | 174 |
| 165 | QVQLVQSGPEVKKPGTSV KVSCKASGFTFTSSAVQW VRQARGQRLEWIGWIVVG SGNTNYAQKFQESVTITRD MSTSTAYMELSSLRSEDTA VYYCAAPHCIGGSCHDAF DIWGQGTMVTVSS | 182 | DIVMTQSPGTLSLSPGERA TLSCRASQSVRSSYLAWYQ QKPGQAPRLLIYGASRRGT GIPDRFSGSGSGTDFTLTIS RLEPEDFAVYYCQQYGSSP WTFGQGTKVEIK | 184 |
| 170 | QVQLVESGAEVKKPGESL KISCKGSGYSFTSYWIVWV RQMPGKGLEWMGIIYPGD SDTKYSPSFQGQVSISADK PISTAYLQWSRLKASDTA MYYCARLGNWLVDYWG QGTLVTVSS | 192 | DIVMTQSPLSLSVTPGQPAS ISCKSSQSLLHSDGKTYLY WYLQKPGQPPQLLMYEVS NRFSGVPDRFSGSGSGTDFT LKISRVESEDVGVYYCMQS IQLPRGITFGQGTRLEIK | 194 |
| 175 | EVQLVESGGGLIQPGGSLR LSCAASGLTVSRNYMSWV RQAPGKGLEWVSLIYSGGS TYYADSVKGRFTISRDNSK NTLYLQMNSLRAEDTAVY YCARDLRGEVWGQGTMV TVSS | 202 | AIQMTQSPSSLSASVGDRVT ITCQASQDISNFLNWYQQK PGKAPKLLIYDASNLETGVP SRFSGSGSGTDFTFTISSLQP EDIATYYCHQYDNLPRTFGQ GTKVDIK | 204 |
| 177 | EVQLVESGGGLVQPGGSL RLSCAASGFTFSNYDMHW VRQATGKGLEWVSLIGTA GDTYYPDSVKGRFTISREN AKNSLYLQMNSLRAGDTA VYYCARGQHTQIGHYYYY YMDVWGKGTTVTVSS | 212 | AIRMTQSPSSLSASVGDRV TITCRASQSISSYLNWYQQ KPGKAPKLLIFAASSLQSGV PSRFSGSGSGTDSTLTISSL QPEDFATYYCQQSYSNPPE GSFGQGTKVEIK | 214 |
| 181 | EVQLVETGGGLIQPGGSLRL SCAASGFTVSSNYMSWVRQ APGKGLEWVSVVYGGGTT YYADSVKGRFTISRDNSKN TLYLQMNSLRAEDTAVYYC ATDNGYSYGFSFDYWGQG TLVIVSS | 222 | QSVLTQPASMSGSPGQSITI SCTGTSSDVGGYNLVSWYQ QHPGKAPKLMIYEGSKRPSG VSNRFSGSKSGNTASLTISG LQAEDEADYYCCSYAGSSN WVFGGGTKLTVL | 224 |

-continued

| Antibody number: | Amino acid sequence | SEQ ID NO: | Amino acid sequence | SEQ ID NO: |
|---|---|---|---|---|
| 182 | QVQLVESGAEVEKPGASVKVSCKASGYTFTGYYMHWVRQAPGQGLEWMGWINPISGGTNYAQKFQGRVTMTRDTSISTAYMDLSRLRSDDTAVYYCARGTYYYDSSGYIPFDYWGQGTLVTVSS | 232 | QSVLTQPASVSGSPGQSITISCTGTSSDVGSYNLVSWYQQHPGKAPKLMIYEGSKRPSGVSNRFSGSKSGNTASLTISGLQAEDEADYYCCSYAGSSTLVFGGGTKLTVL | 234 |
| 183 | QVQLVQSGSELKKPGASVKVSCKASGYTFSSYAMTWVRQAPGQGLEWMGWINTNTGNPTYAQGFTGRFVFSLDTSVSTAYLQISSLKAEDTAVYYCARALGYCSSTSCYPAWAAFDIWGQGTMVTVSS | 242 | SYELTQPLSVSVALGQTASITCGGNNIGSKNVHWYQQKPGQAPVLVIYRDSNRPSGIPERFSGSNSGNTATLTISRAQAGDEADYNCQVWDSSVVFGGGTKLTVL | 244 |
| 222 | EVQLVESGGGLIQPGGSLRLSCAASGLTVSSNYMSWVRQAPGKGLEWVSVIYSGGSTFYADSVKGRFTISRDNSKNTLYLQMNSLGAEDTAVYYCARGEGSPGNWFDPWGQGTLVTVSS | 252 | DVVMTQSPGTLSLSPGERATLSCRASQSVPSSYLAWYQQKPGQAPRLLIYGASTRATGIPDRFSGSGSGTDFTLTISRLEPEDFAVYYCQHYDTSPRFGGGTKVDIK | 254 |
| 253 | QVQLVQSGPEVKKPGTSVKVSCKASGFTFTTSAVQWVRQARGQRLEWIGWIVVGSQNTNYAQKFQERVTITRDMSTTTAYMELSSLRSEDTAVYFCAAPHCNSTSCYDAFDIWGQGTMVTVSS | 262 | DIQMTQSPGTLSLSPGEGATLSCRASQSVSSSYLAWYQQKPGQAPRLLIYGASSGATGIPDRFSGSGSGTDFTLTISRLEPEDFAVYYCQQYGSSPYTFGQGTKVEIK | 264 |
| 269 | QVQLVESGGGLIQPGGSLRLSCAASGLTVNRNYMSWIRQAPGKGLEWVSVIYSGGSTFYADSVKGRFTISRDNSKNTLSLQMNSLRAEDTAIYYCARDFYEGSFDIWGQGTMVTVSS | 272 | AIQLTQSPSFLSASIGDRVTITCRASQGISSYLAWYQQKPGKAPKLLIYAASTLQSGVPSRFSGSGSGTEFTLTISSLQPEDFASYYCQQLNSYPAPVFGPGTKVDIK | 274 |
| 278 | QVQLVQSGAEVKKPGASVKVSCKASGYIFIRYGISWVRQAPGQGLEWMGWISANNGYTNYAQKLQGRVTMTTDTSTSTAYMELRSLRSDDTAVYYCARDGGILTGYLDYFDHWGQGTLVTVSS | 282 | DIQMTQSPSSLSASVGDRLTITCRASQSIASYLNWYQQKPGKAPKLLIYAASSLQSGVPSRFSGSGSGTDFTLTISSLQPEDFATYHCQQSYSTLGITFGPGTKVDIK | 284 |
| 281 | QVQLVESGGGLVQPGGSLRLSCAASGFPFSIYWMSWVRQAPGKGLEWVANIKQDGSEKYYVDSVKGRFTISRDNAKNSLYLHMNSLRGEDTAVYYCASRYYDFRPEAWFDYWGQGTLVTVSS | 292 | DIVMTQTPLSSPVTLGQPASISCRSSQSLVHRDGNTYLSWLQQRPGQPPRLLIYKISNRFSGVPDRFSGSGAGTDFTLKISRVEAEDVGVYYCMQATQFPHGYTFGQGTKVEIK | 294 |
| 282 | QVQLQESGGGLVQPGGSLRLSCSASGFTVSSNYMTWVRQAPGKGLEWVSVIYSGGSTFYADSVKGRFTISRDNSKNTLYLQMNSLRAEDTAVYYCARDLEEAGGFDYWGQGTLVTVSS | 302 | EIVLTQSPGTLSLSPGEKVTLSCRASQSVSSTYLAWYQQKPGQAPRLLIYGASSRATGVPDRFRGSGSGTDFTLTISRLEPEDFAVYYCQQYGSSLYTFGQGTKVDIK | 304 |
| 285 | QLQLQESGPGLVKPSETLSLTCTVSGDSVSNYYWSWIRQPAGKGLEWIGRIYTSGSTNYNPSLKSRVTMSVDTSKNQFSLKLSSVTAADTAVYYCARDHRASRYSSGWYEWWNCFDPWGQGTLVTVSS | 312 | DIQMTQSPSSLSASVGDRVTITCRASQSISSYLNWYQQKPGKAPKLLIYAASSLQSGVPSRFSGSGSGTDFTLTINSLQPEDFATYYCQQSYSTPALTFGGGTKVDIK | 314 |

-continued

| Antibody number: | Amino acid sequence | SEQ ID NO: | Amino acid sequence | SEQ ID NO: |
|---|---|---|---|---|
| 316 | QVQLVQSGAEVKKPGASV KVSCKASGYTFTGYYMH WVRQAPGQGLEWMGWIN PNSGGTNYTQKFQGRVTM TRDTSISTAYMELSRLRS DDTAVYSCARDMAFSMVR GSFDYWGQGTLVTVSS | 322 | QAVLTQPPSASGSPGQSVTI SCTGTSSDVGGYNYVSWYQ QHPGKAPKLMIYEVSKRPS GVPDRFSGSKSGNTASLTV SGLQAEDEADYYCSSYAGS NHWVFGGGTKLTVL | 324 |
| 318 | QVQLVQSGPEVKKPGTSV KVSCKASGFTLTSSAMQW VRQARGQRLEWIGWIVVG SQNTNYAQKFQERVTITRD MSTSTAYMELSSLRSEDTA VYYCAAGRGYNSDFDYWG QGTLVTVSS | 332 | AIRMTQSPGTLSLSPGERAT LSCRASQSVSSSYLAWYQQR PGQAPRLLIYGTSSRATGIP DRFSGSGSGTDFTLTISRLEP EDFAVYYCQQYGYSVYTFG QGTKVDIK | 334 |
| 334 | QVQLVESEAEVKKPGASV KVSCKASGYTFTSYYMHW VRQAPGQGLQWMGIINPS AGSTSYAQKFQGRVTMTT DTSTTTVYMELSSLRSEDT AVYYCARDSVLVPAANAF DIWGQGTMVTVSS | 342 | EIVMTQSPATLSLSPGERAT LSCRASQSVSSYLAWYQQK PGQAPRLLIYDASNRATGIP ARFSGSGSGTDFTLTISSLEP EDFAVYYCQQRRNWLFTFG PGTKVDIK | 344 |
| 361 | QVQLVQSGAEVKKPGAS VKVSCKASGDTFTSYTLH WVRQAPGQRLEWMGWI NAGNGYTKYSQKFQGRV TITRDTSASTAYMELSSLR SEDTAVYYCAKCTMIVDY FDYWGQGTLVTVSS | 352 | AIRMTQSPSTLSASVGDRVT ITCRASQSISGWLAWYQQK PEKAPKLLIYDASNLESGVP SRFSGSGSGTEFTLTINSLQP DDFATYYCQQYNSYPWTF GQGTKVDIK | 354 |
| 382 | EVQLVQSGAEVKKPGASV KVSCKASGYTFTSYDINW VRQATGQGLEWMGWMN PHSDTTGYAQKFQGRVTM TRNTSITTAYMELSSLRSED TAVYYCAQGPIAVNYMD VWGKGTTVTVSS | 362 | QPVLTQPPSVSVAPGKTARI TCGGSNIGSKSVHWYQQKP GQAPVLIIYYDSDRPSGIPER FSGSNSGNTATLTISRVEAG DEADFYCQVWDSSTDHVV FGGGTKLTVL | 364 |
| 384 | EVQLVESGGGLVKPGESL RLSCAASGFTFSDYYMTW IRQAPGKGLEWVSYIRSSG HTIYYADSVKGRFTISRDN AKNSLYLQMNSLRVEDTA VYYCARGGVLRFLEWPLN AFDIWGQGTMVTVSS | 372 | DIQLTQSPSSLSASVGDRVT ITCRASQGISNYLAWYQQK PGKVPKLLIYAASTLQSGVP SRFSGSGSGTDFTLTISSLQP EDVATYYCQKYNNALGTF GQGTKVEIK | 374 |
| 394 | EVQLVQSGAEVKKPGASV KVSCKASGYTFTGYYMH WVRQAPGQGLEWMGWIS PNSGGTNYAQKFQGRVTM TRDTSITTAYMDLSRLSDD TAVYYCARGYYYEALDAF DIWGQGTMVTVSS | 382 | QSVVTQPASVSGSPGQSITIS CTGTSSDVGGYNFVSWYQ QHPGKAPKLMIYEVSNRPS GVSNRFSGSKSGITASLTISG LQAEDEADYYCNSYTSNST RVFGGGTKLTVL | 384 |
| 398 | QVQLVESGGGLVQPGGSLR LSCAASGFTVSSNYMTWVR QAPGKGLEWVSVIYSGGSTY YADSVKGRFTISRDNSKNTL YLQMNSLRADDTAVYYCA RDSTADYDFWSGYYVGAF HIWGQGTMVTVSS | 392 | QTVLTQPASVSGSPGQSITIS CTGTSSDVGGYNYVSWYQ QHPGKAPKLMIYEVTKRPSG VPDRFSGSKSGNTASLTVS GLQAEDEADYYCSSYAGS NNWVFGGGTKLTVL | 394 |

Nucleotide Sequence of Heavy Chain and Light Chain
Variable Regions of Selected Antibodies

| Antibody number: | Heavy chain Nucleotide Sequence | SEQ ID NO: | Light chain Nucleotide sequence | SEQ ID NO: |
|---|---|---|---|---|
| 2 | gaggtgcagctggtgcagtctggggctga ggtgaagaagcctgggtcctcggtgaagg tctcctgcaaggcttctggaggcaccttcag caactatgctatcagctgggtgcgacaggc ccctggacaagggcttgagtggatgggag ggatcatccctatctttggtacagcaaactac gcacagaacttccaggcagagtcacgatt accgcggacgaatccatgagcacagccta catggagctgagcagcctgagatctgagg acacggccgtatattactgtgcgggaggtg ggaggtattgtagtggtggtaggtgccactc tgcctactctgcctactggggccagggaac cctggtcaccgtctcctcag | 1 | gccatccagttgacccagtctccaggcaccct gtctttgcctccaggggaaagagccaccctct cctgcagggccagtcagagtgttagcagcag ctacttagcctggtaccagcagaaacctggcc aggctcccaggctcctcatctatggtgcatcca gcagggccactggcatcccagacaggttcag tggcagtgggtctgggacagacttcactctca ccatcagcagactggaccctgaagattttgca gtgtattactgtcagcaatatggtagctcactca ctttcggcggagggaccaaagtggatatcaaa c | 3 |
| 22 | caggtgcagctggtggagtctgggggagg cttggtccaccctgggggtccctgagact ctcctgttcagcctctggattcaccttcagta actatgctgcactgggtccgccaggctc cagggaagggactggaatatgtttcagcta ttagtagtagtgggatatcacatactacgc ggactccgtaaagggcagattcaccatctc cagagacaattccaagaactcactgtatctt caaatgaacagtctgagagctgaggacac ggctgtttattactgtgtgaaagatgtaacga ggacctactacgtagtctttgactactgggc cagggaaccctggtcaccgtctcctcag | 11 | gccatccagttgacccagtctccatcctccctg tctgcatctgtgggagacagagtcaccatcact tgccgggcaagtcagagcattagcagttattta aattggtatcagcaggaaccagggaaagccc ctaaaactcctgatctatgctgcatccagtttgca aggtggggtcccatcaaggttcagtggcagtg gatctgggacagatttcactctcaccatcagca gtctgcaacctgaagattttgcaacttactactg tcaacagagttacactaccccgtacactttttgg ccaggggaccaaagtggatatcaaac | 13 |
| 40 | caggtgcagctggtggagtctgggggagg cttggtccagcctgggggtccctgagact ctcctgtgcagtctctggattcaccgtcagta ggaactacatgagctgggtccgccaggct ccagggaaggggctggagtgggtctcact tatttatagcggtggtagcacattctacgca gactccgtgaagggcagattcaccatctcc agagacaattccaagaacacgctgtatcttc aaatgaacagcctgagagccgaggacac ggctgtgtattactgtgcgagagatctgtttc ataggagtggttatcacgactactgggcc agggaaccctggtcaccgtctcctcag | 21 | gtcatctggatgacccagtctccatcctccctgt ctgcatctgtaggagacagagtcaccatcactt gccaggcagtcaggacattaacaactatttaa attggtatcagcagaaaccagggaaagccct aagctcctgatcttcgatgcctccaatttggaaa caggggtcccatcaaggttcagtggcagtgg atctggacagattttactttcaccatcagcagc ctacagcctgaagatattgcaacatattactgtc aacagtatgataatctccctgccttcggcggag ggaccaaagtggatatcaaac | 23 |
| 44 | gaagtgcagctggtggagtctgggggagg cgtggtccagcctggggaggtccctgagact ctcctgtgcagcgtctggattcaccttcagta actatgcatgcactgggtccgccaggctc caggcaaggggctggagtgggtggcggtt gtatggtatgatggaagcaagaaatactatg cagactccgtgaagggccgattcaccatct ccagagacaattccaagaacaccctgtatct gcaaatgaacagcctgagagtcgaggaca cggctgtgtattactgcgcgagagattttgc ggtggggaggagatcgctgactcctggg gccagggaaccctggtcaccgtctcctcag | 31 | tcctatgagctgactcagccaccctcggtgtca gtgtcccaggacaaacggccaggatcacctgc tctggagatgcattgccaaaaaaatatgcttattg gtaccagcagaagtcaggccaggcccctgta ctggtcatctatgaggacagcaaacgaccctc cgggatccctgagagattctctgggtccagctc agggacaatggccaccttgactatcagtgggg cccaggtggaggatgaaggtgactactactgt tactcaagagacagcagtggtgatcattgggt gttcggcgcagggaccaagctgaccgtccta g | 33 |
| 45 | caggtgcagctggtggagtctgggggag gcgtggtccagcctgggaggtccctgag actctcctgtgcagcctctggattcaccttc agtacctatgctatgcactgggtccgcca ggctccaggcaaggggctggagtggg ggctgttcttcatatgatggaagcaataaa tactacgcagactccgtgaagggccgatt caccatctccagagacaattccaagaaca cgctgtatctgcaaatgaacagcctgaga gctgaggacacggctgtgtattactgtgc gaaaggggctcgtacgcgtactactact acatggacgtctggggcaaagggaccac ggtcaccgtctcctca | 41 | gacatccagttgacccagtctccatcctccctg tctgcatctgtaggagacagagtcaccatcact tgccaggcgagtcaggacattagcaactattta aattggtatcagcagaaaccagggaaagcccct aagctcctgatctacgatgcatccaatttggaa acaggggtcccatcaaggttcagtggagggtg gatctgggacagattttactttcaccatcaccag cctgcagcctgaagatattgcaacatattactgt caacagtatgataatctcccgctcactttcggcg agggaccaaagtggatatcaaac | 43 |
| 54 | gttcagctggtgcaggagtcgggcccagg actggtgaagcttcggagaccctgtccct cacctgcactgtctctggtggctccgtcagt agtggtagttactactggagctggatccgg cagcccccagggaagggactggagtgga | 51 | gaaatagtgatgacgcagtctccaggcaccct gtctttgtctccaggggaaagagccaccctctc ctgcagggccagtcagagtgttagcagcagcta cttagcctggtaccagcagaaacctggccagg ctcccaggctcctcatctatggtgcatccagcag | 53 |

-continued

| | Heavy chain | | Light chain | |
|---|---|---|---|---|
| Antibody number: | Nucleotide Sequence | SEQ ID NO: | Nucleotide sequence | SEQ ID NO: |
| | ttgggtatatgtatttcagtgggagcaccaa ctataatccctccctcaagagtcgagtcacc atatcattagccacgtccaagaaccagttct ccctgaagctgagctctgtgaccgctgcgga cacggccgtctattactgtgcgagaggggat tacgattttggagtggtcccccggtcggg tggacgtctgggcaaagggaccacggtc accgtctcctcag | | ggccactggcatcccagacaggttcagtggc agtgggtctgggacagacttcactctcaccatc agcagactggagcctgaagattttgcagtgtat tactgtcagcactatggtagttcacccgtaactt ttggccagggaccaaagtggatatcaaac | |
| 55 | caggtgcagctggtgcagtctgggcctga ggtgaagaagcctgggacctcagtgaagg tctcctgcaaggcttctggattcacctttact agctctgctgtgcagtgggtgcgacagg ctcgtggacaacgccttgagtggataggaa tggatcgtcgttggcagtggtaacacaaa ctacgcacagaagttccaggaaaagctca ccattaccagggacatgtccacaagcaca gcctacatggagatgagcagcctgagat ccgaggacacggccgtgtattactgtgcg gcaccggcctgtggtaccagctgctctga tgcctttgatatctggggccaagggacaat ggtcaccgtctcttcag | 61 | gacatccagatgacccagtctccaggcaccct gtctttgtctccaggggaaagagccaccctctc ctgcagggccagtcagagtgttagcagcagcta cttagcctggtaccagcagaaacctggccagg ctcccaggctcctcatctatggtgcatccagca gggccactggcatcccagacaggttcagtgg cagtgggtctgggacagacttcactctcaccat cagcagactggagcctgaagattttggagtgt attactgtcagcagtatggtagctcaccgtgga cgttcggccaagggaccaaggtggaaatcaa ac | 63 |
| 58 | caggtgcagctggtggagtctgggggag gcttggtacagcctggcaggtccctgaga ctctcctgtgcagcctctggattcacctttgat gattatgccatgcactgggtccggcaacc tccagggaagggcctggagtgggtctca ggtgtcagttggaacagtggtaccatagg ctatgcggactctgtgaagggccgattcat catctccagagacaacgccaagaactcc ctgtatctgcaaatgaacagtctgaaagct gaggacacggccttgtattactgtgcaag agaagtgggggggacttttggagtccttat ttcacgcgaggggggacttgattactggg gccagggaaccctggtcaccgtctcctca g | 71 | tcctatgagctgacacagccaccctcggtgtca gtggcccccaggacagacggccagaattacctgt gggggaaacaccattggaagtaaaagtgtgc actggtaccagcagagaccaggccaggccc ctgtgctggtcgtctatgatgatagcgaccggc cctcagggatccctgagcgattctctgcca actctgggaacacggccaccctgaccatcag cagggtcgaagccggggatgaggccgactat tactgtcaggtgtgggatagtagtagtgatcgg gtggtattcggcggagggaccaagctgaccg tcctag | 13 |
| 61 | caggtgcagctgcaggagtcgggccca ggactggtgaagccttcggagaccctgtc cctcatctgcactgtctctggtggctccgtc agcagtggtaatttctactggagctggatc cggcagcccccagggaagggactggag tggattggatctatctattacactgggagcc ccaactacaaccctccctcaagagtcga gtcaccatatccctagacacgtccaagaa ccagttctccctgaagctgagctctgtgac cgctgcggacacggccgtgtattactgtg cgagagagatcattattatgatagaagtg gttcttacaactctgatgcttttgatatctggg gccaagggacaatggtcaccgtctcttca g | 81 | gatatcgtgatgactcagtctccagccaccctg tctgtgtctccaggggaaagaggcaccctctc ctgcagggccagtcagagtgttagcagcaactt agctggtaccagcagaaacccgggccaggt cccaggctcctcatctatggtgcatccacgag ggccactggtatcccagccaggttcagtggca gtgggtctgggacagagttcactctcaccatca gcagcctgcagtctgaagattttgcagtttatta ctgccagcagtataataactggcctccgctcac tttcggcggagggaccaaagtggatatcaaac | 83 |
| 75 | caggtgcagctggtggagtctgggggag gcgtggttcagcctggggaggtccctgag actctcctgtgcagcctctggattcacccttc aataactatccttttgcactgggtccgccag gctccaggcaaggggctggagtgggtg gcagttatttcacaggatggaggcaataa atactacgtagactccgtgaagggccgatt caccatctccagagacaattccaagaaca cactgtatctgcaaatgaacaacctgaga gctgaggacacggctctgtattactgtgc gagagatgttgtagtggtggtagctgcta ggaaccactactacaacggtatggacgtc tggggccaagggaccacggtcaccgtct cctca | 91 | gacatccagttgacccagtctccatcttccgtgt ctgcatctgtaggagacagagtcaccatcactt gtcgggcgagtcagggtattagcagctggtta gcctggtatcagcagaaaccagggaaagccc ctaagctcctgatctatgctgtatccagtttgca aagtggggtcccatcaaggttcagcggcagtg gatctgggacagatttcactctcaccatcagca gcctgcagcctgaagattttgcaacttactattg tcaacaggctaagagtttccctttcactttcggc cctgggaccaaggtggagattaaac | 93 |
| 88 | cagctgcagctgcaggagtcgggccca ggactggtgaagccttcacagaccctgtc cctcacctgcactgtctctggtggctccat cagtagtggtagttataattggacctggat ccggcagcccgccgggaagggactgga | 101 | caatctgccctgactcagccaccctcggtgtct gaagcccccaggcagagggtcaccatctcct gttctggaagcagctccaacatcggaaataat gctgtaaactggtaccagcagttcccaggaaa ggctcccaaactcctcatctattatgatgatctg | 103 |

-continued

| | Heavy chain | | Light chain | |
|---|---|---|---|---|
| Antibody number: | Nucleotide Sequence | SEQ ID NO: | Nucleotide sequence | SEQ ID NO: |
| | gtggattgggcgtatatataatagtgggag caccaactacaaccctccctcaagagtc gagtcaccatatcagtagacacgtccaaga accagttgtccctgaaggtgaggtctgtga ccgccgcagacacggccgtgtattactgtg cgagacattgcagtggtggtacctgctac ccgaagtactactacgtatggacgtctg gggccaagggaccacggtcaccgtctcc tca | | ctgccctcaggggtctctgaccgattctctggc tccaagtctggcacctcagcctcctggccatc agtggggtccagtctgaggatgaggctgattat tactgtgcagcatgggatgacagcctgaatgt cgtggtattcggcggagggaccaagctgacc gtcctag | |
| 111 | caggtgcagctggtggagtcgggcccag gactggtgaagccttcggagaccctgtcc ctcacctgcactgtctctggtggctccatc agcagtaatagttacttctggggctggatc cgccagcccccagggacggggctggag tggattgggaatatctattatactggagca cctactacaacccgtcgttcgagagtcga gtcaccatgtccgtagacacgtcgaagaa ccagttctccctgaggctgagctctgtgac cgccgcagacacggctgtgtattactgtg cgagacatgtcagggcctacgactatgat gccccttttgatatctggggccaagggac aatggtcaccgtctcttcag | 111 | gtcatctggatgacccagtctccatcctcccctgt ctgcatctgtaggagacagagtcaccatcactt gccgggcaagtcagggcattagaaatgattta ggctggtatcagcagaaaccagggaaagcc cctaagcgcctgatctatgctgcatccagtttg caaagtggggtcccatcaaggttcagcggca gtggatctgggacacaattcactctcacaatca gcagcctgcagcctgaagattttgcaacttatt actgtctacagattaatagttatccgctcactttc ggcggagggaccaaggtggaaatcaaac | 113 |
| 132 | caggtacagctgcagcagtggggcgca ggactgttgaagccttcggagaccctgtc cctcacctgcgctgtctatggtgggtccttc agtggttactactggagctggatccgccag ccccagggaaggggctggagtggattg gggaaatcaatcatagtggaagcaccaa ctacaacccgtccctcaagagtcgagtca ccatatcagtagacacgtccaagaaccag ttctccctgaagctgagttctgtgaccgcc gcggacacggctgtgtattactgtgcgag aactgattactatgatagtatagactgggg ccaggggaaccctggtcaccgtctcctcag | 121 | cagtctgtgctgactcaggagccctcactgact gtgtccccaggagggacagtcactctcacctg tggctccagcactggagctgtcaccagtggtc attatccctactggttccagcagaagcctggcc aagtcccccaggcactgatttatgatacaagg aacaaacactcctggaccccctgcccggttctc aggctccctccttggggcaaagctgccctgac cctttcgggtgcgcagcctgaggatgaggctg aatattactgcttgctctccctcagtggtgctcgg gtgttcggcggagggaccaagctgaccgtcc tag | 123 |
| 140 | gaggtgcagctggtggagtctgggggag gcttggtacagcctgggggtccctgagac tctcctgtgcagcctctggattcaccttcagta cctacgacatccactgggtccgccaagcta caggaaaaggtctggagtgggtctcagctat tggtactgctggtgacacatactattcaggct ccgtgaagggccgattcaccatctccagag aaaatgccaagaacctccttgtatcttcaaatg aacagcctgagagccggggacacggctg tgtattactgtgcaaggggtagtgggaccta cttctactactttgactactggggccagggaa ccctggtcaccgtctcctcag | 131 | gacatcgtgatgactcagtctccatcctcccctgt ctgcatctgtaggagacagaatcaccatcactt gccgggcaagtcagagcattaacaactattta aattggtatcagcagaaaccagggaaagccc ctaagctcctgatctatgctgcatcccgtttgca aactggggtcccatcaaggttcagtggcagtg gatctgggacagattccactctcaccatcaaca tctgcaacctgaagattttgcaacttactactg tcaacagctttacagtgcccctcgtgacgtt cggccaagggaccaaagtggatatcaaac | 133 |
| 148 | caggtgcagctggtggagtcgggcccag gactggtgaagccttcggagaccctgtccc tcacctgcactgtctctggtggctcgatcag cagttcttactactgggggctggatccgccag ccccagggaaggggctggagtggattg ggagtgtctattatagtgggagcacctacta caacccgtccctcaagagtcgagtcaccat atccgtagacacgtccaagaaccagttctcc ctgaggctgagctctgtgaccgccgcaga cacggctgtgtattattgtgcgaggctgatg accacgaagactactactccggtatggac gtctggggccaagggaccacggtcaccgt ctcctca | 141 | gccatccagatgacccagtctccatcctcactg tctgcatctgtaggagacagagtcaccatcact tgtcgggcgagtcagggcattagcagtatttta gccgtggttcagcagaaaccagggaaagcccc taagtccctgatctatgctgcatccagtttgcaaa gtggggtcccatcaaggttcagcggcggtgga tctgggacagatttcactctcaccatcagcagc ctgcagcctgaagattttgcaacttattactgcc aacagtatcatagttacccgatcaccttcggcc aagggacgactggagattaaac | 143 |
| 150 | caggtgcagctggtggagtctggaggagg cttgatccagcctggggggtccctgagact ctcctgtgcagcctctggggtcaccgtcagt agcaactacatgagttgggtccgccaggct ccagggaaggggctggagtgggtctcaat tatttatagtggtggtaccacatactacgcag actccgtgaagggccgattcaccatctcca gagactcttccatgaacacgctgtatcttcaa atgaacagcctgagagccgaggacacgg | 151 | gaaatagtgatgacgcagtctccatcctccctg tctgcatctgtaggagacagagtcaccatcact tgccgggccagtcagggcattagcagttatta gcctggtatcagcaaaaaccagggaaagccc ctaagctcctgatctatgctgcatccactttgca aagtggggtcccatcaaggttcagcggcagtg gatctgggacagatttcactctcaccatcagca gcctgcagcctgaagattttgcaacttattactg tcaacagcttgatagttacccccccgggtacac | 153 |

-continued

| Heavy chain | | Light chain | |
|---|---|---|---|
| Antibody number: Nucleotide Sequence | SEQ ID NO: | Nucleotide sequence | SEQ ID NO: |
| ccgtgtattactgtgcgagagatctgatggt gtacggtatagacgtctggggccaaggga ccacggtcaccgtctcctca | | tttggccaggggaccaaagtggatatcaaac | |
| 158 gaggtgcagctgttggagtctggaggag acttgatccagcctggggggtccctgaga ctctcctgtgcagcctctgggtcaccgtc agtagcaactacatgagctgggtccgccag gctccagggaaggggctggagtgggtct caattatttatcccggtgggagcacattcta cgcagactccgtgaagggccgattcacc atctccagagacaattccaagaacacgtgt atcttcaaatgcacagcctgagagccgag gacacggccgtgtattactgtgcgagaga tcttggctcaggggacatgacgtctggg gcaaagggaccacggtcaccgtctcctca | 161 | gacatcgtgatgactcagtctccatccttcctgtct gcatctgtaggagacagagtcaccatcacttgcc gggccagtcagggcattagcagttatttagcctg gtatcagcaaaaaccggggaaagcccctaagct cctgatccaagctgcatccactttgcaaagtggg gtcccatcaaggttcagcggcagtggatctggg acagaattcactctcacaatcagcagcctgcagcc tgaagattttgcaacttattactgtcaacagcttaata gttaccggtacacttttggccaggggaccaagg tggagatcaaac | 163 |
| 159 gaggtgcagctggtggagtctgggggag gcgtggtccagcctggggaggtccctgag actctcctgtgcagcctctggattcaccttc agtagctatggcatgcactgggtccgcca ggctccaggcaaggggctgagtgggtg gcacttatatcatatgatggaggtaatagat actatgcagactccgtgaagggccgattc accatctccagagacaattccaagaacac gctgtatctgcaaatgaacagactgagag ctgaagacacggctatgtattactgtgcga aagatcgtgatgatgggtgggattggtact acttcatggacgtctggggcaaagggacc acggtcaccgtctcctca | 171 | gacatccagttgacccagtctccaggcaccct gtctttgtctccaggggaaagagccaccctctc ctgcagggccagtcagagtgttagcggcaact acttagcctggtaccagcataaacctggccag gctcccagactcctcatctatggtgcatccacc agggccactggcatcccagacaggttcagtg gcagtggatctgggacagacttcactctcacc atcagcagactggagcctgaagattttgcagt gtattactgtcagcagtatggtagctcgtacact tttggccaggggaccaaggtggagatcaaac | 173 |
| 165 caggttcagctggtgcagtctgggcctga ggtgaagaagcctgggacctcagtgaag gtctcctgcaaggcttctggattcaccttta ctagctctgctgtgcagtgggtgcgacag gctcgtggacagcgccttgagtggatagg atggatcgtcgttggcagtggtaacacaa actacgcacagaagttccaggaaagcgtc accattaccagggacatgtccacaagcac agcctacatgagctgagcagcctgagat ccgaggacacggccgtgtattactgtgcg gccccacattgtattggtggtagctgccatga tgcttttgatatctggggccaagggacaat ggtcaccgtctcttcag | 181 | gatatcgtgatgacccagtctccaggcaccct atctttgtctccaggggaaagagccaccctctc ctgcagggccagtcagagtgttagaagcagcta cttagcctggtaccagcagaaacctggccagg ctcccaggctcctcatctatggtgcatccaggag gggcactggcatcccagacaggttcagtggca gtgggtctgggacagacttcactctcaccatca gcagactggagcctgaagattttgcagtgtatt actgtcagcagtatggtagctcaccctggacgt tcggccaagggaccaaggtggaaatcaaac | 183 |
| 170 caggtgcagctggtggagtcaggagcag aggtgaaaaagcccggggagtctctgaa gatctcctgtaaggggttctggatacagctttt accagctactggatcgtctgggtgcgcca gatgccgggaaaggcctggagtggatg gggatcatctatcctggtgactctgatacc aaatacagtccgtccttccaaggccaggt cagcatctcagccgacaagcccatcagca ccgcctacctgcagtggagcaggctgaa ggcctcggacaccgccatgtattactgtg cgagactagggaattggctggtggactac tggggccagggaaccctggtcaccgtct cctcag | 191 | gatattgtgatgactcagtctcctctctctctgtc cgtcaccctggacagccggcctccatctcct gcaagtctagtcagagcctcctgcatagtgatg gaaagacctatttgtattggtacctgcagaagc caggccagcctccacagctcctgatgtatgaa gtttccaaccggttctctggagtgccagatagg ttcagtggcagcgggtcagggacagacttcac acttaaaatcagccgggtggagtctgaggatg ttggggtttattactgcatgcaaagtatacagctt cctcgcgggatcaccttcggccaagggacac gactggagattaaac | 193 |
| 175 gaggtgcagctggtggagtctggaggag gcttgatccagcctggggggtccctgaga ctctcctgtgcagcctctgggctcaccgtc agtcgcaattacatgagctgggtccgcca ggctccagggaaggggctggagtgggt ctcacttatttatagcggtggtagcacatac tacgcagactccgtgaagggccgattcac catctccagagacaattccaagaacacgc tgtatcttcaaatgaacagcctgagagccg aggacacggccgtgtattactgtgcgagag atctacgcggagaagtctggggccaaggg acaatggtcaccgtctcttcag | 201 | gccatccagatgacccagtctccatcctccctgt ctgcatctgtaggagacagagtcaccatcacttg ccaggcgagtcaggacattagcaacttttttaaatt ggtatcagcagaaaccagggaaagcccctaag ctcctgatctacgatgcatccaatttggaaacag gggtcccatcaaggttcagtggaagtggatctg ggacagatttttcaccatcagtagcctgcag cctgaagatattgcaacatattactgtcaccagta tgataatctccctcgaacgttcggccaagggac caaagtggatatcaaac | 203 |

-continued

| Antibody number: | Heavy chain Nucleotide Sequence | SEQ ID NO: | Light chain Nucleotide sequence | SEQ ID NO: |
|---|---|---|---|---|
| 177 | gaggtgcagctggtggagtctgggggag gcttggtacagcctgggggtccctgaga ctctcctgtgcagcctctggattcaccttca gtaactacgacatgcactgggtccgccaa gctacaggaaaaggtctggagtgggtctca cttattggtactgctggtgacacatactatc cagactccgtgaagggccgattcaccatc tccagagaaaatgccaagaactccttgtat cttcaaatgaacagcctgagagccgggg acacggctgtgtattactgtgcaagaggg caacacactcaaatcggtcactactactac tactacatggacgtctggggcaaagggac cacggtcaccgtctcctca | 211 | gccatccggatgacccagtctccatcgtccct gtctgcatctgtaggagacagagtcaccatca cttgccgggcaagtcagagcattagcagctatt taaattggtatcagcagaaaccagggaaagcc cctaagctcctgatctttgctgcatccagtttgc aaagtgggtccatcaaggttcagtggcagt ggatctgggacagttccactctaaccatcag cagtctgcaacctgaagattttgcaacttactac tgtcaacagagttacagtaaccctccggaggg cagttttggccaggggaccaaagtggagatta aac | 213 |
| 181 | gaagtgcagctggtggagactggaggag gcttgatccagcctgggggtccctgaga ctctcctgtgcagcctctgggttcaccgtc agtagcaactacatgagctgggtccgcca ggctccagggaaggggctggagtgggt ctcagttgtttatggcggtggtaccacatac tacgcagactccgtgaagggccgattcac catctccagagacaattccaagaacacgc tgtatcttcaaatgaacagcctgagagccg aggacacggccgtatattactgtgcgact gacaatggatacagctatggttttttcatttg actactggggccagggaaccctggtcatc gtctcctcag | 221 | cagtctgtgctgactcagcctgcctccatgtctg ggtctcctggacagtcgatcaccatctcctgca ctggaaccagcagtgatgttggggttataac cttgtctcctggtaccaacagcacccaggcaa agccccaaactcatgatttatgagggcagtaa gcggccctcaggggtttctaatcgcttctctgg ctccaagtctggcaacacggcctccctgacaa tctctggggctccaggctgaggacgaggctgat tattactgctgctcatatgcaggtagtagtaattg ggtgttcggcggagggaccaagctgaccgtc ctag | 223 |
| 182 | caggtgcagctggtggagtctgggctg aggtggagaagcctggggcctcagtgaa ggtctcctgcaaggcttctggatacaccttt caccggctactatatgcactgggtgcgac aggcccctggacaagggcttgagtggatg ggatggatcaacccctatcagtggtggcac aaaactatgcacagaagtttcagggcagg gtcaccatgaccagggacacgtccatca gcacagcctacatggacctgagcaggct gagatctgacgacacggccgtgtattact gtgcgagaggaacgtattactatgatagt agtggttacatcccatttgactactggggc cagggaaccctggtcaccgtctcctcag | 231 | cagtctgtgctgactcagcctgcctccgtatctg ggtctcctggacagtcgatcaccatctcctgcac tggaaccagcagtgatgttgggagttataaccttt gtctcctggtaccaacagcacccaggcaaagc ccccaaactcatgatttatgagggcagtaagcg gccctcaggggtttctaatcgcttctctggctcca agtctggcaacacggcctccctgacaatctctgg gctccaggctgaggacgaggctgattattactg ctgctcatatgcaggtagtagcactttggtattcg gcggagggaccaagctgaccgtcctag | 233 |
| 183 | caggttcagctggtgcagtctgggtctga gttgaagaagcctggggcctcagtgaag gtttcctgcaaggcttctggatacaccttca gtagctatgctatgacttgggtgcgacag gcccctggacaagggcttgagtggatgg gatggatcaacaccaacactgggaaccc aacgtatgcccagggcttcacaggacggt ttgtcttctccttggacacctctgtcagcac ggcatatctgcagatcagcagcctaaagg ctgaggacactgccgtgtattactgtgcga gagctctgggatattgtagtagtaccagct gctatcccgcttgggctgcttttgatatctg gggccaagggacaatggtcaccgtctctt cag | 241 | tcctatgagctgactcagccactctcagtgtca gtggcccctgggacagacgccagtattacctg tgggggaaacaacattggaagtaaaaatgtgc actggtaccagcagaagccaggccaggcccct gtgctggtcatctatagggatagcaaccggcc ctctgggatccctgagcgattctctggctccaa ctcggggaacacggccacccctgaccatcagc agagcccaagccggggatgaggctgactata actgtcaggtgtgggacagcagcgtggtattc ggcggagggaccaagctgaccgtcctag | 243 |
| 222 | gaggtgcagctggtggagtctggaggag gcttgatccagcctgggggtccctgaga ctctcctgtgcagcctctgggctcaccgtc agtagcaactacatgagttgggtccgcca ggctccagggaaggggctggagtgggt ctcagttatttatagtggtggtagcacgttct acgcagactccgtgaagggccgattcac catctccagagacaattccaagaacacgc tgtatcttcaaatgaacagcctgggagccg aggacacggccgtgtattactgtgcgaga ggagaaggtagtcctggaaactggttcga cccctggggccagggaaccctggtcacc gtctcctcag | 251 | gatgttgtgatgactcagtctccaggcaccctg tctttgtctctcaggggaaagagccaccctctcc tgcagggccagtcagagtgttcccagcagcta cttagcctggtaccagcagaaacctggccag gctcccaggctcctcatctatggtgcatccacc agggccactggcatcccagacaggttcagtg gcagtgggtctgggacagacttcactctcacc atcagcagactggaccctgaggattttgcagt gtattactgtcagcactatgataccctcacccgt ttcggcggagggaccaagtggagatatcaaac | 253 |

-continued

| Heavy chain | | Light chain | |
|---|---|---|---|
| Antibody number: Nucleotide Sequence | SEQ ID NO: | Nucleotide sequence | SEQ ID NO: |
| 253 caggtccagctggtacagtctgggcctga ggtgaagaagcctgggacctcagtgaag gtctcctgcaaggcttctggattcacctta ctacctctgctgtgcagtgggtgcgacag gctcgtggacaacgccttgagtggatagg atggatcgtcgttggcagtggtaacacaa actacgcacagaagttccaggaaagagt caccattaccagggacatgtccacaacca cagcctacatggagctgagcagcctgag atccgaggacacggccgtgtatttctgtgc ggcgcctcattgtaatagtaccagctgcta tgacgcttttgatatctggggccaaggga caatggtcaccgtctcttcag | 261 | gacatccagatgacccagtctccaggcaccctg tctttgtctccaggggaaggagccaccctctcctgc agggccagtcagagtgttagcagcagctacttag cctggtaccagcagaaacctggccaggctccca ggctcctcatctatggtgcatctagtggggccact ggcatcccagacagattcagtggcagtgggtct gggacagacttcactctcaccatcagcagactg gagcctgaagattttgcagtgtattactgtcagca gtatggtagctcaccttacacttttggccagggg accaaggtggaaatcaaac | 263 |
| 269 caggtgcagctggtggagtctggaggagg cttgatccagcctggggggtccctgagactct cctgtgcagcctctgggctcaccgtcaatag gaactacatgagctggatccgccaggctcc agggaaggggctggagtgggtctcagttat ttatagcggtggtagtacattttacgcagact ccgtgaagggccgattcaccatctccagag acaattccaagaacacactgtctcttcaaat gaacagctgagagccgaggacacggcc atttattactgtgcgagagacttctacgagg gttcttttgatatctggggccaagggacaatg gtcaccgtctcttcag | 271 | gccatccagttgacccagtctccttccttcctgtct gcatctataggagacagagtcaccatcacttgcc gggccagtcagggcattagcagttatttagcctg gtatcagcaaaaaccagggaaagcccctaagc tcctgatctatgctgcatccacttTgcaaagtggg gtcccatcaaggttcagcggcagtggatctggg acagaattcactctcacaatcagcagcctgcagc ctgaagattttgcatcttattactgtcaacagctta atagttacccgctccggttttcggccctgggac caaagtggatatcaaac | 273 |
| 278 caggtacagctggtgcagtctgggcctga ggtgaagaagcctggggcctcagtgaag gtctcctgcaaggcttctggttacatcttat cagatatggtattagctgggtgcgacagg ccctcgacaaggcttgagtggatggg atggatcagcgctaacaatggttacacaa actatgcacagaagctccagggcagagt caccatgaccacagacacatccacgagc acagcctacatggagctgagaggcctga gatctgacgacacggccgtgtattactgtgc gagagatgggggtattttgactggttatctc gactactttgaccactggggccagggaac cctggtcaccgtctcctcag | 281 | gacatccagatgacccagtctccatcctccctg tctgcatctgtaggagacagactcaccatcact tgccgggcaagtcagagcattgccagctattt aaattggtatcagcagaaaccagggaaagc cctaagctcctgatctgatctatgctgcatccagtttgc aaagtggggtcccatcaaggttcagtggcagt ggatctgggacagatttcactctcaccatcagc agtctgcaacctgaagattttgcaacttaccact gtcaacagagttacagtaccctcggaatcactt cggccctgggaccaaagtggatatcaaac | 283 |
| 281 caggtgcagctggtggagtctggggagg cttggtccagcctggggggtccctgagact ctcctgtgcagcctctggattcccctttagta tctattggatgagctgggtccgccaggctc cagggaaggggctggagtgggtggccaa cataaagcaagatggaagtgagaaatactat gtggactctgtgaagggccgattcaccatctc ccagagacaacgccaagaactcactgtatc tgcacatgaacagcctgagaggcgaggac acggctgtgtattactgtgcgagccgatatt acgattttgaccggaggcttggttttgacta ctggggccagggaaccctggtcaccgtct cctcag | 291 | gatattgtgatgacccagactccactctcctcac ctgtcacccttggacagccggcctccatctcctg caggtctagtcaaagcctcgtacacagggatgg aaacacccacttgagctggcttcagcagaggcc aggccagcctccaaagactcctaatttataagattt ctaaccggttctctggggtcccagacagattcag tggcagtggggcaggggacagattttcacactgaa aatcagcagggtggaagctgaggatgtcgggg tttattactgcatgcaagctacacaattttcctcatg ggtacacttttggccaggggaccaaggtggag atcaaac | 293 |
| 282 caggtgcagctgcaggagtctgggggag gcttggtccagcctggggggtccctgaga ctctcctgttcagcctctggattcaccgtca gtagcaactacatgacctgggtccgccag gctccagggaaggggctggagtgggtct cagttatttatagcggtggtagcacattcta cgcagactccgtgaagggcagattcacc atctccagagacaattccaagaacacgctgt atcttcaaatgaacagcctgagagccgag gacaccgctgtgtattactgtgcgagagat ctggaagaggccggggggatttgactactg gggccagggaaccctggtcaccgtctcct cag | 301 | gaaattgtgttgacgcagtctccaggcaccct gtctttgtctccaggggaaaagtcaccctctc ctgcagggccagtcagagtgttagcagcacct acttagcctggtaccagcagaaacctggccag gctcccaggctcctcatctatggtgcatccagc agggccactggcgtcccagacaggttccgtg gcagtgggtctgggacagacttcactctcacc atcagcagactggagcctgaagattttgcagt gtattactgtcagcagtatggtagctcgctgtac acttttggccaggggaccaaagtggatatcaa ac | 303 |
| 285 cagctgcagctgcaggagtcgggcccag gactggtgaagccttcggagaccctgtcc ctcacctgcactgtctccggtgactccgtc | 311 | gacatccagatgacccagtctccatcctccctg tctgcatctgtaggagacagagtcaccatcact tgccgggcaagtcagagcattagcagctattt | 313 |

-continued

| | Heavy chain | | Light chain | |
|---|---|---|---|---|
| Antibody number: | Nucleotide Sequence | SEQ ID NO: | Nucleotide sequence | SEQ ID NO: |
| | agtaattactactggagctggatccggca gcccgccgggaagggactggagtggatt gggcgtatctataccagtgggagcaccaa ctacaaccccctccctcaagagtcgagtcac catgtcagtagacacgtccaagaaccagtt ctccctgaagctgagctctgtgaccgccg cggacacggccgtgtattactgtgcgagag atcaccgggcttcccggtatagcagtggc tggtacgaatggtggaactgcttcgaccc ctggggccagggaaccctggtcaccgtc tcctcag | | aaattggtatcagcagaaaccagggaaagcc cctaagctcctgatctatgctgcatccagtttgc aaagtggggtcccgtcaaggttcagtggcagt ggatctgggacagatttcactctcaccatcaac agtctgcaacctgaagattttgcaacttactact gtcaacagagttacagtaccccgcgctcact ttcggcggagggaccaaagtggatatcaaac | |
| 316 | caggttcagctggtgcagtctggggctga ggtgaagaagcctggggcctcagtgaagg tctcctgcaaggcttctggatacaccttcac cggctactatatgcactgggtgcgacagg cccctggacaagggcttgagtggatggg atggatcaaccctaacagtggtggcacaa actatacacagaagtttcagggcagggtc accatgaccagggacacgtccatcagca cagcctacatggagctgagcaggctgag atctgacgacacggccgtgtattcctgtgc gagagatatggcgtttagtatggttcggggtt cctttgactactggggccagggaaccctg gtcaccgtctcctcag | 321 | caggctgtgctgactcagcctcctccgcgtc cgggtctcctggacagtcagtcaccatctcctg cactggaaccagcagtgacgttggtggttata actatgtctcctggtaccaacagcacccaggc aaagcccccaaactcatgatttatgaggtcagt aagcggccctcaggggtccctgatcgcttctc tggctccaagtctggcaacacggcctcctga ccgtctctggggctccaggctgaggatgaggct gattattactgcagctcatatgcaggcagcaac cattgggtgttcggcggagggaccaagctga ccgtcctag | 323 |
| 318 | caggtgcagctggtgcagtctgggcctga ggtgaagaagcctggggacctcagtgaag gtctcctgcaaggcgtctggattcacccttt actagctctgctatgcagtgggtgcgaca ggctcgtggacaacgccttgagtggatag gatggatcgtcgttggcagtggcaacaca aactacgcacagaagttccaggaaagagt caccattaccagggacatgtccacaagca cagcctacatggagctgagcagcctgag atccgaggacacggccgtgtattattgtgc ggccggccgtggctacaattcggactttg actactggggccagggaaccctggtcac cgtctcctcag | | gccatccggatgacccagtctccaggcaccct gtctttgtctccaggggaaagagccaccctctc ctgcagggccagtcagagtgttagcagcagcta cttagcctggtaccagcagagacctggccag gctcccaggctcctcatctatggtacatccagc agggccactggcatcccagacaggttcagtg gcagtgggtctgggacagacttcactctcacc atcagcagactggagcctgaagattttgcagt gtattactgtcagcagtatggttactcagtgtac actttggccaggggaccaaagtggatatcaa ac | 333 |
| 334 | caggtgcagctggtggagtctgaggctga ggtgaagaagcctggggcctcagtgaag gtttcctgcaaggcatctggatacaccttca ccagctactatatgcactgggtgcgacag gcccctggacaagggcttcagtggatgg gaataatcaaccctagtgctggtagcaca agctacgcacagaagttccagggcagag tcaccatgaccacggacacgtccacgacca cagtctacatggagctgagcagcctgaga tctgaggacacggccgtgtattactgtgcg agagattctgtactagtaccagctgctaatg cttttgatatctggggccaagggacaatggt caccgtctcttcag | | gaaatagtgatgacgcagtctccagcccaccct gtctttgtctccaggggaaagagccaccctctc ctgcagggccagtcagagtgttagtagctactta gcctggtaccaacagaaacctggccaggctc ccaggctcctcatctatgatgcatccaacagg gccactggcatcccagccaggttcagtggca gtgggtctgggacagacttcactctcaccatca gcagcctagagcctgaagattttgcagtttatta ctgtcagcagcgtcgcaactggctattcactttc ggccctgggaccaaagtggatatcaaac | 343 |
| 361 | caggtgcagctggtgcagtctggggctga ggtgaagaagcctggggcctcagtgaag gtttcctgcaaggcttctggagacaccttc actagctatactctgcattgggtgcgccag gcccccggacaaagggcttgagtggatgg gatggatcaacgctggcaatggttacaca aaatattcacagaagttccagggcagagtc accattaccagggacacatccgcgagcac agcctacatggagctgagcctgagat ctgaagacacggctgtgtattactgtgcga atgtactatgatagtagactactttgactact ggggccagggaaccctggtcaccgtctc ctcag | | gccatccggatgacccagtctccttccaccctg tctgcatctgtaggagacagagtcaccatcact tgccgggccagtcagagtattagtggctggtt ggctggtatcagcagaaaccagagaaagcc cctaagctcctgatctatgatgcctccaatttgga aagtgggtcccatcaaggttcagcggcagt ggatctgggacagaattcactctcaccatcaac agcctgcagcctgatgattttgcaacttattact gccaacagtataatagttaccccgtggacgttcg gccaagggaccaaagtggatatcaaac | 353 |
| 382 | gaggtgcagctggtgcagtctggggctg aggtgaagaagcctggggcctcagtgaa ggtctcctgcaaggcttctgggtacacctt caccagttatgatatcaactgggtgcgaca ggccactggacaagggcttgagtggatg | 361 | cagcctgtgctgactcagccaccctcagtgtc agtggcccaggaaagacggccaggattac ctgtgggggaagcaacattggaagtaaaagtg tgcactggtaccagcagaagccaggccaggc cctgtgctgatcatctattatgatagcgaccggc | 363 |

-continued

| Antibody number: | Heavy chain Nucleotide Sequence | SEQ ID NO: | Light chain Nucleotide sequence | SEQ ID NO: |
|---|---|---|---|---|
| | ggatggatgaaccctcacagtgataccac aggctatgcacagaagttccagggcaga gtcaccatgaccaggaacacctccataac cacagcctacatggagctgagcagcctg agatctgaggacacggccgtgtattactgt gctcagggacccatagcagtgaactacat ggacgtctggggcaaagggaccacggtc accgtctcctca | | cctcagggatccctgagcgattctctggctcc aactctgggaacacggccaccctgaccatca gcagggtcgaagccggggatgaggccgact tttactgtcaggtgtgggatagtagtactgatca tgtggtattcggcggggggaccaagctgacc gtcctag | |
| 384 | gaggtgcagctggtggagtctgggggag gcttggtcaagcctggagagtccctgaga ctctcctgtgcagcctctggattcaccttca gtgactactacatgacctggatccgccag gctccagggaaggggctggagtgggttt catacattaggagtagtggtcatactatata ctacgcagactctgtgaagggccgattca ccatctccagggacaacgccaagaactc actgtatctacaaatgaacagcctgagagtc gaggacacggccgtgtattactgtgcgag aggaggggttttacgattttttggagtggcc tctcaatgcttttgatatctggggccaagg gacaatggtcaccgtctcttcag | 371 | gacatccagttgacccagtctccatcctccctg tctgcatctgtaggagacagagtcaccatcact tgccgggcgagtcagggcattagcaattattta gcctggtatcagcagaaaccagggaaagttcc taagctcctgatctatgctgcatccactttgcaat cagggggtcccatctcggttcagtggcagtgga tctgggacagatttcactctcaccatcagcagc ctgcagcctgaagatgttgcaacttattactgtc aaaagtataacaatgccctcgggacgttcggc caagggaccaaggtggagatcaaac | 373 |
| 394 | gaggtgcagctggtgcagtctggggctg aggtgaagaagcctggggcctcagtgaa ggtctcctgcaaggcttctggatacacctt caccggctactatatgcactgggtgcgac aggcccctggacaagggcttgagtggat gggatggatcagccctaacagtggtggc acaaactatgcacagaagtttcagggcag ggtcaccatgaccagggacacgtccatca ccacagcctacatggacctgagcaggct gagatctgacgacacggccgtgtattactgt gcgagaggttattactatgaagccctcgatg cttttgatatctggggccaagggacaatgg tcaccgtctcttcag | 381 | cagtctgtcgtgacgcagcctgcctccgtgtct gggtctcctggacagtcgatcaccatctcctgc actggaaccagcagtgacgttggtggttataa ctttgtctcctggtaccaacagcacccaggcaa agcccccaaactcatgatttatgaggtcagtaa tcggccctcaggggtttctaatcgcttctctggc tccaagtctggcatcacggcctccctgaccatc tctgggctccaggctgaggacgaggctgatta ttactgcaactcatatacaagcaacagtactcg ggtattcggcggagggaccaagctgaccgtc ctag | 383 |
| 398 | caggtgcagctggtggagtctgggggag gcttggtccagcctggggggtccctgaga ctctcctgtgcagcctctggattcaccgtca gtagcaactatgacctgggtccgccagg ctccagggaaggggctggagtgggtctca gttatttatagcggtggtagcacatactacg cagactccgtgaagggcagattcaccatc tccagagacaattccaagaacacgctatat cttcaaatgaacagcctgagagccgacg acacggctgtatattactgtgcgagagact ctacagccgattacgattttggagtggtta ttatgtaggtgctttcatatctggggccaa gggacaatggtcaccgtctcttcag | 391 | cagactgtgctgactcagcctgcctccgtgtct gggtctcctggacagtcgatcaccatctcctgc actggaaccagcagtgacgttggtggttacaa ctatgtctcctggtaccaacagcacccaggca aagcccccaaactcatgatttatgaggtcacta agcggccctcaggggtccctgatcgcttctct ggctccaagtctggcaacacggcctccctgac cgtctctggctccaggctgaggacgaggctg attattactgcagctcatatgcaggcagcaaca attgggtgttcggcggagggaccaagctgac cgtcctag | 393 |

Amino Acid Sequences of CDRs

| Ab number | Heavy chain CDR CDR1-IMGT | SEQ ID NO. | CDR2-IMGT | SEQ ID NO. | CDR3-IMGT | SEQ ID NO. |
|---|---|---|---|---|---|---|
| 2 | GGTFSNYA | 5 | IIPIFGTA | 6 | AGGGRYCSGGRCHSAYSAY | 7 |
| 22 | GFTFSNYA | 15 | ISSSGDIT | 16 | VKDVTRTYYVVFDY | 17 |
| 40 | GFTVSRNY | 25 | IYSGGST | 26 | ARDLFHRSGYHDY | 27 |
| 44 | GFTFSNYG | 35 | VWYDGSKK | 36 | ARDFAVGEEIADS | 37 |

| Ab number | Heavy chain CDR CDR1-IMGT | SEQ ID NO. | CDR2-IMGT | SEQ ID NO. | CDR3-IMGT | SEQ ID NO. |
|---|---|---|---|---|---|---|
| 45 | GFTFSTYA | 45 | LSYDGSNK | 46 | AKGGSYAYYYYMDV | 47 |
| 54 | GGSVSSGSYY | 55 | MYFSGST | 56 | ARGDYDFWSGPPGRVDV | 57 |
| 55 | GFTFTSSA | 65 | IVVGSGNT | 66 | AAPACGTSCSDAFDI | 67 |
| 58 | GFTFDDYA | 75 | VSWNSGTI | 76 | AREVGGTFGVLISREGGLDY | 77 |

-continued

| Heavy chain CDR | | | | | |
|---|---|---|---|---|---|
| Ab number | CDR1-IMGT | SEQ ID NO. | CDR2-IMGT | SEQ ID NO. | CDR3-IMGT | SEQ ID NO. |

| Ab number | CDR1-IMGT | SEQ ID NO. | CDR2-IMGT | SEQ ID NO. | CDR3-IMGT | SEQ ID NO. |
|---|---|---|---|---|---|---|
| 61 | GGSVSSGNFY | 85 | IYYTGSP | 86 | AREIYYYDRSGYNSDAFDI | 87 |
| 75 | GFTFNNYP | 95 | ISQDGGNK | 96 | ARDVVVVAARNHYYNGMDV | 97 |
| 88 | GGSISSGSYN | 105 | IYNSGST | 106 | ARHCSGGTCYPKYYYGMDV | 107 |
| 111 | GGSISSNSYF | 115 | IYYTGST | 116 | ARHVRAYDYDAPFDI | 117 |
| 132 | GGSFSGYY | 125 | INHSGST | 126 | ARTDYYDSID | 127 |
| 140 | GFTFSTYD | 135 | IGTAGDT | 136 | ARGSGTYFYYFDY | 137 |
| 148 | GGSISSSYY | 145 | VYYSGST | 146 | ARLMTTEDYYSGMDV | 147 |
| 150 | GVTVSSNY | 155 | IYSGGTT | 156 | ARDLMVYGIDV | 157 |
| 158 | GVTVSSNY | 165 | IYPGGST | 166 | ARDLGSGDMDV | 167 |
| 159 | GFTFSSYG | 175 | ISYDGGNR | 176 | AKDRDDGWDWYYFMDV | 177 |
| 165 | GFTFTSSA | 185 | IVVGSGNT | 186 | AAPHCIGGSCHDAFDI | 187 |
| 170 | GYSFTSYW | 195 | IYPGDSDT | 196 | ARLGNWLVDY | 197 |
| 175 | GLTVSRNY | 205 | TYSGGST | 206 | ARDLRGEV | 207 |
| 177 | GFTFSNYD | 215 | IGTAGDT | 216 | ARGQHTQIGHYYYYYMDV | 217 |
| 181 | GFTVSSNY | 225 | VYGGGTT | 226 | ATDNGYSYGFSFDY | 227 |
| 182 | GYTFTGYY | 235 | INPISGGT | 236 | ARGTYYYDSSGYIPFDY | 237 |
| 183 | GYTFSSYA | 245 | INTNTGNP | 246 | ARALGYCSSTSCYPAWAAFDI | 247 |
| 222 | GLTVSSNY | 255 | IYSGGST | 256 | ARGEGSPGNWFDP | 257 |
| 253 | GFTFTTSA | 265 | IVVGSGNT | 266 | AAPHCNSTSCYDAFDI | 267 |
| 269 | GLTVNRNY | 275 | IYSGGST | 276 | ARDFYEGSFDI | 277 |
| 278 | GYIFIRYG | 285 | ISANNGYT | 286 | ARDGGILTGYLDYFDH | 287 |
| 281 | GFPFSIYW | 295 | IKQDGSEK | 296 | ASRYYDFRPEAWFDY | 297 |
| 282 | GFTVSSNY | 305 | IYSGGST | 306 | ARDLEEAGGFDY | 307 |
| 285 | GDSVSNYY | 315 | IYTSGST | 316 | ARDHRASRYSSGWYEWWNCFDP | 317 |
| 316 | GYTFTGYY | 325 | INPNSGGT | 326 | ARDMAFSMVRGSFDY | 327 |
| 318 | GFTLTSSA | 335 | IVVGSGNT | 336 | AAGRGYNSDFDY | 337 |
| 334 | GYTFTSYY | 345 | INPSAGST | 346 | ARDSVLVPAANAFDI | 347 |
| 361 | GDTFTSYT | 355 | INAGNGYT | 356 | AKCTMIVDYFDY | 357 |
| 382 | GYTFTSYD | 365 | MNPHSDTT | 366 | AQGPIAVNYMDV | 367 |
| 384 | GFTFSDYY | 375 | IRSSGHTI | 376 | ARGGVLRFLEWPLNAFDI | 377 |
| 394 | GYTFTGYY | 385 | ISPNSGGT | 386 | ARGYYYEALDAFDI | 387 |
| 398 | GFTVSSNY | 395 | IYSGGST | 396 | ARDSTADYDFWSGYYVGAFHI | 397 |

| Light Chain CDR | | | | | |
|---|---|---|---|---|---|
| Ab number | CDR1-IMGT | SEQ ID NO. | CDR2-IMGT | SEQ ID NO. | CDR3-IMGT | SEQ ID NO. |
| 2 | QSVSSSY | 8 | GAS | 9 | QQYGSSLT | 10 |
| 22 | QSISSY | 18 | AAS | 19 | QQSYTTPYT | 20 |
| 40 | QDINNY | 28 | DAS | 29 | QQYDNLPA | 30 |
| 44 | ALPKKY | 38 | EDS | 39 | YSRDSSGDHWV | 40 |
| 45 | QDISNY | 48 | DAS | 49 | QQYDNLPLT | 50 |
| 54 | QSVSSSY | 58 | GAS | 59 | QHYGSSPVT | 60 |
| 55 | QSVSSSY | 68 | GAS | 69 | QQYGSSPWT | 70 |
| 58 | TIGSKS | 78 | DDS | 79 | QVWDSSSDRVV | 80 |
| 61 | QSVSSN | 88 | GAS | 89 | QQYNNWPPLT | 90 |
| 75 | QGISSW | 98 | AVS | 99 | QQAKSFPFT | 100 |
| 88 | SSNIGNNA | 108 | YDD | 109 | AAWDDSLNVVV | 110 |

Light Chain CDR

| Ab number | CDR1-IMGT | SEQ ID NO. | CDR2-IMGT | SEQ ID NO. | CDR3-IMGT | SEQ ID NO. |
|---|---|---|---|---|---|---|
| 111 | QGIRND | 118 | AAS | 119 | LQINSYPLT | 120 |
| 132 | TGAVTSGHY | 128 | DTR | 129 | LLSSSGARV | 130 |
| 140 | QSINNY | 138 | AAS | 139 | QQSYSAPPWT | 140 |
| 148 | QGISDY | 148 | AAS | 149 | QQYHSYPIT | 150 |
| 150 | QGISSY | 158 | AAS | 159 | QQLDSYPPGYT | 160 |
| 158 | QGISSY | 168 | AAS | 169 | QQLNSYRYT | 170 |
| 159 | QSISGNY | 178 | GAS | 179 | QQYGSSYT | 180 |
| 165 | QSVRSSY | 188 | GAS | 189 | QQYGSSPWT | 190 |
| 170 | QSLLHSDGKTY | 198 | EVS | 199 | MQSIQLPRGIT | 200 |
| 175 | QDISNF | 208 | DAS | 209 | HQYDNLPRT | 210 |
| 177 | QSISSY | 218 | AAS | 219 | QQSYSNPPEGS | 220 |
| 181 | SSDVGGYNL | 228 | EGS | 229 | CSYAGSSNWV | 230 |
| 182 | SSDVGSYNL | 238 | EGS | 239 | CSYAGSSTLV | 240 |
| 183 | NIGSKN | 248 | RDS | 249 | QVWDSSVV | 250 |
| 222 | QSVPSSY | 258 | GAS | 259 | QHYDTSPR | 260 |
| 253 | QSVSSSY | 268 | GAS | 269 | QQYGSSPYT | 270 |
| 269 | QGISSY | 278 | AAS | 279 | QQLNSYPAPV | 280 |
| 278 | QSIASY | 288 | AAS | 289 | QQSYSTLGIT | 290 |
| 281 | QSLVHRDGNTY | 298 | KIS | 299 | MQATQFPHGYT | 300 |
| 282 | QSVSSTY | 308 | GAS | 309 | QQYGSSLYT | 310 |
| 285 | QSISSY | 318 | AAS | 319 | QQSYSTPALT | 320 |
| 316 | SSDVGGYNY | 328 | EVS | 329 | SSYAGSNHWV | 330 |
| 318 | QSVSSSY | 338 | GTS | 339 | QQYGYSVYT | 340 |
| 334 | QSVSSY | 348 | DAS | 349 | QQRRNWLFT | 350 |
| 361 | QSISGW | 358 | DAS | 359 | QQYNSYPWT | 360 |
| 382 | NIGSKS | 368 | YDS | 369 | QVWDSSTDHVV | 370 |
| 384 | QGISNY | 378 | AAS | 379 | QKYNNALGT | 380 |
| 394 | SSDVGGYNF | 388 | EVS | 389 | NSYTSNSTRV | 390 |
| 398 | SSDVGGYNY | 398 | EVT | 399 | SSYAGSNNWV | 400 |

Amino Acid Sequence of Heavy Chain and Light Chain Variable Regions of Selected Antibodies

| Antibody number: | Heavy chain Amino Acid Sequence | SEQ ID NO: | Light chain Amino Acid sequence | SEQ ID NO: |
|---|---|---|---|---|
| Beta 6 | EVQLVESGPGLVKPSET LSLTCTVSGGSISSSHY WGWIRQPPGKGLEWIGS IYYSESAYYNPSLKSRVT | 402 | EIVMTQSPATLSLSPGERAT LSCRTSQSVTSYLAWYQQR PGQAPRLLIYDASDRATGIP ARFSGSGSGTDFTLTISNLE | 404 |

-continued

| Antibody number: | Heavy chain Amino Acid Sequence | SEQ ID NO: | Light chain Amino Acid sequence | SEQ ID NO: |
|---|---|---|---|---|
| | MSIDTSKNQFSLKLNSVT AADTAVYYCARVTEPR WTSCYFDYWGQGTLVT VSS | | PEDFAVYYCQLRSNWPPIT FGQGTRLETK | |
| Beta 10 | EVQLVESGPGLVKPSET LSLTCTVSGGSISSSSYY WGWIRQPPGKGLEWIGS IYYSGSTYYNPSLKSRVT ISVDTSKNQFSLKLSSVT AADTAVFFCARERSAPL AGNWFDPWGQGTLVTV SS | 412 | DIQMTQSPSFLSASVGDRV TITCRASQGISSYLAWYQQ KPGKAPKLLIYAASTLQSG VPSRFSGSGSGTEFTLTISSL QPEDFATYYCQQLNTYPSI TFGQGTRLEIK | 414 |
| Beta 20 | EVQLVESGGGVVQPGRPLRL SCAASGFPFSNYGMHWVR QAPGKGLEWVAVIWYDGS NKYYADSVKGRFTISRDNS KNTLYLQMNNLRAEDTAIY YCAKDGYTAHYYYYMDV WGKGTTVTVSS | 422 | AIQLTQSPGTLSLSPGERATLS CRASQSVSSSYLAWYQQKPG QAPRLLIYGASSRATGIPGRFS GSGSGTDFTLTISRLEPEDFAV YYCQQYGSSPGITFGGGTKV DIK | 424 |
| Beta 22 | EVQLVESGGGVVQPGRSL RLSCAASGFTFSNYGIHWV RQAPGKGLEWVAVISYDG SHKYYADSVKGRFTISRDN SKNTLYLQMNSLKTEDTA VYYCAKDSSAAIPYYYYG MDVWGQGTTVTVSS | 432 | AIQMTQSPDSLAVSLGERATI NCKSSQSILYNSNNKTYLAW YQQKPGQPPKLLIFWASTRES GVPDRFSGSGSGTDFTLTISSL QAEDVAVYYCQQYYSIPLIFG PGTKVDIK | 434 |
| Beta 23 | QLQLQESGPGLVKPSETLSL TCTVSGGSISSSSYYWGWIR QPPGKGLEWIGNVYYSGGT YCNPSLKSRVTISVDTSKNQ FSLNLSSVTAADTAVYYCA RIWFGEPAGGYFDYWGQG TLVTVSS | 442 | SYELTQPPSVSVSPGQTASITCS GHKLGDKNACWYQQKPGQSP VLVIYEYNKRPSGIPERFSGSNS GNTATLTISGTQAMDEADYYC QAWDTGTHVFGTGTKVTVL | 444 |
| Beta 24 | QVQLVQSGPGLVKPSQTLS LTCSVSDGSISSSDYYWSW IRQPPGKGLEWIGYIYYTG STYYNPSLKSRVSISVDRS KNQFSLKLSSVTAADTAVY YCARLVVPSPKGSWFDPW GQGTLVTVSS | 452 | SYELTQPASVSGSPGQSITISCT GTSIDVGNYNLASWYQQHPGK APKLIIYEGSRRPSGVSNRFSGA KSGNTASLTISGLQAEDEADYY CCSYVGSSTYVFGSGTKVTVL | 454 |
| Beta 25 | QVQLVQSGPEVKKPGTSVK VSCKASGFTFTSSAMQWVR QARGQRLEWIGWIVVGSGN TNYAQKFQERVTITRDMST STAYMELSSLRSEDTAVYY CAAVYCSGGSCNDAFDIWG QGTMVTVSS | 462 | EIVMTQSPGTLSLSPGERATLS CRASQSVSSSYLAWYQQKPG QAPRLLIYGASSRATGIPDRES GSGSGTDFTLTISRLEPEDFAV YYCQQYGSSPFTFGGGTKVEI K | 464 |
| Beta 26 | QVQLQQSGPGLVKPSETLSL TCTVSGASISNYYWSWIRQP PGKGLEWVGYIYYTGSTNH NPSLKSRVTISLDTSKNQFS LRLSSVTAADTAVYYCARA YCSGGSCFDTFDIWGQGTM VTVSS | 472 | SYELTQPPSVSVAPGQTARIT CGGNNIGSKSVHWFQQKPGQ APVLVVYDDSDRPSGIPERFS GSNSGNTASLTISRVEAGDEA DYYCQVWDSASDSGVFGTGT KLTVP | 474 |
| Beta 27 | EVQLLESGGGLVQPGGSLR LSCAASGLTVRSNYMNWV RQAPGKGLEWVSLIYSGGS TFYADSVKGRFTISRHDSKN TLYLQMNSLRAEDTAVYYC ARDLVVYGMDVWGQGTT VTVSS | 482 | DIQMTQSPGTLSLSPGERATLS CRASQVSSSSLAWYQQKHGQ APRLLIYGTSSRATGIPDRFSGS GSGTDFTLTISGLEPEDFA VYY CQQYGSSPLFGGGTKVEIK | 484 |
| Beta 29 | EVQLVESGGGVVQPGRSL RLSCAASGFTFSNYGMHRV RQAPGKGLEWVALISYEES NRYYGDSVRGRFTISRDNS KNTLYLQMNSLRPEDTAV | 492 | DIQLTQSPDSLAVSLGERATIN CKSSQSVLYSSNNKNYLAWY QQKPGQPPKLLIYWASTRESG VPDRFSGSGSGTDFTLTISSLQ AEDVAVYYCQQYFGSPSITFG | 494 |

-continued

| Antibody number: | Heavy chain Amino Acid Sequence | SEQ ID NO: | Light chain Amino Acid sequence | SEQ ID NO: |
|---|---|---|---|---|
| | YYCAKDQGPATVMVTAIR GAMDVWGQGTTVTSS | | QGTRLEIK | |
| Beta 30 | QVQLVQSGAEVKKPGASV KVSCKASGYTFTDYYMH WVRQAPGQGLEWMGWIN SKDGGANYAQKFQGRVTL TRDTSIDTAYIELSRLRSDD TAVYYCARSASTVTEPPTN WFDPWGQGTLVTVSS | 502 | DVVMTQSPSSLSASVGDRVT VTCRASQGIRNDLGWYQQKP GKAPKRLIYAASSLQSGVPSR FSGSGSGTDFTLTISSLQPEDF ATYYCLQHNSYLRFTFGPGTK VDIK | 504 |
| Beta 32 | EVQLVQSGAEVKKPGASVK VSCKASGYTFTGYYMHWV RQAPGQGLEWMGWINPNS GGTNYAQKFQGRVTMTRD TSITTGYMELSSLRSDDTAL YYCARVGAHDYYDSSDNW FDPWGQGTLVTVFS | 512 | DIQMTQSPSSVSASVGDRLTIT CRASQGISSWLAWYQQKPGK APKLLIYAASSLQSGVPSRFSG SGSGTDFTLTISSLQPEDFATYY CQQANSFPWTFGQGTKVEIK | 514 |
| Beta 33 | QVQLVQSGAEVKKPGASV KVSCKASGYPLTGYYIHW VRQAPGQGLEWMGWLNP NSGGTKYAQKFQGRVTMT RDTSISTGYMELSRLSDD TAVYYCARDGGGIDDYVQ EDGMDVWGQGPMVTVSS | 522 | QSALTQPPSVSVSPGQTARIT CSGDALSKQHAYWYQQKPG QAPVLVIYKDSERPSGIPERFS GSSSGTIVTLTISGVQAEDEA DYYCQSADNSGSRYVFGTGT KVTVL | 524 |
| Beta 34 | EVQLVESGGGLVQPGGSL RLSCAASGFTFSSYSMNWV RQAPGKGLEWVSYISGINSA IYYADSVKGRFTISRDNAK NSLYLQMNSLRVEDTAVY YCARDKYLGIKDMWGQG TMVTVSS | 532 | DIQMTQSPATLSLSPGERATLS CRASQSVSTYLAWYQQKPGQ APRLVIYDASNRATGIPARFSG GGSGTDFTLTISSLEPEDFAVYY CQQRLNWPLTFGGGTKVDIK | 534 |
| Beta 38 | EVQLVQSGAEVKKPGESL KISCKGSGYSFTNYWIGWV RQMPGKGLEWMGIIYPGD SGTRYSPSFQGQVTISADK SIRTAYLQWSSLKASDSAM YYCARSRVGATGGYYDYY MDVWGQGTTVTVSS | 542 | QSVLTQPPSASGTPGQRVTIS CSGSSSNLGGNTVNWYQQLP GTAPKLLIYSNNQRPSGVPDR FSGSKSGTSASLAISGLQSEDE ADYYCAAWDDSLNGPVFGT GTKVTVL | 544 |
| Beta 40 | QVQLVESGPGQVKPSETLS LTCTVSGGSISSSSYYWGW IRQPPGKGLEWIGSIYYSGS AYYNPSLKSRVTISVDTSK NQFSLKLNSVTAADTAVF YCARHAAPSPGDNWFDPW GQGTLVTVSS | 552 | QSVLTQPPSVSVSPGQTARIT CSGDALSTQNGNWYQQKPG QAPVMVICKDSERPSGIPERFS GSRSGTTVTLTISGVQAEDEA DYHCQSADNRAHVVFGGGT KLTVL | 554 |
| Beta 43 | EVQLVESGGGVVQPGRSLR LSCAASGFTFSSYGMHWVR QAPGKGLEWVAVIWYDGS NNFYADSVKGRFTISRDNF KNTLYLQMNSLRAEDTAV YYCARSYCSGGFCFGYYYG LDVWGQGTTVTVSS | 562 | SYELTQPPSVSVAPGKTATIT CGGNNIGTKSVHWYQQKPG QAPVLVIYYNSDRPSGIPERFS GSNSGNTVTLTISRVEAGDEA DYYCQVWDSGSDHYVFGTG TKVTVV | 564 |
| Beta 44 | QVQLVQSGAEVKKPGASV KVSCKASGYTFTSYGISWV RQAPGQGLEWMGWISPYN GNTHYAQKLQGRVTMTTD TSTSTAYMELRSLSDDTA VYYCARDGELLGWFDPW GQGTLVTVSS | 572 | QSVVTQPASVSGSPGQSITISCT GTSSDVGSYNLVSWYQQHPGK APKLMIYAGSKRPSGVSNRFSG SKSGNTASLTISGLQAEDEADY YCCSYAGSSTWVFGGGTKLTV L | 574 |
| Beta 45 | PGQLVESGGSLVQPGGALR LSCEASGFTFSDYAMSWV RQAPGKGLEWVSVINSSGG ITNYADSVKGRFTISRNNS KNTLYLQMNSLRGDDTAI YYCAKGPPRINTFYRHYYG MDVWGQGITVTVSS | 582 | AIQLTQSPSSLSASVGDRVTIT CQASQDIRNYLNWYQQKPG KAPKLLIYDASNLETGVPSRFS GSGSGTDFTFTIGSLQPEDIAT YYCQQYDNLRATFGGGTKVE IK | 584 |

-continued

| Antibody number: | Heavy chain Amino Acid Sequence | SEQ ID NO: | Light chain Amino Acid sequence | SEQ ID NO: |
|---|---|---|---|---|
| Beta 47 | QVQLVESGPEMKKPGTSV KVSCKASGFTFITSAVQWV RQARGQRLEWMGWIAVG SQNTNYAQKFQDRVTINR DMSTSTAYMELSSLRSEDT AVYYCAAPHCNRTSCHDG FDIWGQGTMVTVSS | 592 | EIVLTQSPGTLSLSPGERATLS CRASQSVSRNYLAWYQQKP GQVPRLLIYGASSRATGIPDR FRGSGSGTDFTLTINRLESEDF AVYYCQQYGSSLFTFGPGTK VDIK | 594 |
| Beta 48 | EVQLVESGGGLVKPGESL RLSCAASGFTFSSYAMNW VRQAPGKGLEWVSSISTGS YFIYYSDSVKGRFTISRDN AKNSLYLQMNSLRAADTA IYYCARGKEDTSAAFDIW GQGTMVTVSS | 602 | AIQMTQSLPPATLAPGERATL SCRASQSVSNNLAWYQQKP GQAPRLLIYGASTRATGIPAR FSGSGSGTEFTLTISSLQSEDF AVYYCQQYNNWPPWTFGQG TKVDIK | 604 |
| Beta 49 | EVQLVQSGAEVKKPGSSV KVSCKASGGTFSSSVISWV RQAPGQGLEWMGGIIPLFG SANYAQKFQGRVTITADES TSTAYMEMTSLRSEDTAV YYCAKVSQWALILFWGQG TLVTVSS | 612 | AIRMTQSPGTLSLSPGERATLS CRASQSVSSSYLAWYQQKPG QAPRLLIYGASSRATGIPDRFS GSGSGTDFTLTISRLEPEDFAV YYCQQYGTSPSWTFGQGTKV EIK | 614 |
| Beta 50 | EVQLVQSGAEVKKPGSSV KVSCKASRGTFNTYVFTW VRQAPGQGLEWMGGIIPFF GTADYAQKFQGRVTITAD DSTSTAYMELSSLRSEDTA VYYCSRLSQWDLLPMWG QGTLVTVSS | 622 | DIVMTQSPGTLSLSPGERATL SCRASQSFTSSYLAWYQQKP GQAPRLLIYGASSRATGIPDRF SGTGSGTDFTLTISRLEPEDFA VYYCQQYGTSPRMYTFGQGT KVDIK | 624 |
| Beta 51 | QLQLVESGAEVKKPGASVK VSCKVSGYTLTELSMHWVR QAPGKGLEWMGGFDPEDG ETIYAQKFQGRVTMTEDTSI DTVYMELSSLRSEDTAVYY CAIDRKHWLVGLDYWGQG TLVTVSS | 632 | AIRMTQSPSSLSASVGDRVTI TCRASQGIRNYLAWFQQKPG KAPKSLIYAASSLQSGVPSKF SGSGSGTDFTLTISSLQPEDFA TYYCQQYNSYPLTFGQGTRL EIK | 634 |
| Beta 53 | QVQLVQSGAEVKKPGESL RISCKGSGHNSPSYWISWV RQMPGKGLEWMGRIDPSD SYTNYSPSFQGHVTISADK SISTAYLQWSSLQASDTAI YYCARHVVALTHLYPDY WGQGTLVTVSS | 642 | DIQMTQSPATLSVSPGERATL SCRASQSVSSTLAWYQQKPG QAPRLLIYGASTRATGIPARFS GSGSGTEFTLTISSLQSEDFAV YYCQQYNNWSTWTFGQGTK VDIK | 644 |
| Beta 54 | QVQLQESGPGLVKPSETLS LTCTVFGGSITSSNHYWV WIRQPPGKGLEWIGSMYYS GSTAYNPSLTNRVTISVDT SKNQFSLKLSSVTAADTAV YYCARQIGPKRPSQVADW FDPWGQGTLVTVSS | 652 | DIQLTQSPSFLSASVGDRVTIT CRASQGISSYLAWYQQKPGK APKLLIYAASTLQSGVPSRFS GSGSGTEFTLTISSLQPEDFAT YYCQQLNSYPLTFGGGTKVEI K | 654 |
| Beta 55 | QVQLQESGPGLVKPSETLS LTCTVSGDSISSSRYYWGW IRQPPGKGLEWIGTFYYSGI TYYNPSLKSRVTIFVDTSK NQFSLKLSSVTAADTAVYY CARPRPPDYYDNSGALLFD IWGQGTMVTVSS | 662 | AIRMTQSPSTLSASVGDRVTIA CRASQSISAWLAWYQQKPGKA PKLLIYKASSLESGVPSRFSGSG SGTEFTLTINSLQPDDFATYYC QQYISSSPWTFGQGTKVEIK | 664 |
| Beta 56 | QLQLQESGPGLVRPSQTLSL SCTVSGGSISSATHYWSWIR QHPGRGLEWIGYIYYTGGT FYNPSLKSRLTISVDTSKNQ FSLKLSAVTAADTAVYYCA RVIAARPGSTYFDFWGRGTL VTVSS | 672 | QSALTQPASVSGSPGQSITISCT GTSSDVSGYNYVSWYQQHPD KAPKLLIYDVTNRPTGVSNRFS ASKSGNTASLTISGLQAEDEAD YYCSSDTNSIPRYVVFGGGTKL TVL | 674 |

Nucleotide Sequence of Heavy Chain and Light Chain Variable Regions of Selected Antibodies

| Antibody number: | Heavy chain Nucleotide Sequence | SEQ ID NO: | Light chain Nucleotide sequence | SEQ ID NO: |
|---|---|---|---|---|
| Beta 6 | gaggtgcagctggtggagtcgggcccag gactggtgaagccttcggagaccctgtccc tcacctgcactgtctctggtgggtccatcag cagtagtagtcactactggggctggatccg ccagcccccagggaaggggctggagtgg attgggagtatttattatagtgagagtgcctact acaaacccgtccctcaagagtcgagtcacca tgtcaatagacacgtccaagaaccagttctc cctgaagctgaactctgtgaccgccgcgga cacggccgtgtattactgtgcgagagtcact gagcctcggtggacttcttgttactttgactac tggggccagggaaccctggtcaccgtctc ctcag | 401 | gaaatagtgatgacgcagtctccagccaccct gtctttgtctccaggggaaagagccaccctctcc tgcaggaccagtcagagtgttaccagctactta gcctggtaccaacagagacctggccaggctc ccaggctcctcatctatgatgcatccgacaggg ccactggcatcccagccaggttcagtggcagtg ggtctgggacagacttcactctcaccatcagca acctagagcctgaagattttgcagtttattactgtc agctgcgtagcaactggcctccgatcaccttc ggccaagggacacgactggagactaaac | 403 |
| Beta10 | gaagtgcagctggtggagtcgggcccag gactggtgaagccttcggagaccctgtccc tcacctgcactgtctctgggggctccatcag cagtagtagttactactggggctggatccg ccagcccccagggaaggggctggagtgg attgggagtatctattatagtgggagcacct actacaaaccgtccctcaagagtcgagtca ccatatcagtagacacgtccaagaaccagt tctccctgaagctgagctctgtgaccgcc cggacacggccgtgttttctgtgcgagag agaggagcgctcctctcgcgggcaactgg ttcgaccctggggccagggaaccctggt caccgtctcttcag | 411 | gacatccagatgacccagtctccatccttcctg tctgcatctgtaggagacagagtcaccatcact tgccgggccagtcagggcattagcagttattta gcctggtatcagcaaaaaccagggaaagccc ctaagctcctgatctatgctgcatccactttgca aagtggggtcccatcaaggttcagcggcagtg gatctgggacagaattcactctcacaatcagca gcctgcagcctgaagattttgcaacttattactg tcaacagcttaatacttacccttcgatcaccttc ggccaagggacacgactggagattaaac | 413 |
| Beta20 | gaagtgcagctggtggagtctggggagg cgtggtccagcctggggaggcccctgagac tctcctgtgcagcctctggattcccttcagt aactatggcatgcactggtccgccaggct ccaggcaaggggctggaatgggtggcag ttatatggtatgatggaagtaataaatactat gcagactccgtgaagggccgattcaccatc tccagagacaattccaagaacacgctgtat ctgcaaatgaacaacctgagagctgagga cacggctatatattactgtgcgaaagatggg tacacggcccactactactactactacatgg acgtctggggcaaagggaccacggtcacc gtctcctca | 421 | gccatccagttgacccagtctccaggcaccctg tctttgtctccaggggaaagagccaccctctcct gcagggccagtcagagtgttagcagcagctactt agcctggtaccagcagaaacctggccaggctcc caggctcctaatctatggtgcatccagcagggcc actggcatcccaggcaggttcagtggcagtgg gtctgggacagacttcactctcaccatcagcag actggagcctgaagattttgcagtgtattactgtc agcagtatggtagctcacctgggatcactttcgg cggagggaccaaagtggatatcaaac | 423 |
| Beta22 | gaagtgcagctggtggagtctggggag gcgtggtccagcctggggaggtccctgag actctcctgtgcagcctctggattcaccttc agtaactatggcatacactgggtccgcca ggctccaggcaaggggctggagtgggt ggcagttatttcatatgatggaagtcataaa tattatgcagactctgtgaagggccgattc accatctccagagacaattccaagaacac gctatatctgcaaatgaacagcctgaaaa ctgaggacacggctgtgtattactgtgcga aagatagttcagctgctattccctactacta ctacggtatggacgtctggggccaaggg accacggtcaccgtctcttca | 431 | gccatccagatgacccagtctccagactccct ggctgtgtctctgggcgagagggccaccatc aactgcaagtccagccagagtattttatacaac tccaacaataagacctactagcttggtaccag cagaaaccaggacagcctcctaagctgctcat tttctgggcatctacccgggaatccgggtcc ctgaccgattcagtggcagcgggtctgggac agatttcactctcaccatcagcagcctgcaggct gaagatgtggcagtttattactgtcagcaatatta tagtattcccttatttcggccctgggaccaaa gtggatatcaaac | 433 |
| Beta23 | cagctgcagctgcaggagtcgggccca ggactggtgaagccttcggagaccctgtc cctcacctgcactgtctctggtggctccat cagcagtagtagttactactggggctgga tccgccagccccagggaaggggctgg agtggattgggaatgtctactatagtgggg gcacctactgcaaccgtccctcaagagt cgagtcaccatatcagtagacacgtccaa gaatcagttctccctgaactgagctccgt gaccgccgcggacacggccgtgtattact gtgcgagaatatggttcggggagcctgc gggtgggtactttgactactggggccagg gaaccctggtcaccgtctcctcag | 441 | tcctatgagctgactcagccaccctcagtgtcc gtgtccccaggacagacagccagcatcacct gctctggacataagttgggggataaaaatgcttg ctggtatcagcagaagccaggccagtcccctg tgctggtcatctatgaatataacaagcggccctc agggatccctgagcgattctctggctccaactc tgggaacacagccactctgaccatcagcggg acccaggctatggatgaggctgactattactgt caggcgtgggacaccggcactcatgtcttcgg aactgggaccaaggtcaccgtcctag | 443 |
| Beta24 | caggtccagctggtacagtcgggcccag gactggtgaagccttcacagaccctgtcc ctcacctgctctgtctctgatggctccatca gcagtagtgattactactggagctggatcc | 451 | tcctatgagctgactcagcctgcctccgtgtct gggtctcctggacagtcgatcaccatctcctgc actgggaccagcattgatgttggaattataac cttgcctcctggtaccaacagcacccaggcaa | 453 |

-continued

| Antibody number: | Heavy chain Nucleotide Sequence | SEQ ID NO: | Light chain Nucleotide sequence | SEQ ID NO: |
|---|---|---|---|---|
| | gccagcccccgggaagggcctggagtg gattgggtacatctattacactgggagcac ctactacaacccgtccctcaagagtcgag tttccatatcagtagacaggtccaagaacca attctccctgaagctgagttctgtgactgcc gcagacacggccgtttactattgtgccag actcgtagtaccatctccgaagggctcctg gttcgacccctggggccagggaaccctgg tcaccgtctcctcaa | | agcccccaaactcatcatttatgagggcagtag gcggccctcagggggtttctaatcgcttctctgg cgccaagtctggcaacacggcctccctgaca atctctgggctccaggctgaggacgaggctga ttattactgctgctcatatgtaggtagtagcactt atgtcttcggatctgggaccaaggtcaccgtcct ag | |
| Beta25 | caggtccagctggtacagtctgggcctga ggtgaagaagcctgggacctcagtgaag gtctcctgcaaggcttctggattcaccttta ctagctctgctatgcagtgggtgcgacag gctcgtggacaacgccttgagtggatagg atggatcgtcgttggcagtggtaacacaa actacgcacagaagttccaggaaagagt caccattaccagggacatgtccacaagca cagctcactggagctgagcagcctgag atccgaggacacggccgtgtattactgtg cggcagtttattgtagtggtggtagctgta atgatgctttttgatatctggggccaaggga caatggtcaccgtctcttcag | 461 | gaaatagtgatgacgcagtctccaggcaccct gtctttgtctccaggggaaagagccaccctctc ctgcagggccagtcagagtgttagcagcagcta cttagcctggtaccagcagaaacctggccagg ctcccaggctcctcatctatggtgcatccagcag ggccactggcatcccagacaggttcagtggc agtgggtctgggacagacttcactctcaccatc agcagcctgcagcctgaagattttgcagtgtat tactgtcagcagtatggtagctcacccttcactt tcggcggagggaccaaggtggaaatcaaac | 463 |
| Beta26 | caggtacagctgcagcagtcgggcccag gactggtgaagccctcggagaccctgtcc ctcacctgcactgtctctggtgcctccatta gtaattattactggagttggatccggcagc cccagggaagggactggagtgggttgg atatatctattacactgggagcaccaacca caaccccctccctcaagagtcgagtcacca tatcactagacacgtccaagaatcagttct ccctgaggctgagctctgtgaccgctgcg gacacggccgtctattactgtgcgcgagc ctattgtagtggtagctgcttcgatactt ttgatatctggggccaagggacaatggtc accgtctcttcag | 471 | tcctatgagctgacacagccaccctcggtgtca gtgccccaggacagacggccagaattacctgt ggggaaacaacattggaagtaaaagtgtgc actggttccagcagaagccaggccaggcccc tgtgctggtcgtctatgatgatagcgaccggcc ctcagggatccctgagcgattctctggctccaa ctctgggaacacggcctccctgaccatcagcag ggtcgaagccggggatgaggccgactattact gtcaggtgtgggatagtgctagtgattcaggtg tcttcggaactgggaccaagctcaccgtccca g | 473 |
| Beta27 | gaagtgcagctgttggagtctggaggag gcttggtccagcctgggggggtccctgaga ctctcctgtgcagcctctgggttaaccgtc agaagcaactacatgaactgggtccgcca ggctccagggaaggggctggagtgggtc tcacttatttatagcggtggtagtacattcta cgcagactccgtgaagggccgattcacc atctccagacacgattccaagaacacact gtatcttcaaatgaacagctgagagctga ggacacggccgtgtattactgtgcgcgag atttggtagtctacggaatggacgtctggg gccaagggaccacggtcaccgtctcctca | 481 | gacatccagatgacccagtctccaggcaccct gtctttgtctccaggggaaagagccaccctctc ctgcagggccagtcagagtgttagcagcagctc cttagcctggtaccagcagaaacatggccagg ctcccaggctcctcatctatggtacatccagcag ggccactggcatcccagacaggttcagtggc agtgggtctgggacagacttcactctcaccatc agtggactggagcctgaagattttgcagtgtat tactgtcagcagtatggtagctcaccccttttcg gcggggggaccaaggtggaaatcaaac | 483 |
| Beta29 | gaggtgcagctggtggagtctgggggga ggcgtggtccagcctggggagtccctga gactctcctgtgcagcctctggattcacctt cagtaattatggcgatgcaccgggtccgc caggctccaggcaaggggctggagtgg gtggcacttatttcatatgaagaaagtaata gatattatggagactccgtgagggggccg attcaccatctccagagacaattccaaga acactctgtatctgcaaatgaacagcctga gacctgaggacacggctgtgtattactgt gcgaaagatcaaggcccggctactgtgat ggtgactgctattcggggcgctatggac gtctggggccaagggaccacggtcacc gtctcctcag | 491 | gacatccagttgacccagtctccagattccctg gctgtgtctctgggcgagagggccaccatca actgcaagtccagccagagtgttttatacagct ccaacaataagaactacttagcttggtaccag cagaaaccaggccagcctcctaaactcctcat ttactgggcgtctacccgggaatccggggtcc ctgaccgattcagtggcagcgggtctgggaca gatttcactctcaccatcagcagcctgcaggct gaagatgtggcagtatattactgtcagcaatatt ttggttctccttcgatcaccttcggccaagggga cacgactggagattaaac | 493 |
| Beta30 | caggtgcagctggtgcagtctggggctga ggtgaagaagcctgggggcctcagtgaag gtctcctgcaaggcttctggatacaccttca ccgactactatatgcactggtgcgcaa gcccctggacaagggcttgagtggatgg gatggatcaactctaaagatggtggcgcg aactatgcacagaagtttcagggcaggt caccctgaccaggacgtcatcgac acagcctacatagaactgagcaggctcaga | 501 | gatgttgtgatgactcagtctccatcctccctgt ctgcatctgtaggcgacagagtcaccgtcactg ccgggcaagtcagggcattagaaatgatttag gctggtatcagcagaaaccagggaaagctcc taagcgcctgatctatctgctgcatccagtttgcaa agtggtgtcccatcaaggttcagcggcagtgg atctggacagacttcactctcacaatcagcag cctgcagcctgaagattttgcaacttattactgt ctacagcataatagttaccctccgtttcacttttcgg | 503 |

-continued

| Antibody number: | Heavy chain Nucleotide Sequence | SEQ ID NO: | Light chain Nucleotide sequence | SEQ ID NO: |
|---|---|---|---|---|
| | tctgacgacacggccgtgtattactgtgcg agatccgcctctacagtaaccgaaccacc gacaaactggttcgaccnctggggccag ggaaccctggtcaccgtctcctcag | | ccctgggaccaaagtggatatcaaac | |
| Beta32 | gaagtgcagctggtgcagtctggggctga ggtgaagaagcctggggcctcagtgaag gtctcctgcaaggcttctggatacaccttca ccggctactatatgcactgggtgcgacag gcccctggacaagggcttgagtggatgg gatggatcaaccctaacagtggtggcaca aactatgcacagaagtttcagggcagggt caccatgaccagggacacgtccatcacc acaggctacatggagctgagcagcctga gatctgacgacacggccctgtattactgtg cgagagttggggctcacgattactatgata gtagtgacaactggttcgaccnctggggc cagggaaccctggtcaccgtcttctcag | 511 | gacatccagatgacccagtctccatcttccgtg tctgcatctgtaggagacagactcaccatcact tgtcgggcgagtcagggtattagcagctggtt agcctggtatcagcagaaaccagggaaagcc cctaagctcctgatctatgctgcatccagtttgc aaagtggggtcccatcaaggttcagcggcagt ggatctgggacagatttcactctcaccatcagc agcctgcagcctgaagattttgcaacttactatt gtcaacaggctaacagtttcccgtggacgttcg gccaagggaccaaggtggagatcaaac | 513 |
| Beta33 | caggtgcagctggtgcagtctggggctga ggtgaagaagcctggggcctcagtgaag gtctcctgcaaggcttctggataccccctc accggctactatatacactgggtgcgaca ggcccctggacaaggacttgagtggatgg gatggctcaaccctaacagtggtggcaca aagtatgcacagaagtttcagggcagggt caccatgaccagggacacgtccatcagc acaggctacatggagctgagcaggctgag atctgacgacacggccgtgtactactgtgc gagagatggggggggaatagatgattac gttcaggaggacggtatggacgtctgggg ccaagggcccatggtcaccgtctcttca | 521 | caatctgccctgactcagccaccctcggtgtc agtgtcccaggacagacggccaggatcacc tgctctggagatgcattgtcaaagcaacatgct tattggtaccagcagaagccaggccaggccc ctgtattggtgatatataaagacagtgagaggc cctcagggatccctgagcgattctctggctcca gctcagggacaatagtcaccttgaccatcagtg gagtccaggcagaagacgaggctgactattac tgtcaatcagcagacaacagtggtagtagatat gtcttcggaactgggaccaaggtcaccgtcct ag | 523 |
| Beta34 | gaagtgcagctggtggagtctgggggag gcttggtacagcctggggggtccctgag actctcctgtgcagcctctggattcaccttc agtagctatagcatgaactgggtccgcca ggctccagggaaggggctggagtgggtct catacattagtagtaataatagtgccatata ttacgcagactctgtgaaggggccgcttca ccatctccagagacaacgccaagaactc actgtatctgcaaatgaacagcctgagag tcgaggacacggctgtgtattactgtgcg agagataaatacttaggtataaaagatatg tggggccaagggacaatggtcaccgtctct tcag | 531 | gacatccagatgacccagtctccagccaccct gtctttgtctccaggggaaagagccaccctctc ctgcagggccagtcagagtgttagcacctactta gcctggtaccaacagaaacctggccaggctc ccaggctcgtcatctatgatgcatccaacagg gccactggcatcccagccaggttcagtggcgg tgggtctgggacagacttcactctcaccatcag cagcctagagcctgaagattttgcagtttattac tgtcaacagcgtctcaactggcctctcactttcg gcggagggaccaaagtggatatcaaac | 533 |
| Beta38 | gaggtgcagctggtacagtctggagcaga ggtgaaaaagccggggagtctctgaaga tctcctgtaagggctctggatacagctttacc aactactggatcggctgggtgcgccagatg cccgggaaaggcctggagtggatggggat catctatcctggtgactctggtaccagatac agcccgtccttccaaggccaggtcaccatc tcagccgacaagtccatcagaaccgcctac ctgcagtggagcagcctgaaggcctcgga cagcgccatgtattactgtgcgaggtctaga gtgggagctactgggggctattatgactacta tatggacgtctggggccaagggaccacgg tcaccgtctcctca | 541 | cagtctgtgttgacgcagccaccctcagcgtctg ggaccccggcagagggtcaccatctcttgttc tggaagcagctccaacctcggaggtaatactgta aactggtaccagcagctcccaggaacggcccc caaactcctcatctatagtaataatcagcggccctc aggggtccctgaccgattctctggctccaagtct ggcacctcagcctccctggccatcagtgggctc cagtctgaggatgaggctgattattactgtgcagc atgggatgacagcctgaatggtcccgtcttcgg aactgggaccaaggtcaccgtcctag | 543 |
| Beta40 | caggtgcagctggtggagtcgggcccag gacaggtgaagccttcggagaccctgtccc tcacctgcactgtctctggtggctccatcag cagtagtagttactactggggctggatccgc cagcccccagggaagggactggagtggat tgggagtatctattatagtgggagcgcctac tataacccgtccctcaagagtcgagtcacca tatccgtagacacgtccaagaaccagttctc cctgaagctgaactctgtgaccgccgaga cacggctgtcttttactgtgcgagacacgca gctcccagtccggggacaactggttcga cccctggggccagggaaccctggtcaccg tctcctcag | 551 | cagtctgtgttgactcagccaccctcggtgtca gtgtcccaggacagacggcccgatcacct gctctggagatgcattgtcaacgcaaaatggt aattggtaccagcagaagccaggccaggcc cctgtgatggtgatatgtaaagacagtgagag gccctcagggatccctgagcgattctctggct ccaggtcagggacaacagtcacgttgaccat cagtggagtccaggcagaagacgaagctga ctatcactgtcaatcagcagacaacagggcac atgtagtattcggcggagggaccaagctgac cgtcctag | 553 |

-continued

| Antibody number: | Heavy chain Nucleotide Sequence | SEQ ID NO: | Light chain Nucleotide sequence | SEQ ID NO: |
|---|---|---|---|---|
| Beta43 | gaggtgcagctggtggagtctgggggag gcgtggtccagcctggggaggtccctgaga ctctcctgtgcagcgtctggattcacctttag tagttatggcatgcactgggtccgccaggc tccaggcaaggggctggagtgggtggca gttatatgtatgatggaagtaataacttctat gcagactccgtgaagggccgattcaccatc tccagagacaatttcaagaacacgctgtattt gcaaatgaacagcctgagagccgaggac acggctgtgtattactgtgcgagatcatattg tagtggtggtttctgcttcggctactactatg gtttggacgtgtggggccaagggaccacgg tcaccgtctcctca | 561 | tcctatgagctgactcagccaccctcagtgtca gtggccccaggaaagacggccacgattacct gtgggggaaacaacattggaactaaaagtgtg cactggtaccagcagaagccaggccaggccc ctgtcgttggtcatctattataatagcgaccggc ctctcgggatccctgagcgattctctggctccaa ctctgggaacacggtcaccctgaccatcagca gggtcgaagccggggatgaggccgactatta ctgtcaggtgtgggatagtggtagtgatcattat gtcttcggaactgggaccaaggtcaccgtcgt ag | 563 |
| Beta44 | caggtgcagctggtgcagtctggagctga ggtgaagaagcctggggcctcagtgaag gtctcctgcaaggcttctggttacacctttta ccagctatgtatcagctgggtgcgacag gcccctggacaagggcttgagtggatgg gatggatcagcccttacaatggtaacaca cactatgcacagaagctccagggcagag tcaccatgaccacagacacatccacgagc acagcctacatggagctgagcagcctga gatctgacgacacggccgtatattactgtg cgagagatggggagttattgggctggttc gaccccctggggccagggaaccctggtca ccgtctcctcag | 571 | cagtctgtcgtgacgcagcctgcctccgtgtctg ggtctcctggacagtcgatcaccatctcctgcac tggaaccagcagtgatgttgggagttataacctt gtctcctggtaccaacagcacccaggcaaagc ccccaaactcatgatttatgcgggcagtaagcg gccctcaggggtttctaatcgcttctctggctcca agtctggcaacacggcctcctgacaatctctgg gctccaggctgaggacgaggctgattattactg ctgctcatatgcaggtagtgcacttgggtgttc ggcggagggaccaagctgaccgtcctag | 573 |
| Beta45 | ccaggtcagctggtggaatctgggggaa gcttggtacagcctggggggtccctgag actctcctgtgaagcctctggattcacctttt agcgactatgccatgagctgggtccgcca ggctccagggaaggggctggagtgggt ctcagttattaatagtagtggtggtatcaca aactacgcagactccgtgaagggccggtt caccatctccagaaacaattccaagaaca cgctctatctgcaaatgaacagcctgaga ggcgacgacacggccatatattactgtgc gaagggaccccccgagaattaacaccttct acaggcactactacggtatggacgtctgg ggccaagggatcacggtcaccgtctcctc a | 581 | gccatccagttgacccagtctccatcctccctg tctgcatctgtaggagacagagtcaccatcact tgccaggcgagtcaggacattaggaactattt aaattggtatcagcagaaaccagggaaagcc cctaagctcctgatctacgatgcatccaatttgg aaacaggggtcccatcaaggttcagtggaagt ggatctgggacagattttactttcaccatcggca gcctgcagcctgaagatattgcaacatattact gtcaacaatatgataatctccgggccactttcg gcggagggaccaaggtggagatcaaac | 583 |
| Beta47 | caggtgcagctggtggagtctgggcctg aaaatgaagaagcctgggacctcagtgaa ggtctcctgcaaggcttctggattcacctttt attacgtctgctgttcagtgggtgcgacagg ctcgtggacaacgccttgagtggatggga tggatcgccgttggcagtggtaacacaaa ctacgcacagaaattccaggacagagtc accattaacaggagtgtccacaagcac agcctacatggagctgagcagcctgaga tccgaggacacggccgtgtattactgtgc ggccccgcattgtaatcgtaccagctgcc atgatggttttgatatctggggccaaggga caatggtcaccgtctcttcag | 591 | gaaattgtgttgacgcagtctccaggcaccct gtctttgtctccaggggaaagagccaccctctc ctgcagggccagtcagagtgttagcagaaact acttagcctggtaccagcagaaacctggcca ggttcccaggctcctcatctatggtgcatccag cagggccactggcatcccagacaggttcaga ggtagtgggtctgggacagacttcactctcac catcaacagactggagtctgaagattttgcagt gtattactgtcagcagtatggtagctccctattc actttcggccctgggaccaaagtggatatcaa ac | 593 |
| Beta48 | gaagtgcagctggtggagtcggggggga ggcctggtcaagcctggggagtccctgag actctcctgtgcagcctctggattcaccttc agtagctatgccatgaactgggtccgcca ggctccagggaaggggctggagtgggt ctcatccattagtactggtagttatttcatata ctactcagactcagtgaagggccgattca ccatttccagagacaacgccaagaactca ctgtatctgcaaatgaacagcctgagagc cgcggacacggctatctattactgtgcga gaggaaaggaagatacaagcgctgcttttt gatatctggggccaagggacaatggtca ccgtctcttcag | 601 | gccatccagatgacccagtctcttcctcctgcg actctggctccaggggaaagagccaccctct cctgcagggccagtcagagtgttagcaacaa cttagcctggtaccagcagaaacctggccag gctcccaggctcctcatctatggtgcatccacc agggccactggtatcccagccaggttcagtgg cagtgggtctgggacagagttcactctcaccatc agcagactggagtctgaagatgtttgcagtttatt actgtcagcagtataatagctggcctccgtgg acgttcggccaagggaccaaagtggatatca aac | 603 |
| Beta49 | gaggtgcagctggtgcagtctggggctg aggtgaagaagcctgggtcctcggtgaa ggtctcctgcaaggcttctggaggcacctt cagcagctctgttatcagctgggtgcgac | 611 | gccatccggatgacccagtctccaggcaccct gtctttgtctccaggggaaagagccaccctctc ctgcagggccagtcagagtgttagcagcagcta cttagcctggtaccagcagaaacctggccagg | 613 |

| Antibody number: | Heavy chain Nucleotide Sequence | SEQ ID NO: | Light chain Nucleotide sequence | SEQ ID NO: |
|---|---|---|---|---|
| | aggcccctggacaaggccttgagtggat gggagggatcatccctctctttggttcagc aaaactacgcacagaagttccagggcaga gtcacgattaccgcggacgaatccacga gcacagcctacatggagatgactagcctg agatctgaagacacggccgtgtattactgt gcgaaagtttcccagtgggcgttaatactc ttctggggccagggaaccctggtcaccgt ctcctcag | | ctcccaggctcctcatctatggtgcatccagcag ggccactggcatcccagacaggttcagtggc agtgggtctgggacagacttcactctcaccatc agcagactggagcctgaagattttgcagtgtat tactgtcagcagtatggtacctccttcgtgg acgttcggccaagggaccaaggtggagatca aac | |
| Beta50 | gaggtgcagctggtgcagtctggggctg aggtgaagaagcctgggtcctcggtgaa ggtctcctgcaaggcgtctagaggcacctt caacaacctatgtctttcacctgggtcgaca ggcccctggacaagggcttgagtggatg ggagggatcatccctttctttggtacagca gactacgcacagaagttccagggcagag tcacgattaccgcggacgactccacga cacagcctacatggagctgagcagcctg agatctgaggacacggccgtgtattactgt tcgaggctcagccagtgggacctactacc catgtggggccagggaaccctggtcacc gtctcctcag | 621 | gatattgtgatgactcagtctccaggcaccctg tctttgtctccaggggaaagagccaccctctcc tgcagggccagtcagagttttaccagcagcta cttagcctggtaccagcagaaacctggccagg ctcccaggctcctcatctatggtgcatccagca gggccactggcatcccagacaggttcagtgg cactgggtctgggacagacttcactctcaccat cagcagactggagcctgaagattttgcagtata ttactgtcagcagtatggtacgtcacctcgcat gtacacttttggccaggggaccaaagtggatat caaac | 623 |
| Beta51 | cagctgcagctggtggagtctggggctga ggtgaagaagcctggggcttcagtgaagg tctcctgcaaggtttccggatacacccctcact gaattatccatgcactgggtgcgacaggct cctggaaaagggcttgagtggatgggggg ttttgatcctgaagatggtgagacaatctac gcacagaagttccaggcagagtcaccat gaccgaggacacatctatagacacagtgta catggagctgagcagcctgagatctgagg acacggccgtgtattactgtgcaatagatcg caagcactggctggtaggtcttgactactgg ggccagggaaccctggtcaccgtctcctca g | 631 | gccatccggatgacccagtctccatcctcactg tctgtctctgtaggagacagagtcaccatcact tgtcgggcgagtcagggcattaggaattattta gcctggtttcagcagaaaccagggaaagccc ctaagtccctgatctatgctgcatccagtttgca aagtgggctcccatcaaagttcagcggcagtg gatctgggacagatttcactctcaccatcagca gcctgcagcctgaagattttgcaacttattactg ccaacagtataatagttaccccctcaccttcgg ccaagggacacgactggagattaaac | 633 |
| Beta53 | caggtgcagctggtgcagtccggagcag aggtgaaaaagcccggggagtctctgag gatctcctgtaagggttctggacacaactc tcccagctactgattagctgggtgcgcca gatgcccggaaaggcctggagtggatg gggagaattgatcctagtgactcttatacc aactacgcccgtccttccaaggccatgtc accatctcagctgacaagtccatcagtact gcctacctacagtgagcagcctgcagg cctcggacaccgccatttattactgtgcga gacacgtggttgcattgactcatttgtaccc tgactactggggccagggaaccctggtc accgtctcctcag | 641 | gacatccagatgacccagtctccagccaccct gtctctgtctccaggggaaagagccaccctct cctgcagggccagtcaaagtgttagcagcac cttagcctggtaccagcagaaacctggccag gctcccaggctcctcatctatggtgcatccacc agggccactggtatcccagccaggttcagtgg cagtgggtctgggacagagttcactctcaccatc agcagcctgcagtctgaagattttgcagtttatt actgtcagcaatataataactggtccacgtgga cgttcggccaagggaccaaagtggatatcaa ac | 643 |
| Beta54 | caggtgcagctgcaggagtcgggcccag gactggtgaagccttcggagaccctgtcc ctcacctgcgactgtctttggtggctccatca ccagtagtaatcactactgggtctggatcc gccagcccccagggaaggggctggagt ggattgggagtatgtattatagtgggagca ccgcctacaacccgtccctcacgaatcga gtcaccatatccgtagacacgtccaagaa ccagttctccctgaagctgagctccgtgac cgccgcagacacggctgtgtattactgtg cgagacaaatcgggcccaagaggccctc gcaagtggctgactggttcgaccctggg gccagggaaccctggtcaccgtctcctca g | 651 | gacatccagttgacccagtctccatcctttcctgt ctgcatctgtaggagacagagtcaccatcactt gccgggccagtcagggcattagcagttatttta gcctggtatcagcaaaaacctgggaaagccc taagctcctgatctatgctgcatccactttgca aagtggggtcccatcaaggttcagcggcagt ggatctgggacagaattcactctcacaatcag cagcctgcagcctgaagattttgcaacttattac tgtcaacagcttaatagttaccctctcactttcg gcggagggaccaaggtggaaatcaaac | 653 |
| Beta55 | caggtgcagctgcaggagtcgggcccag gactggtgaagccttcggagaccctgtc cctcacttgcgctctctgtggtgactccatc agcagtagtcgttactactggggctggatc cgccagcccccagggaaggggctggag tggattgggactttctattatagtgggatca cgtactacaacc | 661 | gccatccggatgacccagtctccttccaccct gtctgcatctgtaggagacagagtcaccatcg cttgccgggccagtcagagtattagtgcctggt tggcctggtatcagcagaaacagggaaagc ccctaagctcctgatctataaggcatctagtttt gaaagtggggtcccatcaaggttcagcggca gtggatctgggaca | 663 |

-continued

| Antibody number: | Heavy chain Nucleotide Sequence | SEQ ID NO: | Light chain Nucleotide sequence | SEQ ID NO: |
|---|---|---|---|---|
| | cgtccctcaagagtcgagtcaccatattcgt agacacgtccaagaaccagttctccctgaa gctgagctctgtgaccgccgcagacacgg ctgtttattactgtgcgagaccccgacccc cgattactatgataatagtggtgcgctccttt tgatatctggggccaagggacaatggtcac cgtctcttcag | | gaattcactctcaccatcaacagcctgcagcct gatgattttgccacttattactgccaacagtatat tagttcttctccgtggacgttcggccaagggac caaggtggaaatcaaac | |
| Beta56 | cagctgcagctgcaggagtcgggcccag gactggtgaggccttcacagaccctgtcc tctcctgcactgtctctggtggctccatcagc agtgccactcactactgagctggatccgc cagcacccagggagaggcctggagtgga ttgggtacatctattacactgggggcacctt tacaatccgtccctcaagagtcgacttaccata tcagtggacacgtctaagaaccagttctccc tgaagctgagcgctgtgactgccgcggac acggccgtgtattactgtgcgagagtttatag cagctcgtccgggatctacctactttgacttct ggggccggggaaccctggtcaccgtctcc tcag | 671 | caatctgccctgactcagcctgcctccgtgtct gggtctcctggacagtcgatcaccatctcctgc actggaaccagcagtgacgttagtggctataa ctatgtctcctggtaccaacaacacccagacaa agccccaaactcttgatttatgatgtcactaatc ggcccacaggggtttctaatcgcttctctgcct ccaagtctggcaacacggcctccctgaccatc tctgggctccaggctgaggacgaggctgatta ttactgcagctcagatacaaatagtattcctcgg tatgtggtgttcggcggagggaccaagctgac cgtcctag | 673 |

Amino Acid Sequences of CDRs

| Heavy chain CDR | | | | | | |
|---|---|---|---|---|---|---|
| Ab number | CDR1-IMGT | SEQ ID NO | CDR2-IMGT | SEQ ID NO. | CDR3-IMGT | SEQ ID NO. |
| Beta 6 | GGSISSSSHY | 405 | IYYSESA | 406 | ARVTEPRWTSCYFDY | 407 |
| Beta 10 | GGSISSSSY | 415 | IYYSGST | 416 | ARERSAPLAGNWFDP | 417 |
| Beta 20 | GFPFSNYG | 425 | IWYDGSNK | 426 | AKDGYTAHYYYYMDV | 427 |
| Beta 22 | GFTFSNYG | 435 | ISYDGSHK | 436 | AKDSSAAIPYYYYGMDV | 437 |
| Beta 23 | GGSISSSSY | 445 | VYYSGGT | 446 | ARIWFGEPAGGYFDY | 447 |
| Beta 24 | DGSISSSDY | 455 | IYYTGST | 456 | ARLVVPSPKGSWFDP | 457 |
| Beta 25 | GFTFTSSA | 465 | IVVGSGNT | 466 | AAVYCSGGSCNDAFDI | 467 |
| Beta 26 | GASISNYY | 475 | IYYTGST | 476 | ARAYCSGGSCFDTFDI | 477 |
| Beta 27 | GLTVRSNY | 485 | IYSGGST | 486 | ARDLVVYGMDV | 487 |
| Beta 29 | GFTFSNYG | 495 | ISYEESNR | 496 | AKDQGPATVMVTAIRGAMDV | 497 |
| Beta 30 | GYTFTDYY | 505 | INSKDGGA | 506 | ARSASTVTEPPTNWFDP | 507 |
| Beta 32 | GYTFTGYY | 515 | INPNSGGT | 516 | ARVGAHDYYDSSDNWFDP | 517 |
| Beta 33 | GYPLTGYY | 525 | LNPNSGGT | 526 | ARDGGGIDDYVQEDGMDV | 527 |
| Beta 34 | GFTFSSYS | 535 | ISGINSAI | 536 | ARDKYLGIKDM | 537 |
| Beta 38 | GYSFTNYW | 545 | IYPGDSGT | 546 | ARSRVGATGGYYDYYMDV | 547 |

-continued

| | | Heavy chain CDR | | | | |
|---|---|---|---|---|---|---|
| Ab number | CDR1-IMGT | SEQ ID NO | CDR2-IMGT | SEQ ID NO. | CDR3-IMGT | SEQ ID NO. |
| Beta 40 | GGSISSSSY Y | 555 | IYYSGSA | 556 | ARHAAPSPGDNW FDP | 557 |
| Beta 43 | GFTFSSYG | 565 | IWYDGSNN | 566 | ARSYCSGGFCFG YYYGLDV | 567 |
| Beta 44 | GYTFTSYG | 575 | ISPYNGNT | 576 | ARDGELLGWFDP | 577 |
| Beta 45 | GFTFSDYA | 585 | INSSGGIT | 586 | AKGPPRINTFYRH YYGMDV | 587 |
| Beta 47 | GFTFITSA | 595 | IAVGSGNT | 596 | AAPHCNRTSCHD GFDI | 597 |
| Beta 48 | GFTFSSYA | 605 | ISTGSYFI | 606 | ARGKEDTSAAFDI | 607 |
| Beta 49 | GGTFSSSV | 615 | IIPLFGSA | 616 | AKVSQWALILF | 617 |
| Beta 50 | RGTFNTYV | 625 | IIPFFGTA | 626 | SRLSQWDLLPM | 627 |
| Beta 51 | GYTLTELS | 635 | FDPEDGET | 636 | AIDRKHWLVGLD Y | 637 |
| Beta 53 | GHNSPSYW | 645 | IDPSDSYT | 646 | ARHVVALTHLYP DY | 647 |
| Beta 54 | GGSITSSNH Y | 655 | MYYSGST | 656 | ARQIGPKRPSQVA DWFDP | 657 |
| Beta 55 | GDSISSSRY Y | 665 | FYYSGIT | 666 | ARPRPPDYYDNS GALLFDI | 667 |
| Beta 56 | GGSISSATH Y | 675 | IYYTGGT | 676 | ARVIAARPGSTYF DF | 677 |

| | | Light Chain CDR | | | | |
|---|---|---|---|---|---|---|
| Ab number | CDR1-IMGT | SEQ ID NO. | CDR2-IMGT | SEQ ID NO. | CDR3-IMGT | SEQ ID NO. |
| Beta 6 | QSVTSY | 408 | DAS | 409 | QLRSNWPPIT | 410 |
| Beta 10 | QGISSY | 418 | AAS | 419 | QQLNTYPSIT | 420 |
| Beta 20 | QSVSSSY | 428 | GAS | 429 | QQYGSSPGIT | 430 |
| Beta 22 | QSILYNSNNKTY | 438 | WAS | 439 | QQYYSIPLI | 440 |
| Beta 23 | KLGDKN | 448 | EYN | 449 | QAWDTGTHV | 450 |
| Beta 24 | SIDVGNYNL | 458 | EGS | 459 | CSYVGSSTYV | 460 |
| Beta 25 | QSVSSSY | 468 | GAS | 469 | QQYGSSPFT | 470 |
| Beta 26 | NIGSKS | 478 | DDS | 479 | QVWDSASDSGV | 480 |
| Beta 27 | QSVSSSS | 488 | GTS | 489 | QQYGSSPL | 490 |
| Beta 29 | QSVLYSSNNKNY | 498 | WAS | 499 | QQYFGSPSIT | 500 |
| Beta 30 | QGIRND | 508 | AAS | 509 | LQHNSYLRFT | 510 |
| Beta 32 | QGISSW | 518 | AAS | 519 | QQANSFPWT | 520 |
| Beta 33 | ALSKQH | 528 | KDS | 529 | QSADNSGSRYV | 530 |
| Beta 34 | QSVSTY | 538 | DAS | 539 | QQRLNWPLT | 540 |

-continued

| | Light Chain CDR | | | | | |
|---|---|---|---|---|---|---|
| Ab number | CDR1-IMGT | SEQ ID NO. | CDR2-IMGT | SEQ ID NO. | CDR3-IMGT | SEQ ID NO. |
| Beta 38 | SSNLGGNT | 548 | SNN | 549 | AAWDDSLNGPV | 550 |
| Beta 40 | ALSTQN | 558 | KDS | 559 | QSADNRAHVV | 560 |
| Beta 43 | NIGTKS | 568 | YNS | 569 | QVWDSGSDHYV | 570 |
| Beta 44 | SSDVGSYNL | 578 | AGS | 579 | CSYAGSSTWV | 580 |
| Beta 45 | QDIRNY | 588 | DAS | 589 | QQYDNLRAT | 590 |
| Beta 47 | QSVSRNY | 598 | GAS | 599 | QQYGSSLFT | 600 |
| Beta 48 | QSVSNN | 608 | GAS | 609 | QQYNNWPPWT | 610 |
| Beta 49 | QSVSSSY | 618 | GAS | 619 | QQYGTSPSWT | 620 |
| Beta 50 | QSFTSSY | 628 | GAS | 629 | QQYGTSPRMYT | 630 |
| Beta 51 | QGIRNY | 638 | AAS | 639 | QQYNSYPLT | 640 |
| Beta 53 | QSVSST | 648 | GAS | 649 | QQYNNWSTWT | 650 |
| Beta 54 | QGISSY | 658 | AAS | 659 | QQLNSYPLT | 660 |
| Beta 55 | QSISAW | 668 | KAS | 669 | QQYISSSPWT | 670 |
| Beta 56 | SSDVSGYNY | 678 | DVT | 679 | SSDINSIPR | 680 |

Amino Acid Sequence of Heavy Chain and Light Chain Variable Regions of Selected Antibodies

| | Heavy chain | | Light chain | |
|---|---|---|---|---|
| Antibody number: | Amino acid sequence | SEQ ID NO: | Amino acid sequence | SEQ ID NO: |
| Omi02 | EVQLVESGAEVKKPGSS VKVSCKASGGTFSSYAI NWVRQAPGQGLEWMG GIIPIFRTPHYAQKFQGR VTITADESTGTAYMELSS LRSEDTAVYYCASPSCG GDCPQYLKSSKLDWYF DLWGRGTLVTVSS | 682 | VIWMTQSPGTLSLSPGER ATLSCRASQSVSSTYLA WYQQKPGQAPRLLIYGA SSRATGIPDRFSGSGSGT DFTLTISRLEPEDFAVYY CQHYGSSPLTFGQGTRLE IK | 684 |
| Omi03 | EVQLVESGGGLIQPGGS LRLSCAASEIIVSRNYMS WVRQAPGKGLEWVSVI YSGGSTFYADSVKGRFTI SRDNSKNTLYLQMNSLR AEDTAVYYCARDLDVV GGTDYWGQGTLVTVSS | 692 | EIVLTQSPGTLSLSPGERA TLSCRASQSVSSSYLAWY QQKPGQAPRLLIYGASSR ATGIPDRFSGSGSGTDFT LTISRLEPEDFAVYYCQQ YGSSPGYTFGQGTKVDIK | 694 |
| Omi06 | EVQLLESGPGLVKPSETL SLTCTVSGGSISRYSWS WIRQPAGRGLEWIGRM YSSGGTNYNPSLESRVT MSLDTSKKQFSLKLSSV TAADTAVYYCAAASIDQ VWGTYRDAFDIWGQGT MVTVSS | 702 | AIRMTQSPSSLAASVGDR VTISCRAGQSISSFLHWY QQKVGKAPKLLIYDASSL QSGVPSRFSGSGSGTDFT LTISSLQPEDFAAYYCQQ SYENPLTFGGGTKVDIK | 704 |
| Omi08 | EVQLVESGAEVKRPGASV KVSCKASGYTFTNYFMHWV RQAPGQGLEWMGVINPSD GGASYPQKFQGRVTMTRD TSTSTVYMDLSSLRSEDTA VYSCARGAFDVSGSWYVP FDYWGQGTLVTVSS | 712 | QSVVTQPPSVSGAPGQRVT ISCTGSSSNIGAGYDVHWY QQLPGAAPKLLIYGNTNRP SGVPDRFSGSKSGTSASLAIT GLQAEDEADYYCQSYDITL SGSGYVFGTGTKVTVL | 714 |

-continued

| Antibody number: | Heavy chain Amino acid sequence | SEQ ID NO: | Light chain Amino acid sequence | SEQ ID NO: |
|---|---|---|---|---|
| Omi09 | QVQLVESGGGVVQPGRSL RLSCAASGFTFRTYAVHW VRQAPGKGPEWVAVISYD GSNKYYADSVKGRFTLSR DTSKNTLYLQMNSLRAED TAVYYCASRGDTVTTGDA FDIWGQGTMVTVSS | 722 | SYELTQPPSVSVSPGQTARIT CSGDALPKQYTYWYQQKPG QPPVLVIYKDSERPSGIPERF SGSSSGTTVTLTISGVQAEDE ADYYCQSTDSSATYPGNVVF GGGTKLTVL | 724 |
| Omi12 | EVQLVESGPEVKKPGTSVK VSCKASGFSFSMSAMQWV RRARGQRLEWIGWIVPGS GNANYAQKFQERVTITRDE STNTGYMELSSLRSEDTAVY YCAAPHCNKTNCYDAFDI WGQGTMVTVSS | 732 | AIRMTQSPGTLSLSPGERATL SCRASQSVRSSYLAWYQQKP GQAPRLLIYGASTRATGIPDR FSGSGSGTDFILTINRLEPEDL AVYYCQQFGSSPWTFGQGT KVDIK | 734 |
| Omi16 | EVQLVESGGGVVQPGGSL RLSCAASGIIVSANYMTWV RQAPGKGLEWVSVIYPGG STFYADSVKGRFTISRDNS KNTLYLQMNSLRVEDSAV YYCARDLELAGENDFWGQ GTLVTVSS | 742 | DVVMTQSPGTLALSPGERA TLSCRTSQSVSSNYLAWYQ QKPGQAPRLLIYGASSRAT GIPDRFSGSGSGTDFTLTIS RLEPEDFAVYYCQQFGSSP RYTFGQGTKVEIK | 744 |
| Omi17 | QVQLVESGGGVVQPGGSLR LSCAASGVTVSSNYMSWVR QAPGKGLEWVSVLYAGGST FYADSVKGRFTISRDNSKNT LYLQMNSLRAEDTAAYYC ARDLAVAGFLDSWGQGTL VTVSS | 752 | DIVMTQSPGTLSLSPGERATL SCRASQGVSSIYLAWYQQKP GQAPRLVLYGASSRATGIPD RFSGSGSGTDFTLTISRLEPE DFAVYYCQQYGSSPRYTFG QGTKVEIK | 754 |
| Omi18 | QVQLVESGGGLIQPGGSLR LSCAASGITVSSNYMTWV RQAPGKGLEWVSLLYAGG SAFYADSVKGRFTISRDNS KNTLYLLMNSLRVGDTAV YYCARDLQVYGMDVWGQ GTTVTVSS | 762 | SYELTQPPSVSVAPGQTARI TCGGNNDGAKSVHWYQQK PGQAPVLVVYDDSDRPSGI PERFSGSNSGNTATLTITRIE AGDEADYYCQVWDSSRDH VFGTGTKVTVL | 764 |
| Omi20 | EVQLVESGGGLVQPGGSLR LSCEASEITVSSNYMNWVRQ APGKGLEWVSVLFAGGTTY YADSVKGRFTISRDNSKNTL YLQMNTLRIEDTAIYYCARD LVAYGVDVWGQGTTVTVS S | 772 | AIQMTQSPSFLSASVGDRV TITCRASQGISGDLAWYQQ KPGKAPKLLIYAASTLQSG VPSRFSGSGSGTEFTLTISSL QPEDFATYYCQHLNSYPLT FGGGTKVEIK | 774 |
| Omi23 | QVQLQESGPGLVKSSQTLS LTCTVSGDSISRGGYYWS WIRQHPGKGLEWIGSIYYS GSTYYNPSLKSRFTISVDTS KNQFSLKLSSVTAADTAV YHCAREIGFLDYWGQGTL VTVSS | 782 | AIQMTQSPSSLSASVGDRVT ITCRASQAISNSLAWYQQK PGKAPKLLLYAASTLESGV PSRFSGSGSGTDFTLTISSLQ PEDFATYFCQQYYSTPPRTF GQGTKVDIK | 784 |
| Omi24 | QVQLVESGAEVKKPGSSVK VSCKASGGTFSSHGVIWVR QAPGQGLEWMGGIIPIFPTA NYAQKFQGRVTITADKPSNT AYMELSSLRSEDTAVYYCA RARGEHDSVWGSFHYYFD YWGQGTLVTVSS | 792 | RHWMTQSPATLSVSPGERAT LSCRASQSIGSNLAWYQQKP GQAPRLLIYGAATRATGIPA RFSGSGSGTEFTLTISSLQSED FAVYYCQQYNDWPPRTFGQ GTKVEIK | 794 |
| Omi25 | QVQLVESGGGLVQPGRSLR LSCAASGFTFDDYAMHWVR QVPGKGLEWVSGISWNSGSI VYADFVKGRFTIARDNAKN SLFLQMNSLRAEDTALYYC AKSTALRHQYYYGMDVWG QGTTVTVSS | 802 | AIQMTQSPSSLSASVGDRV TITCRTSQTISSYLNWYQQK PGKAPKLLIYDASSLQSGVP SRFSGSGYGTDFTLTISSLQ PEDFATYFCQQSYNTPYAF GQGTKVEIK | 804 |

-continued

| Antibody number: | Heavy chain | | Light chain | |
|---|---|---|---|---|
| | Amino acid sequence | SEQ ID NO: | Amino acid sequence | SEQ ID NO: |
| Omi26 | QVQLVQSGTEVKKPGASV KVSCKASDYTFTRFGIIWV RQAPGQGLEWMGQINPYN GNTDYAQKFQGRVTLTTD TSTNTAYMELRSLRSDDTA VYYCARSAGSPTGLDYWG QGTLVTVSS | 812 | QSVVTQPPSVSEAPRQRVTI SCSGSNSNIGNNAVNWYQ QLPGKAPKLLVYYDDLLPS GVSDRFSGSKSGTSASLAIS GLQSEDKADYYCAAWDDS LNALVFGGGTKLTVL | 814 |
| Omi27 | EVQLLESGGGLVQPGGSLR LSCVASGLTVSSNYMSWV RQAPGKGLEWVSIIYPGGT TYYADSVKGRFTISRDKS KNTLYLQMNSLRAEDTAV YYCARDLAVAGGMDVWG QGTTVTVSS | 822 | EIVMTQSPSSLSASVGDRVT ITCRASQGIGNDLGWYQQK PGKAPKVLIYAASNLQSGV PSRFSGSGSGTDFTLTISSLQ PEDFATYYCLQDSNYPYTF GQGTKVEIK | 824 |
| Omi28 | EVQLVESGGGLVQPGGSLR LSCAASGVIVSSNYMSWVR QAPGKGLQWVSVIYSGGST FYADSVKGRFTISRDNSKNT LYLQMNSLRAEDTAVYYC ARDLLEAGGTDYWGQGTL VTVSS | 832 | DVVMTQSPGTLSLSPGERA TLSCRASQFIGSSYLAWYQ QKPGQAPRLLIYGASNRAT GVPDRFSGSGSGTDFTLTIS RLEPEDFAVYYCQQYGSAP GTFGQGTKVEIK | 834 |
| Omi29 | QVQLVESGGGLVQPGGSL RLSCAASGLIVSRNYMSW VRQAPGKGLEWVSLIYAG GSTFYSDSVKGRFTISRHSS ENTLFLQMNSLRAEDTAV YYCARDLVHYGMDVWGQ GTTVTVSS | 842 | NFMLTQPASVSGSPGQSITI SCTGTSSDVGGYNYVSWY QQHPGKAPKLMIYDVSNRP SGVSNRFSGSNSGNTASLTI SGLQAEDEADYYCSSYTSG STWVFGGGTKLTVL | 844 |
| Omi30 | EVQLVESGAEVKKPGSSV KVSCKASGGTFSRYAISW VRQAPGQGLEWMGGIIPIF DATNYAQKFHDRVTITAD KSASTAYMELSSLRSDDTA VYYCARERTYCSGGTCYG GYFYYGMDVWGQGTTVT VSS | 852 | QSVLTQPPSASGTPGQRVTI SCSGSSSNIGGDIVNWYLQL PGTAPKLLIYSNNQRPSGVP DRFSGSRSGTSASLAISGLQS EDEGYYYCAAWDDSLNGQ VFGGGTKLTVL | 854 |
| Omi31 | EVQLVQSGAEVKKPGSSVK VSCKASGGTFSSYGISWVR QAPGLGLEWMGGVIPILSAK HYAQRFQGRVTITADKSTGT AYMELSSLRSEDTAVYYCA RDILHHDDLWGRFYYDGM DVWGQGTTVTVSS | 862 | QSVVTQPPSASGTPGQRVTI SCSGSSSDIGSNTVNWYQQ LPGTAPKLLIYTNNQRPSGV PDRFSGSKSGTSASLAITGL QSEDEADYFCAAWDESLN GRVFGGGTKLTVL | 864 |
| Omi32 | EVQLVESGG.VVQPGRSL RLSCAASGTFSNYGMHW VRQAPGKGLEWVAVYWY DGGNKFYADSVK.GRFTIS RDNSKNTLYLQMNSLRVE DTAVYYCARDTAPPDYW GQGTLVTVSS | 872 | AIRMTQSPGTLSLSPGERAT LSCRASQSISSSFLAWYQQ KPGQAPRLLIYGASSRATGI PDRFSGSGSGTDFTLTISRL EPEDFAVYYCQQYGTSPRL TFGGGTKVDIK | 874 |
| Omi33 | EVQLLESGGGVVQPGRSL RLSCAASGFKFSDYGMHW VRQAPGKGLEWVAVYWY DGGTKFYADSVKGRFTISR DNSKNTLYLQMSSLRVED TAVYYCARDTAPPDYWG QGTLVTVSS | 882 | EIVLTQSPGTLSLSPGERATL SCRASQSISSNFLAWYQQKP GQAPRLLIYGASSRATGIPDRF SGSGSGTDFTLTISRLEPEDF AVYYCQQYGTSPRLTFGGGT KVDIK | 884 |
| Omi34 | QVQLVQSGAEVKKPGSSV KVSCKASGGTFSSYGIRW VRQAPGQGLEWMGGIIPV FGATNYAQKFQDRVTITA DKSTATAYMELSSLKSDD TAVYFCARDALSASGWTG PFDSWGQGTLVTVSS | 892 | QSVLTQPPSVSGAPGQRVTIS CTGSSSNIGADYDVHWYQQ LPGAAPKLLIYGNNNRPSGV PDRFSGSKSGTSASLAITGLQ AEDEADYYCQSYDSSQNAF YVFGTGTKVTVL | 894 |

| | Heavy chain | | Light chain | |
|---|---|---|---|---|
| Antibody number: | Amino acid sequence | SEQ ID NO: | Amino acid sequence | SEQ ID NO: |
| Omi35 | QVQLVESGGGLVQPGRSLR LSCAASGFTFDDYAMHWV RQAPGKGLEWVSGSTWNS GTIDYADSVKGRFTISRDN AKNSLYLQMNSLRAEDTA LYYCAKDRFRKGCSSTGC YKENYGMDVWGQGTTVT VSS | 902 | QSVVTQPPSVSVAPGQTARIT CGGTNIGSKSVHWYQQKPGQ APVLVVYDDSDRPSGIPERFS GSNSGNTATLTITWVEAGDE ADYYCQVWDSSSDNVLFGG GTKLTVL | 904 |
| Omi36 | EVQLVESGGGVVQPGGSL RLSCAASGIIVSANYMTWV RQAPGKGLEWVSVIYPGG STFYADSVKGRFTISRDNS KNTLYLQMNSLRVEDSAV YYCARDLELAGENDYWG QGTLVTVSS | 912 | DIVMTQSPGTLSLSPGERATL SCRTSQSVSSNYLAWYQQKP GQAPRLLIYGASSRATGIPDR FSGSGSGTDFTLTISRLEPEDF AVYYCQQFGSSPRYTFGQGT KVEIK | 914 |
| Omi38 | QVQLVESGAEVKKPGSSV KVSCKASGGNFNMYTISW VRQAPGRGLEWMGRFIPIA NKANYAQNFPGRVTITAD KSTSTVYMELRSLTSDDTA VYYCARSGSYDAFDVWG QGTMVTVSS | 922 | AIRMTQSPSTLSASVGDRVT ITCRASQTINSWLAWYQQK PGKAPKLLIYDASNLESGVP SRFSGSGSGTEFTLTISSLQPD DFATYYCQQYESYSPITFGQ GTRLEIK | 924 |
| Omi39 | QVQLVESGGVVVQPGGSL RLSCAASGFSFDDYSMHW VRQAPGKGLEWVSVIYWD GVSKYYADSVKGRFTISRD NSKNSLYLQMNSLRTEDT AVYYCAKDSEDCSSTSCY MDVWGKGTTVTVSS | 932 | EIVLTQSPDSLAVSLGERAT INCKSSQNVLYSSNNKNYL AWYQQKPGQPPQLLIYWA STRESGVPDRFSGSGSGTDF TLTISSLQAEDVAVYYCHQ YYSTPFTFGPGTKVDIK | 934 |
| Omi41 | QVQLVQSGAEVKKPGASV KVSCKAAGYSFMNYGINW VRQAPGQGLEWMGWINT YNGNAKYAQKFQGRVTM TTDTSTSTAYMELRSLRSG DTAVYYCARDPFTGYDDV WGGDYWGQGTLVTVSS | 942 | AIQMTQSPDSLAVSLGERA TINCKSSQSVLYSSNNKNYL AWYQQKPGQPPKLVIYWA STRESGVPDRFSGSGSGTDF TLTISSLQAEDVAVYYCHQ YYSSPRTFGQGTKVEIK | 944 |
| Omi42 | EVQLLETGGGLVQPGRSLR LSCAASGFPFDDYAIHWVR LAPGKGLEWVSSISWDSGSI GYADSVKGRFTISRDNAKN SLYLQMNSLRAEDTALYYC AKGAFPGYSSGWYYGLDV WGQGATVTVSS | 952 | QSVVTQPPSASGSLGQSVTI SCTGTSSDVGGYNYVSWY QQHPGKAPKLMIFEVSKRP SGVPDRFSGSKSGNTASLT VSGLQAEDEADYYCSSYA GNKGVFGGGTKLTVL | 954 |

Nucleotide Sequence of Heavy Chain and Light Chain Variable Regions of Selected Antibodies

| | Heavy chain | | Light chain | |
|---|---|---|---|---|
| Antibody number: | Nucleotide Sequence | SEQ ID NO: | Nucleotide sequence | SEQ ID NO: |
| Omi02 | gaggtgcagctggtggagtctgggctga ggtgaagaagcctgggtcctcggtgaagg tctcctgcaaggcttctggaggcaccttcag cagctatgctatcaactgggtgcgacaggc ccctggacaagggcttgagtggatgggag ggatcatccctatctttcgtacgccgcactac gcacagaaattccagggcagagtcacgatt accgcggacgaatctacgggcacagccta catggagctgagcagcctgcgatctgaag acacgccgtgtattactgtgcgagccct | 681 | gtcatctggatgacccagtctccaggcaccct gtctttgtctccaggggaaagagccaccctctc ctgcagggccagtcagagtgttagcagcaccta cttagcctggtaccagcagaaacctggccagg ctcccaggctcctcatctatggtgcatccagcag ggccactggcatcccagacaggttcagtggc agtgggtctgggacagacttcactctcaccatc agcagactggaacctgaagattttgcagtgtat tactgtcagcactatggtagctcacctctcacct tcggccaagggacacgactggagattaaac | 683 |

-continued

| | Heavy chain | | Light chain | |
|---|---|---|---|---|
| Antibody number: | Nucleotide Sequence | SEQ ID NO: | Nucleotide sequence | SEQ ID NO: |
| | cttgtggtggtgactgcccccagtacttaaa atcatccaaactagactggtacttcgatctct ggggccgtggcaccctggtcaccgtctcct cag | | | |
| Omi03 | gaggtgcagctggtggagtctggaggaggc ttgatccagcctgggggtccctgagactct cctgtgcagcctctgagatcatcgtcagtagg aactacatgagctgggtccgccaggctcca gggaaggggctggagtgggtctcagttatt tatagcggtggtagcacgttctacgcagact ccgtgaagggccgattcaccatctccagag acaattccaagaacacgctgtatcttcaaatga acagcctgagagccgaggacacggccgtg tattactgtgcgagacctcgacgtagtgg gaggtactgactactgggggcagggaaccc tggtcaccgtctcctcag | 691 | gaaattgtgttgacacagtctccaggcaccctg tctttgtctccaggggaaagagccaccctctcc tgcagggccagtcagagtgttagcagcagcta cttagcctggtaccagcagaaacctggccag gctcccaggctcctcatctatggtgcatccagc agggccactggcatcccagacaggttcagtg gcagtgggtctgggacagacttcactctcacc atcagcagactggagcctgaagattttgcagt gtattactgtcagcagtatggtagctcaccagg gtacacttttggccaggggaccaaagtggata tcaaac | 693 |
| Omi06 | gaggtgcagctgttggagtcgggcccagg actggtgaagccttcggagaccctgtcct cacctgcaccgtctctggtggctccatcagc agatactcctggtcctggatccggcagccc gccgggaggggactgagtggatcgggc gtatgtatagcagtgggggcaccaactata accctccctcgagagtcgagtcaccatgtca cttgacacgtccaagaagcagttctccctga agctgagctctgtgaccgccgcggacacg gccgtgtattactgtgcggcggcttcaattga tcaagtatgggggacttatcgtgatgcttttga tatctgggtcaagggacaatggtcaccgtct cttcag | 701 | gccatccggatgacccagtctccatcctccctg gctgcatctgtaggagacagagtcaccatctct tgccgggcaggtcagagcattagcagttttttac attggtatcagcagaaagtagggaaagcccct aagctcctgatctatgatgcgtccagtttgcaaa gtggggtcccatcaaggttcagtggcagtgga ctgggacagatttcactctcaccatcagcagtc tgcaacctgaagatttgcagcttactactgtca acagagttacgaaaacccgcttactttcggcg agggaccaaagtggatatcaaac | 703 |
| Omi08 | gaagtgcagctggtggagtctggggctga ggtgaagaggcctggggcctcagtgaag gtttcctgcaaggcatctggatacaccttcac caactactttatgcactgggtgcgacaggcc cctgcaaaggcttgagtggatgggagtt atcaaccctagtgatggtggcgcaagctac ccacagaagttccagggcagagtcaccat gaccagggacacgtccacgagcacagtct acatggatctgagcagcctgagatctgagg acacggccgtctattcctgtgcgaggggg gcttttgatgttagcggcagctggtacgtcc cctttgactactggggccagggaactctgg tcaccgtctcctcag | 711 | cagtctgtcgtgacgcagccgccctcagtgtct ggggcccagggcagagggtcaccatctcct gcactgggagcagctccaacatcggggcaggt tatgatgtacactggtaccagcagcttccagga gcagcccccaaactcctcatctatgataacac caatcggccctcagggggtccctgaccgattctct ggctccaagtctggcacctccgcctcctggc catcactgggctccaggctgaggatgaggct gattattactgccagtcctatgacatcaccctga gtggttcggggatgtcttcggaactgggaccaa ggtcaccgtcctag | 713 |
| Omi09 | caggtgcagctggtggagtctgggggag gcgtggtccagcctggggaggtccctgag actctcctgtgcagcctctggattcaccttc aggacctatgctgtgcactgggtccgcca ggctccaggcaaggggctggagtgggt ggcagttatatcatatgatggaagtaataa atactacgagactccgttaagggccgatt caccctccagagacacttccaagaaca cgctgtatctgcaaatgaacagcctgaga gctgaggacacggctgtgtattactgtgc gagcagaggggacacggtgactacagg tgacgcttttgatatctggggccaagggac aatggtcaccgtctcttcag | 721 | tcctatgagctgacacagccaccctcggtgtc agtgtcccaggacagacggccaggatcacc tgctctggagatgcattgccaaagcaatatactt attggtaccagcagaagccaggccagccccc tgtgctggtgatatataaagacagtgagaggc cctcagggatccctgagcgattctctggctcca gctcagggacaacagtcacgttgaccatcagt ggagtccaggcagaagatgaggctgactatta ctgtcaatcaacagacagcagtgctacttatcc gggaaatggttttcggcggagggaccaagt tgaccgtcctag | 723 |
| Omi12 | gaggtgcagctggtggagtctgggcctg aggtgaagaagcctggggacctcagtgaag gtctcctgcaaggcgtctggattcagtttta gtatgtctgctatgcagtgggtgcgacggg ctcgtggacaacgccttgagtggataggat ggatcgtccctggcagtggtaacgcaaact acgcgcagaagtttcaggaaagagtcacc attacagggacgagcctcacaaacacag gttatatggagttgagcagcctgagatcc gaggacacggccgtgtattattgtgcggc ccctcattgtaataagaccaactgctatgat gcttttgatatctggggccaagggacaat ggtcaccgtctcttcag | 731 | gccatccggatgacccagtctccaggcaccct gtctttgtctccaggggaaagagccaccctctc ctgcagggccagtcagagcgttaggacagtt acttagcctggtaccagcagaaacctggccag gctcccaggctcctcatctatggtgcatccacc agggccactggcatcccagacaggttcagtg gcagtgggtctgggacagacttcattctcacca tcaacagactggagcctgaagatcttgcagtct attactgtcagcagtttggtagctcaccatggac gttcggccaagggaccaaagtggatatcaaac | 733 |

-continued

| Antibody number: | Heavy chain | | Light chain | |
|---|---|---|---|---|
| | Nucleotide Sequence | SEQ ID NO: | Nucleotide sequence | SEQ ID NO: |
| Omi16 | gaggtgcagctggtggagtctgggggag gtgtggtccagcctggggggtccctgaga ctctcctgtgcagcctctggaatcatagtca gtgccaactacatgacctgggtccgccag ctccaggaaggggctggaatgggtctca gttatttatcccggtggtagcacattctacgc ggactccgtgaagggccgattcaccatctc cagagacaactccaagaacacactgtatctt caaatgaacagcctgagagttgaggactcg gctgtgtattactgtgcgagagatttggagct ggctggtttcaatgacttctgggtcaggga accctggtcaccgtctcctcag | 741 | gatgttgtgatgactcagtctccaggcaccctgg ctttgtctccaggggaaagagccaccctctcctgc aggaccagccagagtgttagcagcaactactta gcctggtaccagcagaaacctggccaggctcc caggctcctcatctatggtgcatccagcagggcc actggcatcccagacaggttcagtggcagtggg tctgggacagacttcactctcaccatcagcagac tggagcctgaagattttgcagtgtattactgtcag cagtttggtagttcacctcggtacacttttggcca ggggaccaaggtggagatcaaac | 743 |
| Omi17 | caggtgcagctggtggagtctgggggag gtgtggtccagcctgggggggtccctgag actctcctgtgcagcctctggagtcaccgt cagtgcaactacatgagctgggtccgcc aggctccaggaaggggctggagtggg tctcagttcttatgccggtggtagcacatt ctacgcagactccgtgaagggccgattca ccatctccagagacaattccaagaacacgc tgtatcttcaaatgaacagcctgagagctga ggacacggctgcgtattactgtgcgagagat ttggcagtggctggtttccttgactcctggg gccagggaaccctggtcaccgtctcctcag | 751 | gatattgtgatgacccagtctccgggcaccctg tctttgtctccaggggaaagagccaccctctcc tgcagggccagtcagggtgttagcagcatcta cttagcctggtaccagcagaaacctggccagg ctcccaggctcgtcctctatggcgcatccagta ggggccactggcatcccagacaggttcagtgg cagtgggtctgggacagacttcactctcaccat cagcagactggagcctgaagattttgcagtgt attactgtcagcagtatggtagctcacctcggt acacttttggccaggggaccaaggtggagatc aaac | 753 |
| Omi18 | caggtgcagctggtggagtctggaggag gcttgatccagccgggggggtccctgaga ctctcctgtgcagcctctggagtcaccgtc agtagcaactacatgacctgggtccgcca ggctccagggaaggggctggagtgggt ctcacttctttatgccggtggtagcgcattc tatgctgactccgtgaagggccgattcac catctccagagacaattccaagaacacgct gtatcttctaatgaacagcctgagagtcgg cgacacggccgtttattactgtgcgagag atctccaggtctacggtatggacgtctggg gccaagggaccacggtcaccgtctcctca | 761 | tcctatgagctgactcagccaccctcggtgtca gtggccccaggacagacggccaggattacctg tgggggaaacaacgatggagctaaaagtgtg cactggtaccagcagaagccaggccaggcc cctgtgctggtcgtctatgatgatagcgaccgg ccctcagggatccctgaacgattctctggctcc aactctgggaacacggccaccctgaccatca ccaggatcgaagccggggatgaggccgact attactgtcaggtctgggatagtagtcgtgatca tgtcttcggaactgggaccaaggtcaccgtcct gg | 763 |
| Omi20 | gaggtgcagctggtggagtctgggggag gcttggtccagcctgggggggtccctgag gctctcctgtgaagcctctgaaataaccgt cagtagcaactacatgaattgggtccgcca ggctccagggaaggggctggagtgggt ctcagttcttttttgccggtggtactacatact acgcagactccgtgaagggccgattcac catctccagagacaattccaagaacacac tgtatcttcaaatgaacaccctgagaattga ggacacggctatttattactgtgcgagaga tctcgtcgcatacggtgtggacgtctggg gccaagggaccacggtcaccgtctcctca | 771 | gccatccagatgacccagtctccatcctcctg tctgcatctgtaggagacagagtcaccatcact tgccgggccagtcagggcattagcggtgattt agcctggtatcagcaaaaaccagggaaagcc cctaagctcctgatctatgctgcatccactttgc aaagtggggtcccatcaaggttcagcggcagt ggatctgggacagaattcactctcacaatcagc agcctgcagcctgaagattttgcaacttattact gtcaacaccttaatagttacccctctcacgttcgg cggagggaccaaggtggaaatcaaac | 773 |
| Omi23 | caggtacagctgcaggagtcgggcccag gactggtgaagtcttcacagaccctgtccc tcacgtgcactgtctctggtgactccatca gccgtggtggttactactggagctggatcc gccagcacccagggaagggcctggagt ggattgggtccatctattacagtgggagca cctactacaacccgtccctcaagagtcgatt taccatatcagtagacacgtctaagaacca gttctccctgaagctgagctctgtgactgc cgcggacacggccgtgtatcactgtgcga gagaaattggttccttgactactggggcc agggaaccctggtcaccgtctcctcag | 781 | gccatccagatgacccagtctccatcctcccctg tctgcatctgtaggagacagagtcaccatcact tgccgggcgagtcaggccattagcaattcttta gcctggtatcagcagaaaccagggaaagccc ctaagctcctactctatgctgcatccacattgga aagtggggtcccatccaggttcagtggcagtg gatctgggacggatttcactctcaccatcagca gcctgcagcctgaagattttgcaacttatttctgt cagcagtactatagtacccctccgaggacgtt cggccaagggaccaaagtggatatcaaac | 783 |
| Omi24 | caggtgcagctggtggagtctggggctg aggtgaagaagcctggggcctcggtgaa ggtctcctgcaaggcttctggaggcacctt cagcagccatggtgtcatctgggtgcgac aggcccctggacaagggcttgagtggat gggagggatcatccccatctttcccacag caaactacgcacagaaattccagggcag | 791 | cgtcattggatgacccagtctccagccaccct gtctgtgtctccaggggaaagagccaccctct cctgcagggccagtcaaagtattggcagcaa cttagcctggtaccagcagaaacctggtcagg ctcccaggctcctcatctatggtgcagccacca gggccactggtatcccagccaggttcagtggc agtgggtctgggacagagttcactctcaccatc | 793 |

-continued

| Antibody number: | Heavy chain | | Light chain | |
|---|---|---|---|---|
| | Nucleotide Sequence | SEQ ID NO: | Nucleotide sequence | SEQ ID NO: |
| | agtcacaattaccgcggacaaaccctcca acacagcctacatggagctgagcagcct gagatctgaggacacggccgtatattact gtgcgagggcaagggagaacatgattc cgtttggggaagttttcattactatttgacta ctggggccagggaaccctggtcaccgtct cctcag | | agcagcctgcagtctgaagattttgcagtttact actgtcagcagtataatgactggcctccgagga cgttcggccaagggaccaaggtggaaatcaa ac | |
| Omi25 | caggtgcagctggtggagtctgggggag gcttggtacagcctggcaggtccctgaga ctctcctgtgcagcctctggattcacgtttgat gattatgccatgcactgggtccggcaagtt ccagggaagggcctggagtgggtctcag gaattagttggaacagtggtagcatagtct atgcggactttgtgaagggccgattcacc atcgccagagacaacgccaagaactccc tgtttctgcaaatgaacagtctgagagctg aggacacggccttgtattactgtgcaaaaa gtacggctctacgtcatcagtactactacg gtatggacgtctggggccaagggaccac ggtcaccgtctcctca | 801 | gccatccagatgacccagtctccatcctccctg tctgcatctgtaggagacagagtcaccatcact tgccggacaagtcagaccattagcagctattta aattggtatcagcagaaaccagggaaagccc ctaagctcctgatatatgacgcatccagtttgca aagtgggggtcccatcaaggttcagtggcagtg gatatgggacagatttcactctcaccatcagca gtctgcaacctgaagattttgcaacttacttctgt caacagagttacaataccccgtacgcttttggc cagggggaccaaggtggagatcaaac | 803 |
| Omi26 | caggttcagctggtgcagtctggcactga ggtgaagaagcctggggcctcagtgaaggt ctcctgcaaggcttctgattacaccttttacca ggttttggtatcatctgggtgcgacaggcc cctggacaagggcttgagtggatgggac agatcaaccttacaatggtaacacagact atgcacagaagttccagggcagagtcac cttgaccacagacacatccacgaacaca gcctacatggaactgaggagcctgagatc tgacgacacggccgtgtattattgtgcgag gtccgctgggagcccaccggccttgact actggggccagggaaccctggtcaccgt ctcctcag | 811 | cagtctgtcgtgacgcagccaccctcggtgtc tgaagccccaggcagagggtcaccatctcc tgttctggaagcaactccaacatcggaaataa tgctgtaaactggtaccagcagctcccagga aaggctcccaaactcctcgtctattatgatgat ctgctgccctcaggggtctctgaccgattctct ggctccaagtctggcacctcagcctccctgg ccatcagtgggctccagtctgaggataaggc tgattattactgtgcagcatgggatgacagcct gaatgccttggtgttcggcggagggaccaag ctgaccgtcctag | 813 |
| Omi27 | gaagtgcagctgttggagtctgggggag gcttggtccagcctgggggggtccctgaga ctctcctgtgtagcctctggactcaccgtca gtagcaactacatgagctgggtccgccaag gctccagggaaggggctggagtgggtct caattatttatcccggtggtaccacatacta cgcagactccgtgaagggcagattcacc acctccagagacaaatccaagaacacgct gtatcttcaaatgaacagcctgagagccg aggacacggctgtgtattactgtgcgaga gatctggcagtggctgggggtatggacgt ctggggccaagggaccacggtcaccgtc tcctca | 821 | gaaatagtgatgacgcagtctccatcctccctg tctgcatctgtaggagacagagttaccatcactt gccgggcaagtcagggcattggaaatgattta gggtggtatcagcagaaaccagggaaagccc ctaaagtcctgatttatgctgcatccaatttacaa agtgggggtcccatcaaggttcagcggcagtg gatctggcacagatttcactctcaccatcagca gcctgcagcctgaagattttgcaacttattactg tctacaagattccaattatccctacacttttggcc aggggaccaaggtggagatcaaac | 823 |
| Omi28 | gaagtgcagctggtggagtctgggggagg cttggtccagcctggggggtccctgagact ctcctgtgcagcctctggagtcatcgtcagt agcaactacatgagctgggtccgccaggct ccagggaaggggctgcaatgggtctcagtt atttatagcggtggtagcactttctacgcag actccgtgaagggcagattcaccatctcca gagacaattccaagaacacgttgtatcttca aatgaacagcctgagagccgaggacacg gctgtgtattactgtgcgagagatttgttaga ggcaggcgaactgactactggggccag ggaaccctggtcaccgtctcctcag | 831 | gatgttgtgatgactcagtctccaggcaccctg tctttgtctccaggggaaagagccaccctctcc tgcagggccagtcagtttattggcagctcctac ttagcctggtaccagcagaaacctggccaggc tcccaggctcctcatctatggtgcatccaacag ggccactggcgtcccagacaggttcagtggc agtgggtctgggacagacttcactctcaccatc agcagactggagcctgaagattttgcagtgtat tactgtcagcagtatgggagtgcacctgggac gttcggccaagggaccaaggtggaaatcaaac | 833 |
| Omi29 | caggtgcagctggtggagtctggaggagg cttggtccagcctgggggggtccctgagact ctcctgtcagcctctggattaatcgtcagta ggaactacatgagctgggtccgccaggct ccagggaaggggctggagtgggtctcact tatttatgccggtggtagcacattctactcag actccgtgaagggccgattcaccatctcca gacacagttccgagaacacgctgtttcttca | 841 | aattttatgctgactcagcctgcctccgtgtctg ggtctcctggacagtcgatcaccatctcctgca ctggaaccagcagtgacgttggtggttataact atgtctcctggtaccaacagcacccaggcaaa gcccccaaactcatgatttatgatgtcagtaatc ggccctcaggggtttctaatcgcttctctggctc caactctggcaacacggcctcctcaccatct ctgggctccaggctgaggacgaggctgattat | 843 |

-continued

| | Heavy chain | | Light chain | |
|---|---|---|---|---|
| Antibody number: | Nucleotide Sequence | SEQ ID NO: | Nucleotide sequence | SEQ ID NO: |
| | aatgaacagcctgagagctgaggacacgg ctgtgtattattgtgcgagagatctagtccac tacggcatggacgtctggggccaagggac cacggtcaccgtctcctca | | tactgcagctcatatacaagcggcagcacttgg gtgttcggcggagggaccaagctgaccgtcc tag | |
| Omi30 | gaagtgcagctggtggagtctgggctg aggtgaagaagcctgggtcctcagtgaa ggtctcctgcaaggcttctggaggcacctt cagcaggtatgctatcagctgggtgcgac aggcccctggacaaggacttgagtggat gggagggatcatccctatctttgatgcaac aaactacgcacagaagttccatgacagag tcaccattaccgcggacaaatccgcgagc acagcctacatggaactgagcagcctga gatctgacgacacggccgtgtattactgtg cgagagaacggacatattgtagtggtggt acttgctacggaggatacttctactacggt atggacgtctggggccaaggaaccacgg tcaccgtctcctca | 851 | cagtctgtgctgactcagccaccctcagcgtct gggaccccgggcagagggtcaccatctcttt gttctggaagcagctccaacatcggaggcgat attgtaaactggtacctccagctcccagggacg gccccccaaactcctcatttatagtaataatcagc ggccctcaggcgtccctgaccgattctctgc tccaggtctggcacctcagcctccctggccat cagtgggctccagtctgaggatgagggttatt attactgtgcagcatgggatgacagcctgaatg gtcaagtgttcggcggagggaccaagctgac cgtcctag | 853 |
| Omi31 | gaggtgcagctggtgcagtctgggctg aggtgaagaagcctgggtcctcggtgaa ggtctcctgcaaggcttctggaggcacctt cagtagctatggtatcagctgggtgcgac aggcccctggactagggcttgagtggatg gggggggtcatccctatcctaagtgcaaa acactacgcgcagcggttccaggggcaga gtcacgatcaccgcggacaagtccacgg gcacagcctacatggagctgagcagcct gagatctgaggacacggccgtatactact gtgcgagagatatccttcatcatgacgacc tttgggggaggttctactacgacggtatgg acgtctggggccaagggaccacggtcac cgtctcctca | 861 | cagtctgtcgtgacgcagccaccctcagcgtct gggaccccgggcagagggtcaccatctcttgt tctggaagcagctccgacatcggaagtaatactgt aaactggtaccagcagctcccaggaacggccc ccaaactcctcatctatactaataatcagcggcc ctcaggggtccctgaccgattctctggctccaag tctgccacctcagcctccctggccatcactgggct ccagtctgaggatgaggctgattatttctgtgcag catgggatgaaagcctgaatggtcgagtgttcgg cggagggaccaagctgaccgtcctag | 863 |
| Omi32 | gaagtgcaactggtggagtctgggggag gcgtggtccagcctggggaggtccctgag actctcctgtgcagcgtctggattcaccttc agtaactatggcatgcactgggtccgcca ggctccaggcaagggactggagtgggtg gcagtttattggtatgatggaggtaataaat tctatgcagactccgtgaagggccgattc accatctccagagacaattccaagaatac gttgtatctgcaaatgaacagcctgagagt cgaggacacggctgtttattactgtgcgag agatacggctcctccggactactggggcc agggaaccctggtcaccgtctcctcag | 871 | gccatccggatgacccagtctccaggcaccct gtctttgtctccaggggaaagagccaccctctc ctgcagggccagtcagagtattagtagcagct tcttagcctggtaccagcagaaacctggccag gctcccaggctcctcatctatggtgcatccagc agggccactggcatcccagacaggttcagtg gcagtgggtctgggacagacttcactctcacc atcagcagactggagcctgaagattttgcagt gtattactgtcagcagtatggtacctcaccaag gctcactttcggcggagggaccaaagtggata tcaaac | 873 |
| Omi33 | gaggtgcagctgttggagtctgggggag gcgtggtccagcctggaaggtccctgag actctcctgtgcagcgtctggattcaaattc agtgactatggcatgcactgggtccgcca ggctccaggcaaggggctggagtgggt ggcagtttattggtatgatggaggtactaa attctatgcagactccgtgaagggccgatt caccatctccagagacaattccaagaata cgttgtatctgcaaatgagcagcctgaga gtcgaggacacggctgttttattactgtgcg agagatacggctcctccggactactggg gccagggaaccctggtcaccgtctcctcag | 881 | gaaattgtgttgacgcagtctccaggcaccct gtctttgtctccaggggaaagagccaccctctc ctgcagggccagtcagagtattagtagcaactt cttagcctggtaccagcagaaacctggccag gctcccaggctcctcatctatggtgcatccagca gggccactggcatcccagacaggttcagtgg cagtgggtctgggacagacttcactctcaccat cagcagactggagcctgaagattttgcagtgt attactgtcagcagtatggtacctcaccaaggc tcactttcggcggagggaccaaagtggatatc aaac | 883 |
| Omi34 | caggttcagctggtgcagtctggggctgag gtgaagaagcctgggtcctcggtgaaggt ctcctgcaaggcttctggaggcaccttcag cagtatggtatcaggtgggtgcgacaggc ccctggacaagggcttgagtggatgggag ggatcatcccgtgtttggtgcaacaaacta cgcacagaagttccaggacagagtcacaa ttaccgcggacaaatccacgccacagcct | 891 | cagtctgtgttgacgcagccgccctcagtgtct ggggccccgggcagagggtcaccatctcct gcactgggagcagctccaacatcggggcaga ttatgatgtacactggtaccagcaacttccagg agcagcccccaaactcctcatctatggtaacaa caaccgggcctcagggggtccctgaccgattct ccggctccaagtctggcacctcagcctccctg gccatcactgggctccaggctgaggatgagg | 893 |

| | Heavy chain | | Light chain | |
|---|---|---|---|---|
| Antibody number: | Nucleotide Sequence | SEQ ID NO: | Nucleotide sequence | SEQ ID NO: |
| | acatggaattgagtagcctgaaatctgacg acacggccgtgtattttgtgcgagagatgc ccttagtgccagtggctggacgggccctt tgactcgtggggccagggaaccctggtca ccgtctcctca | | ctgattattactgccagtcctatgacagcagcc agaatgctttctatgtcttcggaactgggaccaa ggtcaccgtcctag | |
| Omi35 | caggtgcagctggtggagtctggggagg cttggtacagcctggcaggtccctgagact ctcctgtgcagcctctggattcacctttgatg attatgccatgcactgggtccggcaagctc cagggaaggcctggagtgggtctcagg aagtacttggaatagtggtaccatagactat gcggactctgtgaagggccgattccatc tccagagacaacgccaagaactccctgtat ctgcaaatgaacagtctgagagctgaggac acggccttgtattactgtgcaaaagataggt ttcgtaaaggttgtagtagtaccggctgctat aaggagaactacggtatggacgtctgggg ccaagggaccacggtcaccgtctcctca | 901 | cagtctgtggtgactcagccaccctcggtgtca gtggccccaggacagacggccaggattacctg tgaggaaccaacattggaagtaaaagtgtcc actggtaccagcagaagccaggccaggccc ctgtgctggtcgtctatgatgatagcgaccggc cctcagggatccctgagcgattctctggctcca actctgggaacacggccaccctgaccatcac ctgggtcgaagccggggatgaggccgactat tactgtcaggtgtgggatagtagtagtgataat gtgctattcggcggagggaccaagctgaccg tcctag | 903 |
| Omi36 | gaggtgcagctggtggagtctgggggag gtgtggtccagcctgggggtccctgag actctcctgtgcagcctctggaatcatagtc agtgccaactacatgacctgggtccgcca ggctccagggaagggactggaatgggtc tcagttatttaccccggtggtagcacattct acgcggactccgtgaagggccgattcac catctccagagacaactccaagaacacgt tgtatcttcaaatgaacagcctgagagttg aggactcggctgtgtattactgtgcgaga gatttggagctggctggtttcaatgactact ggggccagggaaccctggtcaccgtctc ctcag | 911 | gatattgtgatgactcagtctccaggcaccctg tctttgtctccaggggaaagagccaccctctcc tgcaggaccagtcagagtgttagcagcaacta cttagcctggtaccagcagaaacctggccagg ctcccaggctcctcatctatggtgcatccagca gggccactggcatcccagacaggttcagtgg cagtgggtctgggacagacttcactctcaccat cagcagactggagcctgaagattttgcagtgt attactgtcagcagtttggtagttcacctcggta cacttttggccaggggaccaaggtggagatca aac | 913 |
| Omi38 | caggtgcagctggtggagtctggggctga ggtgaagaagcctgggtcctcggtgaagg tcttcctgcaaggcttctggaggaaacttcaa catgtatactatcagttgggtgcgacaggcc cctggacgaggacttgagtggatgggaag gttcatccctatcgctaataaagcaaactac gcacagaactttccgggcagagtcaccatt accgcggacaaatccactagcacagtctac atggagctgagaagcctgacatctgacgac acggccgtgtattactgtgcgagaagtggg agctacgatgcttttgatgtgtgggggccaag ggacaatggtcaccgtctcttcag | 921 | gccatccggatgacccagtctccttccaccctg tctgcatctgtaggagacagagtcaccatcact tgccggggcagtcagactattaatagttggttg gcctggtatcagcagaaacccgggaaagccc taagctcctgatctatgatgcctccaatttggaa agtggggtcccatcaaggttcagcggcagtg gatctgggacagaattcactctcaccatcagca gcctgcagcctgatgattttgcaacttattactgc caacagtatgaaagttattctccgatcaccttcg gccaagggacgactggagattaaac | 923 |
| Omi39 | caggtgcagctggtggagtctggggag tcgtggtacagcctgggggggtccctgaga ctctcctgtgcagcctctggattcagctttg atgattatagcatgcactgggtccgtcaag ctccggggaagggtctggagtgggtctct gtcatttactgggatggtgttagcaaatact atgcagactctgtgaagggccgattcacc atctccagagacaacagcaaaaactccct gtatttgcaaatgaacagtctgagaactga ggacaccgccgtatattactgtgcaaaag atagtgaggattgtagtagtaccagctgct acatggacgtctggggcaaagggaccac ggtcaccgtctcctca | 931 | gaaattgtgttgacacagtctccagactccctg gctgtgtctctgggcgagagggccaccatca actgcaagtccagccagaatgttttatacagctc caacaataagaattacttagcttggtaccagcag aaaccaggacagcctcctcaactactcatttac tgggcatctacccggggaatccggggtccctg accgattcagtggcagcgggtctgggacaga tttcactctcaccatcagcagcctgcaggctga agatgtggcagtttattactgtcaccaatattata gtactccattcactttcggccctgggaccaaag tggatatcaaac | 933 |
| Omi41 | caggttcagctggtgcagtctggagctga ggtgaagaagcctggggcctcagtgaagg tctcctgcaaggctgctggttacagctttat gaactacggtatcaactgggtgcgacag gcccctggacaagggcttgagtggatgg gatggatcaacacttacaatggtaacgca agtatgcacagaagttccaggccgagt caccatgaccacagacacatccacgagc | 941 | gccatccagatgacccagtctccagactccct ggctgtgtctctgggcgagagggccaccatc aactgcaagtccagccagagtgtttatacagc tccaacaataagaattacttagcttggtaccag cagaaaccaggacagcctcctaagctggtcatt tactgggcatctacccggggaatccggggtccct gaccgattcagtggcagcgggtctgggacaga tttcactctcaccatcagcagcctgcaggctga | 943 |

| | Heavy chain | | Light chain | |
|---|---|---|---|---|
| Antibody number: | Nucleotide Sequence | SEQ ID NO: | Nucleotide sequence | SEQ ID NO: |
| | acagcctacatggagctgaggagcctga gatcgggcgacacggccgtgtattactgt gcgagggacccttttcaccggttatgatga cgtttggggggggactactggggccagg gaaccctggtcaccgtctcctcag | | agatgtggcagtttattactgtcaccaatattata gtagtcctcgcacttttggccaggggaccaaggt ggaaatcaaac | |
| Omi42 | gaggtgcagctgttggagactgggggag gcttggttcagcccggcaggtccctgaga ctctcctgtgcagcctcgggattcccctttg atgattatgccatccactgggtccggctag ctccaggaagggcctggagtgggtctc aagtattagttgggatagtggtagcatagg ctatgcggactctgtgaagggccggttca ccatctccagagacaacgccaagaactc cctgtatctgcaaatgaacagtctgagag ctgaggacacggccttgtattactgtgcaa aggggccttcccgggtatagcagtgg ctggtactacggttggacgtctggggcc aagggccacggtcaccgtctcctca | 951 | cagtctgtcgtgacgcagcctccctccgcgtc ggggtctcttggacagtcagtcaccatctcctg cactggaaccagcagtgacgttggtggttaca actatgtctcttggtaccaacaacacccaggc aaagcccccaaactcatgatttttgaggtcagt aagcggccctcaggggtccctgatcgcttctc tggctccaagtctggcaacacggcctccctga ccgtctctgggctccaggctgaggatgaggc tgattattactgcagctcatatgcaggcaacaaa ggggtcttcggcggagggaccaaattgaccgtc ctcg | 952 |

Amino Acid Sequences of CDRs

| | Heavy Chain CDR | | | | | |
|---|---|---|---|---|---|---|
| Antibody number: | CDR1-IMGT | SEQ ID NO. | CDR2-IMGT | SEQ ID NO. | CDR3-IMGT | SEQ ID NO. |
| Omi02 | GGTFSSYA | 685 | IIPIFRTP | 686 | ASPSCGGDCPQYLKSSKLDWYFDL | 687 |
| Omi03 | EIIVSRNY | 695 | IYSGGST | 696 | ARDLDVVGGTDY | 697 |
| Omi06 | GGSISRYS | 705 | MYSSGGT | 706 | AAASIDQVWGTYRDAFDI | 707 |
| Omi08 | GYTFTNYF | 715 | INPSDGGA | 716 | ARGAFDVSGSWYVPFDY | 717 |
| Omi09 | GFTFRTYA | 725 | ISYDGSNK | 726 | ASRGDTVTTGDAFDI | 727 |
| Omi12 | GFSFSMSA | 735 | IVPGSGNA | 736 | AAPHCNKTNCYDAFDI | 737 |
| Omi16 | GIIVSANY | 745 | IYPGGST | 746 | ARDLELAGFNDF | 747 |
| Omi17 | GVTVSSNY | 755 | LYAGGST | 756 | ARDLAVAGFLDS | 757 |
| Omi18 | GITVSSNY | 765 | LYAGGSA | 766 | ARDLQVYGMDV | 767 |
| Omi20 | EITVSSNY | 775 | LFAGGTT | 776 | ARDLVAYGVDV | 777 |
| Omi23 | GDSISRGGYY | 785 | IYYSGST | 786 | AREIGFLDY | 787 |
| Omi24 | GGTFSSHG | 795 | IIPIFPTA | 796 | ARARGEHDSVWGSFHYYFDY | 797 |
| Omi25 | GFTFDDYA | 805 | ISWNSGSI | 806 | AKSTALRHQYYYGMDV | 807 |
| Omi26 | DYTFTRFG | 815 | INPYNGNT | 816 | ARSAGSPTGLDY | 817 |
| Omi27 | GLTVSSNY | 825 | IYPGGTT | 826 | ARDLAVAGGMDV | 827 |
| Omi28 | GVIVSSNY | 835 | IYSGGST | 836 | ARDLLEAGGTDY | 837 |
| Omi29 | GLIVSRNY | 845 | IYAGGST | 846 | ARDLVHYGMDV | 847 |

-continued

| Heavy Chain CDR | | | | | | |
|---|---|---|---|---|---|---|
| Antibody number: | CDR1-IMGT | SEQ ID NO. | CDR2-IMGT | SEQ ID NO. | CDR3-IMGT | SEQ ID NO. |
| Omi30 | GGTFSRYA | 855 | IIPIFDAT | 856 | ARERTYCSGGTCY GGYFYYGMDV | 857 |
| Omi31 | GGTFSSYG | 865 | VIPILSAK | 866 | ARDILHHDDLWGR FYYDGMDV | 867 |
| Omi32 | GFTFSNYG | 875 | YWYDGGNK | 876 | ARDTAPPDY | 877 |
| Omi33 | GFKFSDYG | 885 | YWYDGGTK | 886 | ARDTAPPDY | 887 |
| Omi34 | GGTFSSYG | 895 | IIPVFGAT | 896 | ARDALSASGWTGP FDS | 897 |
| Omi35 | GFTFDDYA | 905 | STWNSGTI | 906 | AKDRFRKGCSSTG CYKENYGMDV | 907 |
| Omi36 | GIIVSANY | 915 | IYPGGST | 916 | ARDLELAGFNDY | 917 |
| Omi38 | GGNFNMYT | 925 | FIPIANKA | 926 | ARSGSYDAFDV | 927 |
| Omi39 | GFSFDDYS | 935 | IYWDGVSK | 936 | AKDSEDCSSTSCY MDV | 937 |
| Omi41 | GYSFMNYG | 945 | INTYNGNA | 946 | ARDPFTGYDDVWG GDY | 947 |
| Omi42 | GFPFDDYA | 955 | ISWDSGSI | 956 | AKGAFPGYSSGWY YGLDV | 957 |

| Light Chain CDR | | | | | | |
|---|---|---|---|---|---|---|
| Antibody number: | CDR1-IMGT | SEQ ID NO. | CDR2-IMGT | SEQ ID NO. | CDR3-IMGT | SEQ ID NO. |
| Omi02 | QSVSSTY | 688 | GAS | | QHYGSSPLT | 690 |
| Omi03 | QSVSSSY | 698 | GAS | | QQYGSSPGYT | 700 |
| Omi06 | QSISSF | 708 | DAS | | QQSYENPLT | 710 |
| Omi08 | SSNIGAGYD | 718 | GNT | | QSYDITLSGSGYV | 720 |
| Omi09 | ALPKQY | 728 | KDS | | QSTDSSATYPGNVV | 730 |
| Omi12 | QSVRSSY | 738 | GAS | | QQFGSSPWT | 740 |
| Omi16 | QSVSSNY | 748 | GAS | | QQFGSSPRYT | 750 |
| Omi17 | QGVSSIY | 758 | GAS | | QQYGSSPRYT | 760 |
| Omi18 | NDGAKS | 768 | DDS | | QVWDSSRDHV | 770 |
| Omi20 | QGISGD | 778 | AAS | | QHLNSYPLT | 780 |
| Omi23 | QAISNS | 788 | AAS | | QQYYSTPPRT | 790 |
| Omi24 | QSIGSN | 798 | GAA | | QQYNDWPPRT | 800 |
| Omi25 | QTISSY | 808 | DAS | | QQSYNTPYA | 810 |
| Omi26 | NSNIGNNA | 818 | YDD | | AAWDDSLNALV | 820 |
| Omi27 | QGIGND | 828 | AAS | | LQDSNYPYT | 830 |
| Omi28 | QFIGSSY | 838 | GAS | | QQYGSAPGT | 840 |
| Omi29 | SSDVGGYNY | 848 | DVS | | SSYTSGSTWV | 850 |
| Omi30 | SSNIGGDI | 858 | SNN | | AAWDDSLNGQV | 860 |

| Light Chain CDR | | | | | |
|---|---|---|---|---|---|
| Antibody number: | CDR1-IMGT | SEQ ID NO. | CDR2-IMGT | SEQ ID NO. | CDR3-IMGT | SEQ ID NO. |
| Omi31 | SSDIGSNT | 868 | TNN | | AAWDESLNGRV | 870 |
| Omi32 | QSISSSF | 878 | GAS | | QQYGTSPRLT | 880 |
| Omi33 | QSISSNF | 888 | GAS | | QQYGTSPRLT | 890 |
| Omi34 | SSNIGADYD | 898 | GNN | | QSYDSSQNAFYV | 900 |
| Omi35 | NIGSKS | 908 | DDS | | QVWDSSSDNVL | 910 |
| Omi36 | QSVSSNY | 918 | GAS | | QQFGSSPRYT | 920 |
| Omi38 | QTINSW | 928 | DAS | | QQYESYSPIT | 930 |
| Omi39 | QNVLYSSNNKNY | 938 | WAS | | HQYYSTPFT | 940 |
| Omi41 | QSVLYSSNNKNY | 948 | WAS | | HQYYSSPRT | 950 |
| Omi42 | SSDVGGYNY | 958 | EVS | | SSYAGNKGV | 960 | amino acid sequence encoded by IGHV1-58 germline V-gene sequence
SEQ ID NO: 961
MQLVQSGPEVKKPGTSVKVSCKASGFTFTSSAVQWVRQARGQRLEWIGWI

VVGSGNTNYAQKFQERVTITRDMSTSTAYMELSSLRSEDTAVYYCAA

AZD8895 (COV2-2196) heavy chain variable region nucleotide sequence
Genbank: MT763531.1
SEQ ID NO: 962
CAAATGCAGCTGGTGCAGTCTGGGCCTGAGGTGAAGAAGCCTGGGACCTC

AGTGAAGGTCTCCTGCAAGGCTTCTGGATTCACCTTTATGAGCTCTGCTG

TGCAGTGGGTGCGACAGGCTCGTGGACAACGCCTTGAGTGGATAGGATGG

ATCGTCATTGGCAGTGGTAACACAAACTACGCACAGAAGTTCCAGGAAAG

AGTCACCATTACCAGGGACATGTCCACAAGCACAGCCTACATGGAGCTGA

GCAGCCTGAGATCCGAGGACACGGCCGTGTATTACTGTGCGGCCCCATAT

TGTAGTAGTATCAGCTGCAATGATGGTTTTGATATCTGGGGCCAAGGGAC

AATGGTCACCGTCTCTTCA

AZD8895 (COV2-2196) heavy chain variable region amino acid sequence:
GenBank: QLI33947.1
SEQ ID NO: 963
QMQLVQSGPEVKKPGTSVKVSCKASGFTFMSSAVQWVRQARGQRLEWIGW

IVIGSGNTNYAQKFQERVTITRDMSTSTAYMELSSLRSEDTAVYYCAAPY

CSSISCNDGFDIWGQGTMVTVSS

AZD8895 (COV2-2196) light chain variable region nucleotide Sequence:
GenBank: MT763532.1
SEQ ID NO: 964
GAAATTGTGTTGACGCAGTCTCCAGGCACCCTGTCTTTGTCTCCAGGGGA

GAGAGCCACCCTCTCCTGCAGGGCCAGTCAGAGTGTTAGCAGCAGCTACT

TAGCCTGGTACCAGCAGAAACCTGGCCAGGCTCCCAGGCTCCTCATCTAT

GGTGCATCCAGCAGGGCCACTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAGCACTATGGTAGCTCACGGGGTTGGACGTTC

GGCCAAGGGACCAAGGTGGAAATCAAA

AZD8895 (COV2-2196) light chain variable domain amino acid sequence:
GenBank: QLI33948.1
SEQ ID NO: 965
EIVLTQSPGTLSLSPGERATLSCRASQSVSSSYLAWYQQKPGQAPRLLIY

GASSRATGIPDRFSGSGSGTDFTLTISRLEPEDFAVYYCQHYGSSRGWTF

GQGTKVEIK

Spike Glycoprotein amino acid sequence of WIV04 isolate
Genbank Ref. QHR63260.2
SEQ ID NO: 966
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

-continued

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

-continued

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT amino acid sequence encoded by germline IGLV Kappa 3-20

SEQ ID NO: 967

EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSP

---

The invention claimed is:

1. An antibody capable of binding to the spike protein of coronavirus SARS-CoV-2, wherein the antibody comprises: a CDRH1 comprising the amino acid sequence of SEQ ID NO: 955, a CDRH2 comprising the amino acid sequence of SEQ ID NO: 956, a CDRH3 comprising the amino acid sequence of SEQ ID NO: 957, a CDRL1 comprising the amino acid sequence of SEQ ID NO: 958, a CDRL2 comprising the amino acid sequence EVS, and a CDRL3 comprising the amino acid sequence of SEQ ID NO: 960, wherein the antibody comprises a M252Y/S254T/T256E (YTE) mutation according to IMGT numbering.

2. The antibody of claim 1, wherein the antibody comprises a heavy chain variable domain comprising the sequence of SEQ ID NO: 952 and a light chain variable domain comprising the sequence of SEQ ID NO: 954.

3. The antibody of claim 1, wherein the antibody comprises an Fc region.

4. The antibody of claim 2, wherein the antibody comprises an IgG1 constant region.

5. A polynucleotide encoding the light chain variable region and/or heavy chain variable region of the antibody of claim 2.

6. A vector comprising one or more polynucleotides of claim 5.

7. A host cell comprising a polynucleotide encoding the light variable region of the antibody of claim 2 and a polynucleotide encoding the heavy chain variable region of the antibody of claim 2.

8. A method for producing an antibody that is capable of binding to the spike protein of coronavirus SARS-CoV-2, comprising culturing the host cell of claim 7 and isolating the antibody from said culture.

9. A pharmaceutical composition comprising:
   (a) the antibody of claim 1, and
   (b) at least one pharmaceutically acceptable diluent or carrier.

10. A pharmaceutical composition comprising:
    (a) the antibody of claim 4, and
    (b) at least one pharmaceutically acceptable diluent or carrier.

11. A method of treating a disease or complication associated with SARS-CoV-2 infection, comprising administering a therapeutically effective amount of an antibody capable of binding to the spike protein of coronavirus SARS-CoV-2, wherein the antibody comprises: a CDRH1 comprising the amino acid sequence of SEQ ID NO: 955, a CDRH2 comprising the amino acid sequence of SEQ ID NO: 956, a CDRH3 comprising the amino acid sequence of SEQ ID NO: 957, a CDRL1 comprising the amino acid sequence of SEQ ID NO: 958, a CDRL2 comprising the amino acid sequence EVS, and a CDRL3 comprising the amino acid sequence of SEQ ID NO: 960.

12. The method of claim 11, wherein antibody comprises a heavy chain variable domain comprising the sequence of SEQ ID NO: 952 and a light chain variable domain comprising the sequence of SEQ ID NO: 954.

13. The method of claim 12, wherein the antibody comprises an IgG1 constant region.

14. The method of claim 13, wherein the antibody comprises a M252Y/S254T/T256E(YTE) mutation according to IMGT numbering.

15. The method of claim 11, wherein the SARS-CoV-2 infection is caused by a SARS-CoV-2 strain of the lineage alpha, beta, gamma, or delta.

16. The method of claim 11, wherein the SARS-CoV-2 infection is caused by a SARS-CoV-2 strain of the omicron lineage, and wherein the omicron strain is Omicron BA.1, Omicron BA.1.1, Omicron BA.2, and/or Omicron BA.3.

17. A method of identifying the presence of SARS-CoV-2, or a protein fragment thereof, in a sample, comprising: contacting the sample with an antibody capable of binding to the spike protein of coronavirus SARS-CoV-2 and detecting the presence or absence of an antibody-antigen complex wherein the presence of the antibody-antigen complex indicates the presence of SARS-CoV-2, or a fragment thereof, in the sample, wherein the antibody comprises: a CDRH1 comprising the amino acid sequence of SEQ ID NO: 955, a CDRH2 comprising the amino acid sequence of SEQ ID NO: 956, a CDRH3 comprising the amino acid sequence of SEQ ID NO: 957, a CDRL1 comprising the amino acid sequence of SEQ ID NO: 958, a CDRL2 comprising the amino acid sequence EVS, and a CDRL3 comprising the amino acid sequence of SEQ ID NO: 960.

18. The method of claim 12, wherein the SARS-CoV-2 infection is caused by a SARS-CoV-2 strain of the lineage alpha, beta, gamma, or delta.

19. The method of claim 12, wherein the SARS-CoV-2 infection is caused by a SARS-CoV-2 strain of the omicron lineage, and wherein the omicron strain is Omicron BA.1, Omicron BA.1.1, Omicron BA.2, and/or Omicron BA.3.

20. The method of claim 13, wherein the SARS-CoV-2 infection is caused by a SARS-CoV-2 strain of the lineage alpha, beta, gamma, or delta.

21. The method of claim 13, wherein the SARS-CoV-2 infection is caused by a SARS-CoV-2 strain of the omicron lineage, and wherein the omicron strain is Omicron BA.1, Omicron BA.1.1, Omicron BA.2, and/or Omicron BA.3.

22. The method of claim 14, wherein the SARS-CoV-2 infection is caused by a SARS-CoV-2 strain of the lineage alpha, beta, gamma, or delta.

23. The method of claim 14, wherein the SARS-CoV-2 infection is caused by a SARS-CoV-2 strain of the omicron lineage, and wherein the omicron strain is Omicron BA.1, Omicron BA.1.1, Omicron BA.2, and/or Omicron BA.3.

24. A pharmaceutical composition comprising:
    (a) the antibody of claim 2, and
    (b) at least one pharmaceutically acceptable diluent or carrier.

25. The method of claim 11, wherein the antibody is administered in a pharmaceutical composition comprising (a) the antibody, and (b) at least one pharmaceutically acceptable diluent or carrier.

26. The method of claim 12, wherein the antibody is administered in a pharmaceutical comprising (a) the antibody, and
    (b) at least one pharmaceutically acceptable diluent or carrier.

* * * * *

SEQUENCE LISTING

```
Sequence total quantity: 967
SEQ ID NO: 1              moltype = DNA  length = 379
FEATURE                   Location/Qualifiers
source                    1..379
                          mol_type = other DNA
                          organism = Homo sapiens
SEQUENCE: 1
gaggtgcagc tggtgcagtc tggggctgag gtgaagaagc ctgggtcctc ggtgaaggtc    60
tcctgcaagg cttctggagg caccttcagc aactatgcta tcagctgggt gcgacaggcc   120
cctggacaag ggcttgagtg gatgggaggg atcatcccta tctttggtac agcaaactac   180
gcacagaact tccagggcag agtcacgatt accgcggacg aatccatgag cacagcctac   240
atggagctga gcagcctgag atctgaggac acggccgtat attactgtgc ggggaggtggg   300
aggtattgta gtggtggtag gtgccactct gcctactctg cctactgggg ccagggaacc   360
ctggtcaccg tctcctcag                                                379

SEQ ID NO: 2              moltype = AA  length = 126
FEATURE                   Location/Qualifiers
source                    1..126
                          mol_type = protein
                          organism = Homo sapiens
SEQUENCE: 2
EVQLVQSGAE VKKPGSSVKV SCKASGGTFS NYAISWVRQA PGQGLEWMGG IIPIFGTANY    60
AQNFQGRVTI TADESMSTAY MELSSLRSED TAVYYCAGGG RYCSGGRCHS AYSAYWGQGT   120
LVTVSS                                                              126

SEQ ID NO: 3              moltype = DNA  length = 322
FEATURE                   Location/Qualifiers
source                    1..322
                          mol_type = other DNA
                          organism = Homo sapiens
SEQUENCE: 3
gccatccagt tgacccagtc tccaggcacc ctgtctttgc ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggac   240
cctgaagatt ttgcagtgta ttactgtcag caatatggta gctcactcac tttcggcgga   300
gggaccaaag tggatatcaa ac                                            322

SEQ ID NO: 4              moltype = AA  length = 107
FEATURE                   Location/Qualifiers
source                    1..107
                          mol_type = protein
                          organism = Homo sapiens
SEQUENCE: 4
AIQLTQSPGT LSLPPGERAT LSCRASQSVS SSYLAWYQQK PGQAPRLLIY GASSRATGIP    60
DRFSGSGSGT DFTLTISRLD PEDFAVYYCQ QYGSSLTFGG GTKVDIK                 107

SEQ ID NO: 5              moltype = AA  length = 8
FEATURE                   Location/Qualifiers
source                    1..8
                          mol_type = protein
                          organism = Homo sapiens
SEQUENCE: 5
GGTFSNYA                                                              8

SEQ ID NO: 6              moltype = AA  length = 8
FEATURE                   Location/Qualifiers
source                    1..8
                          mol_type = protein
```

```
                         organism = Homo sapiens
SEQUENCE: 6
IIPIFGTA                                                              8

SEQ ID NO: 7             moltype = AA  length = 19
FEATURE                  Location/Qualifiers
source                   1..19
                         mol_type = protein
                         organism = Homo sapiens
SEQUENCE: 7
AGGGRYCSGG RCHSAYSAY                                                 19

SEQ ID NO: 8             moltype = AA  length = 7
FEATURE                  Location/Qualifiers
source                   1..7
                         mol_type = protein
                         organism = Homo sapiens
SEQUENCE: 8
QSVSSSY                                                               7

SEQ ID NO: 9             moltype =   length =
SEQUENCE: 9
000

SEQ ID NO: 10            moltype = AA  length = 8
FEATURE                  Location/Qualifiers
source                   1..8
                         mol_type = protein
                         organism = Homo sapiens
SEQUENCE: 10
QQYGSSLT                                                              8

SEQ ID NO: 11            moltype = DNA  length = 364
FEATURE                  Location/Qualifiers
source                   1..364
                         mol_type = other DNA
                         organism = Homo sapiens
SEQUENCE: 11
caggtgcagc tggtggagtc tgggggaggc ttggtccacc ctggggggtc cctgagactc     60
tcctgttcag cctctggatt caccttcagt aactatgcta tgcactgggt ccgccaggct    120
ccagggaagg gactggaata tgtttcagct attagtagta gtggggatat cacatactac    180
gcggactccg taaagggcag attcaccatc tccagagaca attccaagaa ctcactgtat    240
cttcaaatga acagtctgag agctgaggac acggctgttt attactgtgt gaaagatgta    300
acgaggacct actacgtagt ctttgactac tggggccagg gaaccctggt caccgtctcc    360
tcag                                                                 364

SEQ ID NO: 12            moltype = AA  length = 121
FEATURE                  Location/Qualifiers
source                   1..121
                         mol_type = protein
                         organism = Homo sapiens
SEQUENCE: 12
QVQLVESGGG LVHPGGSLRL SCSASGFTFS NYAMHWVRQA PGKGLEYVSA ISSSGDITYY     60
ADSVKGRFTI SRDNSKNSLY LQMNSLRAED TAVYYCVKDV TRTYYVVFDY WGQGTLVTVS    120
S                                                                   121

SEQ ID NO: 13            moltype = DNA  length = 322
FEATURE                  Location/Qualifiers
source                   1..322
                         mol_type = other DNA
                         organism = Homo sapiens
SEQUENCE: 13
gccatccagt tgacccagtc tccatcctcc ctgtctgcat ctgtgggaga cagagtcacc     60
atcacttgcc gggcaagtca gagcattagc agttatttaa attggtatca gcaggaacca    120
gggaaagccc ctaaactcct gatctatgct gcatccagtt tgcaaggtgg gtcccatca    180
aggttcagtg gcagtggatc tgggacagat ttcactctca ccatcagcag tctgcaacct    240
gaagattttg caacttacta ctgtcaacag agttacacta ccccgtacac ttttggccag    300
gggaccaaag tggatatcaa ac                                            322

SEQ ID NO: 14            moltype = AA  length = 107
FEATURE                  Location/Qualifiers
source                   1..107
                         mol_type = protein
                         organism = Homo sapiens
SEQUENCE: 14
AIQLTQSPSS LSASVGDRVT ITCRASQSIS SYLNWYQQEP GKAPKLLIYA ASSLQGGVPS     60
RFSGSGSGTD FTLTISSLQP EDFATYYCQQ SYTTPYTFGQ GTKVDIK                  107

SEQ ID NO: 15            moltype = AA  length = 8
```

```
FEATURE                 Location/Qualifiers
source                  1..8
                        mol_type = protein
                        organism = Homo sapiens
SEQUENCE: 15
GFTFSNYA                                                                8

SEQ ID NO: 16           moltype = AA  length = 8
FEATURE                 Location/Qualifiers
source                  1..8
                        mol_type = protein
                        organism = Homo sapiens
SEQUENCE: 16
ISSSGDIT                                                                8

SEQ ID NO: 17           moltype = AA  length = 14
FEATURE                 Location/Qualifiers
source                  1..14
                        mol_type = protein
                        organism = Homo sapiens
SEQUENCE: 17
VKDVTRTYYV VFDY                                                         14

SEQ ID NO: 18           moltype = AA  length = 6
FEATURE                 Location/Qualifiers
source                  1..6
                        mol_type = protein
                        organism = Homo sapiens
SEQUENCE: 18
QSISSY                                                                  6

SEQ ID NO: 19           moltype =     length =
SEQUENCE: 19
000

SEQ ID NO: 20           moltype = AA  length = 9
FEATURE                 Location/Qualifiers
source                  1..9
                        mol_type = protein
                        organism = Homo sapiens
SEQUENCE: 20
QQSYTTPYT                                                               9

SEQ ID NO: 21           moltype = DNA  length = 358
FEATURE                 Location/Qualifiers
source                  1..358
                        mol_type = other DNA
                        organism = Homo sapiens
SEQUENCE: 21
caggtgcagc tggtggagtc tggggggaggc ttggtccagc ctggggggtc cctgagactc      60
tcctgtgcag tctctggatt caccgtcagt aggaactaca tgagctgggt ccgccaggct      120
ccagggaagg ggctgagtg gtctcactt atttatagcg gtggtagcac attctacgca        180
gactccgtga aggcagatt caccatctcc agagacaatt ccaagaacac gctgtatctt       240
caaatgaaca gcctgagagc cgaggacacg gctgtgtatt actgtgcgag agatctgttt      300
cataggagtg gttatcacga ctactggggc cagggaaccc tggtcaccgt ctcctcag        358

SEQ ID NO: 22           moltype = AA  length = 119
FEATURE                 Location/Qualifiers
source                  1..119
                        mol_type = protein
                        organism = Homo sapiens
SEQUENCE: 22
QVQLVESGGG LVQPGGSLRL SCAVSGFTVS RNYMSWVRQA PGKGLEWVSL IYSGGSTFYA       60
DSVKGRFTIS RDNSKNTLYL QMNSLRAEDT AVYYCARDLF HRSGYHDYWG QGTLVTVSS        119

SEQ ID NO: 23           moltype = DNA  length = 319
FEATURE                 Location/Qualifiers
source                  1..319
                        mol_type = other DNA
                        organism = Homo sapiens
SEQUENCE: 23
gtcatctgga tgacccagtc tccatcctcc ctgtctgcat ctgtaggaga cagagtcacc       60
atcacttgcc aggcgagtca ggacattaac aactatttaa attggtatca gcagaaacca      120
gggaaagccc ctaagctcct gatcttcgat gcctccaatt tggaaacagg ggtcccatca      180
aggttcagtg gcagtggatc tgggacagat tttactttca ccatcagcag cctacagcct      240
gaagatattg caacatatta ctgtcaacag tatgataatc tccctgcctt cggcggaggg      300
accaaagtgg atatcaaac                                                   319

SEQ ID NO: 24           moltype = AA  length = 106
```

| FEATURE | Location/Qualifiers |
|---|---|
| source | 1..106<br>mol_type = protein<br>organism = Homo sapiens |

SEQUENCE: 24
```
VIWMTQSPSS LSASVGDRVT ITCQASQDIN NYLNWYQQKP GKAPKLLIFD ASNLETGVPS   60
RFSGSGSGTD FTFTISSLQP EDIATYYCQQ YDNLPAFGGG TKVDIK                106
```

| SEQ ID NO: 25 | moltype = AA  length = 8 |
|---|---|
| FEATURE | Location/Qualifiers |
| source | 1..8<br>mol_type = protein<br>organism = Homo sapiens |

SEQUENCE: 25
```
GFTVSRNY                                                            8
```

| SEQ ID NO: 26 | moltype = AA  length = 7 |
|---|---|
| FEATURE | Location/Qualifiers |
| source | 1..7<br>mol_type = protein<br>organism = Homo sapiens |

SEQUENCE: 26
```
IYSGGST                                                             7
```

| SEQ ID NO: 27 | moltype = AA  length = 13 |
|---|---|
| FEATURE | Location/Qualifiers |
| source | 1..13<br>mol_type = protein<br>organism = Homo sapiens |

SEQUENCE: 27
```
ARDLFHRSGY HDY                                                     13
```

| SEQ ID NO: 28 | moltype = AA  length = 6 |
|---|---|
| FEATURE | Location/Qualifiers |
| source | 1..6<br>mol_type = protein<br>organism = Homo sapiens |

SEQUENCE: 28
```
QDINNY                                                              6
```

| SEQ ID NO: 29 | moltype =    length = |
|---|---|

SEQUENCE: 29
000

| SEQ ID NO: 30 | moltype = AA  length = 8 |
|---|---|
| FEATURE | Location/Qualifiers |
| source | 1..8<br>mol_type = protein<br>organism = Homo sapiens |

SEQUENCE: 30
```
QQYDNLPA                                                            8
```

| SEQ ID NO: 31 | moltype = DNA  length = 361 |
|---|---|
| FEATURE | Location/Qualifiers |
| source | 1..361<br>mol_type = other DNA<br>organism = Homo sapiens |

SEQUENCE: 31
```
gaagtgcagc tggtggagtc tgggggaggc gtggtccagc ctggggaggtc cctgagactc   60
tcctgtgcag cgtctggatt caccttcagt aactatggca tgcactgggt ccgccaggct  120
ccaggcaagg ggctggagtg ggtggcggtt atatggtatg atggaagcaa gaaatactat  180
gcagactccg tgaagggccg attcaccatc tccagagaca attccaagaa cacccctgtat  240
ctgcaaatga acagcctgag agtcgaggac acggctgtgt attactgcgc gagagatttt  300
gcggtgggg aggagatcgc tgactcctgg ggccaggaaa ccctggtcac cgtctcctca  360
g                                                                  361
```

| SEQ ID NO: 32 | moltype = AA  length = 120 |
|---|---|
| FEATURE | Location/Qualifiers |
| source | 1..120<br>mol_type = protein<br>organism = Homo sapiens |

SEQUENCE: 32
```
EVQLVESGGG VVQPGRSLRL SCAASGFTFS NYGMHWVRQA PGKGLEWVAV VWYDGSKKYY   60
ADSVKGRFTI SRDNSKNTLY LQMNSLRVED TAVYYCARDF AVGEEIADSW GQGTLVTVSS  120
```

| SEQ ID NO: 33 | moltype = DNA  length = 325 |
|---|---|
| FEATURE | Location/Qualifiers |
| source | 1..325<br>mol_type = other DNA |

```
                        organism = Homo sapiens
SEQUENCE: 33
tcctatgagc tgactcagcc accctcggtg tcagtgtccc caggacaaac ggccaggatc   60
acctgctctg gagatgcatt gccaaaaaaa tatgcttatt ggtaccagca gaagtcaggc  120
caggcccctg tactggtcat ctatgaggac agcaaacgac cctccgggat ccctgagaga  180
ttctctgggt ccagctcagg gacaatggcc accttgacta tcagtggggc ccaggtggaa  240
gatgaaggtg actactactg ttactcaaga gacagcagtg gtgatcattg ggtgttcggc  300
gcagggacca agctgaccgt cctag                                        325

SEQ ID NO: 34           moltype = AA  length = 108
FEATURE                 Location/Qualifiers
source                  1..108
                        mol_type = protein
                        organism = Homo sapiens
SEQUENCE: 34
SYELTQPPSV SVSPGQTARI TCSGDALPKK YAYWYQQKSG QAPVLVIYED SKRPSGIPER   60
FSGSSSGTMA TLTISGAQVE DEGDYYCYSR DSSGDHWVFG AGTKLTVL               108

SEQ ID NO: 35           moltype = AA  length = 8
FEATURE                 Location/Qualifiers
source                  1..8
                        mol_type = protein
                        organism = Homo sapiens
SEQUENCE: 35
GFTFSNYG                                                             8

SEQ ID NO: 36           moltype = AA  length = 8
FEATURE                 Location/Qualifiers
source                  1..8
                        mol_type = protein
                        organism = Homo sapiens
SEQUENCE: 36
VWYDGSKK                                                             8

SEQ ID NO: 37           moltype = AA  length = 13
FEATURE                 Location/Qualifiers
source                  1..13
                        mol_type = protein
                        organism = Homo sapiens
SEQUENCE: 37
ARDFAVGEEI ADS                                                      13

SEQ ID NO: 38           moltype = AA  length = 6
FEATURE                 Location/Qualifiers
source                  1..6
                        mol_type = protein
                        organism = Homo sapiens
SEQUENCE: 38
ALPKKY                                                               6

SEQ ID NO: 39           moltype =     length =
SEQUENCE: 39
000

SEQ ID NO: 40           moltype = AA  length = 11
FEATURE                 Location/Qualifiers
source                  1..11
                        mol_type = protein
                        organism = Homo sapiens
SEQUENCE: 40
YSRDSSGDHW V                                                        11

SEQ ID NO: 41           moltype = DNA  length = 363
FEATURE                 Location/Qualifiers
source                  1..363
                        mol_type = other DNA
                        organism = Homo sapiens
SEQUENCE: 41
caggtgcagc tggtggagtc tgggggaggc gtggtccagc ctgggaggtc cctgagactc   60
tcctgtgcag cctctggatt cacccttcagt acctatgcta tgcactgggt ccgccaggct  120
ccaggcaagg ggctggagtg ggtggctgtt ctttcatatg atggaagcaa taaatactac  180
gcagactccg tgaagggccg attcaccatc tccagagaca attccaagaa cacgctgtat  240
ctgcaaatga acagcctgag agctgaggac acggctgtgt attactgtgc gaaggggggc  300
tcgtacgcgt actactacta catggacgtc tggggcaaag ggaccacggt caccgtctcc  360
tca                                                                363

SEQ ID NO: 42           moltype = AA  length = 121
FEATURE                 Location/Qualifiers
source                  1..121
```

```
                        mol_type = protein
                        organism = Homo sapiens
SEQUENCE: 42
QVQLVESGGG VVQPGRSLRL SCAASGFTFS TYAMHWVRQA PGKGLEWVAV LSYDGSNKYY    60
ADSVKGRFTI SRDNSKNTLY LQMNSLRAED TAVYYCAKGG SYAYYYYMDV WGKGTTVTVS   120
S                                                                  121

SEQ ID NO: 43           moltype = DNA  length = 322
FEATURE                 Location/Qualifiers
source                  1..322
                        mol_type = other DNA
                        organism = Homo sapiens
SEQUENCE: 43
gacatccagt tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaggtggatc tgggacagat tttactttca ccatcaccag cctgcagcct   240
gaagatattg caacatatta ctgtcaacag tatgataatc tcccgctcac tttcggcgga   300
gggaccaaag tggatatcaa ac                                            322

SEQ ID NO: 44           moltype = AA  length = 107
FEATURE                 Location/Qualifiers
source                  1..107
                        mol_type = protein
                        organism = Homo sapiens
SEQUENCE: 44
DIQLTQSPSS LSASVGDRVT ITCQASQDIS NYLNWYQQKP GKAPKLLIYD ASNLETGVPS    60
RFSGGGSGTD FTFTITSLQP EDIATYYCQQ YDNLPLTFGG GTKVDIK                 107

SEQ ID NO: 45           moltype = AA  length = 8
FEATURE                 Location/Qualifiers
source                  1..8
                        mol_type = protein
                        organism = Homo sapiens
SEQUENCE: 45
GFTFSTYA                                                              8

SEQ ID NO: 46           moltype = AA  length = 8
FEATURE                 Location/Qualifiers
source                  1..8
                        mol_type = protein
                        organism = Homo sapiens
SEQUENCE: 46
LSYDGSNK                                                              8

SEQ ID NO: 47           moltype = AA  length = 14
FEATURE                 Location/Qualifiers
source                  1..14
                        mol_type = protein
                        organism = Homo sapiens
SEQUENCE: 47
AKGGSYAYYY YMDV                                                      14

SEQ ID NO: 48           moltype = AA  length = 6
FEATURE                 Location/Qualifiers
source                  1..6
                        mol_type = protein
                        organism = Homo sapiens
SEQUENCE: 48
QDISNY                                                                6

SEQ ID NO: 49           moltype =   length =
SEQUENCE: 49
000

SEQ ID NO: 50           moltype = AA  length = 9
FEATURE                 Location/Qualifiers
source                  1..9
                        mol_type = protein
                        organism = Homo sapiens
SEQUENCE: 50
QQYDNLPLT                                                             9

SEQ ID NO: 51           moltype = DNA  length = 376
FEATURE                 Location/Qualifiers
source                  1..376
                        mol_type = other DNA
                        organism = Homo sapiens
SEQUENCE: 51
```

```
gttcagctgg tgcaggagtc gggcccagga ctggtgaagc cttcggagac cctgtccctc   60
acctgcactg tctctggtgg ctccgtcagt agtggtagtt actactggag ctggatccgg  120
cagcccccag ggaagggact ggagtggatt gggtatatgt atttcagtgg gagcaccaac  180
tataatccct ccctcaagag tcgagtcacc atatcattag ccacgtccaa gaaccagttc  240
tccctgaagc tgagctctgt gaccgctgcg gacacggccg tctattactg tgcgagaggg  300
gattacgatt tttggagtgg tccccccggt cgggtggacg tctggggcaa agggaccacg  360
gtcaccgtct cctcag                                                  376

SEQ ID NO: 52           moltype = AA   length = 125
FEATURE                 Location/Qualifiers
source                  1..125
                        mol_type = protein
                        organism = Homo sapiens
SEQUENCE: 52
VQLVQESGPG LVKPSETLSL TCTVSGGSVS SGSYYWSWIR QPPGKGLEWI GYMYFSGSTN   60
YNPSLKSRVT ISLATSKNQF SLKLSSVTAA DTAVYYCARG DYDFWSGPPG RVDVWGKGTT  120
VTVSS                                                              125

SEQ ID NO: 53           moltype = DNA   length = 325
FEATURE                 Location/Qualifiers
source                  1..325
                        mol_type = other DNA
                        organism = Homo sapiens
SEQUENCE: 53
gaaatagtga tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cactatggta gttcacccgt aacttttggc  300
caggggacca agtggatat caaac                                         325

SEQ ID NO: 54           moltype = AA   length = 108
FEATURE                 Location/Qualifiers
source                  1..108
                        mol_type = protein
                        organism = Homo sapiens
SEQUENCE: 54
EIVMTQSPGT LSLSPGERAT LSCRASQSVS SSYLAWYQQK PGQAPRLLIY GASSRATGIP   60
DRFSGSGSGT DFTLTISRLE PEDFAVYYCQ HYGSSPVTFG QGTKVDIK              108

SEQ ID NO: 55           moltype = AA   length = 10
FEATURE                 Location/Qualifiers
source                  1..10
                        mol_type = protein
                        organism = Homo sapiens
SEQUENCE: 55
GGSVSSGSYY                                                          10

SEQ ID NO: 56           moltype = AA   length = 7
FEATURE                 Location/Qualifiers
source                  1..7
                        mol_type = protein
                        organism = Homo sapiens
SEQUENCE: 56
MYFSGST                                                              7

SEQ ID NO: 57           moltype = AA   length = 17
FEATURE                 Location/Qualifiers
source                  1..17
                        mol_type = protein
                        organism = Homo sapiens
SEQUENCE: 57
ARGDYDFWSG PPGRVDV                                                  17

SEQ ID NO: 58           moltype = AA   length = 7
FEATURE                 Location/Qualifiers
source                  1..7
                        mol_type = protein
                        organism = Homo sapiens
SEQUENCE: 58
QSVSSSY                                                              7

SEQ ID NO: 59           moltype =     length =
SEQUENCE: 59
000

SEQ ID NO: 60           moltype = AA   length = 9
FEATURE                 Location/Qualifiers
source                  1..9
```

```
                    mol_type = protein
                    organism = Homo sapiens
SEQUENCE: 60
QHYGSSPVT                                                              9

SEQ ID NO: 61       moltype = DNA   length = 367
FEATURE             Location/Qualifiers
source              1..367
                    mol_type = other DNA
                    organism = Homo sapiens
SEQUENCE: 61
caggtgcagc tggtgcagtc tgggcctgag gtgaagaagc ctgggacctc agtgaaggtc    60
tcctgcaagg cttctggatt cacctttact agctctgctg tgcagtgggt gcgacaggct   120
cgtggacaac gccttgagtg gataggatgg atcgtcggtg gcagtggtaa cacaaactac   180
gcacagaagt tccaggaaag agtcaccatt accagggaca cgtccacaag cacagcctac   240
atggagatga gcagcctgag atccgaggac acggccgtgt attactgtgc ggcaccggcc   300
tgtggtacca gctgctctga tgcctttgat atctggggcc aagggacaat ggtcaccgtc   360
tcttcag                                                              367

SEQ ID NO: 62       moltype = AA   length = 122
FEATURE             Location/Qualifiers
source              1..122
                    mol_type = protein
                    organism = Homo sapiens
SEQUENCE: 62
QVQLVQSGPE VKKPGTSVKV SCKASGFTFT SSAVQWVRQA RGQRLEWIGW IVVGSGNTNY     60
AQKFQERVTI TRDMSTSTAY MEMSSLRSED TAVYYCAAPA CGTSCSDAFD IWGQGTMVTV   120
SS                                                                   122

SEQ ID NO: 63       moltype = DNA   length = 325
FEATURE             Location/Qualifiers
source              1..325
                    mol_type = other DNA
                    organism = Homo sapiens
SEQUENCE: 63
gacatccaga tgacccagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttggagtgta ttactgtcag cagtatggta gctcaccgtg gacgttcggc   300
caagggacca aggtggaaat caaac                                          325

SEQ ID NO: 64       moltype = AA   length = 108
FEATURE             Location/Qualifiers
source              1..108
                    mol_type = protein
                    organism = Homo sapiens
SEQUENCE: 64
DIQMTQSPGT LSLSPGERAT LSCRASQSVS SSYLAWYQQK PGQAPRLLIY GASSRATGIP     60
DRFSGSGSGT DFTLTISRLE PEDFGVYYCQ QYGSSPWTFG QGTKVEIK                 108

SEQ ID NO: 65       moltype = AA   length = 8
FEATURE             Location/Qualifiers
source              1..8
                    mol_type = protein
                    organism = Homo sapiens
SEQUENCE: 65
GFTFTSSA                                                               8

SEQ ID NO: 66       moltype = AA   length = 8
FEATURE             Location/Qualifiers
source              1..8
                    mol_type = protein
                    organism = Homo sapiens
SEQUENCE: 66
IVVGSGNT                                                               8

SEQ ID NO: 67       moltype = AA   length = 15
FEATURE             Location/Qualifiers
source              1..15
                    mol_type = protein
                    organism = Homo sapiens
SEQUENCE: 67
AAPACGTSCS DAFDI                                                      15

SEQ ID NO: 68       moltype = AA   length = 7
FEATURE             Location/Qualifiers
source              1..7
                    mol_type = protein
```

-continued

```
                        organism = Homo sapiens
SEQUENCE: 68
QSVSSSY                                                              7

SEQ ID NO: 69           moltype =    length =
SEQUENCE: 69
000

SEQ ID NO: 70           moltype = AA   length = 9
FEATURE                 Location/Qualifiers
source                  1..9
                        mol_type = protein
                        organism = Homo sapiens
SEQUENCE: 70
QQYGSSPWT                                                            9

SEQ ID NO: 71           moltype = DNA   length = 382
FEATURE                 Location/Qualifiers
source                  1..382
                        mol_type = other DNA
                        organism = Homo sapiens
SEQUENCE: 71
caggtgcagc tggtggagtc tgggggaggc ttggtacagc ctggcaggtc cctgagactc    60
tcctgtgcag cctctggatt cacctttgat gattatgcca tgcactgggt ccggcaacct   120
ccagggaagg gcctggagtg ggtctcaggt gtcagttgga acagtggtac cataggctat   180
gcggactctg tgaagggccg attcatcatc tccagagaca acgccaagaa ctccctgtat   240
ctgcaaatga acagtctgaa agctgaggac acggccttgt attactgtgc aagagaagtg   300
ggggggactt tggagtcct tatttcacgc gagggggac ttgattactg gggccaggga    360
accctggtca ccgtctcctc ag                                            382

SEQ ID NO: 72           moltype = AA   length = 127
FEATURE                 Location/Qualifiers
source                  1..127
                        mol_type = protein
                        organism = Homo sapiens
SEQUENCE: 72
QVQLVESGGG LVQPGRSLRL SCAASGFTFD DYAMHWVRQP PGKGLEWVSG VSWNSGTIGY    60
ADSVKGRFII SRDNAKNSLY LQMNSLKAED TALYYCAREV GGTFGVLISR EGGLDYWGQG   120
TLVTVSS                                                             127

SEQ ID NO: 73           moltype = DNA   length = 325
FEATURE                 Location/Qualifiers
source                  1..325
                        mol_type = other DNA
                        organism = Homo sapiens
SEQUENCE: 73
tcctatgagc tgacacagcc accctcggtg tcagtggccc caggacagac ggccagaatt    60
acctgtgggg gaaacaccat tggaagtaaa agtgtgcact ggtaccagca gagaccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggcca actattactg tcaggtgtgg gatagtagta gtgatcgggt ggtattcggc   300
ggagggacca agctgaccgt cctag                                         325

SEQ ID NO: 74           moltype = AA   length = 108
FEATURE                 Location/Qualifiers
source                  1..108
                        mol_type = protein
                        organism = Homo sapiens
SEQUENCE: 74
SYELTQPPSV SVAPGQTARI TCGGNTIGSK SVHWYQQRPG QAPVLVVYDD SDRPSGIPER    60
FSGSNSGNTA TLTISRVEAG DEADYYCQVW DSSSDRVVFG GGTKLTVL                108

SEQ ID NO: 75           moltype = AA   length = 8
FEATURE                 Location/Qualifiers
source                  1..8
                        mol_type = protein
                        organism = Homo sapiens
SEQUENCE: 75
GFTFDDYA                                                             8

SEQ ID NO: 76           moltype = AA   length = 8
FEATURE                 Location/Qualifiers
source                  1..8
                        mol_type = protein
                        organism = Homo sapiens
SEQUENCE: 76
VSWNSGTI                                                             8

SEQ ID NO: 77           moltype = AA   length = 20
```

| FEATURE | Location/Qualifiers |
| --- | --- |
| source | 1..20<br>mol_type = protein<br>organism = Homo sapiens |

SEQUENCE: 77
AREVGGTFGV LISREGGLDY                                               20

| SEQ ID NO: 78 | moltype = AA  length = 6 |
| --- | --- |
| FEATURE | Location/Qualifiers |
| source | 1..6<br>mol_type = protein<br>organism = Homo sapiens |

SEQUENCE: 78
TIGSKS                                                              6

| SEQ ID NO: 79 | moltype =   length = |
| --- | --- |

SEQUENCE: 79
000

| SEQ ID NO: 80 | moltype = AA  length = 11 |
| --- | --- |
| FEATURE | Location/Qualifiers |
| source | 1..11<br>mol_type = protein<br>organism = Homo sapiens |

SEQUENCE: 80
QVWDSSSDRV V                                                        11

| SEQ ID NO: 81 | moltype = DNA  length = 385 |
| --- | --- |
| FEATURE | Location/Qualifiers |
| source | 1..385<br>mol_type = other DNA<br>organism = Homo sapiens |

SEQUENCE: 81
```
caggtgcagc tgcaggagtc gggcccagga ctggtgaagc cttcggagac cctgtccctc    60
atctgcactg tctctggtgg ctccgtcagc agtggtaatt tctactggag ctggatccgg   120
cagcccccag ggaagggact ggagtggatt ggatctatct attacactgg gagccccaac   180
tacaacccct ccctcaagag tcgagtcacc atatccctag acacgtccaa gaaccagttc   240
tccctgaagc tgagctctgt gaccgctgcg gacacggccg tgtattactg tgcgagagag   300
atctattatt atgatagaag tggttcttac aactctgatg cttttgatat ctggggccaa   360
gggacaatgg tcaccgtctc ttcag                                         385
```

| SEQ ID NO: 82 | moltype = AA  length = 128 |
| --- | --- |
| FEATURE | Location/Qualifiers |
| source | 1..128<br>mol_type = protein<br>organism = Homo sapiens |

SEQUENCE: 82
QVQLQESGPG LVKPSETLSL ICTVSGGSVS SGNFYWSWIR QPPGKGLEWI GSIYYTGSPN    60
YNPSLKSRVT ISLDTSKNQF SLKLSSVTAA DTAVYYCARE IYYYDRSGSY NSDAFDIWGQ   120
GTMVTVSS                                                           128

| SEQ ID NO: 83 | moltype = DNA  length = 325 |
| --- | --- |
| FEATURE | Location/Qualifiers |
| source | 1..325<br>mol_type = other DNA<br>organism = Homo sapiens |

SEQUENCE: 83
```
gatatcgtga tgactcagtc tccagccacc ctgtctgtgt ctccagggga aagaggcacc    60
ctctcctgca gggccagtca gagtgttagc agcaacttag ctggtacca gcagaaaccg   120
ggccaggctc ccaggctcct catctatggt gcatccacga gggccactgg tatcccagcc   180
aggttcagtg gcagtgggtc tgggacagag ttcactctca ccatcagcag cctgcagtct   240
gaagattttg cagtttatta ctgccagcag tataataact ggcctccgct cactttcggc   300
ggagggacca aagtggatat caaac                                         325
```

| SEQ ID NO: 84 | moltype = AA  length = 108 |
| --- | --- |
| FEATURE | Location/Qualifiers |
| source | 1..108<br>mol_type = protein<br>organism = Homo sapiens |

SEQUENCE: 84
DIVMTQSPAT LSVSPGERGT LSCRASQSVS SNLAWYQQKP GQAPRLLIYG ASTRATGIPA    60
RFSGSGSGTE FTLTISSLQS EDFAVYYCQQ YNNWPPLTFG GGTKVDIK                108

| SEQ ID NO: 85 | moltype = AA  length = 10 |
| --- | --- |
| FEATURE | Location/Qualifiers |
| source | 1..10<br>mol_type = protein<br>organism = Homo sapiens |

SEQUENCE: 85

```
GGSVSSGNFY                                                                            10

SEQ ID NO: 86           moltype = AA  length = 7
FEATURE                 Location/Qualifiers
source                  1..7
                        mol_type = protein
                        organism = Homo sapiens
SEQUENCE: 86
IYYTGSP                                                                                7

SEQ ID NO: 87           moltype = AA  length = 20
FEATURE                 Location/Qualifiers
source                  1..20
                        mol_type = protein
                        organism = Homo sapiens
SEQUENCE: 87
AREIYYYDRS GSYNSDAFDI                                                                 20

SEQ ID NO: 88           moltype = AA  length = 6
FEATURE                 Location/Qualifiers
source                  1..6
                        mol_type = protein
                        organism = Homo sapiens
SEQUENCE: 88
QSVSSN                                                                                 6

SEQ ID NO: 89           moltype =     length =
SEQUENCE: 89
000

SEQ ID NO: 90           moltype = AA  length = 10
FEATURE                 Location/Qualifiers
source                  1..10
                        mol_type = protein
                        organism = Homo sapiens
SEQUENCE: 90
QQYNNWPPLT                                                                            10

SEQ ID NO: 91           moltype = DNA  length = 381
FEATURE                 Location/Qualifiers
source                  1..381
                        mol_type = other DNA
                        organism = Homo sapiens
SEQUENCE: 91
caggtgcagc tggtggagtc tgggggaggc gtgttcagc ctggggaggtc cctgagactc                      60
tcctgtgcag cctctggatt caccttcaat aactatcctt tgcactgggt ccgccaggct                    120
ccaggcaagg ggccggagtg ggtggcagtt atttcacagg atggaggcaa taaatactac                    180
gtagactccg tgaagggccg attcaccatc tccagagaca attccaagaa cacccctgtat                   240
ctgcaaatga acaacctgag agctgaggac acggctctgt attactgtgc gagagatgtt                    300
gtagtggtgg tagctgctag gaaccactac tacaacggta tggacgtctg gggccaaggg                    360
accacggtca ccgtctcctc a                                                              381

SEQ ID NO: 92           moltype = AA  length = 127
FEATURE                 Location/Qualifiers
source                  1..127
                        mol_type = protein
                        organism = Homo sapiens
SEQUENCE: 92
QVQLVESGGG VVQPGRSLRL SCAASGFTFN NYPLHWVRQA PGKGPEWVAV ISQDGGNKYY                      60
VDSVKGRFTI SRDNSKNTLY LQMNNLRAED TALYYCARDV VVVVAARNHY YNGMDVWGQG                    120
TTVTVSS                                                                              127

SEQ ID NO: 93           moltype = DNA  length = 322
FEATURE                 Location/Qualifiers
source                  1..322
                        mol_type = other DNA
                        organism = Homo sapiens
SEQUENCE: 93
gacatccagt tgacccagtc tccatcttcc gtgtctgcat ctgtaggaga cagagtcacc                      60
atcacttgtc gggcgagtca gggtattagc agctggttag cctggtatca gcagaaacca                    120
gggaaagccc ctaagctcct gatctatgct gtatccagtt tgcaaagtgg ggtcccatca                    180
aggttcagcg gcagtggatc tgggacagat ttcactctca ccatcagcag cctgcagcct                    240
gaagattttg caacttacta ttgtcaacag gctaagagtt ccccttttac ttcggccct                     300
gggaccaagg tggagattaa ac                                                             322

SEQ ID NO: 94           moltype = AA  length = 107
FEATURE                 Location/Qualifiers
source                  1..107
                        mol_type = protein
```

```
                            organism = Homo sapiens
SEQUENCE: 94
DIQLTQSPSS VSASVGDRVT ITCRASQGIS SWLAWYQQKP GKAPKLLIYA VSSLQSGVPS    60
RFSGSGSGTD FTLTISSLQP EDFATYYCQQ AKSFPFTFGP GTKVEIK                 107

SEQ ID NO: 95           moltype = AA  length = 8
FEATURE                 Location/Qualifiers
source                  1..8
                        mol_type = protein
                        organism = Homo sapiens
SEQUENCE: 95
GFTFNNYP                                                              8

SEQ ID NO: 96           moltype = AA  length = 8
FEATURE                 Location/Qualifiers
source                  1..8
                        mol_type = protein
                        organism = Homo sapiens
SEQUENCE: 96
ISQDGGNK                                                              8

SEQ ID NO: 97           moltype = AA  length = 20
FEATURE                 Location/Qualifiers
source                  1..20
                        mol_type = protein
                        organism = Homo sapiens
SEQUENCE: 97
ARDVVVVVAA RNHYYNGMDV                                                20

SEQ ID NO: 98           moltype = AA  length = 6
FEATURE                 Location/Qualifiers
source                  1..6
                        mol_type = protein
                        organism = Homo sapiens
SEQUENCE: 98
QGISSW                                                                6

SEQ ID NO: 99           moltype =   length =
SEQUENCE: 99
000

SEQ ID NO: 100          moltype = AA  length = 9
FEATURE                 Location/Qualifiers
source                  1..9
                        mol_type = protein
                        organism = Homo sapiens
SEQUENCE: 100
QQAKSFPFT                                                             9

SEQ ID NO: 101          moltype = DNA  length = 381
FEATURE                 Location/Qualifiers
source                  1..381
                        mol_type = other DNA
                        organism = Homo sapiens
SEQUENCE: 101
cagctgcagc tgcaggagtc gggcccagga ctggtgaagc cttcacagac cctgtccctc    60
acctgcactg tctctggtgg ctccatcagt agtggtagtt ataattggac ctggatccgg   120
cagcccgccg ggaagggact ggagtggatt gggcgtatat ataatagtgg gagcaccaac   180
tacaacccct ccctcaagag tcgagtcacc atatcagtag acacgtccaa gaaccagttg   240
tccctgaagg tgaggtctgt gaccgccgca gacacggccg tgtattactg tgcgagacat   300
tgcagtggtg gtacctgcta cccgaagtac tactacggta tggacgtctg gggccaaggg   360
accacggtca ccgtctcctc a                                             381

SEQ ID NO: 102          moltype = AA  length = 127
FEATURE                 Location/Qualifiers
source                  1..127
                        mol_type = protein
                        organism = Homo sapiens
SEQUENCE: 102
QLQLQESGPG LVKPSQTLSL TCTVSGGSIS SGSYNWTWIR QPAGKGLEWI GRIYNSGSTN    60
YNPSLKSRVT ISVDTSKNQL SLKVRSVTAA DTAVYYCARH CSGGTCYPKY YYGMDVWGQG   120
TTVTVSS                                                             127

SEQ ID NO: 103          moltype = DNA  length = 331
FEATURE                 Location/Qualifiers
source                  1..331
                        mol_type = other DNA
                        organism = Homo sapiens
SEQUENCE: 103
```

```
caatctgccc tgactcagcc accctcggtg tctgaagccc caggcagag ggtcaccatc    60
tcctgttctg gaagcagctc caacatcgga ataatgctg taaactggta ccagcagttc   120
ccaggaaagg ctcccaaact cctcatctat tatgatgatc tgctgccctc agggggtctct  180
gaccgattct ctggctccaa gtctggcacc tcagcctccc tggccatcag tggggtccag   240
tctgaggatg aggctgatta ttactgtgca gcatgggatg acagcctgaa tgtcgtggta   300
ttcggcggag ggaccaagct gaccgtccta g                                 331

SEQ ID NO: 104          moltype = AA   length = 110
FEATURE                 Location/Qualifiers
source                  1..110
                        mol_type = protein
                        organism = Homo sapiens
SEQUENCE: 104
QSALTQPPSV SEAPRQRVTI SCSGSSSNIG NNAVNWYQQF PGKAPKLLIY YDDLLPSGVS    60
DRFSGSKSGT SASLAISGVQ SEDEADYYCA AWDDSLNVVV FGGGTKLTVL              110

SEQ ID NO: 105          moltype = AA   length = 10
FEATURE                 Location/Qualifiers
source                  1..10
                        mol_type = protein
                        organism = Homo sapiens
SEQUENCE: 105
GGSISSGSYN                                                          10

SEQ ID NO: 106          moltype = AA   length = 7
FEATURE                 Location/Qualifiers
source                  1..7
                        mol_type = protein
                        organism = Homo sapiens
SEQUENCE: 106
IYNSGST                                                             7

SEQ ID NO: 107          moltype = AA   length = 19
FEATURE                 Location/Qualifiers
source                  1..19
                        mol_type = protein
                        organism = Homo sapiens
SEQUENCE: 107
ARHCSGGTCY PKYYYGMDV                                                19

SEQ ID NO: 108          moltype = AA   length = 8
FEATURE                 Location/Qualifiers
source                  1..8
                        mol_type = protein
                        organism = Homo sapiens
SEQUENCE: 108
SSNIGNNA                                                            8

SEQ ID NO: 109          moltype =     length =
SEQUENCE: 109
000

SEQ ID NO: 110          moltype = AA   length = 11
FEATURE                 Location/Qualifiers
source                  1..11
                        mol_type = protein
                        organism = Homo sapiens
SEQUENCE: 110
AAWDDSLNVV V                                                        11

SEQ ID NO: 111          moltype = DNA   length = 370
FEATURE                 Location/Qualifiers
source                  1..370
                        mol_type = other DNA
                        organism = Homo sapiens
SEQUENCE: 111
caggtgcagc tggtggagtc gggcccagga ctggtgaagc cttcggagac cctgtccctc    60
acctgcactg tctctggtgg ctccatcagc agtaatagtt acttctgggg ctggatccgc   120
cagcccccag ggacggggct ggagtggatt gggaatatct attatactgg gagcacctac   180
tacaacccgt cgttcgagag tcgagtcacc atgtccgtag acacgtcgaa gaaccagttc   240
tccctgaggc tgagctctgt gaccgccgca gacacggctg tgtattactg tgcgagacat   300
gtcagggcct acgactatga tgccccttt gatatctggg gccaagggac aatggtcacc   360
gtctcttcag                                                         370

SEQ ID NO: 112          moltype = AA   length = 123
FEATURE                 Location/Qualifiers
source                  1..123
                        mol_type = protein
                        organism = Homo sapiens
```

```
SEQUENCE: 112
QVQLVESGPG LVKPSETLSL TCTVSGGSIS SNSYFWGWIR QPPGTGLEWI GNIYYTGSTY    60
YNPSFESRVT MSVDTSKNQF SLRLSSVTAA DTAVYYCARH VRAYDYDAPF DIWGQGTMVT   120
VSS                                                                123

SEQ ID NO: 113           moltype = DNA  length = 322
FEATURE                  Location/Qualifiers
source                   1..322
                         mol_type = other DNA
                         organism = Homo sapiens
SEQUENCE: 113
gtcatctgga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacacaa ttcactctca caatcagcag cctgcagcct   240
gaagattttg caacttatta ctgtctacag attaatagtt atccgctcac tttcggcgga   300
gggaccaagg tggaaatcaa ac                                           322

SEQ ID NO: 114           moltype = AA  length = 107
FEATURE                  Location/Qualifiers
source                   1..107
                         mol_type = protein
                         organism = Homo sapiens
SEQUENCE: 114
VIWMTQSPSS LSASVGDRVT ITCRASQGIR NDLGWYQQKP GKAPKRLIYA ASSLQSGVPS    60
RFSGSGSGTQ FTLTISSLQP EDFATYYCLQ INSYPLTFGG GTKVEIK                107

SEQ ID NO: 115           moltype = AA  length = 10
FEATURE                  Location/Qualifiers
source                   1..10
                         mol_type = protein
                         organism = Homo sapiens
SEQUENCE: 115
GGSISSNSYF                                                          10

SEQ ID NO: 116           moltype = AA  length = 7
FEATURE                  Location/Qualifiers
source                   1..7
                         mol_type = protein
                         organism = Homo sapiens
SEQUENCE: 116
IYYTGST                                                              7

SEQ ID NO: 117           moltype = AA  length = 15
FEATURE                  Location/Qualifiers
source                   1..15
                         mol_type = protein
                         organism = Homo sapiens
SEQUENCE: 117
ARHVRAYDYD APFDI                                                    15

SEQ ID NO: 118           moltype = AA  length = 6
FEATURE                  Location/Qualifiers
source                   1..6
                         mol_type = protein
                         organism = Homo sapiens
SEQUENCE: 118
QGIRND                                                               6

SEQ ID NO: 119           moltype =    length =
SEQUENCE: 119
000

SEQ ID NO: 120           moltype = AA  length = 9
FEATURE                  Location/Qualifiers
source                   1..9
                         mol_type = protein
                         organism = Homo sapiens
SEQUENCE: 120
LQINSYPLT                                                            9

SEQ ID NO: 121           moltype = DNA  length = 349
FEATURE                  Location/Qualifiers
source                   1..349
                         mol_type = other DNA
                         organism = Homo sapiens
SEQUENCE: 121
caggtacagc tgcagcagtg gggcgcagga ctgttgaagc cttcggagac cctgtccctc    60
acctgcgctg tctatggtgg gtccttcagt ggttactact ggagctggat ccgccagccc   120
```

```
ccagggaagg ggctggagtg gattggggaa atcaatcata gtggaagcac caactacaac    180
ccgtccctca agagtcgagt caccatatca gtagacacgt ccaagaacca gttctccctg    240
aagctgagtt ctgtgaccgc cgcggacacg gctgtgtatt actgtgcgag aactgattac    300
tatgatagta tagactgggg ccagggaacc ctggtcaccg tctcctcag               349
```

```
SEQ ID NO: 122          moltype = AA   length = 116
FEATURE                 Location/Qualifiers
source                  1..116
                        mol_type = protein
                        organism = Homo sapiens
SEQUENCE: 122
QVQLQQWGAG LLKPSETLSL TCAVYGGSFS GYYWSWIRQP PGKGLEWIGE INHSGSTNYN    60
PSLKSRVTIS VDTSKNQFSL KLSSVTAADT AVYYCARTDY YDSIDWGQGT LVTVSS       116

SEQ ID NO: 123          moltype = DNA   length = 328
FEATURE                 Location/Qualifiers
source                  1..328
                        mol_type = other DNA
                        organism = Homo sapiens
SEQUENCE: 123
```
```
cagtctgtgc tgactcagga gccctcactg actgtgtccc caggagggac agtcactctc    60
acctgtggct ccagcactgg agctgtcacc agtggtcatt atccctactg gttccagcag    120
aagcctggcc aagtccccag gacactgatt tatgatacaa ggaacaaaca ctcctggacc    180
cctgcccggt tctcaggctc cctccttggg ggcaaagctg ccctgaccct ttcgggtgcg    240
cagcctgagg atgaggctga atattactgc ttgctctcct ctagtggtgc tcgggtgttc    300
ggcggaggga ccaagctgac cgtcctag                                      328
```

```
SEQ ID NO: 124          moltype = AA   length = 109
FEATURE                 Location/Qualifiers
source                  1..109
                        mol_type = protein
                        organism = Homo sapiens
SEQUENCE: 124
QSVLTQEPSL TVSPGGTVTL TCGSSTGAVT SGHYPYWFQQ KPGQVPRTLI YDTRNKHSWT    60
PARFSGSLLG GKAALTLSGA QPEDEAEYYC LLSSSGARVF GGGTKLTVL               109

SEQ ID NO: 125          moltype = AA   length = 8
FEATURE                 Location/Qualifiers
source                  1..8
                        mol_type = protein
                        organism = Homo sapiens
SEQUENCE: 125
GGSFSGYY                                                            8

SEQ ID NO: 126          moltype = AA   length = 7
FEATURE                 Location/Qualifiers
source                  1..7
                        mol_type = protein
                        organism = Homo sapiens
SEQUENCE: 126
INHSGST                                                             7

SEQ ID NO: 127          moltype = AA   length = 10
FEATURE                 Location/Qualifiers
source                  1..10
                        mol_type = protein
                        organism = Homo sapiens
SEQUENCE: 127
ARTDYYDSID                                                          10

SEQ ID NO: 128          moltype = AA   length = 9
FEATURE                 Location/Qualifiers
source                  1..9
                        mol_type = protein
                        organism = Homo sapiens
SEQUENCE: 128
TGAVTSGHY                                                           9

SEQ ID NO: 129          moltype =    length =
SEQUENCE: 129
000

SEQ ID NO: 130          moltype = AA   length = 9
FEATURE                 Location/Qualifiers
source                  1..9
                        mol_type = protein
                        organism = Homo sapiens
SEQUENCE: 130
LLSSSGARV                                                           9
```

```
SEQ ID NO: 131          moltype = DNA  length = 358
FEATURE                 Location/Qualifiers
source                  1..358
                        mol_type = other DNA
                        organism = Homo sapiens
SEQUENCE: 131
gaggtgcagc tggtggagtc tgggggaggc ttggtacagc ctgggggtc cctgagactc       60
tcctgtgcag cctctggatt caccttcagt acctacgaca tccactgggt ccgccaagct    120
acaggaaaag gtctggagtg ggtctcagct attggtactg ctggtagtga atactattca    180
ggctccgtga agggccgatt caccatctcc agagaaaatg ccaagaactc cttgtatctt    240
caaatgaaca gcctgagagc cggggacacg gctgtgtatt actgtgcaag gggtagtggg    300
acctacttct actactttga ctactggggc cagggaaccc tggtcaccgt ctcctcag      358

SEQ ID NO: 132          moltype = AA  length = 119
FEATURE                 Location/Qualifiers
source                  1..119
                        mol_type = protein
                        organism = Homo sapiens
SEQUENCE: 132
EVQLVESGGG LVQPGGSLRL SCAASGFTFS TYDIHWVRQA TGKGLEWVSA IGTAGDTYYS       60
GSVKGRFTIS RENAKNSLYL QMNSLRAGDT AVYYCARGSG TYFYYFDYWG QGTLVTVSS      119

SEQ ID NO: 133          moltype = DNA  length = 325
FEATURE                 Location/Qualifiers
source                  1..325
                        mol_type = other DNA
                        organism = Homo sapiens
SEQUENCE: 133
gacatcgtga tgactcagtc tccatcctcc ctgtctgcat ctgtaggaga cagaatcacc       60
atcacttgcc gggcaagtca gagcattaac aactatttaa attggtatca gcagaaacca    120
gggaaagccc ctaagctcct gatctatgct gcatcccgtt tgcaaactgg ggtcccatca    180
aggttcagtg gcagtggatc tgggacagat tccactctca ccatcaacac tctgcaacct    240
gaagattttg caacttacta ctgtcaacag agttacagtg cccctccgtg gacgttcggc    300
caagggacca aagtggatat caaac                                           325

SEQ ID NO: 134          moltype = AA  length = 108
FEATURE                 Location/Qualifiers
source                  1..108
                        mol_type = protein
                        organism = Homo sapiens
SEQUENCE: 134
DIVMTQSPSS LSASVGDRIT ITCRASQSIN NYLNWYQQKP GKAPKLLIYA ASRLQTGVPS       60
RFSGSGSGTD STLTINTLQP EDFATYYCQQ SYSAPPWTFG QGTKVDIK                  108

SEQ ID NO: 135          moltype = AA  length = 8
FEATURE                 Location/Qualifiers
source                  1..8
                        mol_type = protein
                        organism = Homo sapiens
SEQUENCE: 135
GFTFSTYD                                                                8

SEQ ID NO: 136          moltype = AA  length = 7
FEATURE                 Location/Qualifiers
source                  1..7
                        mol_type = protein
                        organism = Homo sapiens
SEQUENCE: 136
IGTAGDT                                                                 7

SEQ ID NO: 137          moltype = AA  length = 13
FEATURE                 Location/Qualifiers
source                  1..13
                        mol_type = protein
                        organism = Homo sapiens
SEQUENCE: 137
ARGSGTYFYY FDY                                                         13

SEQ ID NO: 138          moltype = AA  length = 6
FEATURE                 Location/Qualifiers
source                  1..6
                        mol_type = protein
                        organism = Homo sapiens
SEQUENCE: 138
QSINNY                                                                  6

SEQ ID NO: 139          moltype =   length =
SEQUENCE: 139
```

```
SEQ ID NO: 140          moltype = AA  length = 10
FEATURE                 Location/Qualifiers
source                  1..10
                        mol_type = protein
                        organism = Homo sapiens
SEQUENCE: 140
QQSYSAPPWT                                                                10

SEQ ID NO: 141          moltype = DNA  length = 366
FEATURE                 Location/Qualifiers
source                  1..366
                        mol_type = other DNA
                        organism = Homo sapiens
SEQUENCE: 141
caggtgcagc tggtggagtc gggcccagga ctggtgaagc cttcggagac cctgtccctc         60
acctgcactg tctctggtgg ctcgatcagc agttcttact actggggctg gatccgccag        120
cccccaggga aggggctgga gtggattggg agtgtctatt atagtgggag cacctactac        180
aacccgtccc tcaagagtcg agtcaccata tccgtggaca cgtccaagaa ccagttctcc        240
ctgaggctga gctctgtgac cgccgcagac acggctgtgt attattgtgc gaggctgatg        300
accacggaag actactactc cggtatggac gtctggggcc aagggaccac ggtcaccgtc        360
tcctca                                                                  366

SEQ ID NO: 142          moltype = AA  length = 122
FEATURE                 Location/Qualifiers
source                  1..122
                        mol_type = protein
                        organism = Homo sapiens
SEQUENCE: 142
QVQLVESGPG LVKPSETLSL TCTVSGGSIS SSYYWGWIRQ PPGKGLEWIG SVYYSGSTYY         60
NPSLKSRVTI SVDTSKNQFS LRLSSVTAAD TAVYYCARLM TTEDYYSGMD VWGQGTTVTV        120
SS                                                                      122

SEQ ID NO: 143          moltype = DNA  length = 322
FEATURE                 Location/Qualifiers
source                  1..322
                        mol_type = other DNA
                        organism = Homo sapiens
SEQUENCE: 143
gccatccaga tgacccagtc tccatcctca ctgtctgcat ctgtaggaga cagagtcacc         60
atcacttgtc gggcgagtca gggcattagc gattatttag cctggtttca gcagaaacca        120
gggaaagccc ctaagtccct gatctatgct gcatccagtt tgcaaagtgg ggtcccatca        180
aggttcagcg gcggtggatc tgggacagat ttcactctca ccatcagcag cctgcagcct        240
gaagattttg caacttatta ctgccaacag tatcatagtt acccgatcac cttcggccaa        300
gggacacgac tggagattaa ac                                                322

SEQ ID NO: 144          moltype = AA  length = 107
FEATURE                 Location/Qualifiers
source                  1..107
                        mol_type = protein
                        organism = Homo sapiens
SEQUENCE: 144
AIQMTQSPSS LSASVGDRVT ITCRASQGIS DYLAWFQQKP GKAPKSLIYA ASSLQSGVPS         60
KFSGGGSGTD FTLTISSLQP EDFATYYCQQ YHSYPITFGQ GTRLEIK                      107

SEQ ID NO: 145          moltype = AA  length = 9
FEATURE                 Location/Qualifiers
source                  1..9
                        mol_type = protein
                        organism = Homo sapiens
SEQUENCE: 145
GGSISSSYY                                                                 9

SEQ ID NO: 146          moltype = AA  length = 7
FEATURE                 Location/Qualifiers
source                  1..7
                        mol_type = protein
                        organism = Homo sapiens
SEQUENCE: 146
VYYSGST                                                                   7

SEQ ID NO: 147          moltype = AA  length = 15
FEATURE                 Location/Qualifiers
source                  1..15
                        mol_type = protein
                        organism = Homo sapiens
SEQUENCE: 147
ARLMTTEDYY SGMDV                                                         15
```

```
SEQ ID NO: 148          moltype = AA   length = 6
FEATURE                 Location/Qualifiers
source                  1..6
                        mol_type = protein
                        organism = Homo sapiens
SEQUENCE: 148
QGISDY                                                                    6

SEQ ID NO: 149          moltype =      length =
SEQUENCE: 149
000

SEQ ID NO: 150          moltype = AA   length = 9
FEATURE                 Location/Qualifiers
source                  1..9
                        mol_type = protein
                        organism = Homo sapiens
SEQUENCE: 150
QQYHSYPIT                                                                 9

SEQ ID NO: 151          moltype = DNA  length = 351
FEATURE                 Location/Qualifiers
source                  1..351
                        mol_type = other DNA
                        organism = Homo sapiens
SEQUENCE: 151
caggtgcagc tggtggagtc tggaggaggc ttgatccagc ctgggggtc cctgagactc          60
tcctgtgcag cctctggggt caccgtcagt agcaactaca tgagttgggt ccgccaggct        120
ccagggaagg ggctggagtg ggtctcaatt atttatatg gtggtaccac atactacgca         180
gactccgtga agggccgatt caccatctcc agagactctt ccatgaacac gctgtatctt        240
caaatgaaca gcctgagagc cgaggacacg gccgtgtatt actgtgcgag agatctgatg        300
gtgtacggta tagacgtctg gggccaaggg accacggtca ccgtctcctc a                 351

SEQ ID NO: 152          moltype = AA   length = 117
FEATURE                 Location/Qualifiers
source                  1..117
                        mol_type = protein
                        organism = Homo sapiens
SEQUENCE: 152
QVQLVESGGG LIQPGGSLRL SCAASGVTVS SNYMSWVRQA PGKGLEWVSI IYSGGTTYYA         60
DSVKGRFTIS RDSSMNTLYL QMNSLRAEDT AVYYCARDLM VYGIDVWGQG TTVTVSS           117

SEQ ID NO: 153          moltype = DNA  length = 328
FEATURE                 Location/Qualifiers
source                  1..328
                        mol_type = other DNA
                        organism = Homo sapiens
SEQUENCE: 153
gaaatagtga tgacgcagtc tccatcctcc ctgtctgcat ctgtaggaga cagagtcacc         60
atcacttgcc gggccagtca gggcattagc agttatttag cctggtatca gcaaaaacca       120
gggaaagccc ctaagctcct gatctatgct gcatccactt tgcaaagtgg ggtcccatca       180
aggttcagcg gcagtggatc tgggacagat ttcactctca ccatcagcag cctgcagcct       240
gaagattttg caacttatta ctgtcaacag cttgatagtt accccccccgg gtacactttt      300
ggccagggga ccaaagtgga tatcaaac                                          328

SEQ ID NO: 154          moltype = AA   length = 109
FEATURE                 Location/Qualifiers
source                  1..109
                        mol_type = protein
                        organism = Homo sapiens
SEQUENCE: 154
EIVMTQSPSS LSASVGDRVT ITCRASQGIS SYLAWYQQKP GKAPKLLIYA ASTLQSGVPS         60
RFSGSGSGTD FTLTISSLQP EDFATYYCQQ LDSYPPGYTF GQGTKVDIK                   109

SEQ ID NO: 155          moltype = AA   length = 8
FEATURE                 Location/Qualifiers
source                  1..8
                        mol_type = protein
                        organism = Homo sapiens
SEQUENCE: 155
GVTVSSNY                                                                  8

SEQ ID NO: 156          moltype = AA   length = 7
FEATURE                 Location/Qualifiers
source                  1..7
                        mol_type = protein
                        organism = Homo sapiens
SEQUENCE: 156
```

-continued

```
SEQ ID NO: 157          moltype = AA  length = 11
FEATURE                 Location/Qualifiers
source                  1..11
                        mol_type = protein
                        organism = Homo sapiens
SEQUENCE: 157
ARDLMVYGID V                                                          11

SEQ ID NO: 158          moltype = AA  length = 6
FEATURE                 Location/Qualifiers
source                  1..6
                        mol_type = protein
                        organism = Homo sapiens
SEQUENCE: 158
QGISSY                                                                6

SEQ ID NO: 159          moltype =   length =
SEQUENCE: 159
000

SEQ ID NO: 160          moltype = AA  length = 11
FEATURE                 Location/Qualifiers
source                  1..11
                        mol_type = protein
                        organism = Homo sapiens
SEQUENCE: 160
QQLDSYPPGY T                                                          11

SEQ ID NO: 161          moltype = DNA  length = 351
FEATURE                 Location/Qualifiers
source                  1..351
                        mol_type = other DNA
                        organism = Homo sapiens
SEQUENCE: 161
gaggtgcagc tgttggagtc tggaggagac ttgatccagc ctgggggtc cctgagactc      60
tcctgtgcag cctctgggt caccgtcagt agcaactaca tgagctgggt ccgccaggct     120
ccaggggaag gctggagtg gtctcaatt atttatcccg gtgggagcac attctacgca     180
gactccgtga agggccgatt caccatctcc agagacaatt ccaagaacac gctgtatctt    240
caaatgcaca gcctgagagc cgaggacacg gccgtgtatt actgtgcgag agatcttggc    300
tcaggggaca tggacgtctg gggcaaaggg accacggtca ccgtctcctc a             351

SEQ ID NO: 162          moltype = AA  length = 117
FEATURE                 Location/Qualifiers
source                  1..117
                        mol_type = protein
                        organism = Homo sapiens
SEQUENCE: 162
EVQLLESGGD LIQPGGSLRL SCAASGVTVS SNYMSWVRQA PGKGLEWVSI IYPGGSTFYA     60
DSVKGRFTIS RDNSKNTLYL QMHSLRAEDT AVYYCARDLG SGDMDVWGKG TTVTVSS       117

SEQ ID NO: 163          moltype = DNA  length = 322
FEATURE                 Location/Qualifiers
source                  1..322
                        mol_type = other DNA
                        organism = Homo sapiens
SEQUENCE: 163
gacatcgtga tgactcagtc tccatccttc ctgtctgcat ctgtaggaga cagagtcacc     60
atcacttgcc gggccagtca gggcattagc agttatttag cctggtatca gcaaaaaccg    120
gggaaagccc ctaagctcct gatccaagct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accggtacac ttttggccag    300
gggaccaagg tggagatcaa ac                                             322

SEQ ID NO: 164          moltype = AA  length = 107
FEATURE                 Location/Qualifiers
source                  1..107
                        mol_type = protein
                        organism = Homo sapiens
SEQUENCE: 164
DIVMTQSPSF LSASVGDRVT ITCRASQGIS SYLAWYQQKP GKAPKLLIQA ASTLQSGVPS     60
RFSGSGSGTE FTLTISSLQP EDFATYYCQQ LNSYRYTFGQ GTKVEIK                  107

SEQ ID NO: 165          moltype = AA  length = 8
FEATURE                 Location/Qualifiers
source                  1..8
                        mol_type = protein
                        organism = Homo sapiens
```

```
SEQUENCE: 165
GVTVSSNY                                                                          8

SEQ ID NO: 166           moltype = AA  length = 7
FEATURE                  Location/Qualifiers
source                   1..7
                         mol_type = protein
                         organism = Homo sapiens
SEQUENCE: 166
IYPGGST                                                                           7

SEQ ID NO: 167           moltype = AA  length = 11
FEATURE                  Location/Qualifiers
source                   1..11
                         mol_type = protein
                         organism = Homo sapiens
SEQUENCE: 167
ARDLGSGDMD V                                                                     11

SEQ ID NO: 168           moltype = AA  length = 6
FEATURE                  Location/Qualifiers
source                   1..6
                         mol_type = protein
                         organism = Homo sapiens
SEQUENCE: 168
QGISSY                                                                            6

SEQ ID NO: 169           moltype =     length =
SEQUENCE: 169
000

SEQ ID NO: 170           moltype = AA  length = 9
FEATURE                  Location/Qualifiers
source                   1..9
                         mol_type = protein
                         organism = Homo sapiens
SEQUENCE: 170
QQLNSYRYT                                                                         9

SEQ ID NO: 171           moltype = DNA  length = 369
FEATURE                  Location/Qualifiers
source                   1..369
                         mol_type = other DNA
                         organism = Homo sapiens
SEQUENCE: 171
gaggtgcagc tggtggagtc tgggggaggc gtggtccagc ctggggaggtc cctgagactc              60
tcctgtgcag cctctggatt caccttcagt agctatggca tgcactgggt ccgccaggct             120
ccaggcaagg ggctggagtg ggtggcactt atatcatatg atggaggtaa tagatactat             180
gcagactccg tgaagggccg attcaccatc tccagagaca attccaagaa cacgctgtat             240
ctgcaaatga acagactgag agctgaagac acggctatgt attactgtgc gaaagatcgt             300
gatgatgggt gggattggta ctacttcatg gacgtctggg gcaaagggac cacggtcacc             360
gtctcctca                                                                       369

SEQ ID NO: 172           moltype = AA  length = 123
FEATURE                  Location/Qualifiers
source                   1..123
                         mol_type = protein
                         organism = Homo sapiens
SEQUENCE: 172
EVQLVESGGG VVQPGRSLRL SCAASGFTFS SYGMHWVRQA PGKGLEWVAL ISYDGGNRYY                60
ADSVKGRFTI SRDNSKNTLY LQMNRLRAED TAMYYCAKDR DDGWDWYYFM DVWGKGTTVT              120
VSS                                                                            123

SEQ ID NO: 173           moltype = DNA  length = 322
FEATURE                  Location/Qualifiers
source                   1..322
                         mol_type = other DNA
                         organism = Homo sapiens
SEQUENCE: 173
gacatccagt tgacccagtc tccaggcacc ctgtctttgt ctccagggga aagagccacc                60
ctctcctgca gggccagtca gagtattagc ggcaactact tagcctggta ccagcataaa              120
cctggccagg ctcccagact cctcatctat ggtgcatcca ccagggccac tggcatccca              180
gacaggttca gtggcagtgg gtctgggaca gacttcactc tcaccatcag cagactgagg             240
cctgaagatt ttgcagtgta ttactgtcag cagtatggta gctcgtacac ttttggccag              300
gggaccaagg tggagatcaa ac                                                       322

SEQ ID NO: 174           moltype = AA  length = 107
FEATURE                  Location/Qualifiers
source                   1..107
```

```
                            mol_type = protein
                            organism = Homo sapiens
SEQUENCE: 174
DIQLTQSPGT LSLSPGERAT LSCRASQSIS GNYLAWYQHK PGQAPRLLIY GASTRATGIP    60
DRFSGSGSGT DFTLTISRLE PEDFAVYYCQ QYGSSYTFGQ GTKVEIK                 107

SEQ ID NO: 175              moltype = AA   length = 8
FEATURE                     Location/Qualifiers
source                      1..8
                            mol_type = protein
                            organism = Homo sapiens
SEQUENCE: 175
GFTFSSYG                                                              8

SEQ ID NO: 176              moltype = AA   length = 8
FEATURE                     Location/Qualifiers
source                      1..8
                            mol_type = protein
                            organism = Homo sapiens
SEQUENCE: 176
ISYDGGNR                                                              8

SEQ ID NO: 177              moltype = AA   length = 16
FEATURE                     Location/Qualifiers
source                      1..16
                            mol_type = protein
                            organism = Homo sapiens
SEQUENCE: 177
AKDRDDGWDW YYFMDV                                                    16

SEQ ID NO: 178              moltype = AA   length = 7
FEATURE                     Location/Qualifiers
source                      1..7
                            mol_type = protein
                            organism = Homo sapiens
SEQUENCE: 178
QSISGNY                                                               7

SEQ ID NO: 179              moltype =      length =
SEQUENCE: 179
000

SEQ ID NO: 180              moltype = AA   length = 8
FEATURE                     Location/Qualifiers
source                      1..8
                            mol_type = protein
                            organism = Homo sapiens
SEQUENCE: 180
QQYGSSYT                                                              8

SEQ ID NO: 181              moltype = DNA  length = 370
FEATURE                     Location/Qualifiers
source                      1..370
                            mol_type = other DNA
                            organism = Homo sapiens
SEQUENCE: 181
caggttcagc tggtgcagtc tgggcctgag gtgaagaagc ctgggacctc agtgaaggtc    60
tcctgcaagg cttctggatt cacctttact agctctgctg tgcagtgggt gcgacaggct   120
cgtggacagc gccttgagtg gataggatgg atcgtcgttg gcagtggtaa cacaaactac   180
gcacagaagt tccaggaaag cgtcaccatt accagggaca tgtccacaag cacagcctac   240
atggagctga gcagcctgag atccgaggac acggccgtgt attactgtgc ggcccccacat   300
tgtattggtg gtagctgcca tgatgctttt gatatctggg gccaagggac aatggtcacc   360
gtctcttcag                                                           370

SEQ ID NO: 182              moltype = AA   length = 123
FEATURE                     Location/Qualifiers
source                      1..123
                            mol_type = protein
                            organism = Homo sapiens
SEQUENCE: 182
QVQLVQSGPE VKKPGTSVKV SCKASGFTFT SSAVQWVRQA RGQRLEWIGW IVVGSGNTNY    60
AQKFQESVTI TRDMSTSTAY MELSSLRSED TAVYYCAAPH CIGGSCHDAF DIWGQGTMVT   120
VSS                                                                  123

SEQ ID NO: 183              moltype = DNA  length = 325
FEATURE                     Location/Qualifiers
source                      1..325
                            mol_type = other DNA
                            organism = Homo sapiens
```

```
SEQUENCE: 183
gatatcgtga tgacccagtc tccaggcacc ctatctttgt ctccagggga aagagccacc   60
ctctcctgca gggccagtca gagtgttaga agcagctact tagcctgta ccagcagaaa  120
cctggccagg ctcccaggct cctcatctat ggtgcatcca ggaggggcac tggcatccca  180
gacaggttca gtggcagtgg gtctgggaca gacttcactc tcaccatcag cagactggag  240
cctgaagatt ttgcagtgta ttactgtcag cagtatggta gctcacctg gacgttcggc   300
caagggacca aggtggaaat caaac                                        325

SEQ ID NO: 184           moltype = AA  length = 108
FEATURE                  Location/Qualifiers
source                   1..108
                         mol_type = protein
                         organism = Homo sapiens
SEQUENCE: 184
DIVMTQSPGT LSLSPGERAT LSCRASQSVR SSYLAWYQQK PGQAPRLLIY GASRRGTGIP   60
DRFSGSGSGT DFTLTISRLE PEDFAVYYCQ QYGSSPWTFG QGTKVEIK               108

SEQ ID NO: 185           moltype = AA  length = 8
FEATURE                  Location/Qualifiers
source                   1..8
                         mol_type = protein
                         organism = Homo sapiens
SEQUENCE: 185
GFTFTSSA                                                             8

SEQ ID NO: 186           moltype = AA  length = 8
FEATURE                  Location/Qualifiers
source                   1..8
                         mol_type = protein
                         organism = Homo sapiens
SEQUENCE: 186
IVVGSGNT                                                             8

SEQ ID NO: 187           moltype = AA  length = 16
FEATURE                  Location/Qualifiers
source                   1..16
                         mol_type = protein
                         organism = Homo sapiens
SEQUENCE: 187
AAPHCIGGSC HDAFDI                                                   16

SEQ ID NO: 188           moltype = AA  length = 7
FEATURE                  Location/Qualifiers
source                   1..7
                         mol_type = protein
                         organism = Homo sapiens
SEQUENCE: 188
QSVRSSY                                                              7

SEQ ID NO: 189           moltype =     length =
SEQUENCE: 189
000

SEQ ID NO: 190           moltype = AA  length = 9
FEATURE                  Location/Qualifiers
source                   1..9
                         mol_type = protein
                         organism = Homo sapiens
SEQUENCE: 190
QQYGSSPWT                                                            9

SEQ ID NO: 191           moltype = DNA  length = 352
FEATURE                  Location/Qualifiers
source                   1..352
                         mol_type = other DNA
                         organism = Homo sapiens
SEQUENCE: 191
caggtgcagc tggtggagtc aggagcagag gtgaaaaagc ccggggagtc tctgaagatc   60
tcctgtaagg gttctggata cagctttacc agctactgga tcgtctgggt gcgccagatg  120
cccgggaaag gcctggagtg gatgggggatc atctatcctg gtgactctga taccaaatac  180
agtccgtcct tccaaggcca ggtcagcatc tcagccgaca agcccatcag caccgcctac  240
ctgcagtgga gcaggctgaa ggcctcggac accgccatgt attactgtgc gagactaggg  300
aattggctgg tggactactg gggccaggga accctggtca ccgtctcctc ag          352

SEQ ID NO: 192           moltype = AA  length = 117
FEATURE                  Location/Qualifiers
source                   1..117
                         mol_type = protein
                         organism = Homo sapiens
```

```
SEQUENCE: 192
QVQLVESGAE VKKPGESLKI SCKGSGYSFT SYWIVWVRQM PGKGLEWMGI IYPGDSDTKY      60
SPSFQGQVSI SADKPISTAY LQWSRLKASD TAMYYCARLG NWLVDYWGQG TLVTVSS       117

SEQ ID NO: 193          moltype = DNA  length = 343
FEATURE                 Location/Qualifiers
source                  1..343
                        mol_type = other DNA
                        organism = Homo sapiens
SEQUENCE: 193
gatattgtga tgactcagtc tcctctctct ctgtccgtca cccctggaca gccggcctcc     60
atctcctgca agtctagtca gagcctcctg catagtgatg gaaagaccta tttgtattgg   120
tacctgcaga agccaggcca gcctccacag ctcctgatgt atgaagtttc caaccggttc   180
tctggagtgc cagataggtt cagtggcagc gggtcaggga cagacttcac acttaaaatc   240
agccgggtgg agtctgagga tgttggggtt tattactgca tgcaaagtat acagcttcct   300
cgcgggatca ccttcggcca agggacacga ctggagatta aac                     343

SEQ ID NO: 194          moltype = AA  length = 114
FEATURE                 Location/Qualifiers
source                  1..114
                        mol_type = protein
                        organism = Homo sapiens
SEQUENCE: 194
DIVMTQSPLS LSVTPGQPAS ISCKSSQSLL HSDGKTYLYW YLQKPGQPPQ LLMYEVSNRF     60
SGVPDRFSGS GSGTDFTLKI SRVESEDVGV YYCMQSIQLP RGITFGQGTR LEIK         114

SEQ ID NO: 195          moltype = AA  length = 8
FEATURE                 Location/Qualifiers
source                  1..8
                        mol_type = protein
                        organism = Homo sapiens
SEQUENCE: 195
GYSFTSYW                                                               8

SEQ ID NO: 196          moltype = AA  length = 8
FEATURE                 Location/Qualifiers
source                  1..8
                        mol_type = protein
                        organism = Homo sapiens
SEQUENCE: 196
IYPGDSDT                                                               8

SEQ ID NO: 197          moltype = AA  length = 10
FEATURE                 Location/Qualifiers
source                  1..10
                        mol_type = protein
                        organism = Homo sapiens
SEQUENCE: 197
ARLGNWLVDY                                                            10

SEQ ID NO: 198          moltype = AA  length = 11
FEATURE                 Location/Qualifiers
source                  1..11
                        mol_type = protein
                        organism = Homo sapiens
SEQUENCE: 198
QSLLHSDGKT Y                                                          11

SEQ ID NO: 199          moltype =     length =
SEQUENCE: 199
000

SEQ ID NO: 200          moltype = AA  length = 11
FEATURE                 Location/Qualifiers
source                  1..11
                        mol_type = protein
                        organism = Homo sapiens
SEQUENCE: 200
MQSIQLPRGI T                                                          11

SEQ ID NO: 201          moltype = DNA  length = 343
FEATURE                 Location/Qualifiers
source                  1..343
                        mol_type = other DNA
                        organism = Homo sapiens
SEQUENCE: 201
gaggtgcagc tggtggagtc tggaggaggc ttgatccagc ctgggggtc cctgagactc     60
tcctgtgcag cctctgggct caccgtcagt cgcaattaca tgagctgggt ccgccaggct   120
ccagggaagg ggctggagtg ggtctcactt atttatagcg gtggtagcac atactacgca   180
```

```
gactccgtga agggccgatt caccatctcc agagacaatt ccaagaacac gctgtatctt    240
caaatgaaca gcctgagagc cgaggacacg ccgtgtatt actgtgcgag agatctacgc    300
ggagaagtct ggggccaagg gacaatggtc accgtctctt cag                     343
```

```
SEQ ID NO: 202          moltype = AA   length = 114
FEATURE                 Location/Qualifiers
source                  1..114
                        mol_type = protein
                        organism = Homo sapiens
SEQUENCE: 202
EVQLVESGGG LIQPGGSLRL SCAASGLTVS RNYMSWVRQA PGKGLEWVSL IYSGGSTYYA    60
DSVKGRFTIS RDNSKNTLYL QMNSLRAEDT AVYYCARDLR GEVWGQGTMV TVSS         114
```

```
SEQ ID NO: 203          moltype = DNA   length = 322
FEATURE                 Location/Qualifiers
source                  1..322
                        mol_type = other DNA
                        organism = Homo sapiens
SEQUENCE: 203
gccatccaga tgacccagtc tccatcctcc ctgtctgcat ctgtaggaga cagagtcacc    60
atcacttgcc aggcgagtca ggacattagc aactttttaa attggtatca gcagaaacca   120
gggaaagccc ctaagctcct gatctacgat gcatccaatt tggaaacagg gtcccatca   180
aggttcagtg gaagtggatc tgggacagat tttactttca ccatcagtag cctgcagcct   240
gaagatattg caacatatta ctgtcaccag tatgataatc tccctcgaac gttcggccaa   300
gggaccaaag tggatatcaa ac                                            322
```

```
SEQ ID NO: 204          moltype = AA   length = 107
FEATURE                 Location/Qualifiers
source                  1..107
                        mol_type = protein
                        organism = Homo sapiens
SEQUENCE: 204
AIQMTQSPSS LSASVGDRVT ITCQASQDIS NFLNWYQQKP GKAPKLLIYD ASNLETGVPS    60
RFSGSGSGTD FTFTISSLQP EDIATYYCHQ YDNLPRTFGQ GTKVDIK                 107
```

```
SEQ ID NO: 205          moltype = AA   length = 8
FEATURE                 Location/Qualifiers
source                  1..8
                        mol_type = protein
                        organism = Homo sapiens
SEQUENCE: 205
GLTVSRNY                                                              8
```

```
SEQ ID NO: 206          moltype = AA   length = 7
FEATURE                 Location/Qualifiers
source                  1..7
                        mol_type = protein
                        organism = Homo sapiens
SEQUENCE: 206
IYSGGST                                                               7
```

```
SEQ ID NO: 207          moltype = AA   length = 8
FEATURE                 Location/Qualifiers
source                  1..8
                        mol_type = protein
                        organism = Homo sapiens
SEQUENCE: 207
ARDLRGEV                                                              8
```

```
SEQ ID NO: 208          moltype = AA   length = 6
FEATURE                 Location/Qualifiers
source                  1..6
                        mol_type = protein
                        organism = Homo sapiens
SEQUENCE: 208
QDISNF                                                                6
```

```
SEQ ID NO: 209          moltype =   length =
SEQUENCE: 209
000
```

```
SEQ ID NO: 210          moltype = AA   length = 9
FEATURE                 Location/Qualifiers
source                  1..9
                        mol_type = protein
                        organism = Homo sapiens
SEQUENCE: 210
HQYDNLPRT                                                             9
```

```
SEQ ID NO: 211            moltype = DNA  length = 372
FEATURE                   Location/Qualifiers
source                    1..372
                          mol_type = other DNA
                          organism = Homo sapiens
SEQUENCE: 211
gaggtgcagc tggtggagtc tgggggaggc ttggtacagc ctgggggtc cctgagactc    60
tcctgtgcag cctctggatt caccttcagt aactacgaca tgcactgggt ccgccaagct  120
acaggaaaag gtctggagtg ggtctcactt attggtactg ctggtgacac atactatcca  180
gactccgtga agggccgatt caccatctcc agagaaaatg ccaagaactc cttgtatctt  240
caaatgaaca gcctgagagc cggggacacg gctgtgtatt actgtgcaag agggcaacac  300
actcaaatcg gtcactacta ctactactac atggacgtct ggggcaaagg gaccacggtc  360
accgtctcct ca                                                      372

SEQ ID NO: 212            moltype = AA  length = 124
FEATURE                   Location/Qualifiers
source                    1..124
                          mol_type = protein
                          organism = Homo sapiens
SEQUENCE: 212
EVQLVESGGG LVQPGGSLRL SCAASGFTFS NYDMHWVRQA TGKGLEWVSL IGTAGDTYYP   60
DSVKGRFTIS RENAKNSLYL QMNSLRAGDT AVYYCARGQH TQIGHYYYYY MDVWGKGTTV  120
TVSS                                                               124

SEQ ID NO: 213            moltype = DNA  length = 328
FEATURE                   Location/Qualifiers
source                    1..328
                          mol_type = other DNA
                          organism = Homo sapiens
SEQUENCE: 213
gccatccgga tgacccagtc tccatcgtcc ctgtctgcat ctgtaggaga cagagtcacc   60
atcacttgcc gggcaagtca gagcattagc agctatttaa attggtatca gcagaaacca  120
gggaaagccc ctaagctcct gatctttgct gcatccagtt tgcaaagtgg ggtcccatca  180
aggttcagtg gcagtggatc tgggacagat tccactctaa ccatcagcag tctgcaacct  240
gaagattttg caacttacta ctgtcaacag agttacagta accctccgga gggcagtttt  300
ggccagggga ccaaagtgga gattaaac                                     328

SEQ ID NO: 214            moltype = AA  length = 109
FEATURE                   Location/Qualifiers
source                    1..109
                          mol_type = protein
                          organism = Homo sapiens
SEQUENCE: 214
AIRMTQSPSS LSASVGDRVT ITCRASQSIS SYLNWYQQKP GKAPKLLIFA ASSLQSGVPS   60
RFSGSGSGTD STLTISSLQP EDFATYYCQQ SYSNPPEGSF GQGTKVEIK              109

SEQ ID NO: 215            moltype = AA  length = 8
FEATURE                   Location/Qualifiers
source                    1..8
                          mol_type = protein
                          organism = Homo sapiens
SEQUENCE: 215
GFTFSNYD                                                             8

SEQ ID NO: 216            moltype = AA  length = 7
FEATURE                   Location/Qualifiers
source                    1..7
                          mol_type = protein
                          organism = Homo sapiens
SEQUENCE: 216
IGTAGDT                                                              7

SEQ ID NO: 217            moltype = AA  length = 18
FEATURE                   Location/Qualifiers
source                    1..18
                          mol_type = protein
                          organism = Homo sapiens
SEQUENCE: 217
ARGQHTQIGH YYYYYMDV                                                 18

SEQ ID NO: 218            moltype = AA  length = 6
FEATURE                   Location/Qualifiers
source                    1..6
                          mol_type = protein
                          organism = Homo sapiens
SEQUENCE: 218
QSISSY                                                               6

SEQ ID NO: 219            moltype =   length =
```

```
SEQUENCE: 219
000

SEQ ID NO: 220           moltype = AA  length = 11
FEATURE                  Location/Qualifiers
source                   1..11
                         mol_type = protein
                         organism = Homo sapiens
SEQUENCE: 220
QQSYSNPPEG S                                                              11

SEQ ID NO: 221           moltype = DNA  length = 361
FEATURE                  Location/Qualifiers
source                   1..361
                         mol_type = other DNA
                         organism = Homo sapiens
SEQUENCE: 221
gaagtgcagc tggtggagac tggaggaggc ttgatccagc ctgggggtc cctgagactc            60
tcctgtgcag cctctgggtt caccgtcagt agcaactaca tgagctgggt ccgccaggct          120
ccagggaagg gctgagtg gtctcagtt gtttatggcg gtggtaccac atactacgca            180
gactccgtga agggccgatt caccatctcc agagacaatt ccaagaacac gctgtatctt          240
caaatgaaca gcctgagagc cgaggacacg gccgtatatt actgtgcgac tgacaatgga          300
tacagctatg gtttttcatt tgactactgg ggccaggaa ccctggtcat cgtctcctca            360
g                                                                         361

SEQ ID NO: 222           moltype = AA  length = 120
FEATURE                  Location/Qualifiers
source                   1..120
                         mol_type = protein
                         organism = Homo sapiens
SEQUENCE: 222
EVQLVETGGG LIQPGGSLRL SCAASGFTVS SNYMSWVRQA PGKGLEWVSV VYGGTTYYA            60
DSVKGRFTIS RDNSKNTLYL QMNSLRAEDT AVYYCATDNG YSYGFSFDYW GQGTLVIVSS          120

SEQ ID NO: 223           moltype = DNA  length = 331
FEATURE                  Location/Qualifiers
source                   1..331
                         mol_type = other DNA
                         organism = Homo sapiens
SEQUENCE: 223
cagtctgtgc tgactcagcc tgcctccatg tctgggtctc ctggacagtc gatcaccatc           60
tcctgcactg gaaccagcag tgatgttggg ggttataacc ttgtctcctg gtaccaacag          120
cacccaggca aagcccccaa actcatgatt tatgagggca gtaagcggcc ctcaggggtt          180
tctaatcgct tctctggctc caagtctggc aacacggcct ccctgacaat ctctgggctc          240
caggctgagg acgaggctga ttattactgc tgctcatatg caggtagtag taattgggtg          300
ttcggcggag ggaccaagct gaccgtccta g                                        331

SEQ ID NO: 224           moltype = AA  length = 110
FEATURE                  Location/Qualifiers
source                   1..110
                         mol_type = protein
                         organism = Homo sapiens
SEQUENCE: 224
QSVLTQPASM SGSPGQSITI SCTGTSSDVG GYNLVSWYQQ HPGKAPKLMI YEGSKRPSGV           60
SNRFSGSKSG NTASLTISGL QAEDEADYYC CSYAGSSNWV FGGGTKLTVL                    110

SEQ ID NO: 225           moltype = AA  length = 8
FEATURE                  Location/Qualifiers
source                   1..8
                         mol_type = protein
                         organism = Homo sapiens
SEQUENCE: 225
GFTVSSNY                                                                    8

SEQ ID NO: 226           moltype = AA  length = 7
FEATURE                  Location/Qualifiers
source                   1..7
                         mol_type = protein
                         organism = Homo sapiens
SEQUENCE: 226
VYGGGTT                                                                     7

SEQ ID NO: 227           moltype = AA  length = 14
FEATURE                  Location/Qualifiers
source                   1..14
                         mol_type = protein
                         organism = Homo sapiens
SEQUENCE: 227
ATDNGYSYGF SFDY                                                            14
```

| SEQ ID NO: 228 | moltype = AA length = 9 |
| --- | --- |
| FEATURE | Location/Qualifiers |
| source | 1..9 |
| | mol_type = protein |
| | organism = Homo sapiens |

SEQUENCE: 228
SSDVGGYNL 9

| SEQ ID NO: 229 | moltype = length = |
| --- | --- |

SEQUENCE: 229
000

| SEQ ID NO: 230 | moltype = AA length = 10 |
| --- | --- |
| FEATURE | Location/Qualifiers |
| source | 1..10 |
| | mol_type = protein |
| | organism = Homo sapiens |

SEQUENCE: 230
CSYAGSSNWV 10

| SEQ ID NO: 231 | moltype = DNA length = 373 |
| --- | --- |
| FEATURE | Location/Qualifiers |
| source | 1..373 |
| | mol_type = other DNA |
| | organism = Homo sapiens |

SEQUENCE: 231
```
caggtgcagc tggtggagtc tggggctgag gtggagaagc ctggggcctc agtgaaggtc   60
tcctgcaagg cttctggata caccttcacc ggctactata tgcactgggt gcgacaggcc  120
cctggacaag ggcttgagtg gatgggatgg atcaaccctg tcagtggtgg cacaaactat  180
gcacagaagt ttcagggcag ggtcaccatg accagggaca cgtccatcag cacagcctac  240
atggacctga gcaggctgag atctgacgac acggccgtgt attactgtgc gagaggaacg  300
tattactatg atagtagtgg ttacatccca tttgactact ggggccaggg aaccctggtc  360
accgtctcct cag                                                     373
```

| SEQ ID NO: 232 | moltype = AA length = 124 |
| --- | --- |
| FEATURE | Location/Qualifiers |
| source | 1..124 |
| | mol_type = protein |
| | organism = Homo sapiens |

SEQUENCE: 232
```
QVQLVESGAE VEKPGASVKV SCKASGYTFT GYYMHWVRQA PGQGLEWMGW INPVSGGTNY   60
AQKFQGRVTM TRDTSISTAY MDLSRLRSDD TAVYYCARGT YYYDSSGYIP FDYWGQGTLV  120
TVSS                                                               124
```

| SEQ ID NO: 233 | moltype = DNA length = 331 |
| --- | --- |
| FEATURE | Location/Qualifiers |
| source | 1..331 |
| | mol_type = other DNA |
| | organism = Homo sapiens |

SEQUENCE: 233
```
cagtctgtgc tgactcagcc tgcctccgta tctgggtctc ctggacagtc gatcaccatc   60
tcctgcactg gaaccagcag tgatgttggg agttataacc ttgtctcctg gtaccaacag  120
cacccaggca aagcccccaa actcatgatt tatgagggca gtaagcggcc ctcagggggtt  180
tctaatcgct tctctggctc caagtctggc aacacggccc cctgacaat ctctgggctc  240
caggctgagg acgaggctga ttattactgc tgctcatatg caggtagtag cactttggta  300
ttcggcggag ggaccaagct gaccgtccta g                                 331
```

| SEQ ID NO: 234 | moltype = AA length = 110 |
| --- | --- |
| FEATURE | Location/Qualifiers |
| source | 1..110 |
| | mol_type = protein |
| | organism = Homo sapiens |

SEQUENCE: 234
```
QSVLTQPASV SGSPGQSITI SCTGTSSDVG SYNLVSWYQQ HPGKAPKLMI YEGSKRPSGV   60
SNRFSGSKSG NTASLTISGL QAEDEADYYC CSYAGSSTLV FGGGTKLTVL              110
```

| SEQ ID NO: 235 | moltype = AA length = 8 |
| --- | --- |
| FEATURE | Location/Qualifiers |
| source | 1..8 |
| | mol_type = protein |
| | organism = Homo sapiens |

SEQUENCE: 235
GYTFTGYY 8

| SEQ ID NO: 236 | moltype = AA length = 8 |
| --- | --- |
| FEATURE | Location/Qualifiers |
| source | 1..8 |
| | mol_type = protein |

```
                         organism = Homo sapiens
SEQUENCE: 236
INPISGGT                                                                       8

SEQ ID NO: 237           moltype = AA   length = 17
FEATURE                  Location/Qualifiers
source                   1..17
                         mol_type = protein
                         organism = Homo sapiens
SEQUENCE: 237
ARGTYYYDSS GYIPFDY                                                            17

SEQ ID NO: 238           moltype = AA   length = 9
FEATURE                  Location/Qualifiers
source                   1..9
                         mol_type = protein
                         organism = Homo sapiens
SEQUENCE: 238
SSDVGSYNL                                                                      9

SEQ ID NO: 239           moltype =     length =
SEQUENCE: 239
000

SEQ ID NO: 240           moltype = AA   length = 10
FEATURE                  Location/Qualifiers
source                   1..10
                         mol_type = protein
                         organism = Homo sapiens
SEQUENCE: 240
CSYAGSSTLV                                                                    10

SEQ ID NO: 241           moltype = DNA  length = 385
FEATURE                  Location/Qualifiers
source                   1..385
                         mol_type = other DNA
                         organism = Homo sapiens
SEQUENCE: 241
caggttcagc tggtgcagtc tgggtctgag ttgaagaagc ctggggcctc agtgaaggtt             60
tcctgcaagg cttctggata caccttcagt agctatgcta tgacttgggt gcgacaggcc            120
cctggacaag ggcttgagtg gatgggatgg atcaacacca acactgggaa cccaacgtat            180
gcccagggct tcacaggacg gtttgtcttc tccttggaca cctctgtcag cacggcatat            240
ctgcaaatca gcagcctaaa ggctgaggac actgccgtgt attactgtgc gagagctctg            300
ggatattgta gtagtaccag ctgctatccc gcttgggctg cttttgatat ctggggccaa            360
gggacaatgg tcaccgtctc ttcag                                                  385

SEQ ID NO: 242           moltype = AA   length = 128
FEATURE                  Location/Qualifiers
source                   1..128
                         mol_type = protein
                         organism = Homo sapiens
SEQUENCE: 242
QVQLVQSGSE LKKPGASVKV SCKASGYTFS SYAMTWVRQA PGQGLEWMGW INTNTGNPTY             60
AQGFTGRFVF SLDTSVSTAY LQISSLKAED TAVYYCARAL GYCSSTSCYP AWAAFDIWGQ            120
GTMVTVSS                                                                     128

SEQ ID NO: 243           moltype = DNA  length = 316
FEATURE                  Location/Qualifiers
source                   1..316
                         mol_type = other DNA
                         organism = Homo sapiens
SEQUENCE: 243
tcctatgagc tgactcagcc actctcagtg tcagtggccc tgggacagac ggccagtatt             60
acctgtgggg gaaacaacat tggaagtaaa aatgtgcact ggtaccagca gaagccaggc            120
caggcccctg tgctggtcat ctataggat agcaaccggc cctctgggat ccctgagcga             180
ttctctggct ccaactcggg gaacacggcc accctgacca tcagcagagc ccaagccggg            240
gatgaggctg actataactg tcaggtgtgg gacagcagcg tggtattcgg cggagggacc            300
aagctgaccg tcctag                                                            316

SEQ ID NO: 244           moltype = AA   length = 105
FEATURE                  Location/Qualifiers
source                   1..105
                         mol_type = protein
                         organism = Homo sapiens
SEQUENCE: 244
SYELTQPLSV SVALGQTASI TCGGNNIGSK NVHWYQQKPG QAPVLVIYRD SNRPSGIPER             60
FSGSNSGNTA TLTISRAQAG DEADYNCQVW DSSVVFGGGT KLTVL                            105

SEQ ID NO: 245           moltype = AA   length = 8
```

| | | |
|---|---|---|
| FEATURE | Location/Qualifiers | |
| source | 1..8 | |
| | mol_type = protein | |
| | organism = Homo sapiens | |
| SEQUENCE: 245 | | |
| GYTFSSYA | | 8 |
| | | |
| SEQ ID NO: 246 | moltype = AA length = 8 | |
| FEATURE | Location/Qualifiers | |
| source | 1..8 | |
| | mol_type = protein | |
| | organism = Homo sapiens | |
| SEQUENCE: 246 | | |
| INTNTGNP | | 8 |
| | | |
| SEQ ID NO: 247 | moltype = AA length = 21 | |
| FEATURE | Location/Qualifiers | |
| source | 1..21 | |
| | mol_type = protein | |
| | organism = Homo sapiens | |
| SEQUENCE: 247 | | |
| ARALGYCSST SCYPAWAAFD I | | 21 |
| | | |
| SEQ ID NO: 248 | moltype = AA length = 6 | |
| FEATURE | Location/Qualifiers | |
| source | 1..6 | |
| | mol_type = protein | |
| | organism = Homo sapiens | |
| SEQUENCE: 248 | | |
| NIGSKN | | 6 |
| | | |
| SEQ ID NO: 249 | moltype = length = | |
| SEQUENCE: 249 | | |
| 000 | | |
| | | |
| SEQ ID NO: 250 | moltype = AA length = 8 | |
| FEATURE | Location/Qualifiers | |
| source | 1..8 | |
| | mol_type = protein | |
| | organism = Homo sapiens | |
| SEQUENCE: 250 | | |
| QVWDSSVV | | 8 |
| | | |
| SEQ ID NO: 251 | moltype = DNA length = 358 | |
| FEATURE | Location/Qualifiers | |
| source | 1..358 | |
| | mol_type = other DNA | |
| | organism = Homo sapiens | |

SEQUENCE: 251
```
gaggtgcagc tggtggagtc tggaggaggc ttgatccagc cggggggtc cctgagactc    60
tcctgtgcag cctctgggct caccgtcagt agcaactaca tgagttgggt ccgccaggct   120
ccagggaagg ggctggagtg ggtctcagtt atttatagtg gtggtagcac gttctacgca   180
gactccgtga agggccgatt caccatctcc agagacaatt ccaagaacac gctgtatctt   240
caaatgaaca gcctgggagc cgaggacacg gccgtgtatt actgtgcgag aggagaaggt   300
agtcctggaa actggttcga ccctggggc cagggaaccc tggtcaccgt ctcctcag    358
```

| | | |
|---|---|---|
| SEQ ID NO: 252 | moltype = AA length = 119 | |
| FEATURE | Location/Qualifiers | |
| source | 1..119 | |
| | mol_type = protein | |
| | organism = Homo sapiens | |
| SEQUENCE: 252 | | |
| EVQLVESGGG LIQPGGSLRL SCAASGLTVS SNYMSWVRQA PGKGLEWVSV IYSGGSTFYA | | 60 |
| DSVKGRFTIS RDNSKNTLYL QMNSLGAEDT AVYYCAREG SPGNWFDPWG QGTLVTVSS | | 119 |
| | | |
| SEQ ID NO: 253 | moltype = DNA length = 322 | |
| FEATURE | Location/Qualifiers | |
| source | 1..322 | |
| | mol_type = other DNA | |
| | organism = Homo sapiens | |

SEQUENCE: 253
```
gatgttgtga tgactcagtc tccaggcacc ctgtctttgt ctccagggga aagagccacc    60
ctctcctgca gggccagtca gagtgttccc agcagctact tagcctggta ccagcagaaa   120
cctggccagg ctcccaggct cctcatctat ggtgcatcca ccagggccac tggcatccca   180
gacaggttca gtggcagtgg gtctgggaca gacttcactc tcaccatcag cagactggag   240
cctgaggatt ttgcagtgta ttactgtcag cactatgata cctcacccg tttcggcgga   300
gggaccaaag tggatatcaa ac                                             322
```

| | | |
|---|---|---|
| SEQ ID NO: 254 | moltype = AA length = 107 | |

-continued

```
FEATURE                 Location/Qualifiers
source                  1..107
                        mol_type = protein
                        organism = Homo sapiens
SEQUENCE: 254
DVVMTQSPGT LSLSPGERAT LSCRASQSVP SSYLAWYQQK PGQAPRLLIY GASTRATGIP     60
DRFSGSGSGT DFTLTISRLE PEDFAVYYCQ HYDTSPRFGG GTKVDIK                  107

SEQ ID NO: 255          moltype = AA   length = 8
FEATURE                 Location/Qualifiers
source                  1..8
                        mol_type = protein
                        organism = Homo sapiens
SEQUENCE: 255
GLTVSSNY                                                               8

SEQ ID NO: 256          moltype = AA   length = 7
FEATURE                 Location/Qualifiers
source                  1..7
                        mol_type = protein
                        organism = Homo sapiens
SEQUENCE: 256
IYSGGST                                                                7

SEQ ID NO: 257          moltype = AA   length = 13
FEATURE                 Location/Qualifiers
source                  1..13
                        mol_type = protein
                        organism = Homo sapiens
SEQUENCE: 257
ARGEGSPGNW FDP                                                        13

SEQ ID NO: 258          moltype = AA   length = 7
FEATURE                 Location/Qualifiers
source                  1..7
                        mol_type = protein
                        organism = Homo sapiens
SEQUENCE: 258
QSVPSSY                                                                7

SEQ ID NO: 259          moltype =   length =
SEQUENCE: 259
000

SEQ ID NO: 260          moltype = AA   length = 8
FEATURE                 Location/Qualifiers
source                  1..8
                        mol_type = protein
                        organism = Homo sapiens
SEQUENCE: 260
QHYDTSPR                                                               8

SEQ ID NO: 261          moltype = DNA   length = 370
FEATURE                 Location/Qualifiers
source                  1..370
                        mol_type = other DNA
                        organism = Homo sapiens
SEQUENCE: 261
caggtccagc tggtacagtc tgggcctgag gtgaagaagc ctgggacctc agtgaaggtc     60
tcctgcaagg cttctggatt cacctttact acctctgctg tgcagtgggt gcgacaggct    120
cgtggacaac gccttgagtg gataggatgg atcgtcgttg gcagtggtaa cacaaactac    180
gcacagaagt tccaggaaag agtcaccatt accaggaca tgtccacaac cacagcctac    240
atggagctga gcagcctgag atccgaggac acggccgtgt atttctgtgc ggcgcctcat    300
tgtaatagta ccagctgcta tgacgctttt gatatctggg gccaagggac aatggtcacc    360
gtctcttcag                                                           370

SEQ ID NO: 262          moltype = AA   length = 123
FEATURE                 Location/Qualifiers
source                  1..123
                        mol_type = protein
                        organism = Homo sapiens
SEQUENCE: 262
QVQLVQSGPE VKKPGTSVKV SCKASGFTFT TSAVQWVRQA RGQRLEWIGW IVVGSGNTNY     60
AQKFQERVTI TRDMSTTTAY MELSSLRSED TAVYFCAAPH CNSTSCYDAF DIWGQGTMVT    120
VSS                                                                  123

SEQ ID NO: 263          moltype = DNA   length = 325
FEATURE                 Location/Qualifiers
source                  1..325
```

```
                        mol_type = other DNA
                        organism = Homo sapiens
SEQUENCE: 263
gacatccaga tgacccagtc tccaggcacc ctgtctttgt ctccagggga aggagccacc    60
ctctcctgca gggccagtca gagtgttagc agcagctact tagcctggta ccagcagaaa   120
cctggccagg ctcccaggct cctcatctat ggtgcatcta gtggggccac tggcatccca   180
gacagattca gtggcagtgg gtctgggaca gacttcactc tcaccatcag cagactggag   240
cctgaagatt ttgcagtgta ttactgtcag cagtatggta gctcacctta cactttggc   300
caggggacca aggtggaaat caaac                                         325

SEQ ID NO: 264          moltype = AA length = 108
FEATURE                 Location/Qualifiers
source                  1..108
                        mol_type = protein
                        organism = Homo sapiens
SEQUENCE: 264
DIQMTQSPGT LSLSPGEGAT LSCRASQSVS SSYLAWYQQK PGQAPRLLIY GASSGATGIP    60
DRFSGSGSGT DFTLTISRLE PEDFAVYYCQ QYGSSPYTFG QGTKVEIK                108

SEQ ID NO: 265          moltype = AA length = 8
FEATURE                 Location/Qualifiers
source                  1..8
                        mol_type = protein
                        organism = Homo sapiens
SEQUENCE: 265
GFTFTTSA                                                              8

SEQ ID NO: 266          moltype = AA length = 8
FEATURE                 Location/Qualifiers
source                  1..8
                        mol_type = protein
                        organism = Homo sapiens
SEQUENCE: 266
IVVGSGNT                                                              8

SEQ ID NO: 267          moltype = AA length = 16
FEATURE                 Location/Qualifiers
source                  1..16
                        mol_type = protein
                        organism = Homo sapiens
SEQUENCE: 267
AAPHCNSTSC YDAFDI                                                    16

SEQ ID NO: 268          moltype = AA length = 7
FEATURE                 Location/Qualifiers
source                  1..7
                        mol_type = protein
                        organism = Homo sapiens
SEQUENCE: 268
QSVSSSY                                                               7

SEQ ID NO: 269          moltype =    length =
SEQUENCE: 269
000

SEQ ID NO: 270          moltype = AA length = 9
FEATURE                 Location/Qualifiers
source                  1..9
                        mol_type = protein
                        organism = Homo sapiens
SEQUENCE: 270
QQYGSSPYT                                                             9

SEQ ID NO: 271          moltype = DNA length = 352
FEATURE                 Location/Qualifiers
source                  1..352
                        mol_type = other DNA
                        organism = Homo sapiens
SEQUENCE: 271
caggtgcagc tggtggagtc tggaggaggc ttgatccagc ctgggggtc cctgagactc     60
tcctgtgcag cctctgggct caccgtcaat aggaactaca tgagctggat ccgccaggct   120
ccagggaagg ggctggagtg ggtctcagtt atttatagcg gtggtagtac atttacgca    180
gactccgtga agggccgatt caccatctcc agagacaatt ccaagaacac actgtctctt   240
caaatgaaca gcctgagagc cgaggacacg gccatttatt actgtgcgag agacttctac   300
gagggttctt ttgatatctg gggccaaggg acaatggtca ccgtctcttc ag           352

SEQ ID NO: 272          moltype = AA length = 117
FEATURE                 Location/Qualifiers
source                  1..117
```

```
                            mol_type = protein
                            organism = Homo sapiens
SEQUENCE: 272
QVQLVESGGG LIQPGGSLRL SCAASGLTVN RNYMSWIRQA PGKGLEWVSV IYSGGSTFYA    60
DSVKGRFTIS RDNSKNTLSL QMNSLRAEDT AIYYCARDFY EGSFDIWGQG TMVTVSS      117

SEQ ID NO: 273              moltype = DNA   length = 325
FEATURE                     Location/Qualifiers
source                      1..325
                            mol_type = other DNA
                            organism = Homo sapiens
SEQUENCE: 273
gccatccagt tgacccagtc tccttccttc ctgtctgcat ctataggaga cagagtcacc    60
atcacttgcc gggccagtca gggcattagc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg catcttatta ctgtcaacag cttaatagtt accccgctcc ggttttcggc   300
cctgggacca aagtggatat caaac                                         325

SEQ ID NO: 274              moltype = AA    length = 108
FEATURE                     Location/Qualifiers
source                      1..108
                            mol_type = protein
                            organism = Homo sapiens
SEQUENCE: 274
AIQLTQSPSF LSASIGDRVT ITCRASQGIS SYLAWYQQKP GKAPKLLIYA ASTLQSGVPS    60
RFSGSGSGTE FTLTISSLQP EDFASYYCQQ LNSYPAPVFG PGTKVDIK                108

SEQ ID NO: 275              moltype = AA    length = 8
FEATURE                     Location/Qualifiers
source                      1..8
                            mol_type = protein
                            organism = Homo sapiens
SEQUENCE: 275
GLTVNRNY                                                              8

SEQ ID NO: 276              moltype = AA    length = 7
FEATURE                     Location/Qualifiers
source                      1..7
                            mol_type = protein
                            organism = Homo sapiens
SEQUENCE: 276
IYSGGST                                                               7

SEQ ID NO: 277              moltype = AA    length = 11
FEATURE                     Location/Qualifiers
source                      1..11
                            mol_type = protein
                            organism = Homo sapiens
SEQUENCE: 277
ARDFYEGSFD I                                                         11

SEQ ID NO: 278              moltype = AA    length = 6
FEATURE                     Location/Qualifiers
source                      1..6
                            mol_type = protein
                            organism = Homo sapiens
SEQUENCE: 278
QGISSY                                                                6

SEQ ID NO: 279              moltype =       length =
SEQUENCE: 279
000

SEQ ID NO: 280              moltype = AA    length = 10
FEATURE                     Location/Qualifiers
source                      1..10
                            mol_type = protein
                            organism = Homo sapiens
SEQUENCE: 280
QQLNSYPAPV                                                           10

SEQ ID NO: 281              moltype = DNA   length = 370
FEATURE                     Location/Qualifiers
source                      1..370
                            mol_type = other DNA
                            organism = Homo sapiens
SEQUENCE: 281
caggtacagc tggtgcagtc tggggctgag gtgaagaagc ctggggcctc agtgaaggtc    60
```

```
tcctgcaagg cttctggtta catctttatc agatatggta ttagctgggt gcgacaggcc   120
cctggacaag ggcttgagtg gatgggatgg atcagcgcta acaatggtta cacaaactat   180
gcacagaagc tccagggcag agtcaccatg accacagaca catccacgag cacagcctac   240
atggagctga ggagcctgag atctgacgac acggccgtgt attactgtgc gagagatggg   300
ggtattttga ctggttatct cgactacttt gaccactggg gccagggaac cctggtcacc   360
gtctcctcag                                                          370

SEQ ID NO: 282         moltype = AA  length = 123
FEATURE                Location/Qualifiers
source                 1..123
                       mol_type = protein
                       organism = Homo sapiens
SEQUENCE: 282
QVQLVQSGAE VKKPGASVKV SCKASGYIFI RYGISWVRQA PGQGLEWMGW ISANNGYTNY   60
AQKLQGRVTM TTDTSTSTAY MELRSLRSDD TAVYYCARDG GILTGYLDYF DHWGQGTLVT   120
VSS                                                                 123

SEQ ID NO: 283         moltype = DNA  length = 325
FEATURE                Location/Qualifiers
source                 1..325
                       mol_type = other DNA
                       organism = Homo sapiens
SEQUENCE: 283
gacatccaga tgacccagtc tccatcctcc ctgtctgcat ctgtaggaga cagactcacc   60
atcacttgcc gggcaagtca gagcattgcc agctatttaa attggtatca gcagaaacca   120
gggaaagccc ctaagctcct gatctatgct gcatccactt tgcaaagtgg ggtcccatca   180
aggttcagtg gcagtggatc tgggacagat ttcactctca ccatcagcag tctgcaacct   240
gaagattttg caacttacca ctgtcaacag agttacagta ccctcggaat cactttcggc   300
cctgggacca agtggatat caaac                                          325

SEQ ID NO: 284         moltype = AA  length = 108
FEATURE                Location/Qualifiers
source                 1..108
                       mol_type = protein
                       organism = Homo sapiens
SEQUENCE: 284
DIQMTQSPSS LSASVGDRLT ITCRASQSIA SYLNWYQQKP GKAPKLLIYA ASSLQSGVPS   60
RFSGSGSGTD FTLTISSLQP EDFATYHCQQ SYSTLGITFG PGTKVDIK                108

SEQ ID NO: 285         moltype = AA  length = 8
FEATURE                Location/Qualifiers
source                 1..8
                       mol_type = protein
                       organism = Homo sapiens
SEQUENCE: 285
GYIFIRYG                                                            8

SEQ ID NO: 286         moltype = AA  length = 8
FEATURE                Location/Qualifiers
source                 1..8
                       mol_type = protein
                       organism = Homo sapiens
SEQUENCE: 286
ISANNGYT                                                            8

SEQ ID NO: 287         moltype = AA  length = 16
FEATURE                Location/Qualifiers
source                 1..16
                       mol_type = protein
                       organism = Homo sapiens
SEQUENCE: 287
ARDGGILTGY LDYFDH                                                   16

SEQ ID NO: 288         moltype = AA  length = 6
FEATURE                Location/Qualifiers
source                 1..6
                       mol_type = protein
                       organism = Homo sapiens
SEQUENCE: 288
QSIASY                                                              6

SEQ ID NO: 289         moltype =   length =
SEQUENCE: 289
000

SEQ ID NO: 290         moltype = AA  length = 10
FEATURE                Location/Qualifiers
source                 1..10
                       mol_type = protein
```

```
                        organism = Homo sapiens
SEQUENCE: 290
QQSYSTLGIT                                                              10

SEQ ID NO: 291          moltype = DNA  length = 367
FEATURE                 Location/Qualifiers
source                  1..367
                        mol_type = other DNA
                        organism = Homo sapiens
SEQUENCE: 291
caggtgcagc tggtggagtc tgggggaggc ttggtccagc ctgggggtc cctgagactc         60
tcctgtgcag cctctggatt ccccttagt atcattgga tgagctgggt ccgccaggct        120
ccagggaagg ggctggagtg ggtggccaac ataaagcaag atggaagtga aaatactat        180
gtggactctg tgaagggccg attcaccatc tccagagaca acgccaagaa ctcactgtat       240
ctgcacatga acagcctgag aggcgaggac acggctgtgt attactgtgc gagccgatat       300
tacgattttc gaccggaggc ttggtttgac tactgggcc agggaaccct ggtcaccgtc        360
tcctcag                                                                367

SEQ ID NO: 292          moltype = AA  length = 122
FEATURE                 Location/Qualifiers
source                  1..122
                        mol_type = protein
                        organism = Homo sapiens
SEQUENCE: 292
QVQLVESGGG LVQPGGSLRL SCAASGFPFS IYWMSWVRQA PGKGLEWVAN IKQDGSEKYY        60
VDSVKGRFTI SRDNAKNSLY LHMNSLRGED TAVYYCASRY YDFRPEAWFD YWGQGTLVTV      120
SS                                                                     122

SEQ ID NO: 293          moltype = DNA  length = 343
FEATURE                 Location/Qualifiers
source                  1..343
                        mol_type = other DNA
                        organism = Homo sapiens
SEQUENCE: 293
gatattgtga tgacccagac tccactctcc tcacctgtca cccttggaca gccggcctcc        60
atctcctgca ggtctagtca aagcctcgta cacaggatg aaacaccta cttgagctgg        120
cttcagcaga ggccaggcca gcctccaaga ctcctaattt ataagatttc taacggttc        180
tctggggtcc cagacagatt cagtggcagt ggggcaggga cagatttcac actgaaaatc       240
agcagggtgg aagctgagga tgtcggggtt tattactgca tgcaagctac acaatttcct       300
catggtaca cttttggcca ggggaccaag gtggagatca aac                         343

SEQ ID NO: 294          moltype = AA  length = 114
FEATURE                 Location/Qualifiers
source                  1..114
                        mol_type = protein
                        organism = Homo sapiens
SEQUENCE: 294
DIVMTQTPLS SPVTLGQPAS ISCRSSQSLV HRDGNTYLSW LQQRPGQPPR LLIYKISNRF        60
SGVPDRFSGS GAGTDFTLKI SRVEAEDVGV YYCMQATQFP HGYTFGQGTK VEIK             114

SEQ ID NO: 295          moltype = AA  length = 8
FEATURE                 Location/Qualifiers
source                  1..8
                        mol_type = protein
                        organism = Homo sapiens
SEQUENCE: 295
GFPFSIYW                                                                 8

SEQ ID NO: 296          moltype = AA  length = 8
FEATURE                 Location/Qualifiers
source                  1..8
                        mol_type = protein
                        organism = Homo sapiens
SEQUENCE: 296
IKQDGSEK                                                                 8

SEQ ID NO: 297          moltype = AA  length = 15
FEATURE                 Location/Qualifiers
source                  1..15
                        mol_type = protein
                        organism = Homo sapiens
SEQUENCE: 297
ASRYYDFRPE AWFDY                                                        15

SEQ ID NO: 298          moltype = AA  length = 11
FEATURE                 Location/Qualifiers
source                  1..11
                        mol_type = protein
                        organism = Homo sapiens
```

```
SEQUENCE: 298
QSLVHRDGNT Y                                                              11

SEQ ID NO: 299          moltype =    length =
SEQUENCE: 299
000

SEQ ID NO: 300          moltype = AA   length = 11
FEATURE                 Location/Qualifiers
source                  1..11
                        mol_type = protein
                        organism = Homo sapiens
SEQUENCE: 300
MQATQFPHGY T                                                              11

SEQ ID NO: 301          moltype = DNA  length = 355
FEATURE                 Location/Qualifiers
source                  1..355
                        mol_type = other DNA
                        organism = Homo sapiens
SEQUENCE: 301
caggtgcagc tgcaggagtc tgggggaggc ttggtccagc ctggggggtc cctgagactc           60
tcctgttcag cctctggatt caccgtcagt agcaactaca tgacctgggt ccgccaggct          120
ccagggaagg ggctggagtg ggtctcagtt atttatagcg gtggtagcac attctacgca          180
gactccgtga aggcagatt caccatctcc agagacaatt ccaagaacac gctgtatctt           240
caaatgaaca gcctgagagc cgaggacacc gctgtgtatt actgtgcgag agatctggaa          300
gaggccgggg gatttgacta ctggggccag ggaaccctgg tcaccgtctc ctcag               355

SEQ ID NO: 302          moltype = AA   length = 118
FEATURE                 Location/Qualifiers
source                  1..118
                        mol_type = protein
                        organism = Homo sapiens
SEQUENCE: 302
QVQLQESGGG LVQPGGSLRL SCSASGFTVS SNYMTWVRQA PGKGLEWVSV IYSGGSTFYA           60
DSVKGRFTIS RDNSKNTLYL QMNSLRAEDT AVYYCARDLE EAGGFDYWGQ GTLVTVSS            118

SEQ ID NO: 303          moltype = DNA  length = 325
FEATURE                 Location/Qualifiers
source                  1..325
                        mol_type = other DNA
                        organism = Homo sapiens
SEQUENCE: 303
gaaattgtgt tgacgcagtc tccaggcacc ctgtctttgt ctccagggga aaaagtcacc           60
ctctcctgca gggccagtca gagtgttagc agcacctact tagcctggta ccagcagaaa         120
cctggccagg ctcccaggct cctcatctat ggtgcatcca gcagggccac tggcgtccca         180
gacaggttcc gtggcagtgg gtctgggaca gacttcactc tcaccatcag cagactggag         240
cctgaagatt ttgcagtgta ttactgtcag cagtatggta gctcgctgta cacttttggc         300
caggggacca agtggatat caaac                                                325

SEQ ID NO: 304          moltype = AA   length = 108
FEATURE                 Location/Qualifiers
source                  1..108
                        mol_type = protein
                        organism = Homo sapiens
SEQUENCE: 304
EIVLTQSPGT LSLSPGEKVT LSCRASQSVS STYLAWYQQK PGQAPRLLIY GASSRATGVP           60
DRFRGSGSGT DFTLTISRLE PEDFAVYYCQ QYGSSLYTFG QGTKVDIK                       108

SEQ ID NO: 305          moltype = AA   length = 8
FEATURE                 Location/Qualifiers
source                  1..8
                        mol_type = protein
                        organism = Homo sapiens
SEQUENCE: 305
GFTVSSNY                                                                   8

SEQ ID NO: 306          moltype = AA   length = 7
FEATURE                 Location/Qualifiers
source                  1..7
                        mol_type = protein
                        organism = Homo sapiens
SEQUENCE: 306
IYSGGST                                                                    7

SEQ ID NO: 307          moltype = AA   length = 12
FEATURE                 Location/Qualifiers
source                  1..12
                        mol_type = protein
```

```
                         organism = Homo sapiens
SEQUENCE: 307
ARDLEEAGGF DY                                                        12

SEQ ID NO: 308           moltype = AA   length = 7
FEATURE                  Location/Qualifiers
source                   1..7
                         mol_type = protein
                         organism = Homo sapiens
SEQUENCE: 308
QSVSSTY                                                              7

SEQ ID NO: 309           moltype =      length =
SEQUENCE: 309
000

SEQ ID NO: 310           moltype = AA   length = 9
FEATURE                  Location/Qualifiers
source                   1..9
                         mol_type = protein
                         organism = Homo sapiens
SEQUENCE: 310
QQYGSSLYT                                                            9

SEQ ID NO: 311           moltype = DNA  length = 385
FEATURE                  Location/Qualifiers
source                   1..385
                         mol_type = other DNA
                         organism = Homo sapiens
SEQUENCE: 311
cagctgcagc tgcaggagtc gggcccagga ctggtgaagc cttcggagac cctgtccctc    60
acctgcactg tctccggtga ctccgtcagt aattactact ggagctggat ccggcagccc   120
gccgggaagg gactggagtg gattgggcgt atctatacca gtgggagcac caactacaac   180
ccctccctca agagtcgagt caccatgtca gtagacacgt ccaagaacca gttctccctg   240
aagctgagct ctgtgaccgc cgcggacacg gccgtgtatt actgtgcgag agatcaccgg   300
gcttcccggt atagcagtgg ctggtacgaa tggtggaact gcttcgaccc ctggggccag   360
ggaaccctgg tcaccgtctc ctcag                                         385

SEQ ID NO: 312           moltype = AA   length = 128
FEATURE                  Location/Qualifiers
source                   1..128
                         mol_type = protein
                         organism = Homo sapiens
SEQUENCE: 312
QLQLQESGPG LVKPSETLSL TCTVSGDSVS NYYWSWIRQP AGKGLEWIGR IYTSGSTNYN    60
PSLKSRVTMS VDTSKNQFSL KLSSVTAADT AVYYCARDHR ASRYSSGWYE WWNCFDPWGQ   120
GTLVTVSS                                                            128

SEQ ID NO: 313           moltype = DNA  length = 325
FEATURE                  Location/Qualifiers
source                   1..325
                         mol_type = other DNA
                         organism = Homo sapiens
SEQUENCE: 313
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcaacag tctgcaacct   240
gaagattttg caacttacta ctgtcaacag agttacagta ccccgcgct cactttcggc   300
ggagggacca aagtggatat caaac                                         325

SEQ ID NO: 314           moltype = AA   length = 108
FEATURE                  Location/Qualifiers
source                   1..108
                         mol_type = protein
                         organism = Homo sapiens
SEQUENCE: 314
DIQMTQSPSS LSASVGDRVT ITCRASQSIS SYLNWYQQKP GKAPKLLIYA ASSLQSGVPS    60
RFSGSGSGTD FTLTINSLQP EDFATYYCQQ SYSTPALTFG GGTKVDIK                108

SEQ ID NO: 315           moltype = AA   length = 8
FEATURE                  Location/Qualifiers
source                   1..8
                         mol_type = protein
                         organism = Homo sapiens
SEQUENCE: 315
GDSVSNYY                                                             8

SEQ ID NO: 316           moltype = AA   length = 7
```

```
FEATURE              Location/Qualifiers
source               1..7
                     mol_type = protein
                     organism = Homo sapiens
SEQUENCE: 316
IYTSGST                                                              7

SEQ ID NO: 317       moltype = AA  length = 22
FEATURE              Location/Qualifiers
source               1..22
                     mol_type = protein
                     organism = Homo sapiens
SEQUENCE: 317
ARDHRASRYS SGWYEWWNCF DP                                            22

SEQ ID NO: 318       moltype = AA  length = 6
FEATURE              Location/Qualifiers
source               1..6
                     mol_type = protein
                     organism = Homo sapiens
SEQUENCE: 318
QSISSY                                                               6

SEQ ID NO: 319       moltype =     length =
SEQUENCE: 319
000

SEQ ID NO: 320       moltype = AA  length = 10
FEATURE              Location/Qualifiers
source               1..10
                     mol_type = protein
                     organism = Homo sapiens
SEQUENCE: 320
QQSYSTPALT                                                          10

SEQ ID NO: 321       moltype = DNA  length = 367
FEATURE              Location/Qualifiers
source               1..367
                     mol_type = other DNA
                     organism = Homo sapiens
SEQUENCE: 321
caggttcagc tggtgcagtc tggggctgag gtgaagaagc tggggcctc  agtgaaggtc    60
tcctgcaagg cttctggata cacccttcacc ggctactata tgcactgggt gcgacaggcc  120
cctggacaag gcttgagtg  gatgggatgg atcaaccct  acagtggtgg cacaaactat   180
acacagaagt tcagggcag  ggtcaccatg accaggaca  cgtccatcag cacagcctac   240
atggagctga gcaggctgag atctgacgac acggccgtgt attcctgtgc gagagatatg   300
gcgtttagta tggttcgggg ttcctttgac tactgggcc  agggaaccct ggtcaccgtc   360
tcctcag                                                            367

SEQ ID NO: 322       moltype = AA  length = 122
FEATURE              Location/Qualifiers
source               1..122
                     mol_type = protein
                     organism = Homo sapiens
SEQUENCE: 322
QVQLVQSGAE VKKPGASVKV SCKASGYTFT GYYMHWVRQA PGQGLEWMGW INPNSGGTNY    60
TQKFQGRVTM TRDTSISTAY MELSRLRSDD TAVYSCARDM AFSMVRGSFD YWGQGTLVTV   120
SS                                                                 122

SEQ ID NO: 323       moltype = DNA  length = 331
FEATURE              Location/Qualifiers
source               1..331
                     mol_type = other DNA
                     organism = Homo sapiens
SEQUENCE: 323
caggctgtgc tgactcagcc tcctccgcg  tccgggtctc ctggacagtc agtcaccatc    60
tcctgcactg gaaccagcag tgacgttggt ggttataact atgtctcctg gtaccaacag   120
cacccaggca aagcccccaa actcatgatt tatgaggtca gtaagcggcc ctcagggqtc   180
cctgatcgct tctctggctc caagtctggc aacacggccg ccctgaccgt ctctgggctc   240
caggctgagg atgaggctga ttattactgc agctcatatg caggcagcaa ccattgggtg   300
ttcggcggag ggaccaagct gaccgtccta g                                 331

SEQ ID NO: 324       moltype = AA  length = 110
FEATURE              Location/Qualifiers
source               1..110
                     mol_type = protein
                     organism = Homo sapiens
SEQUENCE: 324
QAVLTQPPSA SGSPGQSVTI SCTGTSSDVG GYNYVSWYQQ HPGKAPKLMI YEVSKRPSGV    60
```

```
PDRFSGSKSG NTASLTVSGL QAEDEADYYC SSYAGSNHWV FGGGTKLTVL          110

SEQ ID NO: 325            moltype = AA  length = 8
FEATURE                   Location/Qualifiers
source                    1..8
                          mol_type = protein
                          organism = Homo sapiens
SEQUENCE: 325
GYTFTGYY                                                        8

SEQ ID NO: 326            moltype = AA  length = 8
FEATURE                   Location/Qualifiers
source                    1..8
                          mol_type = protein
                          organism = Homo sapiens
SEQUENCE: 326
INPNSGGT                                                        8

SEQ ID NO: 327            moltype = AA  length = 15
FEATURE                   Location/Qualifiers
source                    1..15
                          mol_type = protein
                          organism = Homo sapiens
SEQUENCE: 327
ARDMAFSMVR GSFDY                                                15

SEQ ID NO: 328            moltype = AA  length = 9
FEATURE                   Location/Qualifiers
source                    1..9
                          mol_type = protein
                          organism = Homo sapiens
SEQUENCE: 328
SSDVGGYNY                                                       9

SEQ ID NO: 329            moltype =     length =
SEQUENCE: 329
000

SEQ ID NO: 330            moltype = AA  length = 10
FEATURE                   Location/Qualifiers
source                    1..10
                          mol_type = protein
                          organism = Homo sapiens
SEQUENCE: 330
SSYAGSNHWV                                                      10

SEQ ID NO: 331            moltype = DNA  length = 358
FEATURE                   Location/Qualifiers
source                    1..358
                          mol_type = other DNA
                          organism = Homo sapiens
SEQUENCE: 331
caggtgcagc tggtgcagtc tgggcctgag gtgaagaagc ctgggacctc agtgaaggtc    60
tcctgcaagg cgtctggatt caccttact  agctctgcta tgcagtgggt gcgacaggct   120
cgtggacaac gccttgagtg gataggatgg atcgtcgttg gcagtggcaa cacaaactac   180
gcacagaagt tccaggaaag agtcaccatt accaggaca tgtccacaag cacagcctac    240
atggagctga gcagcctgag atccgaggac acggccgtgt attattgtgc ggccggccgt   300
ggctacaatt cggactttga ctactggggc cagggaaccc tggtcaccgt ctcctcag     358

SEQ ID NO: 332            moltype = AA  length = 119
FEATURE                   Location/Qualifiers
source                    1..119
                          mol_type = protein
                          organism = Homo sapiens
SEQUENCE: 332
QVQLVQSGPE VKKPGTSVKV SCKASGFTLT SSAMQWVRQA RGQRLEWIGW IVVGSGNTNY    60
AQKFQERVTI TRDMSTSTAY MELSSLRSED TAVYYCAAGR GYNSDFDYWG QGTLVTVSS    119

SEQ ID NO: 333            moltype = DNA  length = 325
FEATURE                   Location/Qualifiers
source                    1..325
                          mol_type = other DNA
                          organism = Homo sapiens
SEQUENCE: 333
gccatccgga tgacccagtc tccaggcacc ctgtctttgt ctccagggga aagagccacc    60
ctctcctgca gggccagtca gagtgttagc agcagctact tagcctgta ccagcagaga   120
cctggccagg ctcccaggct cctcatctat ggtacatcca gcagggccac tggcatccca   180
gacaggttca gtggcagtgg gtctgggaca gacttcactc tcaccatcag cagactggag   240
cctgaagatt ttgcagtgta ttactgtcag cagtatggtt actcagtgta cactttggc    300
```

```
cagggggacca aagtggatat caaac                                          325

SEQ ID NO: 334          moltype = AA  length = 108
FEATURE                 Location/Qualifiers
source                  1..108
                        mol_type = protein
                        organism = Homo sapiens
SEQUENCE: 334
AIRMTQSPGT LSLSPGERAT LSCRASQSVS SSYLAWYQQR PGQAPRLLIY GTSSRATGIP     60
DRFSGSGSGT DFTLTISRLE PEDFAVYYCQ QYGYSVYTFG QGTKVDIK                 108

SEQ ID NO: 335          moltype = AA  length = 8
FEATURE                 Location/Qualifiers
source                  1..8
                        mol_type = protein
                        organism = Homo sapiens
SEQUENCE: 335
GFTLTSSA                                                               8

SEQ ID NO: 336          moltype = AA  length = 8
FEATURE                 Location/Qualifiers
source                  1..8
                        mol_type = protein
                        organism = Homo sapiens
SEQUENCE: 336
IVVGSGNT                                                               8

SEQ ID NO: 337          moltype = AA  length = 12
FEATURE                 Location/Qualifiers
source                  1..12
                        mol_type = protein
                        organism = Homo sapiens
SEQUENCE: 337
AAGRGYNSDF DY                                                         12

SEQ ID NO: 338          moltype = AA  length = 7
FEATURE                 Location/Qualifiers
source                  1..7
                        mol_type = protein
                        organism = Homo sapiens
SEQUENCE: 338
QSVSSSY                                                                7

SEQ ID NO: 339          moltype =     length =
SEQUENCE: 339
000

SEQ ID NO: 340          moltype = AA  length = 9
FEATURE                 Location/Qualifiers
source                  1..9
                        mol_type = protein
                        organism = Homo sapiens
SEQUENCE: 340
QQYGYSVYT                                                              9

SEQ ID NO: 341          moltype = DNA  length = 367
FEATURE                 Location/Qualifiers
source                  1..367
                        mol_type = other DNA
                        organism = Homo sapiens
SEQUENCE: 341
caggtgcagc tggtggagtc tgaggctgag gtgaagaagc ctggggcctc agtgaaggtt     60
tcctgcaagg catctggata caccttcacc agctactata tgcactgggt gcgacaggcc    120
cctggacaag ggcttcagtg gatgggaata atcaaccccta gtgctggtag cacaagctac    180
gcacagaagt tccagggcag agtcaccatg accacggaca cgtccacgac cacagtctac    240
atggagctga gcagcctgag atctgaggac acggccgtgt attactgtgc gagagattct    300
gtactagtac cagctgctaa tgcttttgat atctggggcc aagggacaat ggtcaccgtc    360
tcttcag                                                              367

SEQ ID NO: 342          moltype = AA  length = 122
FEATURE                 Location/Qualifiers
source                  1..122
                        mol_type = protein
                        organism = Homo sapiens
SEQUENCE: 342
QVQLVESEAE VKKPGASVKV SCKASGYTFT SYYMHWVRQA PGQGLQWMGI INPSAGSTSY     60
AQKFQGRVTM TTDTSTTTVY MELSSLRSED TAVYYCARDS VLVPAANAFD IWGQGTMVTV    120
SS                                                                   122
```

```
SEQ ID NO: 343           moltype = DNA  length = 322
FEATURE                  Location/Qualifiers
source                   1..322
                         mol_type = other DNA
                         organism = Homo sapiens
SEQUENCE: 343
gaaatagtga tgacgcagtc tccagccacc ctgtctttgt ctccagggga aagagccacc   60
ctctcctgca gggccagtca gagtgttagt agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtcgcaact ggctattcac tttcggccct  300
gggaccaaag tggatatcaa ac                                           322

SEQ ID NO: 344           moltype = AA  length = 107
FEATURE                  Location/Qualifiers
source                   1..107
                         mol_type = protein
                         organism = Homo sapiens
SEQUENCE: 344
EIVMTQSPAT LSLSPGERAT LSCRASQSVS SYLAWYQQKP GQAPRLLIYD ASNRATGIPA   60
RFSGSGSGTD FTLTISSLEP EDFAVYYCQQ RRNWLFTFGP GTKVDIK                107

SEQ ID NO: 345           moltype = AA  length = 8
FEATURE                  Location/Qualifiers
source                   1..8
                         mol_type = protein
                         organism = Homo sapiens
SEQUENCE: 345
GYTFTSYY                                                             8

SEQ ID NO: 346           moltype = AA  length = 8
FEATURE                  Location/Qualifiers
source                   1..8
                         mol_type = protein
                         organism = Homo sapiens
SEQUENCE: 346
INPSAGST                                                             8

SEQ ID NO: 347           moltype = AA  length = 15
FEATURE                  Location/Qualifiers
source                   1..15
                         mol_type = protein
                         organism = Homo sapiens
SEQUENCE: 347
ARDSVLVPAA NAFDI                                                    15

SEQ ID NO: 348           moltype = AA  length = 6
FEATURE                  Location/Qualifiers
source                   1..6
                         mol_type = protein
                         organism = Homo sapiens
SEQUENCE: 348
QSVSSY                                                               6

SEQ ID NO: 349           moltype =     length =
SEQUENCE: 349
000

SEQ ID NO: 350           moltype = AA  length = 9
FEATURE                  Location/Qualifiers
source                   1..9
                         mol_type = protein
                         organism = Homo sapiens
SEQUENCE: 350
QQRRNWLFT                                                            9

SEQ ID NO: 351           moltype = DNA  length = 358
FEATURE                  Location/Qualifiers
source                   1..358
                         mol_type = other DNA
                         organism = Homo sapiens
SEQUENCE: 351
caggtgcagc tggtgcagtc tggggctgag gtgaagaagc ctggggcctc agtgaaggtt   60
tcctgcaagg cttctggaga caccttcact agctatactc tgcattgggt gcgccaggcc  120
cccggacaaa ggcttgagtg gatgggatgg atcaacgctg caatggttac acaaaatat   180
tcacagaagt tccagggcag agtcaccatt accaggaca catccgcgag cacagcctac  240
atggagctga gcagcctgag atctgaagac acggctgtgt attactgtgc gaatgtact   300
atgatagtag actactttga ctactggggc cagggaaccc tggtcaccgt ctcctcag    358
```

```
SEQ ID NO: 352          moltype = AA  length = 119
FEATURE                 Location/Qualifiers
source                  1..119
                        mol_type = protein
                        organism = Homo sapiens
SEQUENCE: 352
QVQLVQSGAE VKKPGASVKV SCKASGDTFT SYTLHWVRQA PGQRLEWMGW INAGNGYTKY   60
SQKFQGRVTI TRDTSASTAY MELSSLRSED TAVYYCAKCT MIVDYFDYWG QGTLVTVSS    119

SEQ ID NO: 353          moltype = DNA  length = 322
FEATURE                 Location/Qualifiers
source                  1..322
                        mol_type = other DNA
                        organism = Homo sapiens
SEQUENCE: 353
gccatccgga tgacccagtc tccttccacc ctgtctgcat ctgtaggaga cagagtcacc   60
atcacttgcc gggccagtca gagtattagt ggctggttgg cctggtatca gcagaaacca  120
gagaaagccc ctaagctcct gatctatgat gcctccaatt tggaaagtgg ggtcccatca  180
aggttcagcg gcagtggatc tgggacagaa ttcactctca ccatcaacag cctgcagcct  240
gatgattttg caacttatta ctgccaacag tataatagtt acccgtggac gttcggccaa  300
gggaccaaag tggatatcaa ac                                           322

SEQ ID NO: 354          moltype = AA  length = 107
FEATURE                 Location/Qualifiers
source                  1..107
                        mol_type = protein
                        organism = Homo sapiens
SEQUENCE: 354
AIRMTQSPST LSASVGDRVT ITCRASQSIS GWLAWYQQKP EKAPKLLIYD ASNLESGVPS   60
RFSGSGSGTE FTLTINSLQP DDFATYYCQQ YNSYPWTFGQ GTKVDIK                 107

SEQ ID NO: 355          moltype = AA  length = 8
FEATURE                 Location/Qualifiers
source                  1..8
                        mol_type = protein
                        organism = Homo sapiens
SEQUENCE: 355
GDTFTSYT                                                            8

SEQ ID NO: 356          moltype = AA  length = 8
FEATURE                 Location/Qualifiers
source                  1..8
                        mol_type = protein
                        organism = Homo sapiens
SEQUENCE: 356
INAGNGYT                                                            8

SEQ ID NO: 357          moltype = AA  length = 12
FEATURE                 Location/Qualifiers
source                  1..12
                        mol_type = protein
                        organism = Homo sapiens
SEQUENCE: 357
AKCTMIVDYF DY                                                       12

SEQ ID NO: 358          moltype = AA  length = 6
FEATURE                 Location/Qualifiers
source                  1..6
                        mol_type = protein
                        organism = Homo sapiens
SEQUENCE: 358
QSISGW                                                              6

SEQ ID NO: 359          moltype =     length =
SEQUENCE: 359
000

SEQ ID NO: 360          moltype = AA  length = 9
FEATURE                 Location/Qualifiers
source                  1..9
                        mol_type = protein
                        organism = Homo sapiens
SEQUENCE: 360
QQYNSYPWT                                                           9

SEQ ID NO: 361          moltype = DNA  length = 357
FEATURE                 Location/Qualifiers
source                  1..357
                        mol_type = other DNA
```

```
                        organism = Homo sapiens
SEQUENCE: 361
gaggtgcagc tggtgcagtc tggggctgag gtgaagaagc ctggggcctc agtgaaggtc    60
tcctgcaagg cttctgggta caccttcacc agttatgata tcaactgggt gcgacaggcc   120
actgtgacaag ggcttgagtg gatgggatgg atgaaccctc acagtgatac cacaggctat  180
gcacagaagt tccagggcag agtcaccatg accaggaaca cctccataac cacagcctac   240
atggagctga gcagcctgag atctgaggac acggccgtgt attactgtgc tcagggaccc   300
atagcagtga actacatgga cgtctggggc aaagggacca cggtcaccgt ctcctca      357

SEQ ID NO: 362          moltype = AA  length = 119
FEATURE                 Location/Qualifiers
source                  1..119
                        mol_type = protein
                        organism = Homo sapiens
SEQUENCE: 362
EVQLVQSGAE VKKPGASVKV SCKASGYTFT SYDINWVRQA TGQGLEWMGW MNPHSDTTGY    60
AQKFQGRVTM TRNTSITTAY MELSSLRSED TAVYYCAQGP IAVNYMDVWG KGTTVTVSS   119

SEQ ID NO: 363          moltype = DNA  length = 325
FEATURE                 Location/Qualifiers
source                  1..325
                        mol_type = other DNA
                        organism = Homo sapiens
SEQUENCE: 363
cagcctgtgc tgactcagcc accctcagtg tcagtggccc caggaaagac ggccaggatt    60
acctgtgggg gaagcaacat tggaagtaaa agtgtgcact ggtaccagca gaagccaggc   120
caggcccctg tgctgatcat ctattatgat agcgaccggc cctcagggat ccctgagcga   180
ttctctggct ccaactctgg gaacacggcc accctgacca tcagcagggt cgaagccggg   240
gatgaggccg acttttactg tcaggtgtgg gatagtagta ctgatcatgt ggtattcggc   300
ggagggacca agctgaccgt cctag                                         325

SEQ ID NO: 364          moltype = AA  length = 108
FEATURE                 Location/Qualifiers
source                  1..108
                        mol_type = protein
                        organism = Homo sapiens
SEQUENCE: 364
QPVLTQPPSV SVAPGKTARI TCGGSNIGSK SVHWYQQKPG QAPVLIIYYD SDRPSGIPER    60
FSGSNSGNTA TLTISRVEAG DEADFYCQVW DSSTDHVVFG GGTKLTVL              108

SEQ ID NO: 365          moltype = AA  length = 8
FEATURE                 Location/Qualifiers
source                  1..8
                        mol_type = protein
                        organism = Homo sapiens
SEQUENCE: 365
GYTFTSYD                                                              8

SEQ ID NO: 366          moltype = AA  length = 8
FEATURE                 Location/Qualifiers
source                  1..8
                        mol_type = protein
                        organism = Homo sapiens
SEQUENCE: 366
MNPHSDTT                                                              8

SEQ ID NO: 367          moltype = AA  length = 12
FEATURE                 Location/Qualifiers
source                  1..12
                        mol_type = protein
                        organism = Homo sapiens
SEQUENCE: 367
AQGPIAVNYM DV                                                        12

SEQ ID NO: 368          moltype = AA  length = 6
FEATURE                 Location/Qualifiers
source                  1..6
                        mol_type = protein
                        organism = Homo sapiens
SEQUENCE: 368
NIGSKS                                                                6

SEQ ID NO: 369          moltype =     length =
SEQUENCE: 369
000

SEQ ID NO: 370          moltype = AA  length = 11
FEATURE                 Location/Qualifiers
source                  1..11
```

```
                        mol_type = protein
                        organism = Homo sapiens
SEQUENCE: 370
QVWDSSTDHV V                                                        11

SEQ ID NO: 371          moltype = DNA  length = 376
FEATURE                 Location/Qualifiers
source                  1..376
                        mol_type = other DNA
                        organism = Homo sapiens
SEQUENCE: 371
gaggtgcagc tggtggagtc tgggggaggc ttggtcaagc ctggagagtc cctgagactc      60
tcctgtgcag cctctggatt caccttcagt gactactaca tgacctggat ccgccaggct     120
ccagggaagg ggctggagtg ggtttcatac attaggagta gtggtcatac tatatactac     180
gcagactctg tgaagggccg attcaccatc tccagggaca cgccaagaa ctcactgtat      240
ctacaaatga acagcctgag agtcgaggac acggccgtgt attactgtgc gagaggaggg     300
gttttacgat ttttggagtg gcctctcaat gcttttgata tctggggcca agggacaatg     360
gtcaccgtct cttcag                                                   376

SEQ ID NO: 372          moltype = AA  length = 125
FEATURE                 Location/Qualifiers
source                  1..125
                        mol_type = protein
                        organism = Homo sapiens
SEQUENCE: 372
EVQLVESGGG LVKPGESLRL SCAASGFTFS DYYMTWIRQA PGKGLEWVSY IRSSGHTIYY      60
ADSVKGRFTI SRDNAKNSLY LQMNSLRVED TAVYYCARGG VLRFLEWPLN AFDIWGQGTM     120
VTVSS                                                               125

SEQ ID NO: 373          moltype = DNA  length = 322
FEATURE                 Location/Qualifiers
source                  1..322
                        mol_type = other DNA
                        organism = Homo sapiens
SEQUENCE: 373
gacatccagt tgacccagtc tccatcctcc ctgtctgcat ctgtaggaga cagagtcacc      60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacaatg ccctcgggac gttcggccaa    300
gggaccaagg tggagatcaa ac                                            322

SEQ ID NO: 374          moltype = AA  length = 107
FEATURE                 Location/Qualifiers
source                  1..107
                        mol_type = protein
                        organism = Homo sapiens
SEQUENCE: 374
DIQLTQSPSS LSASVGDRVT ITCRASQGIS NYLAWYQQKP GKVPKLLIYA ASTLQSGVPS      60
RFSGSGSGTD FTLTISSLQP EDVATYYCQK YNNALGTFGQ GTKVEIK                  107

SEQ ID NO: 375          moltype = AA  length = 8
FEATURE                 Location/Qualifiers
source                  1..8
                        mol_type = protein
                        organism = Homo sapiens
SEQUENCE: 375
GFTFSDYY                                                             8

SEQ ID NO: 376          moltype = AA  length = 8
FEATURE                 Location/Qualifiers
source                  1..8
                        mol_type = protein
                        organism = Homo sapiens
SEQUENCE: 376
IRSSGHTI                                                             8

SEQ ID NO: 377          moltype = AA  length = 18
FEATURE                 Location/Qualifiers
source                  1..18
                        mol_type = protein
                        organism = Homo sapiens
SEQUENCE: 377
ARGGVLRFLE WPLNAFDI                                                 18

SEQ ID NO: 378          moltype = AA  length = 6
FEATURE                 Location/Qualifiers
source                  1..6
                        mol_type = protein
```

```
                        organism = Homo sapiens
SEQUENCE: 378
QGISNY                                                                      6

SEQ ID NO: 379          moltype =    length =
SEQUENCE: 379
000

SEQ ID NO: 380          moltype = AA   length = 9
FEATURE                 Location/Qualifiers
source                  1..9
                        mol_type = protein
                        organism = Homo sapiens
SEQUENCE: 380
QKYNNALGT                                                                   9

SEQ ID NO: 381          moltype = DNA  length = 364
FEATURE                 Location/Qualifiers
source                  1..364
                        mol_type = other DNA
                        organism = Homo sapiens
SEQUENCE: 381
gaggtgcagc tggtgcagtc tggggctgag gtgaagaagc ctggggcctc agtgaaggtc           60
tcctgcaagg cttctggata caccttcacc ggctactata tgcactgggt gcgacaggcc          120
cctgacaagg gcttgagtg gatgggatgg atcagcccta cagtggtgg cacaaactat            180
gcacagaagt ttcagggcag ggtcaccatg accagggaca cgtccatcac cacagcctac          240
atggacctga gcaggctgag atctgacgac acggccgtgt attactgtgc gagaggttat          300
tactatgaag ccctcgatgc ttttgatatc tggggccaag ggacaatggt caccgtctct          360
tcag                                                                      364

SEQ ID NO: 382          moltype = AA   length = 121
FEATURE                 Location/Qualifiers
source                  1..121
                        mol_type = protein
                        organism = Homo sapiens
SEQUENCE: 382
EVQLVQSGAE VKKPGASVKV SCKASGYTFT GYYMHWVRQA PGQGLEWMGW ISPNSGGTNY           60
AQKFQGRVTM TRDTSITTAY MDLSRLRSDD TAVYYCARGY YYEALDAFDI WGQGTMVTVS          120
S                                                                         121

SEQ ID NO: 383          moltype = DNA  length = 331
FEATURE                 Location/Qualifiers
source                  1..331
                        mol_type = other DNA
                        organism = Homo sapiens
SEQUENCE: 383
cagtctgtcg tgacgcagcc tgcctccgtg tctgggtctc ctggacagtc gatcaccatc           60
tcctgcactg gaaccagcag tgacgttggt ggttataact ttgtctcctg gtaccaacag          120
cacccaggca aagcccccaa actcatgatt tatgaggtca gtaatcggcc ctcaggggtt          180
tctaatcgct tctctggctc caagtctggc atcacggcct ccctgaccat ctctgggctc          240
caggctgagg acgaggctga ttattactgc aactcatata caagcaacag tactcgggta          300
ttcggcggag ggaccaagct gaccgtccta g                                         331

SEQ ID NO: 384          moltype = AA   length = 110
FEATURE                 Location/Qualifiers
source                  1..110
                        mol_type = protein
                        organism = Homo sapiens
SEQUENCE: 384
QSVVTQPASV SGSPGQSITI SCTGTSSDVG GYNFVSWYQQ HPGKAPKLMI YEVSNRPSGV           60
SNRFSGSKSG ITASLTISGL QAEDEADYYC NSYTSNSTRV FGGGTKLTVL                    110

SEQ ID NO: 385          moltype = AA   length = 8
FEATURE                 Location/Qualifiers
source                  1..8
                        mol_type = protein
                        organism = Homo sapiens
SEQUENCE: 385
GYTFTGYY                                                                    8

SEQ ID NO: 386          moltype = AA   length = 8
FEATURE                 Location/Qualifiers
source                  1..8
                        mol_type = protein
                        organism = Homo sapiens
SEQUENCE: 386
ISPNSGGT                                                                    8

SEQ ID NO: 387          moltype = AA   length = 14
```

-continued

```
FEATURE                 Location/Qualifiers
source                  1..14
                        mol_type = protein
                        organism = Homo sapiens
SEQUENCE: 387
ARGYYYEALD AFDI                                                            14

SEQ ID NO: 388          moltype = AA  length = 9
FEATURE                 Location/Qualifiers
source                  1..9
                        mol_type = protein
                        organism = Homo sapiens
SEQUENCE: 388
SSDVGGYNF                                                                   9

SEQ ID NO: 389          moltype =   length =
SEQUENCE: 389
000

SEQ ID NO: 390          moltype = AA  length = 10
FEATURE                 Location/Qualifiers
source                  1..10
                        mol_type = protein
                        organism = Homo sapiens
SEQUENCE: 390
NSYTSNSTRV                                                                 10

SEQ ID NO: 391          moltype = DNA  length = 382
FEATURE                 Location/Qualifiers
source                  1..382
                        mol_type = other DNA
                        organism = Homo sapiens
SEQUENCE: 391
caggtgcagc tggtggagtc tgggggaggc ttggtccagc ctggggggtc cctgagactc           60
tcctgtgcag cctctggatt caccgtcagt agcaactaca tgacctgggt ccgccaggct          120
ccagggaagg ggctggagtg ggtctcagtt atttatagcg gtggtagcac atactacgca          180
gactccgtga agggcagatt caccatctcc agagacaatt ccaagaacac gctatatctt          240
caaatgaaca gcctgagagc cgacgacacg gctgtatatt actgtgcgag agactctaca          300
gccgattacg atttttggag tggttattat gtaggtgctt tcatatctg gggccaaggg           360
acaatggtca ccgtctcttc ag                                                   382

SEQ ID NO: 392          moltype = AA  length = 127
FEATURE                 Location/Qualifiers
source                  1..127
                        mol_type = protein
                        organism = Homo sapiens
SEQUENCE: 392
QVQLVESGGG LVQPGGSLRL SCAASGFTVS SNYMTWVRQA PGKGLEWVSV IYSGGSTYYA           60
DSVKGRFTIS RDNSKNTLYL QMNSLRADDT AVYYCARDST ADYDFWSGYY VGAFHIWGQG          120
TMVTVSS                                                                    127

SEQ ID NO: 393          moltype = DNA  length = 331
FEATURE                 Location/Qualifiers
source                  1..331
                        mol_type = other DNA
                        organism = Homo sapiens
SEQUENCE: 393
cagactgtgc tgactcagcc tgcctccgtg tctgggtctc ctggacagtc gatcaccatc           60
tcctgcactg gaaccagcag tgacgttggt ggttacaact atgtctcctg gtaccaacag          120
cacccaggca aagcccccaa actcatgatt tatgaggtca ctaagcggcc ctcaggggtc          180
cctgatcgct tctctggctc caagtctggc aacacggcct ccctgaccgt ctctgggctc          240
caggctgagg atgaggctga ttattactgc agctcatatg caggcagcaa caattgggtg          300
ttcggcggag ggaccaagct gaccgtccta g                                         331

SEQ ID NO: 394          moltype = AA  length = 110
FEATURE                 Location/Qualifiers
source                  1..110
                        mol_type = protein
                        organism = Homo sapiens
SEQUENCE: 394
QTVLTQPASV SGSPGQSITI SCTGTSSDVG GYNYVSWYQQ HPGKAPKLMI YEVTKRPSGV           60
PDRFSGSKSG NTASLTVSGL QAEDEADYYC SSYAGSNNWV FGGGTKLTVL                     110

SEQ ID NO: 395          moltype = AA  length = 8
FEATURE                 Location/Qualifiers
source                  1..8
                        mol_type = protein
                        organism = Homo sapiens
SEQUENCE: 395
```

-continued

```
GFTVSSNY                                                                    8

SEQ ID NO: 396          moltype = AA  length = 7
FEATURE                 Location/Qualifiers
source                  1..7
                        mol_type = protein
                        organism = Homo sapiens
SEQUENCE: 396
IYSGGST                                                                     7

SEQ ID NO: 397          moltype = AA  length = 21
FEATURE                 Location/Qualifiers
source                  1..21
                        mol_type = protein
                        organism = Homo sapiens
SEQUENCE: 397
ARDSTADYDF WSGYYVGAFH I                                                    21

SEQ ID NO: 398          moltype = AA  length = 9
FEATURE                 Location/Qualifiers
source                  1..9
                        mol_type = protein
                        organism = Homo sapiens
SEQUENCE: 398
SSDVGGYNY                                                                   9

SEQ ID NO: 399          moltype =     length =
SEQUENCE: 399
000

SEQ ID NO: 400          moltype = AA  length = 10
FEATURE                 Location/Qualifiers
source                  1..10
                        mol_type = protein
                        organism = Homo sapiens
SEQUENCE: 400
SSYAGSNNWV                                                                 10

SEQ ID NO: 401          moltype = DNA  length = 370
FEATURE                 Location/Qualifiers
source                  1..370
                        mol_type = other DNA
                        organism = Homo sapiens
SEQUENCE: 401
gaggtgcagc tggtggagtc gggcccagga ctggtgaagc cttcggagac cctgtccctc           60
acctgcactg tctctggtgg gtccatcagc agtagtagtc actactgggg ctggatccgc          120
cagcccccag ggaagggct ggagtggatt gggagtattt attatagtga gagtgcctac           180
tacaacccgt ccctcaagag tcgagtcacc atgtcaatag acacgtccaa gaaccagttc          240
tccctgaagc tgaactctgt gaccgccgcg gacacggccg tgtattactg tgcgagagtc          300
actgagcctc ggtggacttc ttgttacttt gactactggg gccagggaac cctggtcacc          360
gtctcctcag                                                                 370

SEQ ID NO: 402          moltype = AA  length = 123
FEATURE                 Location/Qualifiers
source                  1..123
                        mol_type = protein
                        organism = Homo sapiens
SEQUENCE: 402
EVQLVESGPG LVKPSETLSL TCTVSGGSIS SSHYWGWIR QPPGKGLEWI GSIYYSESAY            60
YNPSLKSRVT MSIDTSKNQF SLKLNSVTAA DTAVYYCARV TEPRWTSCYF DYWGQGTLVT          120
VSS                                                                       123

SEQ ID NO: 403          moltype = DNA  length = 325
FEATURE                 Location/Qualifiers
source                  1..325
                        mol_type = other DNA
                        organism = Homo sapiens
SEQUENCE: 403
gaaatagtga tgacgcagtc tccagccacc ctgtctttgt ctccagggga aagagccacc           60
ctctcctgca ggaccagtca gagtgttacc agctacttag cctggtacca acagagacct          120
ggccaggctc ccaggctcct catctatgat gcatccgaca gggccactgg catcccagcc          180
aggttcagtg gcagtgggtc tgggacagac ttcactctca ccatcagcaa cctagagcct          240
gaagattttg cagtttatta ctgtcagctg cgtagcaact ggcctccgat caccttcggc          300
caagggacac gactggagac taaac                                                325

SEQ ID NO: 404          moltype = AA  length = 108
FEATURE                 Location/Qualifiers
source                  1..108
                        mol_type = protein
```

```
                        organism = Homo sapiens
SEQUENCE: 404
EIVMTQSPAT LSLSPGERAT LSCRTSQSVT SYLAWYQQRP GQAPRLLIYD ASDRATGIPA    60
RFSGSGSGTD FTLTISNLEP EDFAVYYCQL RSNWPPITFG QGTRLETK                108

SEQ ID NO: 405          moltype = AA  length = 10
FEATURE                 Location/Qualifiers
source                  1..10
                        mol_type = protein
                        organism = Homo sapiens
SEQUENCE: 405
GGSISSSSHY                                                           10

SEQ ID NO: 406          moltype = AA  length = 7
FEATURE                 Location/Qualifiers
source                  1..7
                        mol_type = protein
                        organism = Homo sapiens
SEQUENCE: 406
IYYSESA                                                              7

SEQ ID NO: 407          moltype = AA  length = 15
FEATURE                 Location/Qualifiers
source                  1..15
                        mol_type = protein
                        organism = Homo sapiens
SEQUENCE: 407
ARVTEPRWTS CYFDY                                                     15

SEQ ID NO: 408          moltype = AA  length = 6
FEATURE                 Location/Qualifiers
source                  1..6
                        mol_type = protein
                        organism = Homo sapiens
SEQUENCE: 408
QSVTSY                                                               6

SEQ ID NO: 409          moltype =    length =
SEQUENCE: 409
000

SEQ ID NO: 410          moltype = AA  length = 10
FEATURE                 Location/Qualifiers
source                  1..10
                        mol_type = protein
                        organism = Homo sapiens
SEQUENCE: 410
QLRSNWPPIT                                                           10

SEQ ID NO: 411          moltype = DNA  length = 370
FEATURE                 Location/Qualifiers
source                  1..370
                        mol_type = other DNA
                        organism = Homo sapiens
SEQUENCE: 411
gaagtgcagc tggtggagtc gggcccagga ctggtgaagc cttcggagac cctgtccctc    60
acctgcactg tctctggggg ctccatcagc agtagtagtt actactgggg ctggatccgc   120
cagcccccag gaaggggct ggagtggatt gggagtatct attatagtgg gagcacctac    180
tacaacccgt ccctcaagag tcgagtcacc atatcagtag acacgtccaa gaaccagttc   240
tccctgaagc tgagctctgt gaccgccgcg gacacggccg tgtttttctg tgcgagagag   300
aggagcgctc ctctcgcggg caactggttc gacccctggg gccaggaac cctggtcacc    360
gtctcttcag                                                          370

SEQ ID NO: 412          moltype = AA  length = 123
FEATURE                 Location/Qualifiers
source                  1..123
                        mol_type = protein
                        organism = Homo sapiens
SEQUENCE: 412
EVQLVESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVFFCARE RSAPLAGNWF DPWGQGTLVT   120
VSS                                                                 123

SEQ ID NO: 413          moltype = DNA  length = 325
FEATURE                 Location/Qualifiers
source                  1..325
                        mol_type = other DNA
                        organism = Homo sapiens
SEQUENCE: 413
```

```
gacatccaga tgacccagtc tccatccttc ctgtctgcat ctgtaggaga cagagtcacc    60
atcacttgcc gggccagtca gggcattagc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatactt acccttcgat caccttcggc   300
caagggacac gactggagat taaac                                         325

SEQ ID NO: 414          moltype = AA  length = 108
FEATURE                 Location/Qualifiers
source                  1..108
                        mol_type = protein
                        organism = Homo sapiens
SEQUENCE: 414
DIQMTQSPSF LSASVGDRVT ITCRASQGIS SYLAWYQQKP GKAPKLLIYA ASTLQSGVPS    60
RFSGSGSGTE FTLTISSLQP EDFATYYCQQ LNTYPSITFG QGTRLEIK               108

SEQ ID NO: 415          moltype = AA  length = 10
FEATURE                 Location/Qualifiers
source                  1..10
                        mol_type = protein
                        organism = Homo sapiens
SEQUENCE: 415
GGSISSSSYY                                                           10

SEQ ID NO: 416          moltype = AA  length = 7
FEATURE                 Location/Qualifiers
source                  1..7
                        mol_type = protein
                        organism = Homo sapiens
SEQUENCE: 416
IYYSGST                                                               7

SEQ ID NO: 417          moltype = AA  length = 15
FEATURE                 Location/Qualifiers
source                  1..15
                        mol_type = protein
                        organism = Homo sapiens
SEQUENCE: 417
ARERSAPLAG NWFDP                                                     15

SEQ ID NO: 418          moltype = AA  length = 6
FEATURE                 Location/Qualifiers
source                  1..6
                        mol_type = protein
                        organism = Homo sapiens
SEQUENCE: 418
QGISSY                                                                6

SEQ ID NO: 419          moltype =    length =
SEQUENCE: 419
000

SEQ ID NO: 420          moltype = AA  length = 10
FEATURE                 Location/Qualifiers
source                  1..10
                        mol_type = protein
                        organism = Homo sapiens
SEQUENCE: 420
QQLNTYPSIT                                                           10

SEQ ID NO: 421          moltype = DNA  length = 369
FEATURE                 Location/Qualifiers
source                  1..369
                        mol_type = other DNA
                        organism = Homo sapiens
SEQUENCE: 421
gaagtgcagc tggtggagtc tgggggaggc gtggtccagc ctgggaggcc cctgagactc    60
tcctgtgcag cctctggatt ccccttcagt aactatggca tgcactgggt ccgccaggct   120
ccaggcaagg ggctggaatg ggtggcagtt atatggtatg atggaagtaa taaatactat   180
gcagactccg tgaagggccg attcaccatc tccagagaca attccaagaa cacgctgtat   240
ctgcaaatga acaacctgag agctgaggac acggctatat attactgtgc gaaagatggg   300
tacacggccc actactacta ctactacatg gacgtctggg gcaaagggac cacggtcacc   360
gtctcctca                                                          369

SEQ ID NO: 422          moltype = AA  length = 123
FEATURE                 Location/Qualifiers
source                  1..123
                        mol_type = protein
                        organism = Homo sapiens
```

```
SEQUENCE: 422
EVQLVESGGG VVQPGRPLRL SCAASGFPFS NYGMHWVRQA PGKGLEWVAV IWYDGSNKYY    60
ADSVKGRFTI SRDNSKNTLY LQMNNLRAED TAIYYCAKDG YTAHYYYYYM DVWGKGTTVT   120
VSS                                                                123

SEQ ID NO: 423          moltype = DNA  length = 328
FEATURE                 Location/Qualifiers
source                  1..328
                        mol_type = other DNA
                        organism = Homo sapiens
SEQUENCE: 423
gccatccagt tgacccagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctaatctat ggtgcatcca gcagggccac tggcatccca   180
ggcaggttca gtggcagtgg gtctgggaca gacttcactc tcaccatcag cagactggag   240
cctgaagatt ttgcagtgta ttactgtcag cagtatggta gctcacctgg gatcactttc   300
ggcggaggga ccaaagtgga tatcaaac                                      328

SEQ ID NO: 424          moltype = AA  length = 109
FEATURE                 Location/Qualifiers
source                  1..109
                        mol_type = protein
                        organism = Homo sapiens
SEQUENCE: 424
AIQLTQSPGT LSLSPGERAT LSCRASQSVS SSYLAWYQQK PGQAPRLLIY GASSRATGIP    60
GRFSGSGSGT DFTLTISRLE PEDFAVYYCQ QYGSSPGITF GGGTKVDIK               109

SEQ ID NO: 425          moltype = AA  length = 8
FEATURE                 Location/Qualifiers
source                  1..8
                        mol_type = protein
                        organism = Homo sapiens
SEQUENCE: 425
GFPFSNYG                                                              8

SEQ ID NO: 426          moltype = AA  length = 8
FEATURE                 Location/Qualifiers
source                  1..8
                        mol_type = protein
                        organism = Homo sapiens
SEQUENCE: 426
IWYDGSNK                                                              8

SEQ ID NO: 427          moltype = AA  length = 16
FEATURE                 Location/Qualifiers
source                  1..16
                        mol_type = protein
                        organism = Homo sapiens
SEQUENCE: 427
AKDGYTAHYY YYYMDV                                                    16

SEQ ID NO: 428          moltype = AA  length = 7
FEATURE                 Location/Qualifiers
source                  1..7
                        mol_type = protein
                        organism = Homo sapiens
SEQUENCE: 428
QSVSSSY                                                               7

SEQ ID NO: 429          moltype =   length =
SEQUENCE: 429
000

SEQ ID NO: 430          moltype = AA  length = 10
FEATURE                 Location/Qualifiers
source                  1..10
                        mol_type = protein
                        organism = Homo sapiens
SEQUENCE: 430
QQYGSSPGIT                                                           10

SEQ ID NO: 431          moltype = DNA  length = 372
FEATURE                 Location/Qualifiers
source                  1..372
                        mol_type = other DNA
                        organism = Homo sapiens
SEQUENCE: 431
gaagtgcagc tggtggagtc tgggggaggc gtggtccagc ctgggaggtc cctgagactc    60
tcctgtgcag cctctggatt caccttcagt aactatggca tacactgggt ccgccaggct   120
```

```
ccaggcaagg ggctggagtg ggtggcagtt atttcatatg atggaagtca taaatattat    180
gcagactctg tgaagggccg attcaccatc tccagagaca attccaagaa cacgctatat    240
ctgcaaatga acagcctgaa aactgaggac acggctgtgt attactgtgc gaaagatagt    300
tcagctgcta ttccctacta ctactacggt atggacgtct ggggccaagg gaccacggtc    360
accgtctctt ca                                                        372
```

```
SEQ ID NO: 432          moltype = AA   length = 124
FEATURE                 Location/Qualifiers
source                  1..124
                        mol_type = protein
                        organism = Homo sapiens
SEQUENCE: 432
EVQLVESGGG VVQPGRSLRL SCAASGFTFS NYGIHWVRQA PGKGLEWVAV ISYDGSHKYY     60
ADSVKGRFTI SRDNSKNTLY LQMNSLKTED TAVYYCAKDS SAAIPYYYYG MDVWGQGTTV    120
TVSS                                                                 124

SEQ ID NO: 433          moltype = DNA  length = 340
FEATURE                 Location/Qualifiers
source                  1..340
                        mol_type = other DNA
                        organism = Homo sapiens
SEQUENCE: 433
gccatccaga tgacccagtc tccagactcc ctggctgtgt ctctgggcga gagggccacc     60
atcaactgca agtccagcca gagtatttta tacaactcca acaataagac ctacttagct    120
tggtaccagc agaaaccagg acagcctcct aagctgctca tttctgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtatt    300
ccccttattt tcggccctgg gaccaaagtg gatatcaaac                          340

SEQ ID NO: 434          moltype = AA   length = 113
FEATURE                 Location/Qualifiers
source                  1..113
                        mol_type = protein
                        organism = Homo sapiens
SEQUENCE: 434
AIQMTQSPDS LAVSLGERAT INCKSSQSIL YNSNNKTYLA WYQQKPGQPP KLLIFWASTR     60
ESGVPDRFSG SGSGTDFTLT ISSLQAEDVA VYYCQQYYSI PLIFGPGTKV DIK           113

SEQ ID NO: 435          moltype = AA   length = 8
FEATURE                 Location/Qualifiers
source                  1..8
                        mol_type = protein
                        organism = Homo sapiens
SEQUENCE: 435
GFTFSNYG                                                               8

SEQ ID NO: 436          moltype = AA   length = 8
FEATURE                 Location/Qualifiers
source                  1..8
                        mol_type = protein
                        organism = Homo sapiens
SEQUENCE: 436
ISYDGSHK                                                               8

SEQ ID NO: 437          moltype = AA   length = 17
FEATURE                 Location/Qualifiers
source                  1..17
                        mol_type = protein
                        organism = Homo sapiens
SEQUENCE: 437
AKDSSAAIPY YYYGMDV                                                    17

SEQ ID NO: 438          moltype = AA   length = 12
FEATURE                 Location/Qualifiers
source                  1..12
                        mol_type = protein
                        organism = Homo sapiens
SEQUENCE: 438
QSILYNSNNK TY                                                         12

SEQ ID NO: 439          moltype =      length =
SEQUENCE: 439
000

SEQ ID NO: 440          moltype = AA   length = 9
FEATURE                 Location/Qualifiers
source                  1..9
                        mol_type = protein
                        organism = Homo sapiens
```

-continued

```
SEQUENCE: 440
QQYYSIPLI                                                              9

SEQ ID NO: 441          moltype = DNA   length = 370
FEATURE                 Location/Qualifiers
source                  1..370
                        mol_type = other DNA
                        organism = Homo sapiens
SEQUENCE: 441
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggaatgtct actatagtgg gggcacctac     180
tgcaacccgt ccctcaagag tcgagtcacc atatcagtag acacgtccaa gaatcagttc     240
tccctgaacc tgagctccgt gaccgccgcg gacacggccg tgtattactg tgcgagaata     300
tggttcgggg agcctgcggg tgggtacttt gactactggg gccagggaac cctggtcacc     360
gtctcctcag                                                            370

SEQ ID NO: 442          moltype = AA    length = 123
FEATURE                 Location/Qualifiers
source                  1..123
                        mol_type = protein
                        organism = Homo sapiens
SEQUENCE: 442
QLQLQESGPG LVKPSETLSL TCTVSGGSIS SSSYYWGWIR QPPGKGLEWI GNVYYSGGTY      60
CNPSLKSRVT ISVDTSKNQF SLNLSSVTAA DTAVYYCARI WFGEPAGGYF DYWGQGTLVT     120
VSS                                                                   123

SEQ ID NO: 443          moltype = DNA   length = 319
FEATURE                 Location/Qualifiers
source                  1..319
                        mol_type = other DNA
                        organism = Homo sapiens
SEQUENCE: 443
tcctatgagc tgactcagcc accctcagtg tccgtgtccc caggacagac agccagcatc      60
acctgctctg gacataagtt gggggataaa aatgcttgct ggtatcagca gaagccaggc     120
cagtcccctg tgctggtcat ctatgaatat aacaagcggc cctcaggat ccctgagcga     180
ttctctggct ccaactctgg gaacacagca ctctgacca tcagcgggac ccaggctatg     240
gatgaggctg actattactg tcaggcgtgg gacaccggca ctcatgtctt cggaactggg     300
accaaggtca ccgtcctag                                                 319

SEQ ID NO: 444          moltype = AA    length = 106
FEATURE                 Location/Qualifiers
source                  1..106
                        mol_type = protein
                        organism = Homo sapiens
SEQUENCE: 444
SYELTQPPSV SVSPGQTASI TCSGHKLGDK NACWYQQKPG QSPVLVIYEY NKRPSGIPER      60
FSGSNSGNTA TLTISGTQAM DEADYYCQAW DTGTHVFGTG TKVTVL                    106

SEQ ID NO: 445          moltype = AA    length = 10
FEATURE                 Location/Qualifiers
source                  1..10
                        mol_type = protein
                        organism = Homo sapiens
SEQUENCE: 445
GGSISSSSYY                                                            10

SEQ ID NO: 446          moltype = AA    length = 7
FEATURE                 Location/Qualifiers
source                  1..7
                        mol_type = protein
                        organism = Homo sapiens
SEQUENCE: 446
VYYSGGT                                                                7

SEQ ID NO: 447          moltype = AA    length = 15
FEATURE                 Location/Qualifiers
source                  1..15
                        mol_type = protein
                        organism = Homo sapiens
SEQUENCE: 447
ARIWFGEPAG GYFDY                                                      15

SEQ ID NO: 448          moltype = AA    length = 6
FEATURE                 Location/Qualifiers
source                  1..6
                        mol_type = protein
                        organism = Homo sapiens
SEQUENCE: 448
```

KLGDKN                                                                             6

SEQ ID NO: 449          moltype =    length =
SEQUENCE: 449
000

SEQ ID NO: 450          moltype = AA   length = 9
FEATURE                 Location/Qualifiers
source                  1..9
                        mol_type = protein
                        organism = Homo sapiens
SEQUENCE: 450
QAWDTGTHV                                                                          9

SEQ ID NO: 451          moltype = DNA  length = 370
FEATURE                 Location/Qualifiers
source                  1..370
                        mol_type = other DNA
                        organism = Homo sapiens
SEQUENCE: 451
caggtccagc tggtacagtc gggcccagga ctggtgaagc cttcacagac cctgtccctc    60
acctgctctg tctctgatgg ctccatcagc agtagtgatt actactggag ctggatccgc   120
cagcccccccg ggaagggcct ggagtggatt gggtacatct attacactgg gagcacctac   180
tacaacccgt ccctcaagag tcgagtttcc atatcagtag acaggtccaa gaaccaattc   240
tccctgaagc tgagttctgt gactgccgca gacacggccg tttactattg tgccagactc   300
gtagtaccat ctccgaaggg ctcctggttc gaccccctgg gccagggaac cctggtcacc   360
gtctcctcaa                                                          370

SEQ ID NO: 452          moltype = AA   length = 123
FEATURE                 Location/Qualifiers
source                  1..123
                        mol_type = protein
                        organism = Homo sapiens
SEQUENCE: 452
QVQLVQSGPG LVKPSQTLSL TCSVSDGSIS SSDYYWSWIR QPPGKGLEWI GYIYYTGSTY     60
YNPSLKSRVS ISVDRSKNQF SLKLSSVTAA DTAVYYCARL VVPSPKGSWF DPWGQGTLVT    120
VSS                                                                 123

SEQ ID NO: 453          moltype = DNA  length = 331
FEATURE                 Location/Qualifiers
source                  1..331
                        mol_type = other DNA
                        organism = Homo sapiens
SEQUENCE: 453
tcctatgagc tgactcagcc tgcctccgtg tctgggtctc ctggacagtc gatcaccatc    60
tcctgcactg gaccagcat tgatgttggg aattataacc ttgcctcctg gtaccaacag    120
cacccaggca aagcccccaa actcatcatt tatgagggca gtaggcggcc ctcagggggtt   180
tctaatcgct tctctggcgc caagtctggc aacacggcct ccctgacaat ctctgggctc   240
caggctgagg acgaggctga ttattactgc tgctcatatg taggtagtag cacttatgtc   300
ttcggatctg ggaccaaggt caccgtccta g                                  331

SEQ ID NO: 454          moltype = AA   length = 110
FEATURE                 Location/Qualifiers
source                  1..110
                        mol_type = protein
                        organism = Homo sapiens
SEQUENCE: 454
SYELTQPASV SGSPGQSITI SCTGTSIDVG NYNLASWYQQ HPGKAPKLII YEGSRRPSGV     60
SNRFSGAKSG NTASLTISGL QAEDEADYYC CSYVGSSTYV FGSGTKVTVL              110

SEQ ID NO: 455          moltype = AA   length = 10
FEATURE                 Location/Qualifiers
source                  1..10
                        mol_type = protein
                        organism = Homo sapiens
SEQUENCE: 455
DGSISSSDYY                                                                        10

SEQ ID NO: 456          moltype = AA   length = 7
FEATURE                 Location/Qualifiers
source                  1..7
                        mol_type = protein
                        organism = Homo sapiens
SEQUENCE: 456
IYYTGST                                                                            7

SEQ ID NO: 457          moltype = AA   length = 15
FEATURE                 Location/Qualifiers
source                  1..15

```
                        mol_type = protein
                        organism = Homo sapiens
SEQUENCE: 457
ARLVVPSPKG SWFDP                                                        15

SEQ ID NO: 458          moltype = AA   length = 9
FEATURE                 Location/Qualifiers
source                  1..9
                        mol_type = protein
                        organism = Homo sapiens
SEQUENCE: 458
SIDVGNYNL                                                                9

SEQ ID NO: 459          moltype =    length =
SEQUENCE: 459
000

SEQ ID NO: 460          moltype = AA   length = 10
FEATURE                 Location/Qualifiers
source                  1..10
                        mol_type = protein
                        organism = Homo sapiens
SEQUENCE: 460
CSYVGSSTYV                                                              10

SEQ ID NO: 461          moltype = DNA   length = 370
FEATURE                 Location/Qualifiers
source                  1..370
                        mol_type = other DNA
                        organism = Homo sapiens
SEQUENCE: 461
caggtccagc tggtacagtc tgggcctgag gtgaagaagc ctgggacctc agtgaaggtc        60
tcctgcaagg cttctggatt cacctttact agctctgcta tgcagtgggt gcgacaggct      120
cgtggacaac gccttgagtg dataggatgg atcgtcgttg cagtggtaa cacaaactac       180
gcacagaagt tccaggaaag agtcaccatt accaggaca tgtccacaag cacagcctac       240
atggagctga gcagcctgag atccgaggac acggccgtgt attactgtgc ggcagtttat      300
tgtagtggtg gtagctgtaa tgatgctttt gatatctggg gccaagggac aatggtcacc      360
gtctcttcag                                                             370

SEQ ID NO: 462          moltype = AA   length = 123
FEATURE                 Location/Qualifiers
source                  1..123
                        mol_type = protein
                        organism = Homo sapiens
SEQUENCE: 462
QVQLVQSGPE VKKPGTSVKV SCKASGFTFT SSAMQWVRQA RGQRLEWIGW IVVGSGNTNY        60
AQKFQERVTI TRDMSTSTAY MELSSLRSED TAVYYCAAVY CSGGSCNDAF DIWGQGTMVT      120
VSS                                                                    123

SEQ ID NO: 463          moltype = DNA   length = 325
FEATURE                 Location/Qualifiers
source                  1..325
                        mol_type = other DNA
                        organism = Homo sapiens
SEQUENCE: 463
gaaatagtga tgacgcagtc tccaggcacc ctgtctttgt ctccagggga aagagccacc        60
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactgagg      240
cctgaagatt ttgcagtgta ttactgtcag cagtatggta gctcaccctt cactttcggc      300
ggagggacca aggtggaaat caaac                                            325

SEQ ID NO: 464          moltype = AA   length = 108
FEATURE                 Location/Qualifiers
source                  1..108
                        mol_type = protein
                        organism = Homo sapiens
SEQUENCE: 464
EIVMTQSPGT LSLSPGERAT LSCRASQSVS SSYLAWYQQK PGQAPRLLIY GASSRATGIP        60
DRFSGSGSGT DFTLTISRLE PEDFAVYYCQ QYGSSPFTFG GGTKVEIK                   108

SEQ ID NO: 465          moltype = AA   length = 8
FEATURE                 Location/Qualifiers
source                  1..8
                        mol_type = protein
                        organism = Homo sapiens
SEQUENCE: 465
GFTFTSSA                                                                 8
```

-continued

| | | |
|---|---|---|
| SEQ ID NO: 466<br>FEATURE<br>source | moltype = AA  length = 8<br>Location/Qualifiers<br>1..8<br>mol_type = protein<br>organism = Homo sapiens | |
| SEQUENCE: 466<br>IVVGSGNT | | 8 |
| SEQ ID NO: 467<br>FEATURE<br>source | moltype = AA  length = 16<br>Location/Qualifiers<br>1..16<br>mol_type = protein<br>organism = Homo sapiens | |
| SEQUENCE: 467<br>AAVYCSGGSC NDAFDI | | 16 |
| SEQ ID NO: 468<br>FEATURE<br>source | moltype = AA  length = 7<br>Location/Qualifiers<br>1..7<br>mol_type = protein<br>organism = Homo sapiens | |
| SEQUENCE: 468<br>QSVSSSY | | 7 |
| SEQ ID NO: 469<br>SEQUENCE: 469<br>000 | moltype =    length = | |
| SEQ ID NO: 470<br>FEATURE<br>source | moltype = AA  length = 9<br>Location/Qualifiers<br>1..9<br>mol_type = protein<br>organism = Homo sapiens | |
| SEQUENCE: 470<br>QQYGSSPFT | | 9 |
| SEQ ID NO: 471<br>FEATURE<br>source | moltype = DNA  length = 367<br>Location/Qualifiers<br>1..367<br>mol_type = other DNA<br>organism = Homo sapiens | |
| SEQUENCE: 471<br>caggtacagc tgcagcagtc gggcccagga ctggtgaagc cttcggagac cctgtccctc<br>acctgcactg tctctggtgc ctccattagt aattattact ggagttggat ccggcagccc<br>ccagggaagg gactggagtg ggttggatat atctattaca ctgggagcac caaccacaac<br>ccctccctca agagtcgagt caccatatca ctagacacgt ccaagaatca gttctccctg<br>aggctgagct ctgtgaccgc tgcggacacg gccgtctatt actgtgcgcg agcctattgt<br>agtggtggta gctgcttcga cttttttgat atctggggcc aagggacaat ggtcaccgtc<br>tcttcag | | 60<br>120<br>180<br>240<br>300<br>360<br>367 |
| SEQ ID NO: 472<br>FEATURE<br>source | moltype = AA  length = 122<br>Location/Qualifiers<br>1..122<br>mol_type = protein<br>organism = Homo sapiens | |
| SEQUENCE: 472<br>QVQLQQSGPG LVKPSETLSL TCTVSGASIS NYYWSWIRQP PGKGLEWVGY IYYTGSTNHN<br>PSLKSRVTIS LDTSKNQFSL RLSSVTAADT AVYYCARAYC SGGSCFDTFD IWGQGTMVTV<br>SS | | 60<br>120<br>122 |
| SEQ ID NO: 473<br>FEATURE<br>source | moltype = DNA  length = 325<br>Location/Qualifiers<br>1..325<br>mol_type = other DNA<br>organism = Homo sapiens | |
| SEQUENCE: 473<br>tcctatgagc tgacacagcc accctcggtg tcagtggccc caggacagac ggccagaatt<br>acctgtgggg gaaacaacat tggaagtaaa agtgtgcact ggttccagca gaagccaggc<br>cagggccctg tgctggtcgt ctatgatgat agcgaccggc cctcagggat ccctgagcga<br>ttctctggct ccaactctgg gaacacggcc tccctgacca tcagcagggt cgaagccggg<br>gatgaggccg actattactg tcaggtgtgg gatagtgcta gtgattcagg tgtcttcgga<br>actgggacca agctcaccgt cccag | | 60<br>120<br>180<br>240<br>300<br>325 |
| SEQ ID NO: 474<br>FEATURE<br>source | moltype = AA  length = 108<br>Location/Qualifiers<br>1..108<br>mol_type = protein<br>organism = Homo sapiens | |
| SEQUENCE: 474 | | |

```
SYELTQPPSV SVAPGQTARI TCGGNNIGSK SVHWFQQKPG QAPVLVVYDD SDRPSGIPER    60
FSGSNSGNTA SLTISRVEAG DEADYYCQVW DSASDSGVFG TGTKLTVP               108

SEQ ID NO: 475           moltype = AA  length = 8
FEATURE                  Location/Qualifiers
source                   1..8
                         mol_type = protein
                         organism = Homo sapiens
SEQUENCE: 475
GASISNYY                                                             8

SEQ ID NO: 476           moltype = AA  length = 7
FEATURE                  Location/Qualifiers
source                   1..7
                         mol_type = protein
                         organism = Homo sapiens
SEQUENCE: 476
IYYTGST                                                              7

SEQ ID NO: 477           moltype = AA  length = 16
FEATURE                  Location/Qualifiers
source                   1..16
                         mol_type = protein
                         organism = Homo sapiens
SEQUENCE: 477
ARAYCSGGSC FDTFDI                                                   16

SEQ ID NO: 478           moltype = AA  length = 6
FEATURE                  Location/Qualifiers
source                   1..6
                         mol_type = protein
                         organism = Homo sapiens
SEQUENCE: 478
NIGSKS                                                               6

SEQ ID NO: 479           moltype =     length =
SEQUENCE: 479
000

SEQ ID NO: 480           moltype = AA  length = 11
FEATURE                  Location/Qualifiers
source                   1..11
                         mol_type = protein
                         organism = Homo sapiens
SEQUENCE: 480
QVWDSASDSG V                                                        11

SEQ ID NO: 481           moltype = DNA  length = 351
FEATURE                  Location/Qualifiers
source                   1..351
                         mol_type = other DNA
                         organism = Homo sapiens
SEQUENCE: 481
gaagtgcagc tgttggagtc tggaggaggc ttggtccagc ctgggggtc cctgagactc     60
tcctgtgcag cctctgggtt aaccgtcaga agcaactaca tgaactgggt ccgccaggct   120
ccagggaagg ggctggagtg ggtctcactt atttatagcg gtggtagtac attctacgca   180
gactccgtga agggccgatt caccatctcc agacacgatt ccaagaacac actgtatctt   240
caaatgaaca gcctgagagc tgaggacacg gccgtgtatt actgtgcgcg agatttggta   300
gtctacggaa tggacgtctg gggccaaggg accacggtca ccgtctcctc a            351

SEQ ID NO: 482           moltype = AA  length = 117
FEATURE                  Location/Qualifiers
source                   1..117
                         mol_type = protein
                         organism = Homo sapiens
SEQUENCE: 482
EVQLLESGGG LVQPGGSLRL SCAASGLTVR SNYMNWVRQA PGKGLEWVSL IYSGGSTFYA    60
DSVKGRFTIS RHDSKNTLYL QMNSLRAEDT AVYYCARDLV VYGMDVWGQG TTVTVSS      117

SEQ ID NO: 483           moltype = DNA  length = 322
FEATURE                  Location/Qualifiers
source                   1..322
                         mol_type = other DNA
                         organism = Homo sapiens
SEQUENCE: 483
gacatccaga tgacccagtc tccaggcacc ctgtctttgt ctccagggga aagagccacc    60
ctctcctgca gggccagtca gagtgttagc agcagctcct tagcctggta ccagcagaaa   120
catggccagg ctcccaggct cctcatctat ggtacatcca gcagggccac tggcatccca   180
gacaggttca gtggcagtgg gtctgggaca gacttcactc tcaccatcag tggactggag   240
```

```
cctgaagatt ttgcagtgta ttactgtcag cagtatggta gctcacccct tttcggcggg    300
gggaccaagg tggaaatcaa ac                                             322

SEQ ID NO: 484         moltype = AA   length = 107
FEATURE                Location/Qualifiers
source                 1..107
                       mol_type = protein
                       organism = Homo sapiens
SEQUENCE: 484
DIQMTQSPGT LSLSPGERAT LSCRASQSVS SSSLAWYQQK HGQAPRLLIY GTSSRATGIP     60
DRFSGSGSGT DFTLTISGLE PEDFAVYYCQ QYGSSPLFGG GTKVEIK                  107

SEQ ID NO: 485         moltype = AA   length = 8
FEATURE                Location/Qualifiers
source                 1..8
                       mol_type = protein
                       organism = Homo sapiens
SEQUENCE: 485
GLTVRSNY                                                               8

SEQ ID NO: 486         moltype = AA   length = 7
FEATURE                Location/Qualifiers
source                 1..7
                       mol_type = protein
                       organism = Homo sapiens
SEQUENCE: 486
IYSGGST                                                                7

SEQ ID NO: 487         moltype = AA   length = 11
FEATURE                Location/Qualifiers
source                 1..11
                       mol_type = protein
                       organism = Homo sapiens
SEQUENCE: 487
ARDLVVYGMD V                                                          11

SEQ ID NO: 488         moltype = AA   length = 7
FEATURE                Location/Qualifiers
source                 1..7
                       mol_type = protein
                       organism = Homo sapiens
SEQUENCE: 488
QSVSSSS                                                                7

SEQ ID NO: 489         moltype =    length =
SEQUENCE: 489
000

SEQ ID NO: 490         moltype = AA   length = 8
FEATURE                Location/Qualifiers
source                 1..8
                       mol_type = protein
                       organism = Homo sapiens
SEQUENCE: 490
QQYGSSPL                                                               8

SEQ ID NO: 491         moltype = DNA   length = 382
FEATURE                Location/Qualifiers
source                 1..382
                       mol_type = other DNA
                       organism = Homo sapiens
SEQUENCE: 491
gaggtgcagc tggtggagtc tgggggaggc gtggtccagc ctggggaggtc cctgagactc     60
tcctgtgcag cctctggatt cacccttcagt aattatggca tgcaccgggt ccgccaggct    120
ccaggcaagg ggctggagtg ggtggcactt atttcatatg aagaaagtaa tagatattat    180
ggagactccg tgaggggccg attcaccatc tccagagaca attccaagaa cactctgtat    240
ctgcaaatga acagcctgag acctgaggac acggctgtgt attactgtgc gaaagatcaa    300
gggcccggcta ctctgatggt gactgctatt cggggcgcta tggacgtctg gggccaaggg    360
accacggtca ccgtctcctc ag                                              382

SEQ ID NO: 492         moltype = AA   length = 127
FEATURE                Location/Qualifiers
source                 1..127
                       mol_type = protein
                       organism = Homo sapiens
SEQUENCE: 492
EVQLVESGGG VVQPGRSLRL SCAASGFTFS NYGMHRVRQA PGKGLEWVAL ISYEESNRYY      60
GDSVRGRFTI SRDNSKNTLY LQMNSLRPED TAVYYCAKDQ GPATVMVTAI RGAMDVWGQG    120
TTVTVSS                                                              127
```

```
SEQ ID NO: 493           moltype = DNA  length = 343
FEATURE                  Location/Qualifiers
source                   1..343
                         mol_type = other DNA
                         organism = Homo sapiens
SEQUENCE: 493
gacatccagt tgacccagtc tccagattcc ctggctgtgt ctctgggcga gagggccacc    60
atcaactgca agtccagcca gagtgtttta tacagctcca acaataagaa ctacttagct   120
tggtaccagc agaaaccagg ccagcctcct aaactcctca tttactgggc gtctacccgg   180
gaatccgggg tccctgaccg attcagtggc agcgggtctg ggacagattt cactctcacc   240
atcagcagcc tgcaggctga agatgtggca gtatattact gtcagcaata ttttggttct   300
ccttcgatca ccttcggcca aggacacga ctggagatta aac                      343

SEQ ID NO: 494           moltype = AA  length = 114
FEATURE                  Location/Qualifiers
source                   1..114
                         mol_type = protein
                         organism = Homo sapiens
SEQUENCE: 494
DIQLTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQYFGS PSITFGQGTR LEIK         114

SEQ ID NO: 495           moltype = AA  length = 8
FEATURE                  Location/Qualifiers
source                   1..8
                         mol_type = protein
                         organism = Homo sapiens
SEQUENCE: 495
GFTFSNYG                                                              8

SEQ ID NO: 496           moltype = AA  length = 8
FEATURE                  Location/Qualifiers
source                   1..8
                         mol_type = protein
                         organism = Homo sapiens
SEQUENCE: 496
ISYEESNR                                                              8

SEQ ID NO: 497           moltype = AA  length = 20
FEATURE                  Location/Qualifiers
source                   1..20
                         mol_type = protein
                         organism = Homo sapiens
SEQUENCE: 497
AKDQGPATVM VTAIRGAMDV                                                20

SEQ ID NO: 498           moltype = AA  length = 12
FEATURE                  Location/Qualifiers
source                   1..12
                         mol_type = protein
                         organism = Homo sapiens
SEQUENCE: 498
QSVLYSSNNK NY                                                        12

SEQ ID NO: 499           moltype =    length =
SEQUENCE: 499
000

SEQ ID NO: 500           moltype = AA  length = 10
FEATURE                  Location/Qualifiers
source                   1..10
                         mol_type = protein
                         organism = Homo sapiens
SEQUENCE: 500
QQYFGSPSIT                                                           10

SEQ ID NO: 501           moltype = DNA  length = 373
FEATURE                  Location/Qualifiers
source                   1..373
                         mol_type = other DNA
                         organism = Homo sapiens
SEQUENCE: 501
caggtgcagc tggtgcagtc tggggctgag gtgaagaagc ctggggcctc agtgaaggtc    60
tcctgcaagg cttctggata caccttcacc gactactata tgcactgggt gcgacaggcc   120
cctggacaag gccttgagtg gatgggatgg atcaactcta agatggtgg cgcgaactat    180
gcacagaagt tcagggcag ggtcaccctg accagggaca cgtcaatcga cacagcctac    240
atagaactga gcaggctcag atctgacgac acggccgtgt attactgtgc gagatccgcc   300
tctacagtaa ccgaaccacc gacaaactgg ttcgacccct ggggccaggg aaccctggtc   360
```

```
accgtctcct cag                                                              373

SEQ ID NO: 502          moltype = AA   length = 124
FEATURE                 Location/Qualifiers
source                  1..124
                        mol_type = protein
                        organism = Homo sapiens
SEQUENCE: 502
QVQLVQSGAE VKKPGASVKV SCKASGYTFT DYYMHWVRQA PGQGLEWMGW INSKDGGANY            60
AQKFQGRVTL TRDTSIDTAY IELSRLRSDD TAVYYCARSA STVTEPPTNW FDPWGQGTLV           120
TVSS                                                                       124

SEQ ID NO: 503          moltype = DNA   length = 325
FEATURE                 Location/Qualifiers
source                  1..325
                        mol_type = other DNA
                        organism = Homo sapiens
SEQUENCE: 503
gatgttgtga tgactcagtc tccatcctcc ctgtctgcat ctgtaggcga cagagtcacc            60
gtcacttgcc gggcaagtca gggcattaga aatgatttag gctggtatca gcagaaacca          120
gggaaagctc ctaagcgcct gatctatgct gcatccagtt tgcaaagtgg tgtcccatca          180
aggttcagcg gcagtggatc tgggacagac ttcactctca caatcagcag cctgcagcct          240
gaagattttg caacttatta ctgtctacag cataatagtt acctccgttt cactttcggc          300
cctgggacca aagtggatat caaac                                                325

SEQ ID NO: 504          moltype = AA   length = 108
FEATURE                 Location/Qualifiers
source                  1..108
                        mol_type = protein
                        organism = Homo sapiens
SEQUENCE: 504
DVVMTQSPSS LSASVGDRVT VTCRASQGIR NDLGWYQQKP GKAPKRLIYA ASSLQSGVPS            60
RFSGSGSGTD FTLTISSLQP EDFATYYCLQ HNSYLRFTFG PGTKVDIK                        108

SEQ ID NO: 505          moltype = AA   length = 8
FEATURE                 Location/Qualifiers
source                  1..8
                        mol_type = protein
                        organism = Homo sapiens
SEQUENCE: 505
GYTFTDYY                                                                     8

SEQ ID NO: 506          moltype = AA   length = 8
FEATURE                 Location/Qualifiers
source                  1..8
                        mol_type = protein
                        organism = Homo sapiens
SEQUENCE: 506
INSKDGGA                                                                     8

SEQ ID NO: 507          moltype = AA   length = 17
FEATURE                 Location/Qualifiers
source                  1..17
                        mol_type = protein
                        organism = Homo sapiens
SEQUENCE: 507
ARSASTVTEP PTNWFDP                                                          17

SEQ ID NO: 508          moltype = AA   length = 6
FEATURE                 Location/Qualifiers
source                  1..6
                        mol_type = protein
                        organism = Homo sapiens
SEQUENCE: 508
QGIRND                                                                       6

SEQ ID NO: 509          moltype =    length =
SEQUENCE: 509
000

SEQ ID NO: 510          moltype = AA   length = 10
FEATURE                 Location/Qualifiers
source                  1..10
                        mol_type = protein
                        organism = Homo sapiens
SEQUENCE: 510
LQHNSYLRFT                                                                  10

SEQ ID NO: 511          moltype = DNA   length = 376
```

```
FEATURE                 Location/Qualifiers
source                  1..376
                        mol_type = other DNA
                        organism = Homo sapiens
SEQUENCE: 511
gaagtgcagc tggtgcagtc tggggctgag gtgaagaagc ctggggcctc agtgaaggtc   60
tcctgcaagg cttctggata caccttcacc ggctactata tgcactgggt gcgacaggcc  120
cctggacaag gcttgagtg gatgggatgg atcaaccca acagtggtgg cacaaactat   180
gcacagaagt tcagggcag ggtcaccatg accaggaca cgtccatcac cacaggctac   240
atggagctga gcagcctgag atctgacgac acggccctgt attactgtgc gagagttggg  300
gctcacgatt actatgatag tagtgacaac tggttcgacc cctggggcca gggaaccctg  360
gtcaccgtct tctcag                                                  376

SEQ ID NO: 512          moltype = AA   length = 125
FEATURE                 Location/Qualifiers
source                  1..125
                        mol_type = protein
                        organism = Homo sapiens
SEQUENCE: 512
EVQLVQSGAE VKKPGASVKV SCKASGYTFT GYYMHWVRQA PGQGLEWMGW INPNSGGTNY   60
AQKFQGRVTM TRDTSITTGY MELSSLRSDD TALYYCARVG AHDYYDSSDN WFDPWGQGTL  120
VTVFS                                                              125

SEQ ID NO: 513          moltype = DNA   length = 322
FEATURE                 Location/Qualifiers
source                  1..322
                        mol_type = other DNA
                        organism = Homo sapiens
SEQUENCE: 513
gacatccaga tgacccagtc tccatcttcc gtgtctgcat ctgtaggaga cagactcacc   60
atcacttgtc gggcgagtca gggtattagc agctggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt tcccgtggac gttcggccaa  300
gggaccaagg tggagatcaa ac                                           322

SEQ ID NO: 514          moltype = AA   length = 107
FEATURE                 Location/Qualifiers
source                  1..107
                        mol_type = protein
                        organism = Homo sapiens
SEQUENCE: 514
DIQMTQSPSS VSASVGDRLT ITCRASQGIS SWLAWYQQKP GKAPKLLIYA ASSLQSGVPS   60
RFSGSGSGTD FTLTISSLQP EDFATYYCQQ ANSFPWTFGQ GTKVEIK                107

SEQ ID NO: 515          moltype = AA   length = 8
FEATURE                 Location/Qualifiers
source                  1..8
                        mol_type = protein
                        organism = Homo sapiens
SEQUENCE: 515
GYTFTGYY                                                            8

SEQ ID NO: 516          moltype = AA   length = 8
FEATURE                 Location/Qualifiers
source                  1..8
                        mol_type = protein
                        organism = Homo sapiens
SEQUENCE: 516
INPNSGGT                                                            8

SEQ ID NO: 517          moltype = AA   length = 18
FEATURE                 Location/Qualifiers
source                  1..18
                        mol_type = protein
                        organism = Homo sapiens
SEQUENCE: 517
ARVGAHDYYD SSDNWFDP                                                18

SEQ ID NO: 518          moltype = AA   length = 6
FEATURE                 Location/Qualifiers
source                  1..6
                        mol_type = protein
                        organism = Homo sapiens
SEQUENCE: 518
QGISSW                                                              6

SEQ ID NO: 519          moltype =    length =
SEQUENCE: 519
```

```
000

SEQ ID NO: 520           moltype = AA  length = 9
FEATURE                  Location/Qualifiers
source                   1..9
                         mol_type = protein
                         organism = Homo sapiens
SEQUENCE: 520
QQANSFPWT                                                                  9

SEQ ID NO: 521           moltype = DNA  length = 375
FEATURE                  Location/Qualifiers
source                   1..375
                         mol_type = other DNA
                         organism = Homo sapiens
SEQUENCE: 521
caggtgcagc tggtgcagtc tggggctgag gtgaagaagc tggggcctc agtgaaggtc        60
tcctgcaagg cttctggata ccccctcacc ggctactata tacactgggt gcgacaggcc     120
cctggacaag gacttgagtg gatgggatgg ctcaaccctaa acagtggtgg cacaaagtat    180
gcacagaagt tcagggcag ggtcaccatg accaggaca cgtccatcag cacaggctac       240
atggagctga gcaggctgag atctgacgac acggccgtgt actactgtgc gagagatggg    300
gggggaatag atgattacgt tcaggaggac ggtatgacg tctggggcca agggcccatg     360
gtcaccgtct cttca                                                         375

SEQ ID NO: 522           moltype = AA  length = 125
FEATURE                  Location/Qualifiers
source                   1..125
                         mol_type = protein
                         organism = Homo sapiens
SEQUENCE: 522
QVQLVQSGAE VKKPGASVKV SCKASGYPLT GYYIHWVRQA PGQGLEWMGW LNPNSGGTKY         60
AQKFQGRVTM TRDTSISTGY MELSRLRSDD TAVYYCARDG GIDDYVQED GMDVWGQGPM        120
VTVSS                                                                    125

SEQ ID NO: 523           moltype = DNA  length = 325
FEATURE                  Location/Qualifiers
source                   1..325
                         mol_type = other DNA
                         organism = Homo sapiens
SEQUENCE: 523
caatctgccc tgactcagcc accctcggtg tcagtgtccc caggacagac ggccaggatc       60
acctgctctg gagatgcatt gtcaaagcaa catgcttatt ggtaccagca gaagccaggc     120
caggcccctg tattggtgat atataaagac agtgagaggc cctcagggat ccctgagcga    180
ttctctggct ccagctcagg gacaatagtc acgttgacca tcagtggagt ccaggcagaa     240
gacgaggctg actattactg tcaatcagca gacaacagtg gtagtagata tgtcttcgga    300
actgggacca aggtcaccgt cctag                                              325

SEQ ID NO: 524           moltype = AA  length = 108
FEATURE                  Location/Qualifiers
source                   1..108
                         mol_type = protein
                         organism = Homo sapiens
SEQUENCE: 524
QSALTQPPSV SVSPGQTARI TCSGDALSKQ HAYWYQQKPG QAPVLVIYKD SERPSGIPER         60
FSGSSSGTIV TLTISGVQAE DEADYYCQSA DNSGSRYVFG TGTKVTVL                    108

SEQ ID NO: 525           moltype = AA  length = 8
FEATURE                  Location/Qualifiers
source                   1..8
                         mol_type = protein
                         organism = Homo sapiens
SEQUENCE: 525
GYPLTGYY                                                                   8

SEQ ID NO: 526           moltype = AA  length = 8
FEATURE                  Location/Qualifiers
source                   1..8
                         mol_type = protein
                         organism = Homo sapiens
SEQUENCE: 526
LNPNSGGT                                                                   8

SEQ ID NO: 527           moltype = AA  length = 18
FEATURE                  Location/Qualifiers
source                   1..18
                         mol_type = protein
                         organism = Homo sapiens
SEQUENCE: 527
ARDGGGIDDY VQEDGMDV                                                       18
```

```
SEQ ID NO: 528          moltype = AA  length = 6
FEATURE                 Location/Qualifiers
source                  1..6
                        mol_type = protein
                        organism = Homo sapiens
SEQUENCE: 528
ALSKQH                                                                    6

SEQ ID NO: 529          moltype =     length =
SEQUENCE: 529
000

SEQ ID NO: 530          moltype = AA  length = 11
FEATURE                 Location/Qualifiers
source                  1..11
                        mol_type = protein
                        organism = Homo sapiens
SEQUENCE: 530
QSADNSGSRY V                                                             11

SEQ ID NO: 531          moltype = DNA  length = 355
FEATURE                 Location/Qualifiers
source                  1..355
                        mol_type = other DNA
                        organism = Homo sapiens
SEQUENCE: 531
gaagtgcagc tggtggagtc tgggggaggc ttggtacagc ctgggggtc cctgagactc         60
tcctgtgcag cctctggatt caccttcagt agctatagca tgaactgggt ccgccaggct       120
ccagggaagg ggctggagtg ggtctcatac attagtgca ttaatagtgc catatattac        180
gcagactctg tgaagggccg cttcaccatc tccagagaca acgccaagaa ctcactgtat       240
ctgcaaatga acagcctgag agtcgaggac acggctgtgt attactgtgc gagagataaa       300
tacttaggta taaagatat gtggggccaa gggacaatgg tcaccgtctc ttcag             355

SEQ ID NO: 532          moltype = AA  length = 118
FEATURE                 Location/Qualifiers
source                  1..118
                        mol_type = protein
                        organism = Homo sapiens
SEQUENCE: 532
EVQLVESGGG LVQPGGSLRL SCAASGFTFS SYSMNWVRQA PGKGLEWVSY ISGINSAIYY        60
ADSVKGRFTI SRDNAKNSLY LQMNSLRVED TAVYYCARDK YLGIKDMWGQ GTMVTVSS         118

SEQ ID NO: 533          moltype = DNA  length = 322
FEATURE                 Location/Qualifiers
source                  1..322
                        mol_type = other DNA
                        organism = Homo sapiens
SEQUENCE: 533
gacatccaga tgacccagtc tccagccacc ctgtctttgt ctccagggga aagagccacc        60
ctctcctgca gggccagtca gagtgttagc acctacttag cctggtacca acagaaacct       120
ggccaggctc ccaggctcgt catctatgat gcatccaaca gggccactgg catcccagcc       180
aggttcagtg gcgtgggtc tgggacagac ttcactctca ccatcagcag cctagagcct       240
gaagattttg cagtttatta ctgtcaacag cgtctcaact ggcctctcac tttcggcgga       300
gggaccaaag tggatatcaa ac                                                322

SEQ ID NO: 534          moltype = AA  length = 107
FEATURE                 Location/Qualifiers
source                  1..107
                        mol_type = protein
                        organism = Homo sapiens
SEQUENCE: 534
DIQMTQSPAT LSLSPGERAT LSCRASQSVS TYLAWYQQKP GQAPRLVIYD ASNRATGIPA        60
RFSGGGSGTD FTLTISSLEP EDFAVYYCQQ RLNWPLTFGG GTKVDIK                    107

SEQ ID NO: 535          moltype = AA  length = 8
FEATURE                 Location/Qualifiers
source                  1..8
                        mol_type = protein
                        organism = Homo sapiens
SEQUENCE: 535
GFTFSSYS                                                                  8

SEQ ID NO: 536          moltype = AA  length = 8
FEATURE                 Location/Qualifiers
source                  1..8
                        mol_type = protein
                        organism = Homo sapiens
SEQUENCE: 536
```

```
ISGINSAI                                                              8

SEQ ID NO: 537            moltype = AA  length = 11
FEATURE                   Location/Qualifiers
source                    1..11
                          mol_type = protein
                          organism = Homo sapiens
SEQUENCE: 537
ARDKYLGIKD M                                                         11

SEQ ID NO: 538            moltype = AA  length = 6
FEATURE                   Location/Qualifiers
source                    1..6
                          mol_type = protein
                          organism = Homo sapiens
SEQUENCE: 538
QSVSTY                                                                6

SEQ ID NO: 539            moltype =     length =
SEQUENCE: 539
000

SEQ ID NO: 540            moltype = AA  length = 9
FEATURE                   Location/Qualifiers
source                    1..9
                          mol_type = protein
                          organism = Homo sapiens
SEQUENCE: 540
QQRLNWPLT                                                             9

SEQ ID NO: 541            moltype = DNA  length = 375
FEATURE                   Location/Qualifiers
source                    1..375
                          mol_type = other DNA
                          organism = Homo sapiens
SEQUENCE: 541
gaggtgcagc tggtacagtc tggagcagag gtgaaaaagc cggggagtc tctgaagatc      60
tcctgtaagg gctctggata cagctttacc aactactgga tcggctgggt gcgccagatg    120
cccgggaaag gcctggagtg gatggggatc atctatcctg gtgactctgg taccagatac    180
agcccgtcct tccaaggcca ggtcaccatc tcagccgaca gtccatcag aaccgcctac    240
ctgcagtgga gcagcctgaa ggcctcggac agcgccatgt attactgtgc gaggtctaga    300
gtgggagcta ctgggggcta ttatgactac tatatggacg tctggggcca agggaccacg    360
gtcaccgtct cctca                                                    375

SEQ ID NO: 542            moltype = AA  length = 125
FEATURE                   Location/Qualifiers
source                    1..125
                          mol_type = protein
                          organism = Homo sapiens
SEQUENCE: 542
EVQLVQSGAE VKKPGESLKI SCKGSGYSFT NYWIGWVRQM PGKGLEWMGI IYPGDSGTRY     60
SPSFQGQVTI SADKSIRTAY LQWSSLKASD SAMYYCARSR VGATGGYYDY YMDVWGQGTT    120
VTVSS                                                               125

SEQ ID NO: 543            moltype = DNA  length = 331
FEATURE                   Location/Qualifiers
source                    1..331
                          mol_type = other DNA
                          organism = Homo sapiens
SEQUENCE: 543
cagtctgtgt tgacgcagcc accctcagcg tctgggaccc ccgggcagag ggtcaccatc     60
tcttgttctg gaagcagctc caacctcgga ggtaatactg taaactggta ccagcagctc    120
ccaggaacgg cccccaaact cctcatctat agtaataatc agcggccctc agggggtcct    180
gaccgattct ctggctccaa gtctggcacc tcagcctccc tggccatcag tgggctccag    240
tctgaggatg aggctgatta ttactgtgca gcatgggatg acagcctgaa tggtcccgtc    300
ttcggaactg ggaccaaggt caccgtccta g                                  331

SEQ ID NO: 544            moltype = AA  length = 110
FEATURE                   Location/Qualifiers
source                    1..110
                          mol_type = protein
                          organism = Homo sapiens
SEQUENCE: 544
QSVLTQPPSA SGTPGQRVTI SCSGSSSNLG GNTVNWYQQL PGTAPKLLIY SNNQRPSGVP     60
DRFSGSKSGT SASLAISGLQ SEDEADYYCA AWDDSLNGPV FGTGTKVTVL              110

SEQ ID NO: 545            moltype = AA  length = 8
FEATURE                   Location/Qualifiers
source                    1..8
```

```
                        mol_type = protein
                        organism = Homo sapiens
SEQUENCE: 545
GYSFTNYW                                                             8

SEQ ID NO: 546          moltype = AA  length = 8
FEATURE                 Location/Qualifiers
source                  1..8
                        mol_type = protein
                        organism = Homo sapiens
SEQUENCE: 546
IYPGDSGT                                                             8

SEQ ID NO: 547          moltype = AA  length = 18
FEATURE                 Location/Qualifiers
source                  1..18
                        mol_type = protein
                        organism = Homo sapiens
SEQUENCE: 547
ARSRVGATGG YYDYYMDV                                                 18

SEQ ID NO: 548          moltype = AA  length = 8
FEATURE                 Location/Qualifiers
source                  1..8
                        mol_type = protein
                        organism = Homo sapiens
SEQUENCE: 548
SSNLGGNT                                                             8

SEQ ID NO: 549          moltype =    length =
SEQUENCE: 549
000

SEQ ID NO: 550          moltype = AA  length = 11
FEATURE                 Location/Qualifiers
source                  1..11
                        mol_type = protein
                        organism = Homo sapiens
SEQUENCE: 550
AAWDDSLNGP V                                                        11

SEQ ID NO: 551          moltype = DNA  length = 370
FEATURE                 Location/Qualifiers
source                  1..370
                        mol_type = other DNA
                        organism = Homo sapiens
SEQUENCE: 551
caggtgcagc tggtggagtc gggcccagga caggtgaagc cttcggagac cctgtccctc    60
acctgcactg tctctggtgg ctccatcagc agtagtagtt actactgggg ctggatccgc   120
cagcccccag ggaagggact ggagtggatt ggagtatct attatagtgg gagcgcctac    180
tataaccccgt ccctcaagag tcgagtcacc atatccgtag acacgtccaa gaaccagttc   240
tccctgaagc tgaactctgt gaccgccgca gacacggctg tcttttactg tgcgagacac   300
gcagctccca gtccggggga caactggttc gaccccctggg gccaggaaac cctggtcacc   360
gtctcctcag                                                          370

SEQ ID NO: 552          moltype = AA  length = 123
FEATURE                 Location/Qualifiers
source                  1..123
                        mol_type = protein
                        organism = Homo sapiens
SEQUENCE: 552
QVQLVESGPG QVKPSETLSL TCTVSGGSIS SSSYYWGWIR QPPGKGLEWI GSIYYSGSAY    60
YNPSLKSRVT ISVDTSKNQF SLKLNSVTAA DTAVFYCARH AAPSPGDNWF DPWGQGTLVT   120
VSS                                                                 123

SEQ ID NO: 553          moltype = DNA  length = 322
FEATURE                 Location/Qualifiers
source                  1..322
                        mol_type = other DNA
                        organism = Homo sapiens
SEQUENCE: 553
cagtctgtgt tgactcagcc accctcggtg tcagtgtccc caggacagac ggcccggatc    60
acctgctctg gagatgcatt gtcaacgcaa aatggtaatt ggtaccagca gaagccaggc   120
caggcccctg tgatggtgat atgtaaagac agtgagaggc cctcagggat ccctgagcgc   180
ttctctggct ccaggtcagg gacaacagtc acgttgacca tcagtggagt ccaggcagaa   240
gacgaagctg actatcactg tcaatcagca gacaacaggg cacatgtagt attcggcgga   300
gggaccaagc tgaccgtcct ag                                            322

SEQ ID NO: 554          moltype = AA  length = 107
```

| FEATURE | Location/Qualifiers |
|---|---|
| source | 1..107<br>mol_type = protein<br>organism = Homo sapiens |

SEQUENCE: 554
```
QSVLTQPPSV SVSPGQTARI TCSGDALSTQ NGNWYQQKPG QAPVMVICKD SERPSGIPER   60
FSGSRSGTTV TLTISGVQAE DEADYHCQSA DNRAHVVFGG GTKLTVL                107
```

| SEQ ID NO: 555<br>FEATURE<br>source | moltype = AA length = 10<br>Location/Qualifiers<br>1..10<br>mol_type = protein<br>organism = Homo sapiens |
|---|---|

SEQUENCE: 555
```
GGSISSSSYY                                                         10
```

| SEQ ID NO: 556<br>FEATURE<br>source | moltype = AA length = 7<br>Location/Qualifiers<br>1..7<br>mol_type = protein<br>organism = Homo sapiens |
|---|---|

SEQUENCE: 556
```
IYYSGSA                                                            7
```

| SEQ ID NO: 557<br>FEATURE<br>source | moltype = AA length = 15<br>Location/Qualifiers<br>1..15<br>mol_type = protein<br>organism = Homo sapiens |
|---|---|

SEQUENCE: 557
```
ARHAAPSPGD NWFDP                                                   15
```

| SEQ ID NO: 558<br>FEATURE<br>source | moltype = AA length = 6<br>Location/Qualifiers<br>1..6<br>mol_type = protein<br>organism = Homo sapiens |
|---|---|

SEQUENCE: 558
```
ALSTQN                                                             6
```

| SEQ ID NO: 559 | moltype = length = |
|---|---|

SEQUENCE: 559
```
000
```

| SEQ ID NO: 560<br>FEATURE<br>source | moltype = AA length = 10<br>Location/Qualifiers<br>1..10<br>mol_type = protein<br>organism = Homo sapiens |
|---|---|

SEQUENCE: 560
```
QSADNRAHVV                                                         10
```

| SEQ ID NO: 561<br>FEATURE<br>source | moltype = DNA length = 378<br>Location/Qualifiers<br>1..378<br>mol_type = other DNA<br>organism = Homo sapiens |
|---|---|

SEQUENCE: 561
```
gaggtgcagc tggtggagtc tgggggaggc gtggtccagc ctggggaggtc cctgagactc   60
tcctgtgcag cgtctggatt cacctttagt agttatgcca tgcactgggt ccgccaggct  120
ccaggcaagg ggctggagtg ggtggcagtt atatggtatg atggaagtaa taacttctat  180
gcagactccg tgaagggccg attcaccatc tccagagaca atttcaagaa cacgctgtat  240
ttgcaaatga acagcctgag agccgaggac acggctgtgt attactgtgc gagatcatat  300
tgtagtggtg gtttctgctt cggctactac tatggttttgg acgtgtgggg ccaagggacc  360
acggtcaccg tctcctca                                                378
```

| SEQ ID NO: 562<br>FEATURE<br>source | moltype = AA length = 126<br>Location/Qualifiers<br>1..126<br>mol_type = protein<br>organism = Homo sapiens |
|---|---|

SEQUENCE: 562
```
EVQLVESGGG VVQPGRSLRL SCAASGFTFS SYGMHWVRQA PGKGLEWVAV IWYDGSNNFY   60
ADSVKGRFTI SRDNFKNTLY LQMNSLRAED TAVYYCARSY CSGGFCFGYY YGLDVWGQGT  120
TVTVSS                                                             126
```

| SEQ ID NO: 563<br>FEATURE<br>source | moltype = DNA length = 325<br>Location/Qualifiers<br>1..325 |
|---|---|

```
                              mol_type = other DNA
                              organism = Homo sapiens
SEQUENCE: 563
tcctatgagc tgactcagcc accctcagtg tcagtgggcc caggaaagac ggccacgatt      60
acctgtgggg gaaacaacat tggaactaaa agtgtgcact ggtaccagca gaagccaggc     120
caggcccctg tgttggtcat ctattataat agcgaccggc cctccgggat ccctgagcga     180
ttctctggct ccaactctgg gaacacggtc accgaccca tcagcaggt cgaagccggg      240
gatgaggccg actattactg tcaggtgtgg gatagtggta gtgatcatta tgtcttcgga     300
actgggacca aggtcaccgt cgtag                                           325

SEQ ID NO: 564            moltype = AA  length = 108
FEATURE                   Location/Qualifiers
source                    1..108
                          mol_type = protein
                          organism = Homo sapiens
SEQUENCE: 564
SYELTQPPSV SVAPGKTATI TCGGNNIGTK SVHWYQQKPG QAPVLVIYYN SDRPSGIPER      60
FSGSNSGNTV TLTISRVEAG DEADYYCQVW DSGSDHYVFG TGTKVTVV                  108

SEQ ID NO: 565            moltype = AA  length = 8
FEATURE                   Location/Qualifiers
source                    1..8
                          mol_type = protein
                          organism = Homo sapiens
SEQUENCE: 565
GFTFSSYG                                                                8

SEQ ID NO: 566            moltype = AA  length = 8
FEATURE                   Location/Qualifiers
source                    1..8
                          mol_type = protein
                          organism = Homo sapiens
SEQUENCE: 566
IWYDGSNN                                                                8

SEQ ID NO: 567            moltype = AA  length = 19
FEATURE                   Location/Qualifiers
source                    1..19
                          mol_type = protein
                          organism = Homo sapiens
SEQUENCE: 567
ARSYCSGGFC FGYYYGLDV                                                   19

SEQ ID NO: 568            moltype = AA  length = 6
FEATURE                   Location/Qualifiers
source                    1..6
                          mol_type = protein
                          organism = Homo sapiens
SEQUENCE: 568
NIGTKS                                                                  6

SEQ ID NO: 569            moltype =    length =
SEQUENCE: 569
000

SEQ ID NO: 570            moltype = AA  length = 11
FEATURE                   Location/Qualifiers
source                    1..11
                          mol_type = protein
                          organism = Homo sapiens
SEQUENCE: 570
QVWDSGSDHY V                                                           11

SEQ ID NO: 571            moltype = DNA  length = 358
FEATURE                   Location/Qualifiers
source                    1..358
                          mol_type = other DNA
                          organism = Homo sapiens
SEQUENCE: 571
caggtgcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagccctt acaatggtaa cacacactat     180
gcacagaagc tccagggcag agtcaccatg accacagaca catccacgag cacagcctac     240
atggagctga ggagcctgag atctgacgac acggccgtat attactgtgc gagagatggg     300
gagttattgg gctggttcga ccctggggc cagggaaccc tggtcaccgt ctcctcag        358

SEQ ID NO: 572            moltype = AA  length = 119
FEATURE                   Location/Qualifiers
source                    1..119
```

```
                        mol_type = protein
                        organism = Homo sapiens
SEQUENCE: 572
QVQLVQSGAE VKKPGASVKV SCKASGYTFT SYGISWVRQA PGQGLEWMGW ISPYNGNTHY    60
AQKLQGRVTM TTDTSTSTAY MELRSLRSDD TAVYYCARDG ELLGWFDPWG QGTLVTVSS    119

SEQ ID NO: 573          moltype = DNA   length = 331
FEATURE                 Location/Qualifiers
source                  1..331
                        mol_type = other DNA
                        organism = Homo sapiens
SEQUENCE: 573
cagtctgtcg tgacgcagcc tgcctccgtg tctgggtctc ctggacagtc gatcaccatc    60
tcctgcactg gaaccagcag tgatgttggg agttataacc ttgtctcctg gtaccaacag   120
cacccaggca aagcccccaa actcatgatt tatgcgggca gtaagcggcc ctcaggggtt   180
tctaatcgct tctctggctc caagtctggc aacacggcct ccctgacaat ctctgggctc   240
caggctgagg acgaggctga ttattactgc tgctcatatg caggtagtag cacttgggtg   300
ttcggcggag ggaccaagct gaccgtccta g                                  331

SEQ ID NO: 574          moltype = AA   length = 110
FEATURE                 Location/Qualifiers
source                  1..110
                        mol_type = protein
                        organism = Homo sapiens
SEQUENCE: 574
QSVVTQPASV SGSPGQSITI SCTGTSSDVG SYNLVSWYQQ HPGKAPKLMI YAGSKRPSGV    60
SNRFSGSKSG NTASLTISGL QAEDEADYYC CSYAGSSTWV FGGGTKLTVL              110

SEQ ID NO: 575          moltype = AA   length = 8
FEATURE                 Location/Qualifiers
source                  1..8
                        mol_type = protein
                        organism = Homo sapiens
SEQUENCE: 575
GYTFTSYG                                                              8

SEQ ID NO: 576          moltype = AA   length = 8
FEATURE                 Location/Qualifiers
source                  1..8
                        mol_type = protein
                        organism = Homo sapiens
SEQUENCE: 576
ISPYNGNT                                                              8

SEQ ID NO: 577          moltype = AA   length = 12
FEATURE                 Location/Qualifiers
source                  1..12
                        mol_type = protein
                        organism = Homo sapiens
SEQUENCE: 577
ARDGELLGWF DP                                                        12

SEQ ID NO: 578          moltype = AA   length = 9
FEATURE                 Location/Qualifiers
source                  1..9
                        mol_type = protein
                        organism = Homo sapiens
SEQUENCE: 578
SSDVGSYNL                                                             9

SEQ ID NO: 579          moltype =   length =
SEQUENCE: 579
000

SEQ ID NO: 580          moltype = AA   length = 10
FEATURE                 Location/Qualifiers
source                  1..10
                        mol_type = protein
                        organism = Homo sapiens
SEQUENCE: 580
CSYAGSSTWV                                                           10

SEQ ID NO: 581          moltype = DNA   length = 378
FEATURE                 Location/Qualifiers
source                  1..378
                        mol_type = other DNA
                        organism = Homo sapiens
SEQUENCE: 581
ccaggtcagc tggtggaatc tgggggaagc ttggtacagc ctggggggc cctgagactc    60
```

```
tcctgtgaag cctctggatt caccttagc gactatgcca tgagctgggt ccgccaggct      120
ccagggaagg ggctggagtg ggtctcagtt attaatagta gtggtggtat cacaaactac      180
gcagactccg tgaagggccg gttcaccatc tccagaaaca attccaagaa cacgctctat      240
ctgcaaatga acagcctgag aggcgacgac acggccatat attactgtgc gaagggaccc      300
ccgagaatta acccttcta caggcactac tacggtatgg acgtctgggg ccaagggatc       360
acggtcaccg tctcctca                                                    378

SEQ ID NO: 582          moltype = AA  length = 126
FEATURE                 Location/Qualifiers
source                  1..126
                        mol_type = protein
                        organism = Homo sapiens
SEQUENCE: 582
PGQLVESGGS LVQPGGALRL SCEASGFTFS DYAMSWVRQA PGKGLEWVSV INSSGGITNY       60
ADSVKGRFTI SRNNSKNTLY LQMNSLRGDD TAIYYCAKGP PRINTFYRHY YGMDVWGQGI      120
TVTVSS                                                                 126

SEQ ID NO: 583          moltype = DNA  length = 322
FEATURE                 Location/Qualifiers
source                  1..322
                        mol_type = other DNA
                        organism = Homo sapiens
SEQUENCE: 583
gccatccagt tgacccagtc tccatcctcc ctgtctgcat ctgtaggaga cagagtcacc       60
atcacttgcc aggcgagtca ggacattagg aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcggcag cctgcagcct     240
gaagatattg caacatatta ctgtcaacaa tatgataatc tccgggccac tttcggcgga     300
gggaccaagg tggagatcaa ac                                              322

SEQ ID NO: 584          moltype = AA  length = 107
FEATURE                 Location/Qualifiers
source                  1..107
                        mol_type = protein
                        organism = Homo sapiens
SEQUENCE: 584
AIQLTQSPSS LSASVGDRVT ITCQASQDIR NYLNWYQQKP GKAPKLLIYD ASNLETGVPS       60
RFSGSGSGTD FTFTIGSLQP EDIATYYCQQ YDNLRATFGG GTKVEIK                   107

SEQ ID NO: 585          moltype = AA  length = 8
FEATURE                 Location/Qualifiers
source                  1..8
                        mol_type = protein
                        organism = Homo sapiens
SEQUENCE: 585
GFTFSDYA                                                                 8

SEQ ID NO: 586          moltype = AA  length = 8
FEATURE                 Location/Qualifiers
source                  1..8
                        mol_type = protein
                        organism = Homo sapiens
SEQUENCE: 586
INSSGGIT                                                                 8

SEQ ID NO: 587          moltype = AA  length = 19
FEATURE                 Location/Qualifiers
source                  1..19
                        mol_type = protein
                        organism = Homo sapiens
SEQUENCE: 587
AKGPPRINTF YRHYYGMDV                                                    19

SEQ ID NO: 588          moltype = AA  length = 6
FEATURE                 Location/Qualifiers
source                  1..6
                        mol_type = protein
                        organism = Homo sapiens
SEQUENCE: 588
QDIRNY                                                                   6

SEQ ID NO: 589          moltype =     length =
SEQUENCE: 589
000

SEQ ID NO: 590          moltype = AA  length = 9
FEATURE                 Location/Qualifiers
source                  1..9
                        mol_type = protein
```

```
                        organism = Homo sapiens
SEQUENCE: 590
QQYDNLRAT                                                                 9

SEQ ID NO: 591          moltype = DNA  length = 370
FEATURE                 Location/Qualifiers
source                  1..370
                        mol_type = other DNA
                        organism = Homo sapiens
SEQUENCE: 591
caggtgcagc tggtggagtc tgggcctgaa atgaagaagc ctgggacctc agtgaaggtc    60
tcctgcaagg cttctggatt cacctttatt acgtctgctg ttcagtgggt gcgacaggct   120
cgtggacaac gccttgagtg gatgggatgg atcgccgttg gcagtggtaa cacaaactac   180
gcacagaaat tccaggacag agtcaccatt aacaggacag tgtccacaga cacagcctac   240
atggagctga gcagcctgag atccgaggac acggccgtgt attactgtgc ggcccccgcat   300
tgtaatcgta ccagctgcca tgatggtttt gatatctggg gccaagggac aatggtcacc   360
gtctcttcag                                                           370

SEQ ID NO: 592          moltype = AA  length = 123
FEATURE                 Location/Qualifiers
source                  1..123
                        mol_type = protein
                        organism = Homo sapiens
SEQUENCE: 592
QVQLVESGPE MKKPGTSVKV SCKASGFTFI TSAVQWVRQA RGQRLEWMGW IAVGSGNTNY    60
AQKFQDRVTI NRDMSTSTAY MELSSLRSED TAVYYCAAPH CNRTSCHDGF DIWGQGTMVT   120
VSS                                                                 123

SEQ ID NO: 593          moltype = DNA  length = 325
FEATURE                 Location/Qualifiers
source                  1..325
                        mol_type = other DNA
                        organism = Homo sapiens
SEQUENCE: 593
gaaattgtgt tgacgcagtc tccaggcacc ctgtctttgt ctccagggga aagagccacc    60
ctctcctgca gggccagtca gagtgttagc agaaactact tagcctggta ccagcagaaa   120
cctggccagg ttcccaggct cctcatctat ggtgcatcca gcagggccac tggcatccca   180
gacaggttca gaggtagtgg gtctgggaca gacttcactc tcaccatcaa cagactggag   240
tctgaagatt ttgcagtgta ttactgtcag cagtatggta gctccctatt cactttcggc   300
cctgggacca aagtggatat caaac                                         325

SEQ ID NO: 594          moltype = AA  length = 108
FEATURE                 Location/Qualifiers
source                  1..108
                        mol_type = protein
                        organism = Homo sapiens
SEQUENCE: 594
EIVLTQSPGT LSLSPGERAT LSCRASQSVS RNYLAWYQQK PGQVPRLLIY GASSRATGIP    60
DRFRGSGSGT DFTLTINRLE SEDFAVYYCQ QYGSSLFTFG PGTKVDIK                108

SEQ ID NO: 595          moltype = AA  length = 8
FEATURE                 Location/Qualifiers
source                  1..8
                        mol_type = protein
                        organism = Homo sapiens
SEQUENCE: 595
GFTFITSA                                                              8

SEQ ID NO: 596          moltype = AA  length = 8
FEATURE                 Location/Qualifiers
source                  1..8
                        mol_type = protein
                        organism = Homo sapiens
SEQUENCE: 596
IAVGSGNT                                                              8

SEQ ID NO: 597          moltype = AA  length = 16
FEATURE                 Location/Qualifiers
source                  1..16
                        mol_type = protein
                        organism = Homo sapiens
SEQUENCE: 597
AAPHCNRTSC HDGFDI                                                    16

SEQ ID NO: 598          moltype = AA  length = 7
FEATURE                 Location/Qualifiers
source                  1..7
                        mol_type = protein
                        organism = Homo sapiens
```

```
SEQUENCE: 598
QSVSRNY                                                                      7

SEQ ID NO: 599         moltype =    length =
SEQUENCE: 599
000

SEQ ID NO: 600         moltype = AA   length = 9
FEATURE                Location/Qualifiers
source                 1..9
                       mol_type = protein
                       organism = Homo sapiens
SEQUENCE: 600
QQYGSSLFT                                                                    9

SEQ ID NO: 601         moltype = DNA   length = 361
FEATURE                Location/Qualifiers
source                 1..361
                       mol_type = other DNA
                       organism = Homo sapiens
SEQUENCE: 601
gaagtgcagc tggtggagtc ggggggaggc ctggtcaagc ctggggagtc cctgagactc           60
tcctgtgcag cctctggatt caccttcagt agctatgcca tgaactgggt ccgccaggct          120
ccagggaagg gctggagtg gtctcatcc attagtactg gtagttattt catatactac            180
tcagactcag tgaagggccg attcaccatt tccagagaca acgccaagaa ctcactgtat          240
ctgcaaatga acagcctgag agccgcggac acggctatct attactgtgc gagaggaaag          300
gaagatacaa gcgctgcttt tgatatctgg ggccaaggga caatggtcac cgtctcttca          360
g                                                                          361

SEQ ID NO: 602         moltype = AA   length = 120
FEATURE                Location/Qualifiers
source                 1..120
                       mol_type = protein
                       organism = Homo sapiens
SEQUENCE: 602
EVQLVESGGG LVKPGESLRL SCAASGFTFS SYAMNWVRQA PGKGLEWVSS ISTGSYFIYY            60
SDSVKGRFTI SRDNAKNSLY LQMNSLRAAD TAIYYCARGK EDTSAAFDIW GQGTMVTVSS           120

SEQ ID NO: 603         moltype = DNA   length = 325
FEATURE                Location/Qualifiers
source                 1..325
                       mol_type = other DNA
                       organism = Homo sapiens
SEQUENCE: 603
gccatccaga tgacccagtc tcttcctcct gcgactctgg ctccagggga aagagccacc           60
ctctcctgca gggccagtca gagtgttagc aacaacttag cctggtacca gcagaaacct          120
ggccaggctc ccaggctcct catctatggt gcatccacca gggccactgg tatcccagcc          180
aggttcagtg gcagtgggtc tgggacagag ttcactctca ccatcagcag cctgcagtct          240
gaagattttg cagtttatta ctgtcagcag tataataact ggcctccgtg gacgttcggc          300
caagggacca agtggatat caaac                                                 325

SEQ ID NO: 604         moltype = AA   length = 108
FEATURE                Location/Qualifiers
source                 1..108
                       mol_type = protein
                       organism = Homo sapiens
SEQUENCE: 604
AIQMTQSLPP ATLAPGERAT LSCRASQSVS NNLAWYQQKP GQAPRLLIYG ASTRATGIPA            60
RFSGSGSGTE FTLTISSLQS EDFAVYYCQQ YNNWPPWTFG QGTKVDIK                       108

SEQ ID NO: 605         moltype = AA   length = 8
FEATURE                Location/Qualifiers
source                 1..8
                       mol_type = protein
                       organism = Homo sapiens
SEQUENCE: 605
GFTFSSYA                                                                     8

SEQ ID NO: 606         moltype = AA   length = 8
FEATURE                Location/Qualifiers
source                 1..8
                       mol_type = protein
                       organism = Homo sapiens
SEQUENCE: 606
ISTGSYFI                                                                     8

SEQ ID NO: 607         moltype = AA   length = 13
FEATURE                Location/Qualifiers
source                 1..13
```

```
                        mol_type = protein
                        organism = Homo sapiens
SEQUENCE: 607
ARGKEDTSAA FDI                                                        13

SEQ ID NO: 608          moltype = AA   length = 6
FEATURE                 Location/Qualifiers
source                  1..6
                        mol_type = protein
                        organism = Homo sapiens
SEQUENCE: 608
QSVSNN                                                                 6

SEQ ID NO: 609          moltype =     length =
SEQUENCE: 609
000

SEQ ID NO: 610          moltype = AA   length = 10
FEATURE                 Location/Qualifiers
source                  1..10
                        mol_type = protein
                        organism = Homo sapiens
SEQUENCE: 610
QQYNNWPPWT                                                            10

SEQ ID NO: 611          moltype = DNA  length = 355
FEATURE                 Location/Qualifiers
source                  1..355
                        mol_type = other DNA
                        organism = Homo sapiens
SEQUENCE: 611
gaggtgcagc tggtgcagtc tggggctgag gtgaagaagc ctgggtcctc ggtgaaggtc      60
tcctgcaagg cttctggagg caccttcagc agctctgtta tcagctgggt gcgacaggcc    120
cctggacagg gccttgagtg gatgggaggg atcatccctc tctttggttc agcaaactac    180
gcacagaagt tccagggcag agtcacgatt accgcggacg aatcgacgag cacagcctac    240
atggagatga ctagcctgag atctgaagac acggccgtgt attactgtgc gaaagtttcc    300
cagtgggcgt taatactctt ctggggccag ggaaccctgg tcaccgtctc ctcag         355

SEQ ID NO: 612          moltype = AA   length = 118
FEATURE                 Location/Qualifiers
source                  1..118
                        mol_type = protein
                        organism = Homo sapiens
SEQUENCE: 612
EVQLVQSGAE VKKPGSSVKV SCKASGGTFS SSVISWVRQA PGQGLEWMGG IIPLFGSANY     60
AQKFQGRVTI TADESTSTAY MEMTSLRSED TAVYYCAKVS QWALILFWGQ GTLVTVSS     118

SEQ ID NO: 613          moltype = DNA  length = 328
FEATURE                 Location/Qualifiers
source                  1..328
                        mol_type = other DNA
                        organism = Homo sapiens
SEQUENCE: 613
gccatccgga tgacccagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta cctcaccttc gtggacgttc    300
ggccaaggga ccaaggtgga gatcaaac                                       328

SEQ ID NO: 614          moltype = AA   length = 109
FEATURE                 Location/Qualifiers
source                  1..109
                        mol_type = protein
                        organism = Homo sapiens
SEQUENCE: 614
AIRMTQSPGT LSLSPGERAT LSCRASQSVS SSYLAWYQQK PGQAPRLLIY GASSRATGIP     60
DRFSGSGSGT DFTLTISRLE PEDFAVYYCQ QYGTSPSWTF GQGTKVEIK                109

SEQ ID NO: 615          moltype = AA   length = 8
FEATURE                 Location/Qualifiers
source                  1..8
                        mol_type = protein
                        organism = Homo sapiens
SEQUENCE: 615
GGTFSSSV                                                               8

SEQ ID NO: 616          moltype = AA   length = 8
FEATURE                 Location/Qualifiers
```

```
source                      1..8
                            mol_type = protein
                            organism = Homo sapiens
SEQUENCE: 616
IIPLFGSA                                                                    8

SEQ ID NO: 617              moltype = AA  length = 11
FEATURE                     Location/Qualifiers
source                      1..11
                            mol_type = protein
                            organism = Homo sapiens
SEQUENCE: 617
AKVSQWALIL F                                                               11

SEQ ID NO: 618              moltype = AA  length = 7
FEATURE                     Location/Qualifiers
source                      1..7
                            mol_type = protein
                            organism = Homo sapiens
SEQUENCE: 618
QSVSSSY                                                                     7

SEQ ID NO: 619              moltype =     length =
SEQUENCE: 619
000

SEQ ID NO: 620              moltype = AA  length = 10
FEATURE                     Location/Qualifiers
source                      1..10
                            mol_type = protein
                            organism = Homo sapiens
SEQUENCE: 620
QQYGTSPSWT                                                                 10

SEQ ID NO: 621              moltype = DNA  length = 355
FEATURE                     Location/Qualifiers
source                      1..355
                            mol_type = other DNA
                            organism = Homo sapiens
SEQUENCE: 621
gaggtgcagc tggtgcagtc tggggctgag gtgaagaagc ctgggtcctc ggtgaaggtc            60
tcctgcaagg cgtctagagg caccttcaac acctatgttt tcacctgggt gcgacaggcc          120
cctggacaag ggcttgagtg gatgggaggg atcatccctt tctttggtac agcagactac          180
gcacagaagt tccagggcag agtcacgatt accgcggacg actccacgag cacagcctac          240
atggagctga gcagcctgag atctgaggac acggccgtgt attactgttc gaggctcagc          300
cagtgggacc tactacccat gtggggccag ggaaccctgg tcaccgtctc ctcag              355

SEQ ID NO: 622              moltype = AA  length = 118
FEATURE                     Location/Qualifiers
source                      1..118
                            mol_type = protein
                            organism = Homo sapiens
SEQUENCE: 622
EVQLVQSGAE VKKPGSSVKV SCKASRGTFN TYVFTWVRQA PGQGLEWMGG IIPFFGTADY           60
AQKFQGRVTI TADDSTSTAY MELSSLRSED TAVYYCSRLS QWDLLPMWGQ GTLVTVSS            118

SEQ ID NO: 623              moltype = DNA  length = 331
FEATURE                     Location/Qualifiers
source                      1..331
                            mol_type = other DNA
                            organism = Homo sapiens
SEQUENCE: 623
gatattgtga tgactcagtc tccaggcacc ctgtctttgt ctccagggga aagagccacc            60
ctctcctgca gggccagtca gagttttacc agcagctact tagcctggta ccagcagaaa          120
cctggccagg ctcccaggct cctcatctat ggtgcatcca gcagggccac tggcatccca          180
gacaggttca gtggcactgg gtctgggaca gacttcactc tcaccatcag cagactggag          240
cctgaagatt ttgcagtata ttactgtcag cagtatggta cgtcacctcg catgtacact          300
tttggccagg ggaccaaagt ggatatcaaa c                                         331

SEQ ID NO: 624              moltype = AA  length = 110
FEATURE                     Location/Qualifiers
source                      1..110
                            mol_type = protein
                            organism = Homo sapiens
SEQUENCE: 624
DIVMTQSPGT LSLSPGERAT LSCRASQSFT SSYLAWYQQK PGQAPRLLIY GASSRATGIP           60
DRFSGTGSGT DFTLTISRLE PEDFAVYYCQ QYGTSPRMYT FGQGTKVDIK                     110

SEQ ID NO: 625              moltype = AA  length = 8
```

```
FEATURE                 Location/Qualifiers
source                  1..8
                        mol_type = protein
                        organism = Homo sapiens
SEQUENCE: 625
RGTFNTYV                                                                        8

SEQ ID NO: 626          moltype = AA  length = 8
FEATURE                 Location/Qualifiers
source                  1..8
                        mol_type = protein
                        organism = Homo sapiens
SEQUENCE: 626
IIPFFGTA                                                                        8

SEQ ID NO: 627          moltype = AA  length = 11
FEATURE                 Location/Qualifiers
source                  1..11
                        mol_type = protein
                        organism = Homo sapiens
SEQUENCE: 627
SRLSQWDLLP M                                                                   11

SEQ ID NO: 628          moltype = AA  length = 7
FEATURE                 Location/Qualifiers
source                  1..7
                        mol_type = protein
                        organism = Homo sapiens
SEQUENCE: 628
QSFTSSY                                                                         7

SEQ ID NO: 629          moltype =     length =
SEQUENCE: 629
000

SEQ ID NO: 630          moltype = AA  length = 11
FEATURE                 Location/Qualifiers
source                  1..11
                        mol_type = protein
                        organism = Homo sapiens
SEQUENCE: 630
QQYGTSPRMY T                                                                   11

SEQ ID NO: 631          moltype = DNA  length = 361
FEATURE                 Location/Qualifiers
source                  1..361
                        mol_type = other DNA
                        organism = Homo sapiens
SEQUENCE: 631
cagctgcagc tggtggagtc tggggctgag gtgaagaagc ctggggcttc agtgaaggtc              60
tcctgcaagg tttccggata caccctcact gaattatcca tgcactgggt gcgacaggct             120
cctggaaaag ggcttgagtg gatggggggt tttgatcctg aagatggtga gacaatctac             180
gcacagaagt tccagggcag agtcaccatg accgaggaca catctataga cacagtgtac             240
atggagctga gcagcctgag atctgaggac acggccgtgt attactgtgc aatagatcgc             300
aagcactggc tggtaggtct tgactactgg ggccaggaa ccctggtcac cgtctcctca              360
g                                                                             361

SEQ ID NO: 632          moltype = AA  length = 120
FEATURE                 Location/Qualifiers
source                  1..120
                        mol_type = protein
                        organism = Homo sapiens
SEQUENCE: 632
QLQLVESGAE VKKPGASVKV SCKVSGYTLT ELSMHWVRQA PGKGLEWMGG FDPEDGETIY              60
AQKFQGRVTM TEDTSIDTVY MELSSLRSED TAVYYCAIDR KHWLVGLDYW GQGTLVTVSS             120

SEQ ID NO: 633          moltype = DNA  length = 322
FEATURE                 Location/Qualifiers
source                  1..322
                        mol_type = other DNA
                        organism = Homo sapiens
SEQUENCE: 633
gccatccgga tgacccagtc tccatcctca ctgtctgcat ctgtaggaga cagagtcacc              60
atcacttgtc gggcgagtca gggcattagg aattatttag cctggtttca gcagaaacca             120
gggaaagccc ctaagtccct gatctatgct gcatccagtt tgcaaagtgg ggtcccatca             180
aagttcagcg gcagtggatc tgggacagat tcactctca ccatcagcag cctgcagcct              240
gaagattttg caacttatta ctgccaacag tataatagtt accccctcac cttcggccaa             300
gggacacgac tggagattaa ac                                                      322
```

```
SEQ ID NO: 634            moltype = AA   length = 107
FEATURE                   Location/Qualifiers
source                    1..107
                          mol_type = protein
                          organism = Homo sapiens
SEQUENCE: 634
AIRMTQSPSS LSASVGDRVT ITCRASQGIR NYLAWFQQKP GKAPKSLIYA ASSLQSGVPS   60
KFSGSGSGTD FTLTISSLQP EDFATYYCQQ YNSYPLTFGQ GTRLEIK                107

SEQ ID NO: 635            moltype = AA   length = 8
FEATURE                   Location/Qualifiers
source                    1..8
                          mol_type = protein
                          organism = Homo sapiens
SEQUENCE: 635
GYTLTELS                                                             8

SEQ ID NO: 636            moltype = AA   length = 8
FEATURE                   Location/Qualifiers
source                    1..8
                          mol_type = protein
                          organism = Homo sapiens
SEQUENCE: 636
FDPEDGET                                                             8

SEQ ID NO: 637            moltype = AA   length = 13
FEATURE                   Location/Qualifiers
source                    1..13
                          mol_type = protein
                          organism = Homo sapiens
SEQUENCE: 637
AIDRKHWLVG LDY                                                      13

SEQ ID NO: 638            moltype = AA   length = 6
FEATURE                   Location/Qualifiers
source                    1..6
                          mol_type = protein
                          organism = Homo sapiens
SEQUENCE: 638
QGIRNY                                                               6

SEQ ID NO: 639            moltype =    length =
SEQUENCE: 639
000

SEQ ID NO: 640            moltype = AA   length = 9
FEATURE                   Location/Qualifiers
source                    1..9
                          mol_type = protein
                          organism = Homo sapiens
SEQUENCE: 640
QQYNSYPLT                                                            9

SEQ ID NO: 641            moltype = DNA  length = 364
FEATURE                   Location/Qualifiers
source                    1..364
                          mol_type = other DNA
                          organism = Homo sapiens
SEQUENCE: 641
caggtgcagc tggtgcagtc cggagcagag gtgaaaaagc ccggggagtc tctgaggatc   60
tcctgtaagg gttctggaca caactctccc agctactgga ttagctgggt gcgccagatg  120
cccgggaaag gcctggagtg gatggggaga attgatccta gtgactctta taccaactac  180
agcccgtcct tccaaggcca tgtcaccatc tcagctgaca gtccatcag tactgcctac   240
ctacagtgga gcagcctgca ggcctcggac accgccattt attactgtgc gagacacgtg  300
gttgcattga ctcatttgta ccctgactac tggggccagg aacccctggt caccgtctcc  360
tcag                                                               364

SEQ ID NO: 642            moltype = AA   length = 121
FEATURE                   Location/Qualifiers
source                    1..121
                          mol_type = protein
                          organism = Homo sapiens
SEQUENCE: 642
QVQLVQSGAE VKKPGESLRI SCKGSGHNSP SYWISWVRQM PGKGLEWMGR IDPSDSYTNY   60
SPSFQGHVTI SADKSISTAY LQWSSLQASD TAIYYCARHV VALTHLYPDY WGQGTLVTVS  120
S                                                                  121

SEQ ID NO: 643            moltype = DNA  length = 325
FEATURE                   Location/Qualifiers
```

```
source                  1..325
                        mol_type = other DNA
                        organism = Homo sapiens
SEQUENCE: 643
gacatccaga tgacccagtc tccagccacc ctgtctgtgt ctccagggga aagagccacc    60
ctctcctgca gggccagtca aagtgttagc agcaccttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcaa tataataact ggtccacgtg gacgttcggc   300
caagggacca aagtggatat caaac                                         325

SEQ ID NO: 644          moltype = AA  length = 108
FEATURE                 Location/Qualifiers
source                  1..108
                        mol_type = protein
                        organism = Homo sapiens
SEQUENCE: 644
DIQMTQSPAT LSVSPGERAT LSCRASQSVS STLAWYQQKP GQAPRLLIYG ASTRATGIPA    60
RFSGSGSGTE FTLTISSLQS EDFAVYYCQQ YNNWSTWTFG QGTKVDIK                108

SEQ ID NO: 645          moltype = AA  length = 8
FEATURE                 Location/Qualifiers
source                  1..8
                        mol_type = protein
                        organism = Homo sapiens
SEQUENCE: 645
GHNSPSYW                                                              8

SEQ ID NO: 646          moltype = AA  length = 8
FEATURE                 Location/Qualifiers
source                  1..8
                        mol_type = protein
                        organism = Homo sapiens
SEQUENCE: 646
IDPSDSYT                                                              8

SEQ ID NO: 647          moltype = AA  length = 14
FEATURE                 Location/Qualifiers
source                  1..14
                        mol_type = protein
                        organism = Homo sapiens
SEQUENCE: 647
ARHVVALTHL YPDY                                                      14

SEQ ID NO: 648          moltype = AA  length = 6
FEATURE                 Location/Qualifiers
source                  1..6
                        mol_type = protein
                        organism = Homo sapiens
SEQUENCE: 648
QSVSST                                                                6

SEQ ID NO: 649          moltype =     length =
SEQUENCE: 649
000

SEQ ID NO: 650          moltype = AA  length = 10
FEATURE                 Location/Qualifiers
source                  1..10
                        mol_type = protein
                        organism = Homo sapiens
SEQUENCE: 650
QQYNNWSTWT                                                           10

SEQ ID NO: 651          moltype = DNA  length = 379
FEATURE                 Location/Qualifiers
source                  1..379
                        mol_type = other DNA
                        organism = Homo sapiens
SEQUENCE: 651
caggtgcagc tgcaggagtc gggcccagga ctggtgaagc cttcggagac cctgtccctc    60
acctgcactg tctttggtgg ctccatcacc agtagtaatc actactgggg ctggatccgc   120
cagccccag ggaaggggct ggagtggatt gggagtatgt attatagtgg gagcaccgcc    180
tacaacccgt ccctcacgaa tcgagtcacc atatccgtag acacgtccaa gaaccagttc   240
tccctgaagc tgagctccgt gaccgccgca gacacggctg tgtattactg tgcgagacaa   300
atcgggccca gaggccctc gcaagtggct gactggttcg accctggg ccagggaacc     360
ctggtcaccg tctcctcag                                                379

SEQ ID NO: 652          moltype = AA  length = 126
```

```
FEATURE                 Location/Qualifiers
source                  1..126
                        mol_type = protein
                        organism = Homo sapiens
SEQUENCE: 652
QVQLQESGPG LVKPSETLSL TCTVFGGSIT SSNHYWVWIR QPPGKGLEWI GSMYYSGSTA   60
YNPSLTNRVT ISVDTSKNQF SLKLSSVTAA DTAVYYCARQ IGPKRPSQVA DWFDPWGQGT  120
LVTVSS                                                             126

SEQ ID NO: 653          moltype = DNA  length = 322
FEATURE                 Location/Qualifiers
source                  1..322
                        mol_type = other DNA
                        organism = Homo sapiens
SEQUENCE: 653
gacatccagt tgacccagtc tccatccttc ctgtctgcat ctgtaggaga cagagtcacc   60
atcacttgcc gggccagtca gggcattagc agttatttag cctggtatca gcaaaaacct  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaacag cttaatagtt acccgctcac tttcggcgga  300
gggaccaagg tggaaatcaa ac                                           322

SEQ ID NO: 654          moltype = AA  length = 107
FEATURE                 Location/Qualifiers
source                  1..107
                        mol_type = protein
                        organism = Homo sapiens
SEQUENCE: 654
DIQLTQSPSF LSASVGDRVT ITCRASQGIS SYLAWYQQKP GKAPKLLIYA ASTLQSGVPS   60
RFSGSGSGTE FTLTISSLQP EDFATYYCQQ LNSYPLTFGG GTKVEIK                107

SEQ ID NO: 655          moltype = AA  length = 10
FEATURE                 Location/Qualifiers
source                  1..10
                        mol_type = protein
                        organism = Homo sapiens
SEQUENCE: 655
GGSITSSNHY                                                          10

SEQ ID NO: 656          moltype = AA  length = 7
FEATURE                 Location/Qualifiers
source                  1..7
                        mol_type = protein
                        organism = Homo sapiens
SEQUENCE: 656
MYYSGST                                                             7

SEQ ID NO: 657          moltype = AA  length = 18
FEATURE                 Location/Qualifiers
source                  1..18
                        mol_type = protein
                        organism = Homo sapiens
SEQUENCE: 657
ARQIGPKRPS QVADWFDP                                                 18

SEQ ID NO: 658          moltype = AA  length = 6
FEATURE                 Location/Qualifiers
source                  1..6
                        mol_type = protein
                        organism = Homo sapiens
SEQUENCE: 658
QGISSY                                                              6

SEQ ID NO: 659          moltype =     length =
SEQUENCE: 659
000

SEQ ID NO: 660          moltype = AA  length = 9
FEATURE                 Location/Qualifiers
source                  1..9
                        mol_type = protein
                        organism = Homo sapiens
SEQUENCE: 660
QQLNSYPLT                                                           9

SEQ ID NO: 661          moltype = DNA  length = 382
FEATURE                 Location/Qualifiers
source                  1..382
                        mol_type = other DNA
```

-continued

```
                         organism = Homo sapiens
SEQUENCE: 661
caggtgcagc tgcaggagtc gggcccagga ctggtgaagc cttcggagac cctgtccctc   60
acttgcactg tctctggtga ctccatcagc agtagtcgtt actactgggg ctggatccgc  120
cagcccccag ggaaggggct ggagtggatt gggacttttc tattatagtg gatcacgtac  180
tacaacccgt ccctcaagag tcgagtcacc atattcgtag acacgtccaa gaaccagttc  240
tccctgaagc tgagctctgt gaccgccgca gacacggctg tttattactg tgcgagaccc  300
cgaccccccg attactatga taatagtggt gcgctccttt ttgatatctg gggccaaggg  360
acaatggtca ccgtctcttc ag                                           382

SEQ ID NO: 662           moltype = AA  length = 127
FEATURE                  Location/Qualifiers
source                   1..127
                         mol_type = protein
                         organism = Homo sapiens
SEQUENCE: 662
QVQLQESGPG LVKPSETLSL TCTVSGDSIS SSRYYWGWIR QPPGKGLEWI GTFYYSGITY   60
YNPSLKSRVT IFVDTSKNQF SLKLSSVTAA DTAVYYCARP RPPDYYDNSG ALLFDIWGQG  120
TMVTVSS                                                            127

SEQ ID NO: 663           moltype = DNA  length = 325
FEATURE                  Location/Qualifiers
source                   1..325
                         mol_type = other DNA
                         organism = Homo sapiens
SEQUENCE: 663
gccatccgga tgacccagtc tccttccacc ctgtctgcat ctgtaggaga cagagtcacc   60
atcgcttgcc gggccagtca gagtattagt gcctggttgg cctggtatca gcagaaacca  120
gggaaagccc ctaagctcct gatctataag gcatctagtt tagaaagtgg ggtcccatca  180
aggttcagcg gcagtggatc tgggacagaa ttcactctca ccatcaacag cctgcagcct  240
gatgattttg ccacttatta ctgccaacag tatattagtt cttctccgtg gacgttcggc  300
caagggacca aggtggaaat caaac                                        325

SEQ ID NO: 664           moltype = AA  length = 108
FEATURE                  Location/Qualifiers
source                   1..108
                         mol_type = protein
                         organism = Homo sapiens
SEQUENCE: 664
AIRMTQSPST LSASVGDRVT IACRASQSIS AWLAWYQQKP GKAPKLLIYK ASSLESGVPS   60
RFSGSGSGTE FTLTINSLQP DDFATYYCQQ YISSSPWTFG QGTKVEIK               108

SEQ ID NO: 665           moltype = AA  length = 10
FEATURE                  Location/Qualifiers
source                   1..10
                         mol_type = protein
                         organism = Homo sapiens
SEQUENCE: 665
GDSISSSRYY                                                          10

SEQ ID NO: 666           moltype = AA  length = 7
FEATURE                  Location/Qualifiers
source                   1..7
                         mol_type = protein
                         organism = Homo sapiens
SEQUENCE: 666
FYYSGIT                                                              7

SEQ ID NO: 667           moltype = AA  length = 19
FEATURE                  Location/Qualifiers
source                   1..19
                         mol_type = protein
                         organism = Homo sapiens
SEQUENCE: 667
ARPRPPDYYD NSGALLFDI                                                19

SEQ ID NO: 668           moltype = AA  length = 6
FEATURE                  Location/Qualifiers
source                   1..6
                         mol_type = protein
                         organism = Homo sapiens
SEQUENCE: 668
QSISAW                                                               6

SEQ ID NO: 669           moltype =   length =
SEQUENCE: 669
000

SEQ ID NO: 670           moltype = AA  length = 10
```

| FEATURE | Location/Qualifiers |
|---|---|
| source | 1..10 |
| | mol_type = protein |
| | organism = Homo sapiens |

SEQUENCE: 670
QQYISSSPWT                                                                10

| SEQ ID NO: 671 | moltype = DNA   length = 370 |
|---|---|
| FEATURE | Location/Qualifiers |
| source | 1..370 |
| | mol_type = other DNA |
| | organism = Homo sapiens |

SEQUENCE: 671
```
cagctgcagc tgcaggagtc gggcccagga ctggtgaggc cttcacagac cctgtccctc   60
tcctgcactg tctctggtgg ctccatcagc agtgccactc actactggag ctggatccgc  120
cagcacccag ggagaggcct ggagtggatt gggtacatct attacactgg ggcacccttt  180
tacaatccgt ccctcaagag tcgacttacc atatcagtgg acacgtctaa gaaccagttc  240
tccctgaagc tgagcgctgt gactgccgcg gacacggccg tgtattactg tgcgagagtt  300
atagcagctc gtccgggatc tacctacttt gacttctggg gccggggaac cctggtcacc  360
gtctcctcag                                                         370
```

| SEQ ID NO: 672 | moltype = AA   length = 123 |
|---|---|
| FEATURE | Location/Qualifiers |
| source | 1..123 |
| | mol_type = protein |
| | organism = Homo sapiens |

SEQUENCE: 672
```
QLQLQESGPG LVRPSQTLSL SCTVSGGSIS SATHYWSWIR QHPGRGLEWI GYIYYTGGTF   60
YNPSLKSRLT ISVDTSKNQF SLKLSAVTAA DTAVYYCARV IAARPGSTYF DFWGRGTLVT  120
VSS                                                                123
```

| SEQ ID NO: 673 | moltype = DNA   length = 337 |
|---|---|
| FEATURE | Location/Qualifiers |
| source | 1..337 |
| | mol_type = other DNA |
| | organism = Homo sapiens |

SEQUENCE: 673
```
caatctgccc tgactcagcc tgcctccgtg tctgggtctc ctggacagtc gatcaccatc   60
tcctgcactg gaaccagcag tgacgttagt ggctataact atgtctcctg gtaccaacaa  120
cacccagaca agccccccaa actcttgatt tatgatgtca ctaatcggcc cacaggggtt  180
tctaatcgct tctctgcctc caagtctggc aacacggcct ccctgaccat ctctgggctc  240
caggctgagg acgaggctga ttattactgc agctcagata caaatagtat tcctcggtat  300
gtggtgttcg gcggagggac caagctgacc gtcctag                           337
```

| SEQ ID NO: 674 | moltype = AA   length = 112 |
|---|---|
| FEATURE | Location/Qualifiers |
| source | 1..112 |
| | mol_type = protein |
| | organism = Homo sapiens |

SEQUENCE: 674
```
QSALTQPASV SGSPGQSITI SCTGTSSDVS GYNYVSWYQQ HPDKAPKLLI YDVTNRPTGV   60
SNRFSASKSG NTASLTISGL QAEDEADYYC SSDTNSIPRY VVFGGGTKLT VL          112
```

| SEQ ID NO: 675 | moltype = AA   length = 10 |
|---|---|
| FEATURE | Location/Qualifiers |
| source | 1..10 |
| | mol_type = protein |
| | organism = Homo sapiens |

SEQUENCE: 675
GGSISSATHY                                                                10

| SEQ ID NO: 676 | moltype = AA   length = 7 |
|---|---|
| FEATURE | Location/Qualifiers |
| source | 1..7 |
| | mol_type = protein |
| | organism = Homo sapiens |

SEQUENCE: 676
IYYTGGT                                                                    7

| SEQ ID NO: 677 | moltype = AA   length = 15 |
|---|---|
| FEATURE | Location/Qualifiers |
| source | 1..15 |
| | mol_type = protein |
| | organism = Homo sapiens |

SEQUENCE: 677
ARVIAARPGS TYFDF                                                          15

| SEQ ID NO: 678 | moltype = AA   length = 9 |
|---|---|
| FEATURE | Location/Qualifiers |

```
source                       1..9
                             mol_type = protein
                             organism = Homo sapiens
SEQUENCE: 678
SSDVSGYNY                                                                    9

SEQ ID NO: 679               moltype =    length =
SEQUENCE: 679
000

SEQ ID NO: 680               moltype = AA   length = 9
FEATURE                      Location/Qualifiers
source                       1..9
                             mol_type = protein
                             organism = Homo sapiens
SEQUENCE: 680
SSDTNSIPR                                                                    9

SEQ ID NO: 681               moltype = DNA   length = 394
FEATURE                      Location/Qualifiers
source                       1..394
                             mol_type = other DNA
                             organism = Homo sapiens
SEQUENCE: 681
gaggtgcagc tggtggagtc tgggggctgag gtgaagaagc ctgggtcctc ggtgaaggtc        60
tcctgcaagg cttctggagg caccttcagc agctatgcta tcaactgggt gcgacaggcc       120
cctggacaag ggcttgagtg gatgggaggg atcatcccta tctttcgtac gccgcactac       180
gcacagaaat tccagggcag agtcacgatt accgcggacg aatctacggg cacagcctac       240
atggagctga gcagcctgcg atctgaagac acggccgtgt attactgtgc gagcccctct       300
tgtggtggtg actgccccca gtacttaaaa tcatccaaac tagactggta cttcgatctc       360
tggggccgtg gcaccctggt caccgtctcc tcag                                   394

SEQ ID NO: 682               moltype = AA   length = 131
FEATURE                      Location/Qualifiers
source                       1..131
                             mol_type = protein
                             organism = Homo sapiens
SEQUENCE: 682
EVQLVESGAE VKKPGSSVKV SCKASGGTFS SYAINWVRQA PGQGLEWMGG IIPIFRTPHY         60
AQKFQGRVTI TADESTGTAY MELSSLRSED TAVYYCASPS CGGDCPQYLK SSKLDWYFDL        120
WGRGTLVTVS S                                                            131

SEQ ID NO: 683               moltype = DNA   length = 325
FEATURE                      Location/Qualifiers
source                       1..325
                             mol_type = other DNA
                             organism = Homo sapiens
SEQUENCE: 683
gtcatctgga tgacccagtc tccaggcacc ctgtctttgt ctccagggga aagagccacc        60
ctctcctgca gggccagtca gagtgttagc agcacctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggaa       240
cctgaagatt ttgcagtgta ttactgtcag cactatggta gctcacctct caccttcggc       300
caagggacac gactggagat taaac                                             325

SEQ ID NO: 684               moltype = AA   length = 108
FEATURE                      Location/Qualifiers
source                       1..108
                             mol_type = protein
                             organism = Homo sapiens
SEQUENCE: 684
VIWMTQSPGT LSLSPGERAT LSCRASQSVS STYLAWYQQK PGQAPRLLIY GASSRATGIP         60
DRFSGSGSGT DFTLTISRLE PEDFAVYYCQ HYGSSPLTFG QGTRLEIK                     108

SEQ ID NO: 685               moltype = AA   length = 8
FEATURE                      Location/Qualifiers
source                       1..8
                             mol_type = protein
                             organism = Homo sapiens
SEQUENCE: 685
GGTFSSYA                                                                     8

SEQ ID NO: 686               moltype = AA   length = 8
FEATURE                      Location/Qualifiers
source                       1..8
                             mol_type = protein
                             organism = Homo sapiens
SEQUENCE: 686
IIPIFRTP                                                                     8
```

SEQ ID NO: 687          moltype = AA   length = 24
FEATURE                 Location/Qualifiers
source                  1..24
                        mol_type = protein
                        organism = Homo sapiens
SEQUENCE: 687
ASPSCGGDCP QYLKSSKLDW YFDL                                         24

SEQ ID NO: 688          moltype = AA   length = 7
FEATURE                 Location/Qualifiers
source                  1..7
                        mol_type = protein
                        organism = Homo sapiens
SEQUENCE: 688
QSVSSTY                                                            7

SEQ ID NO: 689          moltype =      length =
SEQUENCE: 689
000

SEQ ID NO: 690          moltype = AA   length = 9
FEATURE                 Location/Qualifiers
source                  1..9
                        mol_type = protein
                        organism = Homo sapiens
SEQUENCE: 690
QHYGSSPLT                                                          9

SEQ ID NO: 691          moltype = DNA   length = 355
FEATURE                 Location/Qualifiers
source                  1..355
                        mol_type = other DNA
                        organism = Homo sapiens
SEQUENCE: 691
gaggtgcagc tggtggagtc tggaggaggc ttgatccagc ctgggggtc cctgagactc    60
tcctgtgcag cctctgagat catcgtcagt aggaactaca tgagctgggt ccgccaggct  120
ccagggaagg ggctggagtg ggtctcagtt atttatagcg gtggtagcac gttctacgca  180
gactccgtga agggccgatt caccatctcc agagacaac gctgtatctt                240
caaatgaaca gcctgagagc cgaggacacg gccgtgtatt actgtgcgag agacctcgac  300
gtagtgggag gtactgacta ctggggccag ggaaccctgg tcaccgtctc ctcag       355

SEQ ID NO: 692          moltype = AA   length = 118
FEATURE                 Location/Qualifiers
source                  1..118
                        mol_type = protein
                        organism = Homo sapiens
SEQUENCE: 692
EVQLVESGGG LIQPGGSLRL SCAASEIIVS RNYMSWVRQA PGKGLEWVSV IYSGGSTFYA   60
DSVKGRFTIS RDNSKNTLYL QMNSLRAEDT AVYYCARDLD VVGGTDYWGQ GTLVTVSS    118

SEQ ID NO: 693          moltype = DNA   length = 328
FEATURE                 Location/Qualifiers
source                  1..328
                        mol_type = other DNA
                        organism = Homo sapiens
SEQUENCE: 693
gaaattgtgt tgacacagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccagg gtacactttt  300
ggccagggga ccaaagtgga tatcaaac                                     328

SEQ ID NO: 694          moltype = AA   length = 109
FEATURE                 Location/Qualifiers
source                  1..109
                        mol_type = protein
                        organism = Homo sapiens
SEQUENCE: 694
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPGYTF GQGTKVDIK              109

SEQ ID NO: 695          moltype = AA   length = 8
FEATURE                 Location/Qualifiers
source                  1..8
                        mol_type = protein
                        organism = Homo sapiens
SEQUENCE: 695

-continued

```
EIIVSRNY                                                              8

SEQ ID NO: 696          moltype = AA  length = 7
FEATURE                 Location/Qualifiers
source                  1..7
                        mol_type = protein
                        organism = Homo sapiens
SEQUENCE: 696
IYSGGST                                                               7

SEQ ID NO: 697          moltype = AA  length = 12
FEATURE                 Location/Qualifiers
source                  1..12
                        mol_type = protein
                        organism = Homo sapiens
SEQUENCE: 697
ARDLDVVGGT DY                                                         12

SEQ ID NO: 698          moltype = AA  length = 7
FEATURE                 Location/Qualifiers
source                  1..7
                        mol_type = protein
                        organism = Homo sapiens
SEQUENCE: 698
QSVSSSY                                                               7

SEQ ID NO: 699          moltype =   length =
SEQUENCE: 699
000

SEQ ID NO: 700          moltype = AA  length = 10
FEATURE                 Location/Qualifiers
source                  1..10
                        mol_type = protein
                        organism = Homo sapiens
SEQUENCE: 700
QQYGSSPGYT                                                            10

SEQ ID NO: 701          moltype = DNA  length = 373
FEATURE                 Location/Qualifiers
source                  1..373
                        mol_type = other DNA
                        organism = Homo sapiens
SEQUENCE: 701
gaggtgcagc tgttggagtc gggcccagga ctggtgaagc cttcggagac cctgtccctc     60
acctgcaccg tctctggtgg ctccatcagc agatactcct ggtcctggat ccggcagccc    120
gccgggaggg gactggagtg gatcgggcgt atgtataggca gtggggcac caactataac    180
ccctccctcg agagtcgagt caccatgtca cttgacacgt ccaagaagca gttctccctg    240
aagctgagct ctgtgaccgc cgcggacacg gccgtgtatt actgtgcggc ggcttcaatt    300
gatcaagtat gggggactta tcgtgatgct tttgatatct ggggtcaagg gacaatggtc    360
accgtctctt cag                                                      373

SEQ ID NO: 702          moltype = AA  length = 124
FEATURE                 Location/Qualifiers
source                  1..124
                        mol_type = protein
                        organism = Homo sapiens
SEQUENCE: 702
EVQLLESGPG LVKPSETLSL TCTVSGGSIS RYSWSWIRQP AGRGLEWIGR MYSSGGTNYN     60
PSLESRVTMS LDTSKKQFSL KLSSVTAADT AVYYCAAASI DQVWGTYRDA FDIWGQGTMV    120
TVSS                                                                124

SEQ ID NO: 703          moltype = DNA  length = 322
FEATURE                 Location/Qualifiers
source                  1..322
                        mol_type = other DNA
                        organism = Homo sapiens
SEQUENCE: 703
gccatccgga tgacccagtc tccatcctcc ctggctgcat ctgtaggaga cagagtcacc     60
atctcttgcc gggcaggtca gagcattagc agctttttac attggtatca gcagaaagta    120
gggaaagccc ctaagctcct gatctatgat cgtccagtt tgcaaagtgg ggtcccatca    180
aggttcagtg gcagtggatc tgggacagat ttcactctca ccatcagcag tctgcaacct    240
gaagattttg cagcttacta ctgtcaacag agttacgaaa cccgcttac tttcggcgga    300
gggaccaaag tggatatcaa ac                                            322

SEQ ID NO: 704          moltype = AA  length = 107
FEATURE                 Location/Qualifiers
source                  1..107
                        mol_type = protein
```

```
                    organism = Homo sapiens
SEQUENCE: 704
AIRMTQSPSS LAASVGDRVT ISCRAGQSIS SFLHWYQQKV GKAPKLLIYD ASSLQSGVPS      60
RFSGSGSGTD FTLTISSLQP EDFAAYYCQQ SYENPLTFGG GTKVDIK                   107

SEQ ID NO: 705          moltype = AA   length = 8
FEATURE                 Location/Qualifiers
source                  1..8
                        mol_type = protein
                        organism = Homo sapiens
SEQUENCE: 705
GGSISRYS                                                                8

SEQ ID NO: 706          moltype = AA   length = 7
FEATURE                 Location/Qualifiers
source                  1..7
                        mol_type = protein
                        organism = Homo sapiens
SEQUENCE: 706
MYSSGGT                                                                 7

SEQ ID NO: 707          moltype = AA   length = 18
FEATURE                 Location/Qualifiers
source                  1..18
                        mol_type = protein
                        organism = Homo sapiens
SEQUENCE: 707
AAASIDQVWG TYRDAFDI                                                    18

SEQ ID NO: 708          moltype = AA   length = 6
FEATURE                 Location/Qualifiers
source                  1..6
                        mol_type = protein
                        organism = Homo sapiens
SEQUENCE: 708
QSISSF                                                                  6

SEQ ID NO: 709          moltype =     length =
SEQUENCE: 709
000

SEQ ID NO: 710          moltype = AA   length = 9
FEATURE                 Location/Qualifiers
source                  1..9
                        mol_type = protein
                        organism = Homo sapiens
SEQUENCE: 710
QQSYENPLT                                                               9

SEQ ID NO: 711          moltype = DNA  length = 373
FEATURE                 Location/Qualifiers
source                  1..373
                        mol_type = other DNA
                        organism = Homo sapiens
SEQUENCE: 711
gaagtgcagc tggtggagtc tgggggctgag gtgaagaggc ctggggcctc agtgaaggtt     60
tcctgcaagg catctggata caccttcacc aactactttta tgcactgggt gcgacaggcc   120
cctggacaag gccttgagtg gatgggagtt atcaaccccta gtgatggtgg cgcaagctac   180
ccacagaagt tccagggcag agtcaccatg accagggaca cgtccacgag cacagtctac   240
atggatctga gcagcctgag atctgaggac acggccgtct attcctgtgc gagggggggct   300
tttgatgtta gcggcagctg gtacgtcccc tttgactact ggggccaggg aactctggtc   360
accgtctcct cag                                                       373

SEQ ID NO: 712          moltype = AA   length = 124
FEATURE                 Location/Qualifiers
source                  1..124
                        mol_type = protein
                        organism = Homo sapiens
SEQUENCE: 712
EVQLVESGAE VKRPGASVKV SCKASGYTFT NYFMHWVRQA PGQGLEWMGV INPSDGGASY      60
PQKFQGRVTM TRDTSTSTVY MDLSSLRSED TAVYSCARGA FDVSGSWYVP FDYWGQGTLV    120
TVSS                                                                 124

SEQ ID NO: 713          moltype = DNA  length = 340
FEATURE                 Location/Qualifiers
source                  1..340
                        mol_type = other DNA
                        organism = Homo sapiens
SEQUENCE: 713
```

```
cagtctgtcg tgacgcagcc gccctcagtg tctggggccc cagggcagag ggtcaccatc    60
tcctgcactg ggagcagctc caacatcggg gcaggttatg atgtacactg gtaccagcag   120
cttccaggag cagcccccaa actcctcatc tatggtaaca ccaatcggcc ctcagggatc   180
cctgaccgat tctctggctc caagtctggc acctccgcct ccctggccat cactgggctc   240
caggctgagg atgaggctga ttattactgc cagtcctatg acatcaccct gagtggttcg   300
gggtatgtct tcggaactgg gaccaaggtc accgtcctag                         340

SEQ ID NO: 714           moltype = AA  length = 113
FEATURE                  Location/Qualifiers
source                   1..113
                         mol_type = protein
                         organism = Homo sapiens
SEQUENCE: 714
QSVVTQPPSV SGAPGQRVTI SCTGSSSNIG AGYDVHWYQQ LPGAAPKLLI YGNTNRPSGV    60
PDRFSGSKSG TSASLAITGL QAEDEADYYC QSYDITLSGS GYVFGTGTKV TVL          113

SEQ ID NO: 715           moltype = AA  length = 8
FEATURE                  Location/Qualifiers
source                   1..8
                         mol_type = protein
                         organism = Homo sapiens
SEQUENCE: 715
GYTFTNYF                                                              8

SEQ ID NO: 716           moltype = AA  length = 8
FEATURE                  Location/Qualifiers
source                   1..8
                         mol_type = protein
                         organism = Homo sapiens
SEQUENCE: 716
INPSDGGA                                                              8

SEQ ID NO: 717           moltype = AA  length = 17
FEATURE                  Location/Qualifiers
source                   1..17
                         mol_type = protein
                         organism = Homo sapiens
SEQUENCE: 717
ARGAFDVSGS WYVPFDY                                                   17

SEQ ID NO: 718           moltype = AA  length = 9
FEATURE                  Location/Qualifiers
source                   1..9
                         mol_type = protein
                         organism = Homo sapiens
SEQUENCE: 718
SSNIGAGYD                                                             9

SEQ ID NO: 719           moltype =   length =
SEQUENCE: 719
000

SEQ ID NO: 720           moltype = AA  length = 13
FEATURE                  Location/Qualifiers
source                   1..13
                         mol_type = protein
                         organism = Homo sapiens
SEQUENCE: 720
QSYDITLSGS GYV                                                       13

SEQ ID NO: 721           moltype = DNA  length = 367
FEATURE                  Location/Qualifiers
source                   1..367
                         mol_type = other DNA
                         organism = Homo sapiens
SEQUENCE: 721
caggtgcagc tggtggagtc tggggggaggc gtggtccagc ctgggaggtc cctgagactc    60
tcctgtgcag cctctggatt caccttcagg acctatgctg tgcactgggt ccgccaggct   120
ccaggcaagg ggccagagtg ggtggcagtt atatcatatg atggaagtaa taaatactac   180
gcagactccg ttaagggccg attcacccta tccagagaca cttccaagaa cacgctgtat   240
ctgcaaatga acagcctgag agctgaggac acggctgtgt attactgcgc gagcagaggg   300
gacacggtga ctacaggtga cgcttttgat atctggggcc aagggacaat ggtcaccgtc   360
tcttcag                                                             367

SEQ ID NO: 722           moltype = AA  length = 122
FEATURE                  Location/Qualifiers
source                   1..122
                         mol_type = protein
                         organism = Homo sapiens
```

-continued

```
SEQUENCE: 722
QVQLVESGGG VVQPGRSLRL SCAASGFTFR TYAVHWVRQA PGKGPEWVAV ISYDGSNKYY    60
ADSVKGRFTL SRDTSKNTLY LQMNSLRAED TAVYYCASRG DTVTTGDAFD IWGQGTMVTV   120
SS                                                                  122

SEQ ID NO: 723          moltype = DNA   length = 334
FEATURE                 Location/Qualifiers
source                  1..334
                        mol_type = other DNA
                        organism = Homo sapiens
SEQUENCE: 723
tcctatgagc tgacacagcc accctcggtg tcagtgtccc caggacagac ggccaggatc    60
acctgctctg gagatgcatt gccaaagcaa tatacttatt ggtaccagca gaagccaggc   120
cagccccctg tgctggtgat atataaagac agtgagaggc ccctgagcga               180
ttctctggct ccagctcagg gacaacagtg acgttgacca tcagtggagt ccaggcagaa   240
gatgaggctg actattactg tcaatcaaca gacagcagtg ctacttatcc gggaaatgtg   300
gttttcggcg gagggaccaa gttgaccgtc ctag                                334

SEQ ID NO: 724          moltype = AA    length = 111
FEATURE                 Location/Qualifiers
source                  1..111
                        mol_type = protein
                        organism = Homo sapiens
SEQUENCE: 724
SYELTQPPSV SVSPGQTARI TCSGDALPKQ YTYWYQQKPG QPPVLVIYKD SERPSGIPER    60
FSGSSSGTTV TLTISGVQAE DEADYYCQST DSSATYPGNV VFGGGTKLTV L            111

SEQ ID NO: 725          moltype = AA    length = 8
FEATURE                 Location/Qualifiers
source                  1..8
                        mol_type = protein
                        organism = Homo sapiens
SEQUENCE: 725
GFTFRTYA                                                              8

SEQ ID NO: 726          moltype = AA    length = 8
FEATURE                 Location/Qualifiers
source                  1..8
                        mol_type = protein
                        organism = Homo sapiens
SEQUENCE: 726
ISYDGSNK                                                              8

SEQ ID NO: 727          moltype = AA    length = 15
FEATURE                 Location/Qualifiers
source                  1..15
                        mol_type = protein
                        organism = Homo sapiens
SEQUENCE: 727
ASRGDTVTTG DAFDI                                                     15

SEQ ID NO: 728          moltype = AA    length = 6
FEATURE                 Location/Qualifiers
source                  1..6
                        mol_type = protein
                        organism = Homo sapiens
SEQUENCE: 728
ALPKQY                                                                6

SEQ ID NO: 729          moltype =       length =
SEQUENCE: 729
000

SEQ ID NO: 730          moltype = AA    length = 14
FEATURE                 Location/Qualifiers
source                  1..14
                        mol_type = protein
                        organism = Homo sapiens
SEQUENCE: 730
QSTDSSATYP GNVV                                                      14

SEQ ID NO: 731          moltype = DNA   length = 370
FEATURE                 Location/Qualifiers
source                  1..370
                        mol_type = other DNA
                        organism = Homo sapiens
SEQUENCE: 731
gaggtgcagc tggtggagtc tgggcctgag gtgaagaagc tgggacctc agtgaaggtc     60
tcctgcaagg cgtctggatt cagttttagt atgtctgcta tgcagtgggt gcgacgggct   120
```

```
cgtggacaac gccttgagtg gataggatgg atcgtccctg gcagtggtaa cgcaaactac    180
gcgcagaagt ttcaggaaag agtcaccatt actaggacg agtccacaaa cacaggttat     240
atggagttga gcagcctgag atccgaggac acggccgtgt attattgtgc ggcccctcat    300
tgtaataaga ccaactgcta tgatgctttt gatatctggg gccaagggac aatggtcacc    360
gtctcttcag                                                           370

SEQ ID NO: 732              moltype = AA  length = 123
FEATURE                     Location/Qualifiers
source                      1..123
                            mol_type = protein
                            organism = Homo sapiens
SEQUENCE: 732
EVQLVESGPE VKKPGTSVKV SCKASGFSFS MSAMQWVRRA RGQRLEWIGW IVPGSGNANY     60
AQKFQERVTI TRDESTNTGY MELSSLRSED TAVYYCAAPH CNKTNCYDAF DIWGQGTMVT    120
VSS                                                                  123

SEQ ID NO: 733              moltype = DNA  length = 325
FEATURE                     Location/Qualifiers
source                      1..325
                            mol_type = other DNA
                            organism = Homo sapiens
SEQUENCE: 733
gccatccgga tgacccagtc tccaggcacc ctgtctttgt ctccagggga aagagccacc     60
ctctcctgca gggccagtca gagcgttagg agcagttact tagcctggta ccagcagaaa    120
cctggccagg ctcccaggct cctcatctat ggtgcatcca ccagggccac tggcatccca    180
gacaggttca gtggcagtgg gtctgggaca gacttcattc tcaccatcaa cagactggag    240
cctgaagatc ttgcagtcta ttactgtcag cagtttggta gctcaccatg gacgttcggc    300
caagggacca agtggatat caaac                                           325

SEQ ID NO: 734              moltype = AA  length = 108
FEATURE                     Location/Qualifiers
source                      1..108
                            mol_type = protein
                            organism = Homo sapiens
SEQUENCE: 734
AIRMTQSPGT LSLSPGERAT LSCRASQSVR SSYLAWYQQK PGQAPRLLIY GASTRATGIP     60
DRFSGSGSGT DFILTINRLE PEDLAVYYCQ QFGSSPWTFG QGTKVDIK                 108

SEQ ID NO: 735              moltype = AA  length = 8
FEATURE                     Location/Qualifiers
source                      1..8
                            mol_type = protein
                            organism = Homo sapiens
SEQUENCE: 735
GFSFSMSA                                                               8

SEQ ID NO: 736              moltype = AA  length = 8
FEATURE                     Location/Qualifiers
source                      1..8
                            mol_type = protein
                            organism = Homo sapiens
SEQUENCE: 736
IVPGSGNA                                                               8

SEQ ID NO: 737              moltype = AA  length = 16
FEATURE                     Location/Qualifiers
source                      1..16
                            mol_type = protein
                            organism = Homo sapiens
SEQUENCE: 737
AAPHCNKTNC YDAFDI                                                     16

SEQ ID NO: 738              moltype = AA  length = 7
FEATURE                     Location/Qualifiers
source                      1..7
                            mol_type = protein
                            organism = Homo sapiens
SEQUENCE: 738
QSVRSSY                                                                7

SEQ ID NO: 739              moltype =   length =
SEQUENCE: 739
000

SEQ ID NO: 740              moltype = AA  length = 9
FEATURE                     Location/Qualifiers
source                      1..9
                            mol_type = protein
                            organism = Homo sapiens
```

```
SEQUENCE: 740
QQFGSSPWT                                                                    9

SEQ ID NO: 741          moltype = DNA   length = 355
FEATURE                 Location/Qualifiers
source                  1..355
                        mol_type = other DNA
                        organism = Homo sapiens
SEQUENCE: 741
gaggtgcagc tggtggagtc tgggggaggt gtggtccagc ctggggggtc cctgagactc            60
tcctgtgcag cctctggaat catagtcagt gccaactaca tgacctgggt ccgccaggct           120
ccagggaagg ggctggaatg ggtctcagtt atttatcccg gtggtagcac attctacgcg           180
gactccgtga agggccgatt caccatctcc agagacaact ccaagaacac actgtatctt           240
caaatgaaca gcctgagagt tgaggactcg gctgtgtatt actgtgcgag agatttggag           300
ctggctggtt tcaatgactt ctggggtcag ggaaccctgg tcaccgtctc ctcag                355

SEQ ID NO: 742          moltype = AA   length = 118
FEATURE                 Location/Qualifiers
source                  1..118
                        mol_type = protein
                        organism = Homo sapiens
SEQUENCE: 742
EVQLVESGGG VVQPGGSLRL SCAASGIIVS ANYMTWVRQA PGKGLEWVSV IYPGGSTFYA            60
DSVKGRFTIS RDNSKNTLYL QMNSLRVEDS AVYYCARDLE LAGFNDFWGQ GTLVTVSS            118

SEQ ID NO: 743          moltype = DNA   length = 328
FEATURE                 Location/Qualifiers
source                  1..328
                        mol_type = other DNA
                        organism = Homo sapiens
SEQUENCE: 743
gatgttgtga tgactcagtc tccaggcacc ctggctttgt ctccagggga aagagccacc            60
ctctcctgca ggaccagcca gagtgttagc agcaactact tagcctggta ccagcagaaa           120
cctggccagg ctcccaggct cctcatctat ggtgcatcca gcagggccac tggcatccca           180
gacaggttca gtggcagtgg gtctgggaca gacttcactc tcaccatcag cagactggag           240
cctgaagatt ttgcagtgta ttactgtcag cagtttggta gttcacctcg gtacactttt           300
ggccagggga ccaaggtgga gatcaaac                                              328

SEQ ID NO: 744          moltype = AA   length = 109
FEATURE                 Location/Qualifiers
source                  1..109
                        mol_type = protein
                        organism = Homo sapiens
SEQUENCE: 744
DVVMTQSPGT LALSPGERAT LSCRTSQSVS SNYLAWYQQK PGQAPRLLIY GASSRATGIP            60
DRFSGSGSGT DFTLTISRLE PEDFAVYYCQ QFGSSPRYTF GQGTKVEIK                       109

SEQ ID NO: 745          moltype = AA   length = 8
FEATURE                 Location/Qualifiers
source                  1..8
                        mol_type = protein
                        organism = Homo sapiens
SEQUENCE: 745
GIIVSANY                                                                     8

SEQ ID NO: 746          moltype = AA   length = 7
FEATURE                 Location/Qualifiers
source                  1..7
                        mol_type = protein
                        organism = Homo sapiens
SEQUENCE: 746
IYPGGST                                                                      7

SEQ ID NO: 747          moltype = AA   length = 12
FEATURE                 Location/Qualifiers
source                  1..12
                        mol_type = protein
                        organism = Homo sapiens
SEQUENCE: 747
ARDLELAGFN DF                                                               12

SEQ ID NO: 748          moltype = AA   length = 7
FEATURE                 Location/Qualifiers
source                  1..7
                        mol_type = protein
                        organism = Homo sapiens
SEQUENCE: 748
QSVSSNY                                                                      7
```

```
SEQ ID NO: 749          moltype =   length =
SEQUENCE: 749
000

SEQ ID NO: 750          moltype = AA   length = 10
FEATURE                 Location/Qualifiers
source                  1..10
                        mol_type = protein
                        organism = Homo sapiens
SEQUENCE: 750
QQFGSSPRYT                                                                10

SEQ ID NO: 751          moltype = DNA   length = 355
FEATURE                 Location/Qualifiers
source                  1..355
                        mol_type = other DNA
                        organism = Homo sapiens
SEQUENCE: 751
caggtgcagc tggtggagtc tgggggaggt gtggtccagc ctggggggtc cctgagactc         60
tcctgtgcag cctctggagt caccgtcagt agcaactaca tgagctgggt ccgccaggct        120
ccagggaagg ggctggagtg ggtctcagtt ctttatgccg gtggtagcac attctacgca        180
gactccgtga agggccgatt caccatctcc agagacaatt ccaagaacac gctgtatctt        240
caaatgaaca gcctgagagc tgaggacacg gctgcgtatt actgtgcgag agatttggca        300
gtggctggtt tccttgactc ctggggccag ggaaccctgg tcaccgtctc ctcag             355

SEQ ID NO: 752          moltype = AA   length = 118
FEATURE                 Location/Qualifiers
source                  1..118
                        mol_type = protein
                        organism = Homo sapiens
SEQUENCE: 752
QVQLVESGGG VVQPGGSLRL SCAASGVTVS SNYMSWVRQA PGKGLEWVSV LYAGGSTFYA         60
DSVKGRFTIS RDNSKNTLYL QMNSLRAEDT AAYYCARDLA VAGFLDSWGQ GTLVTVSS         118

SEQ ID NO: 753          moltype = DNA   length = 328
FEATURE                 Location/Qualifiers
source                  1..328
                        mol_type = other DNA
                        organism = Homo sapiens
SEQUENCE: 753
gatattgtga tgacccagtc tccgggcacc ctgtctttgt ctccagggga aagagccacc         60
ctctcctgca gggccagtca gggtgttagc agcatctact tagcctggta ccagcagaaa        120
cctggccagg ctcccaggct cgtcctctat ggcgcatcca gtagggccac tggcatccca        180
gacaggttca gtggcagtgg gtctgggaca gacttcactc tcaccatcag cagactggag        240
cctgaagatt ttgcagtgta ttactgtcag cagtatggta gctcacctcg gtacactttt        300
ggccagggga ccaaggtgga gatcaaac                                           328

SEQ ID NO: 754          moltype = AA   length = 109
FEATURE                 Location/Qualifiers
source                  1..109
                        mol_type = protein
                        organism = Homo sapiens
SEQUENCE: 754
DIVMTQSPGT LSLSPGERAT LSCRASQGVS SIYLAWYQQK PGQAPRLVLY GASSRATGIP         60
DRFSGSGSGT DFTLTISRLE PEDFAVYYCQ QYGSSPRYTF GQGTKVEIK                   109

SEQ ID NO: 755          moltype = AA   length = 8
FEATURE                 Location/Qualifiers
source                  1..8
                        mol_type = protein
                        organism = Homo sapiens
SEQUENCE: 755
GVTVSSNY                                                                   8

SEQ ID NO: 756          moltype = AA   length = 7
FEATURE                 Location/Qualifiers
source                  1..7
                        mol_type = protein
                        organism = Homo sapiens
SEQUENCE: 756
LYAGGST                                                                    7

SEQ ID NO: 757          moltype = AA   length = 12
FEATURE                 Location/Qualifiers
source                  1..12
                        mol_type = protein
                        organism = Homo sapiens
SEQUENCE: 757
ARDLAVAGFL DS                                                             12
```

```
SEQ ID NO: 758          moltype = AA  length = 7
FEATURE                 Location/Qualifiers
source                  1..7
                        mol_type = protein
                        organism = Homo sapiens
SEQUENCE: 758
QGVSSIY                                                                    7

SEQ ID NO: 759          moltype =     length =
SEQUENCE: 759
000

SEQ ID NO: 760          moltype = AA  length = 10
FEATURE                 Location/Qualifiers
source                  1..10
                        mol_type = protein
                        organism = Homo sapiens
SEQUENCE: 760
QQYGSSPRYT                                                                10

SEQ ID NO: 761          moltype = DNA  length = 351
FEATURE                 Location/Qualifiers
source                  1..351
                        mol_type = other DNA
                        organism = Homo sapiens
SEQUENCE: 761
caggtgcagc tggtggagtc tggaggaggc ttgatccagc cggggggtc cctgagactc            60
tcctgtgcag cctctgggat caccgtcagt agcaactaca tgacctgggt ccgccaggct          120
ccagggaagg ggctggagtg ggtctcactt ctttatgccg gtggtagcgc attctatgct          180
gactccgtga agggccgatt caccatctcc agagacaatt ccaagaacac gctgtatctt          240
ctaatgaaca gcctgagagt cggcgacacg gccgtttatt actgtgcgag agatctccag          300
gtctacggta tggacgtctg ggaccaaggg accacggtca ccgtctcctc a                   351

SEQ ID NO: 762          moltype = AA  length = 117
FEATURE                 Location/Qualifiers
source                  1..117
                        mol_type = protein
                        organism = Homo sapiens
SEQUENCE: 762
QVQLVESGGG LIQPGGSLRL SCAASGITVS SNYMTWVRQA PGKGLEWVSL LYAGGSAFYA           60
DSVKGRFTIS RDNSKNTLYL LMNSLRVGDT AVYYCARDLQ VYGMDVWGQG TTVTVSS             117

SEQ ID NO: 763          moltype = DNA  length = 322
FEATURE                 Location/Qualifiers
source                  1..322
                        mol_type = other DNA
                        organism = Homo sapiens
SEQUENCE: 763
tcctatgagc tgactcagcc accctcggtg tcagtggccc caggacagac ggccaggatt           60
acctgtgggg gaaacaacga tgagctaaa agtgtgcact ggtaccagca gaagccaggc          120
caggcccctg tgctggtcgt ctatgatgat agcgaccggc cctcaggat ccctgaacga          180
ttctctggct ccaactctgg gaacacggcc accctgacca tcaccaggat cgaagccggg          240
gatgaggccg actattactg tcaggtctgg atagtagtc gtgatcatgt cttcggaact           300
gggaccaagg tcaccgtcct gg                                                  322

SEQ ID NO: 764          moltype = AA  length = 107
FEATURE                 Location/Qualifiers
source                  1..107
                        mol_type = protein
                        organism = Homo sapiens
SEQUENCE: 764
SYELTQPPSV SVAPGQTARI TCGGNNDGAK SVHWYQQKPG QAPVLVVYDD SDRPSGIPER           60
FSGSNSGNTA TLTITRIEAG DEADYYCQVW DSSRDHVFGT GTKVTVL                       107

SEQ ID NO: 765          moltype = AA  length = 8
FEATURE                 Location/Qualifiers
source                  1..8
                        mol_type = protein
                        organism = Homo sapiens
SEQUENCE: 765
GITVSSNY                                                                   8

SEQ ID NO: 766          moltype = AA  length = 7
FEATURE                 Location/Qualifiers
source                  1..7
                        mol_type = protein
                        organism = Homo sapiens
SEQUENCE: 766
```

-continued

```
LYAGGSA                                                                     7

SEQ ID NO: 767         moltype = AA  length = 11
FEATURE                Location/Qualifiers
source                 1..11
                       mol_type = protein
                       organism = Homo sapiens
SEQUENCE: 767
ARDLQVYGMD V                                                               11

SEQ ID NO: 768         moltype = AA  length = 6
FEATURE                Location/Qualifiers
source                 1..6
                       mol_type = protein
                       organism = Homo sapiens
SEQUENCE: 768
NDGAKS                                                                      6

SEQ ID NO: 769         moltype =   length =
SEQUENCE: 769
000

SEQ ID NO: 770         moltype = AA  length = 10
FEATURE                Location/Qualifiers
source                 1..10
                       mol_type = protein
                       organism = Homo sapiens
SEQUENCE: 770
QVWDSSRDHV                                                                 10

SEQ ID NO: 771         moltype = DNA  length = 351
FEATURE                Location/Qualifiers
source                 1..351
                       mol_type = other DNA
                       organism = Homo sapiens
SEQUENCE: 771
gaggtgcagc tggtggagtc tgggggaggc ttggtccagc ctggggggtc cctgaggctc          60
tcctgtgaag cctctgaaat aaccgtcagt agcaactaca tgaattgggt ccgccaggct         120
ccagggaagg ggctggagtg ggtctcagtt cttttgccg gtgtactac atactacgca           180
gactccgtga agggccgatt caccatctcc agagacaatt ccaagaacac actgtatctt         240
caaatgaaca ccctgagaat tgaggacacg gctatttatt actgtgcgag agatctcgtc         300
gcatacggtg tggacgtctg gggccaaggg accacggtca ccgtctcctc a                  351

SEQ ID NO: 772         moltype = AA  length = 117
FEATURE                Location/Qualifiers
source                 1..117
                       mol_type = protein
                       organism = Homo sapiens
SEQUENCE: 772
EVQLVESGGG LVQPGGSLRL SCEASEITVS SNYMNWVRQA PGKGLEWVSV LFAGGTTYYA          60
DSVKGRFTIS RDNSKNTLYL QMNTLRIEDT AIYYCARDLV AYGVDVWGQG TTVTVSS            117

SEQ ID NO: 773         moltype = DNA  length = 322
FEATURE                Location/Qualifiers
source                 1..322
                       mol_type = other DNA
                       organism = Homo sapiens
SEQUENCE: 773
gccatccaga tgacccagtc tccatccttc ctgtctgcat ctgtaggaga cagagtcacc          60
atcacttgcc gggccagtca gggcattagc ggtgatttag cctggtatca gcaaaaacca        120
gggaaagccc ctaagctcct gatctatgct gcatccactt tgcaaagtgg ggtcccatca        180
aggttcagcg gcagtggatc tgggacagaa ttcactctca caatcagcag cctgcagcct        240
gaagattttg caacttatta ctgtcaacac cttaatagtt accctctcac gttcggcgga        300
gggaccaagg tggaaatcaa ac                                                 322

SEQ ID NO: 774         moltype = AA  length = 107
FEATURE                Location/Qualifiers
source                 1..107
                       mol_type = protein
                       organism = Homo sapiens
SEQUENCE: 774
AIQMTQSPSF LSASVGDRVT ITCRASQGIS GDLAWYQQKP GKAPKLLIYA ASTLQSGVPS          60
RFSGSGSGTE FTLTISSLQP EDFATYYCQH LNSYPLTFGG GTKVEIK                      107

SEQ ID NO: 775         moltype = AA  length = 8
FEATURE                Location/Qualifiers
source                 1..8
                       mol_type = protein
                       organism = Homo sapiens
```

```
SEQUENCE: 775
EITVSSNY                                                                          8

SEQ ID NO: 776          moltype = AA  length = 7
FEATURE                 Location/Qualifiers
source                  1..7
                        mol_type = protein
                        organism = Homo sapiens
SEQUENCE: 776
LFAGGTT                                                                           7

SEQ ID NO: 777          moltype = AA  length = 11
FEATURE                 Location/Qualifiers
source                  1..11
                        mol_type = protein
                        organism = Homo sapiens
SEQUENCE: 777
ARDLVAYGVD V                                                                     11

SEQ ID NO: 778          moltype = AA  length = 6
FEATURE                 Location/Qualifiers
source                  1..6
                        mol_type = protein
                        organism = Homo sapiens
SEQUENCE: 778
QGISGD                                                                            6

SEQ ID NO: 779          moltype =     length =
SEQUENCE: 779
000

SEQ ID NO: 780          moltype = AA  length = 9
FEATURE                 Location/Qualifiers
source                  1..9
                        mol_type = protein
                        organism = Homo sapiens
SEQUENCE: 780
QHLNSYPLT                                                                         9

SEQ ID NO: 781          moltype = DNA  length = 352
FEATURE                 Location/Qualifiers
source                  1..352
                        mol_type = other DNA
                        organism = Homo sapiens
SEQUENCE: 781
caggtacagc tgcaggagtc gggcccagga ctggtgaagt cttcacagac cctgtccctc                60
acgtgcactg tctctggtga ctccatcagc cgtggtggtt actactggag ctggatccgc               120
cagcacccag ggaagggcct ggagtggatt gggtccatct attacagtgg gagcacctac               180
tacaacccgt ccctcaagag tcgatttacc atatcagtag acacgtctaa gaaccagttc               240
tccctgaagc tgagctctgt gactgccgcg gacacggccg tgtatcactg tgcgagagaa               300
attggttttc ttgactactg gggccaggga accctggtca ccgtctcctc ag                       352

SEQ ID NO: 782          moltype = AA  length = 117
FEATURE                 Location/Qualifiers
source                  1..117
                        mol_type = protein
                        organism = Homo sapiens
SEQUENCE: 782
QVQLQESGPG LVKSSQTLSL TCTVSGDSIS RGGYYWSWIR QHPGKGLEWI GSIYYSGSTY                60
YNPSLKSRFT ISVDTSKNQF SLKLSSVTAA DTAVYHCARE IGFLDYWGQG TLVTVSS                  117

SEQ ID NO: 783          moltype = DNA  length = 325
FEATURE                 Location/Qualifiers
source                  1..325
                        mol_type = other DNA
                        organism = Homo sapiens
SEQUENCE: 783
gccatccaga tgacccagtc tccatcctcc ctgtctgcat ctgtaggaga cagagtcacc                60
atcacttgcc gggcgagtca ggcattagc aattctttag cctggtatca gcagaaacca               120
gggaaagccc ctaagctcct actctatgct gcatccacat ggaaagtgg ggtcccatcc                180
aggttcagtg gcagtggatc tgggacggat ttcactctca ccatcagcag cctgcagcct               240
gaagattttg caacttattt ctgtcagcag tactatagta cccctccgag gacgttcggc               300
caagggacca aagtggatat caaac                                                    325

SEQ ID NO: 784          moltype = AA  length = 108
FEATURE                 Location/Qualifiers
source                  1..108
                        mol_type = protein
                        organism = Homo sapiens
```

```
SEQUENCE: 784
AIQMTQSPSS LSASVGDRVT ITCRASQAIS NSLAWYQQKP GKAPKLLLYA ASTLESGVPS    60
RFSGSGSGTD FTLTISSLQP EDFATYFCQQ YYSTPPRTFG QGTKVDIK                108

SEQ ID NO: 785          moltype = AA   length = 10
FEATURE                 Location/Qualifiers
source                  1..10
                        mol_type = protein
                        organism = Homo sapiens
SEQUENCE: 785
GDSISRGGYY                                                           10

SEQ ID NO: 786          moltype = AA   length = 7
FEATURE                 Location/Qualifiers
source                  1..7
                        mol_type = protein
                        organism = Homo sapiens
SEQUENCE: 786
IYYSGST                                                              7

SEQ ID NO: 787          moltype = AA   length = 9
FEATURE                 Location/Qualifiers
source                  1..9
                        mol_type = protein
                        organism = Homo sapiens
SEQUENCE: 787
AREIGFLDY                                                            9

SEQ ID NO: 788          moltype = AA   length = 6
FEATURE                 Location/Qualifiers
source                  1..6
                        mol_type = protein
                        organism = Homo sapiens
SEQUENCE: 788
QAISNS                                                               6

SEQ ID NO: 789          moltype =     length =
SEQUENCE: 789
000

SEQ ID NO: 790          moltype = AA   length = 10
FEATURE                 Location/Qualifiers
source                  1..10
                        mol_type = protein
                        organism = Homo sapiens
SEQUENCE: 790
QQYYSTPPRT                                                           10

SEQ ID NO: 791          moltype = DNA   length = 382
FEATURE                 Location/Qualifiers
source                  1..382
                        mol_type = other DNA
                        organism = Homo sapiens
SEQUENCE: 791
caggtgcagc tggtggagtc tgggggctgag gtgaagaagc ctgggtcctc ggtgaaggtc   60
tcctgcaagg cttctggagg caccttcagc agccatggtg tcatctgggt gcgacaggcc  120
cctggacaag ggcttgagtg gatgggaggg atcatcccca tctttcccac agcaaactac  180
gcacagaaat tccagggcag agtcacaatt accgcggaca acctccaa cacagcctac    240
atggagctga gcagcctgag atctgaggac acggccgtat attactgtgc gagggcaagg  300
ggagaacatg attccgtttg gggaagtttt cattactatt ttgactactg gggccaggga  360
accctggtca ccgtctcctc ag                                           382

SEQ ID NO: 792          moltype = AA   length = 127
FEATURE                 Location/Qualifiers
source                  1..127
                        mol_type = protein
                        organism = Homo sapiens
SEQUENCE: 792
QVQLVESGAE VKKPGSSVKV SCKASGGTFS SHGVIWVRQA PGQGLEWMGG IIPIFPTANY    60
AQKFQGRVTI TADKPSNTAY MELSSLRSED TAVYYCARAR GEHDSVWGSF HYYFDYWGQG   120
TLVTVSS                                                            127

SEQ ID NO: 793          moltype = DNA   length = 325
FEATURE                 Location/Qualifiers
source                  1..325
                        mol_type = other DNA
                        organism = Homo sapiens
SEQUENCE: 793
cgtcattgga tgacccagtc tccagccacc ctgtctgtgt ctccagggga aagagccacc   60
```

```
ctctcctgca gggccagtca aagtattggc agcaacttag cctggtacca gcagaaacct    120
ggtcaggctc ccaggctcct catctatggt gcagccacca gggccactgg tatcccagcc    180
aggttcagtg gcagtgggtc tgggacagag ttcactctca ccatcagcag cctgcagtct    240
gaagattttg cagtttacta ctgtcagcag tataatgact ggcctccgag gacgttcggc    300
caagggacca aggtggaaat caaac                                          325

SEQ ID NO: 794         moltype = AA  length = 108
FEATURE                Location/Qualifiers
source                 1..108
                       mol_type = protein
                       organism = Homo sapiens
SEQUENCE: 794
RHWMTQSPAT LSVSPGERAT LSCRASQSIG SNLAWYQQKP GQAPRLLIYG AATRATGIPA     60
RFSGSGSGTE FTLTISSLQS EDFAVYYCQQ YNDWPPRTFG QGTKVEIK                 108

SEQ ID NO: 795         moltype = AA  length = 8
FEATURE                Location/Qualifiers
source                 1..8
                       mol_type = protein
                       organism = Homo sapiens
SEQUENCE: 795
GGTFSSHG                                                               8

SEQ ID NO: 796         moltype = AA  length = 8
FEATURE                Location/Qualifiers
source                 1..8
                       mol_type = protein
                       organism = Homo sapiens
SEQUENCE: 796
IIPIFPTA                                                               8

SEQ ID NO: 797         moltype = AA  length = 20
FEATURE                Location/Qualifiers
source                 1..20
                       mol_type = protein
                       organism = Homo sapiens
SEQUENCE: 797
ARARGEHDSV WGSFHYYFDY                                                 20

SEQ ID NO: 798         moltype = AA  length = 6
FEATURE                Location/Qualifiers
source                 1..6
                       mol_type = protein
                       organism = Homo sapiens
SEQUENCE: 798
QSIGSN                                                                 6

SEQ ID NO: 799         moltype =    length =
SEQUENCE: 799
000

SEQ ID NO: 800         moltype = AA  length = 10
FEATURE                Location/Qualifiers
source                 1..10
                       mol_type = protein
                       organism = Homo sapiens
SEQUENCE: 800
QQYNDWPPRT                                                            10

SEQ ID NO: 801         moltype = DNA  length = 369
FEATURE                Location/Qualifiers
source                 1..369
                       mol_type = other DNA
                       organism = Homo sapiens
SEQUENCE: 801
caggtgcagc tggtggagtc tgggggaggc ttggtacagc ctgcaggtc cctgagactc       60
tcctgtgcag cctctggatt cacgtttgat gattatgcca tgcactgggt ccggcaagtt    120
ccagggaagg gcctggagtg ggtctcagga attagttgga acagtggtag catagtctat    180
gcggactttg tgaagggccg attcaccatc gccagagaca acgccaagaa ctccctgttt    240
ctgcaaatga acagtctgag agctgaggac acggccttgt attactgtgc aaaaagtacg    300
gctctacgtc atcagtacta ctacggtatg gacgtctggg gccaagggac cacggtcacc    360
gtctcctca                                                            369

SEQ ID NO: 802         moltype = AA  length = 123
FEATURE                Location/Qualifiers
source                 1..123
                       mol_type = protein
                       organism = Homo sapiens
SEQUENCE: 802
```

```
QVQLVESGGG LVQPGRSLRL SCAASGFTFD DYAMHWVRQV PGKGLEWVSG ISWNSGSIVY    60
ADFVKGRFTI ARDNAKNSLF LQMNSLRAED TALYYCAKST ALRHQYYYGM DVWGQGTTVT   120
VSS                                                                123

SEQ ID NO: 803          moltype = DNA  length = 322
FEATURE                 Location/Qualifiers
source                  1..322
                        mol_type = other DNA
                        organism = Homo sapiens
SEQUENCE: 803
gccatccaga tgacccagtc tccatcctcc ctgtctgcat ctgtaggaga cagagtcacc    60
atcacttgcc ggacaagtca gaccattagc agctatttaa attggtatca gcagaaacca   120
gggaaagccc ctaagctcct gatatatgac gcatccagtt tgcaaagtgg ggtcccatca   180
aggttcagtg gcagtggata tgggacagat ttcactctca ccatcagcag tctgcaacct   240
gaagattttg caacttactt ctgtcaacag agttacaata ccccgtacgc ttttggccag   300
gggaccaagg tggagatcaa ac                                            322

SEQ ID NO: 804          moltype = AA  length = 107
FEATURE                 Location/Qualifiers
source                  1..107
                        mol_type = protein
                        organism = Homo sapiens
SEQUENCE: 804
AIQMTQSPSS LSASVGDRVT ITCRTSQTIS SYLNWYQQKP GKAPKLLIYD ASSLQSGVPS    60
RFSGSGYGTD FTLTISSLQP EDFATYFCQQ SYNTPYAFGQ GTKVEIK                 107

SEQ ID NO: 805          moltype = AA  length = 8
FEATURE                 Location/Qualifiers
source                  1..8
                        mol_type = protein
                        organism = Homo sapiens
SEQUENCE: 805
GFTFDDYA                                                              8

SEQ ID NO: 806          moltype = AA  length = 8
FEATURE                 Location/Qualifiers
source                  1..8
                        mol_type = protein
                        organism = Homo sapiens
SEQUENCE: 806
ISWNSGSI                                                              8

SEQ ID NO: 807          moltype = AA  length = 16
FEATURE                 Location/Qualifiers
source                  1..16
                        mol_type = protein
                        organism = Homo sapiens
SEQUENCE: 807
AKSTALRHQY YYGMDV                                                    16

SEQ ID NO: 808          moltype = AA  length = 6
FEATURE                 Location/Qualifiers
source                  1..6
                        mol_type = protein
                        organism = Homo sapiens
SEQUENCE: 808
QTISSY                                                                6

SEQ ID NO: 809          moltype =   length =
SEQUENCE: 809
000

SEQ ID NO: 810          moltype = AA  length = 9
FEATURE                 Location/Qualifiers
source                  1..9
                        mol_type = protein
                        organism = Homo sapiens
SEQUENCE: 810
QQSYNTPYA                                                             9

SEQ ID NO: 811          moltype = DNA  length = 358
FEATURE                 Location/Qualifiers
source                  1..358
                        mol_type = other DNA
                        organism = Homo sapiens
SEQUENCE: 811
caggttcagc tggtgcagtc tggcactgag gtgaagaagc ctggggcctc agtgaaggtc    60
tcctgcaagg cttctgatta cacctttacc aggtttggta tcatctgggt gcgacaggcc   120
cctggacaag ggcttgagtg gatgggacag atcaaccctc acaatggtaa cacagactat   180
```

```
gcacagaagt tccagggcag agtcaccttg accacagaca catccacgaa cacagcctac    240
atggaactga ggagcctgag atctgacgac acgccgtgt attattgtgc gaggtccgct     300
gggagcccta ccggccttga ctactggggc cagggaaccc tggtcaccgt ctcctcag      358
```

```
SEQ ID NO: 812           moltype = AA   length = 119
FEATURE                  Location/Qualifiers
source                   1..119
                         mol_type = protein
                         organism = Homo sapiens
SEQUENCE: 812
QVQLVQSGTE VKKPGASVKV SCKASDYTFT RFGIIWVRQA PGQGLEWMGQ INPYNGNTDY    60
AQKFQGRVTL TTDTSTNTAY MELRSLRSDD TAVYYCARSA GSPTGLDYWG QGTLVTVSS     119

SEQ ID NO: 813           moltype = DNA   length = 331
FEATURE                  Location/Qualifiers
source                   1..331
                         mol_type = other DNA
                         organism = Homo sapiens
SEQUENCE: 813
cagtctgtcg tgacgcagcc accctcggtg tctgaagccc ccaggcagag ggtcaccatc    60
tcctgttctg gaagcaactc caacatcgga ataatgctg taaactggta ccagcagctc    120
ccaggaaagg ctcccaaact cctcgtctat tatgatgatc tgctgccctc aggggtctct    180
gaccgattct ctggctccaa gtctggcacc tcagctcccc tggccatcag tgggctccag   240
tctgaggata aggctgatta ttactgtgca gcatgggatg acagcctgaa tgccttggtg   300
ttcggcggag ggaccaagct gaccgtccta g                                  331

SEQ ID NO: 814           moltype = AA   length = 110
FEATURE                  Location/Qualifiers
source                   1..110
                         mol_type = protein
                         organism = Homo sapiens
SEQUENCE: 814
QSVVTQPPSV SEAPRQRVTI SCSGSNSNIG NNAVNWYQQL PGKAPKLLVY YDDLLPSGVS    60
DRFSGSKSGT SASLAISGLQ SEDKADYYCA AWDDSLNALV FGGGTKLTVL              110

SEQ ID NO: 815           moltype = AA   length = 8
FEATURE                  Location/Qualifiers
source                   1..8
                         mol_type = protein
                         organism = Homo sapiens
SEQUENCE: 815
DYTFTRFG                                                             8

SEQ ID NO: 816           moltype = AA   length = 8
FEATURE                  Location/Qualifiers
source                   1..8
                         mol_type = protein
                         organism = Homo sapiens
SEQUENCE: 816
INPYNGNT                                                             8

SEQ ID NO: 817           moltype = AA   length = 12
FEATURE                  Location/Qualifiers
source                   1..12
                         mol_type = protein
                         organism = Homo sapiens
SEQUENCE: 817
ARSAGSPTGL DY                                                        12

SEQ ID NO: 818           moltype = AA   length = 8
FEATURE                  Location/Qualifiers
source                   1..8
                         mol_type = protein
                         organism = Homo sapiens
SEQUENCE: 818
NSNIGNNA                                                             8

SEQ ID NO: 819           moltype =    length =
SEQUENCE: 819
000

SEQ ID NO: 820           moltype = AA   length = 11
FEATURE                  Location/Qualifiers
source                   1..11
                         mol_type = protein
                         organism = Homo sapiens
SEQUENCE: 820
AAWDDSLNAL V                                                         11
```

-continued

```
SEQ ID NO: 821          moltype = DNA  length = 354
FEATURE                 Location/Qualifiers
source                  1..354
                        mol_type = other DNA
                        organism = Homo sapiens
SEQUENCE: 821
gaagtgcagc tgttggagtc tggggggaggc ttggtccagc ctgggggtc cctgagactc      60
tcctgtgtag cctctggact caccgtcagt agcaactaca tgagctgggt ccgccaggct    120
ccagggaagg ggctggagtg ggtctcaatt atttatcccg gtggtaccac atactacgca    180
gactccgtga agggcagatt caccacctcc agagacaaat ccaagaacac gctgtatctt    240
caaatgaaca gcctgagagc cgaggacacg gctgtgtatt actgtgcgag agatctggca    300
gtggctgggg gtatggacgt ctggggccaa gggaccacgg tcaccgtctc ctca          354

SEQ ID NO: 822          moltype = AA  length = 118
FEATURE                 Location/Qualifiers
source                  1..118
                        mol_type = protein
                        organism = Homo sapiens
SEQUENCE: 822
EVQLLESGGG LVQPGGSLRL SCVASGLTVS SNYMSWVRQA PGKGLEWVSI IYPGGTTYYA     60
DSVKGRFTTS RDKSKNTLYL QMNSLRAEDT AVYYCARDLA VAGGMDVWGQ GTTVTVSS     118

SEQ ID NO: 823          moltype = DNA  length = 322
FEATURE                 Location/Qualifiers
source                  1..322
                        mol_type = other DNA
                        organism = Homo sapiens
SEQUENCE: 823
gaaatagtga tgacgcagtc tccatcctcc ctgtctgcat ctgtaggaga cagagttacc     60
atcacttgcc gggcaagtca gggcattgga aatgatttag gtggtatca gcagaaacca    120
gggaaagccc ctaaagtcct gatttatgct gcatccaatt tacaaagtgg ggtcccatca    180
aggttcagcg gcagtggatc tggcacagat ttcactctca ccatcagcag cctgcagcct    240
gaagattttg caacttatta ctgtctacaa gattccaatt atccctacac ttttggccag    300
gggaccaagg tggagatcaa ac                                             322

SEQ ID NO: 824          moltype = AA  length = 107
FEATURE                 Location/Qualifiers
source                  1..107
                        mol_type = protein
                        organism = Homo sapiens
SEQUENCE: 824
EIVMTQSPSS LSASVGDRVT ITCRASQGIG NDLGWYQQKP GKAPKVLIYA ASNLQSGVPS     60
RFSGSGSGTD FTLTISSLQP EDFATYYCLQ DSNYPYTFGQ GTKVEIK                  107

SEQ ID NO: 825          moltype = AA  length = 8
FEATURE                 Location/Qualifiers
source                  1..8
                        mol_type = protein
                        organism = Homo sapiens
SEQUENCE: 825
GLTVSSNY                                                               8

SEQ ID NO: 826          moltype = AA  length = 7
FEATURE                 Location/Qualifiers
source                  1..7
                        mol_type = protein
                        organism = Homo sapiens
SEQUENCE: 826
IYPGGTT                                                                7

SEQ ID NO: 827          moltype = AA  length = 12
FEATURE                 Location/Qualifiers
source                  1..12
                        mol_type = protein
                        organism = Homo sapiens
SEQUENCE: 827
ARDLAVAGGM DV                                                         12

SEQ ID NO: 828          moltype = AA  length = 6
FEATURE                 Location/Qualifiers
source                  1..6
                        mol_type = protein
                        organism = Homo sapiens
SEQUENCE: 828
QGIGND                                                                 6

SEQ ID NO: 829          moltype =     length =
SEQUENCE: 829
000
```

```
SEQ ID NO: 830            moltype = AA  length = 9
FEATURE                   Location/Qualifiers
source                    1..9
                          mol_type = protein
                          organism = Homo sapiens
SEQUENCE: 830
LQDSNYPYT                                                                  9

SEQ ID NO: 831            moltype = DNA  length = 355
FEATURE                   Location/Qualifiers
source                    1..355
                          mol_type = other DNA
                          organism = Homo sapiens
SEQUENCE: 831
gaagtgcagc tggtggagtc tgggggaggc ttggtccagc ctgggggtc cctgagactc            60
tcctgtgcag cctctggagt catcgtcagt agcaactaca tgagctgggt ccgccaggct          120
ccaggqaagg ggctgcaatg ggtctcagtt atttatagcg gtgqtagcac tttctacgca          180
gactccgtga aqggcaqatt caccatctcc agaqacaatt ccaagaacac gttqtatctt          240
caaatgaaca gcctgaqaqc cqaqgacacq qctqtqtatt actqtqcqaq aqatttqtta          300
gaggcaggcg gaactgacta ctggggccag ggaaccctgg tcaccgtctc ctcag               355

SEQ ID NO: 832            moltype = AA  length = 118
FEATURE                   Location/Qualifiers
source                    1..118
                          mol_type = protein
                          organism = Homo sapiens
SEQUENCE: 832
EVQLVESGGG LVQPGGSLRL SCAASGVIVS SNYMSWVRQA PGKGLQWVSV IYSGGSTFYA           60
DSVKGRFTIS RDNSKNTLYL QMNSLRAEDT AVYYCARDLL EAGGTDYWGQ GTLVTVSS            118

SEQ ID NO: 833            moltype = DNA  length = 325
FEATURE                   Location/Qualifiers
source                    1..325
                          mol_type = other DNA
                          organism = Homo sapiens
SEQUENCE: 833
gatgttgtga tgactcagtc tccaggcacc ctgtctttgt ctccagggga aagagccacc           60
ctctcctgca gggccagtca gtttattggc agctcctact tagcctggta ccagcagaaa         120
cctggccagg ctcccaggct cctcatctat ggtgcatcca acagggccac tggcgtccca         180
gacaggttca gtggcagtgg gtctgggaca gacttcactc tcaccatcag cagactggag         240
cctgaagatt ttgcagtgta ttactgtcag cagtatggga gtgcacctgg gacgttcggc         300
caagggacca aggtggaaat caaac                                                325

SEQ ID NO: 834            moltype = AA  length = 108
FEATURE                   Location/Qualifiers
source                    1..108
                          mol_type = protein
                          organism = Homo sapiens
SEQUENCE: 834
DVVMTQSPGT LSLSPGERAT LSCRASQFIG SSYLAWYQQK PGQAPRLLIY GASNRATGVP           60
DRFSGSGSGT DFTLTISRLE PEDFAVYYCQ QYGSAPGTFG QGTKVEIK                       108

SEQ ID NO: 835            moltype = AA  length = 8
FEATURE                   Location/Qualifiers
source                    1..8
                          mol_type = protein
                          organism = Homo sapiens
SEQUENCE: 835
GVIVSSNY                                                                   8

SEQ ID NO: 836            moltype = AA  length = 7
FEATURE                   Location/Qualifiers
source                    1..7
                          mol_type = protein
                          organism = Homo sapiens
SEQUENCE: 836
IYSGGST                                                                    7

SEQ ID NO: 837            moltype = AA  length = 12
FEATURE                   Location/Qualifiers
source                    1..12
                          mol_type = protein
                          organism = Homo sapiens
SEQUENCE: 837
ARDLLEAGGT DY                                                              12

SEQ ID NO: 838            moltype = AA  length = 7
FEATURE                   Location/Qualifiers
```

```
source                        1..7
                              mol_type = protein
                              organism = Homo sapiens
SEQUENCE: 838
QFIGSSY                                                                   7

SEQ ID NO: 839          moltype =   length =
SEQUENCE: 839
000

SEQ ID NO: 840          moltype = AA   length = 9
FEATURE                 Location/Qualifiers
source                        1..9
                              mol_type = protein
                              organism = Homo sapiens
SEQUENCE: 840
QQYGSAPGT                                                                 9

SEQ ID NO: 841          moltype = DNA   length = 351
FEATURE                 Location/Qualifiers
source                        1..351
                              mol_type = other DNA
                              organism = Homo sapiens
SEQUENCE: 841
caggtgcagc tggtggagtc tggaggaggc ttggtccagc ctgggggtc cctgagactc          60
tcctgtgcag cctctggttt aatcgtcagt aggaactaca tgagctgggt ccgccaggct        120
ccagggaagg ggctgagtg gtctcacttt atttatgccg gtggtagcac attctactca         180
gactccgtga agggccgatt caccatctcc agacacagtt ccgagaacac gctgtttctt        240
caaatgaaca gcctgagagc tgaggacacg gctgtgtatt attgtgcgag agatctagtc        300
cactacggca tggacgtctg ggccaagggg accacggtca ccgtctccta a                 351

SEQ ID NO: 842          moltype = AA   length = 117
FEATURE                 Location/Qualifiers
source                        1..117
                              mol_type = protein
                              organism = Homo sapiens
SEQUENCE: 842
QVQLVESGGG LVQPGGSLRL SCAASGLIVS RNYMSWVRQA PGKGLEWVSL IYAGGSTFYS         60
DSVKGRFTIS RHSSENTLFL QMNSLRAEDT AVYYCARDLV HYGMDVWGQG TTVTVSS           117

SEQ ID NO: 843          moltype = DNA   length = 331
FEATURE                 Location/Qualifiers
source                        1..331
                              mol_type = other DNA
                              organism = Homo sapiens
SEQUENCE: 843
aattttatgc tgactcagcc tgcctccgtg tctgggtctc ctggacagtc gatcaccatc         60
tcctgcactg gaaccagcag tgacgttggt ggttataact atgtctcctg gtaccaacag        120
cacccaggca aagcccccaa actcatgatt tatgatgtca gtaatcggcc ctcagggatt        180
tctaatcgct tctctggctc caactctggc aacacggcct ccctcaccat ctctgggctc        240
caggctgagg acgaggctga ttattactgc agctcatata caagcggcag cacttgggtg        300
ttcggcggag ggaccaagct gaccgtccta g                                       331

SEQ ID NO: 844          moltype = AA   length = 110
FEATURE                 Location/Qualifiers
source                        1..110
                              mol_type = protein
                              organism = Homo sapiens
SEQUENCE: 844
NFMLTQPASV SGSPGQSITI SCTGTSSDVG GYNYVSWYQQ HPGKAPKLMI YDVSNRPSGV         60
SNRFSGSNSG NTASLTISGL QAEDEADYYC SSYTSGSTWV FGGGTKLTVL                   110

SEQ ID NO: 845          moltype = AA   length = 8
FEATURE                 Location/Qualifiers
source                        1..8
                              mol_type = protein
                              organism = Homo sapiens
SEQUENCE: 845
GLIVSRNY                                                                  8

SEQ ID NO: 846          moltype = AA   length = 7
FEATURE                 Location/Qualifiers
source                        1..7
                              mol_type = protein
                              organism = Homo sapiens
SEQUENCE: 846
IYAGGST                                                                   7

SEQ ID NO: 847          moltype = AA   length = 11
```

```
FEATURE                 Location/Qualifiers
source                  1..11
                        mol_type = protein
                        organism = Homo sapiens
SEQUENCE: 847
ARDLVHYGMD V                                                              11

SEQ ID NO: 848          moltype = AA  length = 9
FEATURE                 Location/Qualifiers
source                  1..9
                        mol_type = protein
                        organism = Homo sapiens
SEQUENCE: 848
SSDVGGYNY                                                                  9

SEQ ID NO: 849          moltype =   length =
SEQUENCE: 849
000

SEQ ID NO: 850          moltype = AA  length = 10
FEATURE                 Location/Qualifiers
source                  1..10
                        mol_type = protein
                        organism = Homo sapiens
SEQUENCE: 850
SSYTSGSTWV                                                                10

SEQ ID NO: 851          moltype = DNA  length = 390
FEATURE                 Location/Qualifiers
source                  1..390
                        mol_type = other DNA
                        organism = Homo sapiens
SEQUENCE: 851
gaagtgcagc tggtggagtc tgggggctgag gtgaagaagc ctgggtcctc agtgaaggtc         60
tcctgcaagg cttctggagg caccttcagc aggtatgcta tcagctgggt gcgacaggcc        120
cctggacaag gacttgagtg gatgggaggg atcatcccta tctttgatgc aacaaactac        180
gcacagaagt tccatgacag agtcaccatt accgcggaca aatccgcgag cacagcctac        240
atggaactga gcagcctgag atctgacgac acggccgtgt attactgtgc gagagaacgg        300
acatattgta gtggtggtac ttgctacgga ggatacttct actacggtat ggacgtctgg        360
ggccaaggaa ccacggtcac cgtctcctca                                         390

SEQ ID NO: 852          moltype = AA  length = 130
FEATURE                 Location/Qualifiers
source                  1..130
                        mol_type = protein
                        organism = Homo sapiens
SEQUENCE: 852
EVQLVESGAE VKKPGSSVKV SCKASGGTFS RYAISWVRQA PGQGLEWMGG IIPIFDATNY          60
AQKFHDRVTI TADKSASTAY MELSSLRSDD TAVYYCARER TYCSGGTCYG GYFYYGMDVW        120
GQGTTVTVSS                                                               130

SEQ ID NO: 853          moltype = DNA  length = 331
FEATURE                 Location/Qualifiers
source                  1..331
                        mol_type = other DNA
                        organism = Homo sapiens
SEQUENCE: 853
cagtctgtgc tgactcagcc accctcagcg tctgggaccc ccgggcagag ggtcaccatc         60
tcttgttctg gaagcagctc caacatcgga ggcgataatc agcgctggta cctccagctc        120
ccagggacgg cccccaaact cctcatttat agtaatcaga gcgccctc aggctccct          180
gaccgattct ctggctccag gtctggcacc tcagcctccc tggccatcag tgggctccag        240
tctgaggatg aggttatta ttactgtgca gcatgggatg acagcctgaa tggtcaagtg         300
ttcggcggag ggaccaagct gaccgtccta g                                       331

SEQ ID NO: 854          moltype = AA  length = 110
FEATURE                 Location/Qualifiers
source                  1..110
                        mol_type = protein
                        organism = Homo sapiens
SEQUENCE: 854
QSVLTQPPSA SGTPGQRVTI SCSGSSSNIG GDIVNWYLQL PGTAPKLLIY SNNQRPSGVP          60
DRFSGSRSGT SASLAISGLQ SEDEGYYYCA AWDDSLNGQV FGGGTKLTVL                   110

SEQ ID NO: 855          moltype = AA  length = 8
FEATURE                 Location/Qualifiers
source                  1..8
                        mol_type = protein
                        organism = Homo sapiens
SEQUENCE: 855
```

```
GGTFSRYA                                                                      8

SEQ ID NO: 856          moltype = AA  length = 8
FEATURE                 Location/Qualifiers
source                  1..8
                        mol_type = protein
                        organism = Homo sapiens
SEQUENCE: 856
IIPIFDAT                                                                      8

SEQ ID NO: 857          moltype = AA  length = 23
FEATURE                 Location/Qualifiers
source                  1..23
                        mol_type = protein
                        organism = Homo sapiens
SEQUENCE: 857
ARERTYCSGG TCYGGYFYYG MDV                                                    23

SEQ ID NO: 858          moltype = AA  length = 8
FEATURE                 Location/Qualifiers
source                  1..8
                        mol_type = protein
                        organism = Homo sapiens
SEQUENCE: 858
SSNIGGDI                                                                      8

SEQ ID NO: 859          moltype =     length =
SEQUENCE: 859
000

SEQ ID NO: 860          moltype = AA  length = 11
FEATURE                 Location/Qualifiers
source                  1..11
                        mol_type = protein
                        organism = Homo sapiens
SEQUENCE: 860
AAWDDSLNGQ V                                                                 11

SEQ ID NO: 861          moltype = DNA  length = 384
FEATURE                 Location/Qualifiers
source                  1..384
                        mol_type = other DNA
                        organism = Homo sapiens
SEQUENCE: 861
gaggtgcagc tggtgcagtc tggggctgag gtgaagaagc ctgggtcctc ggtgaaggtc            60
tcctgcaagg cttctggagg caccttcagt agctatggta tcagctgggt gcgacaggcc          120
cctggactag ggcttgagtg gatggggggg gtcatcccta tcctaagtgc aaaacactac          180
gcgcagcggt tccagggcag agtcacgatc accgcggaca gtccacgggc acagcctac           240
atggagctga gcagcctgag atctgaggac acggccgtat actactgtgc gagagatatc          300
cttcatcatg acgacctttg ggggaggttc tactacgacg gtatggacgt ctggggccaa          360
gggaccacgg tcaccgtctc ctca                                                 384

SEQ ID NO: 862          moltype = AA  length = 128
FEATURE                 Location/Qualifiers
source                  1..128
                        mol_type = protein
                        organism = Homo sapiens
SEQUENCE: 862
EVQLVQSGAE VKKPGSSVKV SCKASGGTFS SYGISWVRQA PGLGLEWMGG VIPILSAKHY            60
AQRFQGRVTI TADKSTGTAY MELSSLRSED TAVYYCARDI LHHDDLWGRF YYDGMDVWGQ          120
GTTVTVSS                                                                   128

SEQ ID NO: 863          moltype = DNA  length = 331
FEATURE                 Location/Qualifiers
source                  1..331
                        mol_type = other DNA
                        organism = Homo sapiens
SEQUENCE: 863
cagtctgtcg tgacgcagcc accctcagcg tctgggaccc ccgggcagag ggtcaccatc            60
tcttgttctg gaagcagctc cgacatcgga agtaatactg taaactggta ccagcagctc          120
ccaggaacgg ccccccaaact cctcatctat actaataatc agcggccctc aggggtccct         180
gaccgattct ctggctccaa gtctggcacc tcagcctccc tggccatcac tgggctccag          240
tctgaggatg aggctgatta tttctgtgca gcatgggata aagcctgaa tggtcgagtg           300
ttcggcggag ggaccaagct gaccgtccta g                                         331

SEQ ID NO: 864          moltype = AA  length = 110
FEATURE                 Location/Qualifiers
source                  1..110
                        mol_type = protein
```

```
                              organism = Homo sapiens
SEQUENCE: 864
QSVVTQPPSA SGTPGQRVTI SCSGSSSDIG SNTVNWYQQL PGTAPKLLIY TNNQRPSGVP    60
DRFSGSKSGT SASLAITGLQ SEDEADYFCA AWDESLNGRV FGGGTKLTVL              110

SEQ ID NO: 865             moltype = AA  length = 8
FEATURE                    Location/Qualifiers
source                     1..8
                           mol_type = protein
                           organism = Homo sapiens
SEQUENCE: 865
GGTFSSYG                                                              8

SEQ ID NO: 866             moltype = AA  length = 8
FEATURE                    Location/Qualifiers
source                     1..8
                           mol_type = protein
                           organism = Homo sapiens
SEQUENCE: 866
VIPILSAK                                                              8

SEQ ID NO: 867             moltype = AA  length = 21
FEATURE                    Location/Qualifiers
source                     1..21
                           mol_type = protein
                           organism = Homo sapiens
SEQUENCE: 867
ARDILHHDDL WGRFYYDGMD V                                              21

SEQ ID NO: 868             moltype = AA  length = 8
FEATURE                    Location/Qualifiers
source                     1..8
                           mol_type = protein
                           organism = Homo sapiens
SEQUENCE: 868
SSDIGSNT                                                              8

SEQ ID NO: 869             moltype =     length =
SEQUENCE: 869
000

SEQ ID NO: 870             moltype = AA  length = 11
FEATURE                    Location/Qualifiers
source                     1..11
                           mol_type = protein
                           organism = Homo sapiens
SEQUENCE: 870
AAWDESLNGR V                                                         11

SEQ ID NO: 871             moltype = DNA  length = 349
FEATURE                    Location/Qualifiers
source                     1..349
                           mol_type = other DNA
                           organism = Homo sapiens
SEQUENCE: 871
gaagtgcaac tggtggagtc tgggggaggc gtggtccagc ctggggaggtc cctgagactc    60
tcctgtgcag cgtctggatt caccttcagt aactatggca tgcactgggt ccgccaggct   120
ccaggcaagg gactggagtg ggtggcagtt tattggtatg atggaggtaa taaattctat   180
gcagactccg tgaagggccg attcaccatc tccagagaca attccaagaa tacgttgtat   240
ctgcaaatga acagcctgag agtcgaggac acggctgttt attactgtgc gagagatacg   300
gctcctccgg actactgggg ccagggaacc ctggtcaccg tctcctcag               349

SEQ ID NO: 872             moltype = AA  length = 116
FEATURE                    Location/Qualifiers
source                     1..116
                           mol_type = protein
                           organism = Homo sapiens
SEQUENCE: 872
EVQLVESGGG VVQPGRSLRL SCAASGFTFS NYGMHWVRQA PGKGLEWVAV YWYDGGNKFY    60
ADSVKGRFTI SRDNSKNTLY LQMNSLRVED TAVYYCARDT APPDYWGQGT LVTVSS       116

SEQ ID NO: 873             moltype = DNA  length = 328
FEATURE                    Location/Qualifiers
source                     1..328
                           mol_type = other DNA
                           organism = Homo sapiens
SEQUENCE: 873
gccatccgga tgacccagtc tccaggcacc ctgtctttgt ctccagggga aagagccacc    60
ctctcctgca gggccagtca gagtattagt agcagcttct tagcctggta ccagcagaaa   120
```

```
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta cctcaccaag gctcactttc    300
ggcgaggga ccaaagtgga tatcaaac                                        328

SEQ ID NO: 874           moltype = AA   length = 109
FEATURE                  Location/Qualifiers
source                   1..109
                         mol_type = protein
                         organism = Homo sapiens
SEQUENCE: 874
AIRMTQSPGT LSLSPGERAT LSCRASQSIS SSFLAWYQQK PGQAPRLLIY GASSRATGIP    60
DRFSGSGSGT DFTLTISRLE PEDFAVYYCQ QYGTSPRLTF GGGTKVDIK                109

SEQ ID NO: 875           moltype = AA   length = 8
FEATURE                  Location/Qualifiers
source                   1..8
                         mol_type = protein
                         organism = Homo sapiens
SEQUENCE: 875
GFTFSNYG                                                              8

SEQ ID NO: 876           moltype = AA   length = 8
FEATURE                  Location/Qualifiers
source                   1..8
                         mol_type = protein
                         organism = Homo sapiens
SEQUENCE: 876
YWYDGGNK                                                              8

SEQ ID NO: 877           moltype = AA   length = 9
FEATURE                  Location/Qualifiers
source                   1..9
                         mol_type = protein
                         organism = Homo sapiens
SEQUENCE: 877
ARDTAPPDY                                                             9

SEQ ID NO: 878           moltype = AA   length = 7
FEATURE                  Location/Qualifiers
source                   1..7
                         mol_type = protein
                         organism = Homo sapiens
SEQUENCE: 878
QSISSSF                                                               7

SEQ ID NO: 879           moltype =      length =
SEQUENCE: 879
000

SEQ ID NO: 880           moltype = AA   length = 10
FEATURE                  Location/Qualifiers
source                   1..10
                         mol_type = protein
                         organism = Homo sapiens
SEQUENCE: 880
QQYGTSPRLT                                                           10

SEQ ID NO: 881           moltype = DNA  length = 349
FEATURE                  Location/Qualifiers
source                   1..349
                         mol_type = other DNA
                         organism = Homo sapiens
SEQUENCE: 881
gaggtgcagc tgttggagtc tggggggaggc gtggtccagc ctggaaggtc cctgagactc    60
tcctgtgcag cgtctggatt caaattcagt gactatggca tgcactgggt ccgccaggct    120
ccaggcaagg ggctggagtg ggtggcagtt tattggtatg atggaaggtac taaattctat    180
gcagactccg tgaagggccg attcaccatc tccagagaca attccaagaa tacgttgtat    240
ctgcaaatga gcagcctgag agtcgaggac acggctgttt attactgtgc gagagatacg    300
gctcctccgg actactgggg ccagggaacc ctggtcaccg tctcctcag                349

SEQ ID NO: 882           moltype = AA   length = 116
FEATURE                  Location/Qualifiers
source                   1..116
                         mol_type = protein
                         organism = Homo sapiens
SEQUENCE: 882
EVQLLESGGG VVQPGRSLRL SCAASGFKFS DYGMHWVRQA PGKGLEWVAV YWYDGGTKFY    60
ADSVKGRFTI SRDNSKNTLY LQMSSLRVED TAVYYCARDT APPDYWGQGT LVTVSS        116
```

-continued

```
SEQ ID NO: 883           moltype = DNA  length = 328
FEATURE                  Location/Qualifiers
source                   1..328
                         mol_type = other DNA
                         organism = Homo sapiens
SEQUENCE: 883
gaaattgtgt tgacgcagtc tccaggcacc ctgtctttgt ctccagggga aagagccacc    60
ctctcctgca gggccagtca gagtattagt agcaacttct tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta cctcaccaag gctcactttc   300
ggcggaggga ccaaagtgga tatcaaac                                      328

SEQ ID NO: 884           moltype = AA  length = 109
FEATURE                  Location/Qualifiers
source                   1..109
                         mol_type = protein
                         organism = Homo sapiens
SEQUENCE: 884
EIVLTQSPGT LSLSPGERAT LSCRASQSIS SNFLAWYQQK PGQAPRLLIY GASSRATGIP    60
DRFSGSGSGT DFTLTISRLE PEDFAVYYCQ QYGTSPRLTF GGGTKVDIK              109

SEQ ID NO: 885           moltype = AA  length = 8
FEATURE                  Location/Qualifiers
source                   1..8
                         mol_type = protein
                         organism = Homo sapiens
SEQUENCE: 885
GFKFSDYG                                                              8

SEQ ID NO: 886           moltype = AA  length = 8
FEATURE                  Location/Qualifiers
source                   1..8
                         mol_type = protein
                         organism = Homo sapiens
SEQUENCE: 886
YWYDGGTK                                                              8

SEQ ID NO: 887           moltype = AA  length = 9
FEATURE                  Location/Qualifiers
source                   1..9
                         mol_type = protein
                         organism = Homo sapiens
SEQUENCE: 887
ARDTAPPDY                                                             9

SEQ ID NO: 888           moltype = AA  length = 7
FEATURE                  Location/Qualifiers
source                   1..7
                         mol_type = protein
                         organism = Homo sapiens
SEQUENCE: 888
QSISSNF                                                               7

SEQ ID NO: 889           moltype =   length =
SEQUENCE: 889
000

SEQ ID NO: 890           moltype = AA  length = 10
FEATURE                  Location/Qualifiers
source                   1..10
                         mol_type = protein
                         organism = Homo sapiens
SEQUENCE: 890
QQYGTSPRLT                                                           10

SEQ ID NO: 891           moltype = DNA  length = 369
FEATURE                  Location/Qualifiers
source                   1..369
                         mol_type = other DNA
                         organism = Homo sapiens
SEQUENCE: 891
caggttcagc tggtgcagtc tggggctgag gtgaagaagc ctgggtcctc ggtgaaggtc    60
tcctgcaagg cttctggagg caccttcagc agttatggta tcaggtgggt gcgacaggcc   120
cctggacaag gcttgagtg gatgggaggg atcatcccg tgtttggtgc aacaaactac     180
gcacagaagt tccaggacag agtcacaatt accgcggaca aatccacggc cacagcctac   240
atggaattga gtagcctgaa atctgacgac acggccgtgt attttgtgc gagagatgcc    300
cttagtgcca gtggctggac gggcccttt gactcgtggg gccagggaac cctggtcacc    360
```

```
                                gtctcctca                                                               369

SEQ ID NO: 892          moltype = AA  length = 123
FEATURE                 Location/Qualifiers
source                  1..123
                        mol_type = protein
                        organism = Homo sapiens
SEQUENCE: 892
QVQLVQSGAE VKKPGSSVKV SCKASGGTFS SYGIRWVRQA PGQGLEWMGG IIPVFGATNY    60
AQKFQDRVTI TADKSTATAY MELSSLKSDD TAVYFCARDA LSASGWTGPF DSWGQGTLVT   120
VSS                                                                 123

SEQ ID NO: 893          moltype = DNA  length = 337
FEATURE                 Location/Qualifiers
source                  1..337
                        mol_type = other DNA
                        organism = Homo sapiens
SEQUENCE: 893
cagtctgtgt tgacgcagcc gccctcagtg tctggggccc cggggcagag ggtcaccatc    60
tcctgcactg ggagcagctc caacatcggg gcagattatg atgtacactg gtaccagcaa   120
cttccaggag cagcccccaa actcctcatc tatggtaaca acaaccggcc ctcagggtc    180
cctgaccgat tctccggctc caagtctggc acctcagcct ccctggccat cactgggctc   240
caggctgagg atgaggctga ttattactgc cagtcctatg acagcagcca gaatgctttc   300
tatgtcttcg gaactgggac caaggtcacc gtcctag                            337

SEQ ID NO: 894          moltype = AA  length = 112
FEATURE                 Location/Qualifiers
source                  1..112
                        mol_type = protein
                        organism = Homo sapiens
SEQUENCE: 894
QSVLTQPPSV SGAPGQRVTI SCTGSSSNIG ADYDVHWYQQ LPGAAPKLLI YGNNNRPSGV    60
PDRFSGSKSG TSASLAITGL QAEDEADYYC QSYDSSQNAF YVFGTGTKVT VL           112

SEQ ID NO: 895          moltype = AA  length = 8
FEATURE                 Location/Qualifiers
source                  1..8
                        mol_type = protein
                        organism = Homo sapiens
SEQUENCE: 895
GGTFSSYG                                                              8

SEQ ID NO: 896          moltype = AA  length = 8
FEATURE                 Location/Qualifiers
source                  1..8
                        mol_type = protein
                        organism = Homo sapiens
SEQUENCE: 896
IIPVFGAT                                                              8

SEQ ID NO: 897          moltype = AA  length = 16
FEATURE                 Location/Qualifiers
source                  1..16
                        mol_type = protein
                        organism = Homo sapiens
SEQUENCE: 897
ARDALSASGW TGPFDS                                                    16

SEQ ID NO: 898          moltype = AA  length = 9
FEATURE                 Location/Qualifiers
source                  1..9
                        mol_type = protein
                        organism = Homo sapiens
SEQUENCE: 898
SSNIGADYD                                                             9

SEQ ID NO: 899          moltype =     length =
SEQUENCE: 899
000

SEQ ID NO: 900          moltype = AA  length = 12
FEATURE                 Location/Qualifiers
source                  1..12
                        mol_type = protein
                        organism = Homo sapiens
SEQUENCE: 900
QSYDSSQNAF YV                                                        12

SEQ ID NO: 901          moltype = DNA  length = 390
```

```
FEATURE              Location/Qualifiers
source               1..390
                     mol_type = other DNA
                     organism = Homo sapiens
SEQUENCE: 901
caggtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcagga agtacttgga atagtggtac catagactat   180
gcggactctg tgaagggccg attcaccatc tccagagaca acgccaagaa ctccctgtat   240
ctgcaaatga acagtctgag agctgaggac acggccttgt attactgtgc aaaagatagg   300
tttcgtaaag gttgtagtag taccggctgc tataaggaga actacggtat ggacgtctgg   360
ggccaaggga ccacggtcac cgtctcctca                                    390

SEQ ID NO: 902       moltype = AA  length = 130
FEATURE              Location/Qualifiers
source               1..130
                     mol_type = protein
                     organism = Homo sapiens
SEQUENCE: 902
QVQLVESGGG LVQPGRSLRL SCAASGFTFD DYAMHWVRQA PGKGLEWVSG STWNSGTIDY    60
ADSVKGRFTI SRDNAKNSLY LQMNSLRAED TALYYCAKDR FRKGCSSTGC YKENYGMDVW   120
GQGTTVTVSS                                                          130

SEQ ID NO: 903       moltype = DNA  length = 325
FEATURE              Location/Qualifiers
source               1..325
                     mol_type = other DNA
                     organism = Homo sapiens
SEQUENCE: 903
cagtctgtgg tgactcagcc accctcggtg tcagtggccc caggacagac ggccaggatt    60
acctgtggag gaaccaacat tggaagtaaa agtgtccact ggtaccagca gaagccaggc   120
caggcccctg tgctggtcgt ctatgatgat agcgaccggc cctcagggat ccctgagcga   180
ttctctggct ccaactctgg gaacacggcc accctgacca tcacctgggt cgaagccggg   240
gatgaggccg actattactg tcaggtgtgg gatagtagta gtgataatgt gctattcggc   300
ggagggacca agctgaccgt cctag                                         325

SEQ ID NO: 904       moltype = AA  length = 108
FEATURE              Location/Qualifiers
source               1..108
                     mol_type = protein
                     organism = Homo sapiens
SEQUENCE: 904
QSVVTQPPSV SVAPGQTARI TCGGTNIGSK SVHWYQQKPG QAPVLVVYDD SDRPSGIPER    60
FSGSNSGNTA TLTITWVEAG DEADYYCQVW DSSSDNVLFG GGTKLTVL                108

SEQ ID NO: 905       moltype = AA  length = 8
FEATURE              Location/Qualifiers
source               1..8
                     mol_type = protein
                     organism = Homo sapiens
SEQUENCE: 905
GFTFDDYA                                                              8

SEQ ID NO: 906       moltype = AA  length = 8
FEATURE              Location/Qualifiers
source               1..8
                     mol_type = protein
                     organism = Homo sapiens
SEQUENCE: 906
STWNSGTI                                                              8

SEQ ID NO: 907       moltype = AA  length = 23
FEATURE              Location/Qualifiers
source               1..23
                     mol_type = protein
                     organism = Homo sapiens
SEQUENCE: 907
AKDRFRKGCS STGCYKENYG MDV                                            23

SEQ ID NO: 908       moltype = AA  length = 6
FEATURE              Location/Qualifiers
source               1..6
                     mol_type = protein
                     organism = Homo sapiens
SEQUENCE: 908
NIGSKS                                                                6

SEQ ID NO: 909       moltype =   length =
SEQUENCE: 909
```

```
000

SEQ ID NO: 910            moltype = AA   length = 11
FEATURE                   Location/Qualifiers
source                    1..11
                          mol_type = protein
                          organism = Homo sapiens
SEQUENCE: 910
QVWDSSSDNV L                                                              11

SEQ ID NO: 911            moltype = DNA   length = 355
FEATURE                   Location/Qualifiers
source                    1..355
                          mol_type = other DNA
                          organism = Homo sapiens
SEQUENCE: 911
gaggtgcagc tggtggagtc tgggggaggt gtggtccagc ctggggggtc cctgagactc          60
tcctgtgcag cctctggaat catagtcagt gccaactaca tgacctgggt ccgccaggct        120
ccagggaagg gactgaatgg ggtctcagtt atttaccccg gtggtagcac attctacgcg        180
gactccgtga agggccgatt caccatctcc agagacaact ccaagaacac gttgtatctt        240
caaatgaaca gcctgagagt tgaggactcg gctgtgtatt actgtgcgag agattttgag        300
ctggctggtt tcaatgacta ctggggccag ggaaccctgg tcaccgtctc ctcag             355

SEQ ID NO: 912            moltype = AA   length = 118
FEATURE                   Location/Qualifiers
source                    1..118
                          mol_type = protein
                          organism = Homo sapiens
SEQUENCE: 912
EVQLVESGGG VVQPGGSLRL SCAASGIIVS ANYMTWVRQA PGKGLEWVSV IYPGGSTFYA          60
DSVKGRFTIS RDNSKNTLYL QMNSLRVEDS AVYYCARDLE LAGFNDYWGQ GTLVTVSS          118

SEQ ID NO: 913            moltype = DNA   length = 328
FEATURE                   Location/Qualifiers
source                    1..328
                          mol_type = other DNA
                          organism = Homo sapiens
SEQUENCE: 913
gatattgtga tgactcagtc tccaggcacc ctgtctttgt ctccagggga aagagccacc          60
ctctcctgca ggaccagtca gagtgttagc agcaactact tagcctggta ccagcagaaa        120
cctggccagg ctcccaggct cctcatctat ggtgcatcca gcagggccac tggcatccca        180
gacaggttca gtggcagtgg gtctgggaca gacttcactc tcaccatcag cagactggag        240
cctgaagatt ttgcagtgta ttactgtcag cagtttggta gttcacctcg gtacactttt        300
ggccagggga ccaaggtgga gatcaaac                                            328

SEQ ID NO: 914            moltype = AA   length = 109
FEATURE                   Location/Qualifiers
source                    1..109
                          mol_type = protein
                          organism = Homo sapiens
SEQUENCE: 914
DIVMTQSPGT LSLSPGERAT LSCRTSQSVS SNYLAWYQQK PGQAPRLLIY GASSRATGIP          60
DRFSGSGSGT DFTLTISRLE PEDFAVYYCQ QFGSSPRYTF GQGTKVEIK                     109

SEQ ID NO: 915            moltype = AA   length = 8
FEATURE                   Location/Qualifiers
source                    1..8
                          mol_type = protein
                          organism = Homo sapiens
SEQUENCE: 915
GIIVSANY                                                                   8

SEQ ID NO: 916            moltype = AA   length = 7
FEATURE                   Location/Qualifiers
source                    1..7
                          mol_type = protein
                          organism = Homo sapiens
SEQUENCE: 916
IYPGGST                                                                    7

SEQ ID NO: 917            moltype = AA   length = 12
FEATURE                   Location/Qualifiers
source                    1..12
                          mol_type = protein
                          organism = Homo sapiens
SEQUENCE: 917
ARDLELAGFN DY                                                             12

SEQ ID NO: 918            moltype = AA   length = 7
```

```
FEATURE                 Location/Qualifiers
source                  1..7
                        mol_type = protein
                        organism = Homo sapiens
SEQUENCE: 918
QSVSSNY                                                                 7

SEQ ID NO: 919          moltype =    length =
SEQUENCE: 919
000

SEQ ID NO: 920          moltype = AA   length = 10
FEATURE                 Location/Qualifiers
source                  1..10
                        mol_type = protein
                        organism = Homo sapiens
SEQUENCE: 920
QQFGSSPRYT                                                             10

SEQ ID NO: 921          moltype = DNA   length = 355
FEATURE                 Location/Qualifiers
source                  1..355
                        mol_type = other DNA
                        organism = Homo sapiens
SEQUENCE: 921
caggtgcagc tggtggagtc tgggggctgag gtgaagaagc ctgggtcctc ggtgaaggtc       60
tcctgcaagg cttctggagg aaacttcaac atgtatacta tcagtttggt gcgacaggcc      120
cctggacgag gacttgagtg gatgggaagg ttcatcccta cgctaataaa agcaaactac      180
gcacagaact ttccgggcag agtcaccatt accgcggaca atccactag cacagtctac       240
atggagctga agcctgac atctgacgac acggccgtgt attactgtgc gagaagtggg        300
agctacgatg cttttgatgt gtggggccaa gggacaatgg tcaccgtctc ttcag           355

SEQ ID NO: 922          moltype = AA   length = 118
FEATURE                 Location/Qualifiers
source                  1..118
                        mol_type = protein
                        organism = Homo sapiens
SEQUENCE: 922
QVQLVESGAE VKKPGSSVKV SCKASGGNFN MYTISWVRQA PGRGLEWMGR FIPIANKANY       60
AQNFPGRVTI TADKSTSTVY MELRSLTSDD TAVYYCARSG SYDAFDVWGQ GTMVTVSS        118

SEQ ID NO: 923          moltype = DNA   length = 325
FEATURE                 Location/Qualifiers
source                  1..325
                        mol_type = other DNA
                        organism = Homo sapiens
SEQUENCE: 923
gccatccgga tgacccagtc tccttccacc ctgtctgcat ctgtaggaga cagagtcacc       60
atcacttgcc gggccagtca gactattaat agttggttgg cctggtatca gcagaaaccc     120
gggaaagccc ctaagctcct gatctatgat gcctccaatt tggaaagtgg ggtcccatca     180
aggttcagcg gcagtggatc tgggacagaa ttcactctca ccatcagcag cctgcagcct     240
gatgattttg caacttatta ctgccaacag tatgaaagtt attctccgat caccttcggc     300
caagggacac gactggagat taaac                                           325

SEQ ID NO: 924          moltype = AA   length = 108
FEATURE                 Location/Qualifiers
source                  1..108
                        mol_type = protein
                        organism = Homo sapiens
SEQUENCE: 924
AIRMTQSPST LSASVGDRVT ITCRASQTIN SWLAWYQQKP GKAPKLLIYD ASNLESGVPS       60
RFSGSGSGTE FTLTISSLQP DDFATYYCQQ YESYSPITFG QGTRLEIK                   108

SEQ ID NO: 925          moltype = AA   length = 8
FEATURE                 Location/Qualifiers
source                  1..8
                        mol_type = protein
                        organism = Homo sapiens
SEQUENCE: 925
GGNFNMYT                                                                8

SEQ ID NO: 926          moltype = AA   length = 8
FEATURE                 Location/Qualifiers
source                  1..8
                        mol_type = protein
                        organism = Homo sapiens
SEQUENCE: 926
FIPIANKA                                                                8
```

```
SEQ ID NO: 927            moltype = AA  length = 11
FEATURE                   Location/Qualifiers
source                    1..11
                          mol_type = protein
                          organism = Homo sapiens
SEQUENCE: 927
ARSGSYDAFD V                                                              11

SEQ ID NO: 928            moltype = AA  length = 6
FEATURE                   Location/Qualifiers
source                    1..6
                          mol_type = protein
                          organism = Homo sapiens
SEQUENCE: 928
QTINSW                                                                     6

SEQ ID NO: 929            moltype =     length =
SEQUENCE: 929
000

SEQ ID NO: 930            moltype = AA  length = 10
FEATURE                   Location/Qualifiers
source                    1..10
                          mol_type = protein
                          organism = Homo sapiens
SEQUENCE: 930
QQYESYSPIT                                                                10

SEQ ID NO: 931            moltype = DNA  length = 369
FEATURE                   Location/Qualifiers
source                    1..369
                          mol_type = other DNA
                          organism = Homo sapiens
SEQUENCE: 931
caggtgcagc tggtggagtc tgggggagtc gtggtacagc ctggggggtc cctgagactc    60
tcctgtgcag cctctggatt cagctttgat gattatagca tgcactgggt ccgtcaagct   120
ccggggaagg gtctggagtg gtctctgtc atttactggg atggtgttag caaatactat    180
gcagactctg tgaagggccg attcaccatc tccagagaca cagcaaaaa ctccctgtat    240
ttgcaaatga acagtctgag aactgaggac accgccgtat attactgtgc aaaagatagt   300
gaggattgta gtagtaccag ctgctacatg gacgtctggg gcaaagggac cacggtcacc   360
gtctcctca                                                           369

SEQ ID NO: 932            moltype = AA  length = 123
FEATURE                   Location/Qualifiers
source                    1..123
                          mol_type = protein
                          organism = Homo sapiens
SEQUENCE: 932
QVQLVESGGV VVQPGGSLRL SCAASGFSFD DYSMHWVRQA PGKGLEWVSV IYWDGVSKYY     60
ADSVKGRFTI SRDNSKNSLY LQMNSLRTED TAVYYCAKDS EDCSSTSCYM DVWGKGTTVT    120
VSS                                                                 123

SEQ ID NO: 933            moltype = DNA  length = 340
FEATURE                   Location/Qualifiers
source                    1..340
                          mol_type = other DNA
                          organism = Homo sapiens
SEQUENCE: 933
gaaattgtgt tgacacagtc tccagactcc ctggctgtgt ctctgggcga gagggccacc     60
atcaactgca agtccagcca gaatgttttt tacagctcca acaataagaa ttacttagct   120
tggtaccagc agaaaccagg acagcctcct caactactca tttactgggc atctacccgg   180
gaatccgggg tccctgaccg attcagtggc agcgggtctg ggacagattt cactctcacc   240
atcagcagcc tgcaggctga agatgtggca gtttattact gtcaccaata ttatagtact   300
ccattcactt tcggccctgg gaccaaagtg gatatcaaac                         340

SEQ ID NO: 934            moltype = AA  length = 113
FEATURE                   Location/Qualifiers
source                    1..113
                          mol_type = protein
                          organism = Homo sapiens
SEQUENCE: 934
EIVLTQSPDS LAVSLGERAT INCKSSQNVL YSSNNKNYLA WYQQKPGQPP QLLIYWASTR     60
ESGVPDRFSG SGSGTDFTLT ISSLQAEDVA VYYCHQYYST PFTFGPGTKV DIK           113

SEQ ID NO: 935            moltype = AA  length = 8
FEATURE                   Location/Qualifiers
source                    1..8
                          mol_type = protein
                          organism = Homo sapiens
```

```
SEQUENCE: 935
GFSFDDYS                                                                            8

SEQ ID NO: 936          moltype = AA  length = 8
FEATURE                 Location/Qualifiers
source                  1..8
                        mol_type = protein
                        organism = Homo sapiens
SEQUENCE: 936
IYWDGVSK                                                                            8

SEQ ID NO: 937          moltype = AA  length = 16
FEATURE                 Location/Qualifiers
source                  1..16
                        mol_type = protein
                        organism = Homo sapiens
SEQUENCE: 937
AKDSEDCSST SCYMDV                                                                  16

SEQ ID NO: 938          moltype = AA  length = 12
FEATURE                 Location/Qualifiers
source                  1..12
                        mol_type = protein
                        organism = Homo sapiens
SEQUENCE: 938
QNVLYSSNNK NY                                                                      12

SEQ ID NO: 939          moltype =     length =
SEQUENCE: 939
000

SEQ ID NO: 940          moltype = AA  length = 9
FEATURE                 Location/Qualifiers
source                  1..9
                        mol_type = protein
                        organism = Homo sapiens
SEQUENCE: 940
HQYYSTPFT                                                                           9

SEQ ID NO: 941          moltype = DNA  length = 370
FEATURE                 Location/Qualifiers
source                  1..370
                        mol_type = other DNA
                        organism = Homo sapiens
SEQUENCE: 941
caggttcagc tggtgcagtc tggagctgag gtgaagaagc tggggcctc  agtgaaggtc       60
tcctgcaagg ctgctggtta cagctttatg aactacggt  tcaactgggt gcgacaggcc      120
cctggacaag gcttgagtg  gatgggatgg atcaacactt acaatggtaa cgcaaagtat      180
gcacagaagt tccagggccg agtcaccatg accacagaca catccacgag cacagcctac      240
atggagctga ggagcctgag atcgggcgac acggccgtgt attactgtgc gagggaccct      300
ttcaccggtt atgatgacgt ttgggggggg gactactggg gccagggaac cctggtcacc      360
gtctcctcag                                                              370

SEQ ID NO: 942          moltype = AA  length = 123
FEATURE                 Location/Qualifiers
source                  1..123
                        mol_type = protein
                        organism = Homo sapiens
SEQUENCE: 942
QVQLVQSGAE VKKPGASVKV SCKAAGYSFM NYGINWVRQA PGQGLEWMGW INTYNGNAKY       60
AQKFQGRVTM TTDTSTSTAY MELRSLRSGD TAVYYCARDP FTGYDDVWGG DYWGQGTLVT      120
VSS                                                                    123

SEQ ID NO: 943          moltype = DNA  length = 340
FEATURE                 Location/Qualifiers
source                  1..340
                        mol_type = other DNA
                        organism = Homo sapiens
SEQUENCE: 943
gccatccaga tgacccagtc tccagactcc ctggctgtgt ctctgggcga gagggccacc       60
atcaactgca agtccagcca gagtgtttta tacagctcca acaataagaa ttacttagct      120
tggtaccagc agaaaccagg acagcctcct aagctggtca tttactgggc atctacccgg      180
gaatccgggg tccctgaccg attcagtggc agcgggtctg ggacagattt cactctcacc      240
atcagcgcc  tgcaggctga gatgtggca  gtttattact gtcaccaata ttatagtagt      300
cctcgcactt ttggccaggg gaccaaggtg gaaatcaaac                             340

SEQ ID NO: 944          moltype = AA  length = 113
FEATURE                 Location/Qualifiers
source                  1..113
```

```
                        mol_type = protein
                        organism = Homo sapiens
SEQUENCE: 944
AIQMTQSPDS LAVSLGERAT INCKSSQSVL YSSNNKNYLA WYQQKPGQPP KLVIYWASTR    60
ESGVPDRFSG SGSGTDFTLT ISSLQAEDVA VYYCHQYYSS PRTFGQGTKV EIK          113

SEQ ID NO: 945          moltype = AA  length = 8
FEATURE                 Location/Qualifiers
source                  1..8
                        mol_type = protein
                        organism = Homo sapiens
SEQUENCE: 945
GYSFMNYG                                                              8

SEQ ID NO: 946          moltype = AA  length = 8
FEATURE                 Location/Qualifiers
source                  1..8
                        mol_type = protein
                        organism = Homo sapiens
SEQUENCE: 946
INTYNGNA                                                              8

SEQ ID NO: 947          moltype = AA  length = 16
FEATURE                 Location/Qualifiers
source                  1..16
                        mol_type = protein
                        organism = Homo sapiens
SEQUENCE: 947
ARDPFTGYDD VWGGDY                                                    16

SEQ ID NO: 948          moltype = AA  length = 12
FEATURE                 Location/Qualifiers
source                  1..12
                        mol_type = protein
                        organism = Homo sapiens
SEQUENCE: 948
QSVLYSSNNK NY                                                        12

SEQ ID NO: 949          moltype =     length =
SEQUENCE: 949
000

SEQ ID NO: 950          moltype = AA  length = 9
FEATURE                 Location/Qualifiers
source                  1..9
                        mol_type = protein
                        organism = Homo sapiens
SEQUENCE: 950
HQYYSSPRT                                                             9

SEQ ID NO: 951          moltype = DNA  length = 375
FEATURE                 Location/Qualifiers
source                  1..375
                        mol_type = other DNA
                        organism = Homo sapiens
SEQUENCE: 951
gaggtgcagc tgttggagac tgggggaggc ttggttcagc ccggcaggtc cctgagactc    60
tcctgtgcag cctcgggatt ccccttttgat gattatgcca tccactgggt ccggctagct  120
ccagggaagg gcctggagtg ggtctcaagt attagttggg atagtggtag cataggctat   180
gcggactctg tgaagggccg gttcaccatc tccagagaca acgccaagaa ctccctgtat   240
ctgcaaatga acagtctgag agctgaggac acggccttgt attactgtgc aaaggggggcc  300
tttcccgggt atagcagtgg ctggtactac ggttttggacg tctggggcca agggccacg   360
gtcaccgtct cctca                                                    375

SEQ ID NO: 952          moltype = AA  length = 125
FEATURE                 Location/Qualifiers
source                  1..125
                        mol_type = protein
                        organism = Homo sapiens
SEQUENCE: 952
EVQLLETGGG LVQPGRSLRL SCAASGFPFD DYAIHWVRLA PGKGLEWVSS ISWDSGSIGY    60
ADSVKGRFTI SRDNAKNSLY LQMNSLRAED TALYYCAKGA FPGYSSGWYY GLDVWGQGAT   120
VTVSS                                                               125

SEQ ID NO: 953          moltype = DNA  length = 328
FEATURE                 Location/Qualifiers
source                  1..328
                        mol_type = other DNA
                        organism = Homo sapiens
```

```
SEQUENCE: 953
cagtctgtcg tgacgcagcc tccctccgcg tcggggtctc ttggacagtc agtcaccatc   60
tcctgcactg gaaccagcag tgacgttggt ggttacaact atgtctcttg gtaccaacaa  120
cacccaggca aagcccccaa actcatgatt tttgaggtca gtaagcggcc ctcagggggtc  180
cctgatcgct tctctggctc caagtctggc aacacggccc cctgaccgt ctctgggctc   240
caggctgagg atgaggctga ttattactgc agctcatatg caggcaacaa aggggtcttc   300
ggcggaggga ccaaattgac cgtcctcg                                      328

SEQ ID NO: 954              moltype = AA   length = 109
FEATURE                     Location/Qualifiers
source                      1..109
                            mol_type = protein
                            organism = Homo sapiens
SEQUENCE: 954
QSVVTQPPSA SGSLGQSVTI SCTGTSSDVG GYNYVSWYQQ HPGKAPKLMI FEVSKRPSGV   60
PDRFSGSKSG NTASLTVSGL QAEDEADYYC SSYAGNKGVF GGGTKLTVL              109

SEQ ID NO: 955              moltype = AA   length = 8
FEATURE                     Location/Qualifiers
source                      1..8
                            mol_type = protein
                            organism = Homo sapiens
SEQUENCE: 955
GFPFDDYA                                                              8

SEQ ID NO: 956              moltype = AA   length = 8
FEATURE                     Location/Qualifiers
source                      1..8
                            mol_type = protein
                            organism = Homo sapiens
SEQUENCE: 956
ISWDSGSI                                                              8

SEQ ID NO: 957              moltype = AA   length = 18
FEATURE                     Location/Qualifiers
source                      1..18
                            mol_type = protein
                            organism = Homo sapiens
SEQUENCE: 957
AKGAFPGYSS GWYYGLDV                                                  18

SEQ ID NO: 958              moltype = AA   length = 9
FEATURE                     Location/Qualifiers
source                      1..9
                            mol_type = protein
                            organism = Homo sapiens
SEQUENCE: 958
SSDVGGYNY                                                             9

SEQ ID NO: 959              moltype =    length =
SEQUENCE: 959
000

SEQ ID NO: 960              moltype = AA   length = 9
FEATURE                     Location/Qualifiers
source                      1..9
                            mol_type = protein
                            organism = Homo sapiens
SEQUENCE: 960
SSYAGNKGV                                                             9

SEQ ID NO: 961              moltype = AA   length = 97
FEATURE                     Location/Qualifiers
source                      1..97
                            mol_type = protein
                            organism = Homo sapiens
SEQUENCE: 961
MQLVQSGPEV KKPGTSVKVS CKASGFTFTS SAVQWVRQAR GQRLEWIGWI VVGSGNTNYA    60
QKFQERVTIT RDMSTSTAYM ELSSLRSEDT AVYYCAA                             97

SEQ ID NO: 962              moltype = DNA   length = 369
FEATURE                     Location/Qualifiers
source                      1..369
                            mol_type = other DNA
                            organism = Homo sapiens
SEQUENCE: 962
caaatgcagc tggtgcagtc tgggcctgag gtgaagaagc ctgggacctc agtgaaggtc    60
tcctgcaagg cttctggatt cacctttatg agctctgctg tgcagtgggt gcgacaggct  120
cgtggacaac gccttgagtg gataggatgg atcgtcattg gcagtggtaa cacaaactac  180
```

-continued

```
gcacagaagt tccaggaaag agtcaccatt accagggaca tgtccacaag cacagcctac    240
atggagctga gcagcctgag atccgaggac acggccgtgt attactgtgc ggcccccat     300
tgtagtagta tcagctgcaa tgatggtttt gatatctggg gccaagggac aatggtcacc    360
gtctcttca                                                            369

SEQ ID NO: 963            moltype = AA   length = 123
FEATURE                   Location/Qualifiers
source                    1..123
                          mol_type = protein
                          organism = Homo sapiens
SEQUENCE: 963
QMQLVQSGPE VKKPGTSVKV SCKASGFTFM SSAVQWVRQA RGQRLEWIGW IVIGSGNTNY     60
AQKFQERVTI TRDMSTSTAY MELSSLRSED TAVYYCAAPY CSSISCNDGF DIWGQGTMVT    120
VSS                                                                  123

SEQ ID NO: 964            moltype = DNA   length = 327
FEATURE                   Location/Qualifiers
source                    1..327
                          mol_type = other DNA
                          organism = Homo sapiens
SEQUENCE: 964
gaaattgtgt tgacgcagtc tccaggcacc ctgtctttgt ctccagggga gagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cactatggta gctcacgggg ttggacgttc    300
ggccaaggga ccaaggtgga aatcaaa                                        327

SEQ ID NO: 965            moltype = AA   length = 109
FEATURE                   Location/Qualifiers
source                    1..109
                          mol_type = protein
                          organism = Homo sapiens
SEQUENCE: 965
EIVLTQSPGT LSLSPGERAT LSCRASQSVS SSYLAWYQQK PGQAPRLLIY GASSRATGIP     60
DRFSGSGSGT DFTLTISRLE PEDFAVYYCQ HYGSSRGWTF GQGTKVEIK               109

SEQ ID NO: 966            moltype = AA   length = 1273
FEATURE                   Location/Qualifiers
source                    1..1273
                          mol_type = protein
                          organism = Homo sapiens
SEQUENCE: 966
MFVFLVLLPL VSSQCVNLTT RTQLPPAYTN SFTRGVYYPD KVFRSSVLHS TQDLFLPFFS     60
NVTWFHAIHV SGTNGTKRFD NPVLPFNDGV YFASTEKSNI IRGWIFGTTL DSKTQSLLIV    120
NNATNVVIKV CEFQFCNDPF LGVYYHKNNK SWMESEFRVY SSANNCTFEY VSQPFLMDLE    180
GKQGNFKNLR EFVFKNIDGY FKIYSKHTPI NLVRDLPQGF SALEPLVDLP IGINITRFQT    240
LLALHRSYLT PGDSSSGWTA GAAAYYVGYL QPRTFLLKYN ENGTITDAVD CALDPLSETK    300
CTLKSFTVEK GIYQTSNFRV QPTESIVRFP NITNLCPFGE VFNATRFASV YAWNRKRISN    360
CVADYSVLYN SASFSTFKCY GVSPTKLNDL CFTNVYADSF VIRGDEVRQI APGQTGKIAD    420
YNYKLPDDFT GCVIAWNSNN LDSKVGGNYN YLYRLFRKSN LKPFERDIST EIYQAGSTPC    480
NGVEGFNCYF PLQSYGFQPT NGVGYQPYRV VVLSFELLHA PATVCGPKKS TNLVKNKCVN    540
FNFNGLTGTG VLTESNKKFL PFQQFGRDIA DTTDAVRDPQ TLEILDITPC SFGGVSVITP    600
GTNTSNQVAV LYQDVNCTEV PVAIHADQLT PTWRVYSTGS NVFQTRAGCL IGAEHVNNSY    660
ECDIPIGAGI CASYQTQTNS PRRARSVASQ SIIAYTMSLG AENSVAYSNN SIAIPTNFTI    720
SVTTEILPVS MTKTSVDCTM YICGDSTECS NLLLQYGSFC TQLNRALTGI AVEQDKNTQE    780
VFAQVKQIYK TPPIKDFGGF NFSQILPDPS KPSKRSFIED LLFNKVTLAD AGFIKQYGDC    840
LGDIAARDLI CAQKFNGLTV LPPLLTDEMI AQYTSALLAG TITSGWTFGA GAALQIPFAM    900
QMAYRFNGIG VTQNVLYENQ KLIANQFNSA IGKIQDSLSS TASALGKLQD VVNQNAQALN    960
TLVKQLSSNF GAISSVLNDI LSRLDKVEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 967            moltype = AA   length = 96
FEATURE                   Location/Qualifiers
source                    1..96
                          mol_type = protein
                          organism = Homo sapiens
SEQUENCE: 967
EIVLTQSPGT LSLSPGERAT LSCRASQSVS SSYLAWYQQK PGQAPRLLIY GASSRATGIP     60
DRFSGSGSGT DFTLTISRLE PEDFAVYYCQ QYGSSP                               96
```